(12) United States Patent
Ito et al.

(10) Patent No.: US 11,479,544 B2
(45) Date of Patent: Oct. 25, 2022

(54) COMPOUND, MATERIAL FOR ORGANIC ELECTROLUMINESCENCE ELEMENT, ORGANIC ELECTROLUMINESCENCE ELEMENT, AND ELECTRONIC DEVICE

(71) Applicant: IDEMITSU KOSAN CO., LTD., Chiyoda-ku (JP)

(72) Inventors: Hirokatsu Ito, Ichihara (JP); Tasuku Haketa, Chiba (JP); Yu Kudo, Chiba (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 83 days.

(21) Appl. No.: 16/491,503

(22) PCT Filed: Mar. 8, 2018

(86) PCT No.: PCT/JP2018/009091
§ 371 (c)(1),
(2) Date: Sep. 5, 2019

(87) PCT Pub. No.: WO2018/164239
PCT Pub. Date: Sep. 13, 2018

(65) Prior Publication Data
US 2020/0024263 A1 Jan. 23, 2020

(30) Foreign Application Priority Data
Mar. 8, 2017 (JP) .............................. JP2017-044370

(51) Int. Cl.
*C07D 405/12* (2006.01)
*C09K 11/06* (2006.01)
*H01L 51/50* (2006.01)

(52) U.S. Cl.
CPC ............ *C07D 405/12* (2013.01); *C09K 11/06* (2013.01); *H01L 51/5056* (2013.01)

(58) Field of Classification Search
CPC .... C07D 405/12; C09K 11/06; H01L 51/5056
See application file for complete search history.

(56) References Cited

U.S. PATENT DOCUMENTS

| | | | |
|---|---|---|---|
| 11,056,654 B2 * | 7/2021 | Kim | C09B 57/00 |
| 2012/0292606 A1 * | 11/2012 | Kato | C09B 57/008 |
| | | | 257/40 |
| 2014/0151666 A1 | 6/2014 | Miyata | |
| 2015/0166515 A1 * | 6/2015 | Itoi | C07D 409/14 |
| | | | 257/40 |
| 2015/0243891 A1 * | 8/2015 | Kato | C07C 255/58 |
| | | | 257/40 |
| 2015/0263292 A1 * | 9/2015 | Kato | H01L 51/006 |
| | | | 257/40 |
| 2015/0270502 A1 * | 9/2015 | Fuchiwaki | C07F 7/0812 |
| | | | 257/40 |
| 2016/0079542 A1 * | 3/2016 | Itoi | H01L 51/006 |
| | | | 257/40 |
| 2016/0093810 A1 * | 3/2016 | Miyake | C07D 405/14 |
| | | | 548/440 |

(Continued)

FOREIGN PATENT DOCUMENTS

| | | | |
|---|---|---|---|
| EP | 3 680 948 A2 | 7/2020 | |
| FR | 3 056 591 A1 | 3/2018 | |

(Continued)

OTHER PUBLICATIONS

CAS Abstract and Indexed Compound, J. Kim et al., WO 2018155826 (2018) (Year: 2018).*
International Search Report dated Apr. 17, 2018 in PCT/JP2018/009091 filed Mar. 8, 2018.
International Search Report dated Apr. 17, 2018 in PCT/JP2018/009091 filed Mar. 8, 2018, 2 pages.

(Continued)

*Primary Examiner* — Alexander R Pagano
(74) *Attorney, Agent, or Firm* — Oblon, McClelland, Maier & Neustadt, L.L.P.

(57) ABSTRACT

A novel compound represented by formula (1):

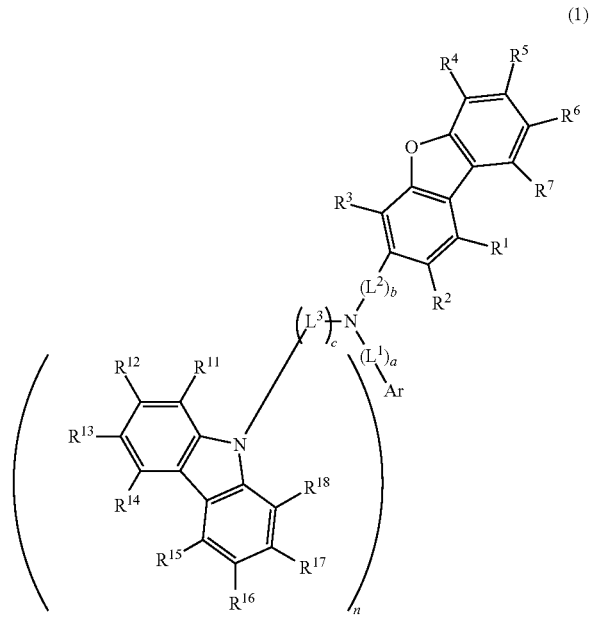

wherein $R^1$ to $R^7$, $R^{11}$ to $R^{18}$, $L^1$ to $L^3$, a to c, n, and Ar are as defined in the description,
provides an organic electroluminescence device having a device lifetime further improved.

25 Claims, 1 Drawing Sheet

(56) References Cited

U.S. PATENT DOCUMENTS

| | | |
|---|---|---|
| 2018/0182974 A1 | 6/2018 | Haketa et al. |
| 2018/0182981 A1 | 6/2018 | Chen et al. |
| 2018/0190915 A1 | 7/2018 | Ji et al. |
| 2018/0198081 A1 | 7/2018 | Zeng et al. |
| 2018/0208615 A1 | 7/2018 | Lin et al. |
| 2018/0237460 A1 | 8/2018 | Ahn et al. |
| 2019/0006591 A1* | 1/2019 | Yamaki .................. H01L 51/006 |
| 2019/0181344 A1 | 6/2019 | Herron et al. |
| 2019/0189946 A1 | 6/2019 | Kim et al. |
| 2019/0203114 A1 | 7/2019 | Ihn et al. |
| 2019/0028021 A1 | 9/2019 | Yoon et al. |
| 2019/0273220 A1 | 9/2019 | Kim et al. |
| 2020/0091435 A1* | 3/2020 | Masuda .............. H01L 51/0061 |
| 2020/0290985 A1* | 9/2020 | Kudo .................... H01L 51/006 |
| 2020/0317653 A1* | 10/2020 | Ito ....................... H01L 51/0059 |
| 2020/0335705 A1* | 10/2020 | Song ................... H01L 51/0054 |
| 2021/0062082 A1* | 3/2021 | Kudo .................. H01L 51/0061 |
| 2021/0066611 A1* | 3/2021 | Ito ....................... H01L 51/0061 |
| 2021/0083194 A1 | 3/2021 | Kawamura et al. |
| 2021/0094937 A1* | 4/2021 | Ito ....................... H01L 51/0061 |

FOREIGN PATENT DOCUMENTS

| | | | | |
|---|---|---|---|---|
| JP | 2011-51936 A | | 3/2011 | |
| JP | 2014-131987 A | | 7/2014 | |
| JP | 2018-108939 A | | 7/2018 | |
| JP | 2018-123083 A | | 8/2018 | |
| KR | 10-2012-0104172 | | 9/2012 | |
| KR | 10-2014-0024734 | | 3/2014 | |
| KR | 20140087806 A | * | 7/2014 | ........... C07D 471/14 |
| KR | 10-2015-0073063 | | 6/2015 | |
| KR | 10-2015-0090021 | | 8/2015 | |
| KR | 20150102735 A | * | 9/2015 | |
| KR | 20150116337 A | * | 10/2015 | |
| KR | 10-2016-0149879 A | | 12/2016 | |
| KR | 20160143627 A | * | 12/2016 | |
| KR | 20160149879 A | * | 12/2016 | |
| KR | 10-2017-0025002 | * | 2/2017 | |
| KR | 10-2017-0071681 | * | 6/2017 | |
| KR | 10-2018-0050891 A | | 5/2018 | |
| KR | 10-2018-0060089 A | | 6/2018 | |
| KR | 10-2018-0060582 A | | 6/2018 | |
| KR | 10-2018-0061461 A | | 6/2018 | |
| KR | 10-2018-0063708 A | | 6/2018 | |
| KR | 10-2018-0078040 A | | 7/2018 | |
| KR | 10-2018-0078177 A | | 7/2018 | |
| KR | 10-2018-0082124 A | | 7/2018 | |
| KR | 10-2018-0096444 A | | 8/2018 | |
| KR | 10-2018-0098130 | | 9/2018 | |
| KR | 10-2019-0057229 A | | 5/2019 | |
| KR | 20200013747 A | | 2/2020 | |
| KR | 20200013748 A | | 2/2020 | |
| WO | WO 2010/061824 A1 | | 6/2010 | |
| WO | WO 2011/040607 A1 | | 4/2011 | |
| WO | WO-2011040607 A1 | * | 4/2011 | ......... H01L 51/0059 |
| WO | WO-2014104545 A1 | * | 7/2014 | .......... C07D 471/04 |
| WO | WO 2016/006711 A1 | | 1/2016 | |
| WO | WO 2016/072690 A1 | | 5/2016 | |
| WO | WO 2018/095385 A1 | | 5/2018 | |
| WO | WO 2018/095386 A1 | | 5/2018 | |
| WO | WO 2018/099431 A1 | | 6/2018 | |
| WO | WO 2018/105888 A1 | | 6/2018 | |
| WO | WO 2018/133836 A1 | | 7/2018 | |
| WO | WO 2018/139662 A1 | | 8/2018 | |
| WO | WO 2018/139767 A1 | | 8/2018 | |
| WO | WO-2018155826 A1 | * | 8/2018 | ............. H01L 51/50 |
| WO | WO 2018/159970 A1 | | 9/2018 | |
| WO | WO 2018/164201 A1 | | 9/2018 | |
| WO | WO 2018/164239 A1 | | 9/2018 | |
| WO | WO-2018226036 A1 | * | 12/2018 | ............. H01L 51/50 |
| WO | WO 2019/063886 A1 | | 4/2019 | |

OTHER PUBLICATIONS

Extended European Search Report dated Jul. 31, 2020 in European Patent Application No. 18764799.5, 6 pages.

Office Action as received in the JP Patent Application No. 2019-503856 dated Nov. 16, 2021 w/English Translation, 4 pages.

Office Action in EPC Application No. 18764799.5, dated May 20, 2022.

Office Action dated Jul. 5, 2022, in Korean Patent Application No. 10-2019-7025927 (with English-language Translation).

\* cited by examiner

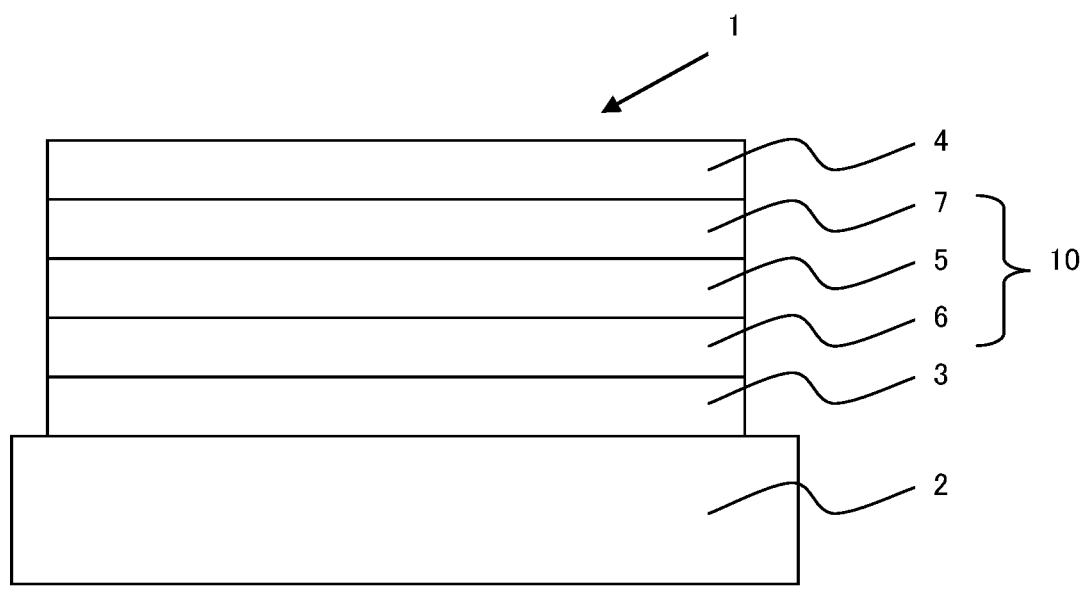

COMPOUND, MATERIAL FOR ORGANIC ELECTROLUMINESCENCE ELEMENT, ORGANIC ELECTROLUMINESCENCE ELEMENT, AND ELECTRONIC DEVICE

TECHNICAL FIELD

The present invention relates to compounds, materials for organic electroluminescence devices comprising the compounds, organic electroluminescence devices comprising the compounds, and electronic devices comprising the organic electroluminescence devices.

BACKGROUND ART

An organic electroluminescence device ("organic EL device") is generally composed of an anode, a cathode, and an organic layer sandwiched between the anode and the cathode. When a voltage is applied between the electrodes, electrons are injected from the cathode and holes are injected from the anode into a light emitting region. The injected electrons recombine with the injected holes in the light emitting region to form excited states. When the excited states return to the ground state, the energy is released as light. Therefore, it is important for obtaining an organic EL device with a high efficiency to develop a compound that transports electrons or holes into the light emitting region efficiently and facilitates the recombination of electrons and holes.

Patent Literature 1 describes a compound wherein a 9,9-diphenylfluorenyl group is bonded to the central nitrogen atom directly or via a linker and two groups selected from a dibenzofuranyl group, a dibenzothiophenyl group, and a carbazolyl group are bonded to the central nitrogen atom each directly or via a linker. The compound is used in a hole transporting layer.

Patent Literature 2 discloses the use of an amine compound wherein a N-carbazolyl group is bonded to the central nitrogen atom directly via a linker in a hole transporting layer. As a specific example of the amine compound, a compound wherein a dibenzofuranyl group is directly bonded to the central nitrogen atom is described.

Patent Literature 3 discloses an amine compound wherein a group represented by formula (1), a group represented by formula (2) or (3), and a group selected from a group represented by formula (2) or (3) and a substituted or unsubstituted aryl group are bonded to the central nitrogen atom:

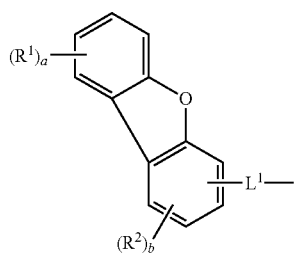

(1)

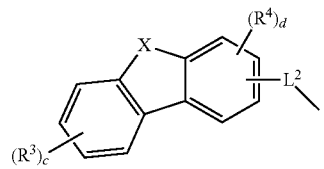

(2)

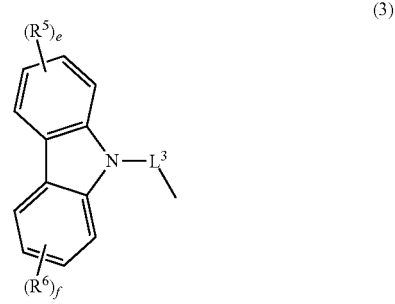

(3)

wherein, X is an oxygen atom or $NAr^1$ and $Ar^1$ is a substituted or unsubstituted aryl group having 6 to 14 ring carbon atoms.

The amine compound is used in a hole transporting layer or a hole injecting layer.

However, Patent Literatures 1 to 3 fail to describe the compound of the present invention.

CITATION LIST

Patent Literature

Patent Literature 1: WO 2016/006711
Patent Literature 2: WO 2016/072690
Patent Literature 3: WO 2010/061824

SUMMARY OF INVENTION

Technical Problem

Various compounds useful for the production of organic EL devices have been reported. However, a compound that further improves the performance of organic EL devices has been still demanded.

The present invention has been made to solve the above problem and an object of the invention is to provide organic EL devices that are further improved in device lifetime and provide novel compounds for achieving such organic EL devices.

Solution to Problem

As a result of extensive research for achieving the above object, the inventors have found that a compound represented by formula (1) provides an organic EL device having a further improved device lifetime.

In an aspect, the invention provides a compound represented by formula (1) (hereinafter also referred to as "compound (1)"):

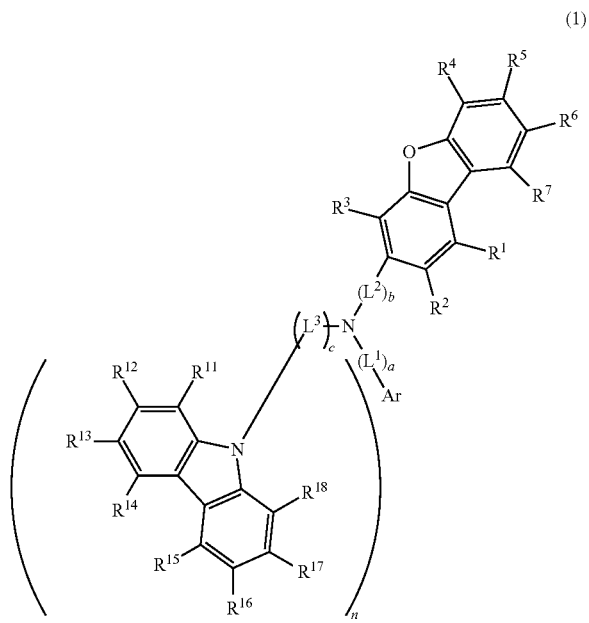

wherein:

$R^1$ to $R^7$ and $R^{11}$ to $R^{18}$ are each independently a hydrogen atom, a substituted or unsubstituted alkyl group having 1 to 30 carbon atoms, a substituted or unsubstituted cycloalkyl group having 3 to 30 ring carbon atoms, a substituted or unsubstituted aryl group having 6 to 30 ring carbon atoms, a substituted or unsubstituted aralkyl group having 7 to 36 carbon atoms, a mono- or di-substituted amino group having a substituent selected from the group consisting of a substituted or unsubstituted alkyl group having 1 to 30 carbon atoms and a substituted or unsubstituted aryl group having 6 to 30 ring carbon atoms, a substituted or unsubstituted alkoxy group having 1 to 30 carbon atoms, a substituted or unsubstituted aryloxy group having 6 to 30 ring carbon atoms, a mono-, di- or tri-substituted silyl group having a substituent selected from the group consisting of a substituted or unsubstituted alkyl group having 1 to 30 carbon atoms and a substituted or unsubstituted aryl group having 6 to 30 ring carbon atoms, a substituted or unsubstituted haloalkyl group having 1 to 30 carbon atoms, a substituted or unsubstituted haloalkoxy group having 1 to 30 carbon atoms, a substituted or unsubstituted heteroaryl group having 5 to 30 ring atoms, a halogen atom, a cyano group, or a nitro group, $R^1$ and $R^2$, adjacent two selected from $R^4$ to $R^7$, adjacent two selected from $R^{11}$ to $R^{14}$, and adjacent two selected from $R^{15}$ to $R^{18}$ may be bonded to each other to form a ring structure, Ar is a substituted or unsubstituted aryl group having 6 to 30 ring carbon atoms, wherein the aryl group is composed of only a six-membered ring, n is 1 or 2, a is 0, 1, 2, or 3, when a is 0, Ar is directly bonded to the central nitrogen atom, and when a is 2 or 3, two or three $L^1$'s may be the same or different, b is 1, 2, or 3, when b is 2 or 3, two or three $L^2$'s may be the same or different, c is 1, 2, or 3, when c is 1, $L^3$ is a group represented by formula (L3-1) or (L3-2), when c is 2 or 3, two or three $L^3$'s may be the same or different and at least one selected from two or three $L^3$'s is a group represented by formula (L3-1) or (L3-2) and $L^3$ not a group represented by formula (L3-1) or (L3-2) is a substituted or unsubstituted aromatic hydrocarbon group having 6 to 18 ring carbon atoms:

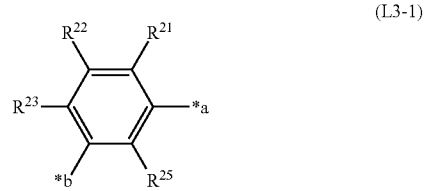

(L3-1)

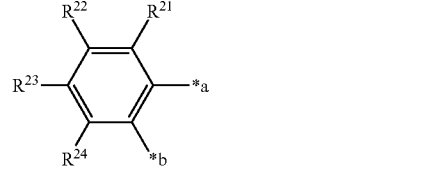

(L3-2)

wherein:

$R^{21}$ to $R^{25}$ are each independently as defined above with respect to $R^1$ to $R^7$,

*a is directly or indirectly bonded to the central nitrogen atom,

*b is directly or indirectly bonded to the nitrogen atom of the carbazole structure, and $L^1$ and $L^2$ are each independently a substituted or unsubstituted aromatic hydrocarbon group having 6 to 18 ring carbon atoms.

In another aspect, the invention provides a material for organic electroluminescence device comprising the compound (1).

In still another aspect, the invention provides an organic electroluminescence device comprising a cathode, an anode, and an organic layer disposed between the cathode and the anode, wherein the organic layer comprises a light emitting layer and at least one layer of the organic layer comprises the compound (1).

In still another aspect, the invention provides an electronic device comprising the organic electroluminescence device.

Advantageous Effects of Invention

The compound (1) provides an organic EL device having a further improved device lifetime.

BRIEF DESCRIPTION OF DRAWINGS

FIG. 1 is a schematic view showing the structure of an organic EL device in an embodiment of the invention.

DESCRIPTION OF EMBODIMENTS

The term of "XX to YY carbon atoms" referred to by "a substituted or unsubstituted group ZZ having XX to YY carbon atoms" used herein is the number of carbon atoms of the unsubstituted group ZZ and does not include any carbon atom in the substituent of the substituted group ZZ.

The term of "XX to YY atoms" referred to by "a substituted or unsubstituted group ZZ having XX to YY atoms" used herein is the number of atoms of the unsubstituted group ZZ and does not include any atom in the substituent of the substituted group ZZ.

The term of "unsubstituted group ZZ" referred to by "substituted or unsubstituted group ZZ" used herein means that no hydrogen atom in the group ZZ is substituted by a substituent.

The definition of "hydrogen atom" used herein includes isotopes different in the neutron numbers, i.e., light hydrogen (protium), heavy hydrogen (deuterium), and tritium.

The number of "ring carbon atoms" referred to herein means the number of the carbon atoms included in the atoms that form the ring itself of a compound in which a series of atoms is bonded to form a ring, for example, a monocyclic compound, a fused ring compound, a cross-linked compound, a carbocyclic compound, and a heterocyclic compound. If the ring has a substituent, the carbon atom in the substituent is not included in the ring carbon atom. Unless otherwise noted, the same applies to the number of "ring carbon atoms" mentioned below. For example, a benzene ring has 6 ring carbon atoms, a naphthalene ring has 10 ring carbon atoms, a pyridinyl group has 5 ring carbon atoms, and a furanyl group has 4 ring carbon atoms. If a benzene ring or a naphthalene ring has, for example, an alkyl substituent, the carbon atom in the alkyl substituent is not counted as the ring carbon atom of the benzene or naphthalene ring. In case of a fluorene ring to which a fluorene substituent is bonded (inclusive of a spirobifluorene ring), the carbon atom in the fluorene substituent is not counted as the ring carbon atom of the fluorene ring.

The number of "ring atom" referred to herein means the number of the atoms that form the ring itself of a compound in which a series of atoms is bonded to form a ring, for example, a monocyclic compound, a fused ring compound, a cross-linked compound, a carbocyclic compound, and a heterocyclic compound. The atom not forming the ring, for example, hydrogen atom bonding to the atom that forms the ring and the atom in the substituent bonding to the atom that forms the ring are not counted as the ring atom. Unless otherwise noted, the same applies to the number of "ring atoms" mentioned below. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent on the ring carbon atom of a pyridine ring or a quinazoline ring are not counted as the ring atom. In case of a fluorene ring to which a fluorene substituent is bonded (inclusive of a spirobifluorene ring), the atom in the fluorene substituent is not counted as the ring atom of the fluorene ring.

The compound in an aspect of the invention ("compound (1)") is represented by formula (1):

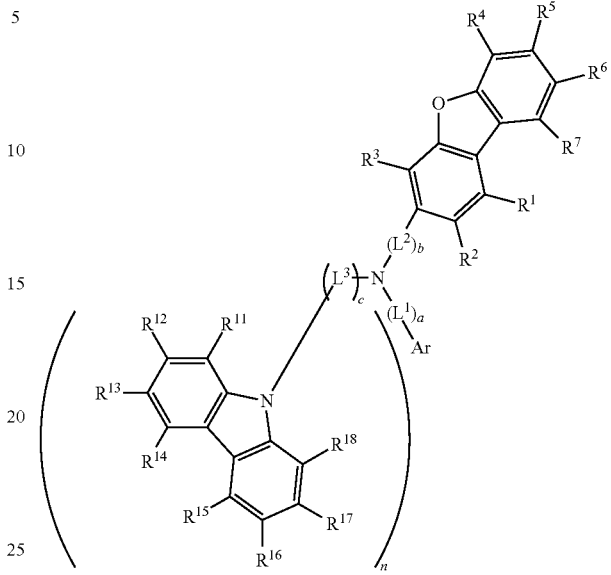

(1)

The compound (1) is preferably represented by formula (2):

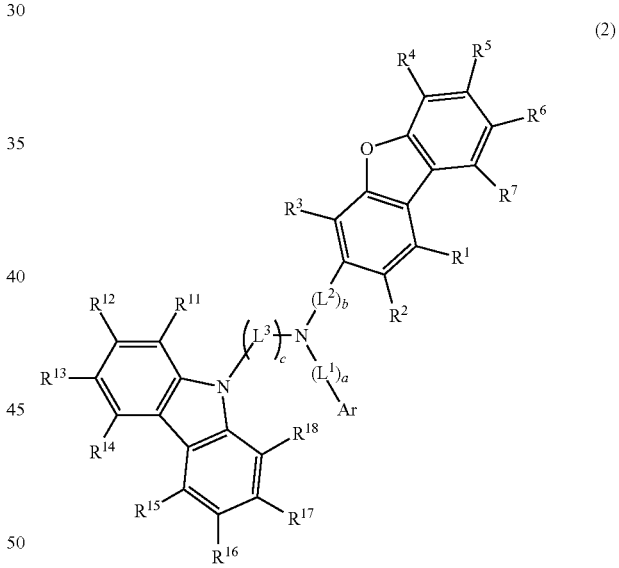

(2)

Each symbol in formulae (1) and (2) will be described below.

$R^1$ to $R^7$ and $R^{11}$ to $R^{18}$ are each independently a hydrogen atom; a substituted or unsubstituted alkyl group having 1 to 30, preferably 1 to 18, and more preferably 1 to 8 carbon atoms; a substituted or unsubstituted cycloalkyl group having 3 to 30, preferably 3 to 10, more preferably 3 to 8, and still more preferably 5 or 6 ring carbon atoms; a substituted or unsubstituted aryl group having 6 to 30, preferably 6 to 25, and more preferably 6 to 18 ring carbon atoms; a substituted or unsubstituted aralkyl group having 7 to 36, preferably 7 to 26, and more preferably 7 to 20 carbon atoms; a substituted or unsubstituted alkoxy group having 1 to 30, preferably 1 to 18, and more preferably 1 to 8 carbon atoms; a substituted or unsubstituted aryloxy group having 6 to 30, preferably 6 to 25, and more preferably 6 to 18 ring carbon atoms; a mono-, di- or tri-substituted silyl group having a substituent selected from the group consisting of a substituted or unsubstituted alkyl group having 1 to 30, preferably 1 to 18, and more preferably 1 to 8 carbon atoms and a substituted or unsubstituted aryl group having 6 to 30, preferably 6 to 25, and more preferably 6 to 18 ring carbon atoms; a substituted or unsubstituted haloalkyl group having 1 to 30, preferably 1 to 18, and more preferably 1 to 8 carbon atoms; a substituted or unsubstituted haloalkoxy group having 1 to 30, preferably 1 to 18, and more preferably 1 to 8 carbon atoms; a substituted or unsubstituted heteroaryl group having 5 to 30, preferably 5 to 24, and more preferably 5 to 13 ring atoms; a halogen atom; a cyano group; or a nitro group.

The alkyl group of the substituted or unsubstituted alkyl group having 1 to 30 carbon atoms is, for example, a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), or a dodecyl group (inclusive of isomeric groups). Of the above, preferred are a methyl group, an ethyl group, a n-propyl group, an isopropyl group, a n-butyl group, an isobutyl group, a s-butyl group, a t-butyl group, and a pentyl group (inclusive of isomeric groups), more preferred are a methyl group, an ethyl group, a n-propyl group, an isopropyl group, a n-butyl group, an isobutyl group, a s-butyl group, and a t-butyl group, and still more preferred are a methyl group and a t-butyl group.

The cycloalkyl group of the substituted or unsubstituted cycloalkyl group having 3 to 30 ring carbon atoms is, for example, a cyclopropyl group, a cyclobutyl group, a cyclopentyl group, a cyclohexyl group, or a cycloheptyl group. Of the above, preferred are a cyclopentyl group and a cyclohexyl group.

The aryl group of the substituted or unsubstituted aryl group having 6 to 30 ring carbon atoms is, for example, a phenyl group, a biphenylyl group, a terphenylyl group, a biphenylenyl group, a naphthyl group, an anthryl group, a benzanthryl group, a phenanthryl group, a benzophenanthryl group, a phenalenyl group, a picenyl group, a pentaphenyl group, a pyrenyl group, a chrysenyl group, a benzochrysenyl group, or a triphenylenyl group. Of the above, preferred are a phenyl group, a biphenylyl group, a terphenylyl group, and a naphthyl group, more preferred are a phenyl group, a biphenylyl group, and a naphthyl group, and still more preferred is a phenyl group.

The aryl portion in the aralkyl group of the substituted or unsubstituted aralkyl group having 7 to 36 ring carbon atoms is selected from the aryl group having 6 to 30, preferably 6 to 25, and more preferably 6 to 18 ring carbon atoms which is mentioned above, and the alkyl portion is selected from the alkyl group having 1 to 30, preferably 1 to 18, and more preferably 1 to 8 carbon atoms which is mentioned above. The aralkyl group is, for example, a benzyl group, a phenethyl group or a phenylpropyl group, with a benzyl group being preferred.

The alkyl portion in the alkoxy group of the substituted or unsubstituted alkoxy group having 1 to 30 carbon atoms is selected from the alkyl group having 1 to 30, preferably 1 to 18, and more preferably 1 to 8 carbon atoms which is mentioned above. The alkoxy group is preferably a t-butoxy group, a propoxy group, an ethoxy group, or a methoxy group, with an ethoxy group and a methoxy group being more preferred and a methoxy group being still more preferred.

The aryl portion in the aryloxy group of the substituted or unsubstituted aryloxy group having 6 to 30 ring carbon atoms is selected from the aryl group having 6 to 30, preferably 6 to 25, and more preferably 6 to 18 ring carbon atoms which is mentioned above. The aryloxy group is preferably a terphenyloxy group, a biphenyloxy group, or a phenoxy group, with a biphenyloxy group and a phenoxy group being preferred and a phenoxy group being more preferred.

The substituent of the mono-, di- or tri-substituted silyl group is selected from the alkyl group having 1 to 30, preferably 1 to 18, and more preferably 1 to 8 carbon atoms which is mentioned above and the aryl group having 6 to 30, preferably 6 to 25, and more preferably 6 to 18 ring carbon atoms which is mentioned above. Preferred is a tri-substituted silyl group, for example, a trimethylsilyl group, a triethylsilyl group, a t-butyldimethylsilyl group, a propyldimethylsilyl group, an isopropyldimethylsilyl group, a triphenylsilyl group, a phenyldimethylsilyl group, a t-butyldiphenylsilyl group, or a tritolylsilyl group.

The haloalkyl group of the substituted or unsubstituted haloalkyl group having 1 to 30 carbon atoms is an alkyl group having 1 to 30, preferably 1 to 18, and more preferably 1 to 8 carbon atoms, wherein at least one hydrogen atom, preferably 1 to 7 hydrogen atoms, or all hydrogen atoms are replaced by a halogen atom. The halogen atom is selected from a fluorine atom, a chlorine atom, a bromine atom, and an iodine atom, and preferably a fluorine atom.

The haloalkyl group is preferably a fluoroalkyl group having 1 to 30, preferably 1 to 18, more preferably 1 to 8 carbon atoms, more preferably a heptafluoropropyl group (inclusive of isomeric groups), a pentafluoroethyl group, a 2,2,2-trifluoroethyl group, or a trifluoromethyl group, still more preferably a pentafluoroethyl group, a 2,2,2-trifluoroethyl group, or a trifluoromethyl group, and particularly preferably a trifluoromethyl group.

The haloalkyl portion in the haloalkoxy group of the substituted or unsubstituted haloalkoxy group is selected from the haloalkyl group having 1 to 30, preferably 1 to 18, and more preferably 1 to 8 carbon atoms which is mentioned above. The haloalkoxy group is preferably a fluoroalkoxy group having 1 to 30, preferably 1 to 18, and more preferably 1 to 8 carbon atoms, more preferably a heptafluoropropoxy group (inclusive of isomeric groups), a pentafluoroethoxy group, a 2,2,2-trifluoroethoxy group, or a trifluoromethoxy group, still more preferably a pentafluoroethoxy group, a 2,2,2-trifluoroethoxy group, or a trifluoromethoxy group, and particularly preferably a trifluoromethoxy group.

The heteroaryl group of the substituted or unsubstituted heteroaryl group having 5 to 30 ring atoms comprises 1 to 5, preferably 1 to 3, and more preferably 1 to 2 ring hetero atoms, which is selected, for example, from a nitrogen atom, a sulfur atom, and an oxygen atom. The free valance of the heteroaryl group is present on a ring carbon atom or may be present on a ring nitrogen atom, if structurally possible.

The heteroaryl group is, for example, a pyrrolyl group, a furyl group, a thienyl group, a pyridyl group, an imidazolyl group, a pyrazolyl group, an indolyl group, an isoindolyl group, a benzofuranyl group, an isobenzofuranyl group, a benzothiophenyl group (a benzothienyl group, the same applies below), an indolizinyl group, a benzimidazolyl group, an indazolyl group, a dibenzofuranyl group, a naphthobenzofuranyl group, a dibenzothiophenyl group (a dibenzothienyl group, the same applies below), a naphthobenzothiophenyl group (a naphthobenzothienyl group, the same applies below), a carbazolyl group, or a benzocarbazolyl group. Of the above, preferred are a furyl group, a thienyl group, a benzofuranyl group, a benzothiophenyl group, a dibenzofuranyl group, a naphthobenzofuranyl group, a dibenzothiophenyl group, a naphthobenzothiophenyl group, a carbazolyl group, and a benzocarbazolyl group, and more preferred are a thienyl group, a benzothiophenyl group, a dibenzofuranyl group, a naphthobenzofuranyl group, a dibenzothiophenyl group, a naphthobenzothiophenyl group, a carbazolyl group, and a benzocarbazolyl group. The substituted heteroaryl group is, for example, a 9-phenylcarbazolyl group, a 9-biphenylylcarbazolyl group, a 9-phenylphenyla carbazolyl group, a 9-naphthylcarbazolyl group, a phenyldibenzofuranyl group, or a phenyldibenzothiophenyl group.

The halogen atom is a fluorine atom, a chlorine atom, a bromine atom, or an iodine atom, with a fluorine atom being preferred.

$R^1$ and $R^2$, adjacent two selected from $R^4$ to $R^7$, adjacent two selected from $R^{11}$ to $R^{14}$, and adjacent two selected from $R^{15}$ to $R^{18}$ may be bonded to each other to form a ring structure.

In an embodiment of the invention, the adjacent two mentioned above may be not bonded to each other, thereby failing to form a ring structure.

Examples of the ring structure include a substituted or unsubstituted aromatic hydrocarbon ring having 6 to 18 ring carbon atoms, a substituted or unsubstituted aliphatic hydrocarbon ring having 5 to 18 ring carbon atoms, a substituted or unsubstituted aromatic heterocyclic ring having 6 to 18 ring atoms, and a substituted or unsubstituted aliphatic heterocyclic ring having 5 to 18 ring atoms.

Examples of the aromatic hydrocarbon ring having 6 to 18 ring carbon atoms include benzene, biphenylene, naphthalene, anthracene, benzanthracene, phenanthrene, benzophenanthrene, phenalene, pyrene, chrysene, and triphenylene.

Examples of the aliphatic hydrocarbon ring having 5 to 18 ring carbon atoms include a cyclopentene ring, a cyclopentadiene ring, a cyclohexene ring, a cyclohexadiene ring, and an aliphatic ring obtained by partially hydrogenating the aromatic hydrocarbon ring having 6 to 18 ring carbon atoms.

Examples of the aromatic heterocyclic ring having 5 to 18 ring atoms include pyrrole, furan, thiophene, pyridine, imidazole, pyrazole, indole, isoindole, benzofuran, isobenzofuran, benzothiophene, benzimidazole, indazole, dibenzofuran, naphthobenzofuran, dibenzothiophene, naphthobenzothiophene, carbazole, and benzocarbazole.

Examples of the aliphatic heterocyclic ring having 5 to 18 ring atoms includes an aliphatic ring obtained by partially hydrogenating the aromatic heterocyclic ring having 5 to 18 ring atoms.

Preferably $R^1$ to $R^7$ and $R^{11}$ to $R^{18}$ are each independently a hydrogen atom, a substituted or unsubstituted alkyl group having 1 to 30 carbon atoms, a substituted or unsubstituted cycloalkyl group having 3 to 30 ring carbon atoms, a substituted or unsubstituted aryl group having 6 to 30 ring carbon atoms, a substituted or unsubstituted alkoxy group having 1 to 30 carbon atoms, a substituted or unsubstituted aryloxy group having 6 to 30 ring carbon atoms, a substituted or unsubstituted heteroaryl group having 5 to 30 ring atoms, a halogen atom, or a cyano group; more preferably a hydrogen atom, a substituted or unsubstituted alkyl group having 1 to 30 carbon atoms, a substituted or unsubstituted aryl group having 6 to 30 ring carbon atoms, a substituted or unsubstituted heteroaryl group having 5 to 30 ring atoms, a halogen atom, or a cyano group; still more preferably a hydrogen atom, a substituted or unsubstituted alkyl group having 1 to 30 carbon atoms, a halogen atom, or a cyano group; and particularly preferably a hydrogen atom or a substituted or unsubstituted alkyl group having 1 to 30 carbon atoms.

In an embodiment of the invention, $R^1$ to $R^7$ and $R^{11}$ to $R^{18}$ may be all hydrogen atoms.

Ar is a substituted or unsubstituted aryl group having 6 to 30, preferably 6 to 25, and more preferably 6 to 18 ring carbon atoms. The aryl group is composed of only a six-membered ring (benzene ring), i.e., the aryl group is a single ring group of a six-membered ring, a fused ring group composed of only a six-membered ring, or a ring assembly group composed of only a six-membered ring. Thus, the aryl group for Ar does not include, for example, an aryl group containing a five-membered ring.

The single ring group of a six-membered ring is a phenyl group.

The fused ring group composed of only a six-membered ring is a monovalent group of a ring system wherein two or more benzene rings are fused. Examples thereof include a naphthyl group, an anthryl group, a benzanthryl group, a phenanthryl group, a benzophenanthryl group, a phenalenyl group, a picenyl group, a pentaphenyl group, a pyrenyl group, a chrysenyl group, a benzochrysenyl group, a perylenyl group, and a triphenylenyl group.

The ring assembly group composed of only a six-membered ring is a monovalent group of a ring system wherein two or more benzene rings are bonded to each other via a single bond. Examples thereof include a monovalent residue of biphenyl and terphenyl.

The aryl group containing a five-membered ring mentioned above includes a fluorene-type aryl group and a fluoranthene-type aryl group. The fluorene-type aryl group has a benzylic alkyl group at its 9-position. The benzylic alkyl group is considered to easily form a radical, thereby reducing the durability (stability) of a compound containing a fluorene-type aryl group. Therefore, the device lifetime may be decreased if a device contains such a compound particularly in a layer adjacent to a light emitting layer. The fluoranthene-type aryl group has an extremely high electron acceptability. If a compound containing the fluoranthene-type aryl group is used in a hole transporting layer adjacent to a light emitting layer, electrons from a cathode are not blocked at the interface between the light emitting layer and the hole transporting layer and enter into the hole transporting layer. This may reduce the device lifetime. For the above reasons, the aryl group and the arylene group in the compound (1) are preferably composed of only a six-membered ring.

The aryl group of the substituted or unsubstituted aryl group having 6 to 30 ring carbon atoms represented by Ar is, for example, a phenyl group, a biphenylyl group, a terphenylyl group, a naphthyl group, an anthryl group, a benzanthryl group, a phenanthryl group, a benzophenanthryl group, a phenalenyl group, a picenyl group, a pentaphenyl group, a pyrenyl group, a chrysenyl group, a benzochrysenyl group, a perylenyl group, or a triphenylenyl group; more preferably a phenyl group, a biphenylyl group, a terphenylyl group, a naphthyl group, a phenanthryl group, or a triphenylenyl group; still more preferably a phenyl group, a 2-, 3-, or 4-biphenylyl group, a 2-, 3-, or 4-o-terphenylyl group, a 2-, 3-, or 4-m-terphenylyl group, a 2-, 3-, or 4-p-terphenylyl group, a 1- or 2-naphthyl group, a 2-, 3-, 4- or 9-phenanthryl group, or a 2-triphenylenyl group.

Preferably, the aryl group of the substituted or unsubstituted aryl group having 6 to 30 ring carbon atoms represented by Ar is a group selected from the following groups:

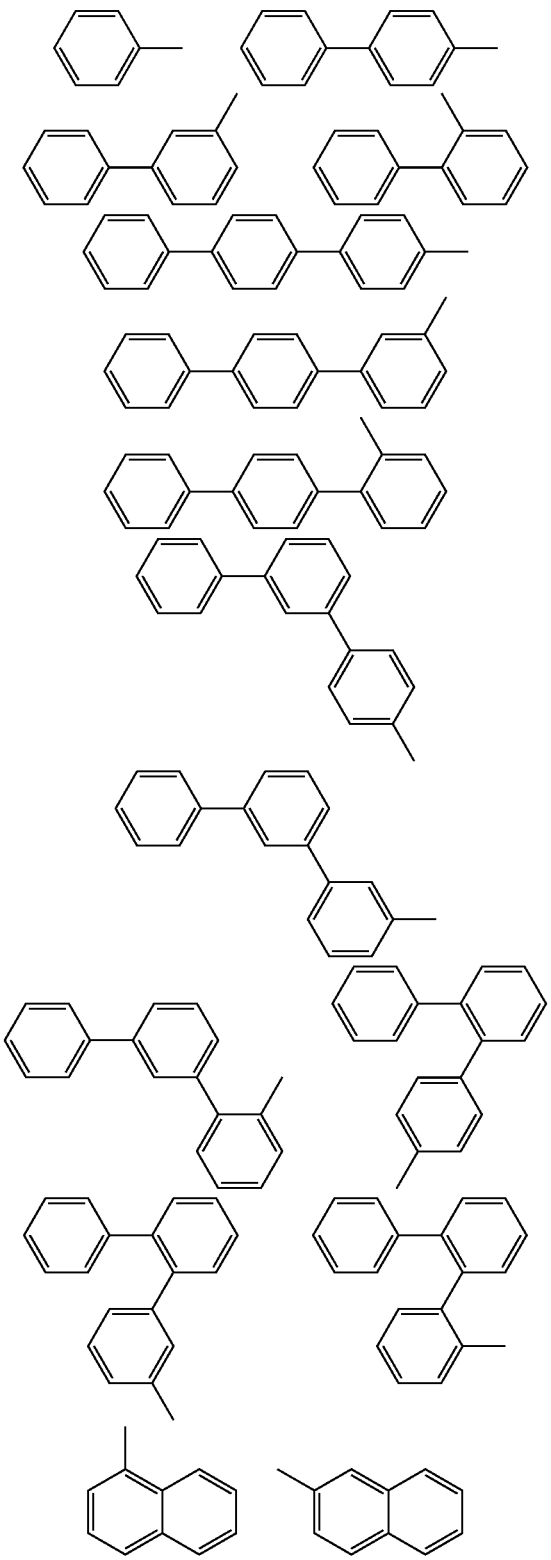

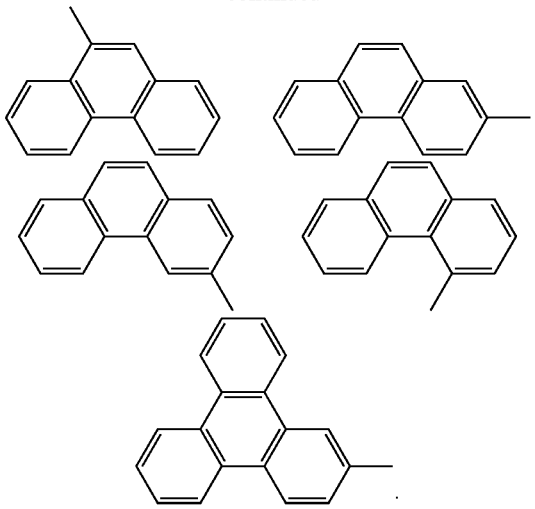

More preferably, the aryl group of the substituted or unsubstituted aryl group having 6 to 30 ring carbon atoms represented by Ar is a group selected from the following groups:

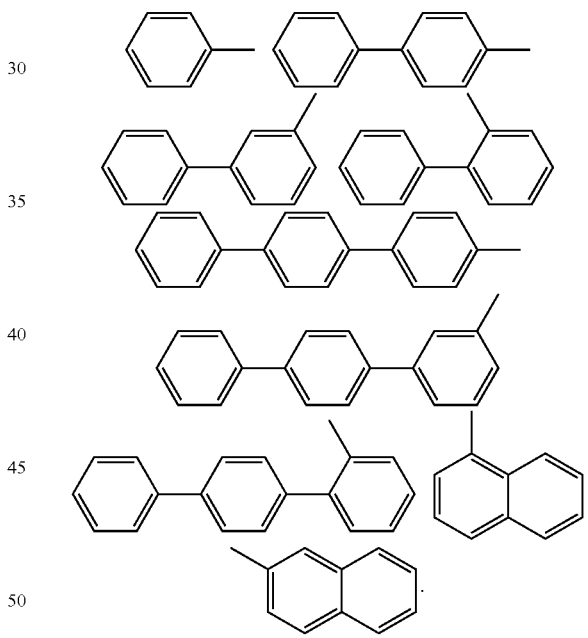

Still more preferably, the aryl group of the substituted or unsubstituted aryl group having 6 to 30 ring carbon atoms represented by Ar is a group selected from the following groups:

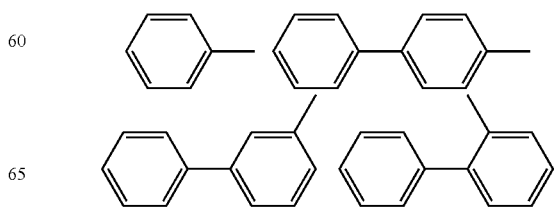

-continued

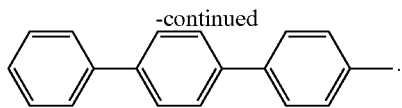

The subscript a is 0, 1, 2, or 3, preferably 0, 1, or 2, and more preferably 0 or 1. In an embodiment of the invention, a is preferably 0. In another embodiment of the invention, a is preferably 1. When a is 0, Ar is directly bonded to the central nitrogen atom. When a is 2 or 3, two or three $L^1$'s may be the same or different. Two optional substituents that may be respectively present on each of adjacent two $L^1$'s are preferably not bonded to each other, i.e., adjacent two $L^1$'s are preferably not crosslinked by optional substituents.

The subscript b is 1, 2, or 3, preferably is 1 or 2, and more preferably 1. When b is 2 or 3, two or three $L^2$'s may be the same or different. Two optional substituents that may be respectively present on each of adjacent two $L^2$'s are preferably not bonded to each other, i.e., adjacent two $L^2$'s are preferably not crosslinked by optional substituents.

The subscript c is 1, 2, or 3 and preferably 2 or 3 in view of device lifetime. When c is 2 or 3, two or three $L^3$'s may be the same or different. Two optional substituents that may be respectively present on each of adjacent two $L^3$'s are preferably not bonded to each other, i.e., adjacent two $L^3$'s are preferably not crosslinked by optional substituents.

More preferably, b is 1 and c is 2 or 3, and still more preferably b is 1 and c is 3, although not limited thereto. Therefore, when b is 1, c may be 1 or 2.

The subscript n is 1 or 2, preferably 1.

$L^1$ is a substituted or unsubstituted aromatic hydrocarbon group having 6 to 18 ring carbon atoms.

The aromatic hydrocarbon group is, for example, a phenylene group, a biphenylylene group, a terphenylylene group, a naphthylene group, an anthrylene group, a benzanthrylene group, a phenanthrylene group, a benzophenanthrylene group, a picenylene group, a pentaphenylene group, a pyrenylene group, a chrysenylene group, a benzochrysenylene group, or a triphenylenylene group; preferably a phenylene group, a biphenylylene group, a terphenylylene group, a naphthylene group, or a phenanthrylene group; more preferably an o-phenylene group, a m-phenylene group, a p-phenylene group, a 4,4'-biphenylylene group, a 4,3'-biphenylylene group, a 4,2'-biphenylylene group, a 4,4''-p-terphenylylene group, a 4,3''-p-terphenylylene group, a 4,2''-p-terphenylylene group, a 4,2'-p-terphenylylene group, a 4,3'-p-terphenylylene group, a 4,4''-m-terphenylylene group, a 4,3''-m-terphenylylene group, a 4,2''-m-terphenylylene group, a 4,3'-m-terphenylylene group, a 1,4-naphthylene group, a 2,6-naphthylene group, or a 2,7-phenanthrylene group; and still more preferably a phenylene group, i.e., an o-phenylene group, a m-phenylene group, or a p-phenylene group.

Of the two free valences of the aromatic hydrocarbon group, one is directly or indirectly bonded to the central nitrogen atom and the other is directly or indirectly bonded to Ar.

$L^2$ is a substituted or unsubstituted aromatic hydrocarbon group having 6 to 18 ring carbon atoms.

The aromatic hydrocarbon group is, for example, a phenylene group, a biphenylylene group, a terphenylylene group, a naphthylene group, an anthrylene group, a benzanthrylene group, a phenanthrylene group, a benzophenanthrylene group, a picenylene group, a pentaphenylene group, a pyrenylene group, a chrysenylene group, a benzochrysenylene group, or a triphenylenylene group; preferably a phenylene group, a biphenylylene group, a terphenylylene group, a naphthylene group, or a phenanthrylene group; more preferably an o-phenylene group, a m-phenylene group, a p-phenylene group, a 4,4'-biphenylylene group, a 4,3'-biphenylylene group, a 4,2'-biphenylylene group, a 4,4''-p-terphenylylene group, a 4,3''-p-terphenylylene group, a 4,2''-p-terphenylylene group, a 4,2'-p-terphenylylene group, a 4,3'-p-terphenylylene group, a 4,4''-m-terphenylylene group, a 4,3''-m-terphenylylene group, a 4,2''-m-terphenylylene group, a 4,3'-m-terphenylylene group, a 1,4-naphthylene group, a 2,6-naphthylene group, or a 2,7-phenanthrylene group; still more preferably an o-phenylene group, a m-phenylene group, a p-phenylene group, a 4,4'-biphenylylene group, a 4,3'-biphenylylene group, a 4,2'-biphenylylene group, a 1,4-naphthylene group, a 2,6-naphthylene group, or a 2,7-phenanthrylene group; and particularly preferably an o-phenylene group, a m-phenylene group, a p-phenylene group, a 4,4'-biphenylylene group, a 4,3'-biphenylylene group, or a 4,2'-biphenylylene group.

Of the two free valences of the aromatic hydrocarbon group, one is directly or indirectly bonded to the central nitrogen atom and the other is directly or indirectly bonded to the 1-position of the dibenzofluorene structure.

In an embodiment, the aromatic hydrocarbon group of the substituted or unsubstituted aromatic hydrocarbon group having 6 to 18 ring carbon atoms represented by $L^1$ is preferably a phenylene group, a biphenylylene group, or a naphthylene group and the aromatic hydrocarbon group of the substituted or unsubstituted aromatic hydrocarbon group having 6 to 18 ring carbon atoms represented by $L^2$ is preferably a phenylene group or a biphenylylene group.

In a more preferred embodiment, the aromatic hydrocarbon group of the substituted or unsubstituted aromatic hydrocarbon group having 6 to 18 ring carbon atoms represented by $L^1$ is a phenylene group and the aromatic hydrocarbon group of the substituted or unsubstituted aromatic hydrocarbon group having 6 to 18 ring carbon atoms represented by $L^2$ is a phenylene group or a biphenylylene group.

In a still more preferred embodiment, the aromatic hydrocarbon group of the substituted or unsubstituted aromatic hydrocarbon group having 6 to 18 ring carbon atoms represented by each of $L^1$ and $L^2$ is a phenylene group.

In another still more preferred embodiment, the aromatic hydrocarbon group of the substituted or unsubstituted aromatic hydrocarbon group having 6 to 18 ring carbon atoms represented by $L^1$ is an o-phenylene group, a m-phenylene group, or a p-phenylene group and the aromatic hydrocarbon group of the substituted or unsubstituted aromatic hydrocarbon group having 6 to 18 ring carbon atoms represented by $L^2$ is an o-phenylene group, a m-phenylene group, a p-phenylene group, a 4,4'-biphenylylene group, a 4,3'-biphenylylene group, a 4,2'-biphenylylene group, a 1,4-naphthylene group, a 2,6-naphthylene group, or a 2,7-phenanthrylene group.

When c is 1, $L^3$ is a group represented by formula (L3-1) or (L3-2). When c is 2 or 3, at least one selected from two or three $L^3$'s is a group represented by formula (L3-1) or (L3-2) and $L^3$ not a group represented by formula (L3-1) or (L3-2) is a substituted or unsubstituted aromatic hydrocarbon group having 6 to 18 ring carbon atoms.

The aromatic hydrocarbon group is, for example, a phenylene group, a biphenylylene group, a terphenylylene group, a naphthylene group, an anthrylene group, a benzanthrylene group, a phenanthrylene group, a benzophenanthrylene group, a picenylene group, a pentaphenylene group, a pyrenylene group, a chrysenylene group, a benzochrysenylene group, or a triphenylenylene group; preferably a phenylene group, a biphenylylene group, a terphenylylene group, a naphthylene group, or a phenanthrylene group; and more preferably a phenylene group, a biphenylylene group, or a terphenylylene group.

Of two free valences of the aromatic hydrocarbon group, one is directly or indirectly bonded to the central nitrogen atom and the other is directly or indirectly bonded to the nitrogen atom of the carbazole structure.

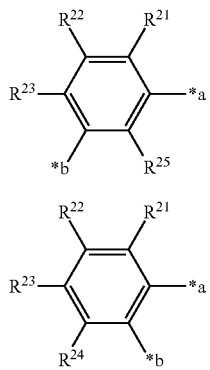

(L3-1)

(L3-2)

wherein:
$R^{21}$ to $R^{25}$ are each independently as defined above with respect to $R^1$ to $R^7$;
*a is directly or indirectly bonded to the central nitrogen atom, and
*b is directly or indirectly bonded to the nitrogen atom of the carbazole structure.

$R^{21}$ to $R^{25}$ are as defined above with respect to $R^1$ to $R^7$ and the preferred examples thereof are also the same as those of $R^1$ to $R^7$. Specifically, $R^{21}$ to $R^{25}$ are each independently preferably a hydrogen atom, a substituted or unsubstituted alkyl group having 1 to 30 carbon atoms, a substituted or unsubstituted cycloalkyl group having 3 to 30 ring carbon atoms, a substituted or unsubstituted aryl group having 6 to 30 ring carbon atoms, a substituted or unsubstituted alkoxy group having 1 to 30 carbon atoms, a substituted or unsubstituted aryloxy group having 6 to 30 ring carbon atoms, a substituted or unsubstituted heteroaryl group having 5 to 30 ring atoms, a halogen atom, or a cyano group; more preferably a hydrogen atom, a substituted or unsubstituted alkyl group having 1 to 30 carbon atoms, a substituted or unsubstituted aryl group having 6 to 30 ring carbon atoms, a substituted or unsubstituted heteroaryl group having 5 to 30 ring atoms, a halogen atom, or a cyano group; and still more preferably a hydrogen atom, a substituted or unsubstituted alkyl group having 1 to 30 carbon atoms, a halogen atom, or a cyano group.

In an embodiment of the invention, $R^{21}$ to $R^{25}$ may be all hydrogen atoms. In this case, formulae (L3-1) and (L3-2) are represented by formulae (L3-1H) and (L3-2H), respectively:

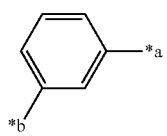

(L3-1H)

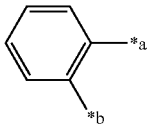

(L3-2H)

wherein, *a and *b are as defined above.

Either of a group represented by formula (L3-1) and a group represented by formula (L3-2) may be selected. In view of device lifetime, a group represented by formula (L3-1) is preferred. Either of a group represented by formula (L3-1H) and a group represented by formula (L3-2H) may be selected. In view of device lifetime, a group represented by formula (L3-1H) is preferred.

In an embodiment of the invention, $-(L^3)_c-$ in formula (1) or formula (2) is preferably a group selected from the following groups:

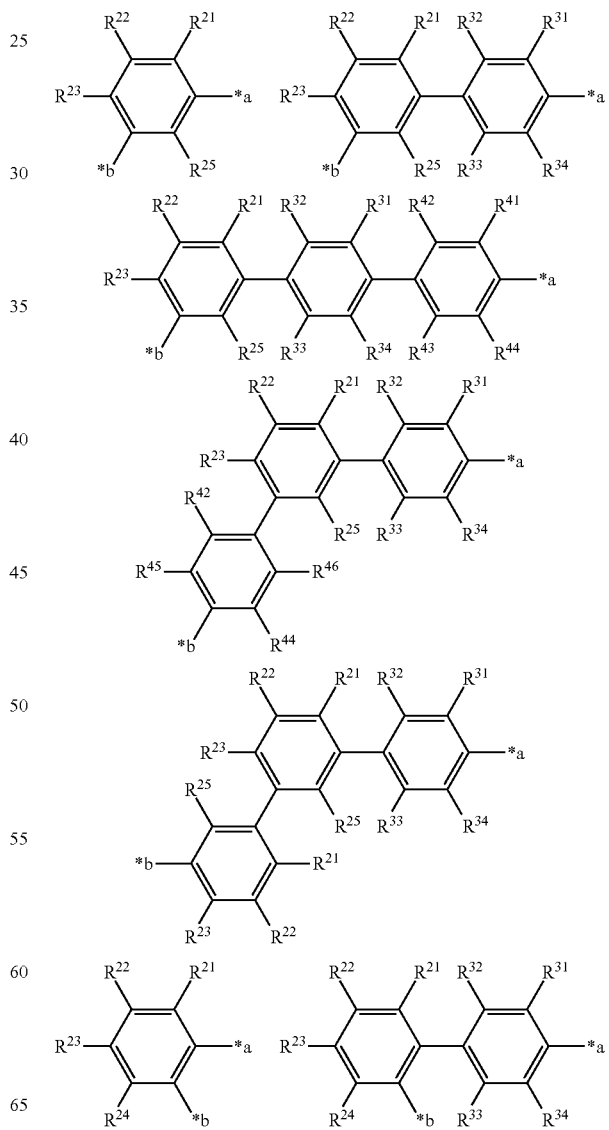

-continued

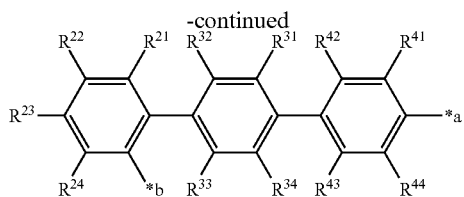

wherein:

$R^{21}$ to $R^{25}$, $R^{31}$ to $R^{34}$, and $R^{41}$ to $R^{46}$ are each independently as defined above with respect to $R^1$ to $R^7$ and preferred examples thereof are also the same as those of $R^1$ to $R^7$; and

*a and *b are as defined above.

In an embodiment of the invention, $-(L^3)_c-$ in formula (1) or formula (2) is preferably a group selected from the following groups:

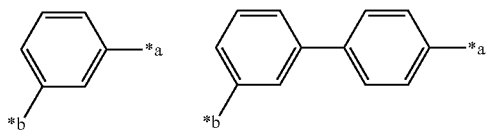

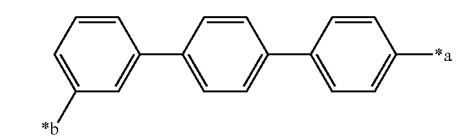

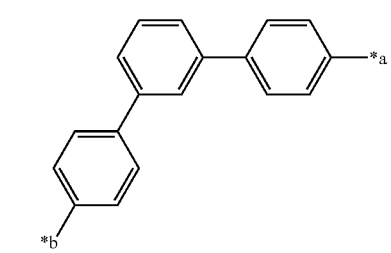

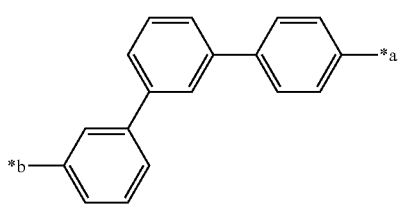

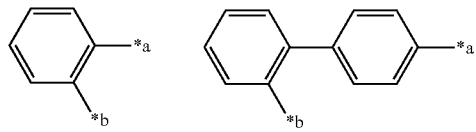

-continued

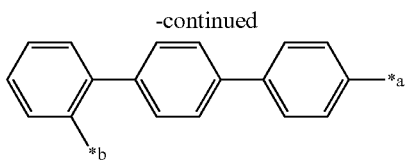

wherein, *a and *b are as defined above.

In an embodiment of the invention, $-(L^3)_c-$ in formula (1) or formula (2) is more preferably a group selected from the following groups:

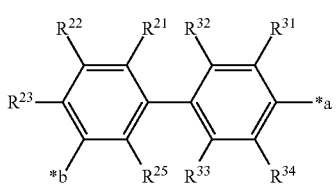

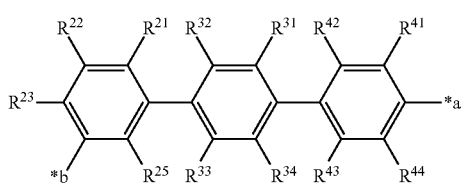

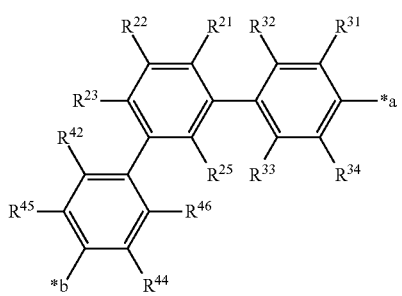

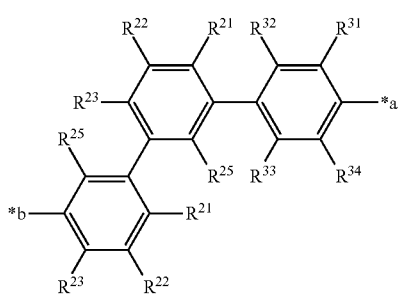

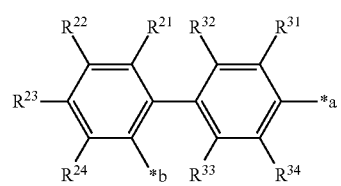

-continued

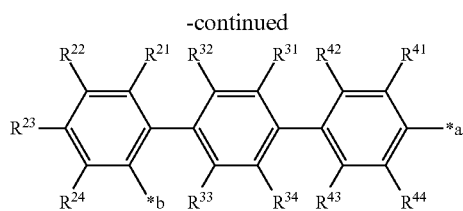

wherein:

$R^{21}$ to $R^{25}$, $R^{31}$ to $R^{34}$, and $R^{41}$ to $R^{46}$ are each independently as defined above with respect to $R^1$ to $R^7$ and preferred examples thereof are also the same as those of $R^1$ to $R^7$; and

*a and *b are as defined above.

In an embodiment of the invention, -(L$^3$)$_c$- in formula (1) or formula (2) is preferably a group selected from the following groups:

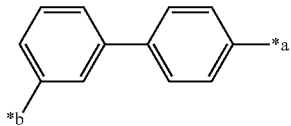

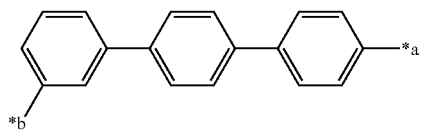

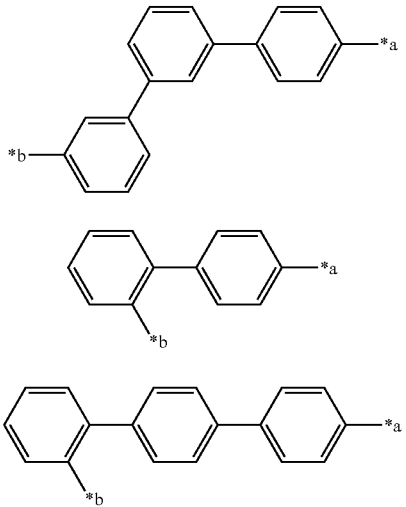

wherein, *a and *b are as defined above.

In a preferred embodiment of the invention, the compound (1) is represented by any of formulae (2-a) to (2-p), wherein each symbol has the same meaning as that of the corresponding symbol mentioned above and preferred examples thereof are also the same as those of the corresponding symbol mentioned above.

(2-a)

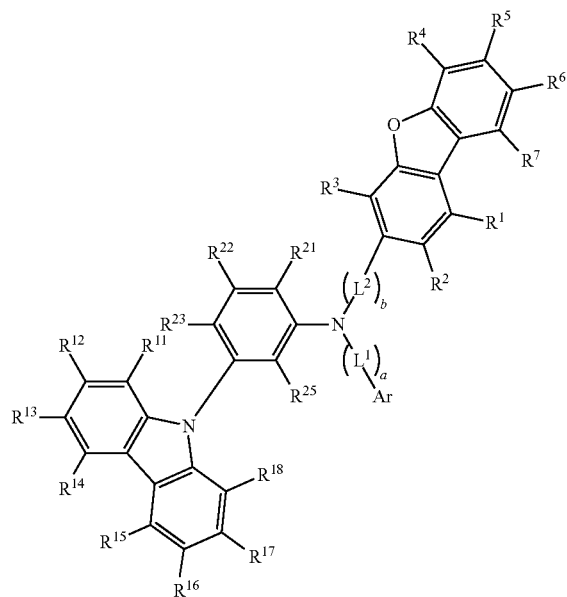

(2-b)

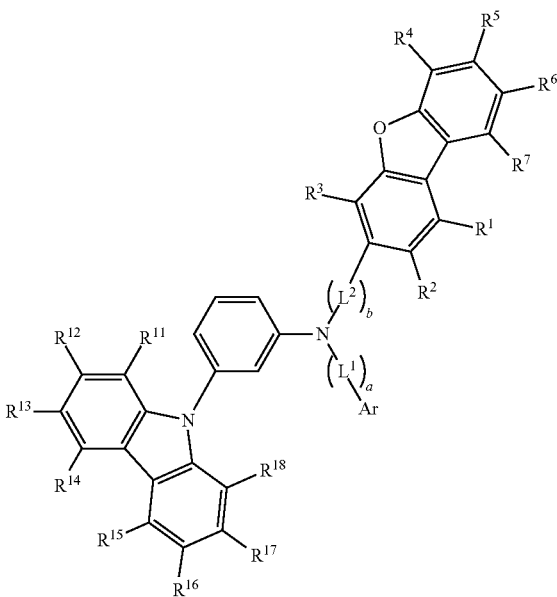

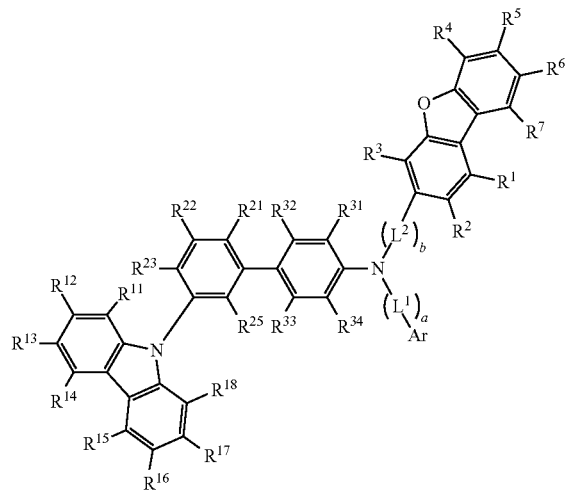
(2-c)
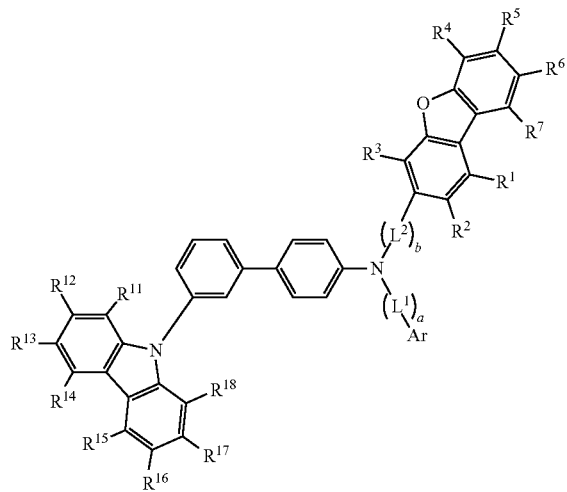
(2-d)
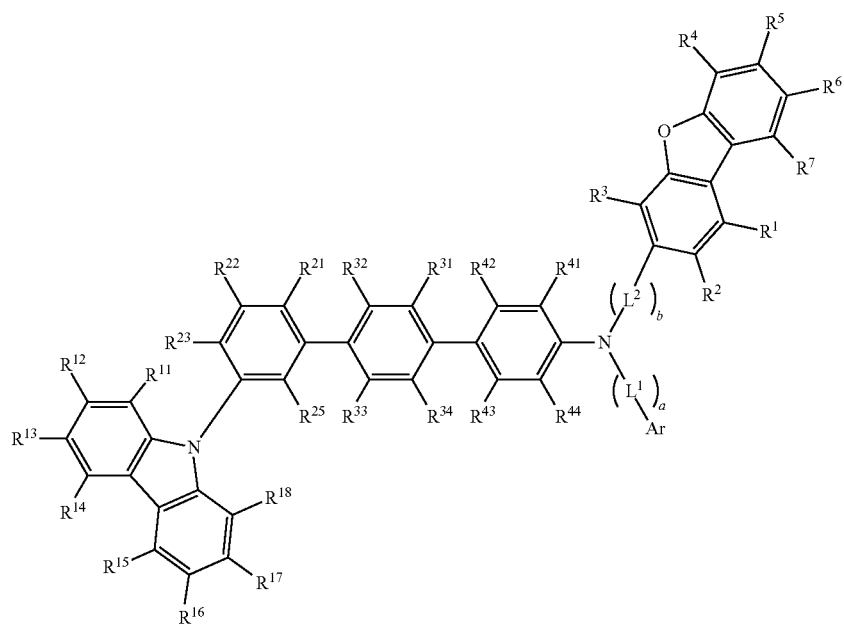
(2-e)

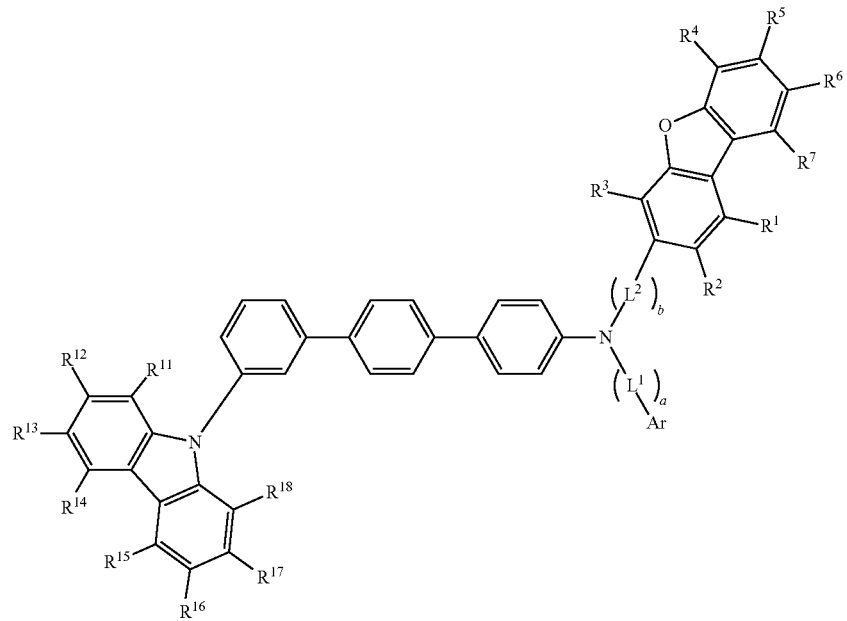
(2-f)
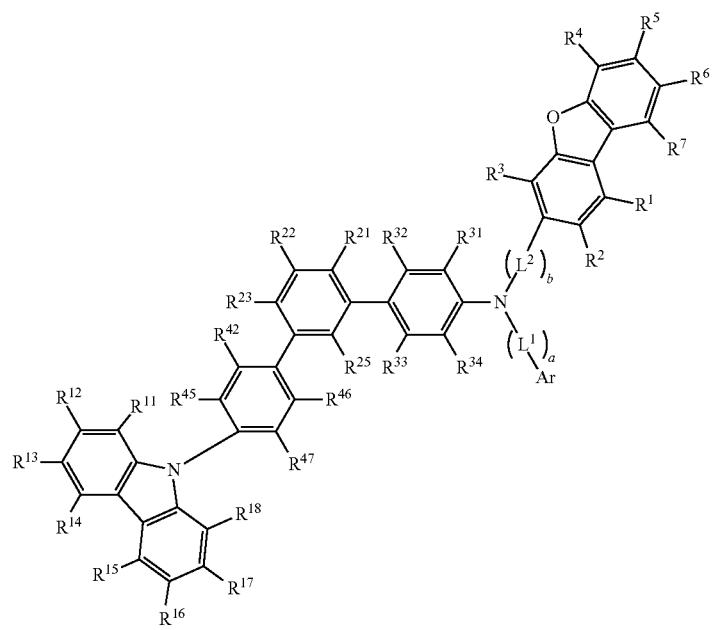
(2-g)

-continued
(2-h)
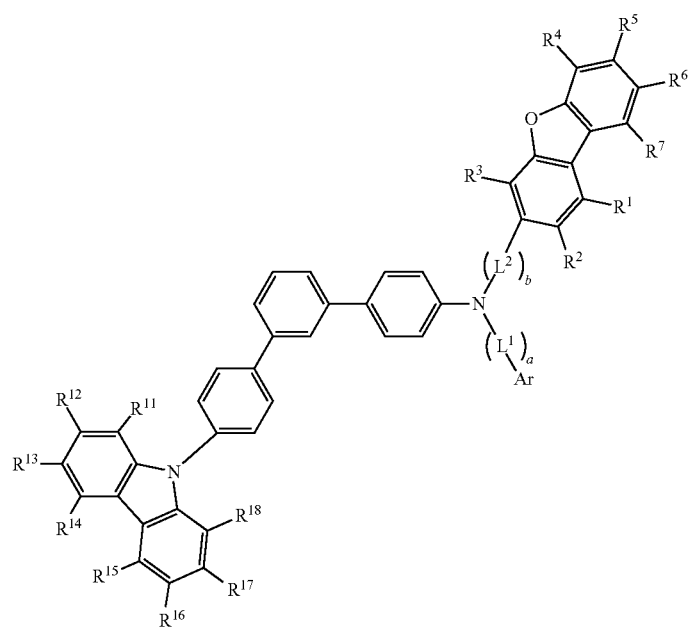
(2-i)
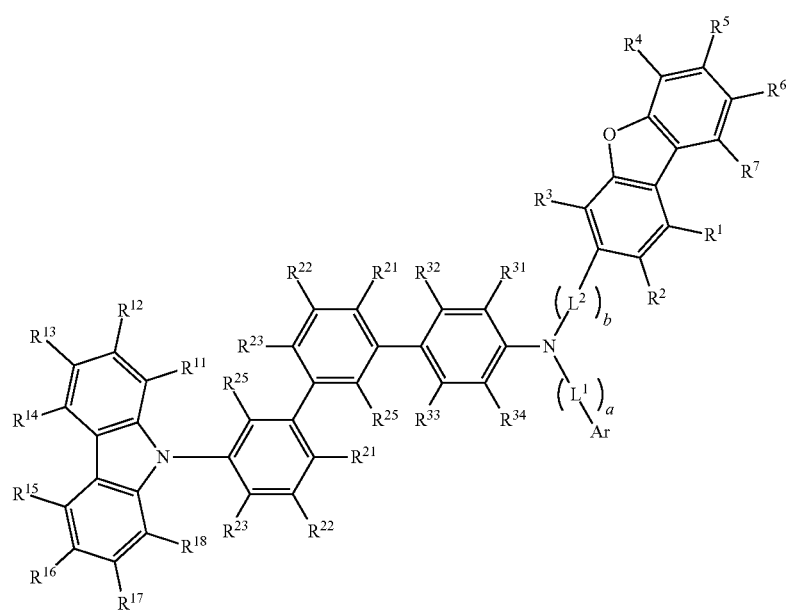

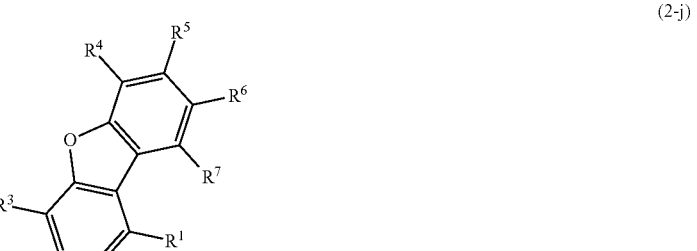
(2-j)
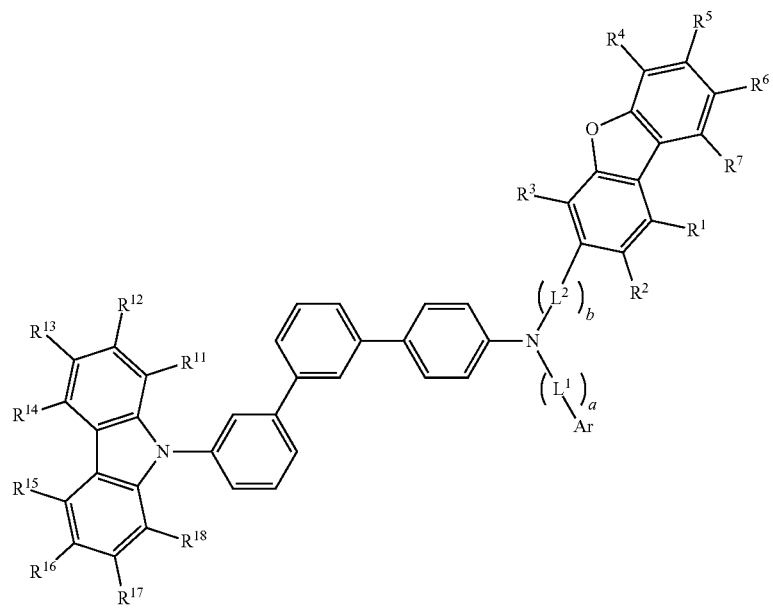
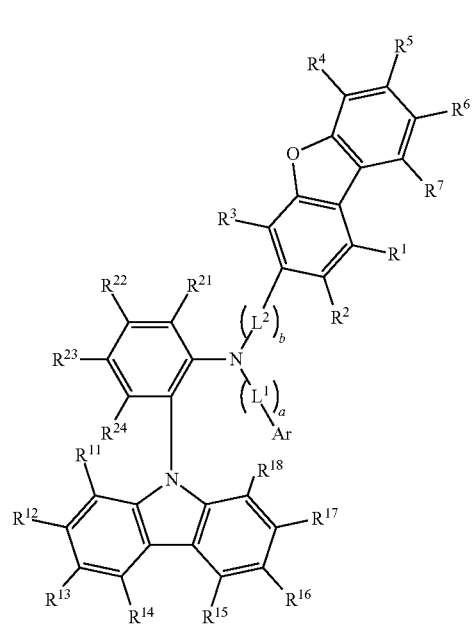
(2-k)
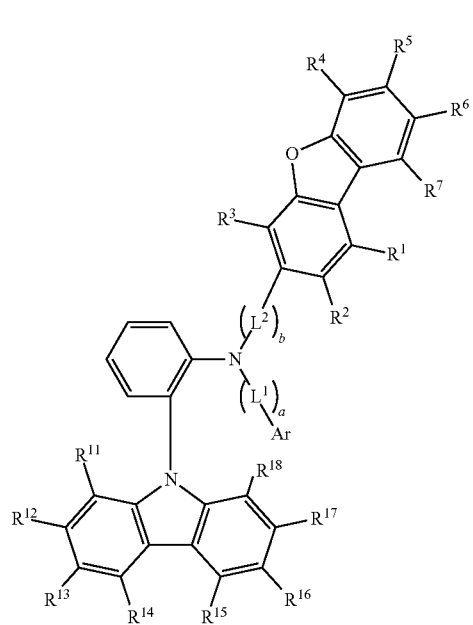
(2-l)

-continued (2-m)
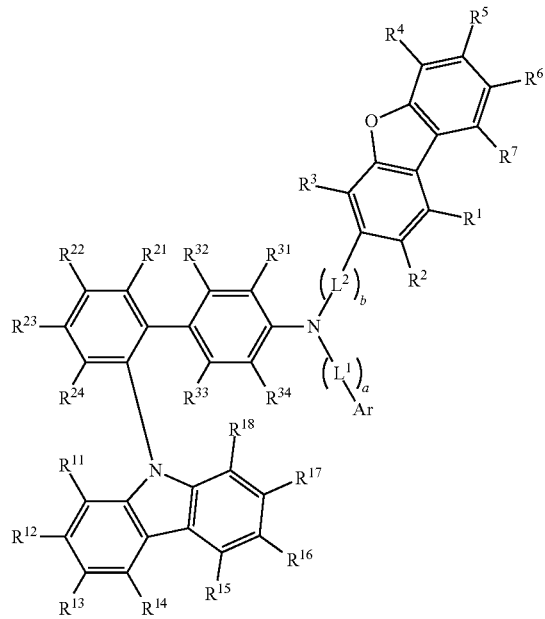

(2-n)
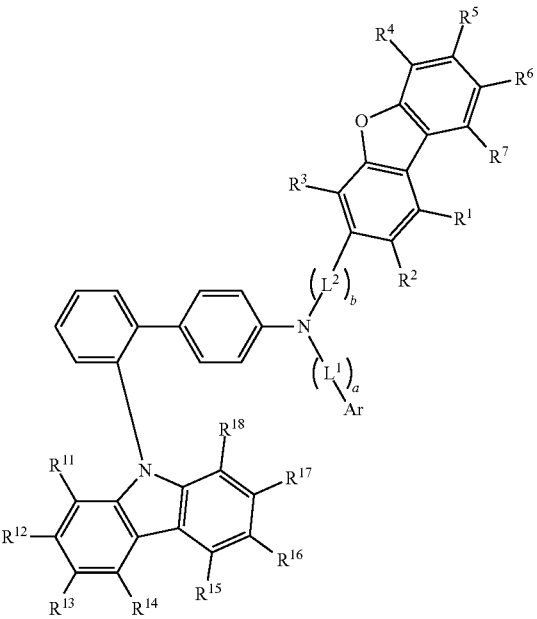

(2-o)
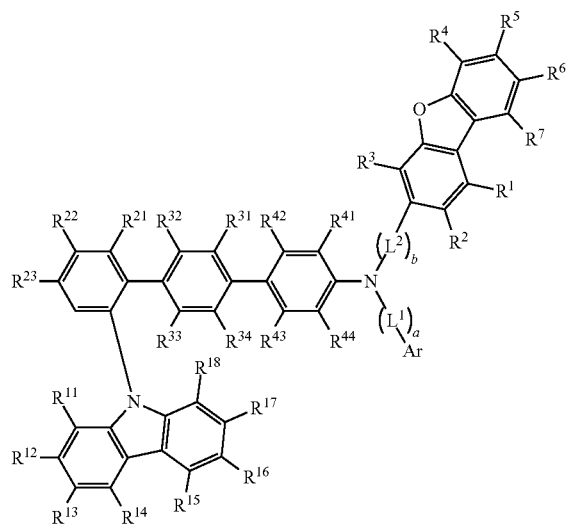

(2-p)
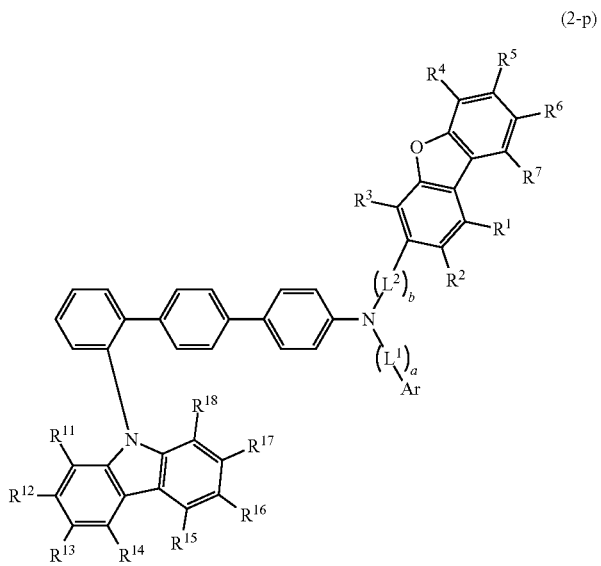

The combinations of the specific examples of the symbols in the compound (1) are described below. However, it should be noted that the combinations are not limited to those described below and the specific examples of each symbol can be suitably selected from its candidate and can be arbitrarily combined with the specific examples of the other symbols.

Combination (1):

In any of formulae relating to the compound of the invention, a is 0 or 1 and b is 1;

$L^1$ is a phenylene group, a biphenylylene group, a terphenylylene group, a naphthylene group, an anthrylene group, a benzanthrylene group, a phenanthrylene group, a benzophenanthrylene group, a picenylene group, a pentaphenylene group, a pyrenylene group, a chrysenylene group, a benzochrysenylene group, or a triphenylenylene group;

$L^2$ is a phenylene group, a biphenylylene group, a terphenylylene group, a naphthylene group, an anthrylene group, a benzanthrylene group, a phenanthrylene group, a benzophenanthrylene group, a picenylene group, a pentaphenylene group, a pyrenylene group, a chrysenylene group, a benzochrysenylene group, or a triphenylenylene group;

Ar is a phenyl group, a biphenylyl group, a terphenylyl group, a naphthyl group, an anthryl group, a benzanthryl group, a phenanthryl group, a benzophenanthryl group, a phenalenyl group, a picenyl group, a pentaphenyl group, a pyrenyl group, a chrysenyl group, a benzochrysenyl group, or a triphenylenyl group; and $R^1$ to $R^7$ and $R^{11}$ to $R^{18}$ are all hydrogen atoms.

Combination (2):

In any of formulae relating to the compound of the invention, a is 0 or 1 and b is 1;

$L^1$ is a phenylene group, a biphenylylene group, a terphenylylene group, a naphthylene group, or a phenanthrylene group;

$L^2$ is a phenylene group, a biphenylylene group, a terphenylylene group, a naphthylene group, or a phenanthrylene group;

Ar is a phenyl group, a biphenylyl group, a terphenylyl group, a naphthyl group, an anthryl group, a benzanthryl group, a phenanthryl group, a benzophenanthryl group, a phenalenyl group, a picenyl group, a pentaphenyl group, a pyrenyl group, a chrysenyl group, a benzochrysenyl group, or a triphenylenyl group; and $R^1$ to $R^7$ and $R^{11}$ to $R^{18}$ are all hydrogen atoms.

Combination (3):

In any of formulae relating to the compound of the invention, a is 0 or 1 and b is 1;

$L^1$ is a phenylene group, a biphenylylene group, a terphenylylene group, a naphthylene group, or a phenanthrylene group;

$L^2$ is a phenylene group, a biphenylylene group, a terphenylylene group, a naphthylene group, or a phenanthrylene group;

Ar is a phenyl group, a biphenylyl group, a terphenylyl group, a naphthyl group, a phenanthryl group, or a triphenylenyl group; and $R^1$ to $R^7$ and $R^{11}$ to $R^{18}$ are all hydrogen atoms.

Combination (4):

In any of formulae relating to the compound of the invention, a is 0 or 1 and b is 1;

$L^1$ is a phenylene group;

$L^2$ is a phenylene group, a biphenylylene group, a naphthylene group, or a phenanthrylene group;

Ar is a phenyl group, a biphenylyl group, a terphenylyl group, a naphthyl group, a phenanthryl group, or a triphenylenyl group; and $R^1$ to $R^7$ and $R^{11}$ to $R^{18}$ are all hydrogen atoms.

Combination (5):

In any of formulae relating to the compound of the invention, a is 0 or 1 and b is 1;

$L^1$ is an o-phenylene group, a m-phenylene group, a p-phenylene group, a 4,4'-biphenylylene group, a 4,3'-biphenylylene group, a 4,2'-biphenylylene group, a 4,4''-p-terphenylylene group, a 4,3''-p-terphenylylene group, a 4,2''-p-terphenylylene group, a 4,2'-p-terphenylylene group, a 4,3'-p-terphenylylene group, a 4,4''-m-terphenylylene group, a 4,3''-m-terphenylylene group, a 4,2''-m-terphenylylene group, a 4,3'-m-terphenylylene group, a 1,4-naphthylene group, a 2,6-naphthylene group, or a 2,7-phenanthrylene group;

$L^2$ is an o-phenylene group, a m-phenylene group, a p-phenylene group, a 4,4'-biphenylylene group, a 4,3'-biphenylylene group, a 4,2'-biphenylylene group, a 4,4''-p-terphenylylene group, a 4,3''-p-terphenylylene group, a 4,2''-p-terphenylylene group, a 4,2'-p-terphenylylene group, a 4,3'-p-terphenylylene group, a 4,4''-m-terphenylylene group, a 4,3''-m-terphenylylene group, a 4,2''-m-terphenylylene group, a 4,3'-m-terphenylylene group, a 1,4-naphthylene group, a 2,6-naphthylene group, or a 2,7-phenanthrylene group;

Ar is a phenyl group, a 2-, 3-, or 4-biphenylyl group, a 2-, 3-, or 4-o-terphenylyl group, a 2-, 3-, or 4-m-terphenylyl group, a 2-, 3-, or 4-p-terphenylyl group, a 1- or 2-naphthyl group, a 2-, 3-, 4-, or 9-phenanthryl group, or a 2-triphenylenyl group; and $R^1$ to $R^7$ and $R^{11}$ to $R^{18}$ are all hydrogen atoms.

Combination (6):

In any of formulae relating to the compound of the invention, a is 0 or 1 and b is 1;

$L^1$ is an o-phenylene group, a m-phenylene group, or a p-phenylene group;

$L^2$ is an o-phenylene group, a m-phenylene group, a p-phenylene group, a 4,4'-biphenylylene group, a 4,3'-biphenylylene group, a 4,2'-biphenylylene group, a 1,4-naphthylene group, a 2,6-naphthylene group, or a 2,7-phenanthrylene group;

Ar is a phenyl group, a 2-, 3-, or 4-biphenylyl group, a 2-, 3-, or 4-o-terphenylyl group, a 2-, 3-, or 4-m-terphenylyl group, a 2-, 3-, or 4-p-terphenylyl group, a 1- or 2-naphthyl group, a 2-, 3-, 4-, or 9-phenanthryl group, or a 2-triphenylenyl group; and $R^1$ to $R^7$ and $R^{11}$ to $R^{18}$ are all hydrogen atoms.

Combination (7):

In any of formulae relating to the compound of the invention, a is 0 or 1 and b is 1;

$L^1$ is an o-phenylene group, a m-phenylene group, or a p-phenylene group;

$L^2$ is an o-phenylene group, a m-phenylene group, a p-phenylene group, a 4,4'-biphenylylene group, a 4,3'-biphenylylene group, or a 4,2'-biphenylylene group;

Ar is a phenyl group, a 2-, 3-, or 4-biphenylyl group, a 2-, 3-, or 4-o-terphenylyl group, a 2-, 3-, or 4-m-terphenylyl group, a 2-, 3-, or 4-p-terphenylyl group, a 1- or 2-naphthyl group, a 2-, 3-, 4-, or 9-phenanthryl group, or a 2-triphenylenyl group; and $R^1$ to $R^7$ and $R^{11}$ to $R^{18}$ are all hydrogen atoms.

Combination (8):

In any of formulae relating to the compound of the invention, a is 0 or 1 and b is 1;

$L^1$ is a p-phenylene group, a 4,4'-biphenylylene group, or a 4,4''-p-terphenylylene group;

$L^2$ is an o-phenylene group, a m-phenylene group, a p-phenylene group, a 4,4'-biphenylylene group, a 4,3'-biphenylylene group, a 4,2'-biphenylylene group, a 4,4''-p-terphenylylene group, a 4,3''-p-terphenylylene group, a 4,2''-p-terphenylylene group, a 4,2'-p-terphenylylene group, a 4,3'-p-terphenylylene group, a 4,4''-m-terphenylylene group, a 4,3''-m-terphenylylene group, a 4,2''-m-terphenylylene group, a 4,3'-m-terphenylylene group, a 1,4-naphthylene group, a 2,6-naphthylene group, or a 2,7-phenanthrylene group;

Ar is a phenyl group, a 2-, 3-, or 4-biphenylyl group, a 2-, 3-, or 4-o-terphenylyl group, a 2-, 3-, or 4-m-terphenylyl group, a 2-, 3-, or 4-p-terphenylyl group, a 1- or 2-naphthyl group, a 2-, 3-, 4-, or 9-phenanthryl group, or a 2-triphenylenyl group; and $R^1$ to $R^7$ and $R^{11}$ to $R^{18}$ are all hydrogen atoms.

Combination (9):

In any of formulae relating to the compound of the invention, a is 0 or 1 and b is 1;

$L^1$ is a p-phenylene group;

$L^2$ is an o-phenylene group, a m-phenylene group, a p-phenylene group, a 4,4'-biphenylylene group, a 4,3'-biphenylylene group, a 4,2'-biphenylylene group, a 4,4''-p-terphenylylene group, a 4,3''-p-terphenylylene group, a 4,2''-p-terphenylylene group, a 4,2'-p-terphenylylene group, a 4,3'-p-terphenylylene group, a 4,4''-m-terphenylylene group, a 4,3''-m-terphenylylene group, a 4,2''-m-terphenylylene group, a 4,3'-m-terphenylylene group, a 1,4-naphthylene group, a 2,6-naphthylene group, or a 2,7-phenanthrylene group;

Ar is a phenyl group, a 2-, 3-, or 4-biphenylyl group, a 2-, 3-, or 4-o-terphenylyl group, a 2-, 3-, or 4-m-terphenylyl group, a 2-, 3-, or 4-p-terphenylyl group, a 1- or 2-naphthyl group, a 2-, 3-, 4-, or 9-phenanthryl group, or a 2-triphenylenyl group; and $R^1$ to $R^7$ and $R^{11}$ to $R^{18}$ are all hydrogen atoms.

Combination (10):

In any of formulae relating to the compound of the invention, a is 0 or 1 and b is 1;

$L^1$ is an o-phenylene group, a m-phenylene group, a p-phenylene group, a 4,4'-biphenylylene group, a 4,3'-biphenylylene group, a 4,2'-biphenylylene group, a 4,4''-p-terphenylylene group, a 4,3''-p-terphenylylene group, a 4,2''-p-terphenylylene group, a 4,2'-p-terphenylylene group, a 4,3'-p-terphenylylene group, a 4,4''-m-terphenylylene group, a 4,3''-m-terphenylylene group, a 4,2''-m-terphenylylene group, a 4,3'-m-terphenylylene group, a 1,4-naphthylene group, a 2,6-naphthylene group, or a 2,7-phenanthrylene group;

$L^2$ is a p-phenylene group, a 4,4'-biphenylylene group, or a 4,4''-p-terphenylylene group;

Ar is a phenyl group, a 2-, 3-, or 4-biphenylyl group, a 2-, 3-, or 4-o-terphenylyl group, a 2-, 3-, or 4-m-terphenylyl group, a 2-, 3-, or 4-p-terphenylyl group, a 1- or 2-naphthyl group, a 2-, 3-, 4-, or 9-phenanthryl group, or a 2-triphenylenyl group; and $R^1$ to $R^7$ and $R^{11}$ to $R^{18}$ are all hydrogen atoms.

Combination (11):

In any of formulae relating to the compound of the invention, a is 0 or 1 and b is 1;

$L^1$ is an o-phenylene group, a m-phenylene group, a p-phenylene group, a 4,4'-biphenylylene group, a 4,3'-biphenylylene group, a 4,2'-biphenylylene group, a 4,4''-p-terphenylylene group, a 4,3''-p-terphenylylene group, a 4,2''-p-terphenylylene group, a 4,2'-p-terphenylylene group, a 4,3'-p-terphenylylene group, a 4,4''-m-terphenylylene group, a 4,3''-m-terphenylylene group, a 4,2''-m-terphenylylene group, a 4,3'-m-terphenylylene group, a 1,4-naphthylene group, a 2,6-naphthylene group, or a 2,7-phenanthrylene group;

$L^2$ is a p-phenylene group;

Ar is a phenyl group, a 2-, 3-, or 4-biphenylyl group, a 2-, 3-, or 4-o-terphenylyl group, a 2-, 3-, or 4-m-terphenylyl group, a 2-, 3-, or 4-p-terphenylyl group, a 1- or 2-naphthyl group, a 2-, 3-, 4-, or 9-phenanthryl group, or a 2-triphenylenyl group; and $R^1$ to $R^7$ and $R^{11}$ to $R^{18}$ are all hydrogen atoms.

Combinations (1) to (11), wherein Ar is a phenyl group, a biphenylyl group, or a terphenylyl group are also preferred and combinations (1) to (11), wherein Ar is a phenyl group or a biphenylyl group are also preferred.

In addition, combinations (1) to (11), wherein Ar is a phenyl group, a 2-, 3-, or 4-biphenylyl group, a 2-, 3-, or 4-o-terphenylyl group, a 2-, 3-, or 4-m-terphenylyl group, or a 2-, 3-, or 4-p-terphenylyl group are also preferred and combinations (1) to (11), wherein Ar is a phenyl group or a 4-biphenylyl group are also preferred.

Combination (12):

In any of formulae relating to the compound of the invention, a is 0 and b is 1;

$L^2$ is an o-phenylene group, a m-phenylene group, a p-phenylene group, a 4,4'-biphenylylene group, a 4,3'-biphenylylene group, a 4,2'-biphenylylene group, a 1,4-naphthylene group, a 2,6-naphthylene group, or a 2,7-phenanthrylene group;

Ar is a phenyl group, a 2-, 3-, or 4-biphenylyl group, a 2-, 3-, or 4-o-terphenylyl group, a 2-, 3-, or 4-m-terphenylyl group, a 2-, 3-, or 4-p-terphenylyl group, a 1- or 2-naphthyl group, a 2-, 3-, 4-, or 9-phenanthryl group, or a 2-triphenylenyl group; and $R^1$ to $R^7$ and $R^{11}$ to $R^{18}$ are all hydrogen atoms.

Combination (13):

In any of formulae relating to the compound of the invention, a is 0 and b is 1;

$L^2$ is an o-phenylene group, a m-phenylene group, a p-phenylene group, a 4,4'-biphenylylene group, a 4,3'-biphenylylene group, or a 4,2'-biphenylylene group;

Ar is a phenyl group, a 2-, 3-, or 4-biphenylyl group, a 2-, 3-, or 4-o-terphenylyl group, a 2-, 3-, or 4-m-terphenylyl group, a 2-, 3-, or 4-p-terphenylyl group, a 1- or 2-naphthyl group, a 2-, 3-, 4-, or 9-phenanthryl group, or a 2-triphenylenyl group; and $R^1$ to $R^7$ and $R^{11}$ to $R^{18}$ are all hydrogen atoms.

Combination (14):

In any of formulae relating to the compound of the invention, a is 0 and b is 1;

$L^2$ is a p-phenylene group or a 4,4'-biphenylylene group;

Ar is a phenyl group, a 2-, 3-, or 4-biphenylyl group, a 2-, 3-, or 4-o-terphenylyl group, a 2-, 3-, or 4-m-terphenylyl group, a 2-, 3-, or 4-p-terphenylyl group, a 1- or 2-naphthyl group, a 2-, 3-, 4-, or 9-phenanthryl group, or a 2-triphenylenyl group; and $R^1$ to $R^7$ and $R^{11}$ to $R^{18}$ are all hydrogen atoms.

Combinations (12) to (14), wherein Ar is a phenyl group, a biphenylyl group, or a terphenylyl group are also preferred and combinations (12) to (14), wherein Ar is a biphenylyl group are also preferred.

In addition, combination (1) to (11), wherein Ar is a phenyl group, a 2-, 3-, or 4-biphenylyl group, a 2-, 3-, or 4-o-terphenylyl group, a 2-, 3-, or 4-m-terphenylyl group, or a 2-, 3-, or 4-p-terphenylyl group are also preferred and combinations (1) to (11), wherein Ar is a 4-biphenylyl group are also preferred.

Combination (15):

In any of formulae relating to the compound of the invention, a is 1 and b is 1;

$L^1$ is an o-phenylene group, a m-phenylene group, or a p-phenylene group;

L² is an o-phenylene group, a m-phenylene group, a p-phenylene group, a 4,4'-biphenylylene group, a 4,3'-biphenylylene group, a 4,2'-biphenylylene group, a 1,4-naphthylene group, a 2,6-naphthylene group, or a 2,7-phenanthrylene group, preferably an o-phenylene group, a m-phenylene group, a p-phenylene group, a 4,4'-biphenylylene group, a 4,3'-biphenylylene group, or a 4,2'-biphenylylene group;

Ar is a 1- or 2-naphthyl group, a 2-, 3-, 4-, or 9-phenanthryl group, or a 2-triphenylenyl group; and $R^1$ to $R^7$ and $R^{11}$ to $R^{18}$ are all hydrogen atoms.

Combination (16)

In any of formulae relating to the compound of the invention, a is 1 and b is 1;

$L^1$ is a p-phenylene group;

L² is an o-phenylene group, a m-phenylene group, a p-phenylene group, a 4,4'-biphenylylene group, a 4,3'-biphenylylene group, a 4,2'-biphenylylene group, a 1,4-naphthylene group, a 2,6-naphthylene group, or a 2,7-phenanthrylene group, preferably an o-phenylene group, a m-phenylene group, a p-phenylene group, a 4,4'-biphenylylene group, a 4,3'-biphenylylene group, or a 4,2'-biphenylylene group;

Ar is a 1- or 2-naphthyl group, a 2-, 3-, 4-, or 9-phenanthryl group, or a 2-triphenylenyl group; and $R^1$ to $R^7$ and $R^{11}$ to $R^{18}$ are all hydrogen atoms.

Combination (17):

In any of formulae relating to the compound of the invention, a is 1 and b is 1;

$L^1$ is an o-phenylene group, a m-phenylene group, or a p-phenylene group;

$L^2$ is a p-phenylene group or a 4,4'-biphenylylene group;

Ar is a 1- or 2-naphthyl group, a 2-, 3-, 4-, or 9-phenanthryl group, or a 2-triphenylenyl group; and $R^1$ to $R^7$ and $R^{11}$ to $R^{18}$ are all hydrogen atoms.

Combination (18)

In any of formulae relating to the compound of the invention, a is 0 and b is 1;

$L^2$ is a p-phenylene group;

Ar is a 4-biphenylyl group; and $R^1$ to $R^7$ and $R^{11}$ to $R^{18}$ are all hydrogen atoms.

The optional substituent referred to by "substituted or unsubstituted" herein is, unless otherwise noted, selected from the group consisting of a substituted or unsubstituted alkyl group having 1 to 30, preferably 1 to 18, more preferably 1 to 8 carbon atoms; a substituted or unsubstituted cycloalkyl group having 3 to 30, preferably 3 to 10, more preferably 3 to 8, still more preferably 5 or 6 ring carbon atoms; a substituted or unsubstituted aryl group having 6 to 30, preferably 6 to 25, more preferably 6 to 18 ring carbon atoms; a substituted or unsubstituted aralkyl group having 7 to 36, preferably 7 to 26, more preferably 7 to 20 ring carbon atoms; a substituted or unsubstituted alkoxy group having 1 to 30, preferably 1 to 18, more preferably 1 to 8 carbon atoms; a substituted or unsubstituted aryloxy group having 6 to 30, preferably 6 to 25, more preferably 6 to 18 ring carbon atoms; a mono-, di-, or tri-substituted silyl group having a substituent selected from a substituted or unsubstituted alkyl group having 1 to 30, preferably 1 to 18, more preferably 1 to 8 carbon atoms and a substituted or unsubstituted aryl group having 6 to 30, preferably 6 to 25, more preferably 6 to 18 ring carbon atoms; a substituted or unsubstituted haloalkyl group having 1 to 30, preferably 1 to 18, more preferably 1 to 8 carbon atoms; a substituted or unsubstituted haloalkoxy group having 1 to 30, preferably 1 to 18, more preferably 1 to 8 carbon atoms; a substituted or unsubstituted heteroaryl group having 5 to 30, preferably 5 to 24, more preferably 5 to 13 ring atoms; a halogen atom; a cyano group; and a nitro group.

The details of the optional substituents are as described above with respect to $R^1$ to $R^7$ and $R^{11}$ to $R^{18}$. Unless otherwise noted, adjacent optional groups may be bonded to each other to form a ring.

Examples of the compound (1) of the invention are shown below, although not limited thereto.

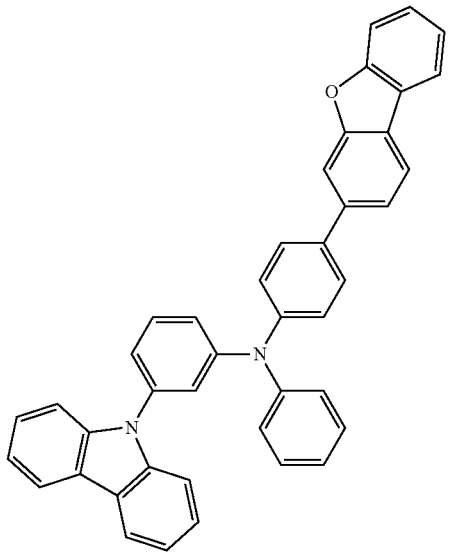
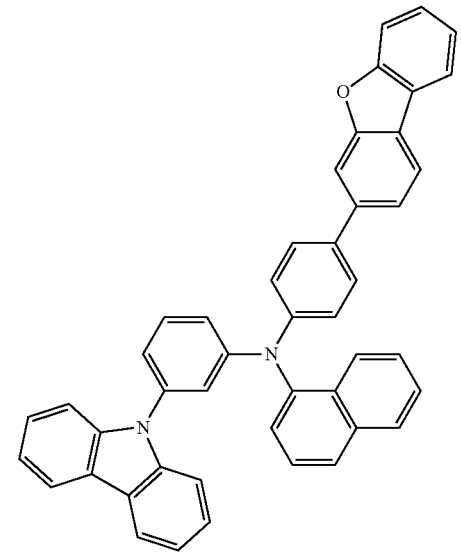

-continued
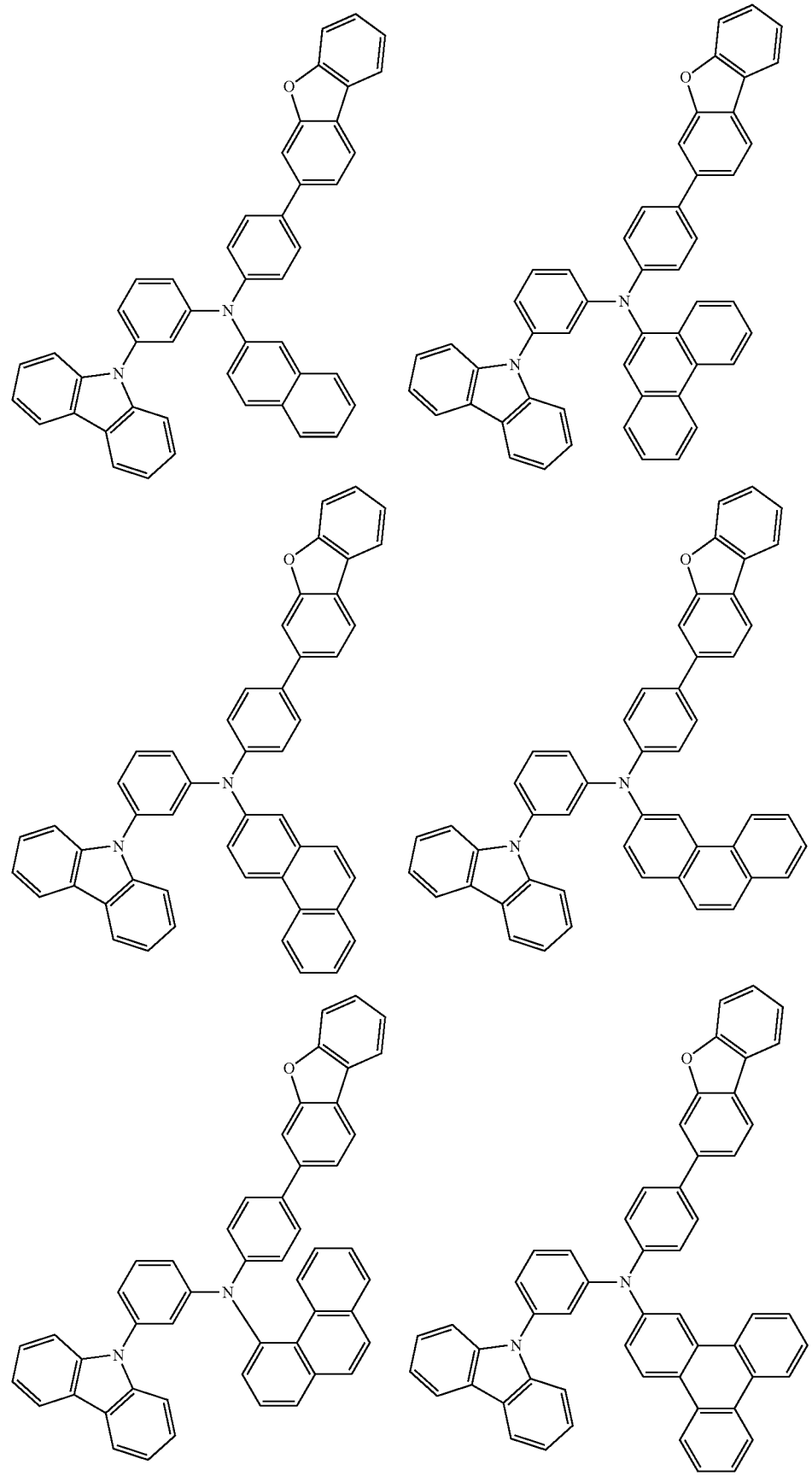

-continued
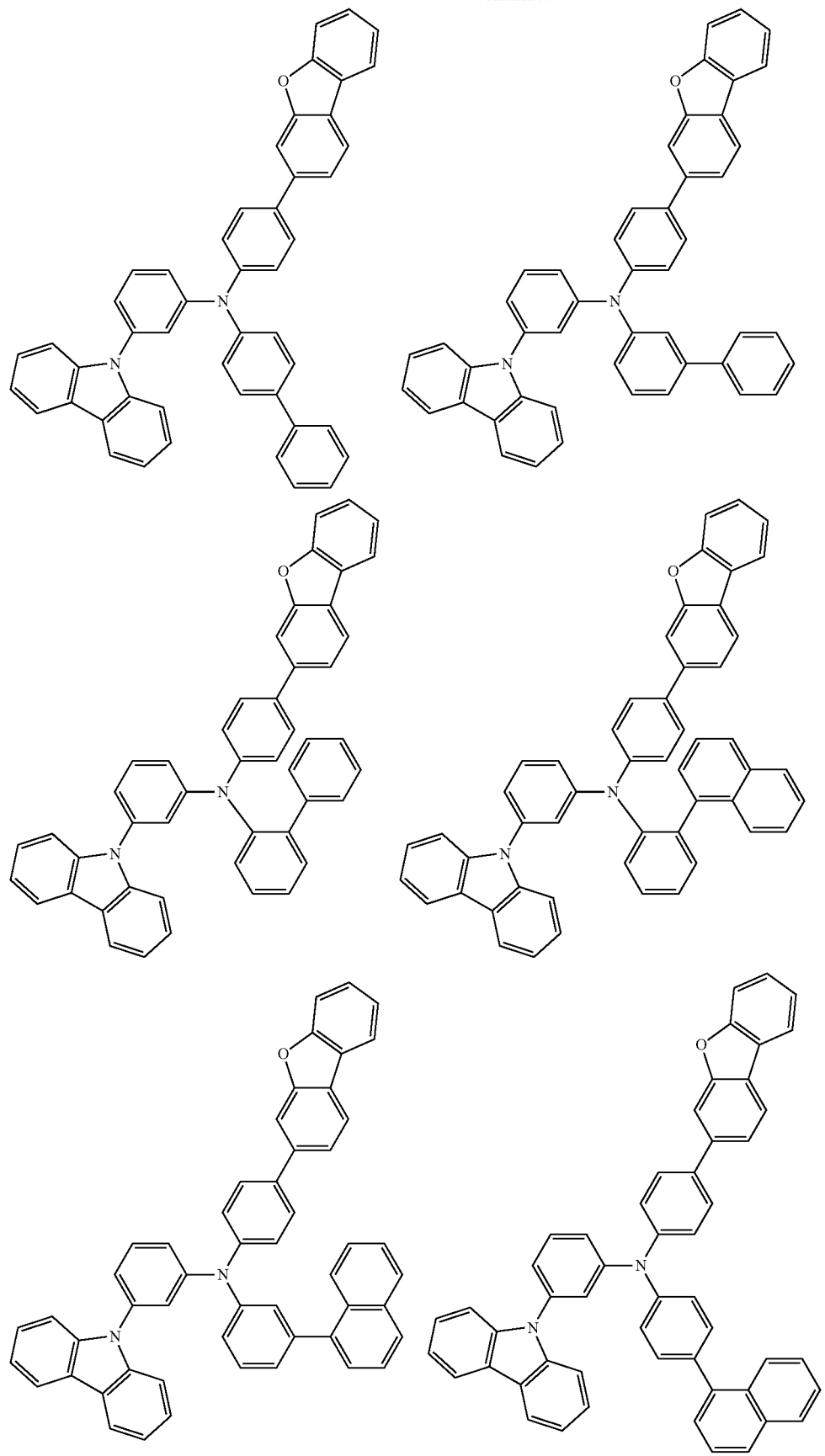

41
42
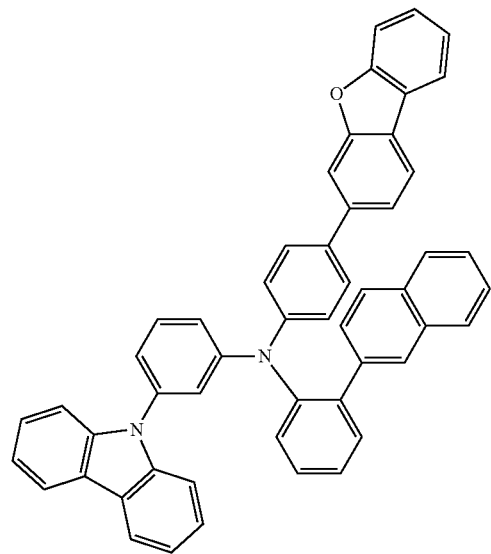
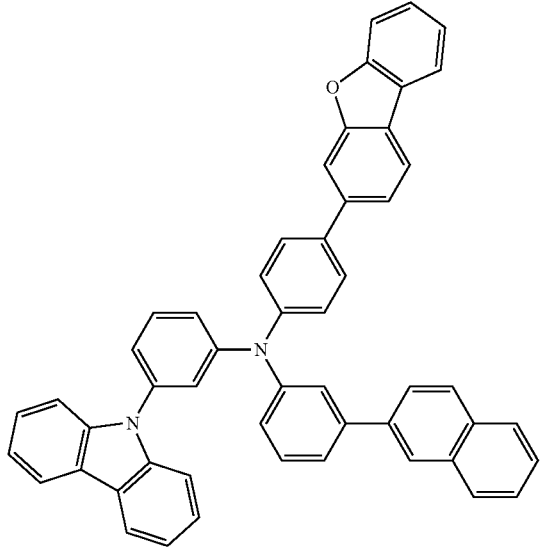
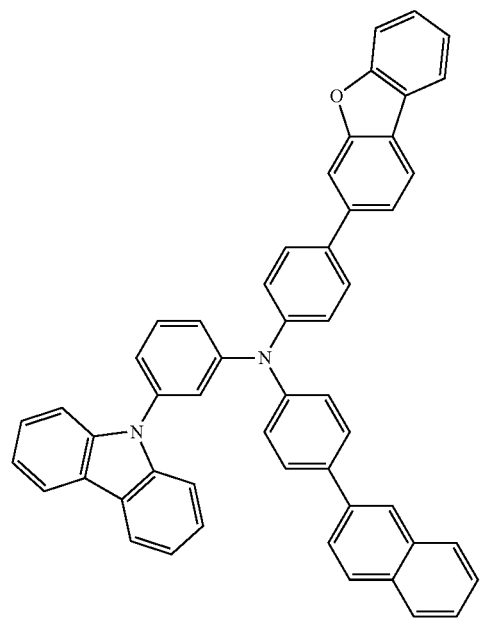
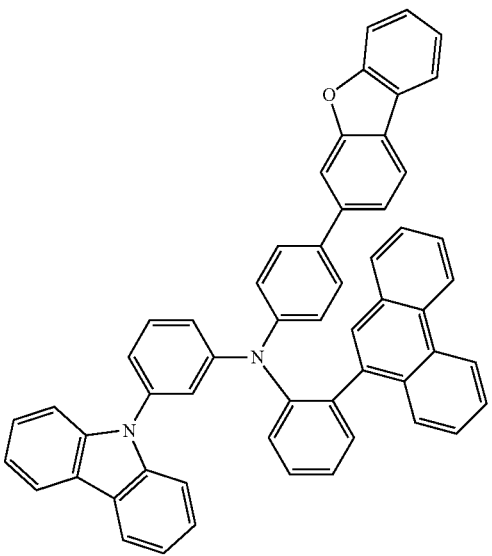

-continued
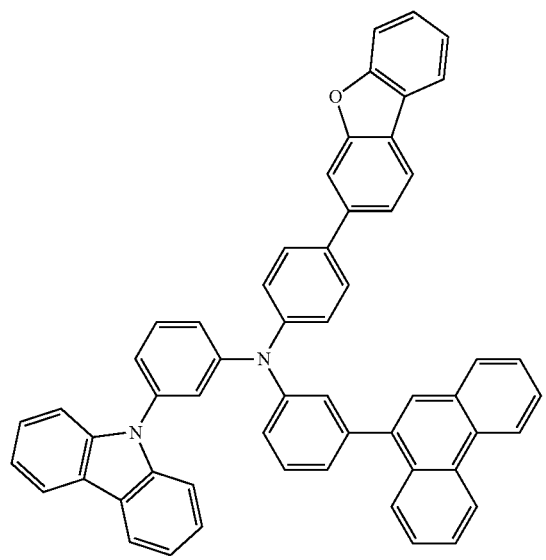
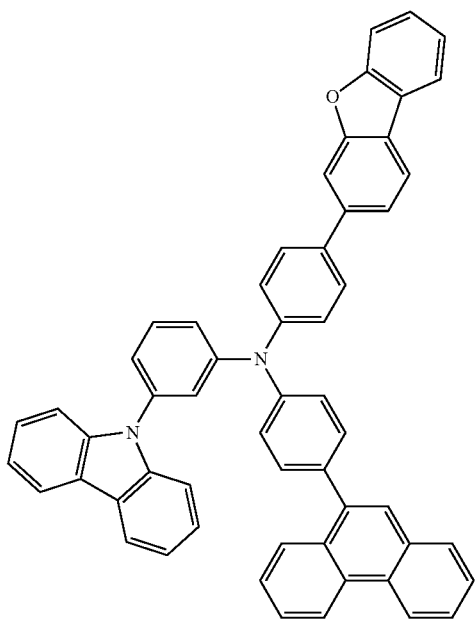
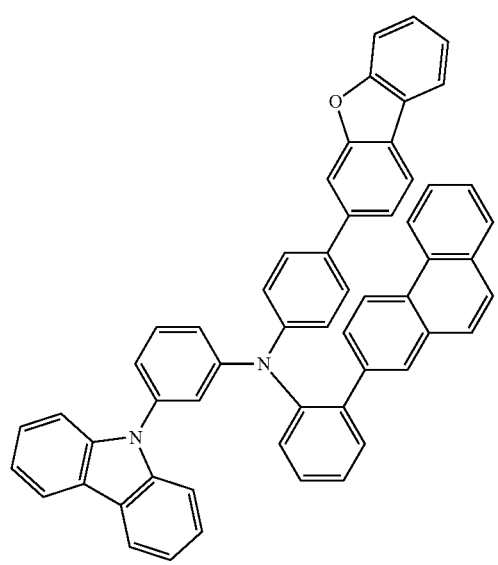
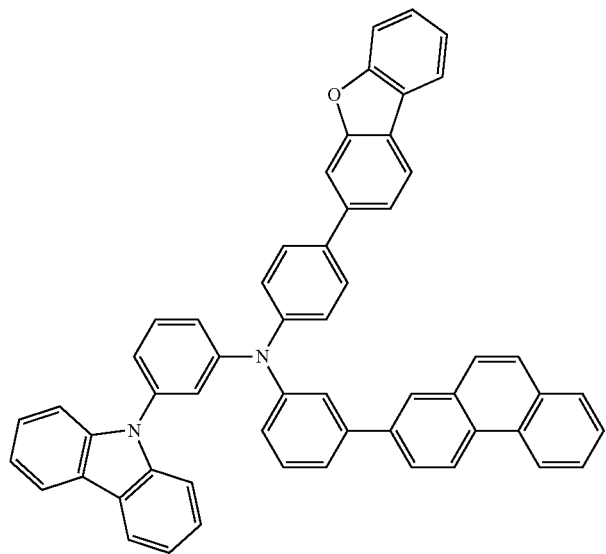

-continued
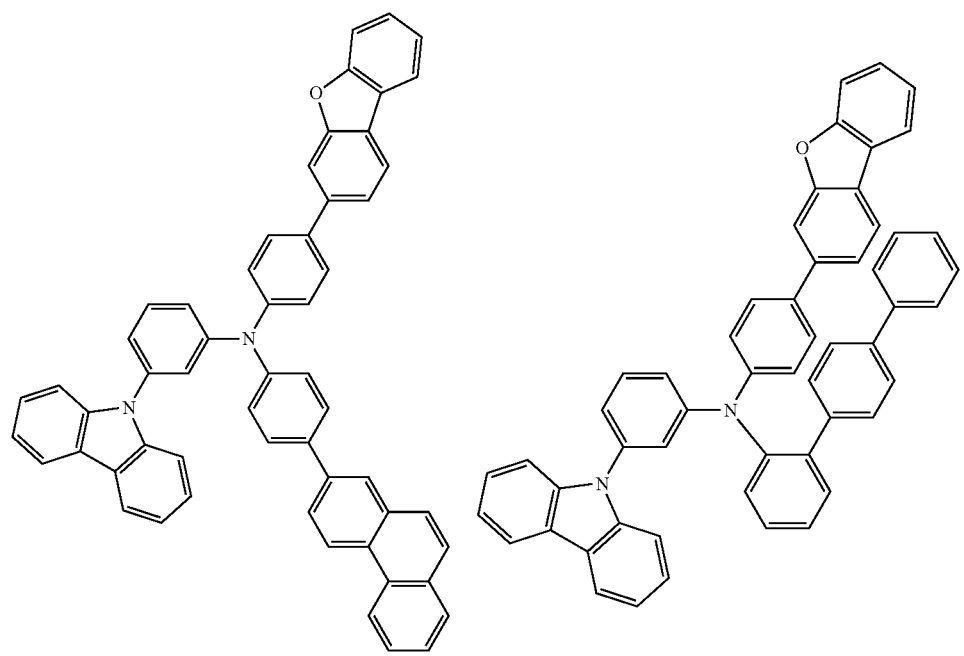
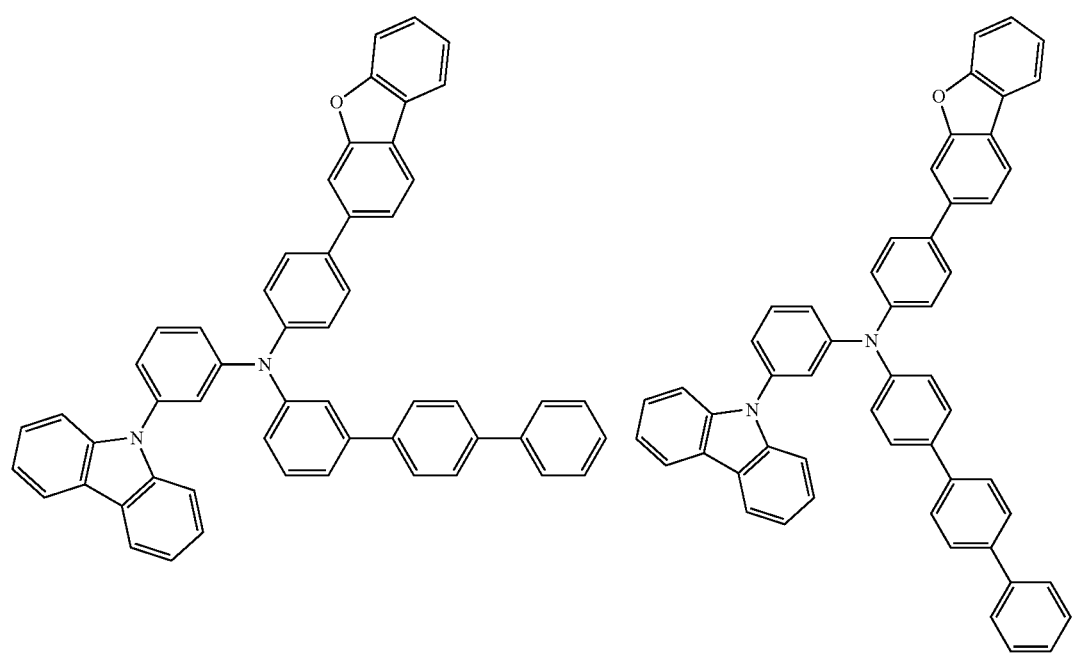

47 48
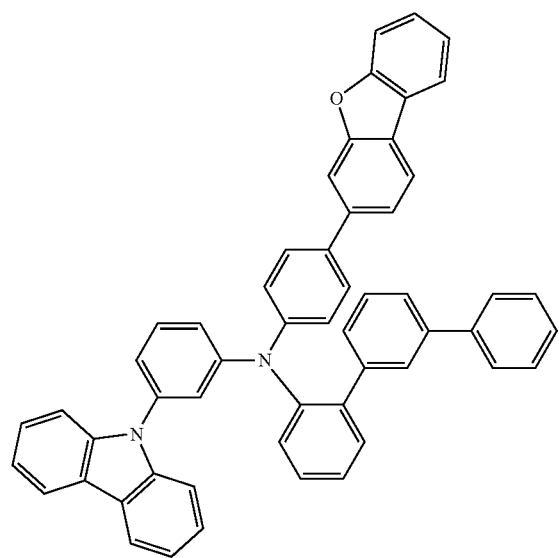 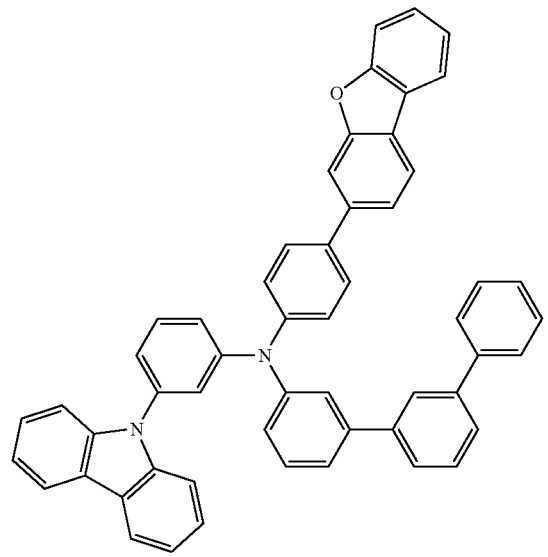
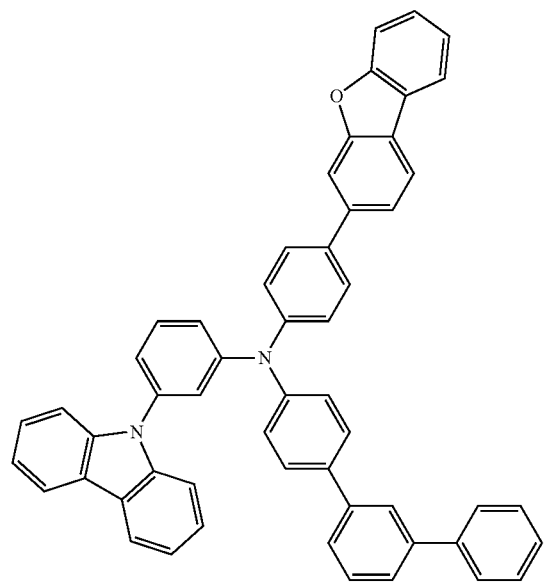 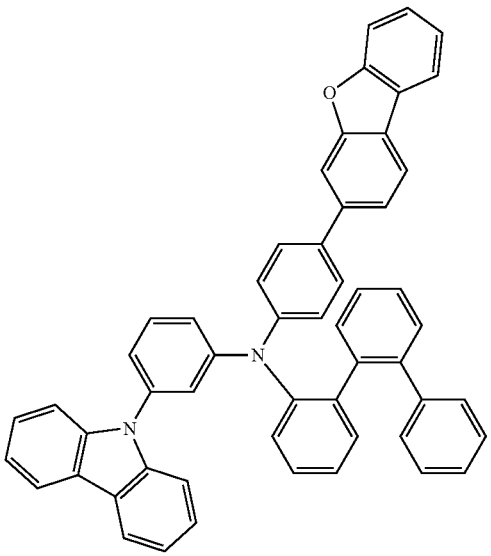

-continued
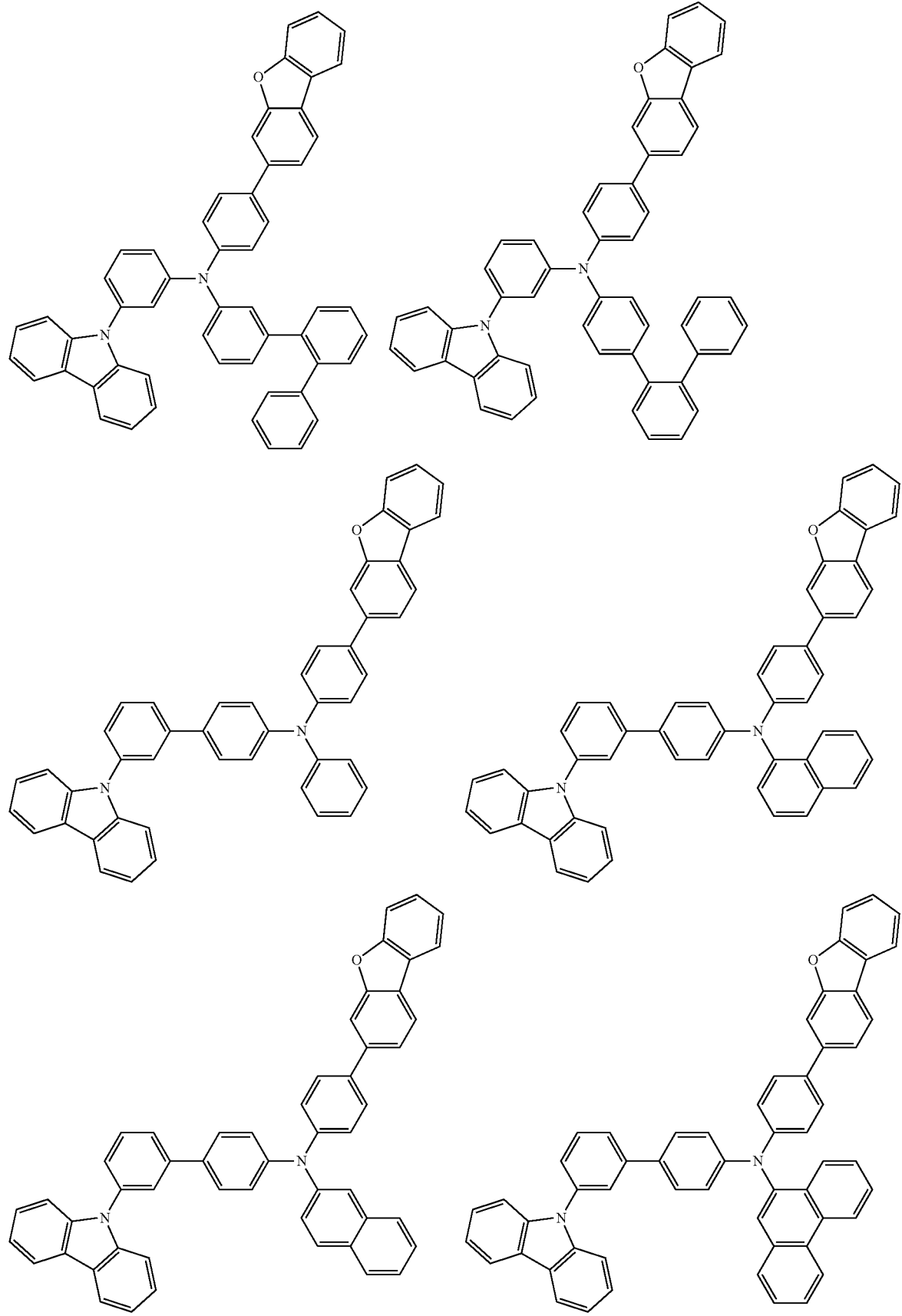

-continued
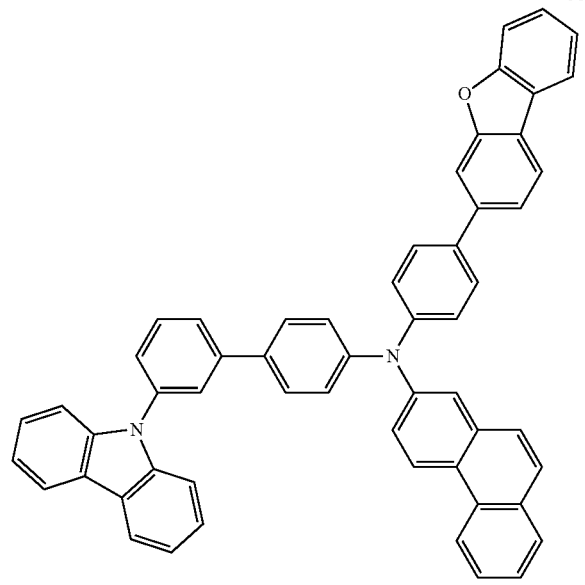
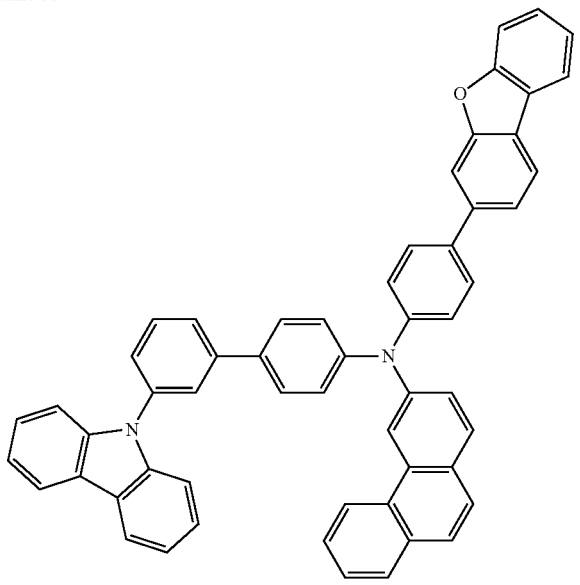
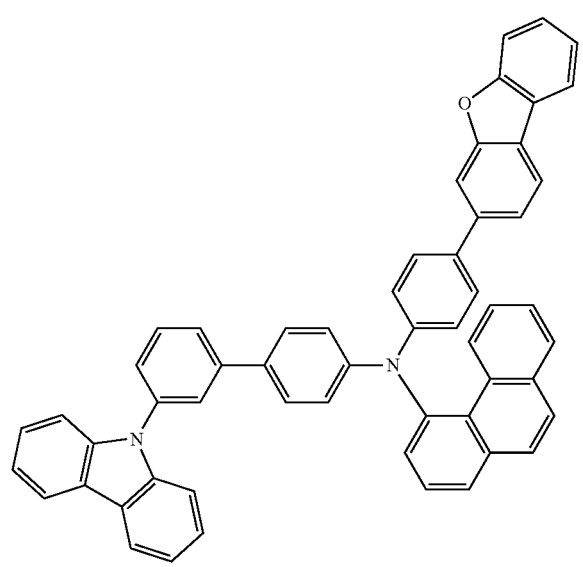
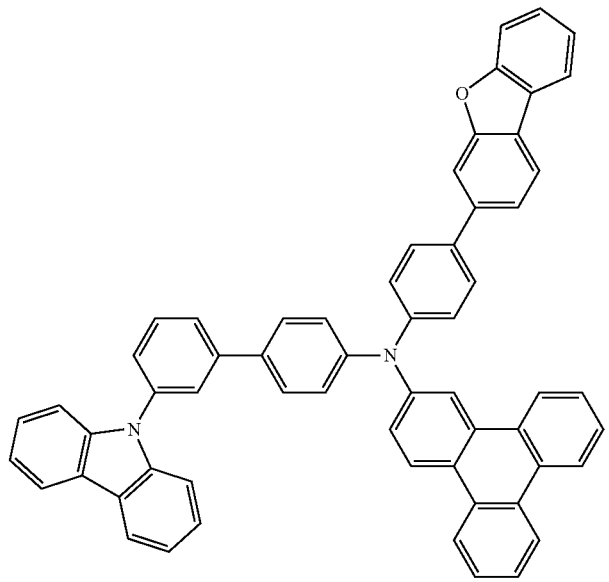
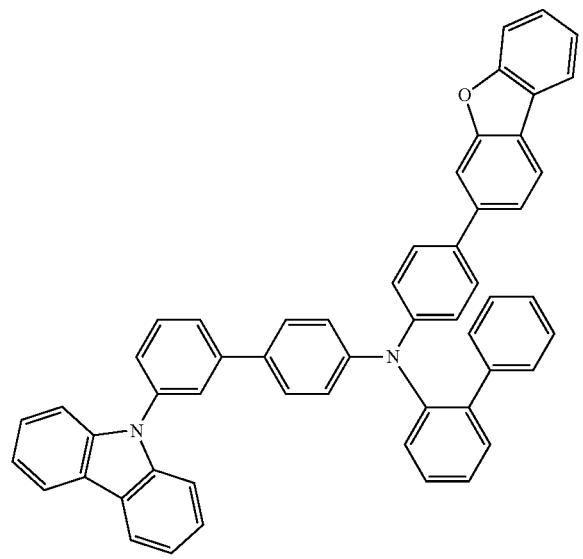
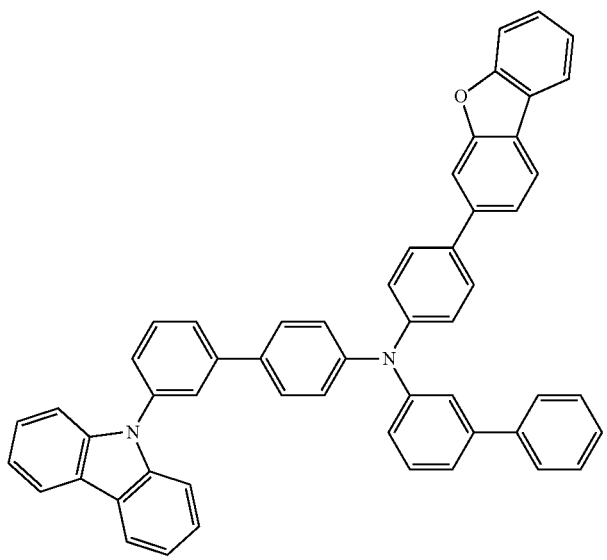

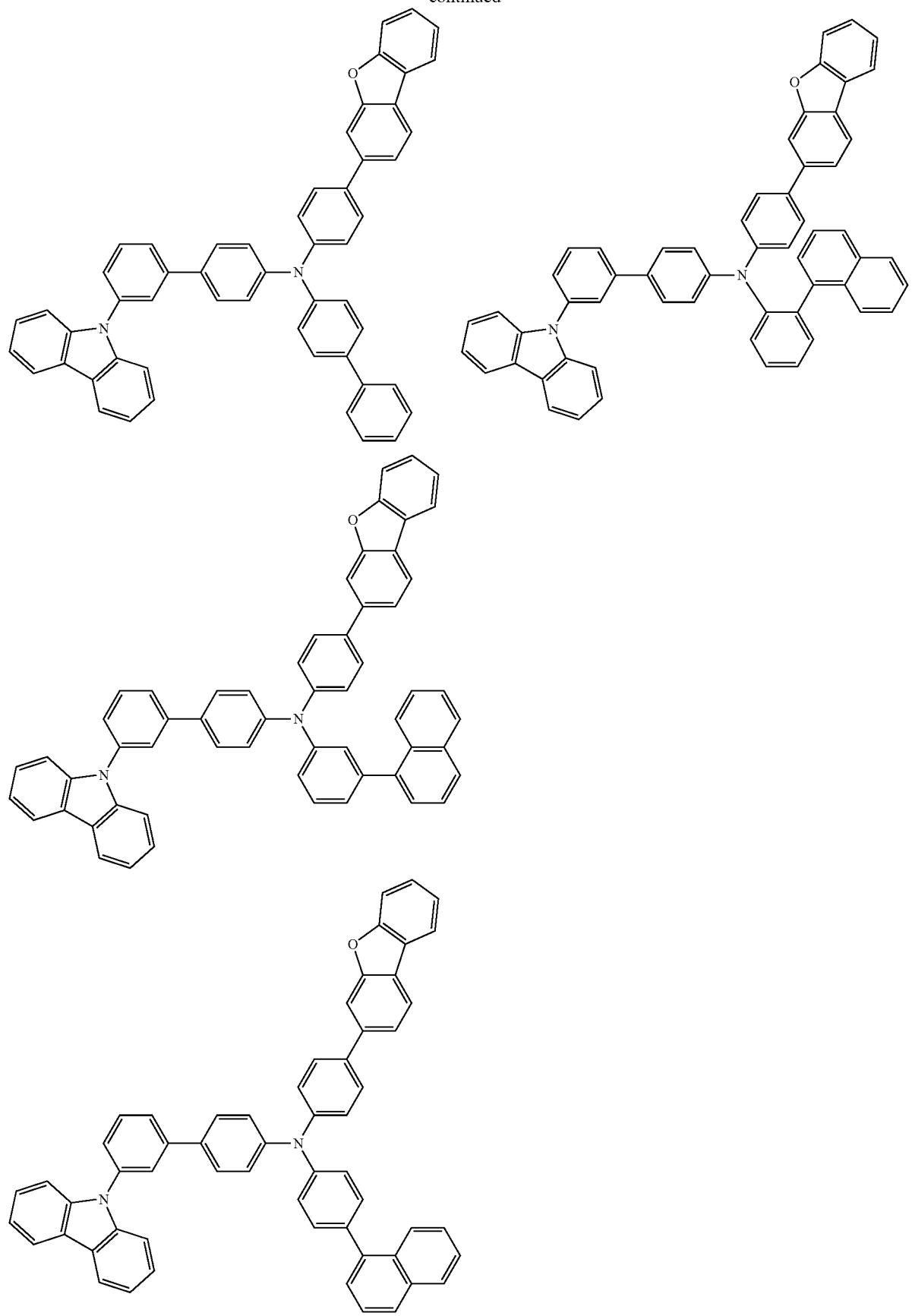

-continued
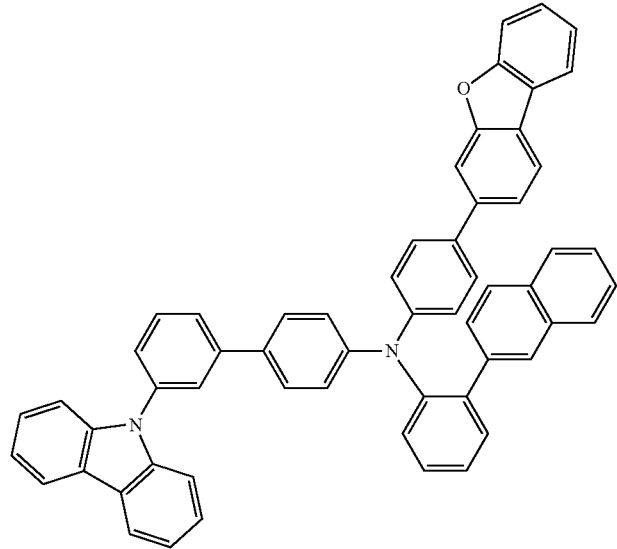
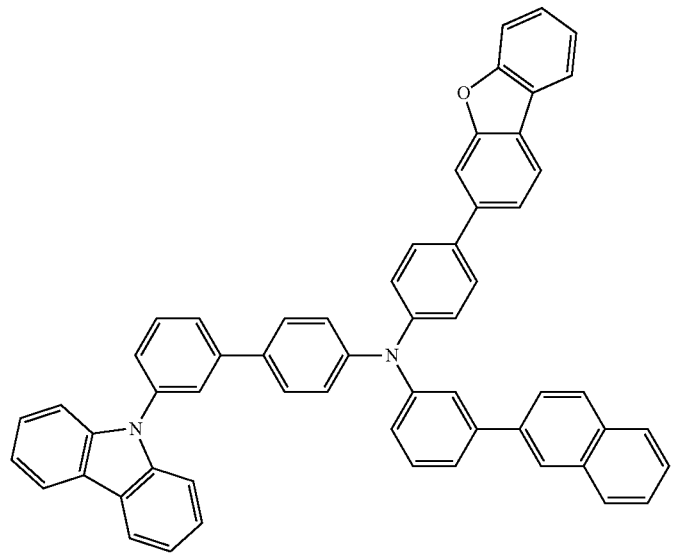
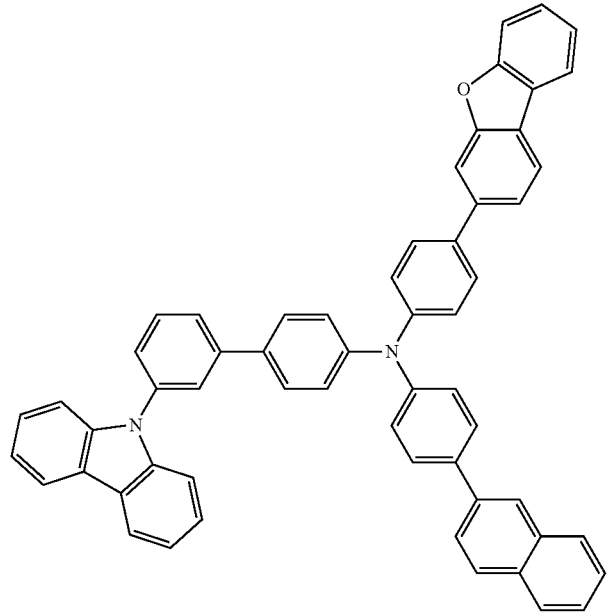

-continued
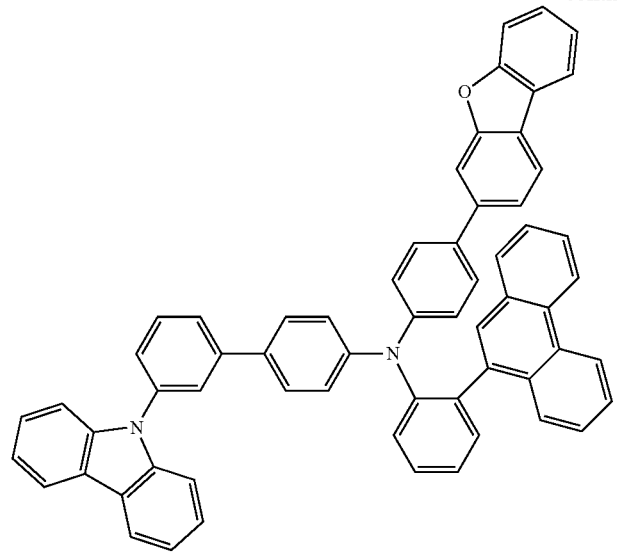
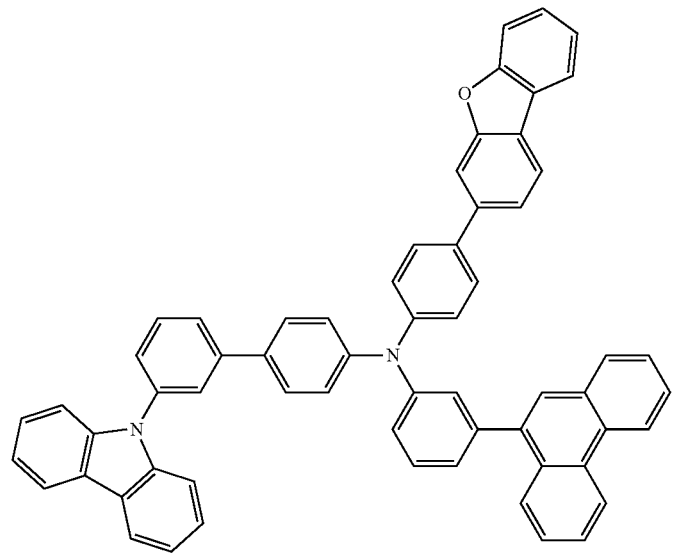
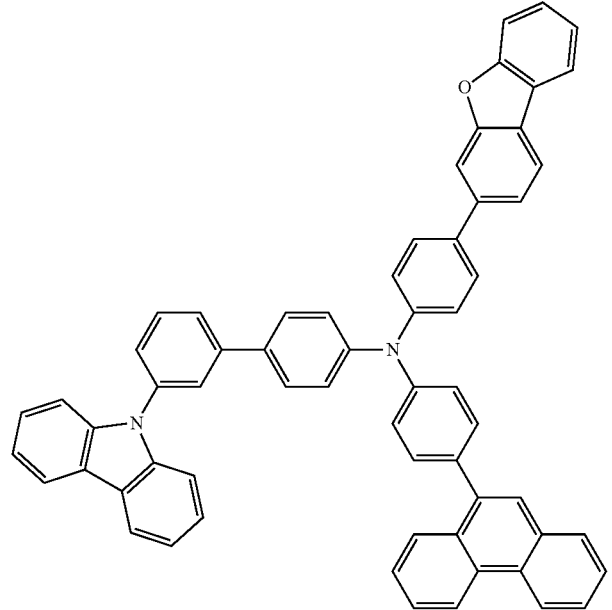

-continued
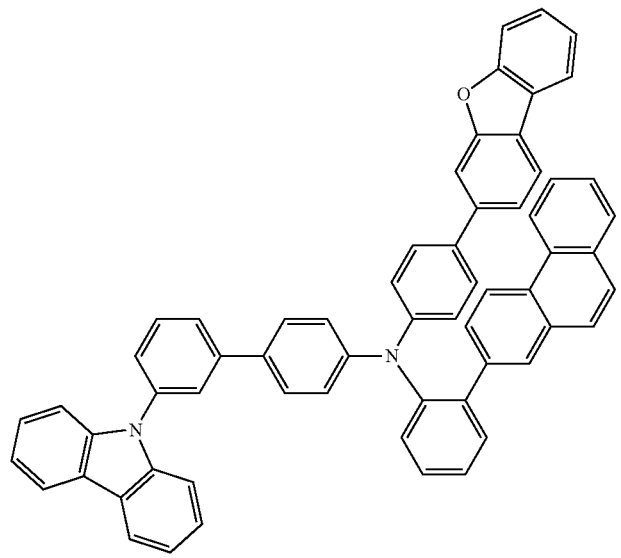
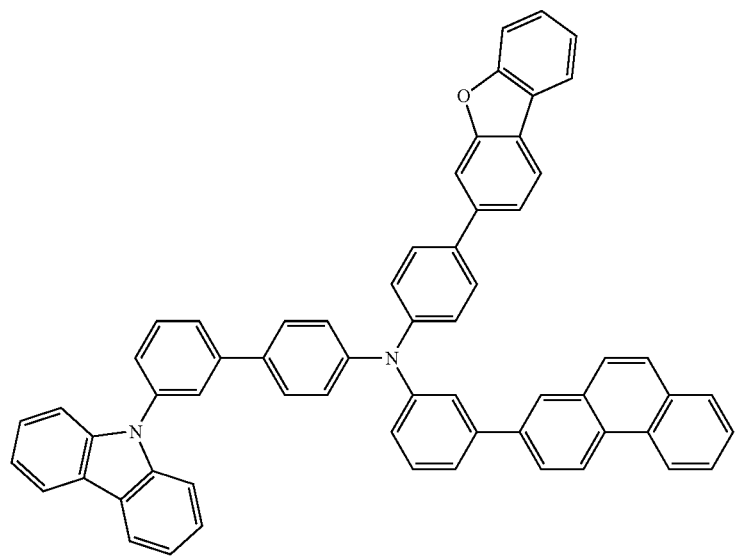

-continued
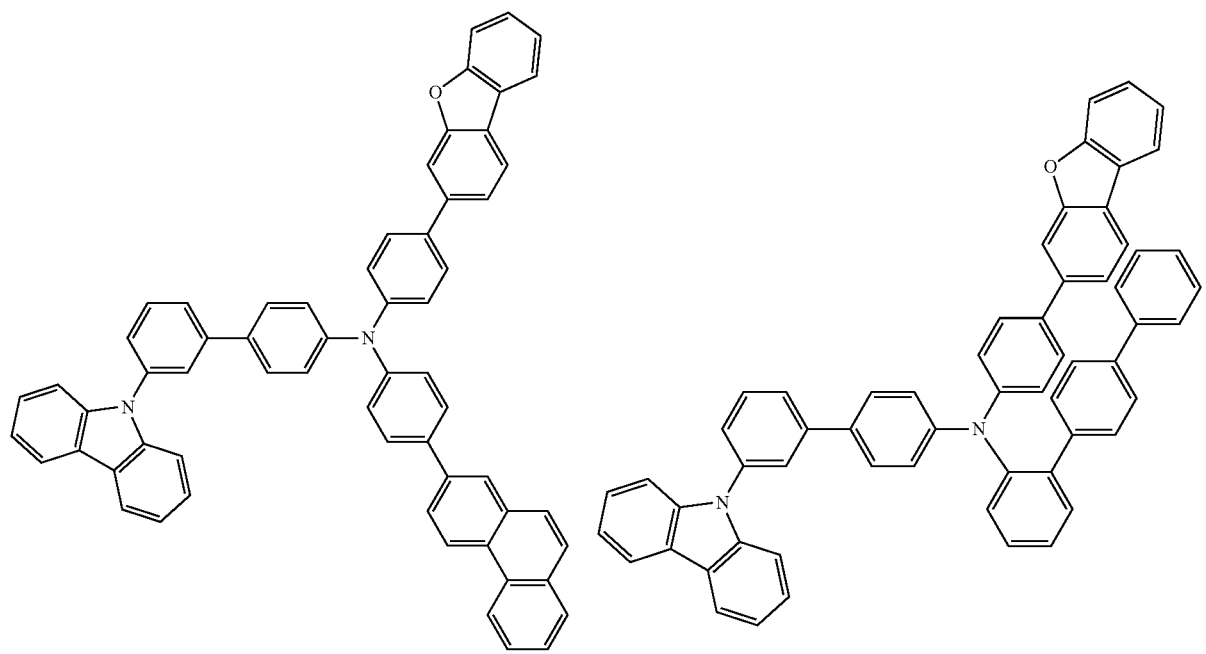
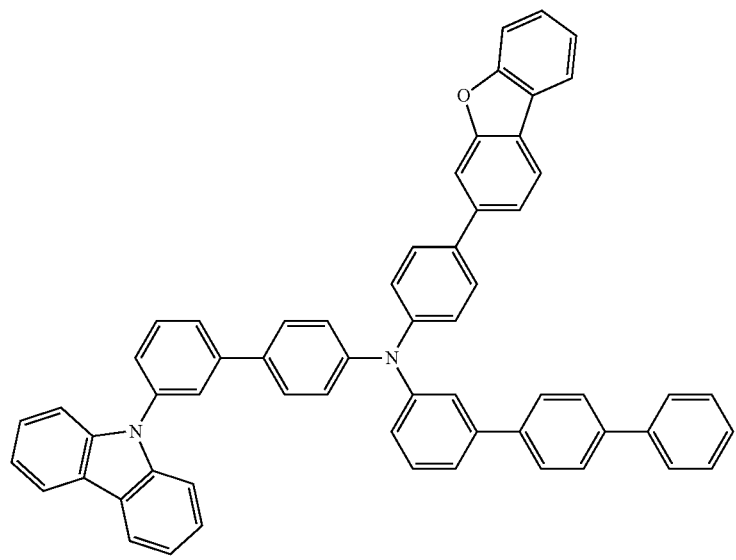

-continued
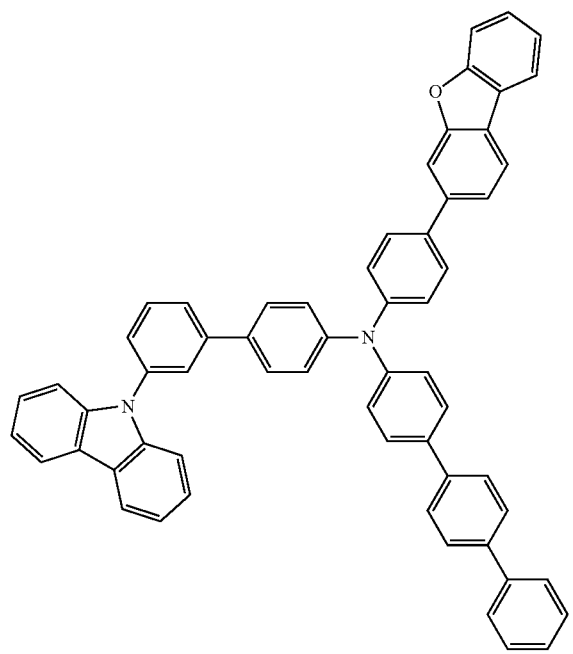
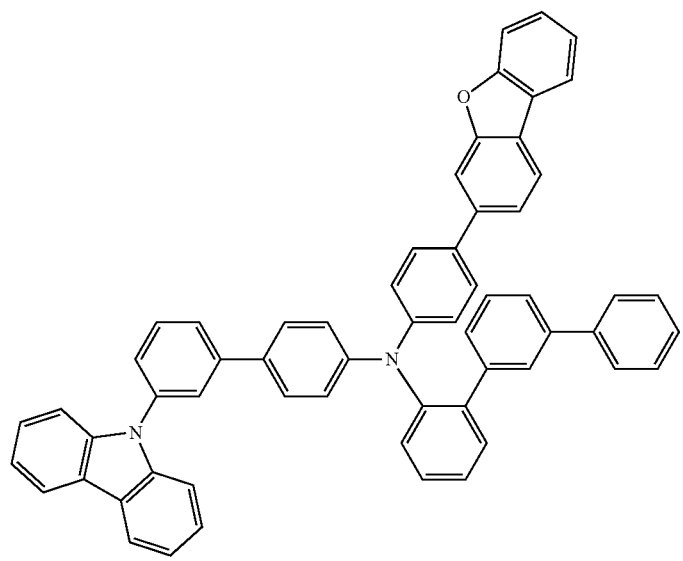

-continued
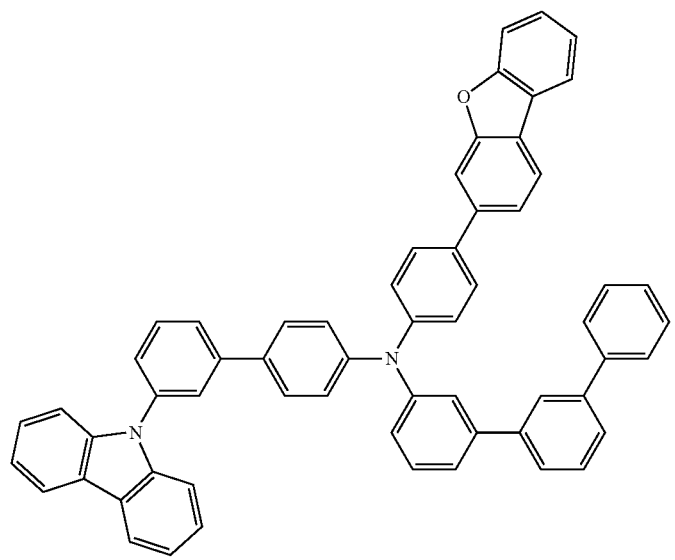
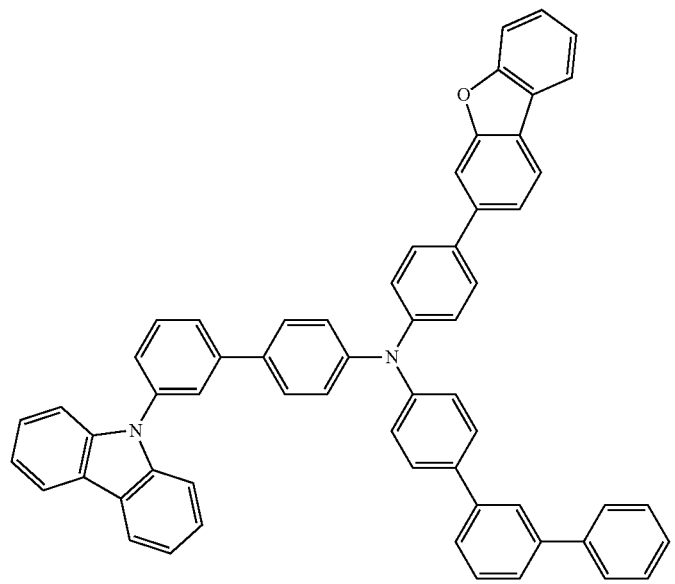
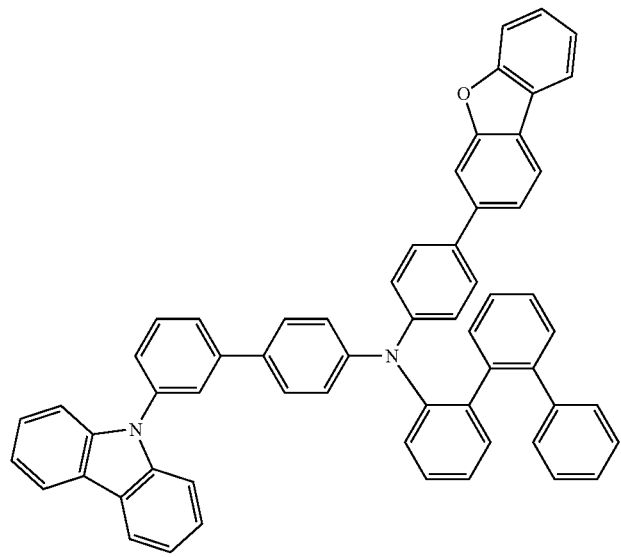

-continued
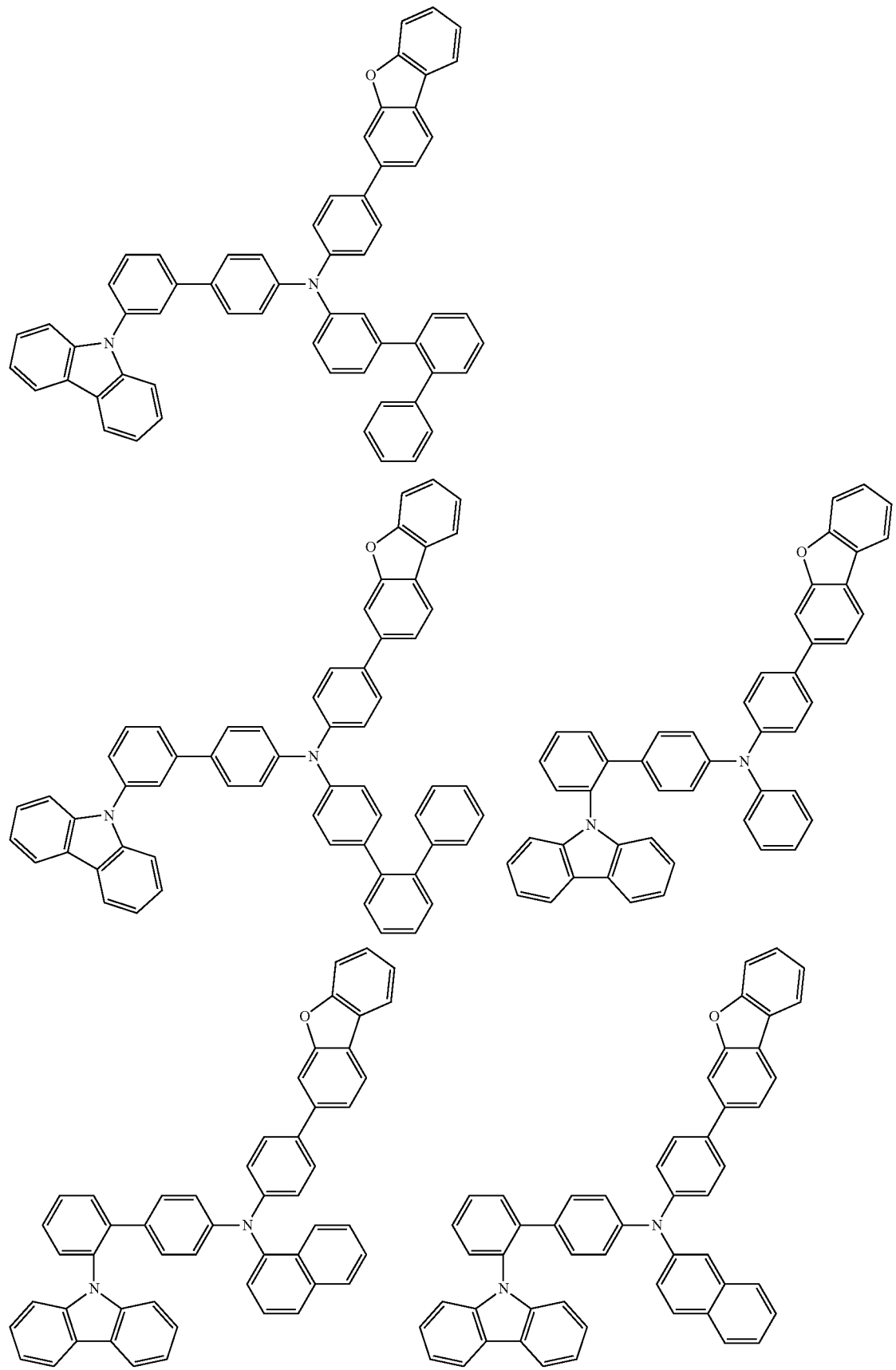

-continued
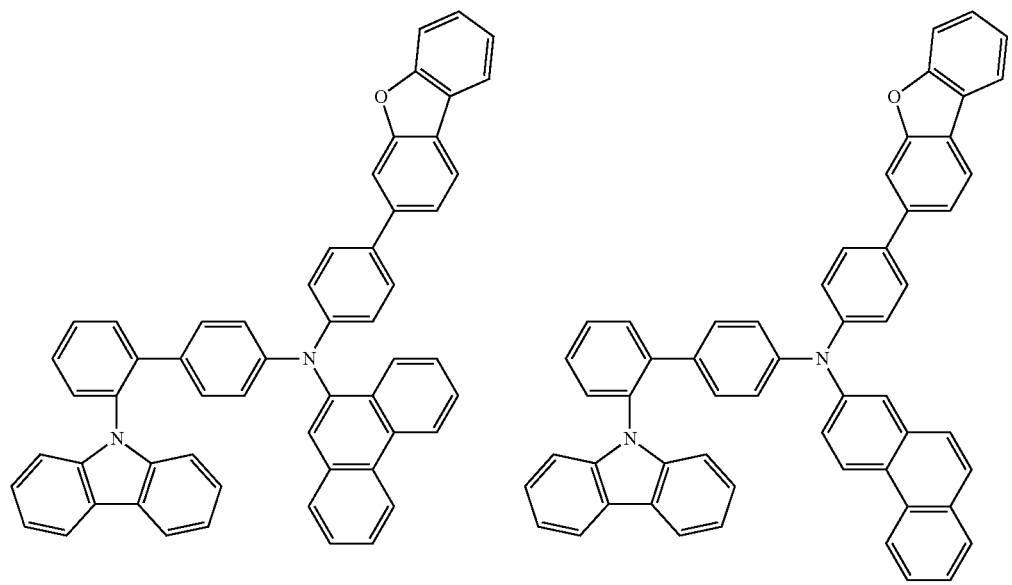
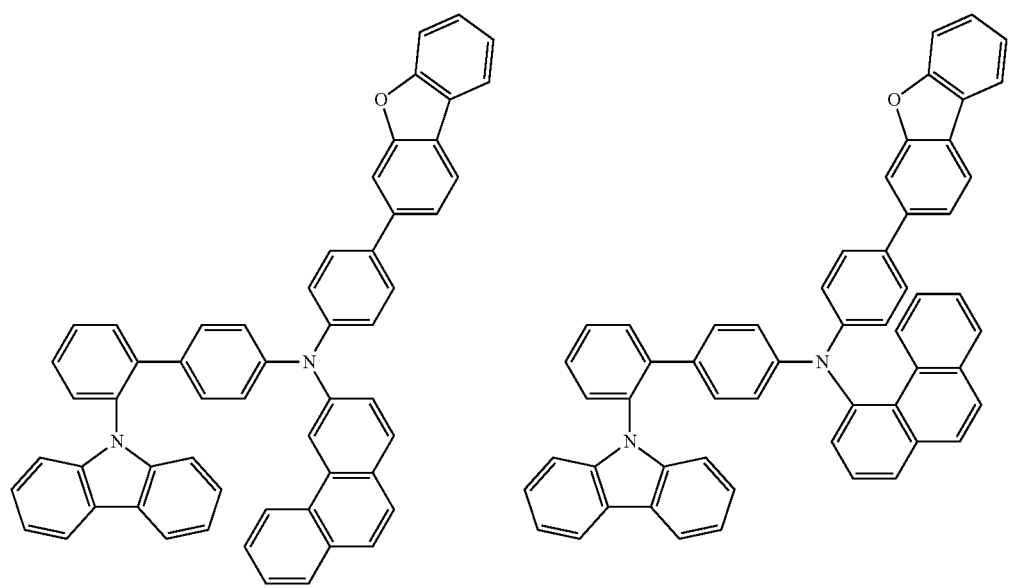

-continued
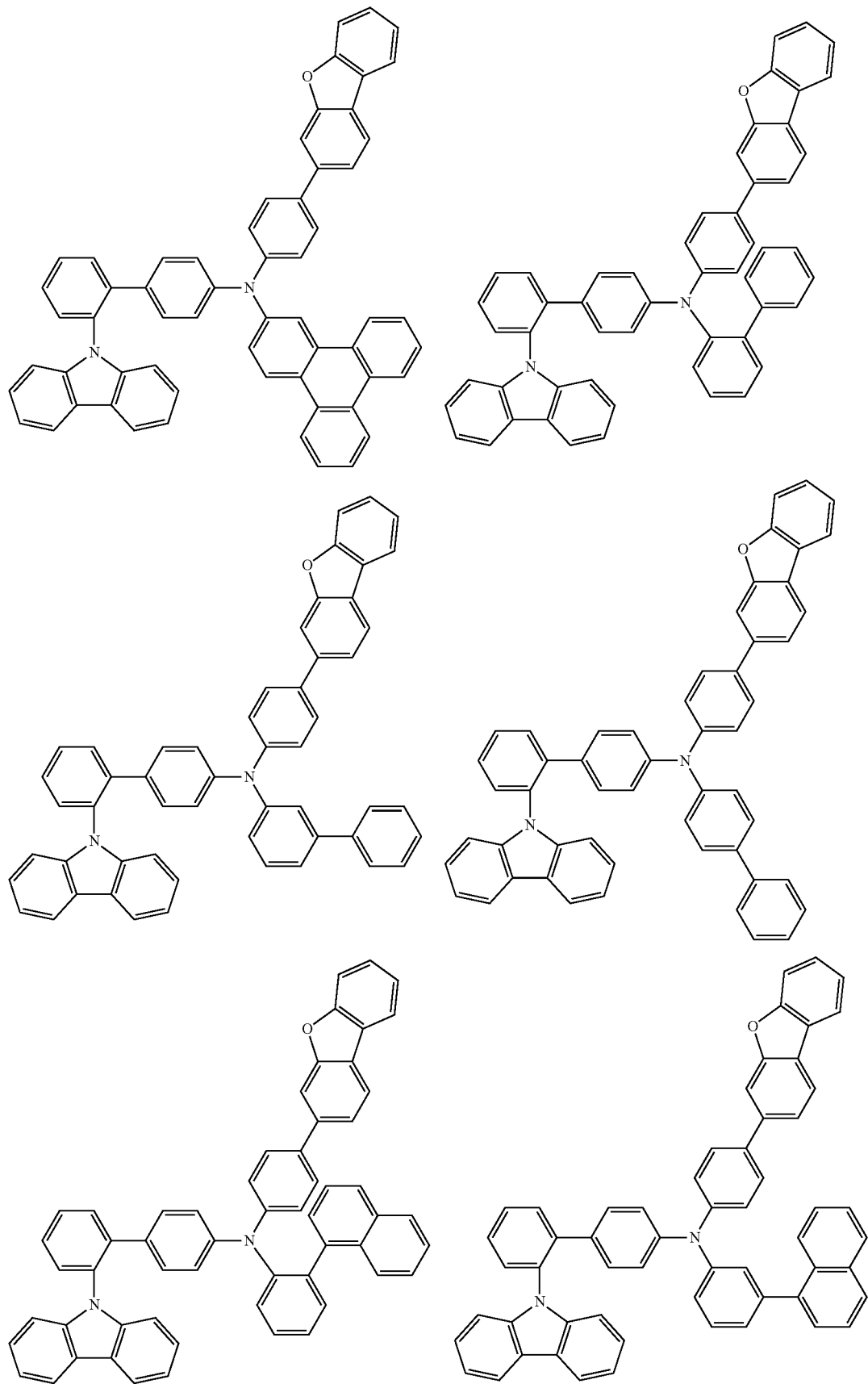

-continued
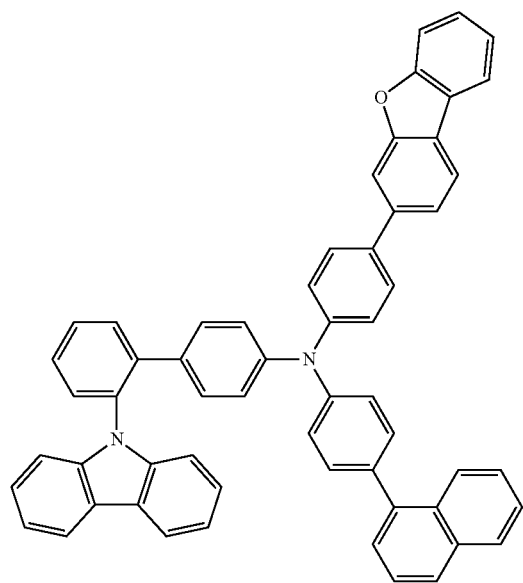
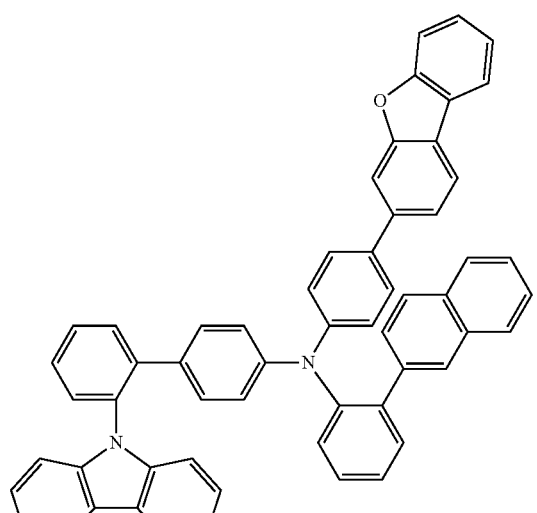
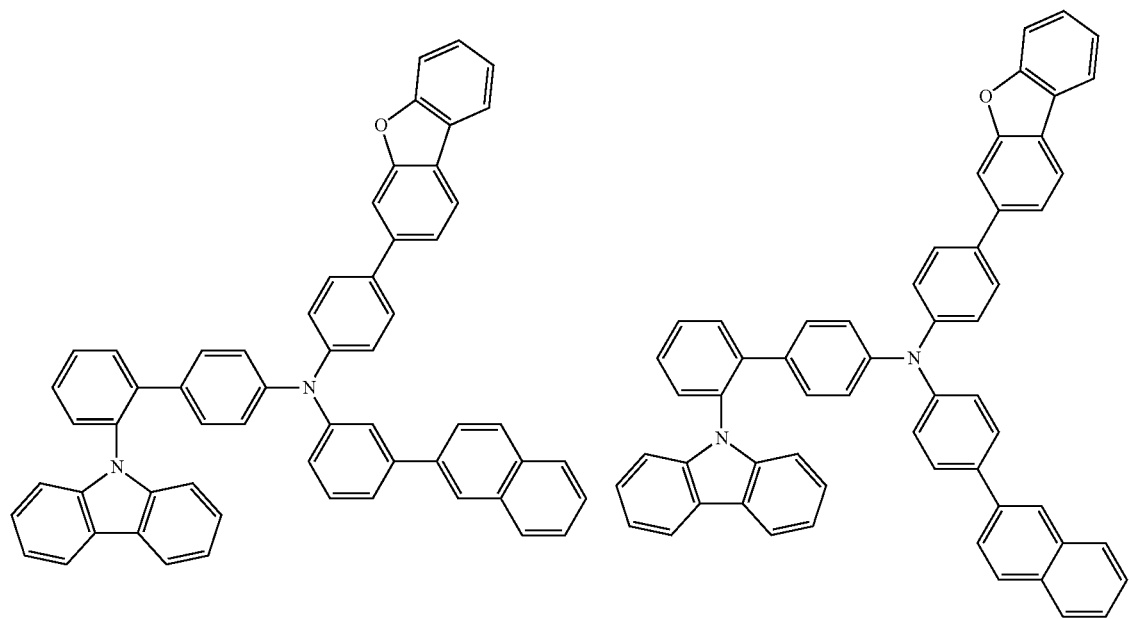

-continued
75
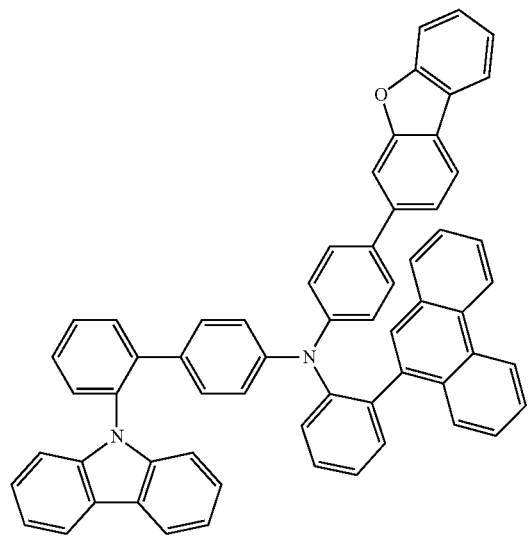
76
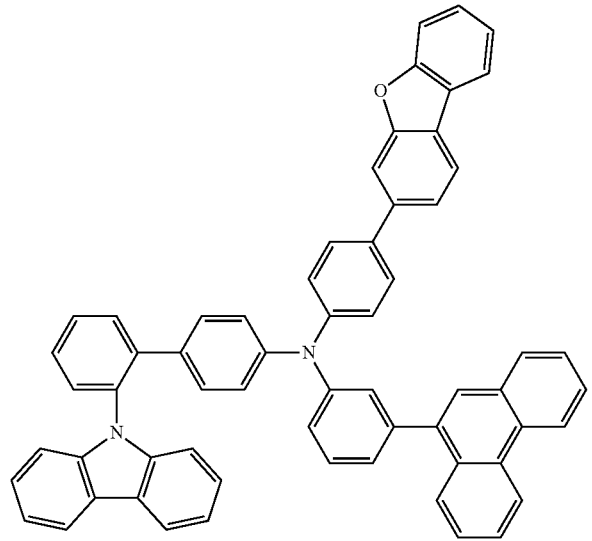
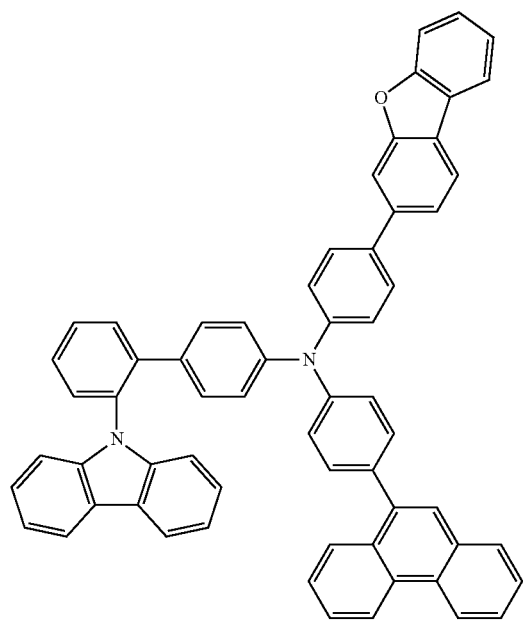
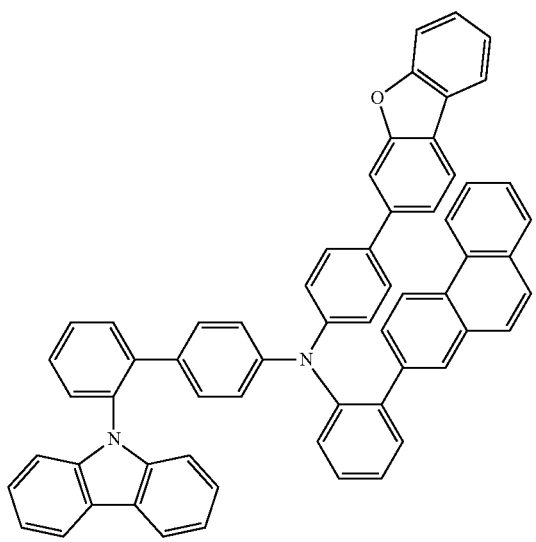

77
78
-continued
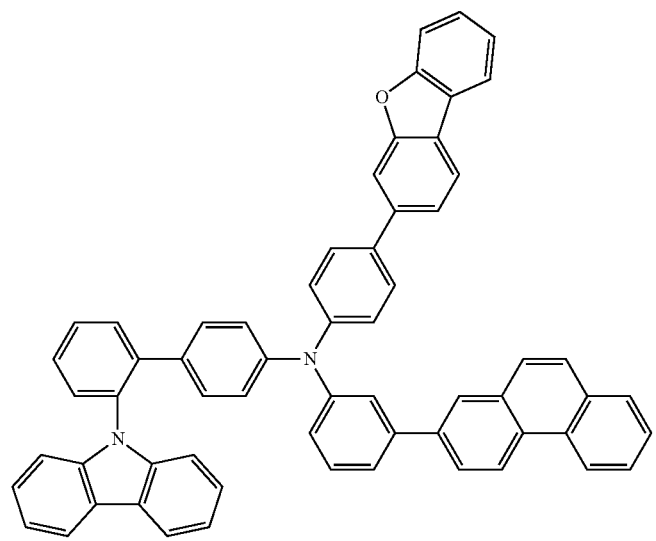
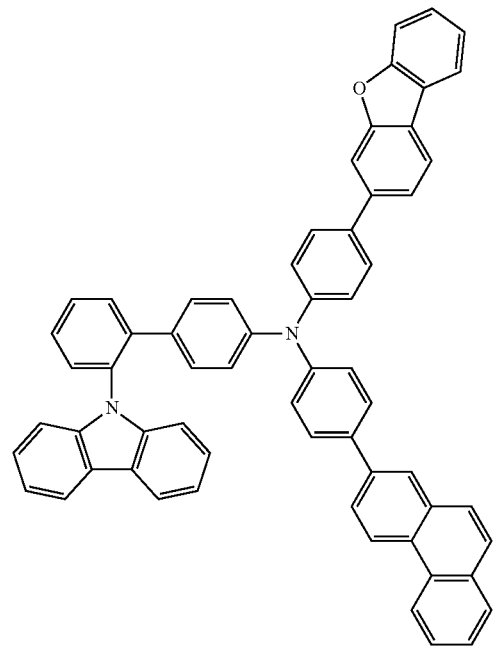
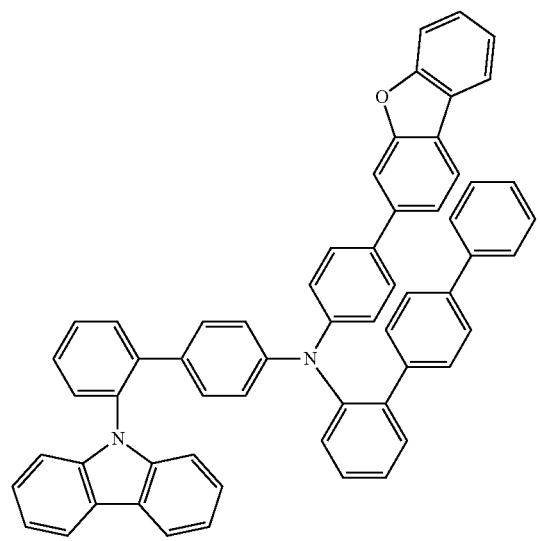
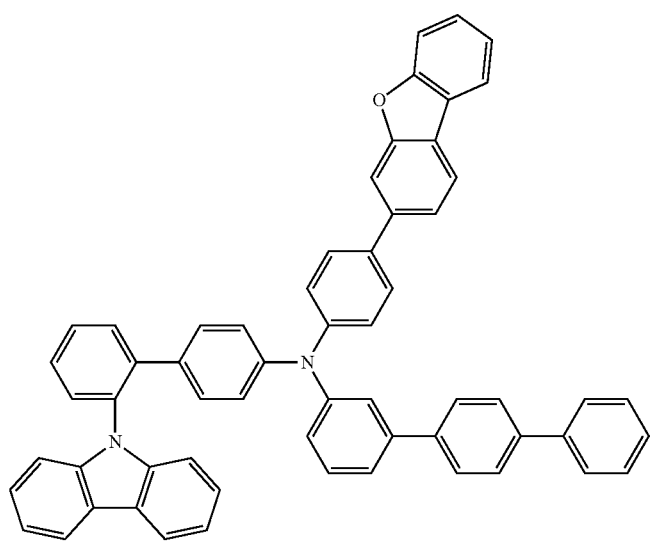

-continued
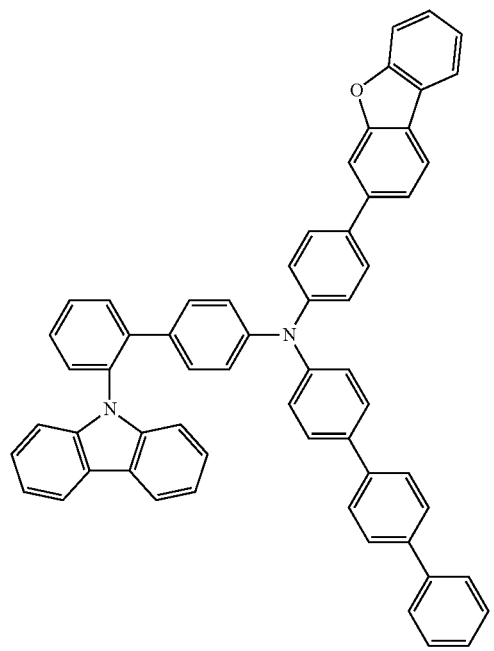
79
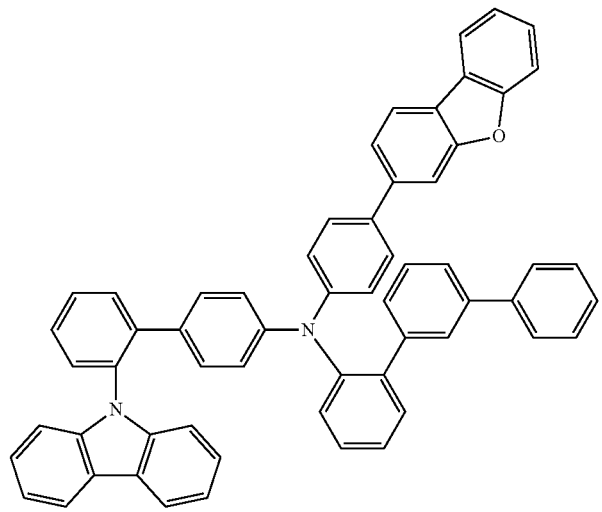
80
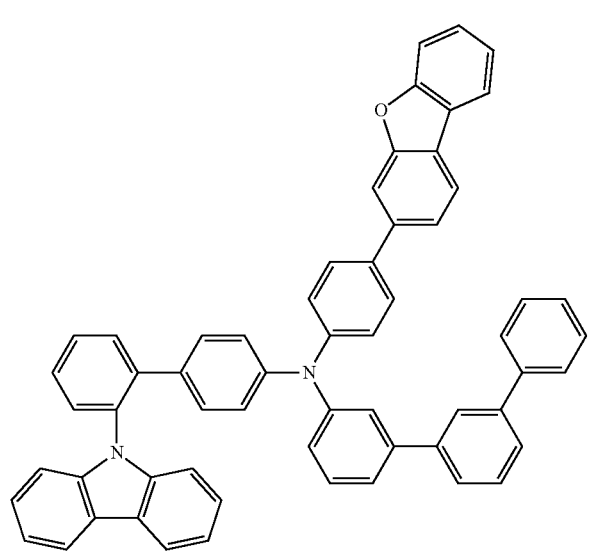
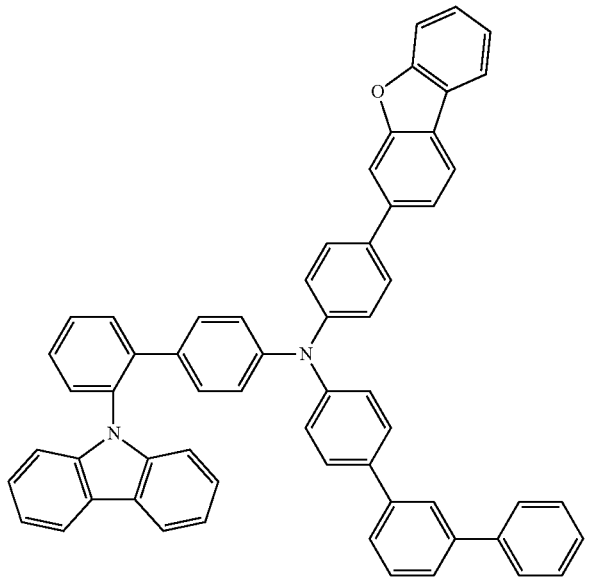

-continued
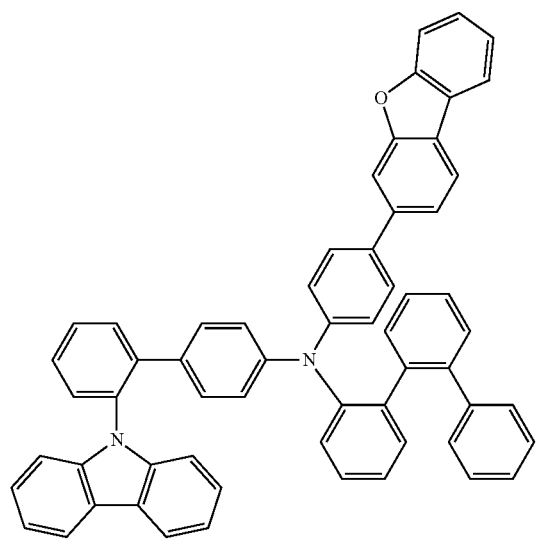
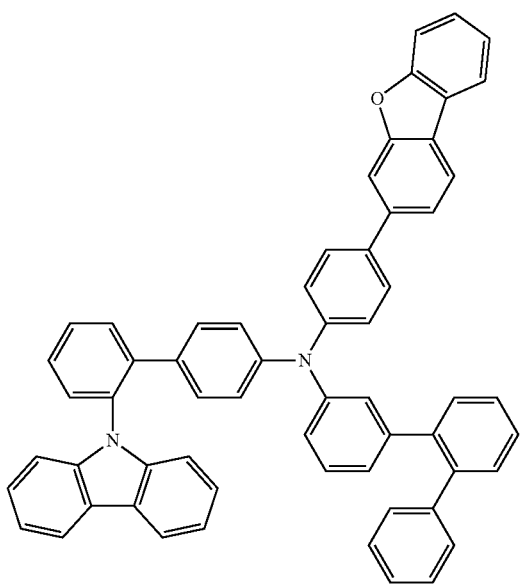
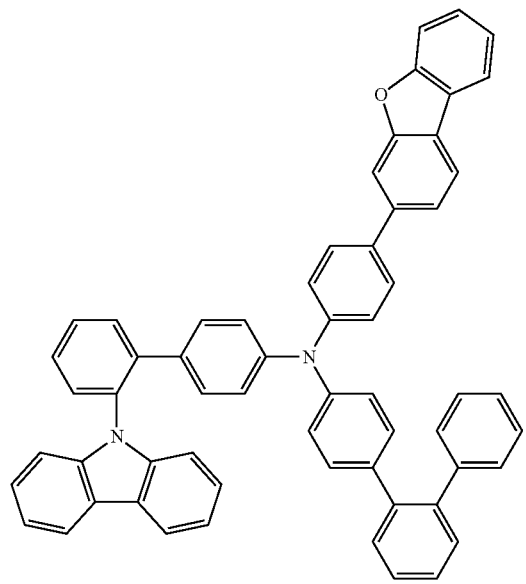
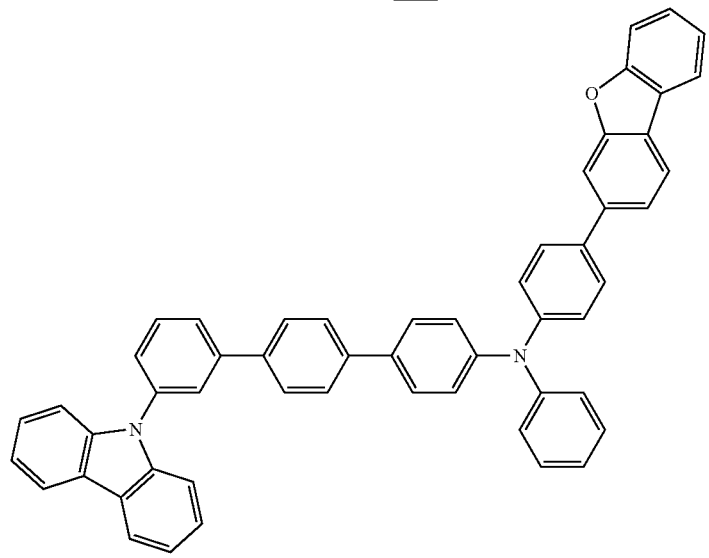

-continued
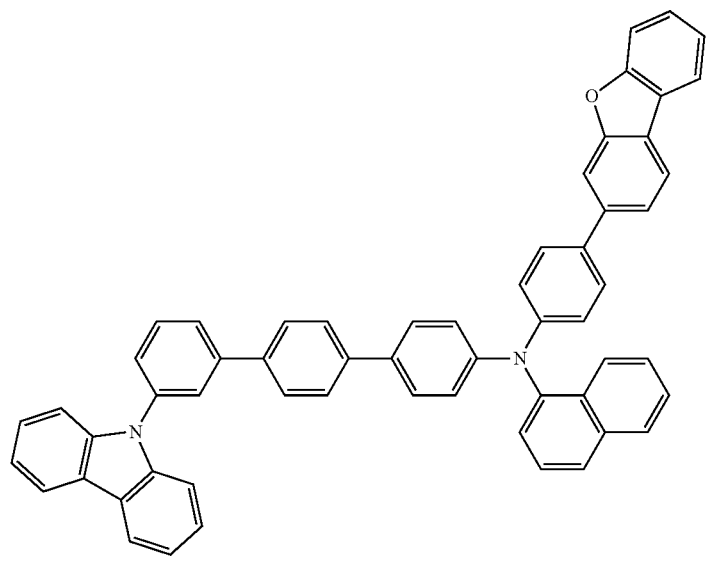
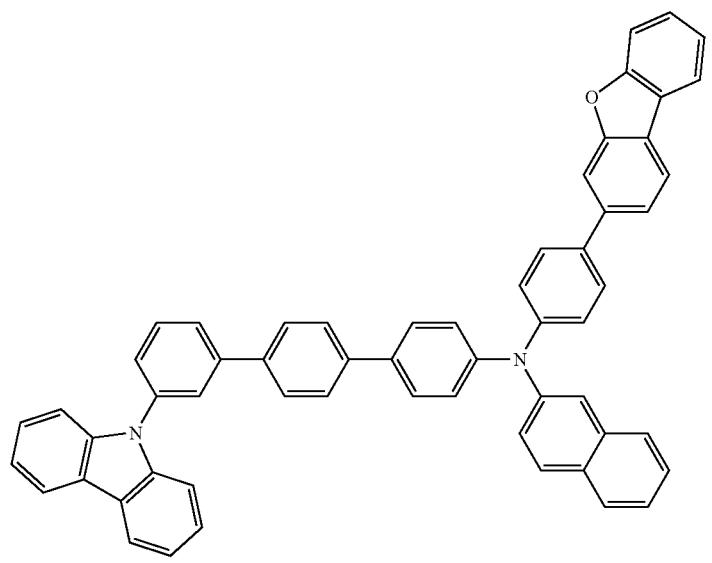
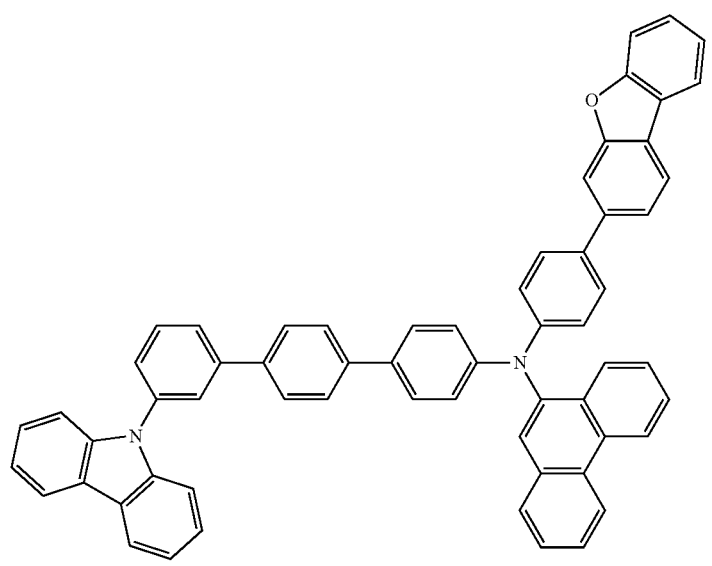

-continued
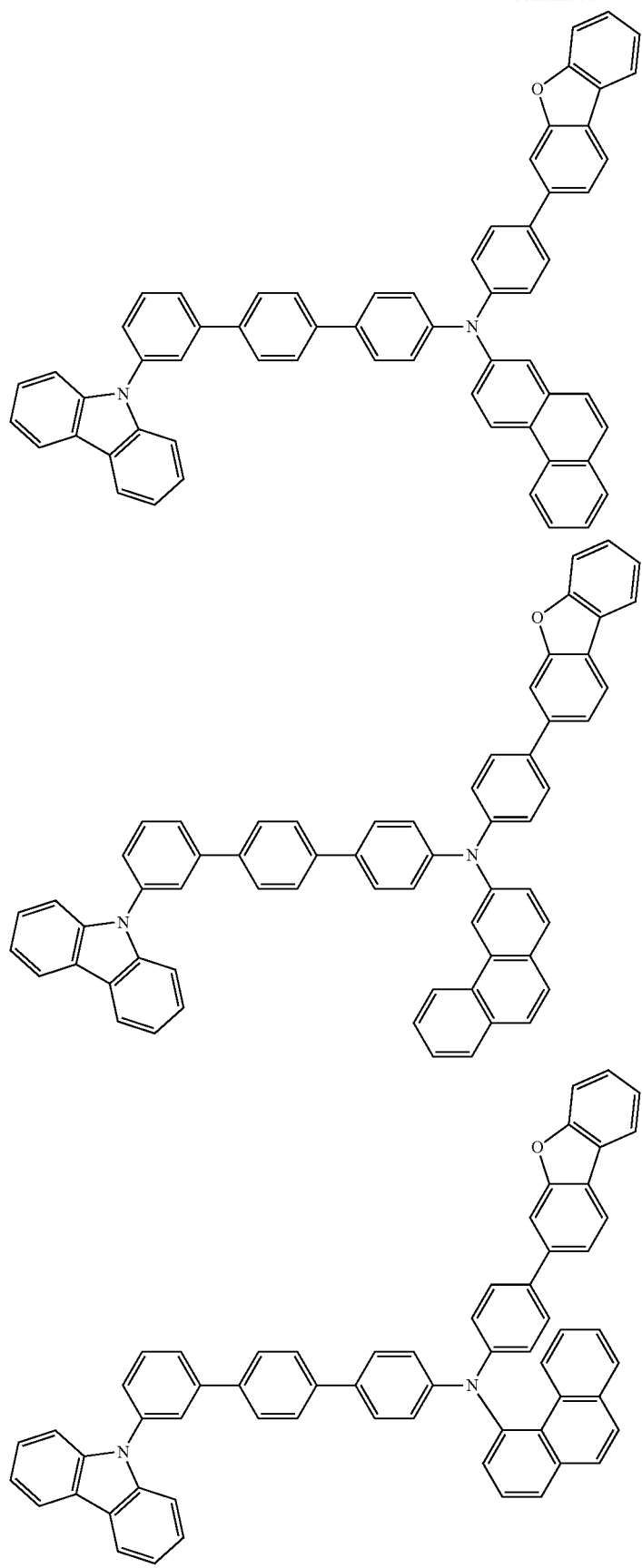

-continued
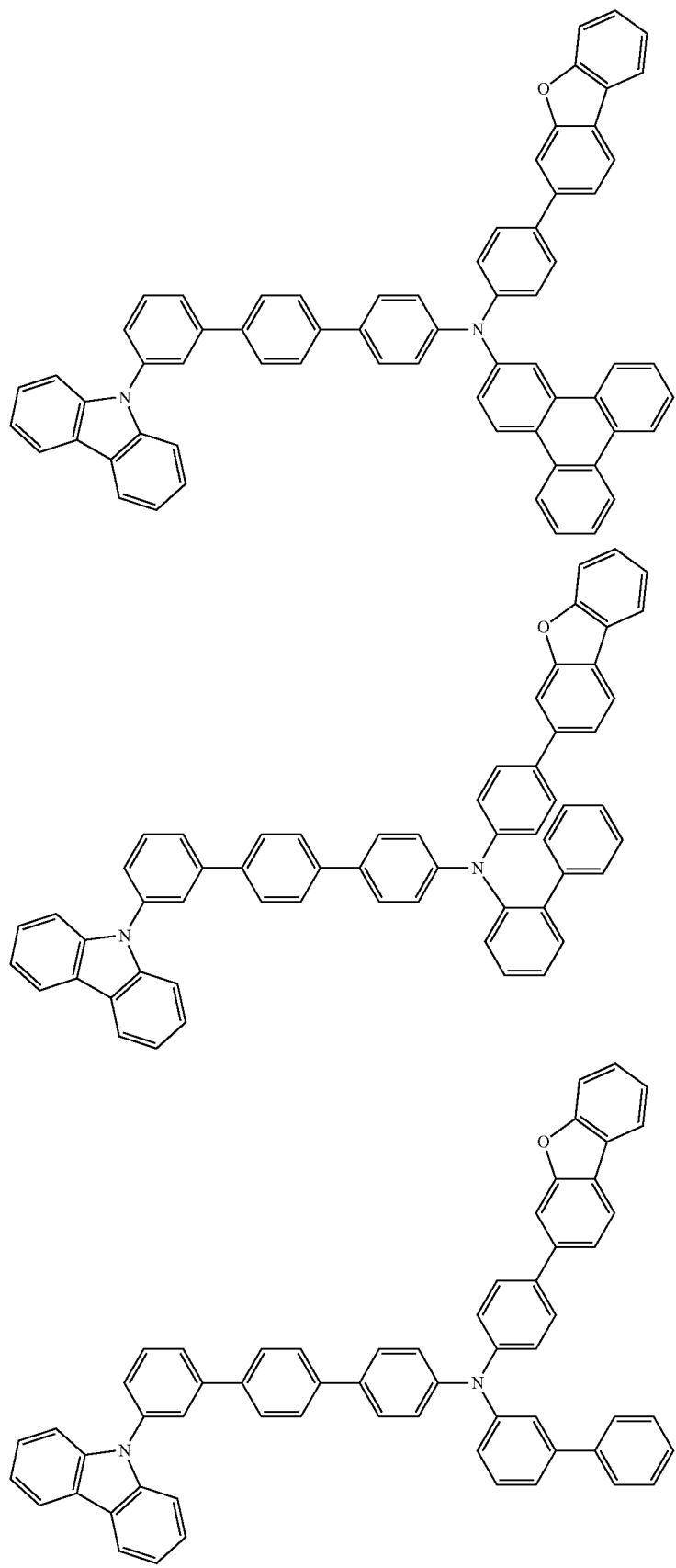

-continued
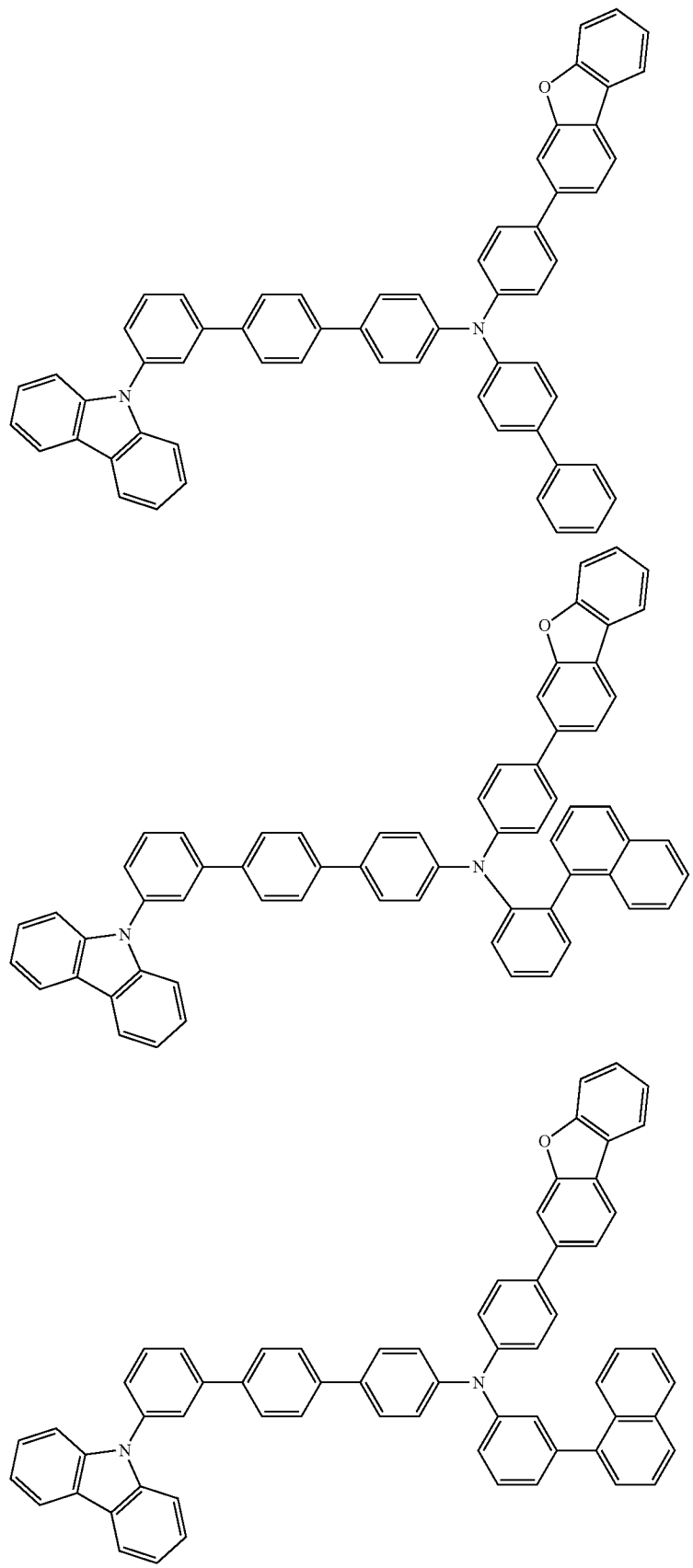

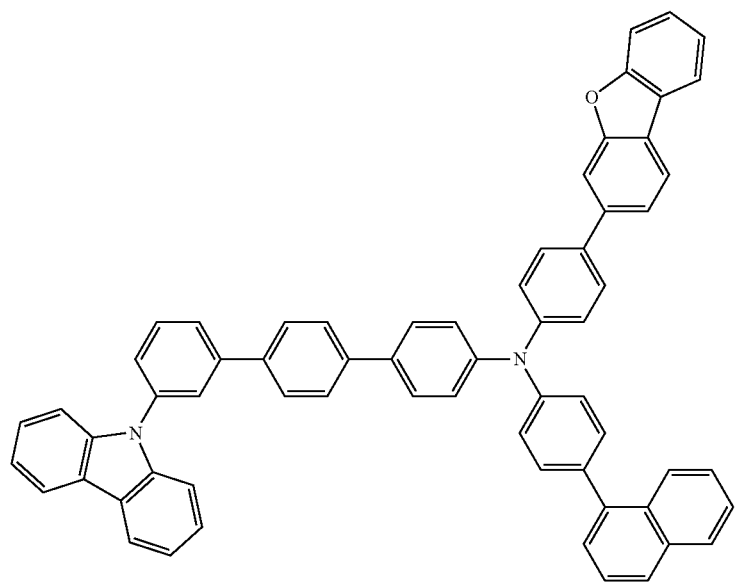
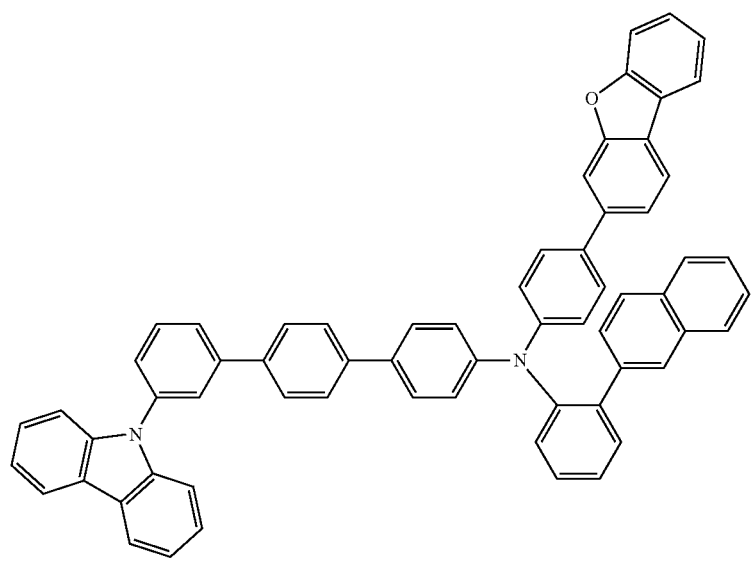
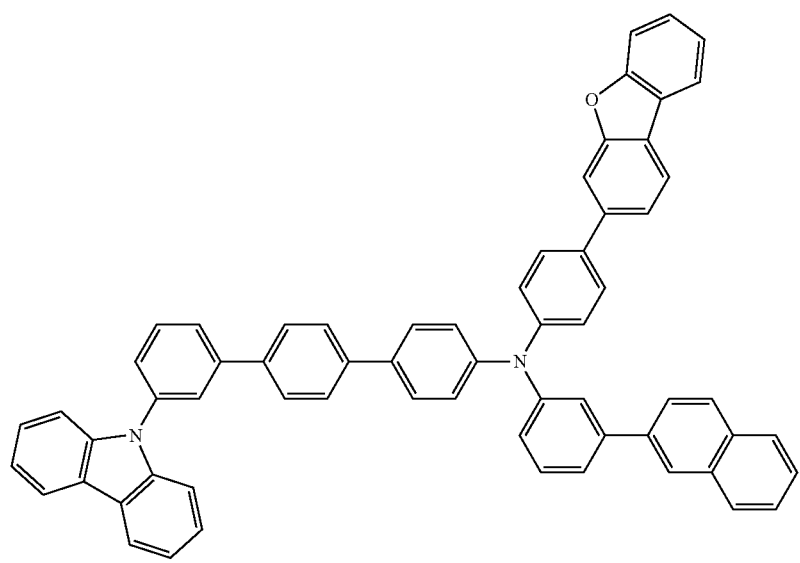

-continued
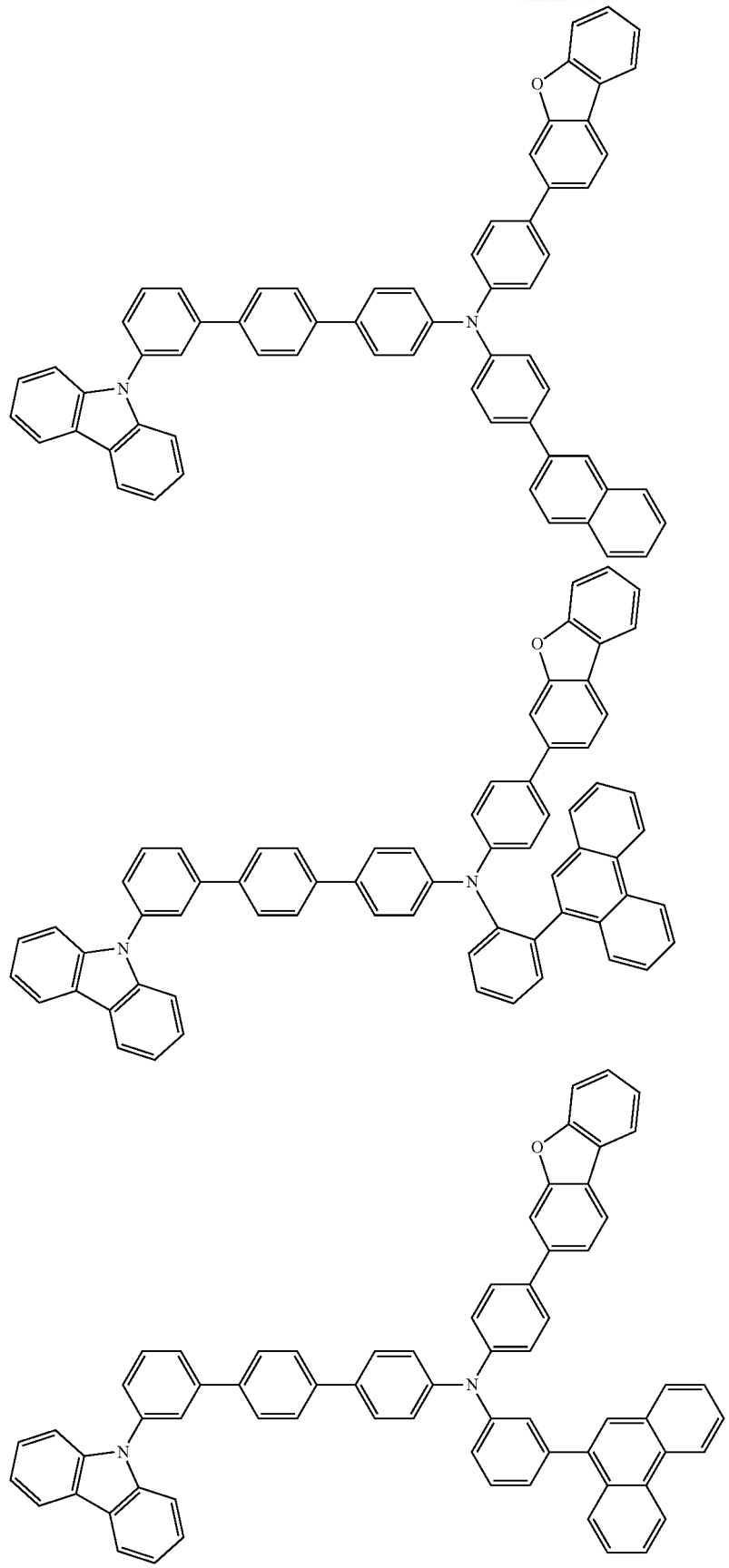

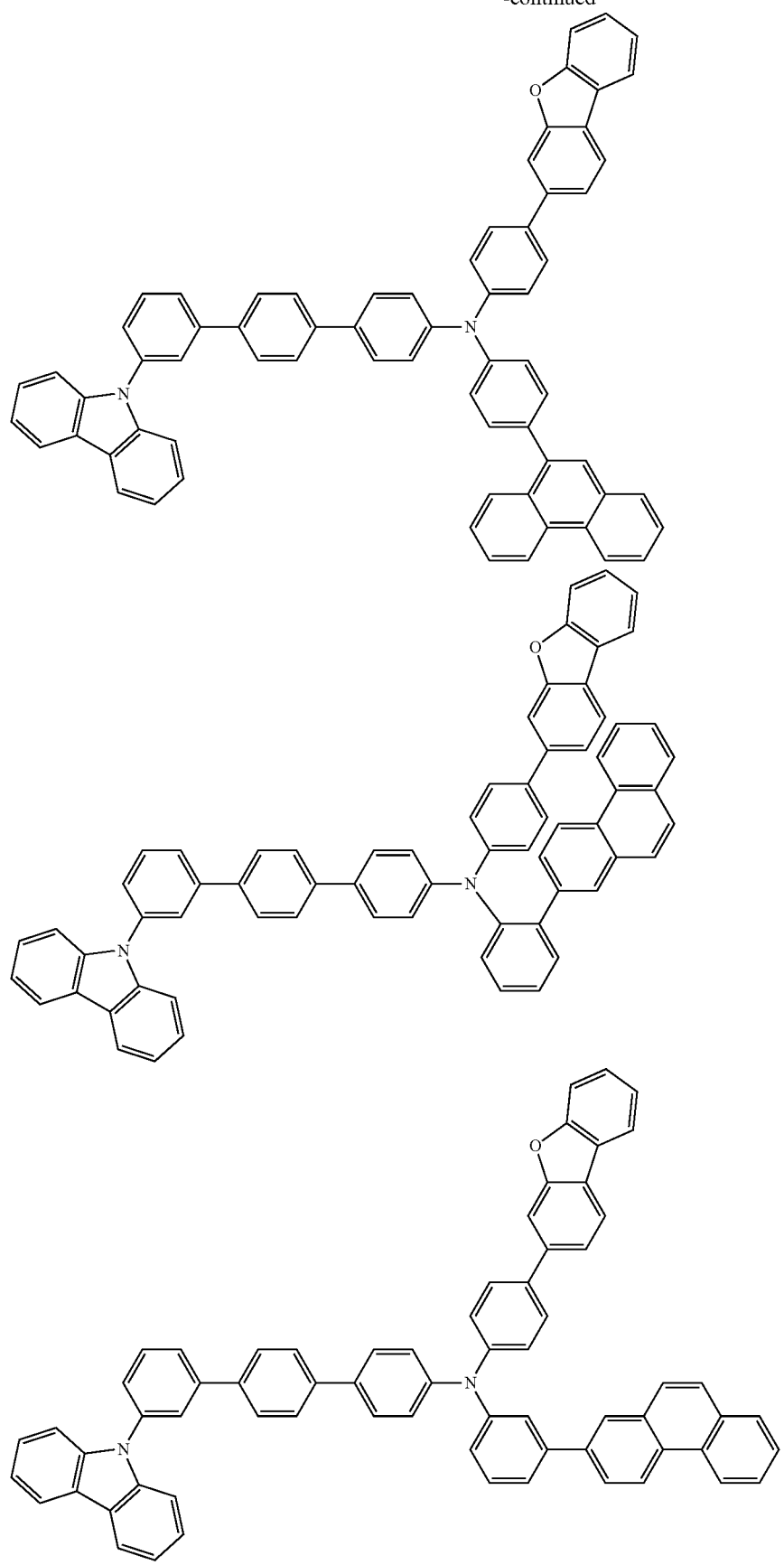

-continued
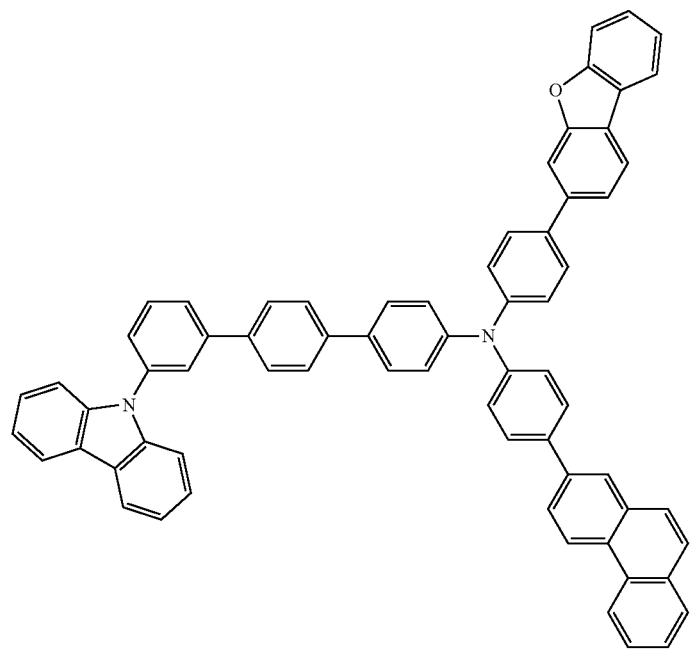
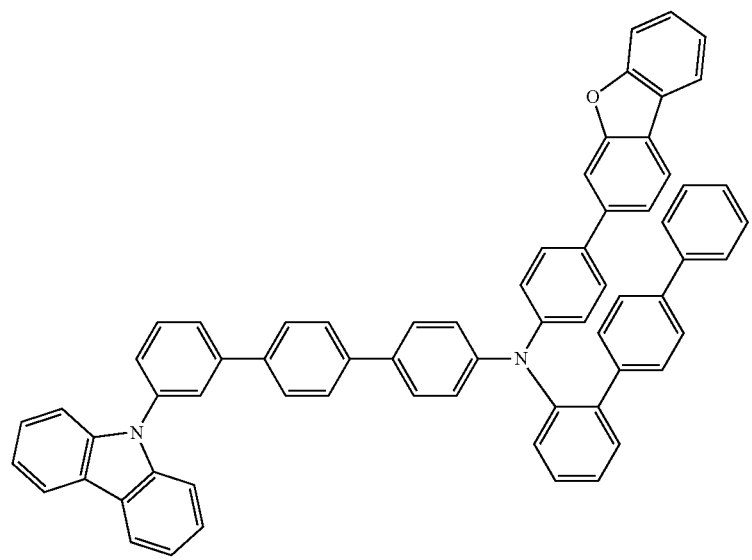

-continued
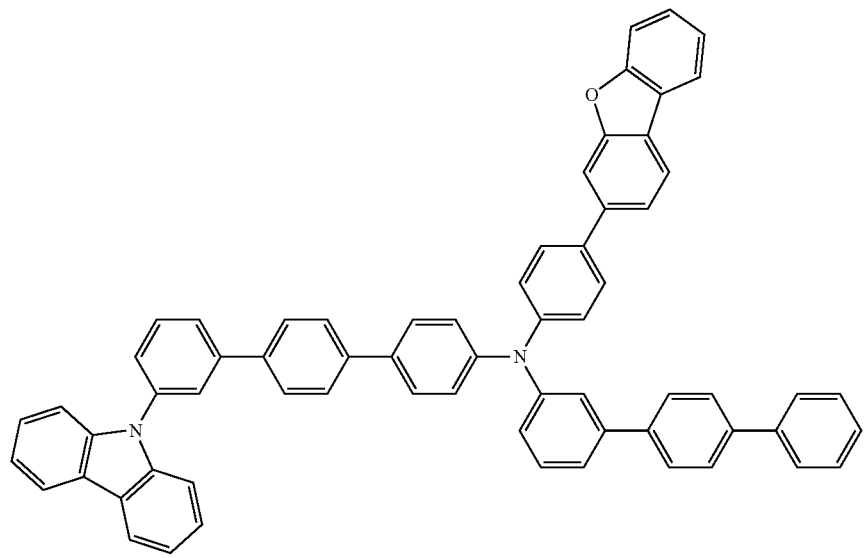
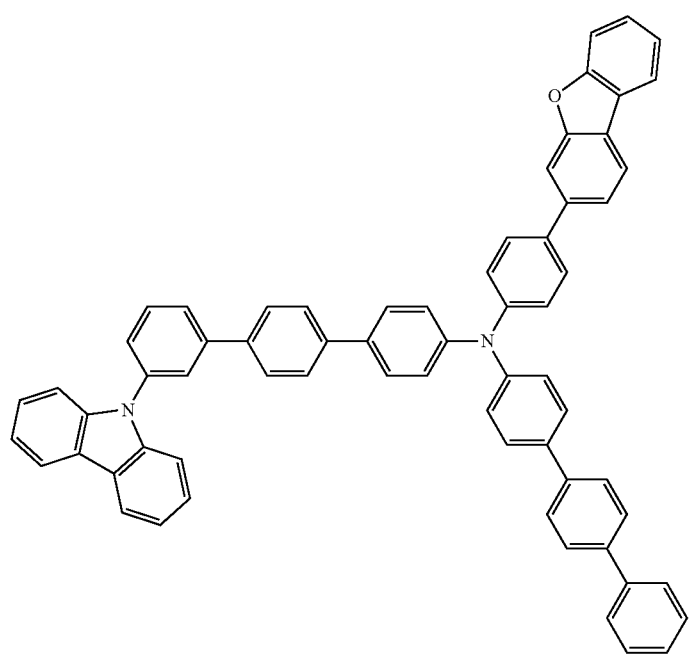

-continued
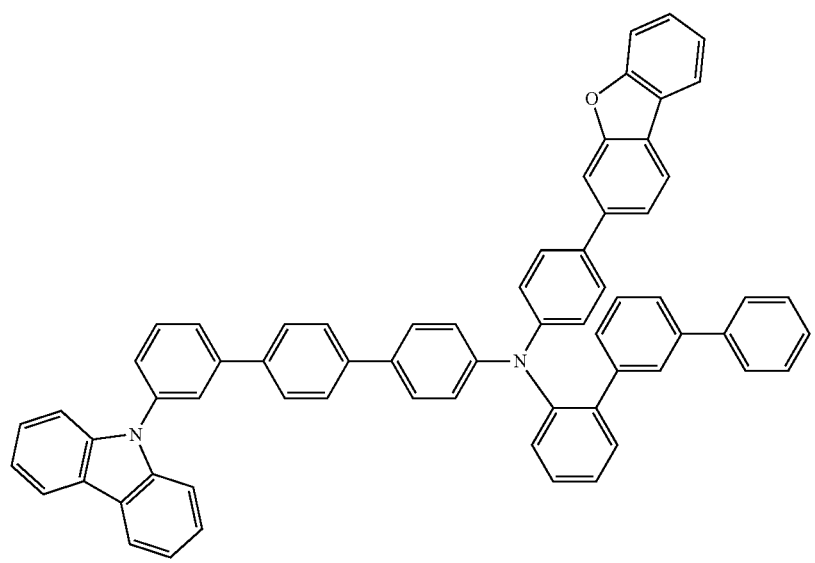
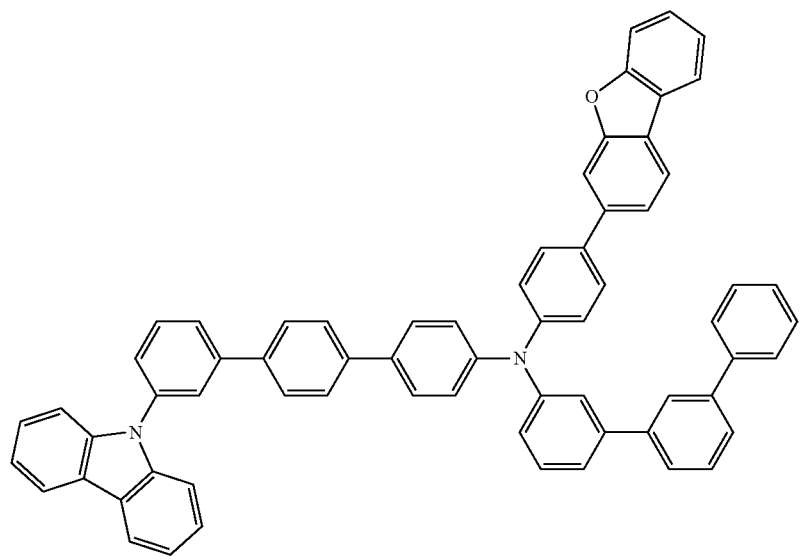
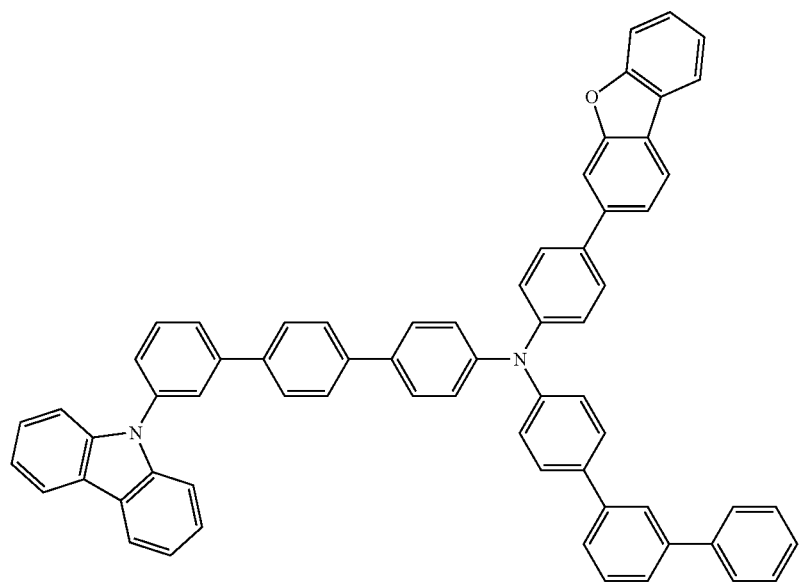

-continued
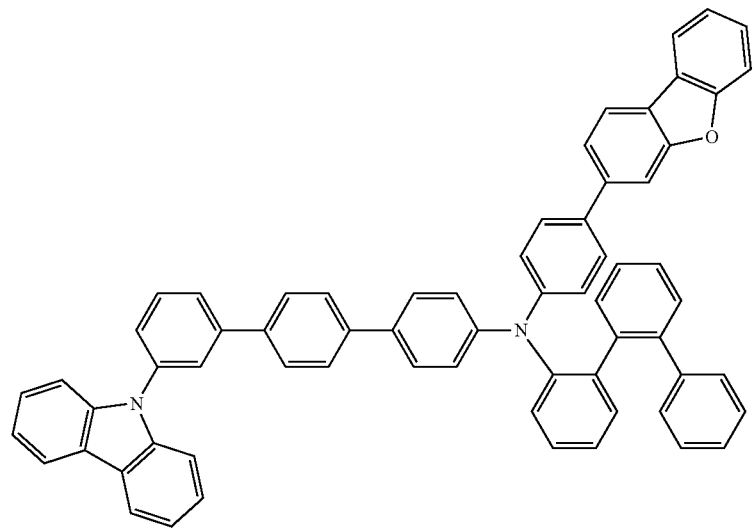
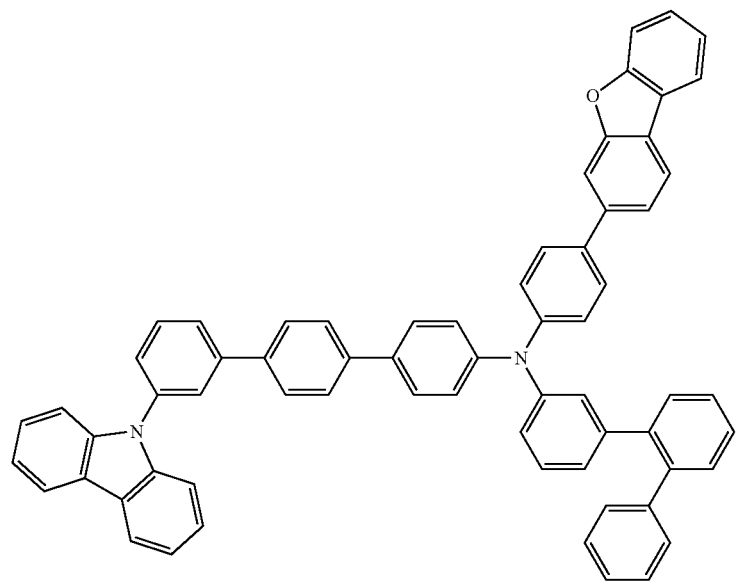
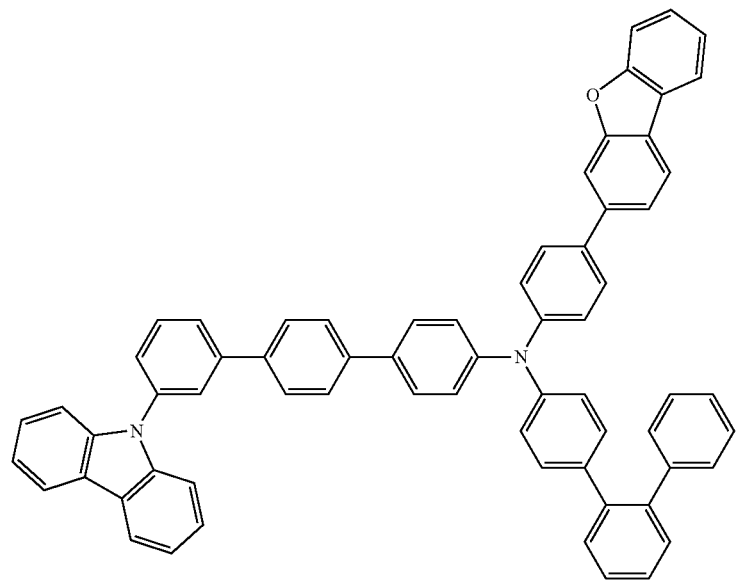

-continued
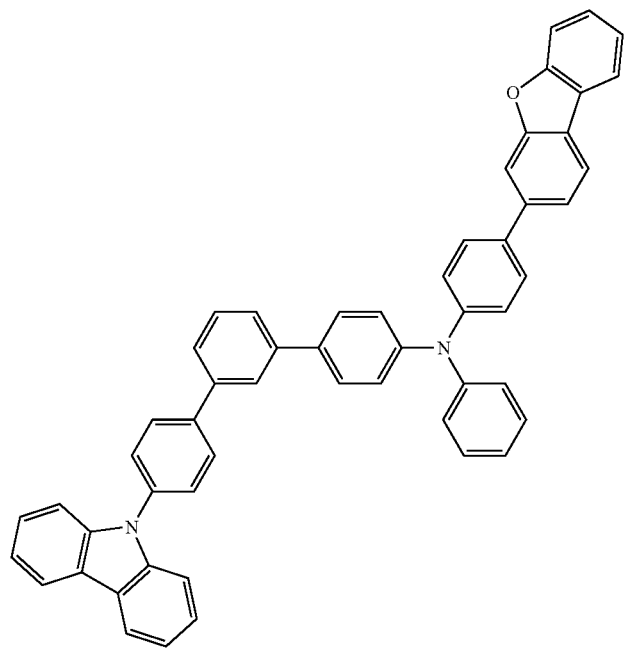
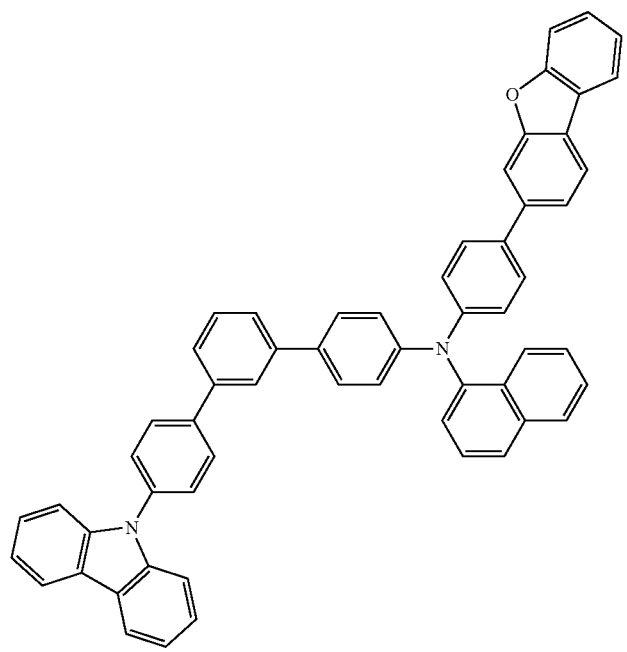

-continued
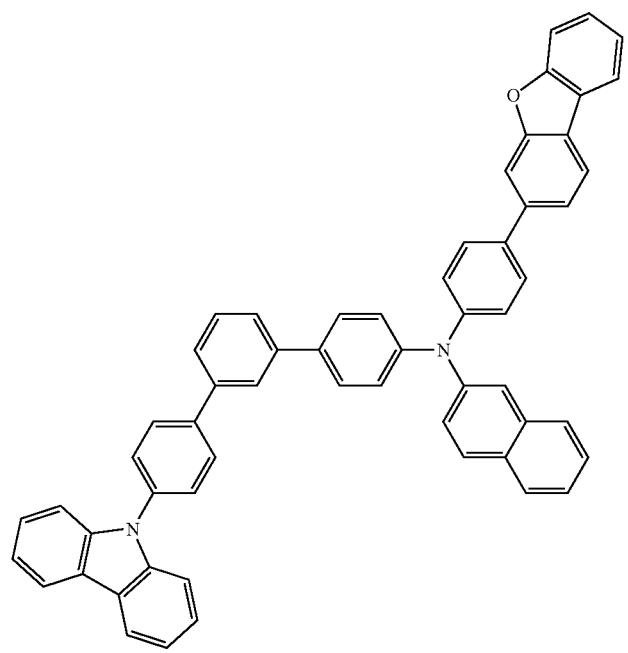
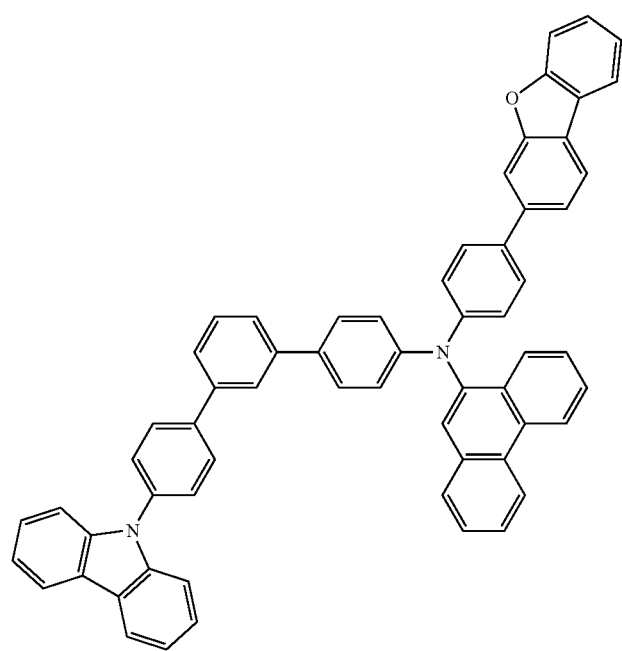

-continued
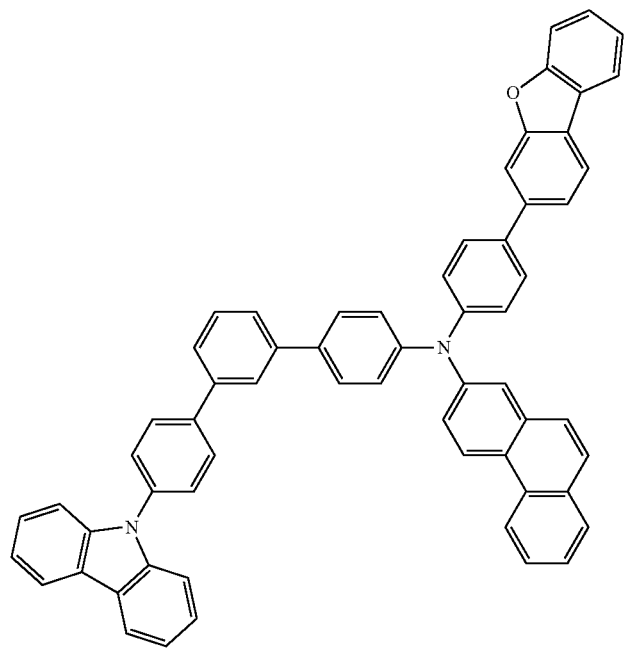
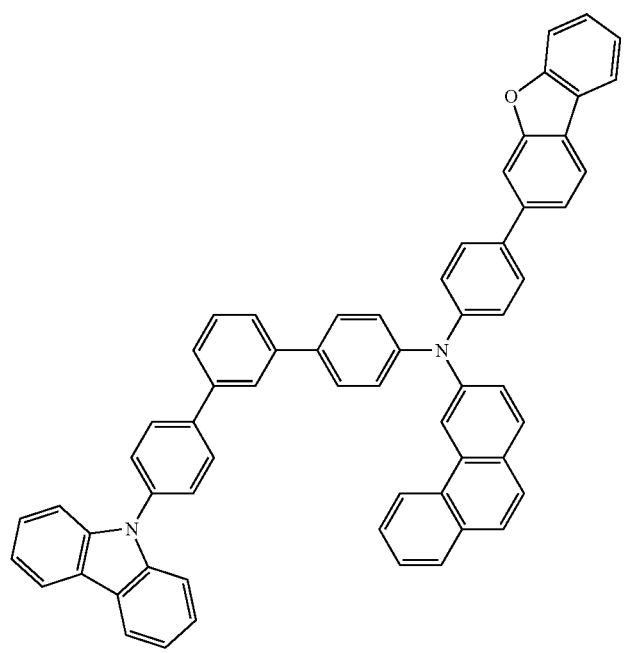

-continued
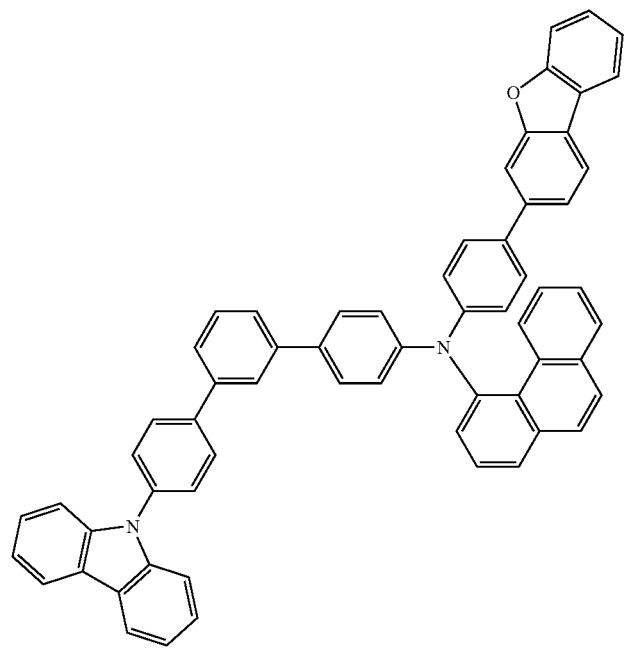
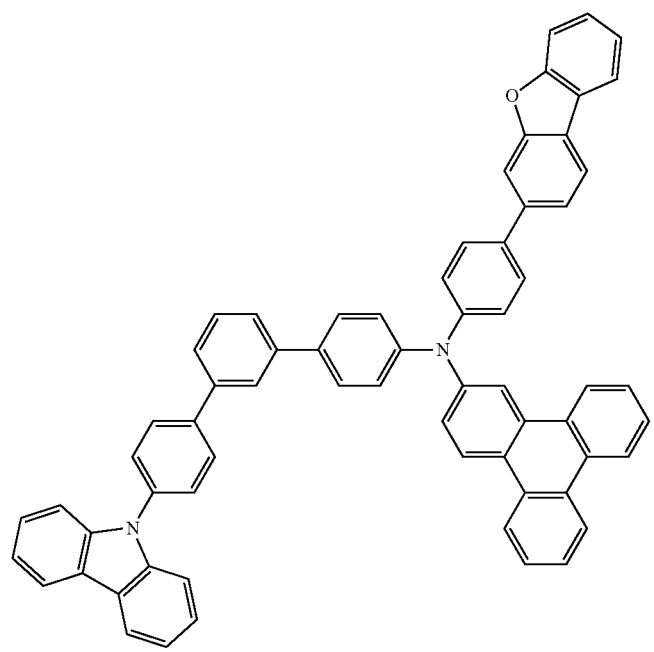

-continued
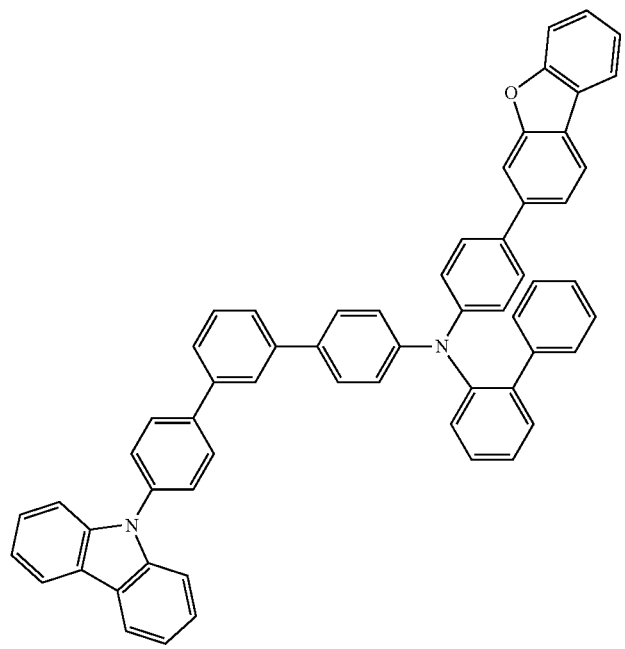
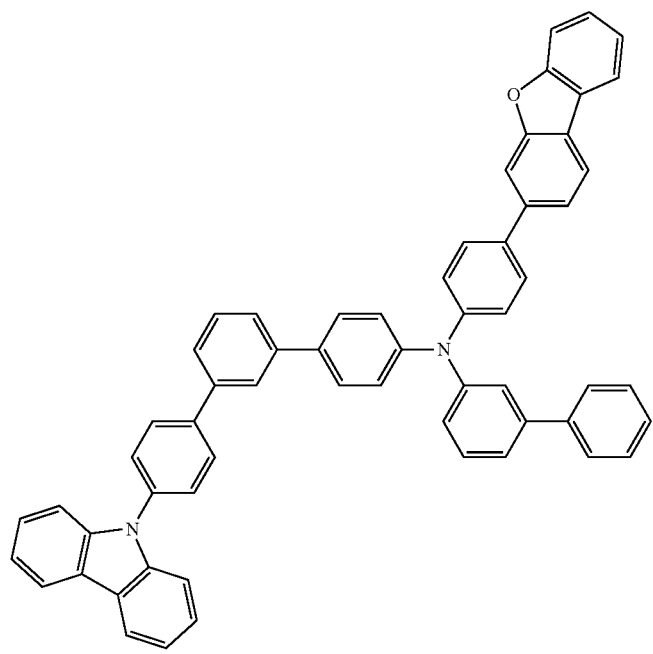

-continued
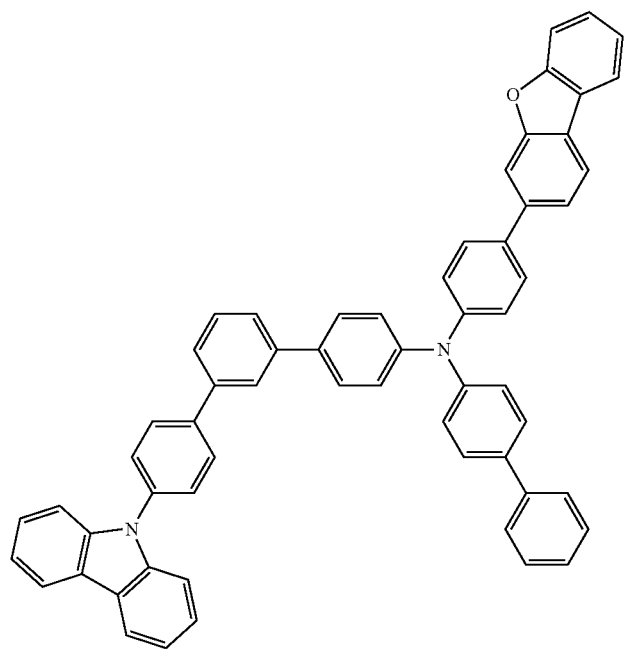
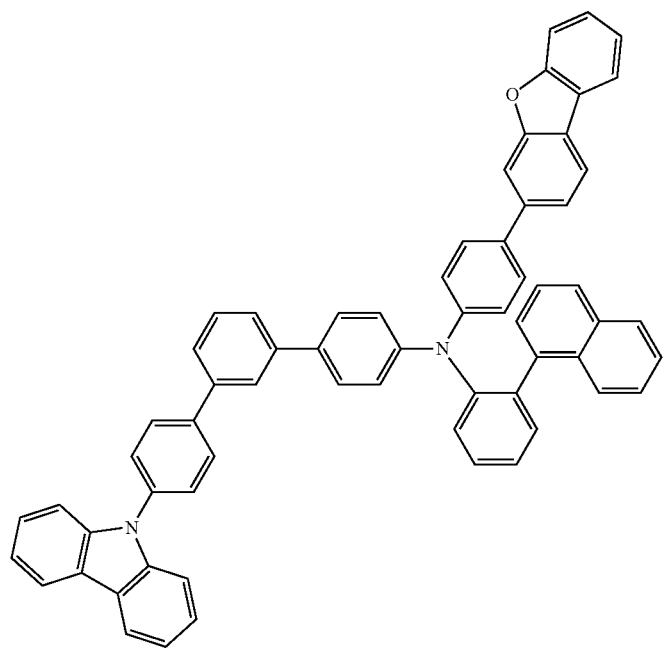

-continued
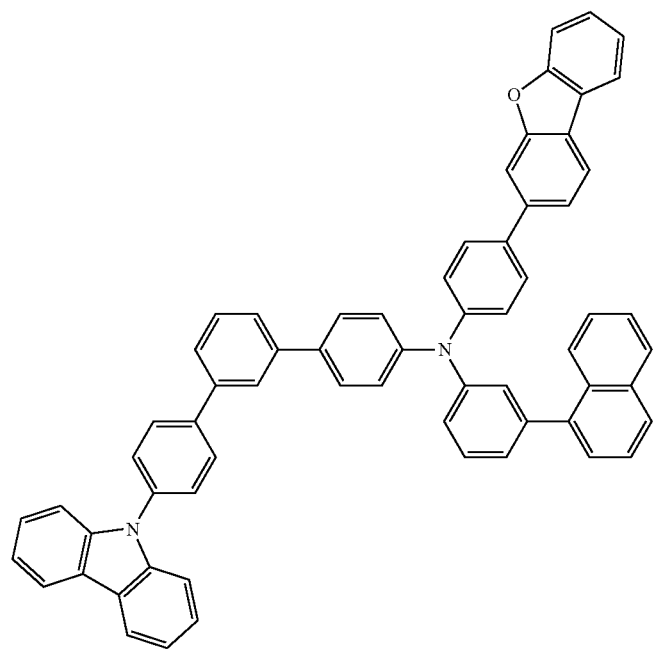
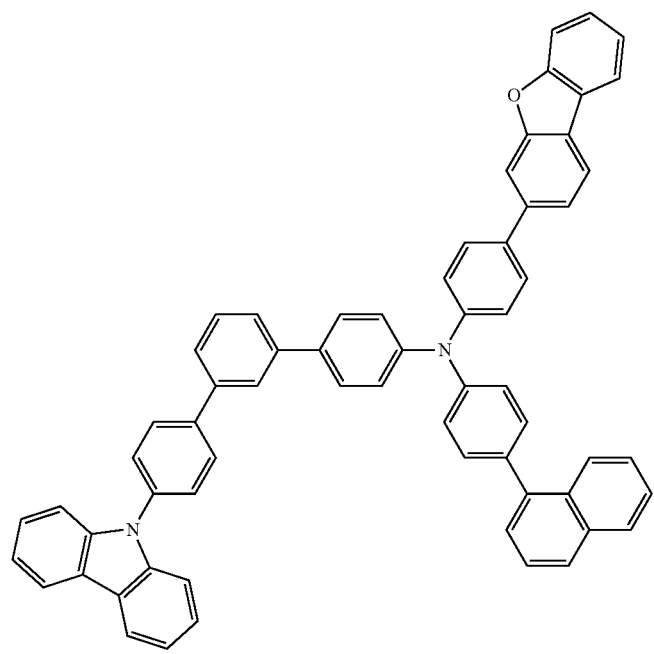

-continued
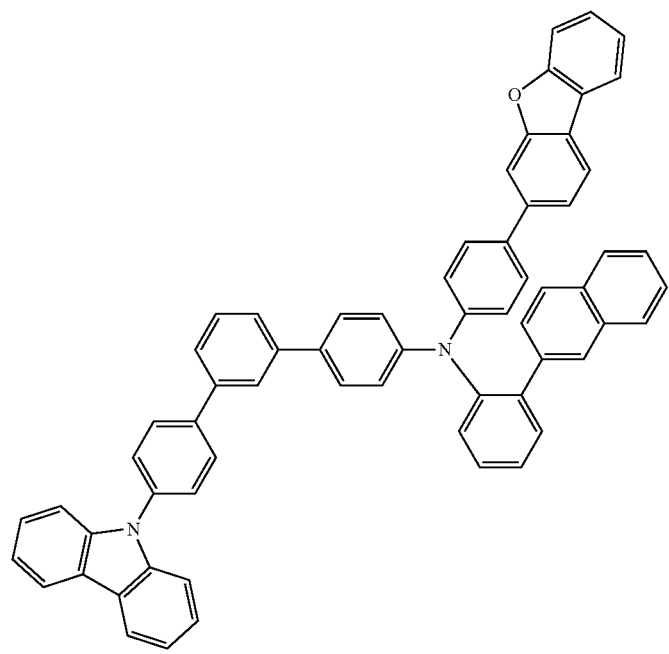
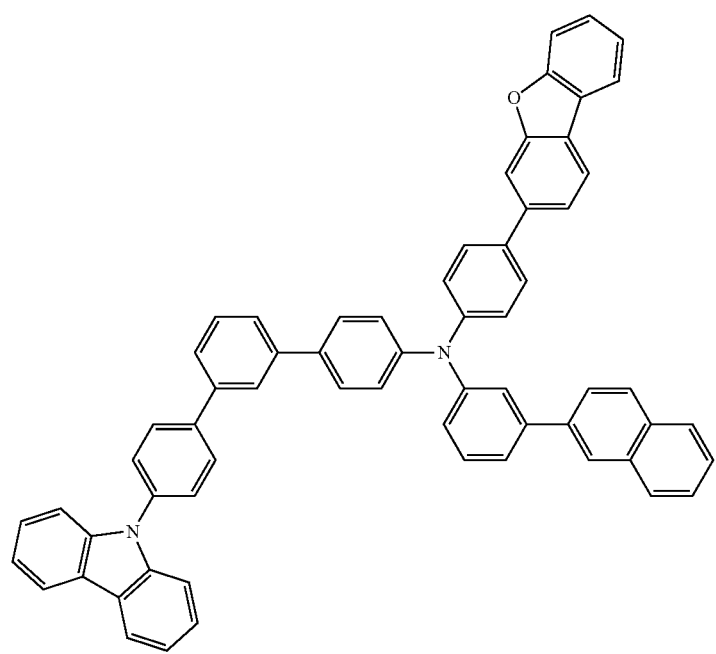

-continued
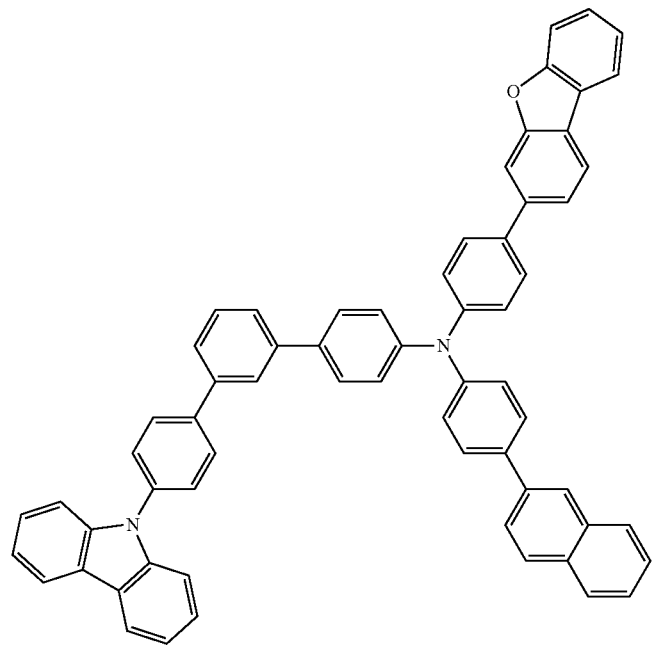
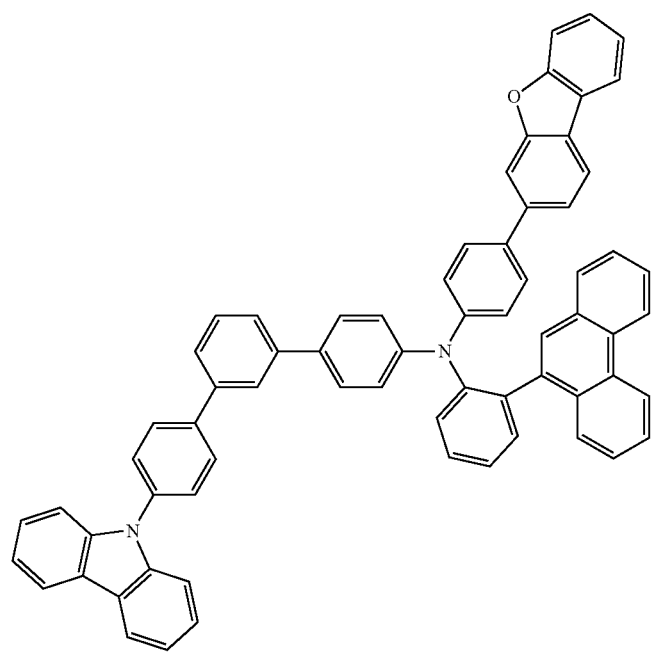

-continued
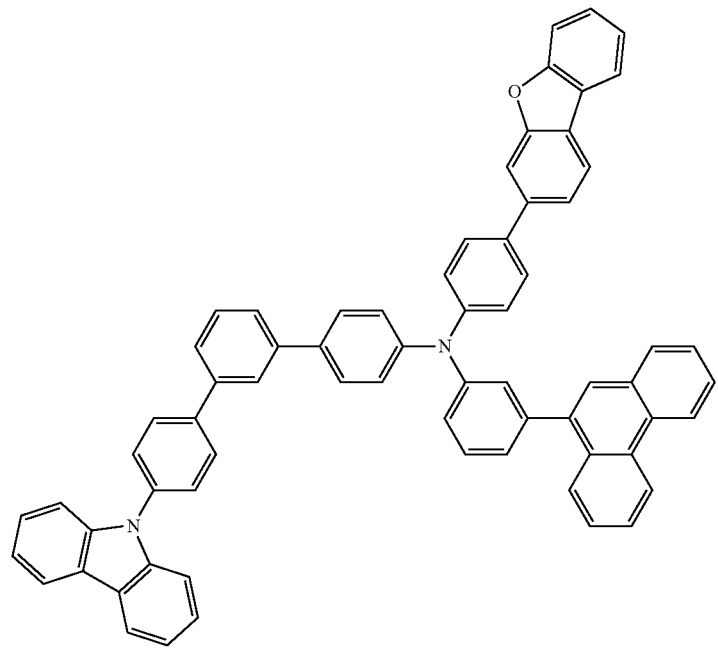
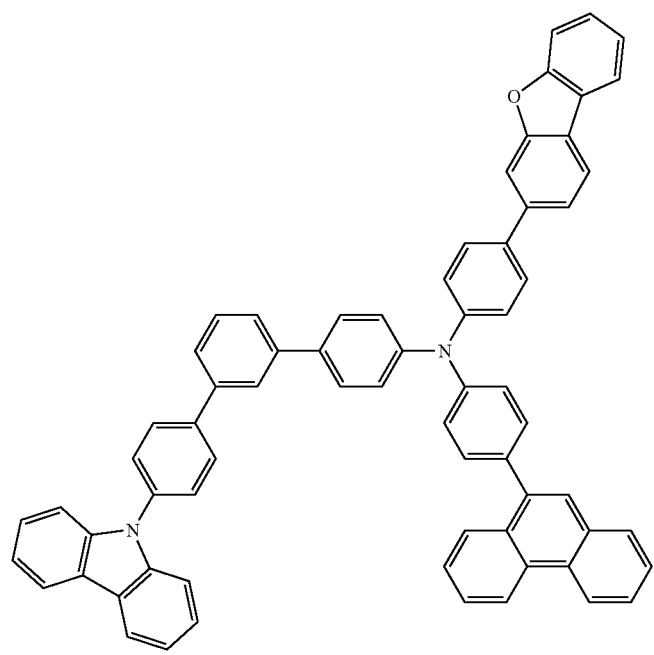

-continued
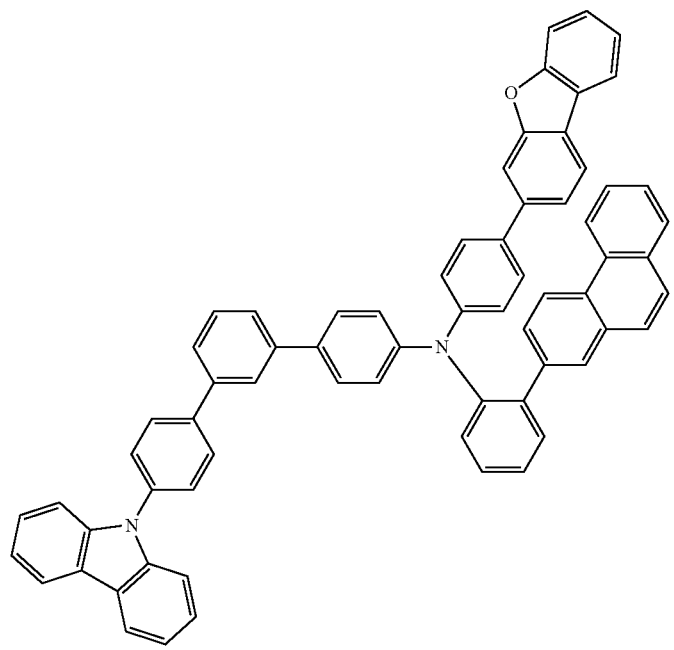
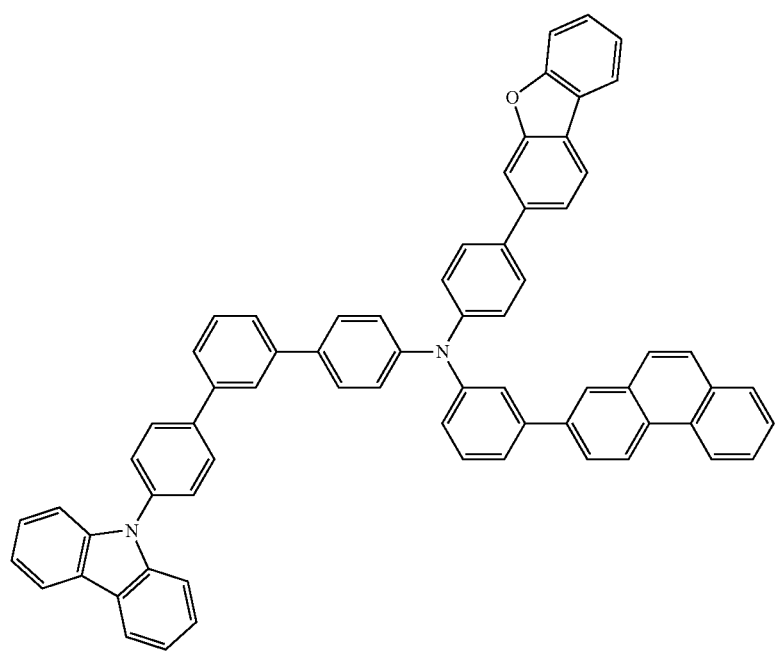

-continued
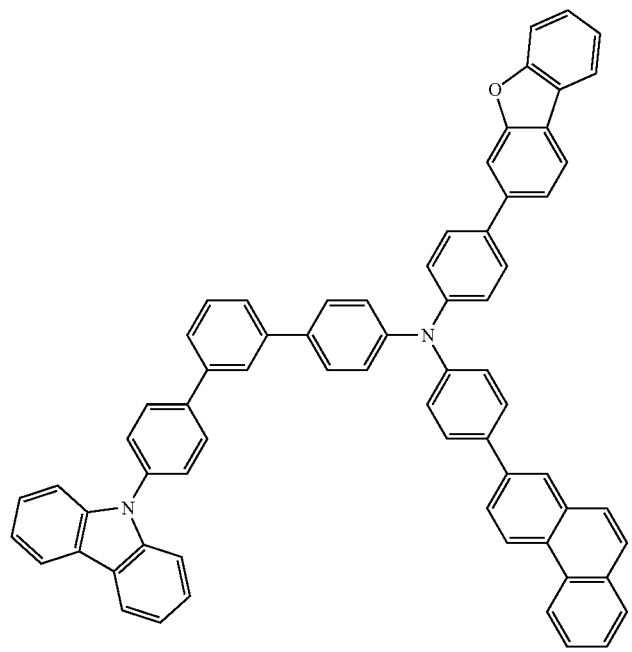
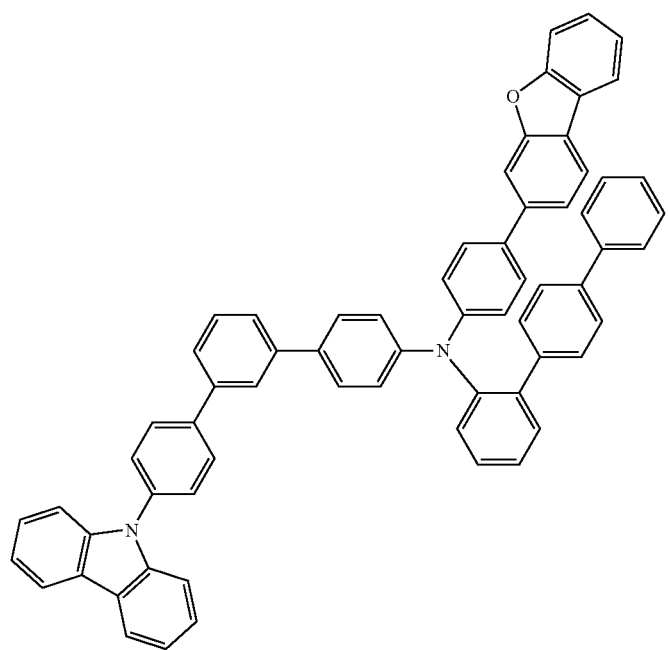

-continued
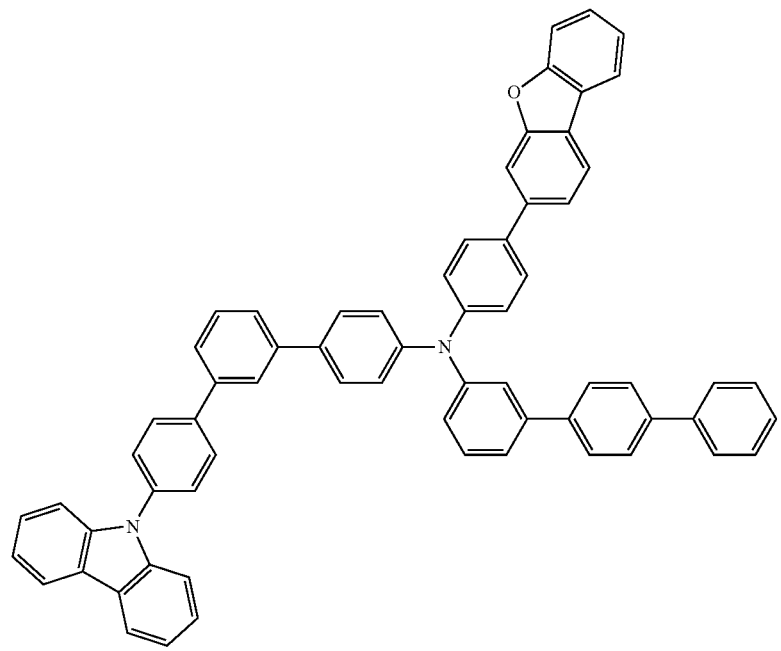
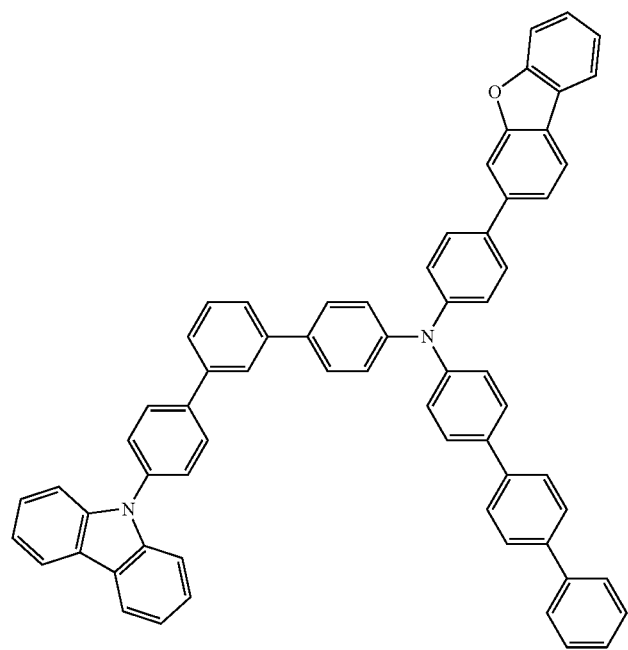

-continued
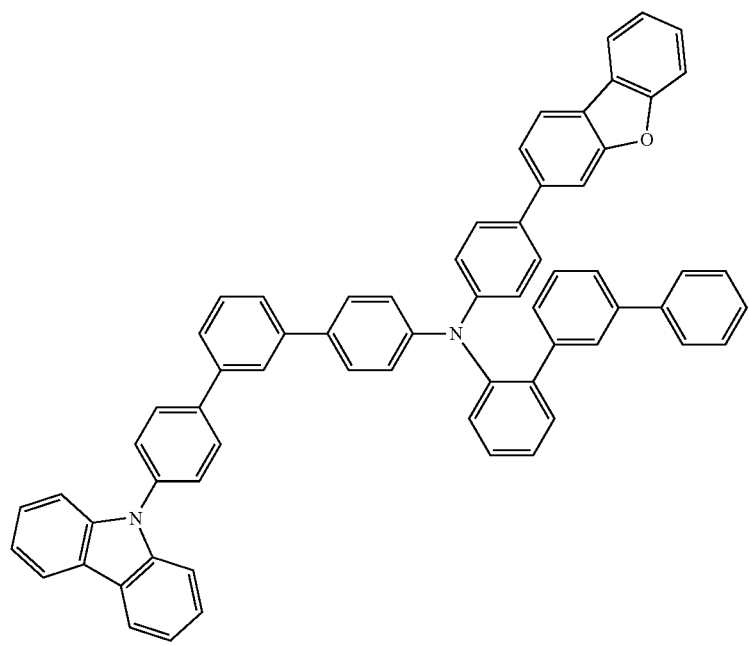
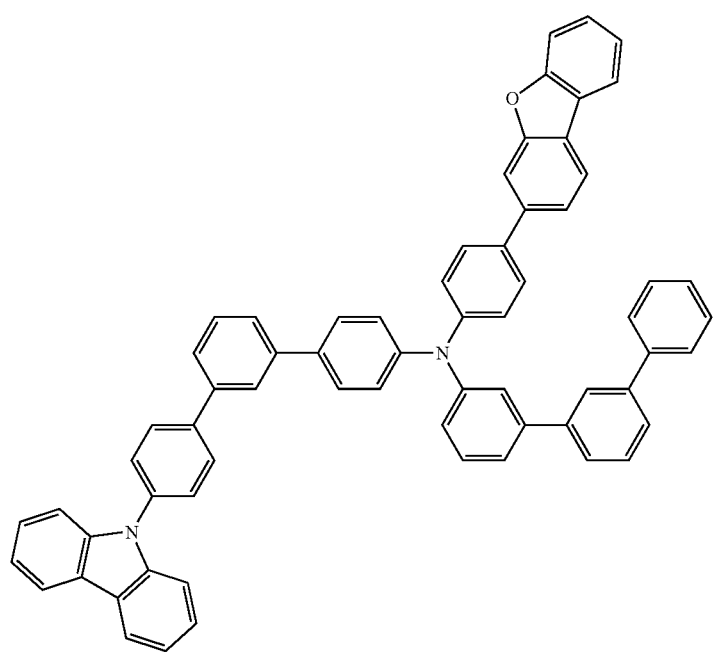

-continued
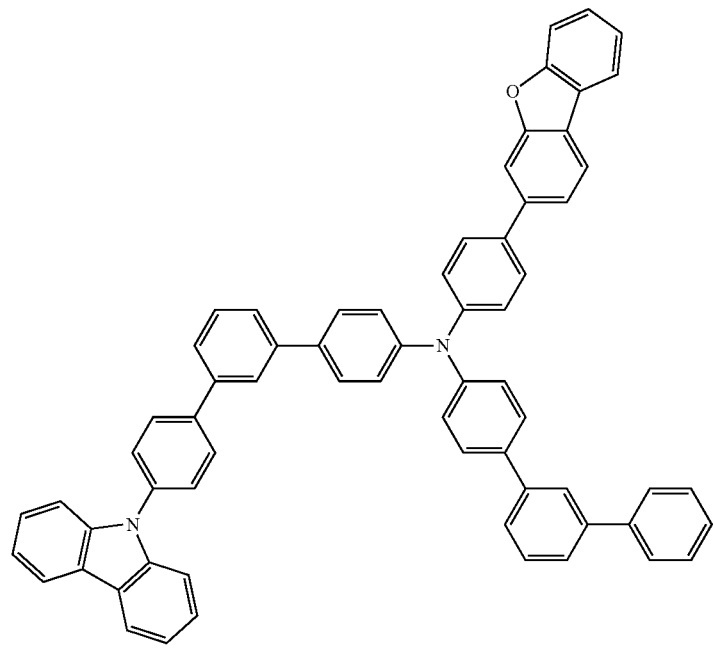
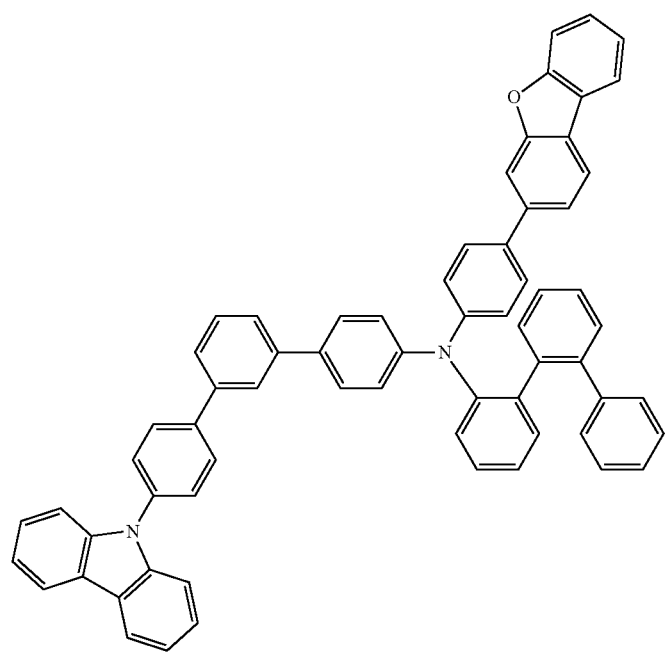

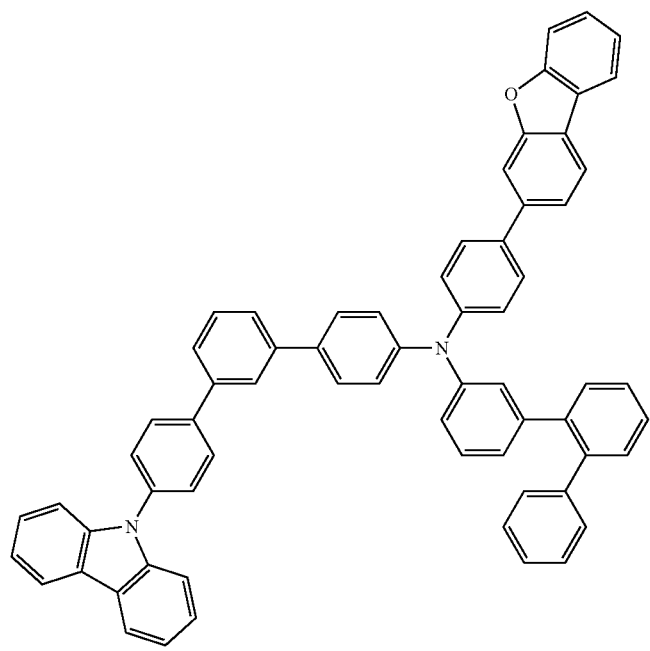

-continued
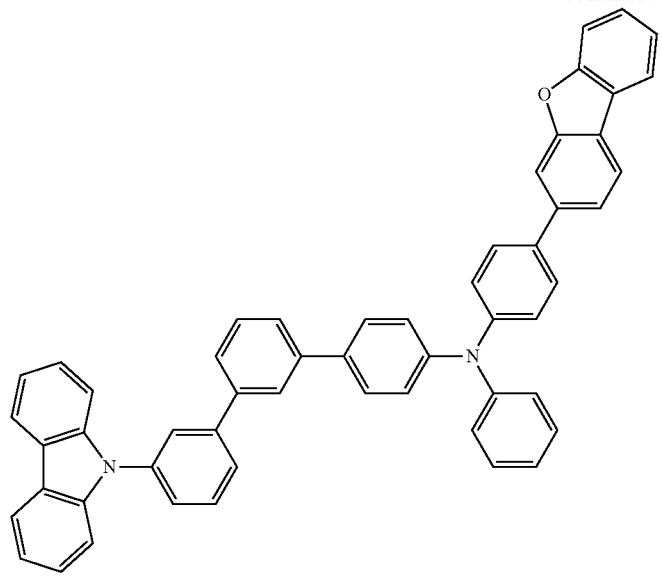
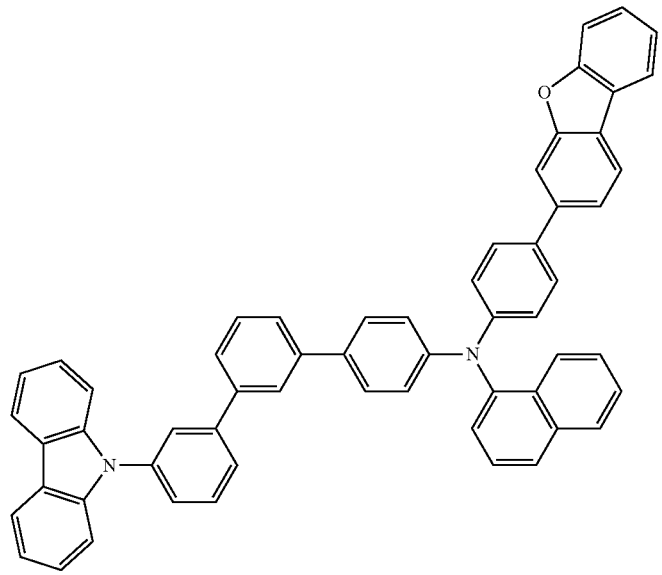
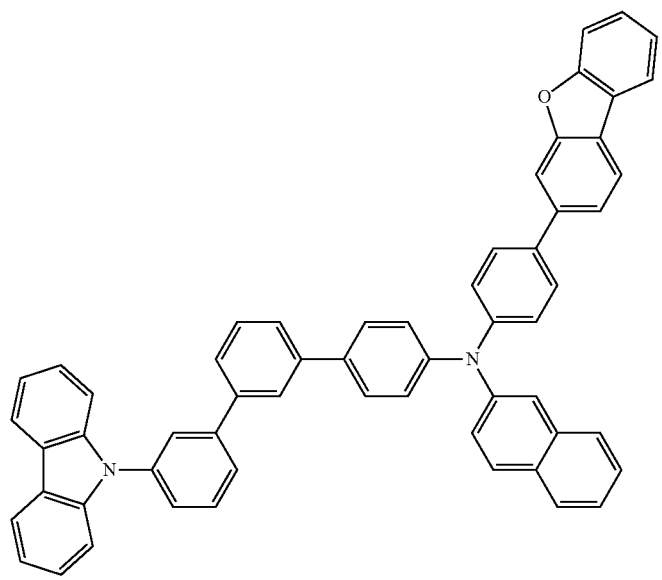

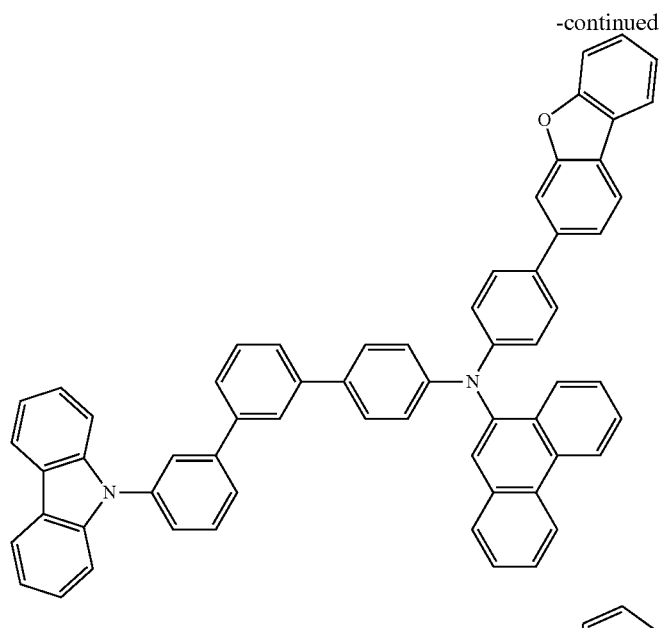
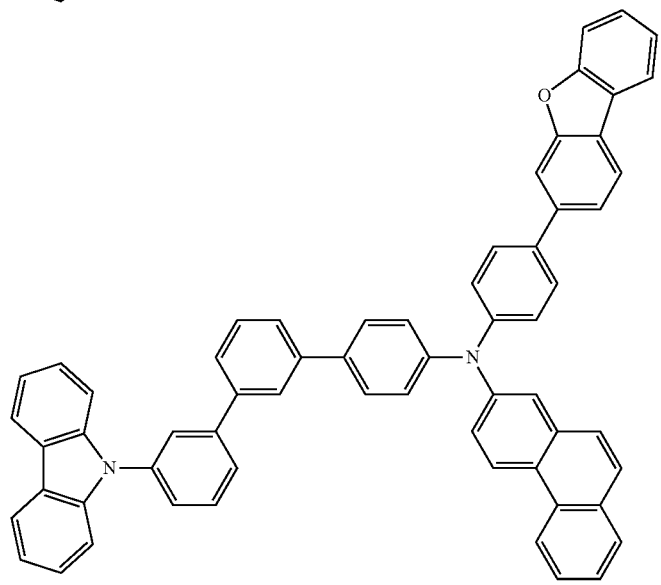
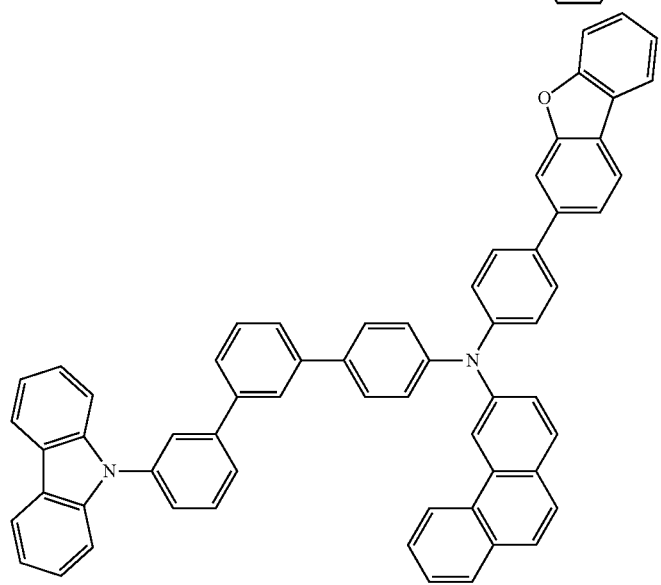

-continued
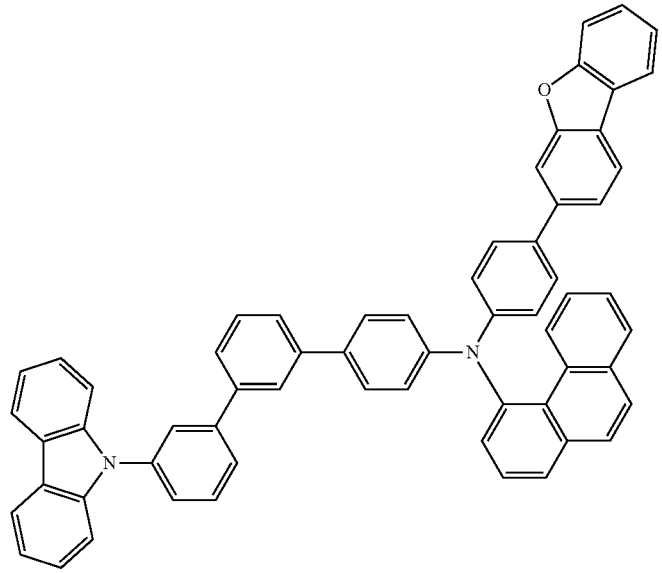
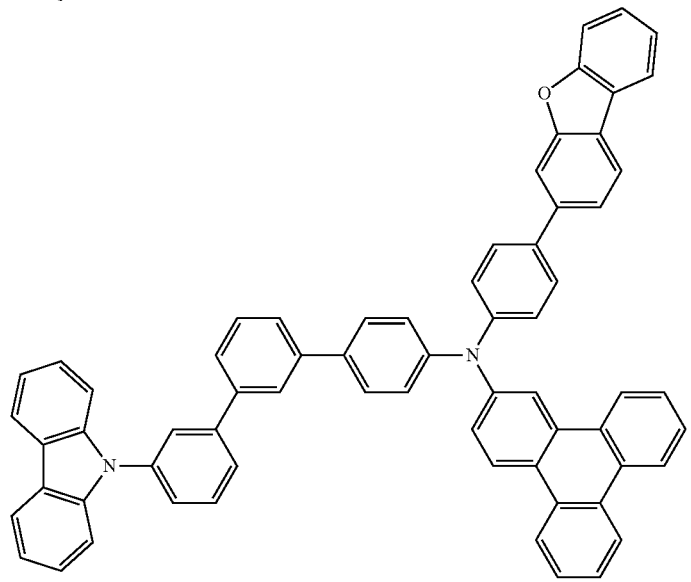
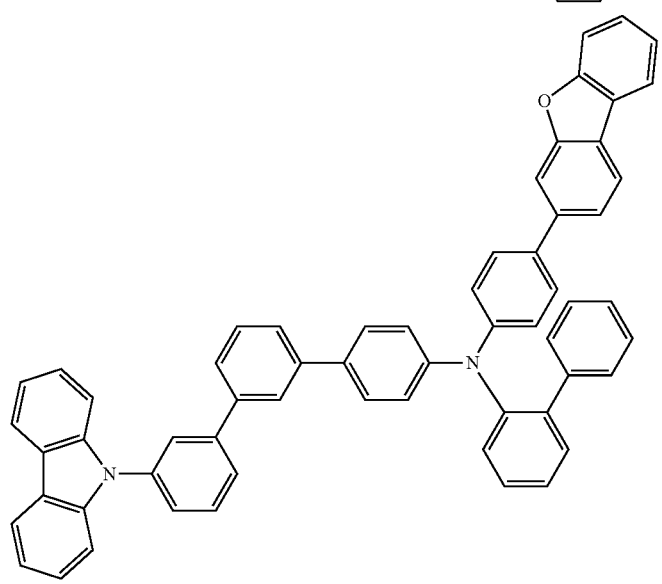

-continued
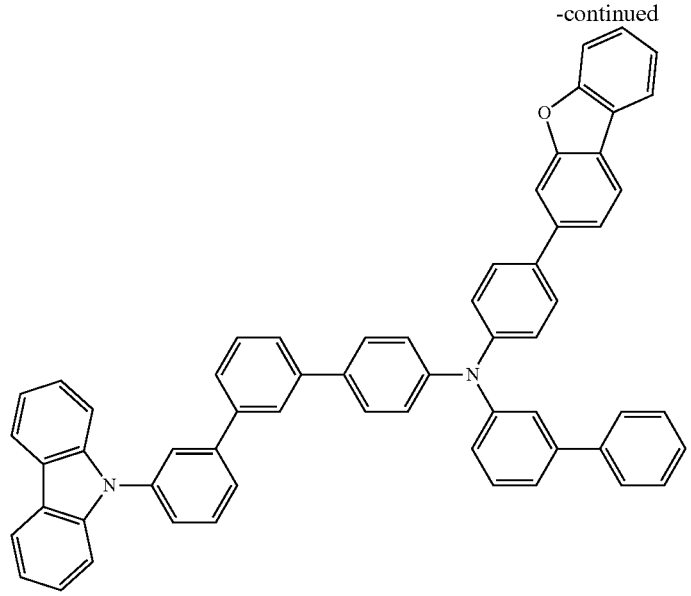
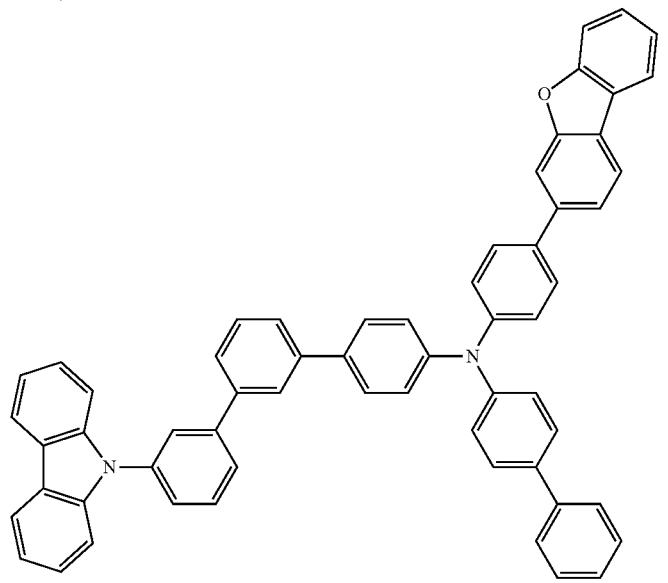
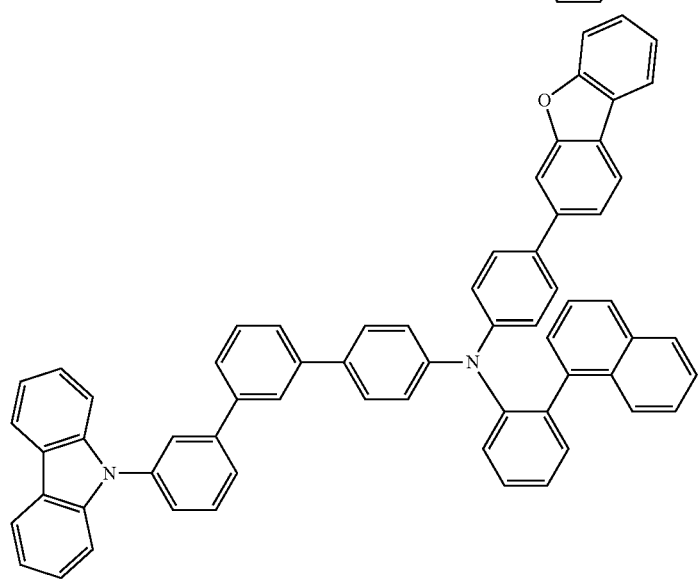

-continued
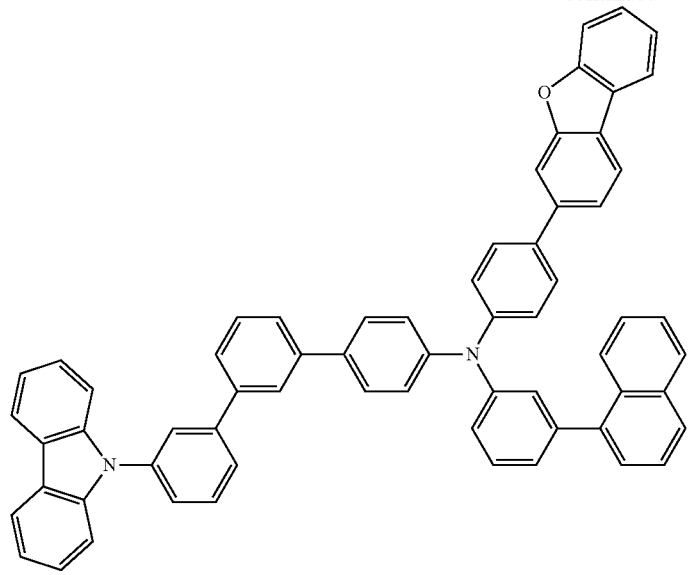
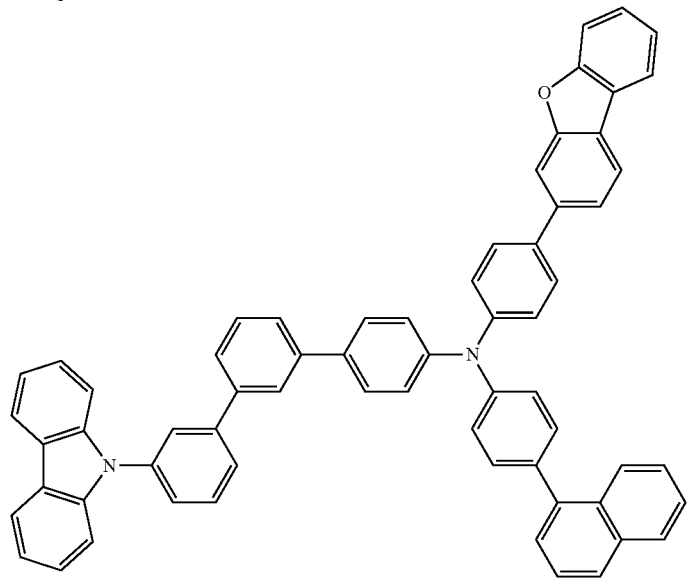
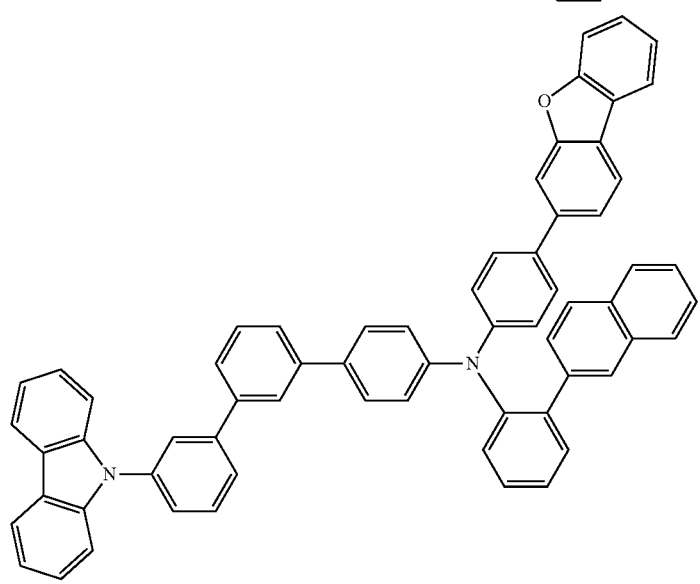

-continued
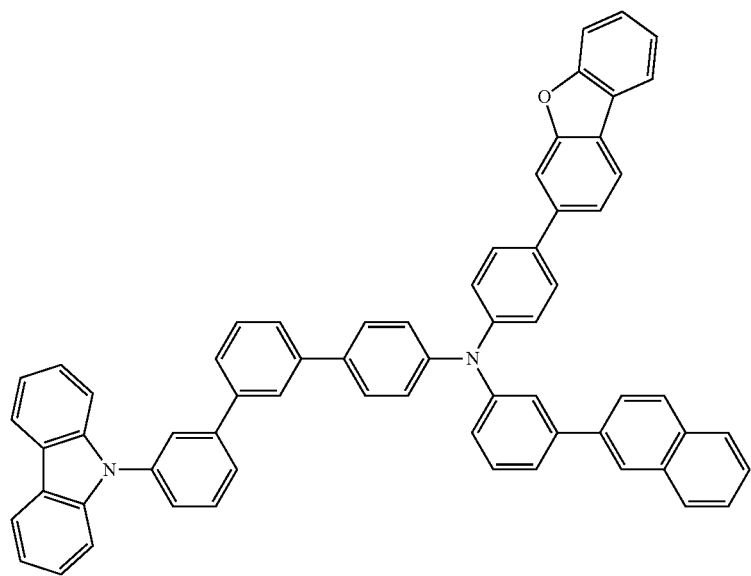
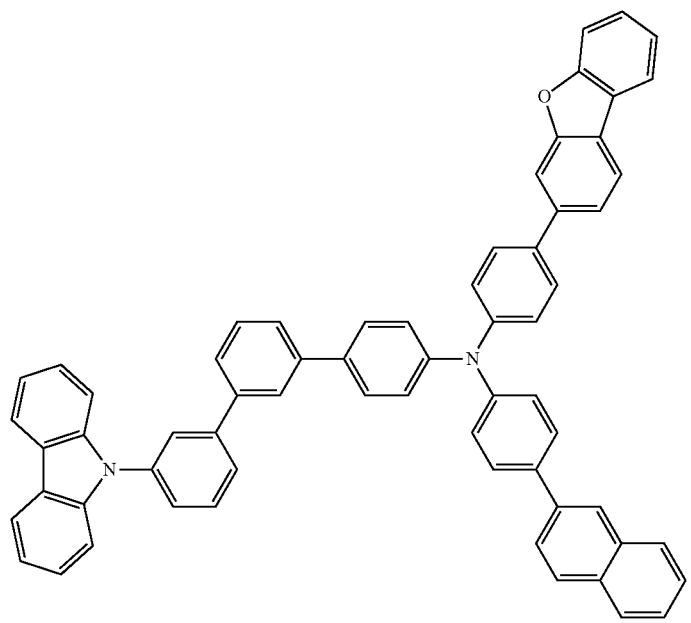

-continued
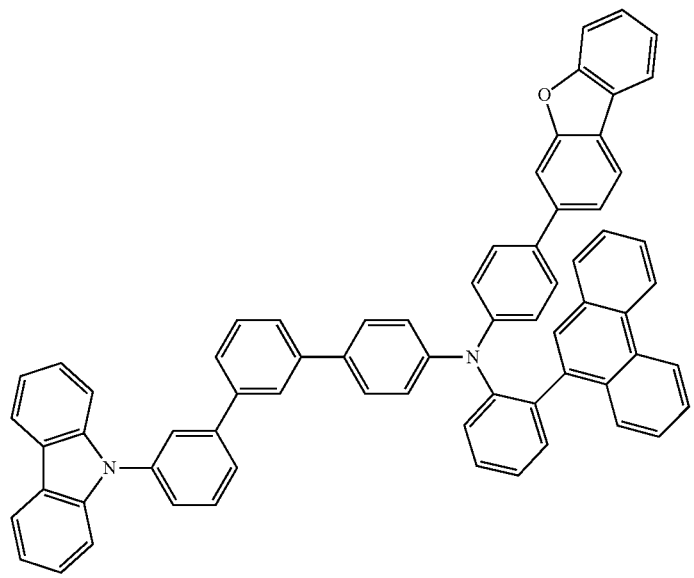
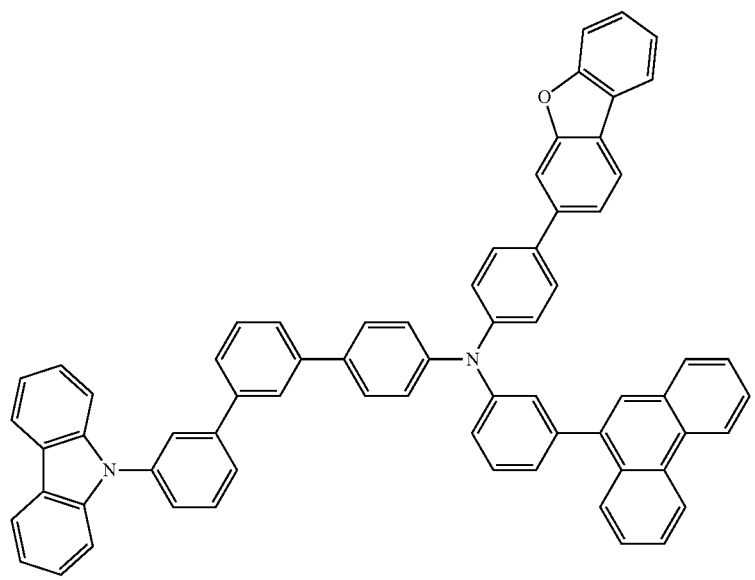

-continued
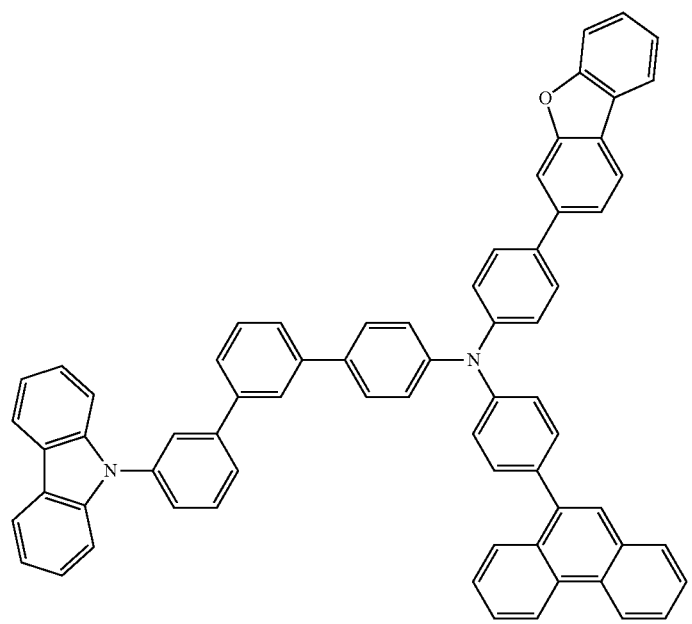
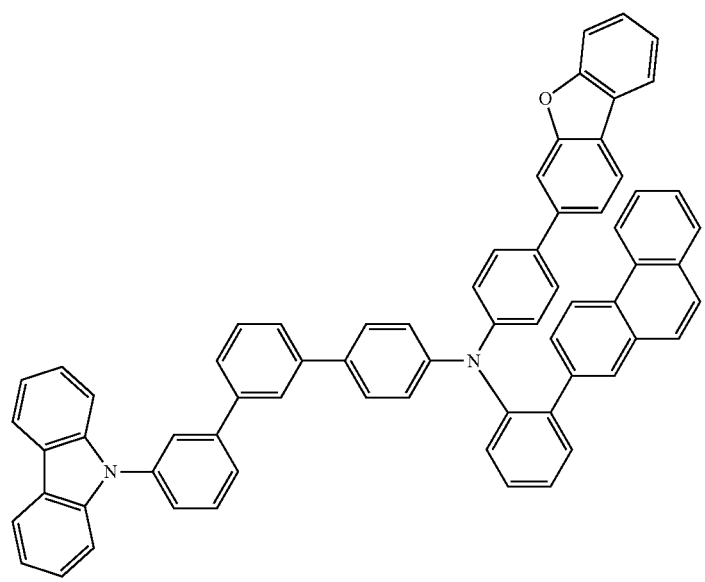

-continued
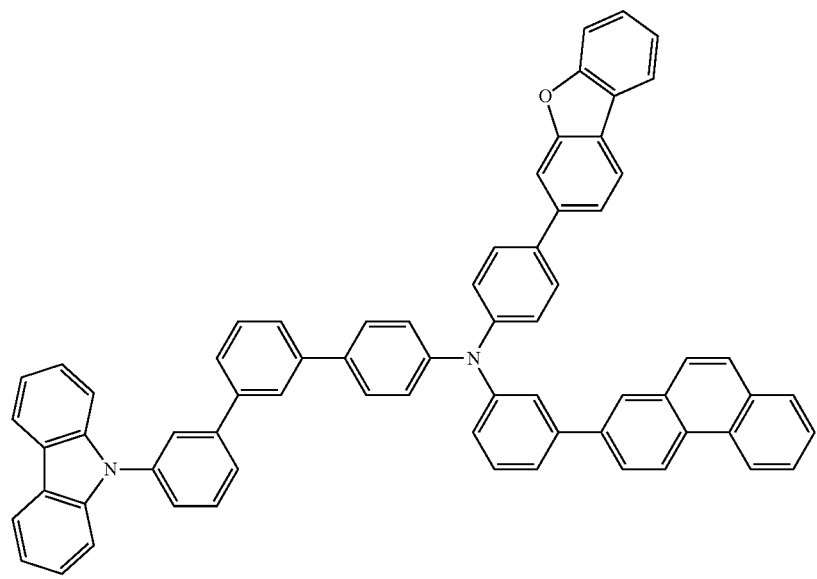
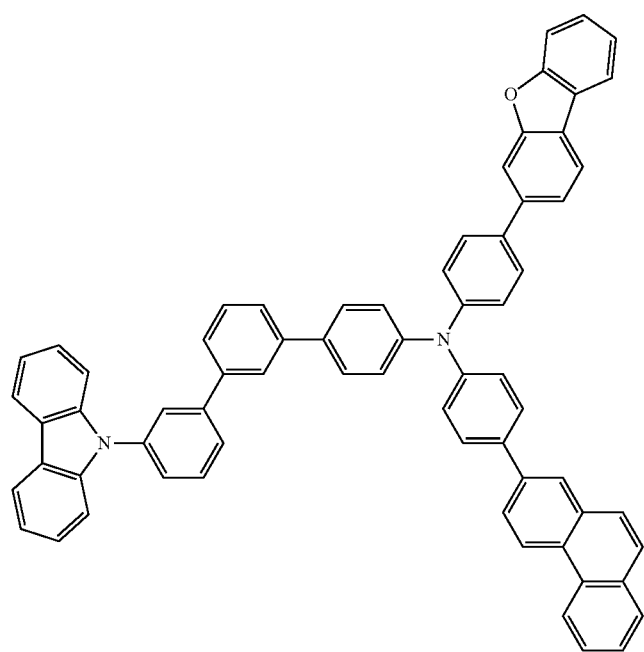

-continued
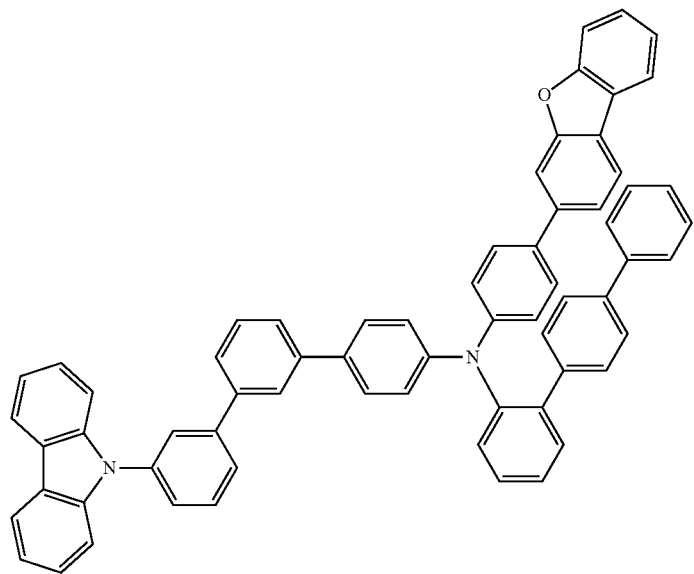
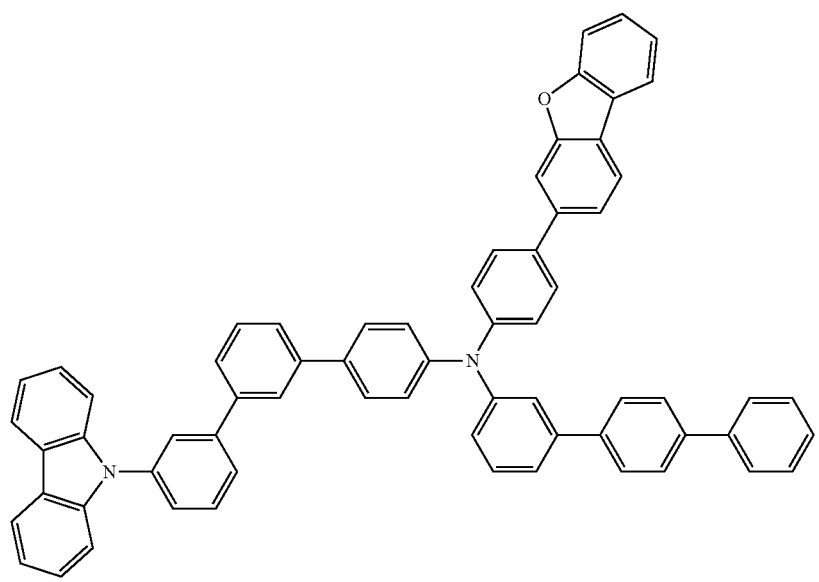

-continued
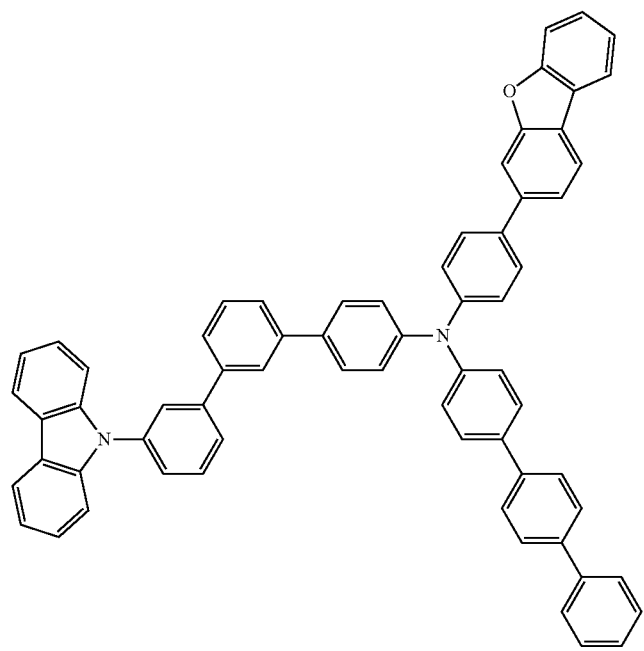
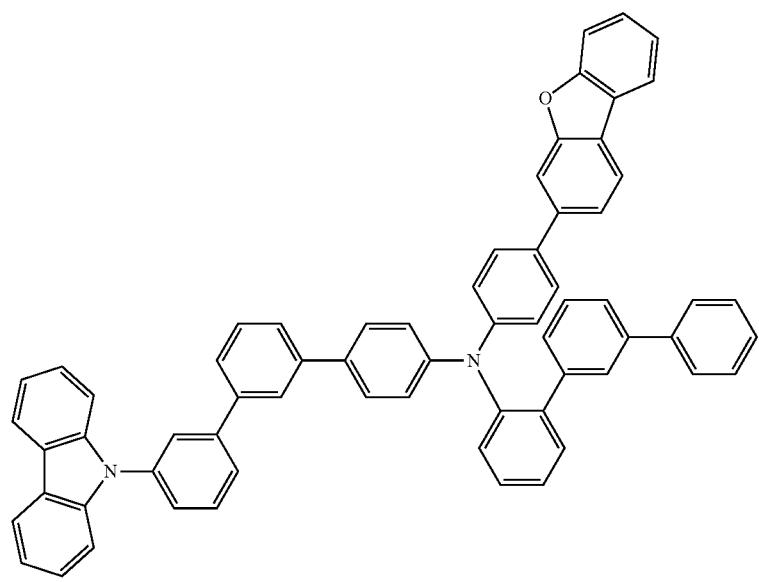

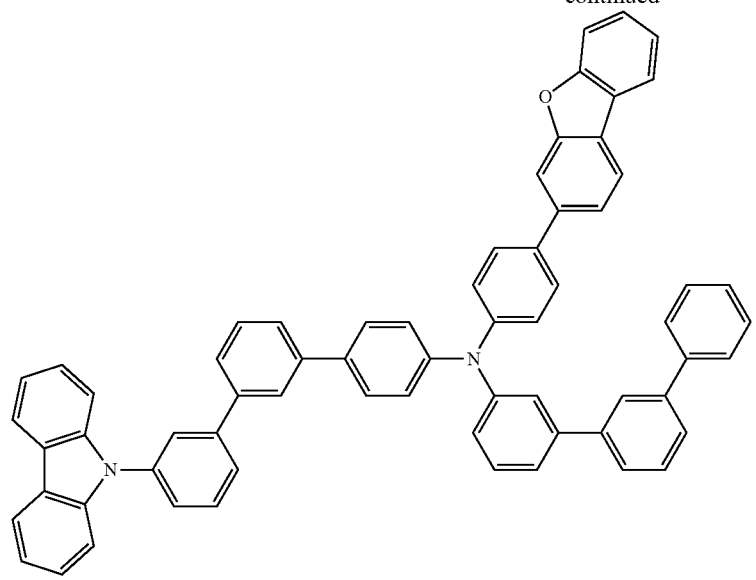
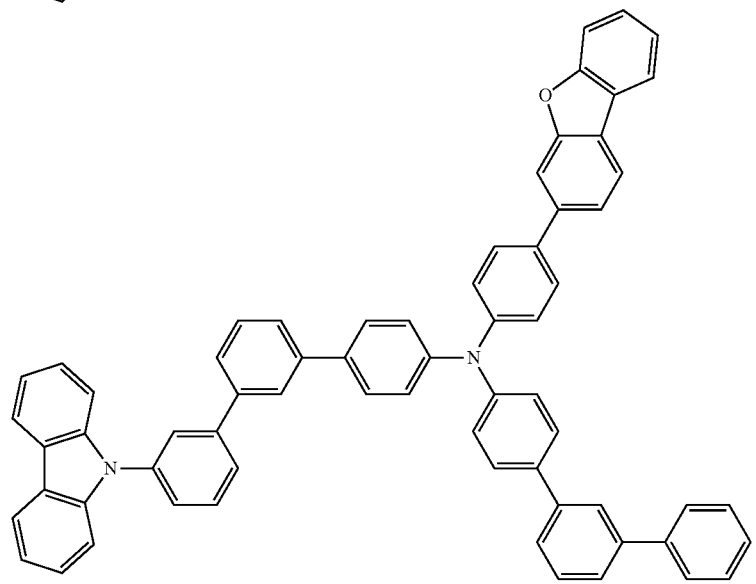
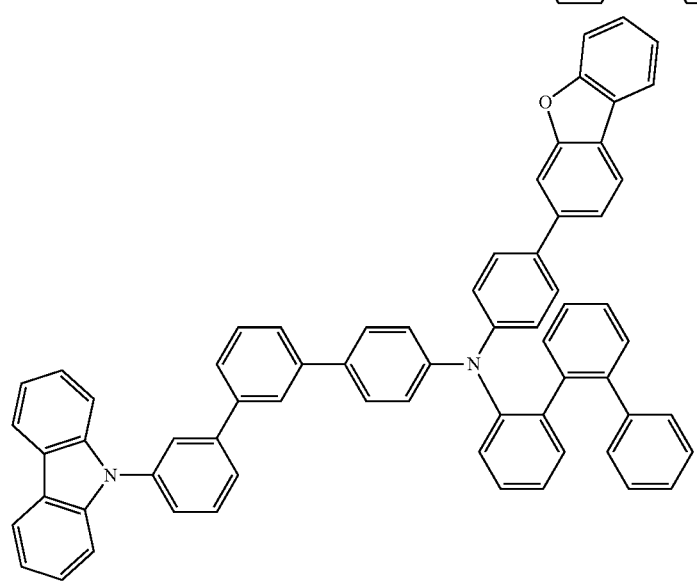

-continued
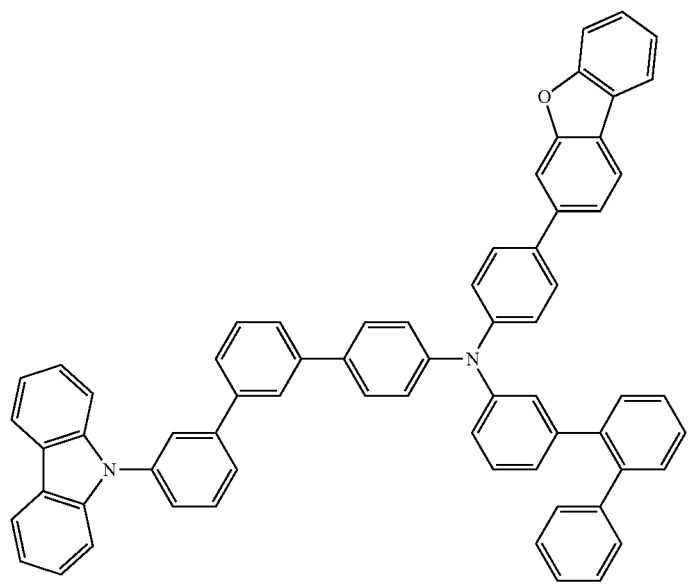
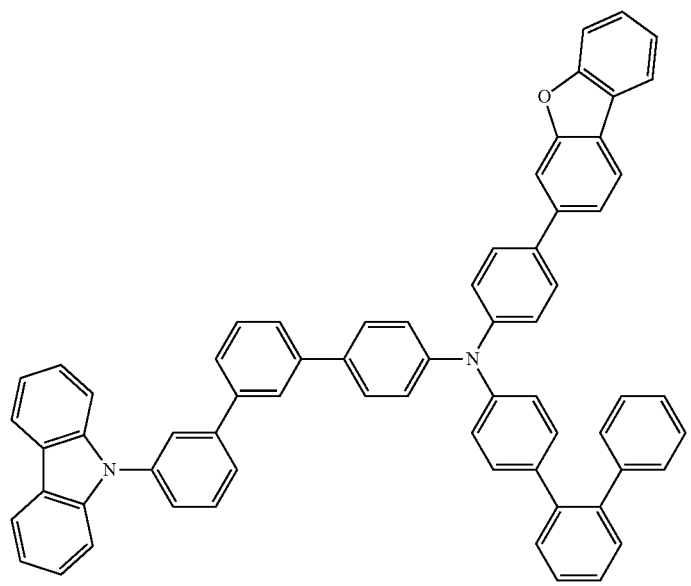
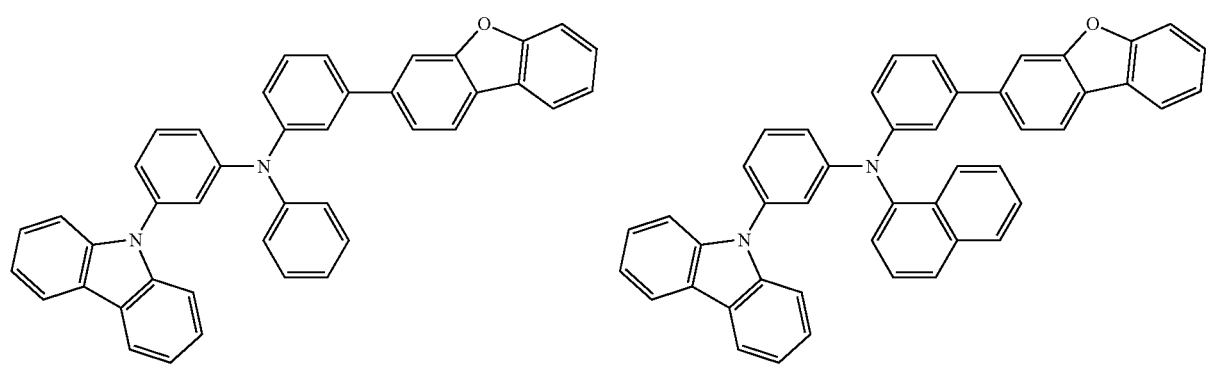

-continued
163
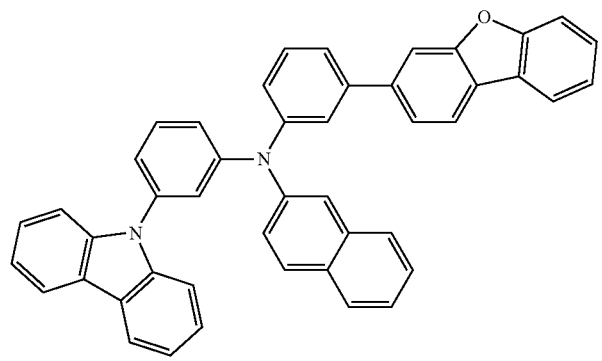
164
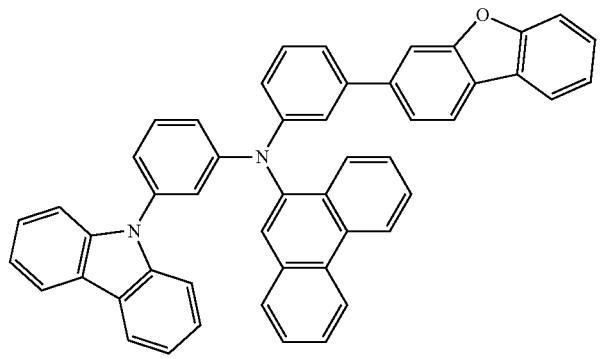
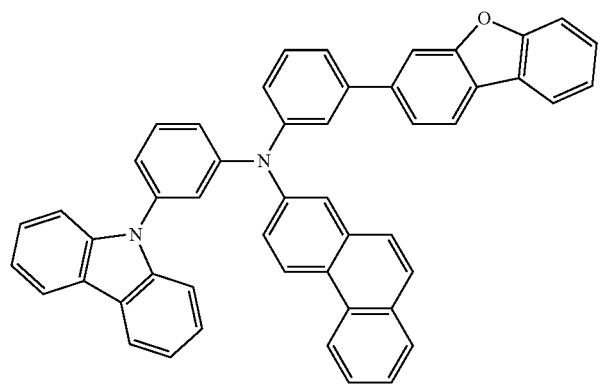
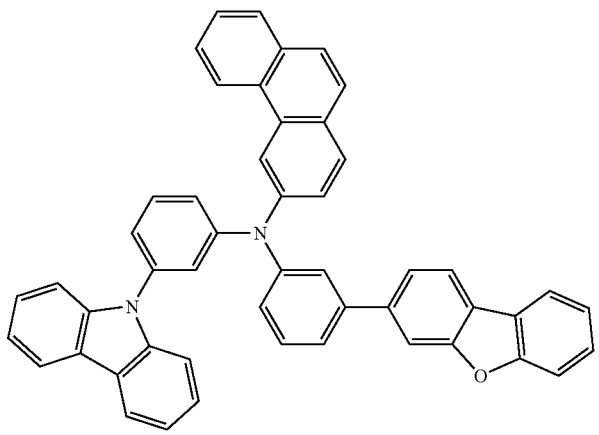
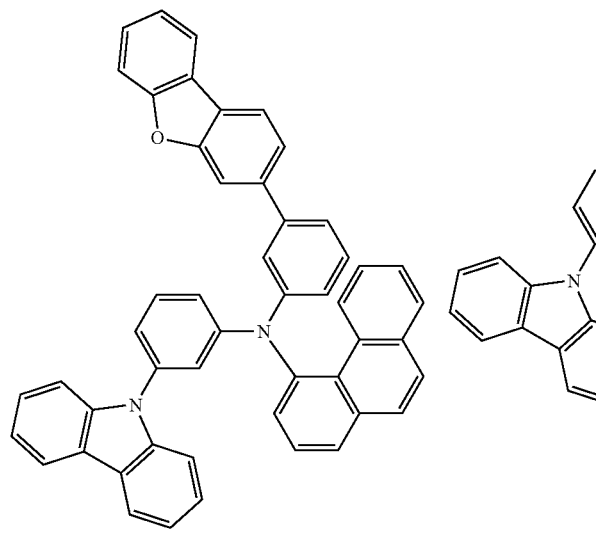
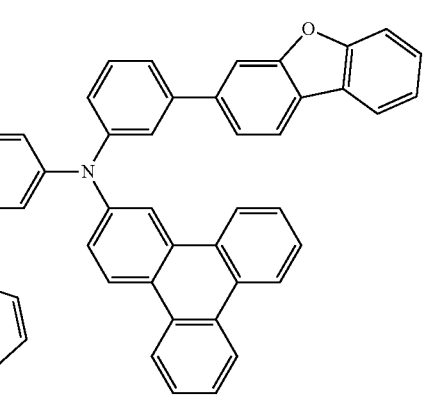

-continued
165
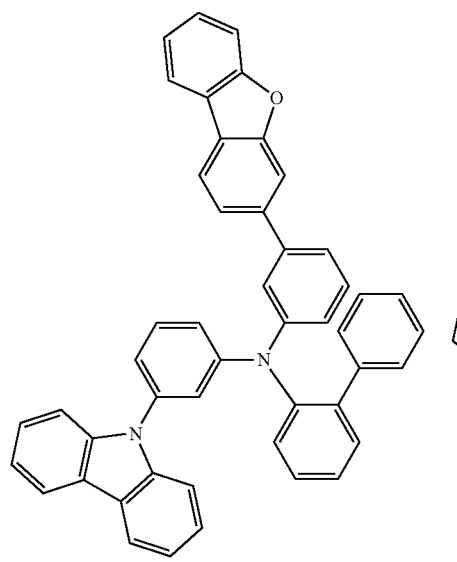
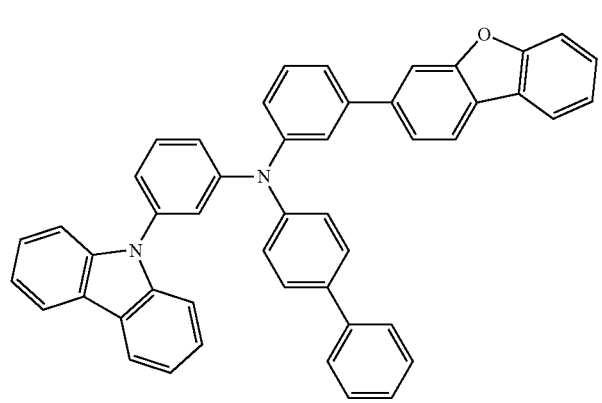
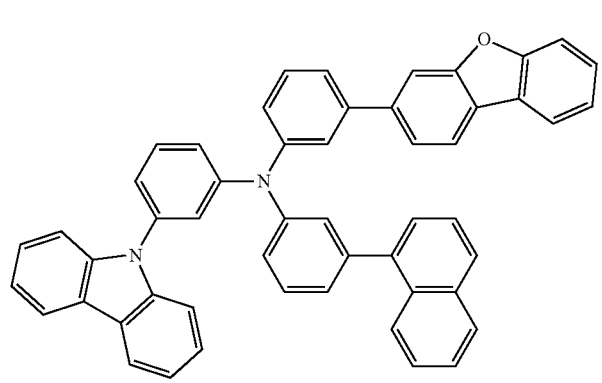
166
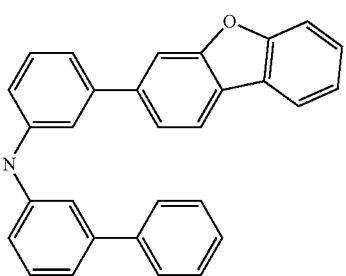
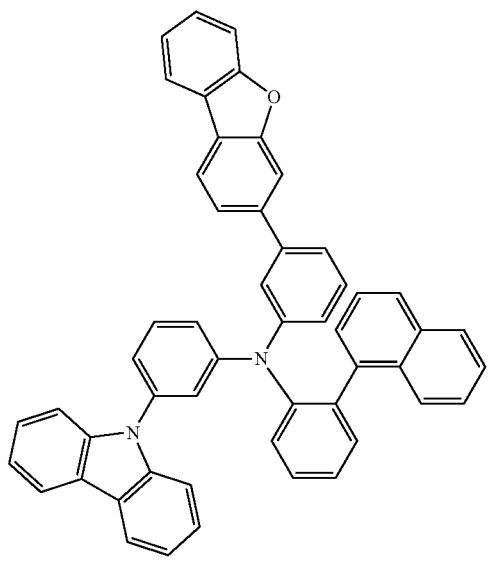
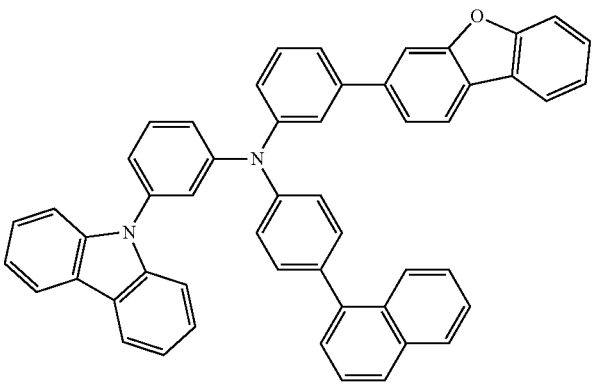

167
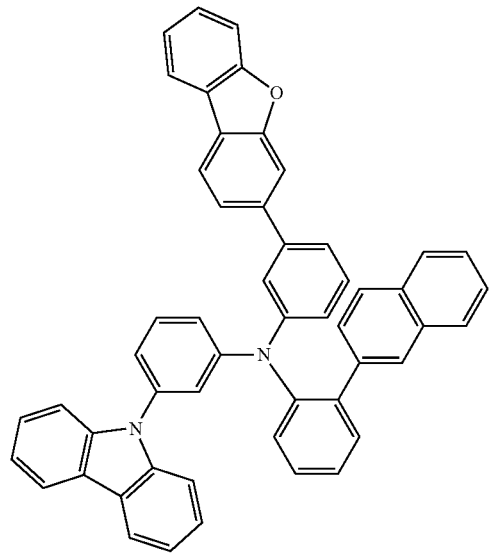
168
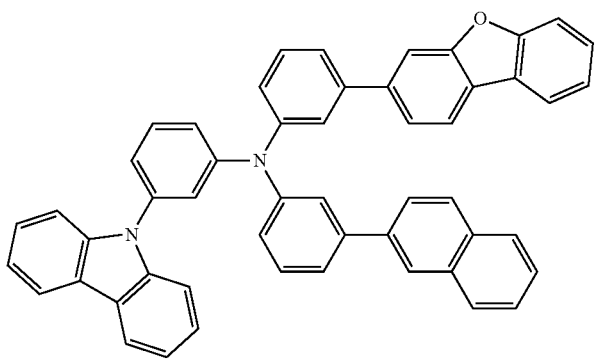
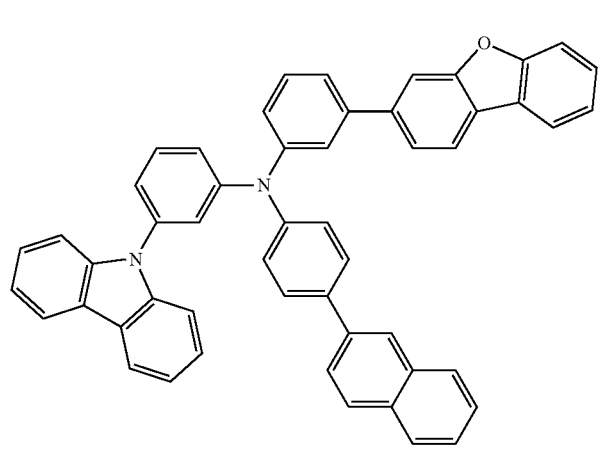
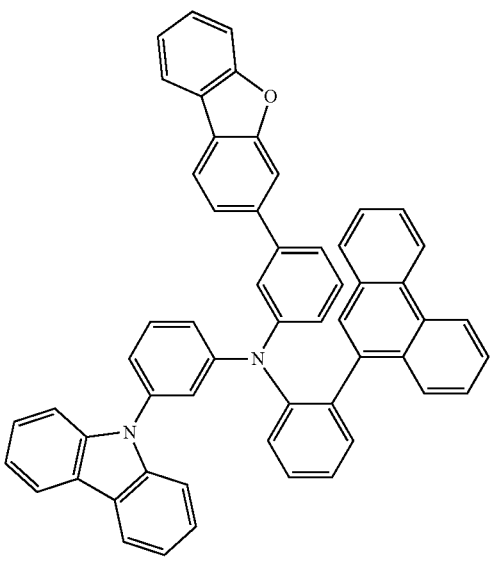
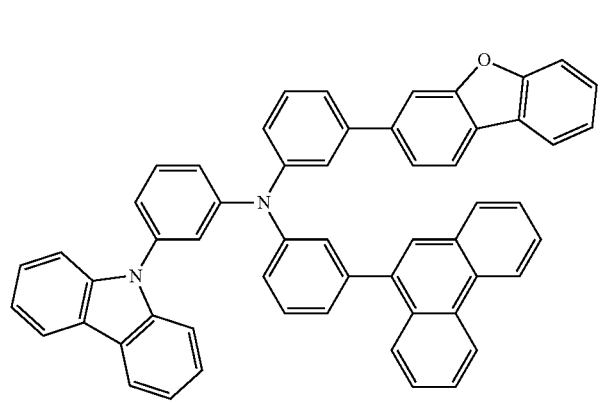
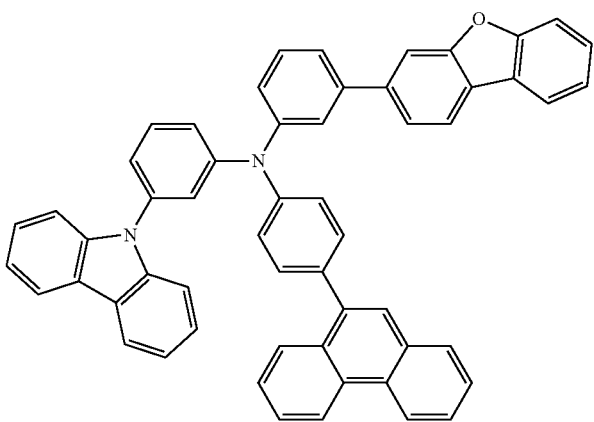

-continued
169
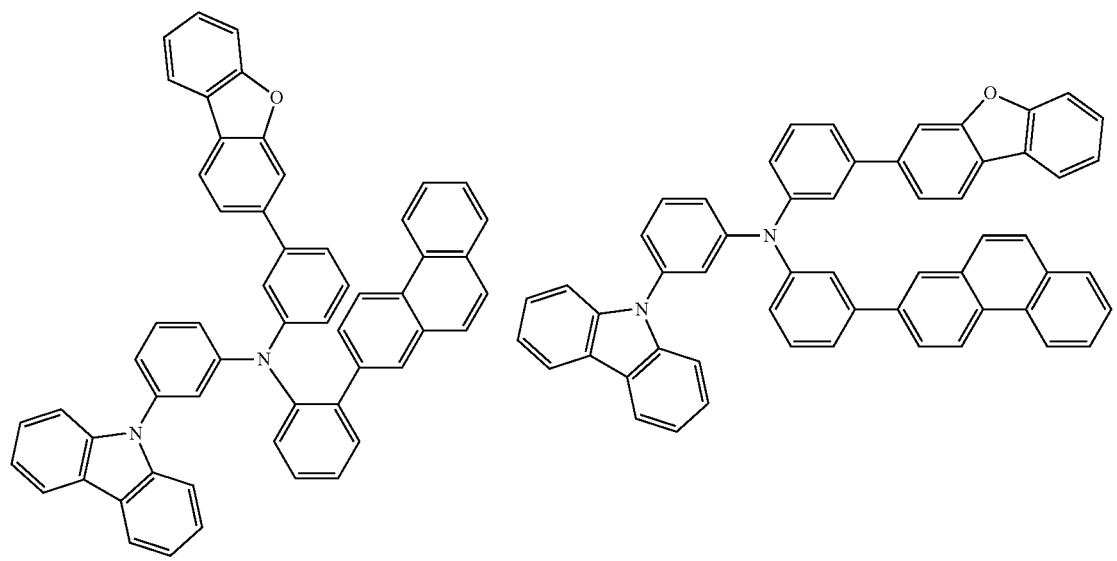
170
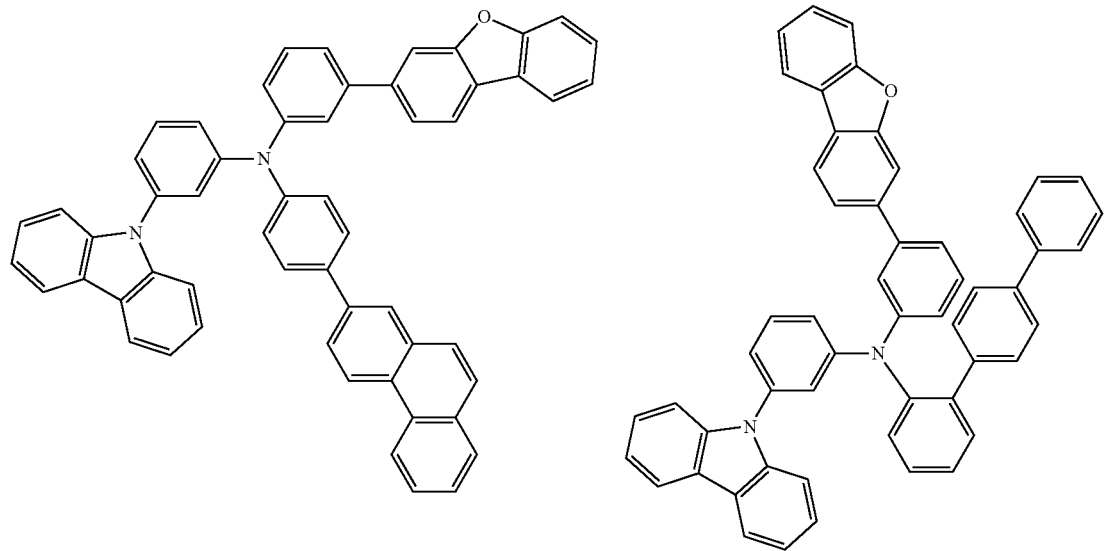
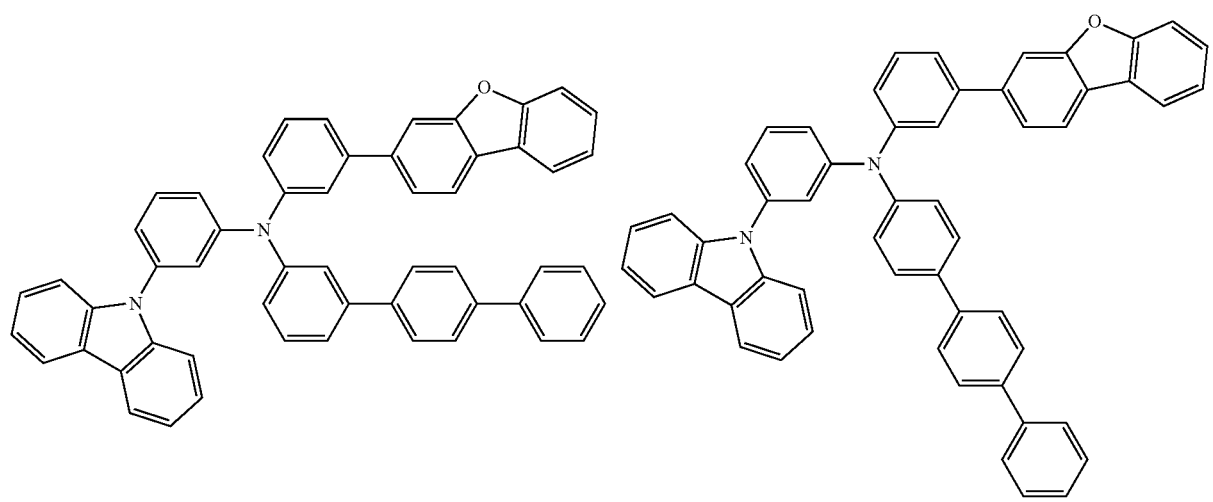

-continued
171
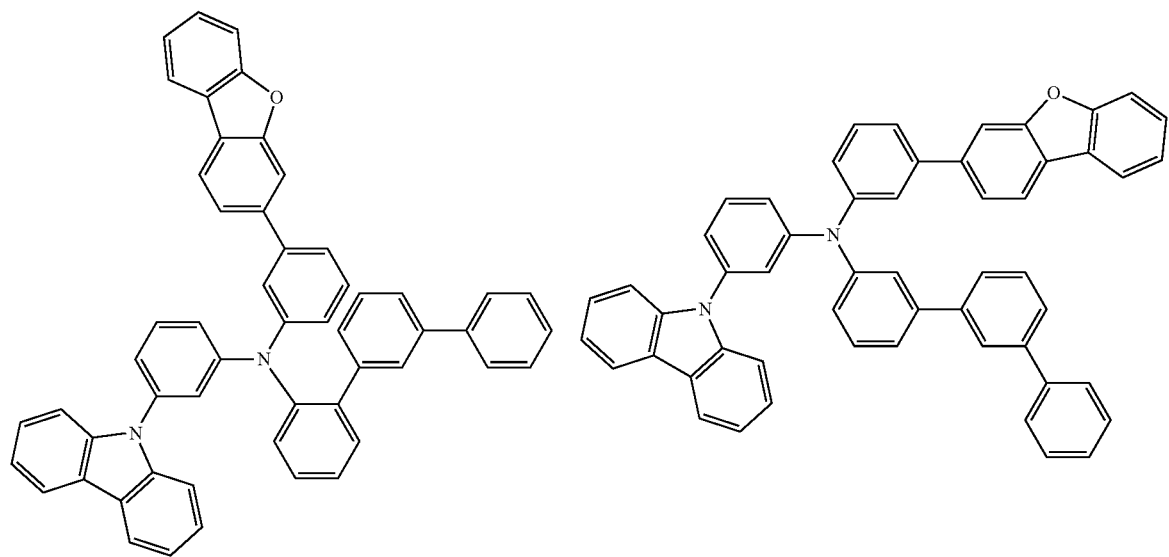
172
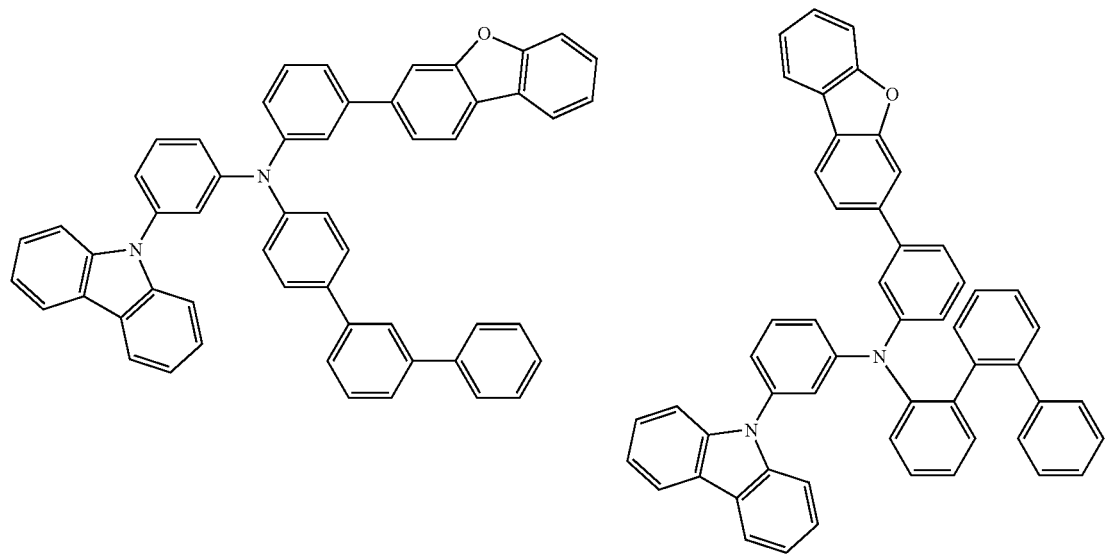
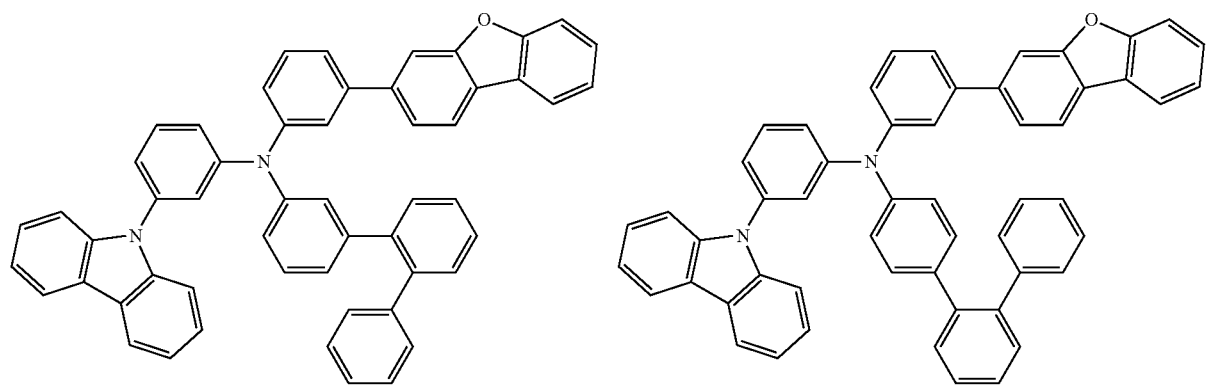

-continued
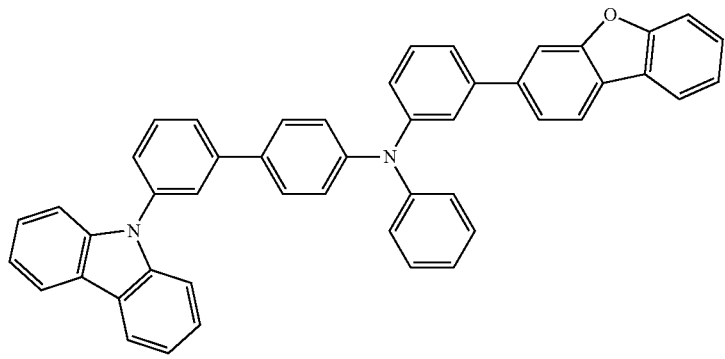
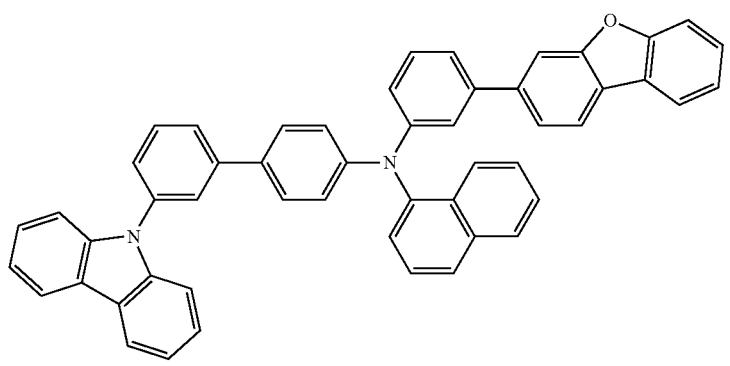
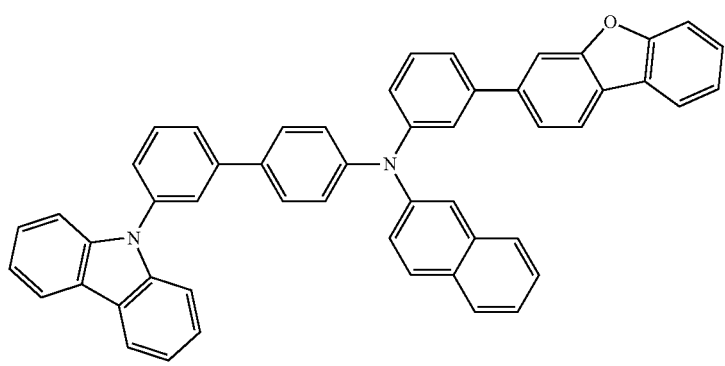
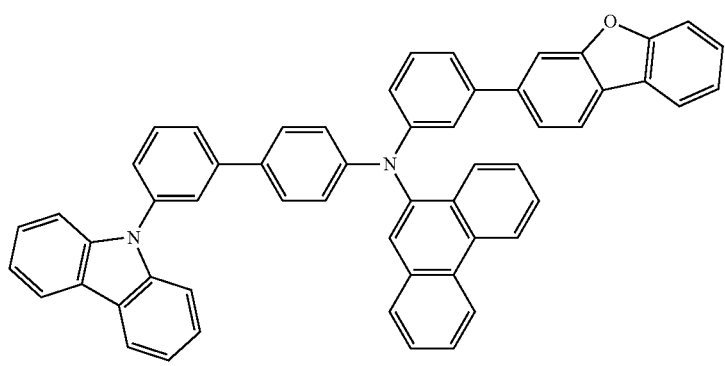

-continued
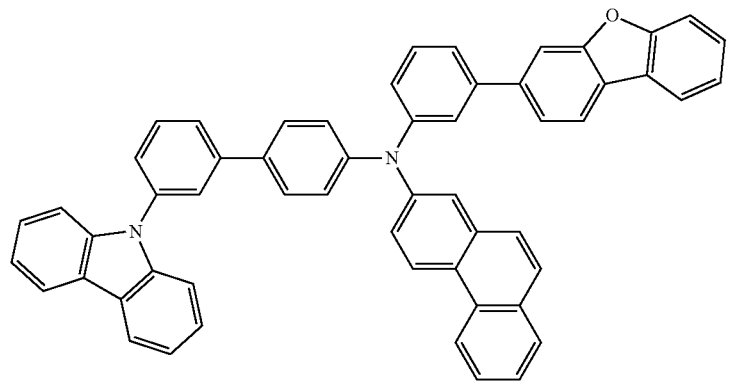
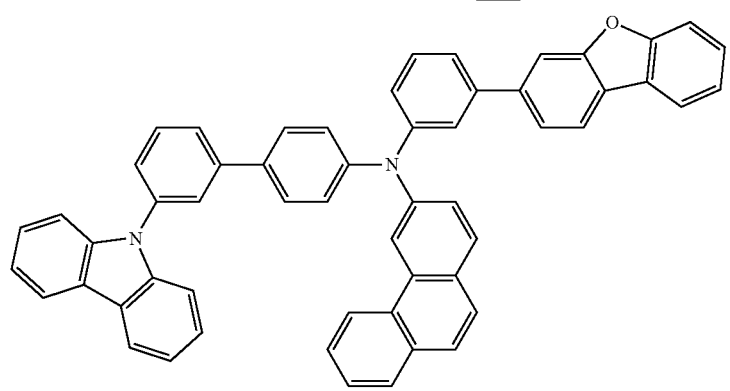
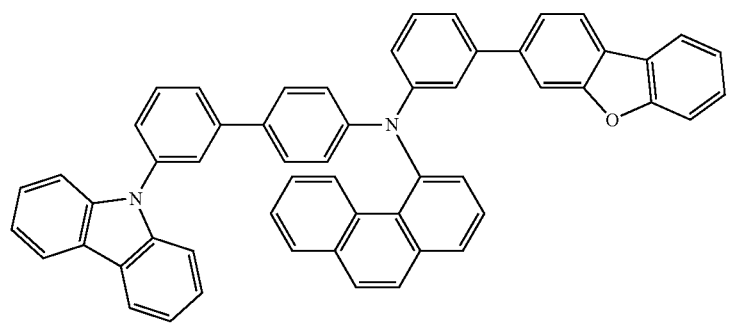
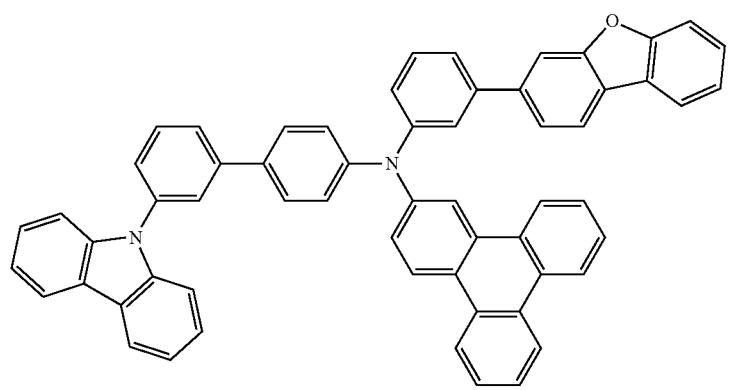

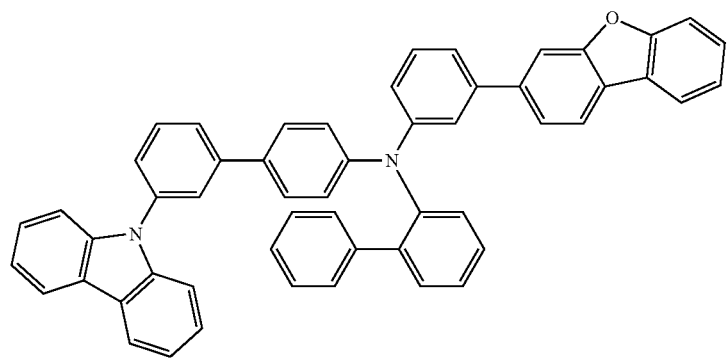
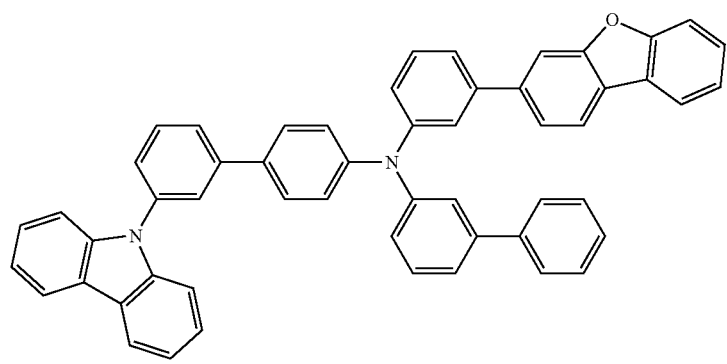
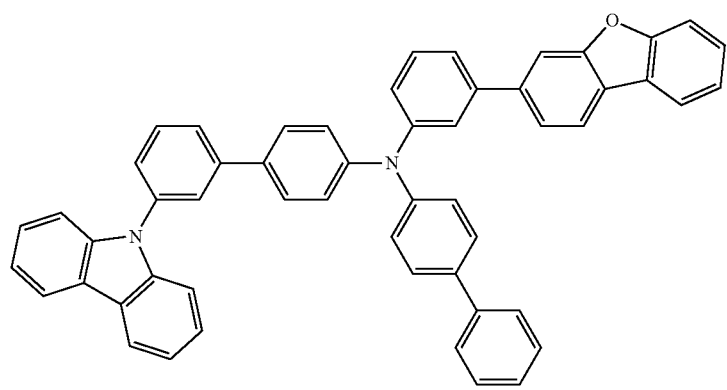
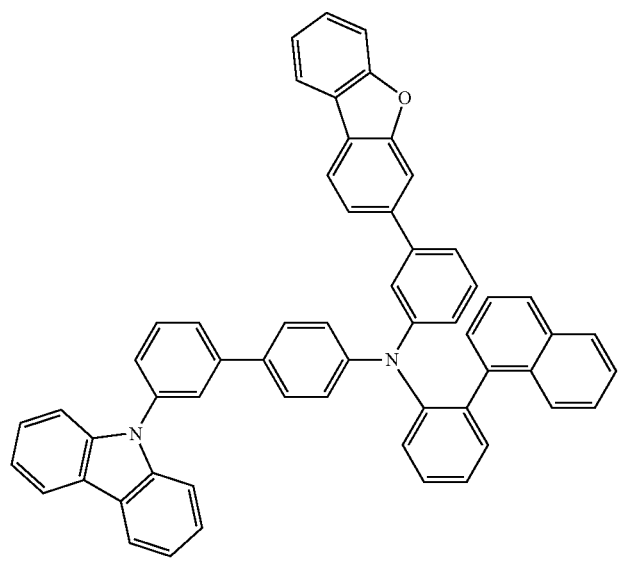

-continued
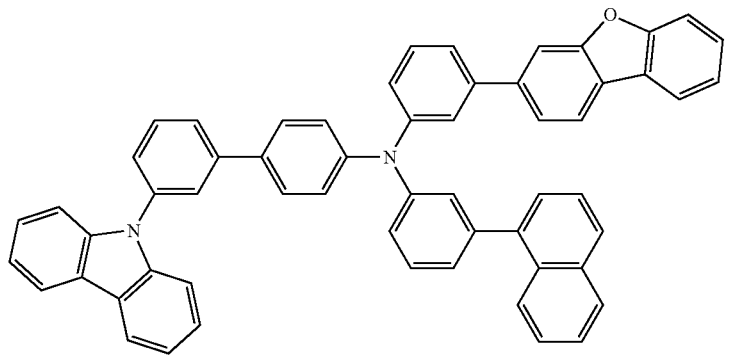
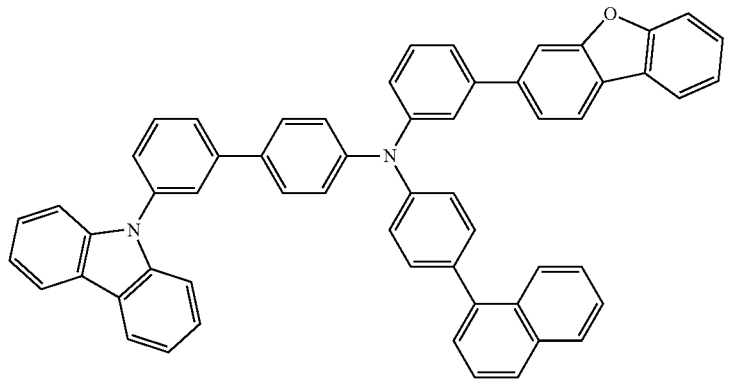
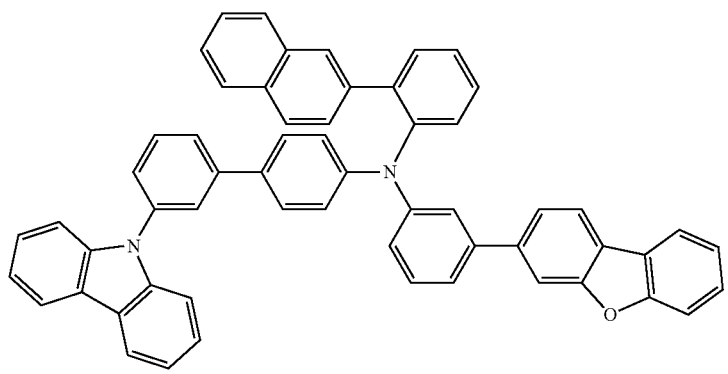
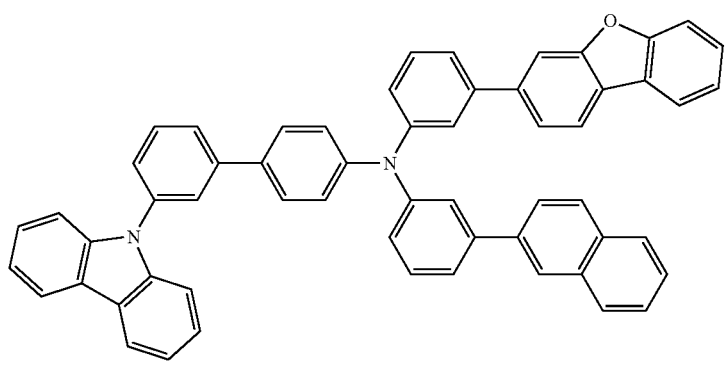

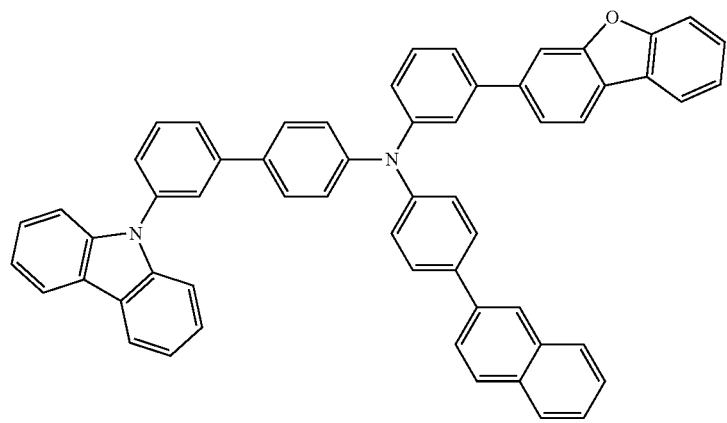
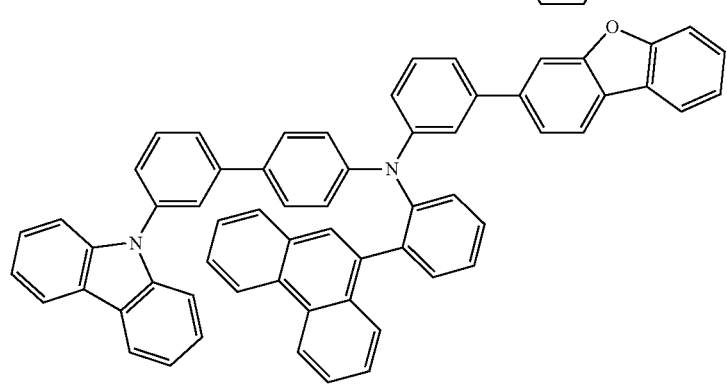
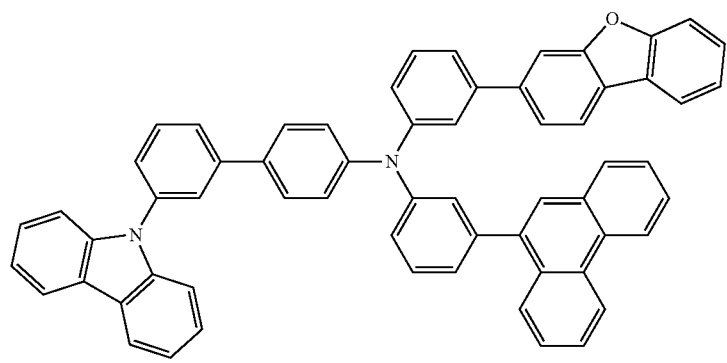
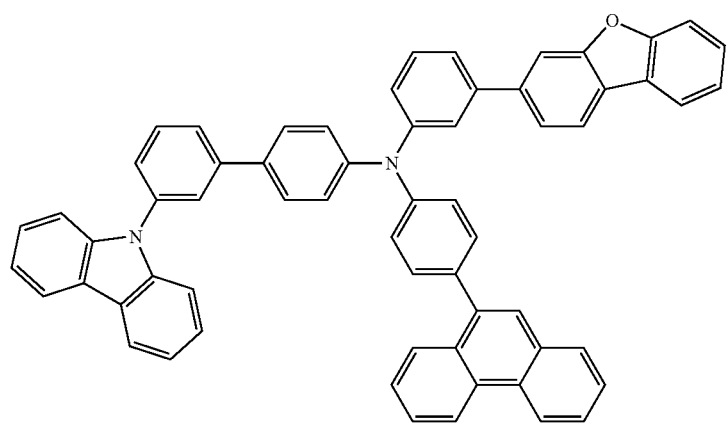

-continued
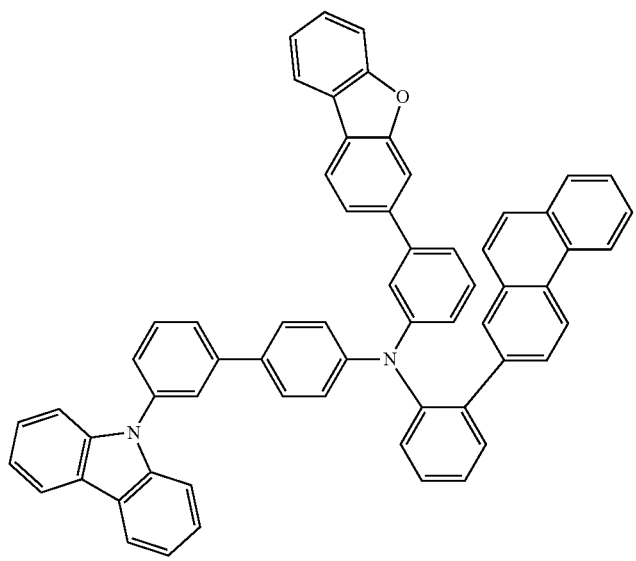
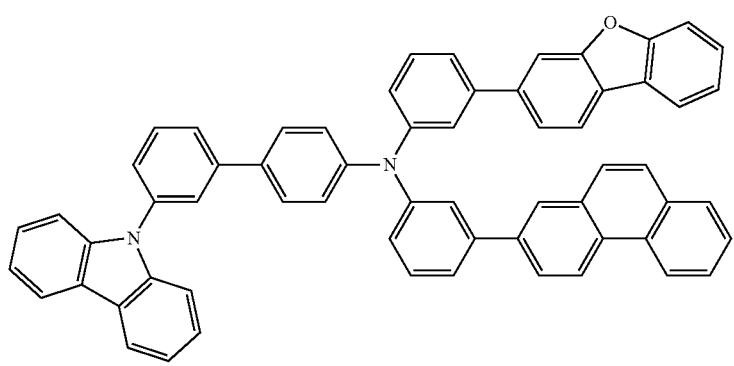
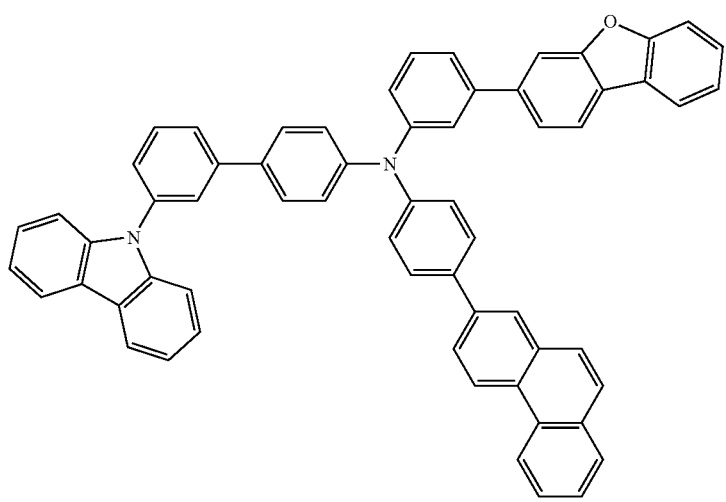

-continued
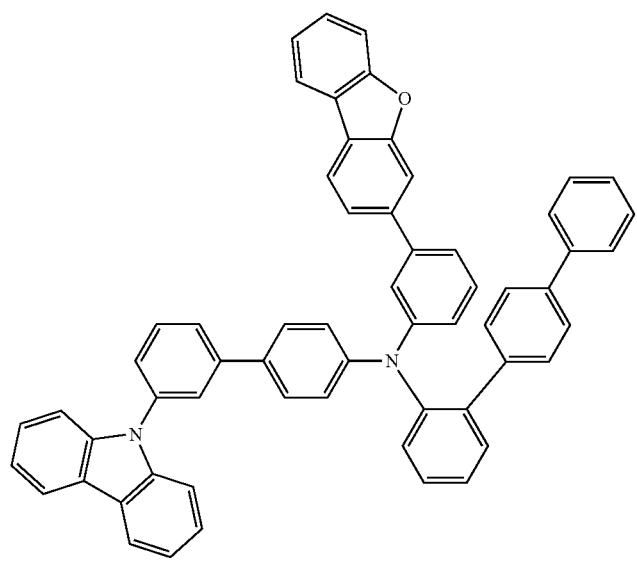
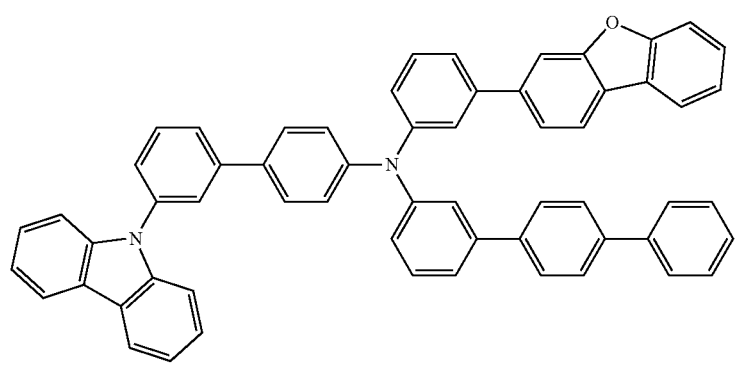
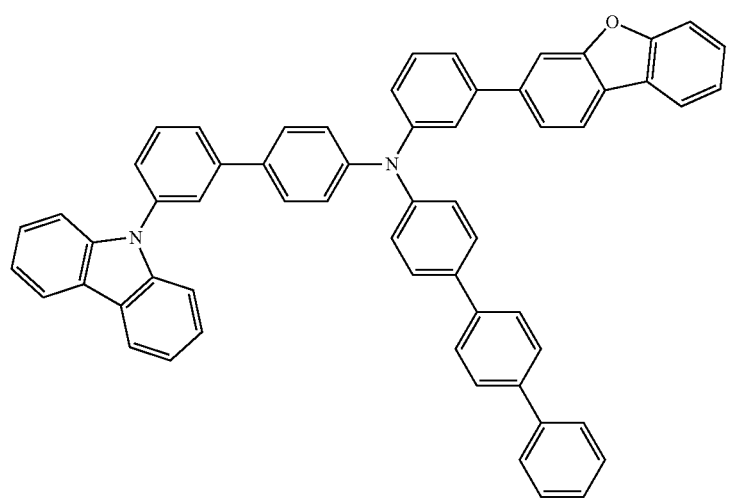

-continued
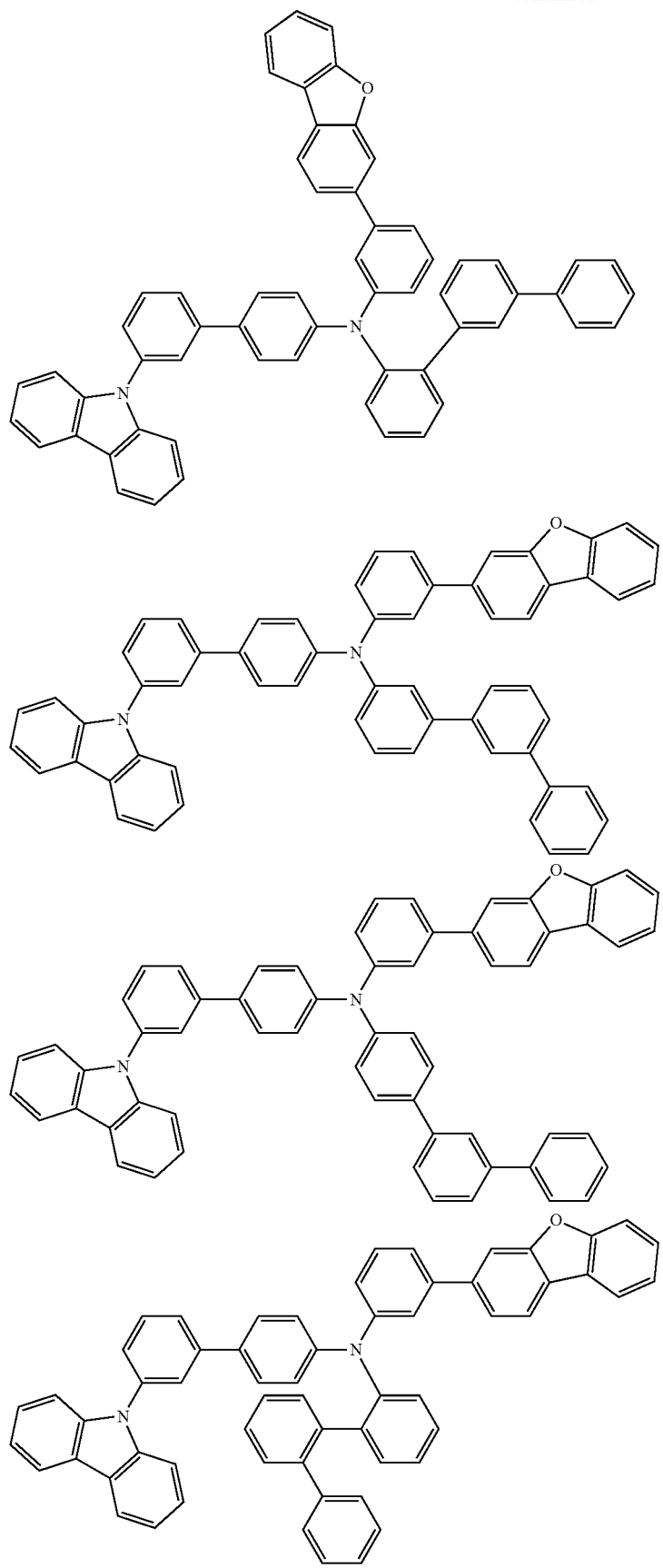

-continued
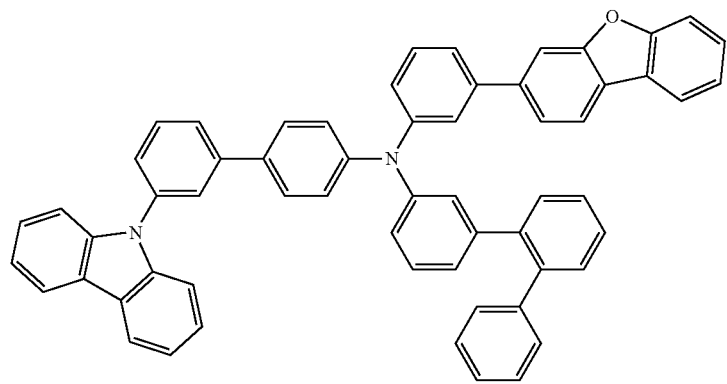
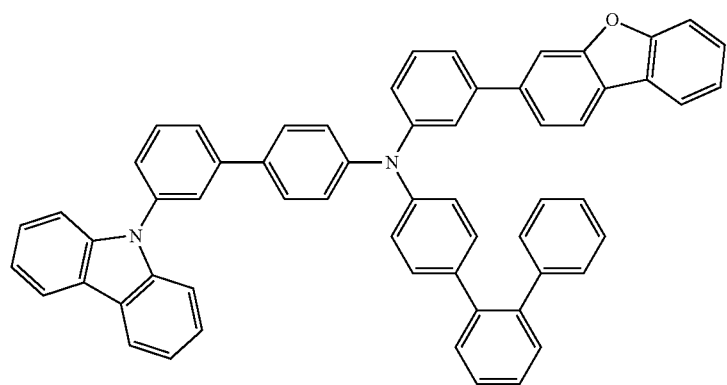
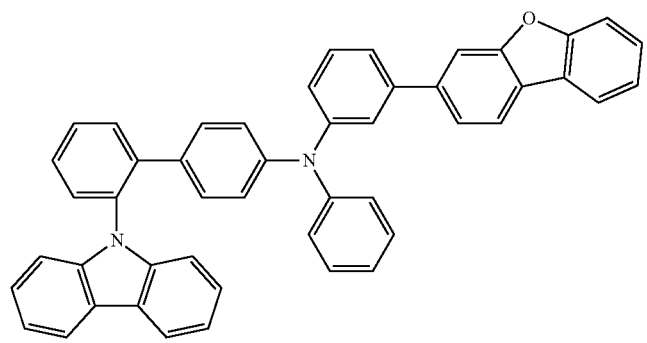
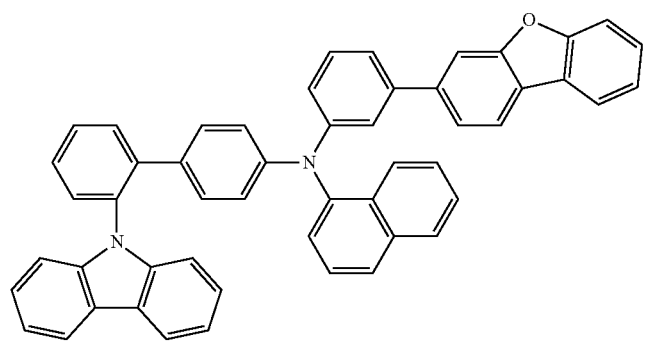

191
-continued
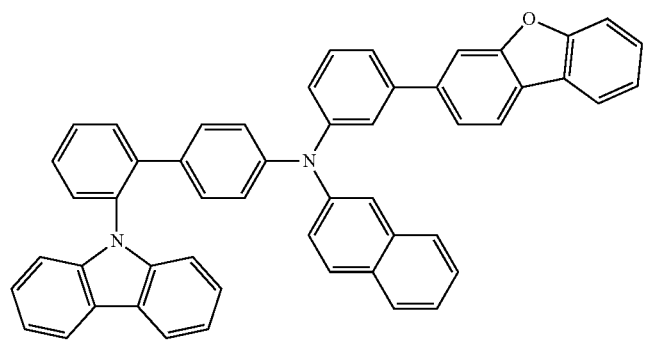
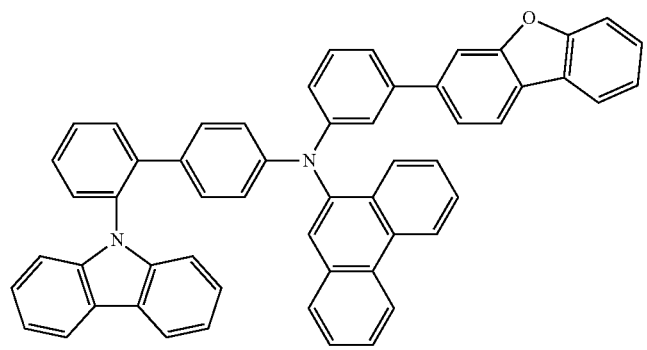
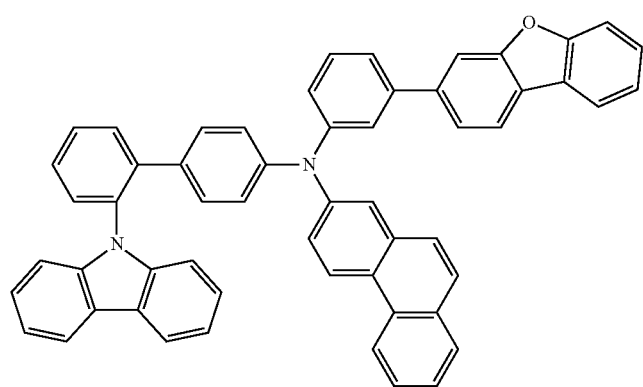
192
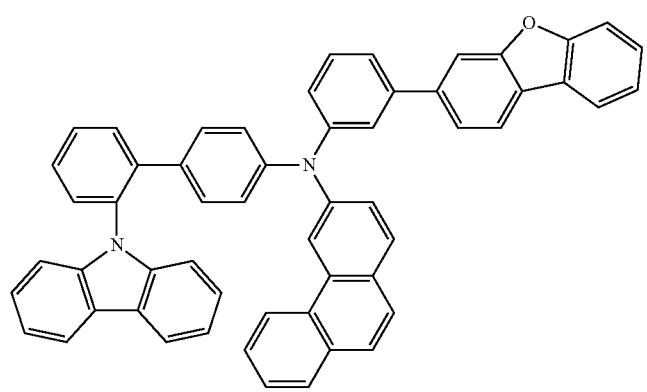
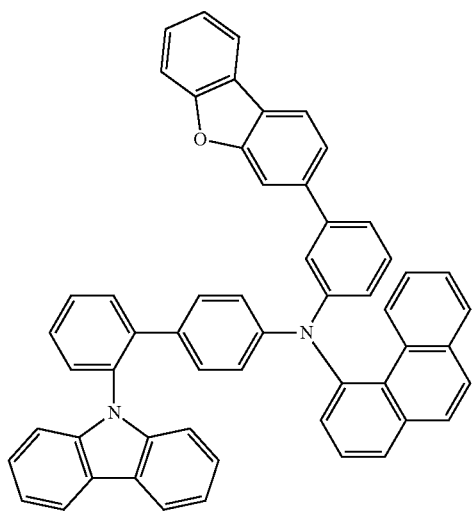

-continued
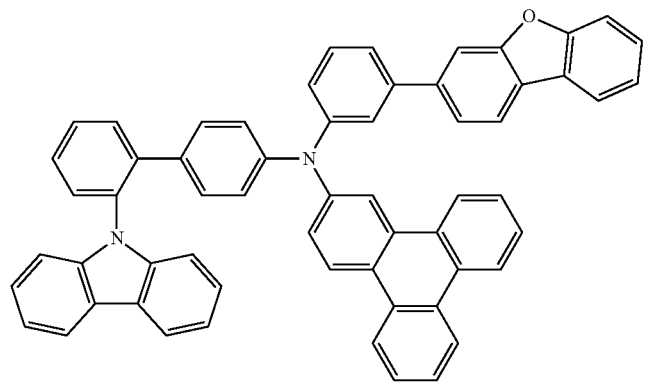
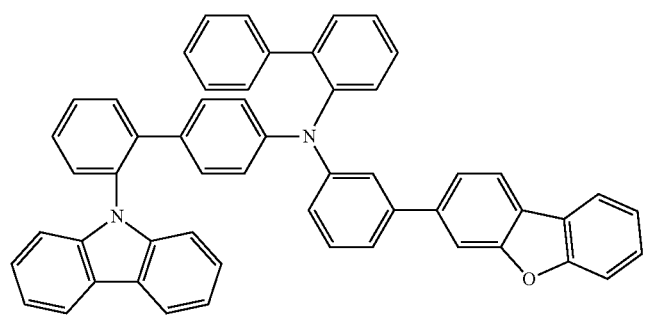
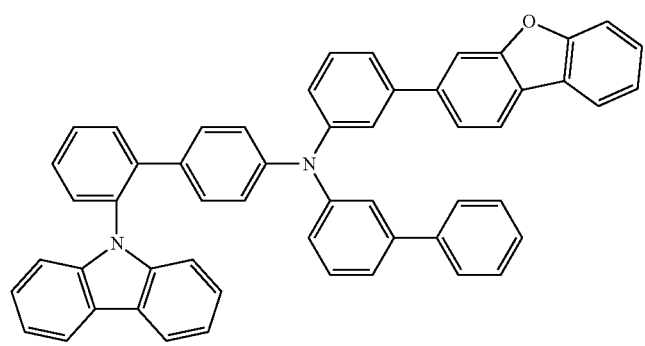
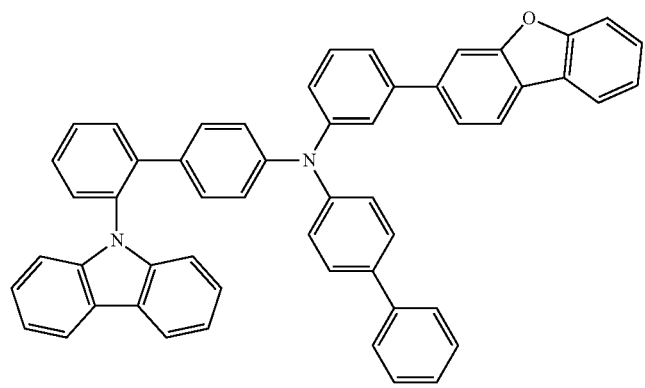

-continued
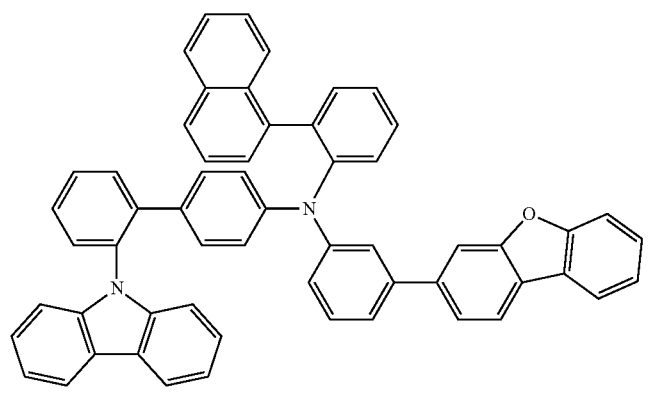
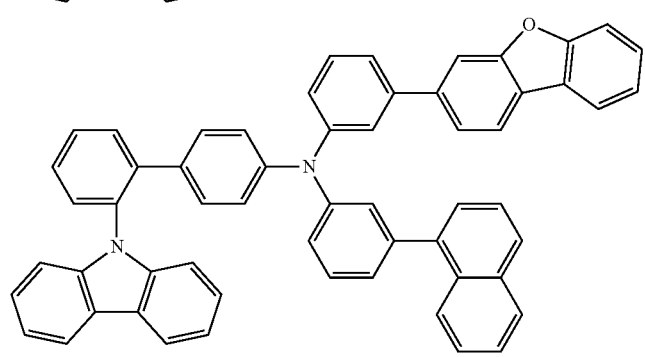
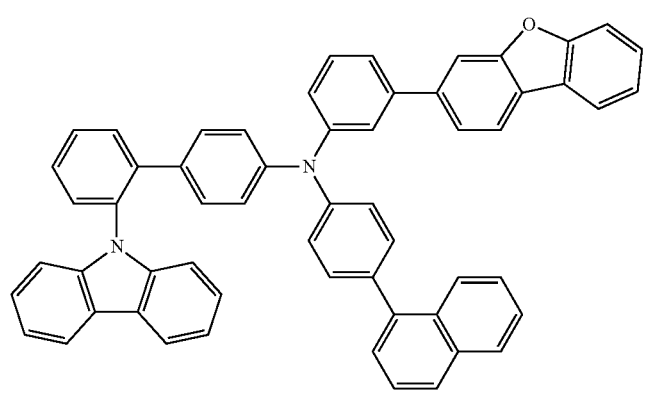
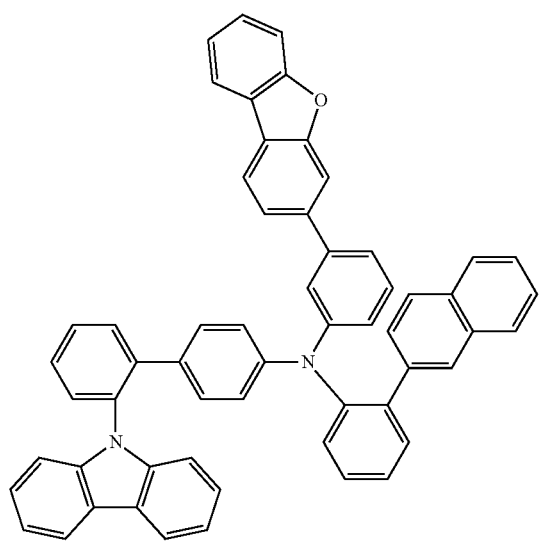
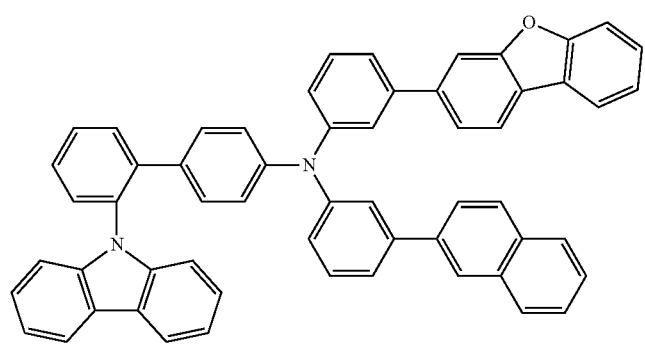

197
-continued
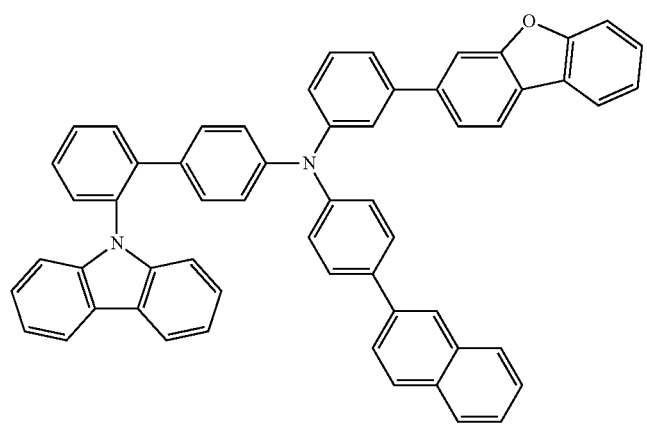
198
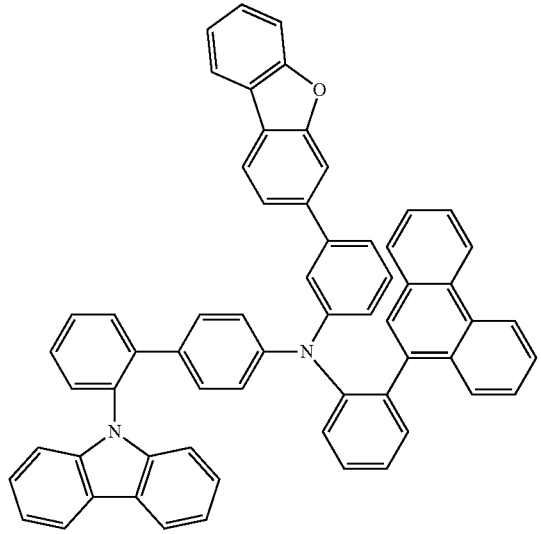
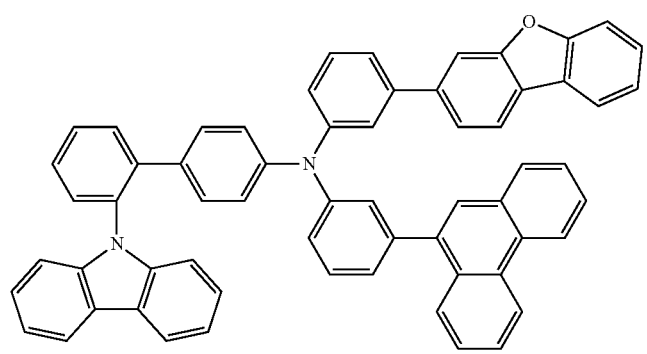
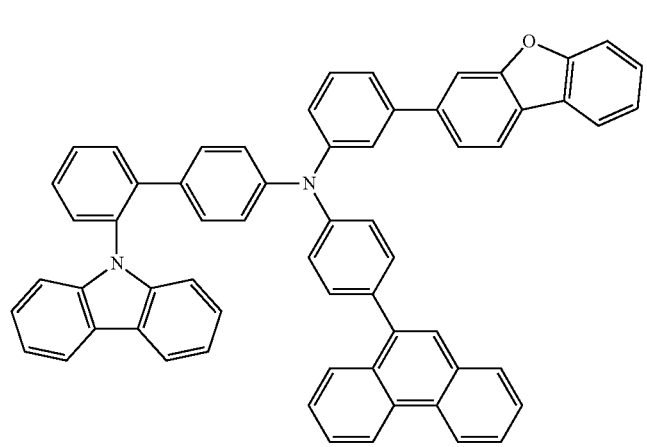
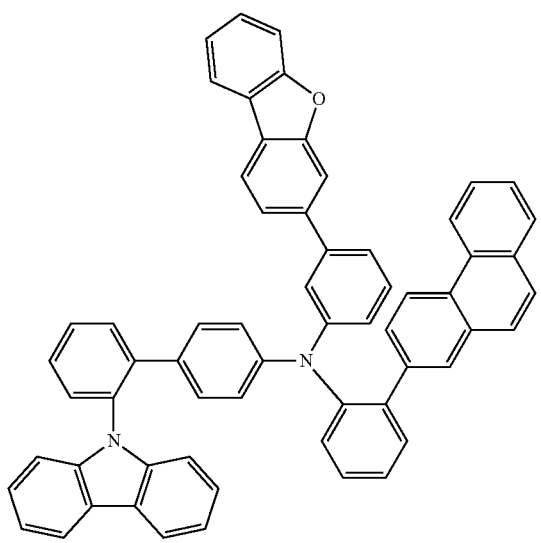

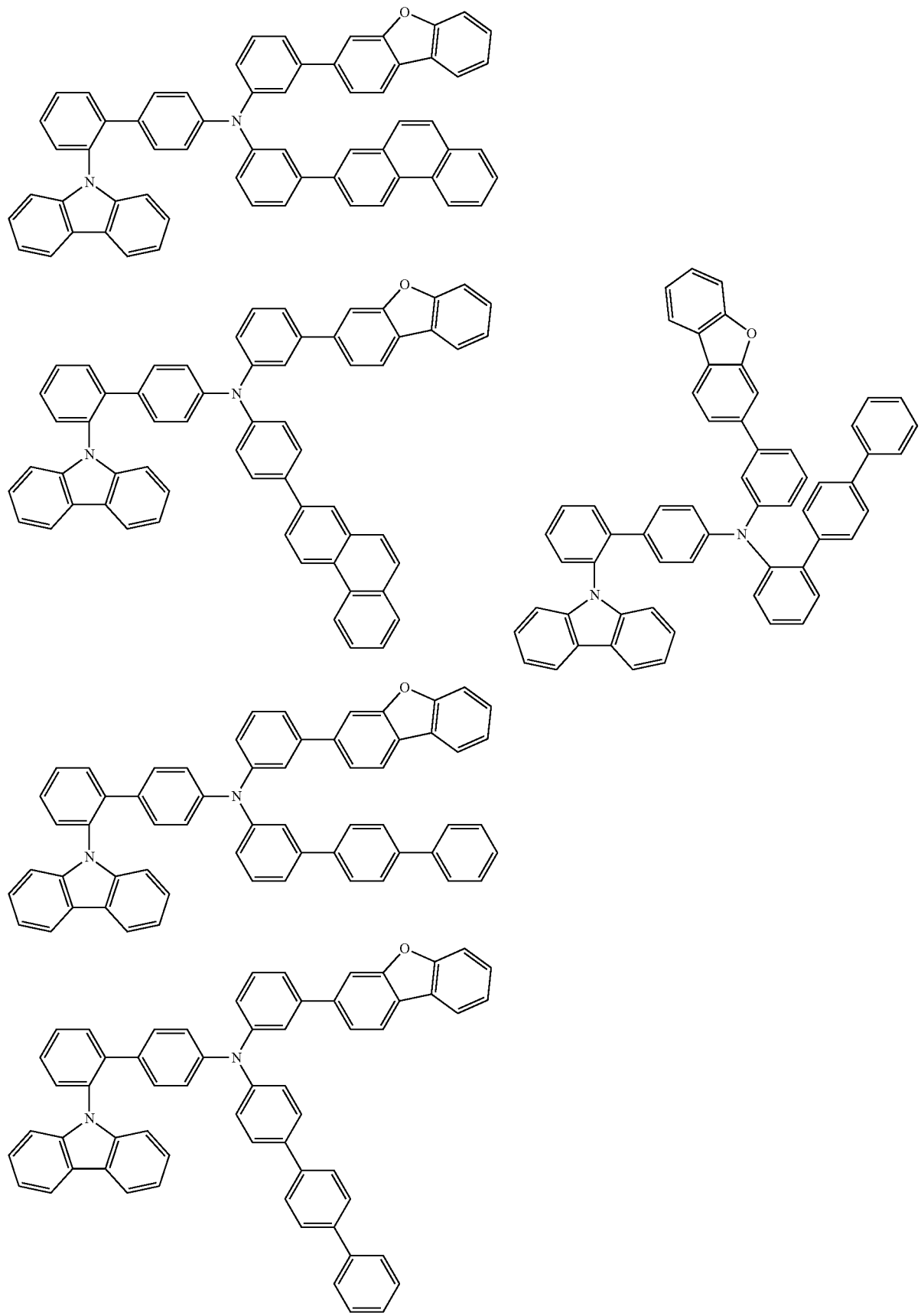

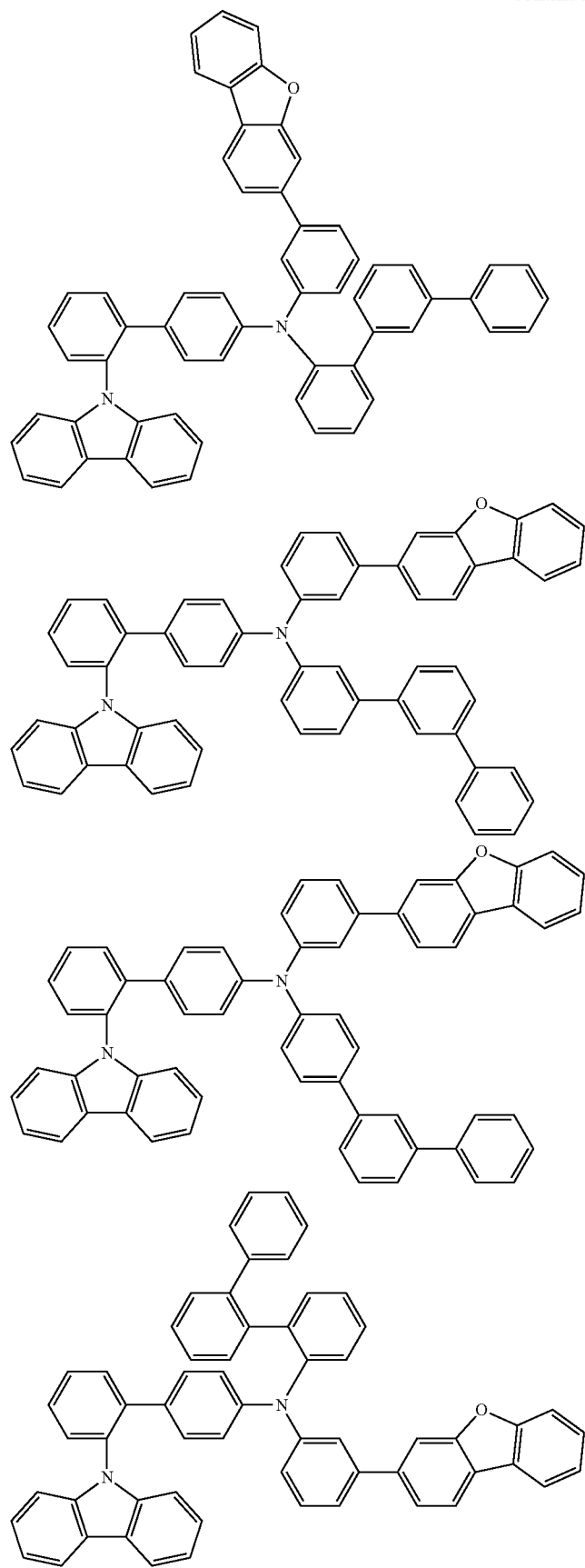

-continued
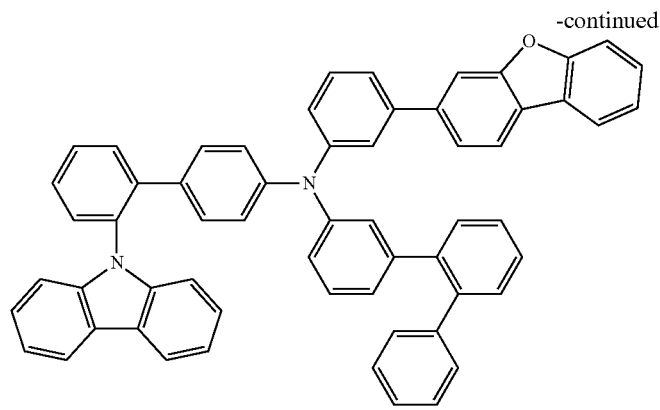
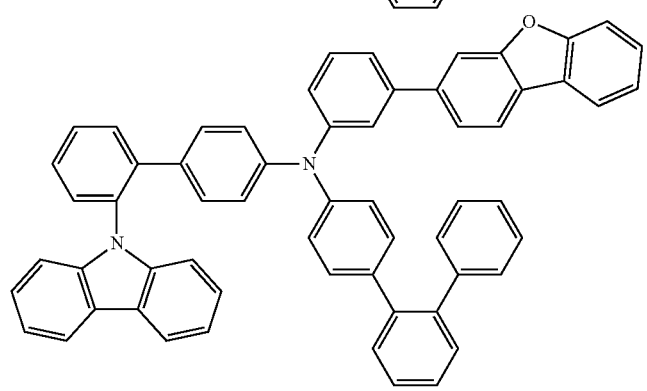
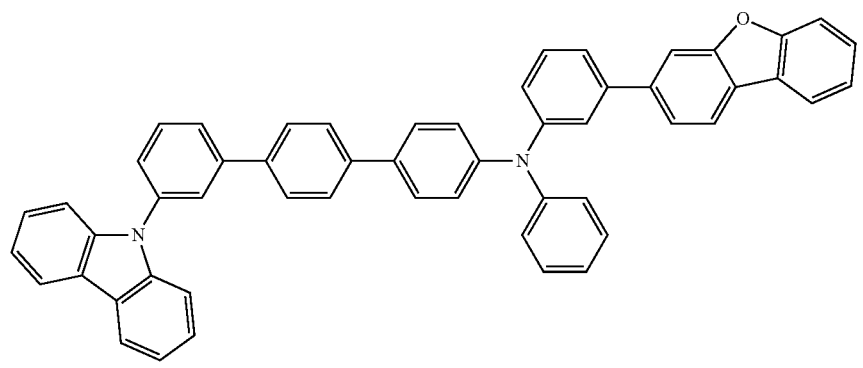
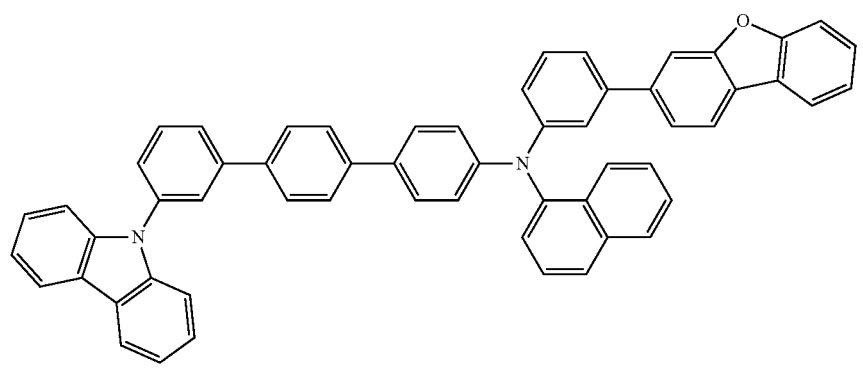

-continued
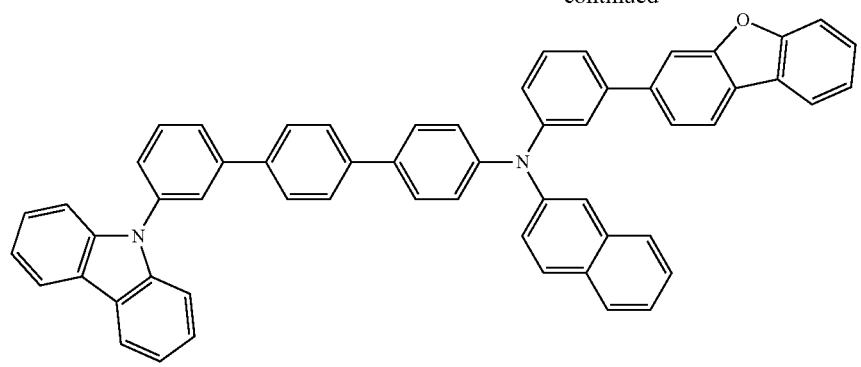
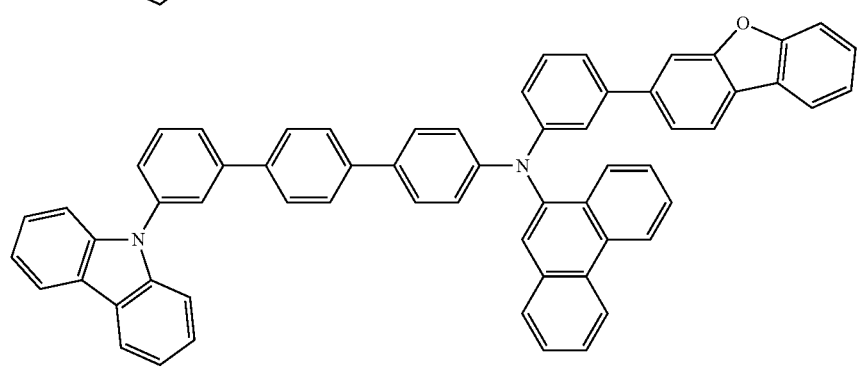
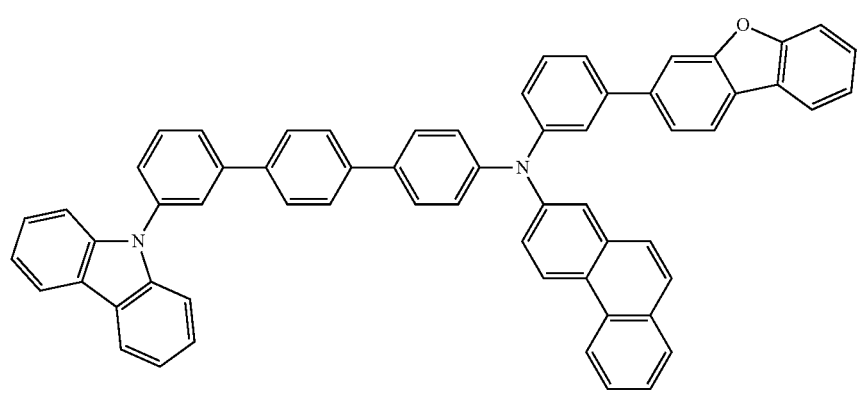
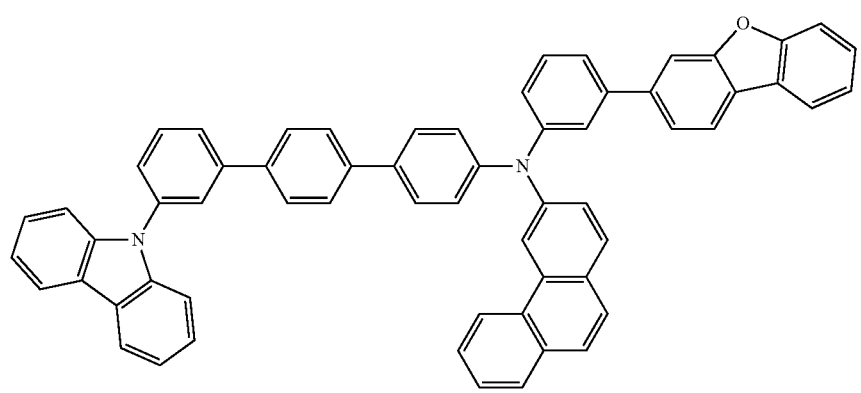

-continued
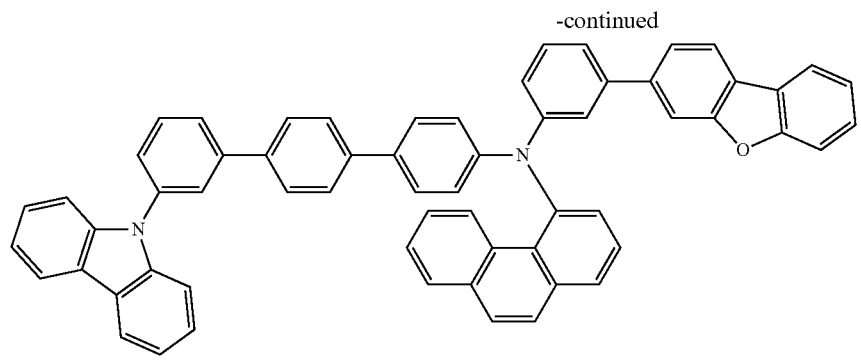
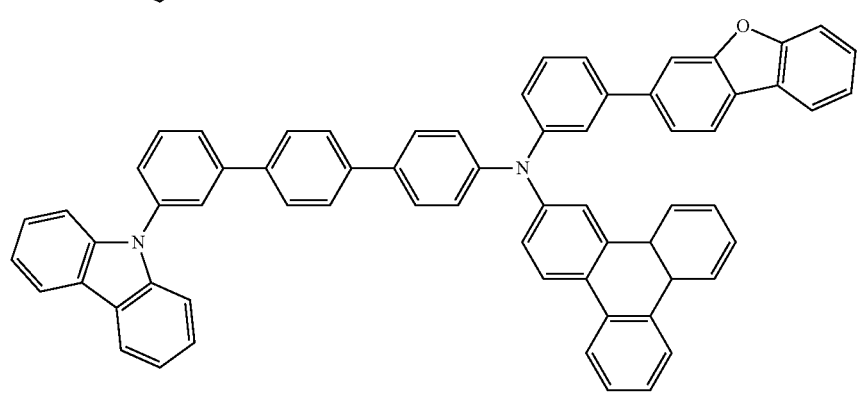
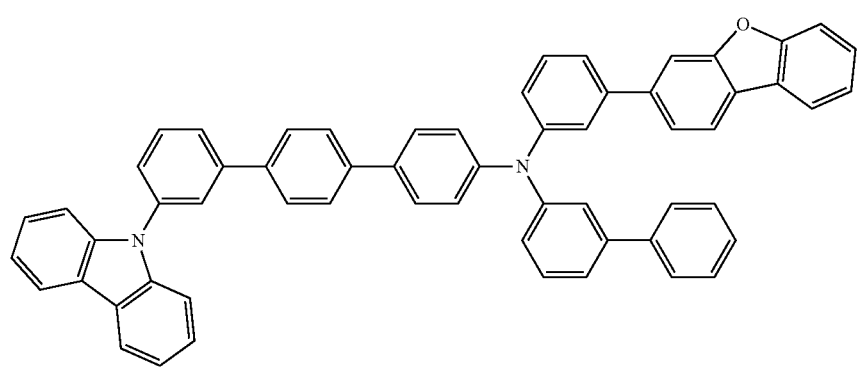
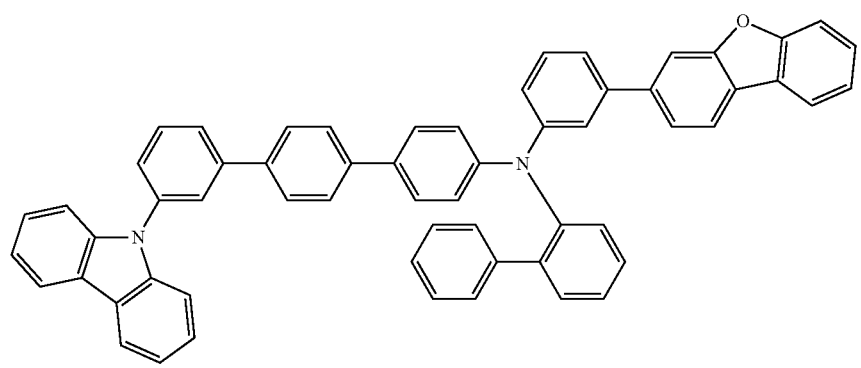

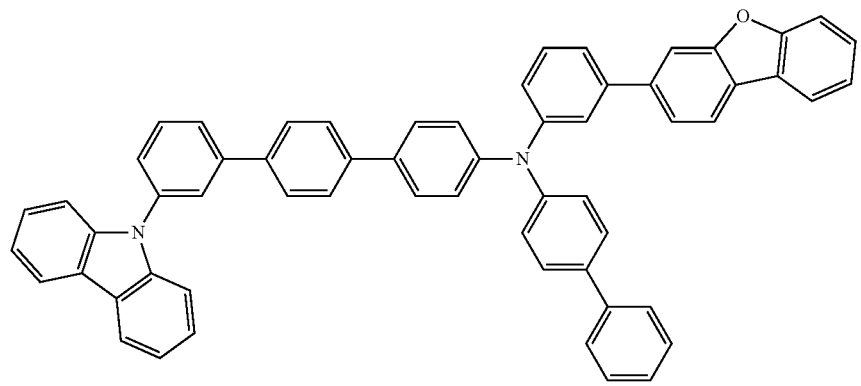
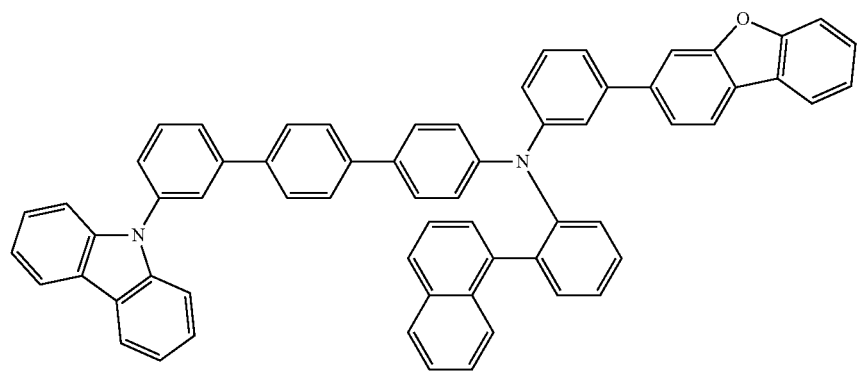
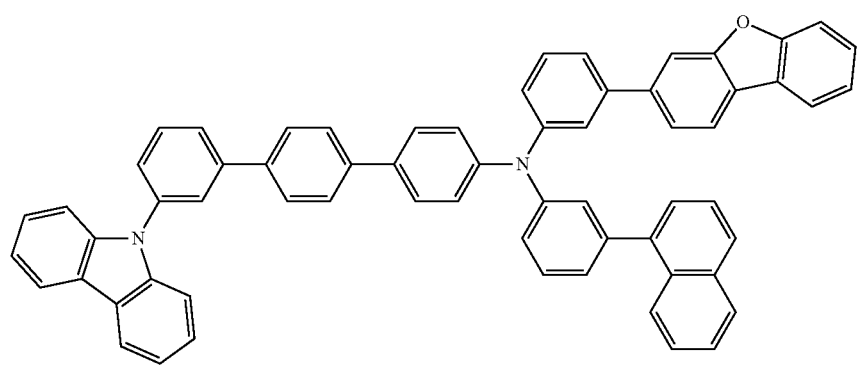
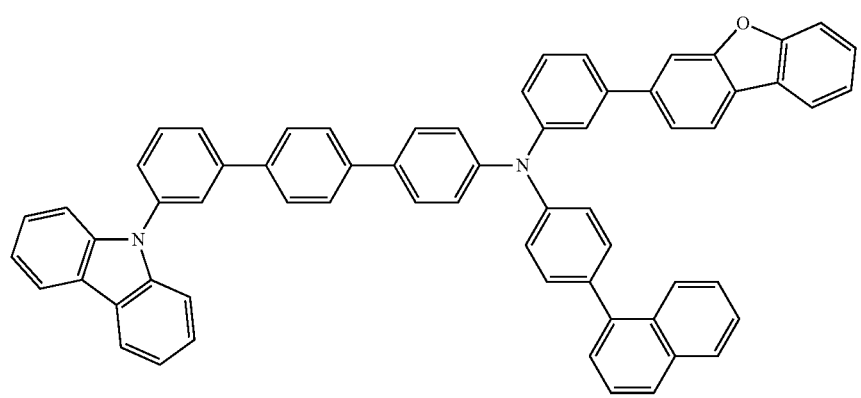

-continued
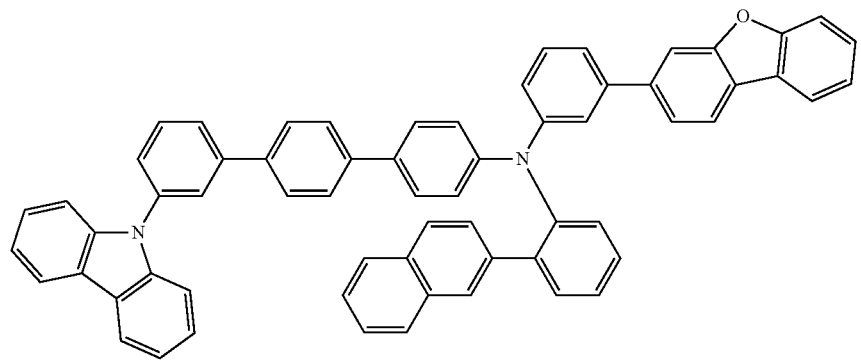
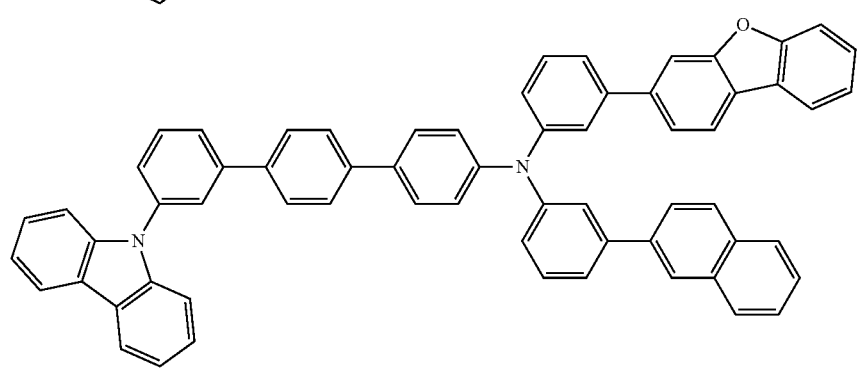
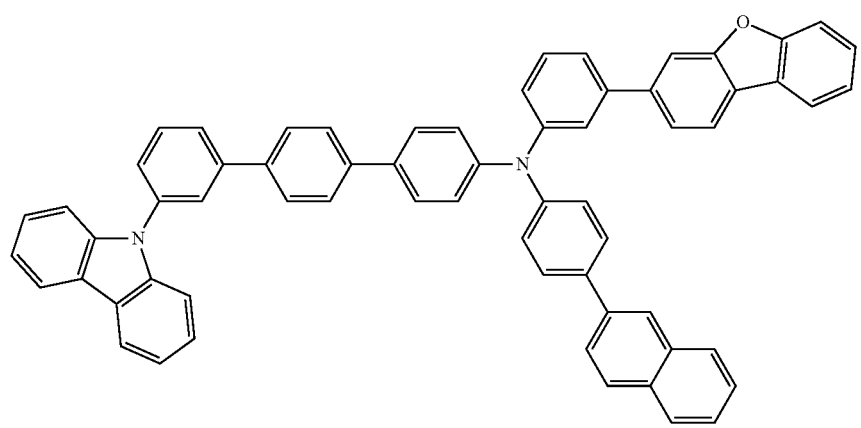
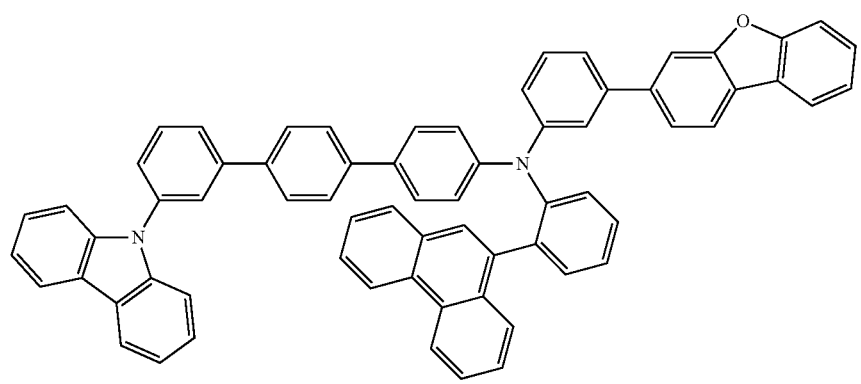

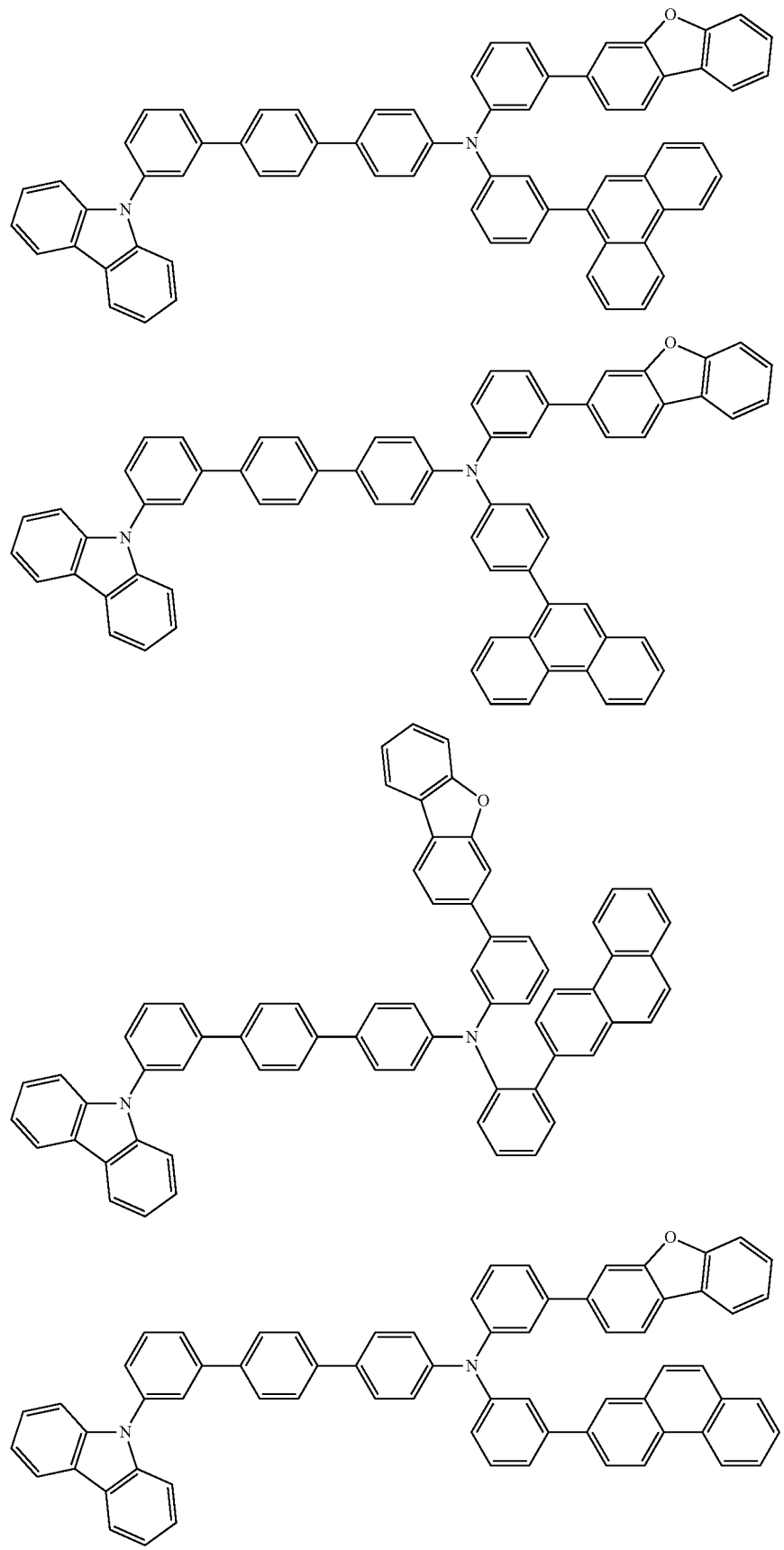

-continued
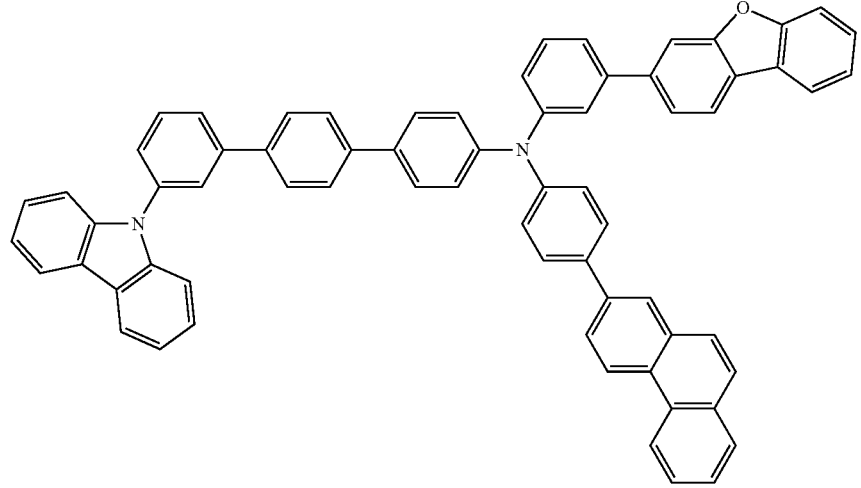
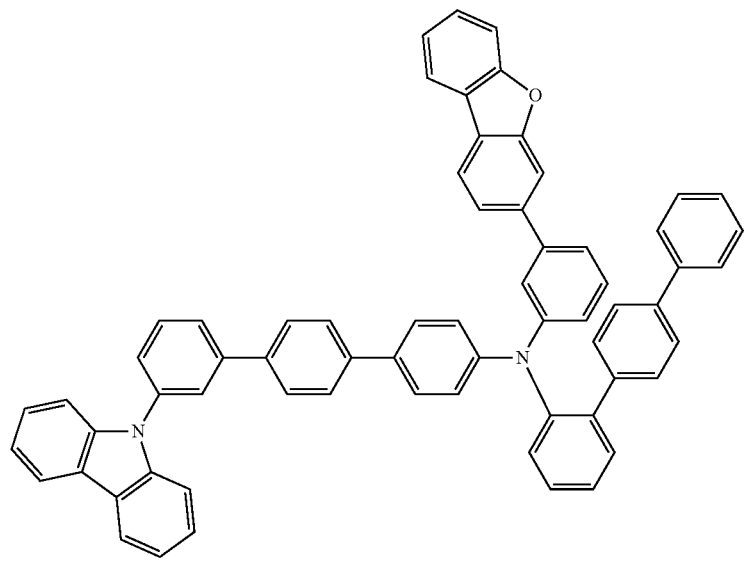
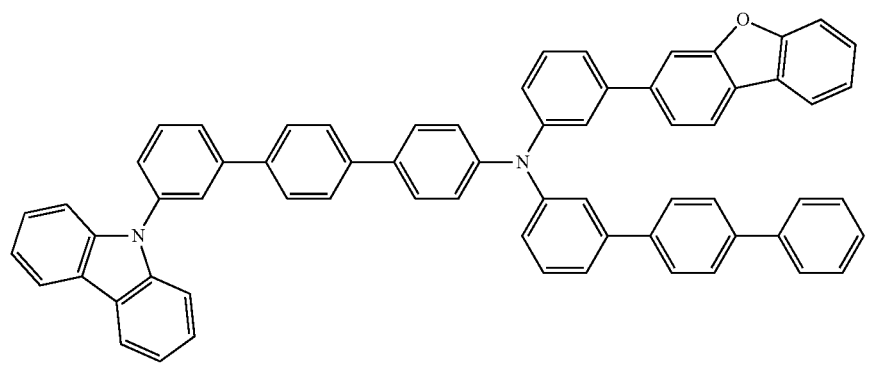

-continued
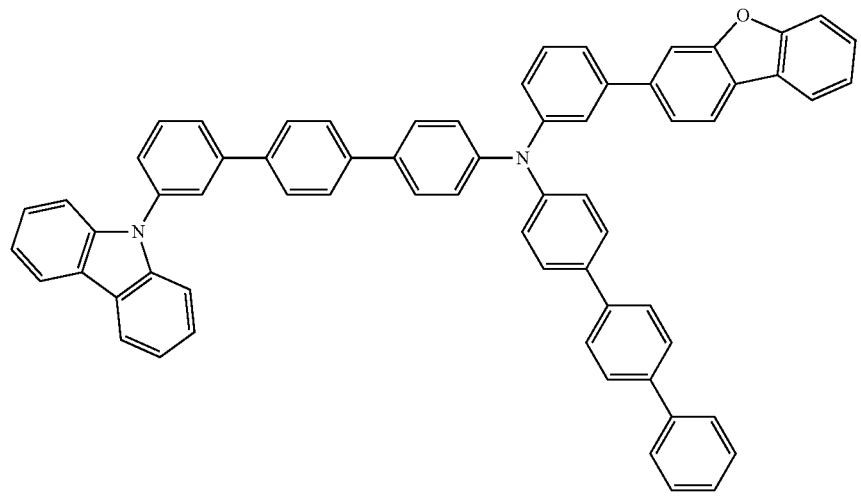
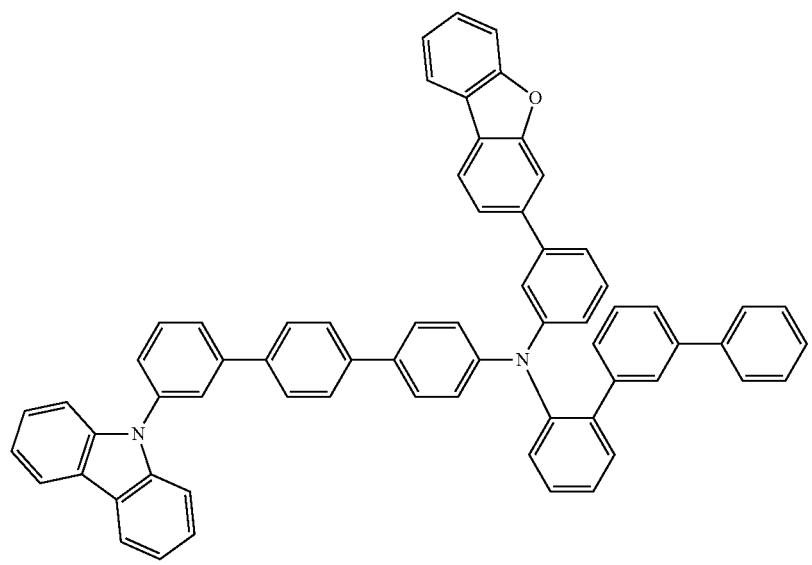
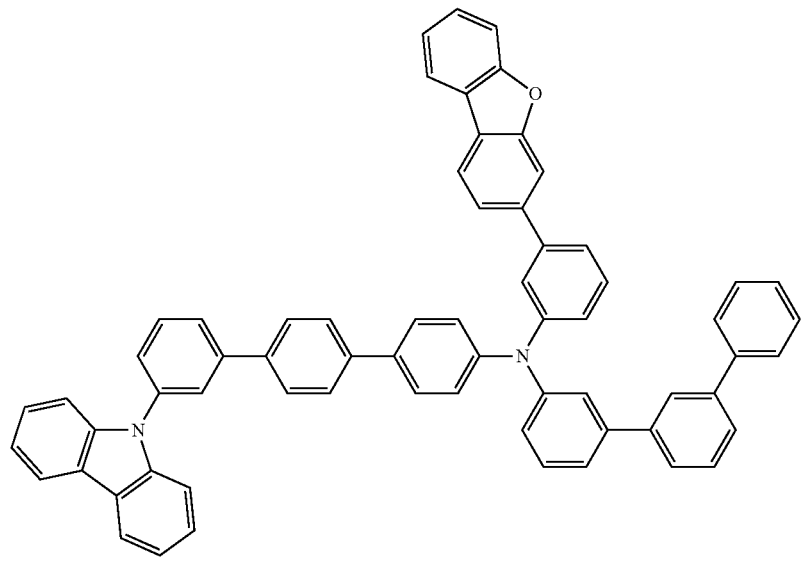

-continued
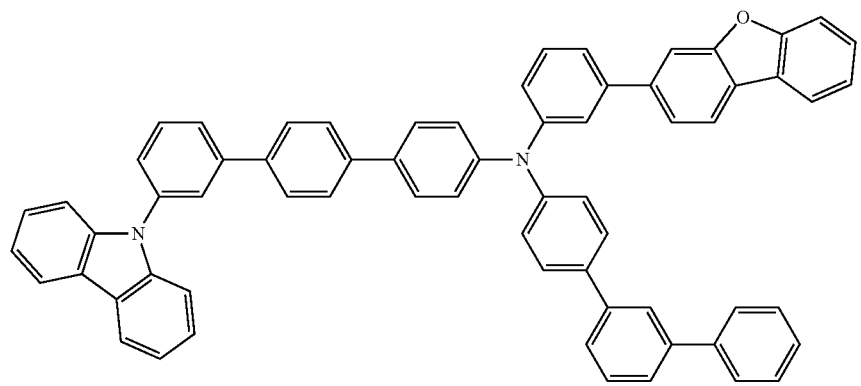
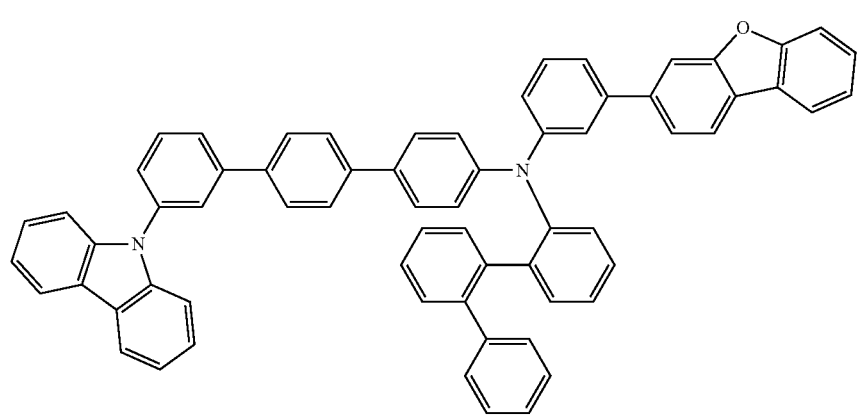
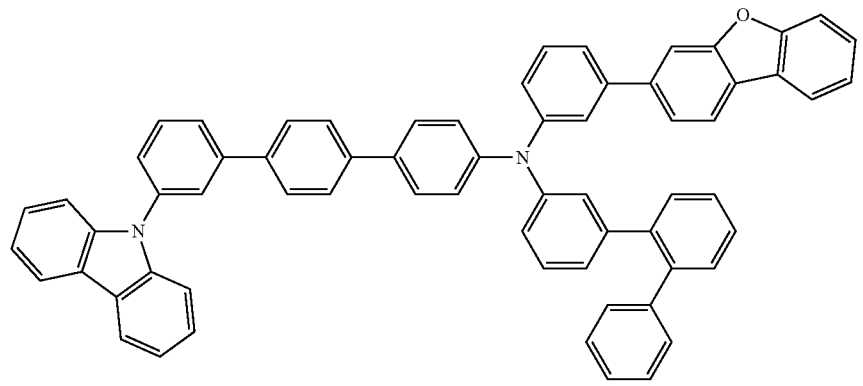
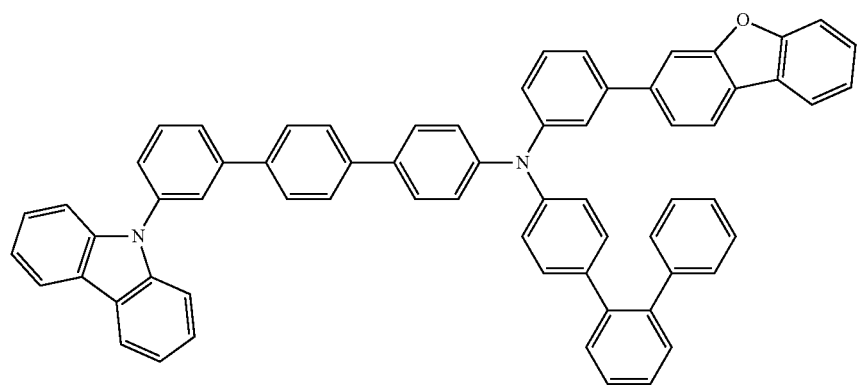

-continued
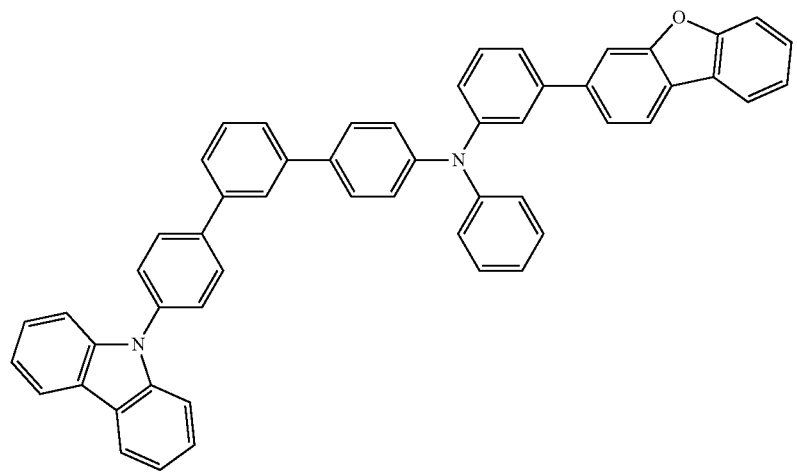
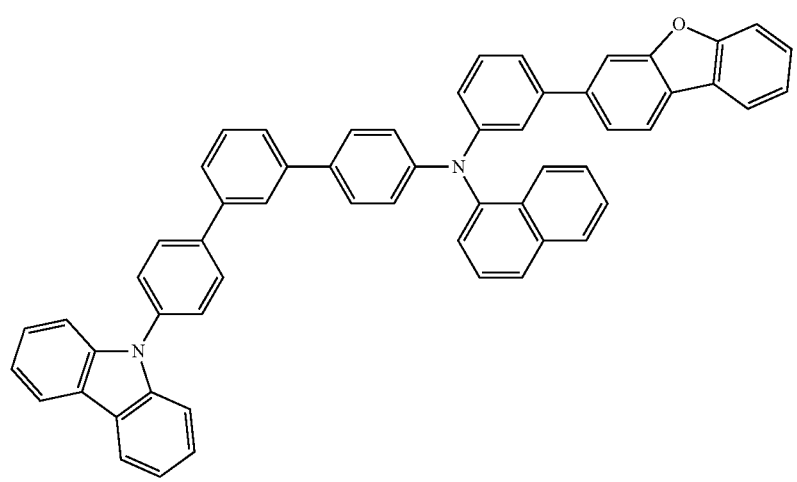
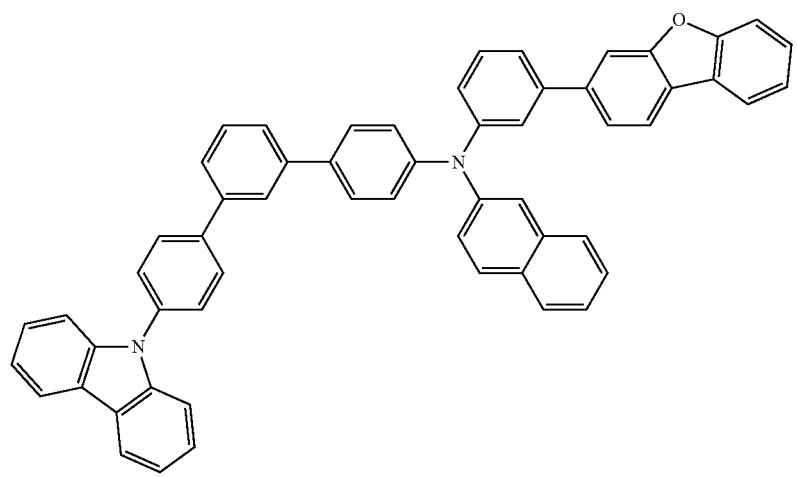

-continued
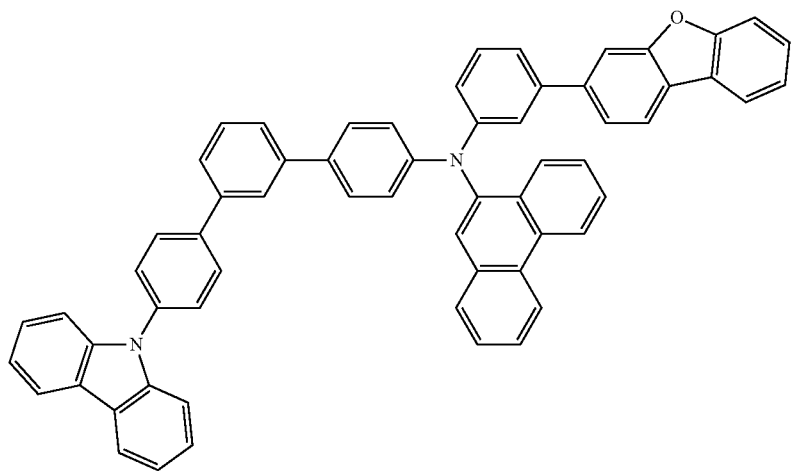
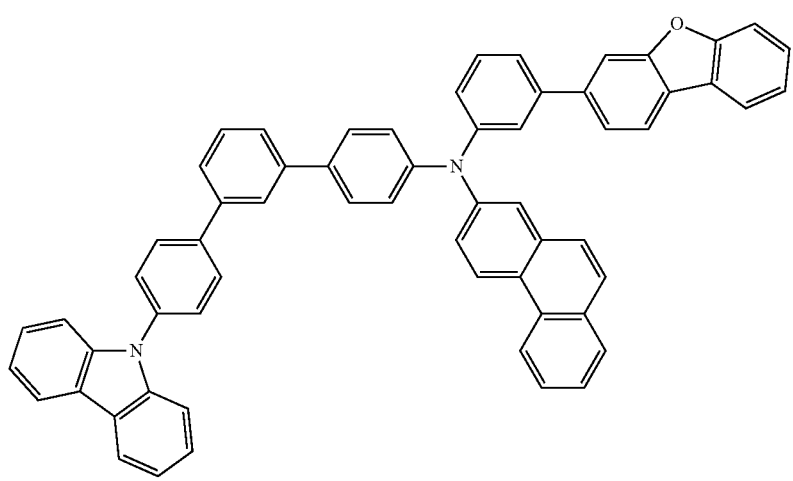
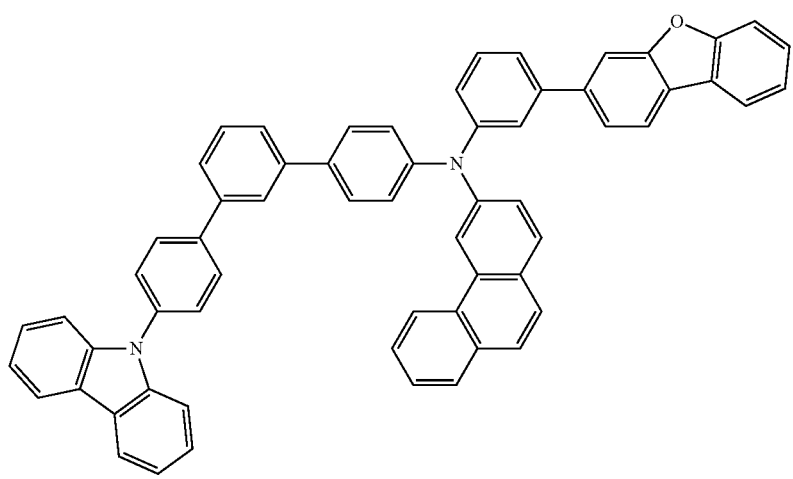

-continued
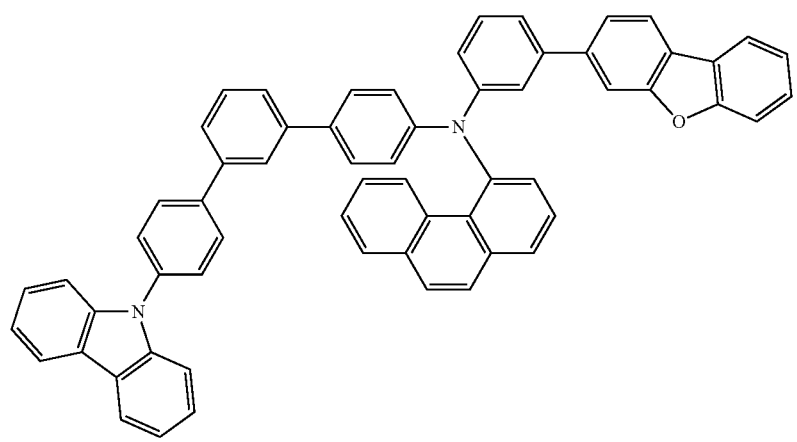
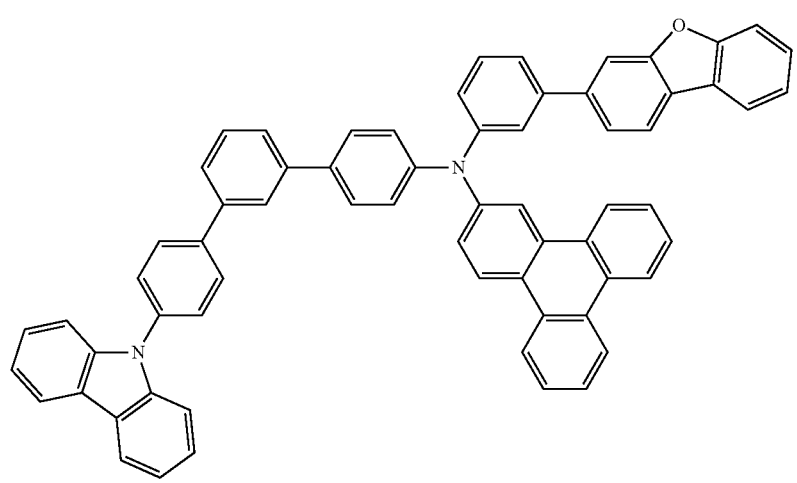
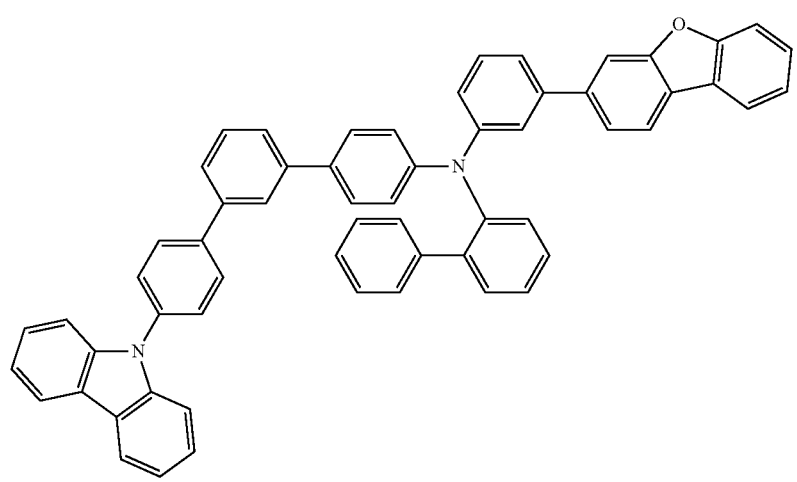

-continued
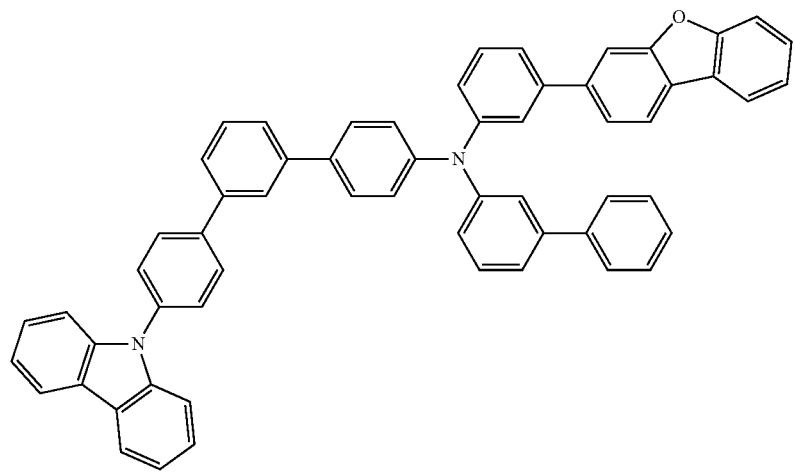
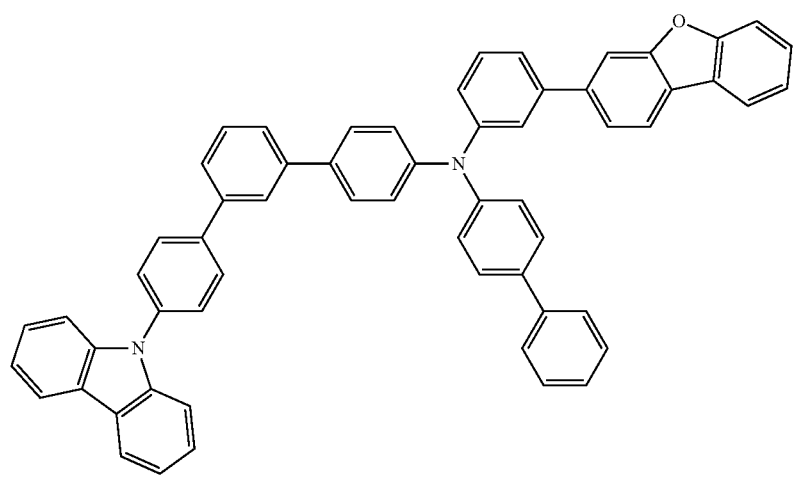
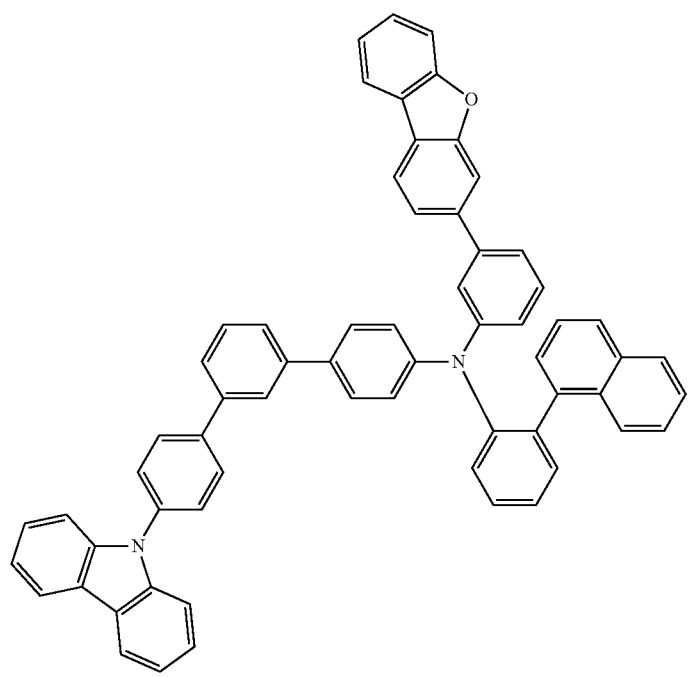

-continued
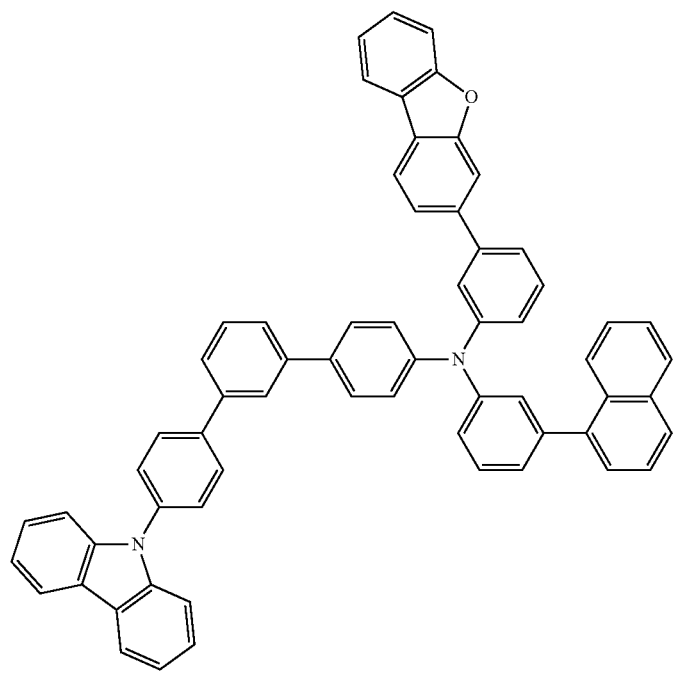
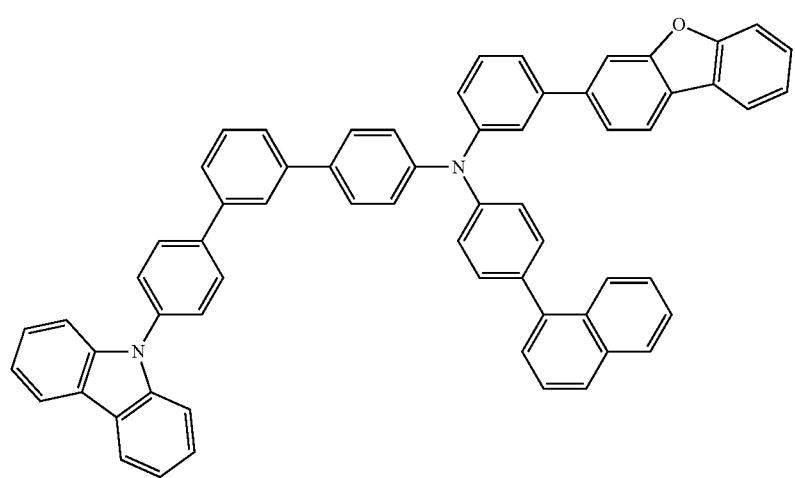

-continued
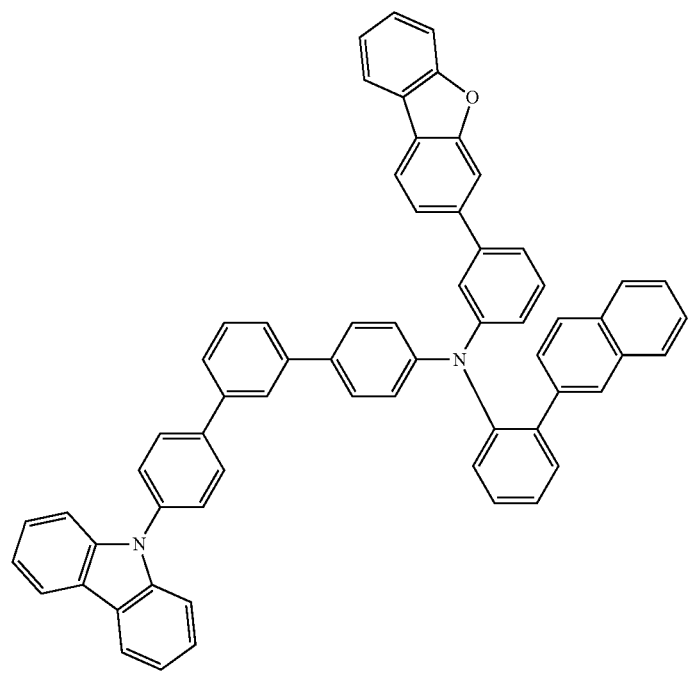
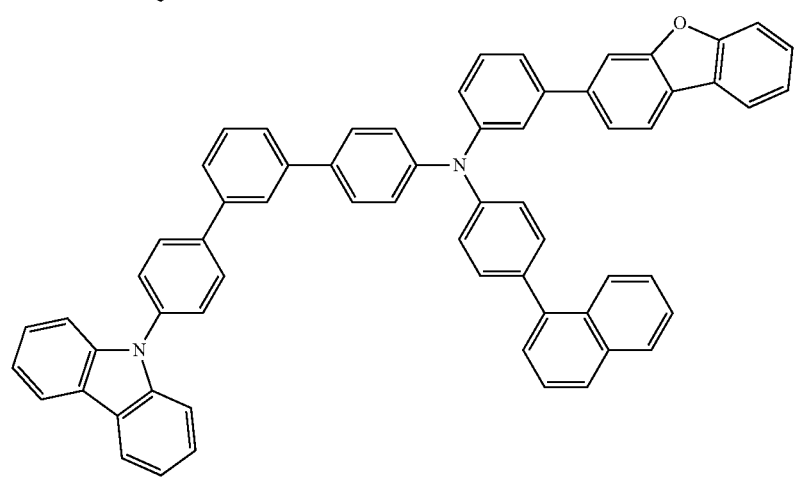
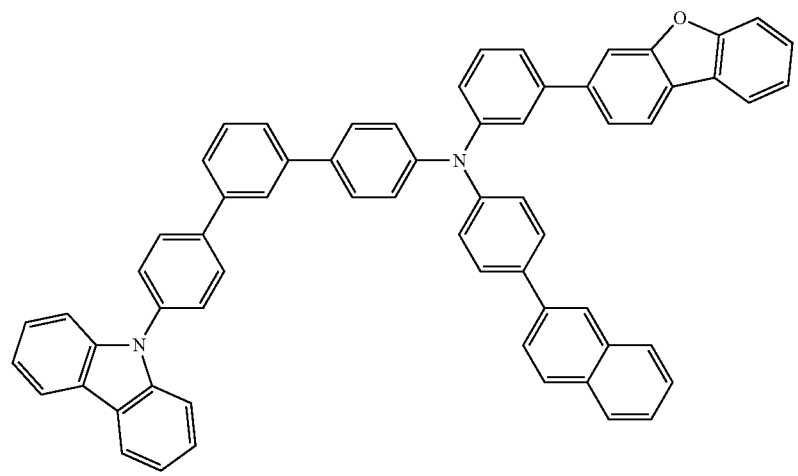

-continued
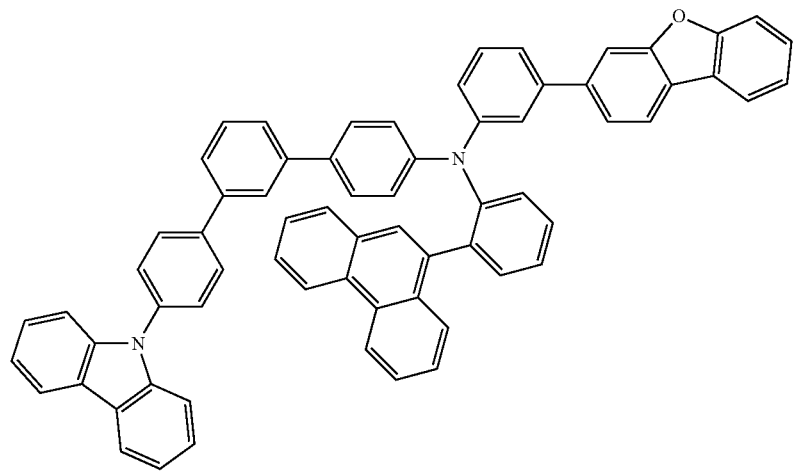
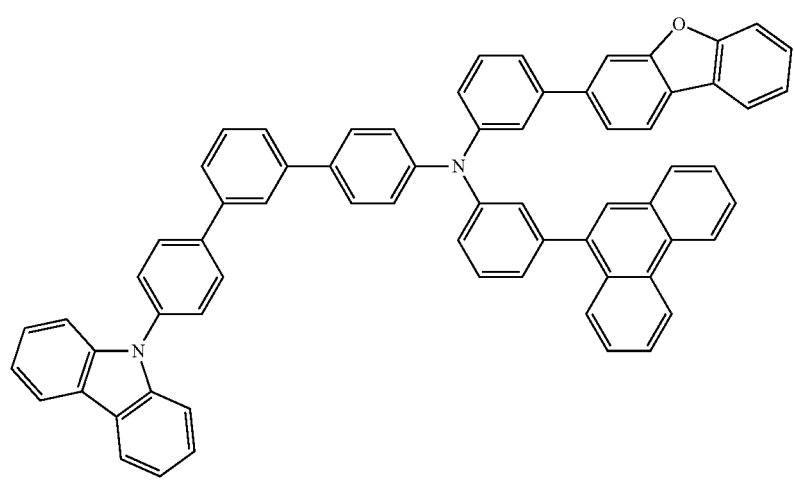
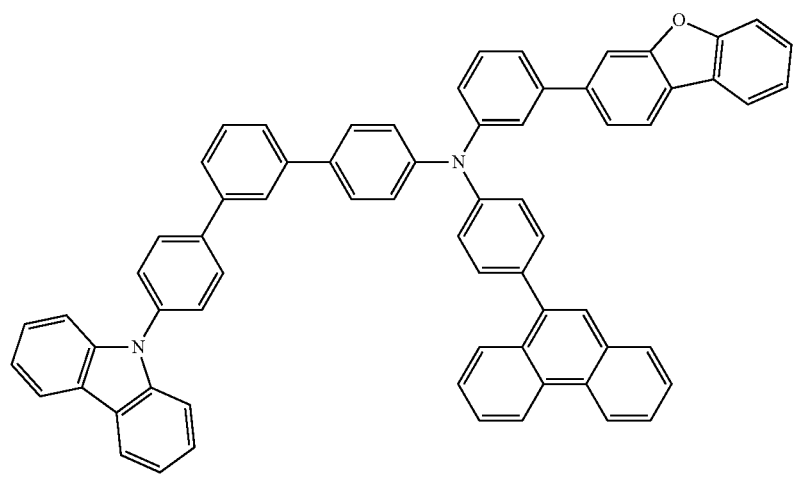

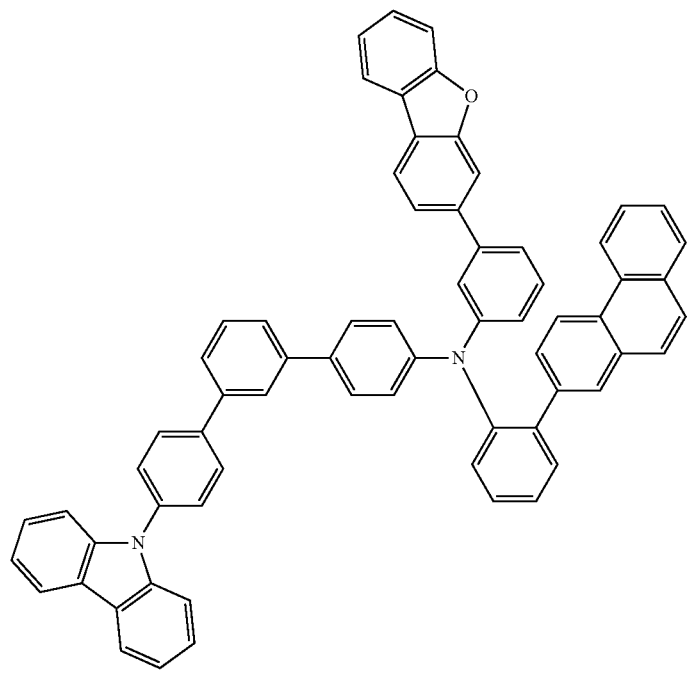
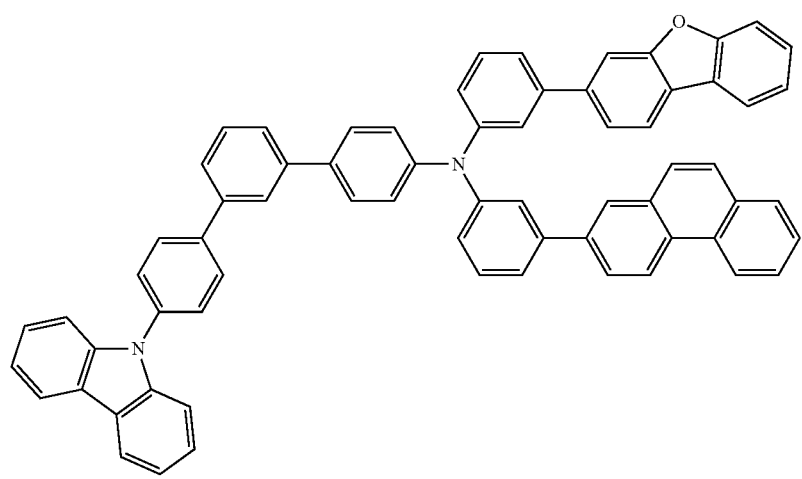
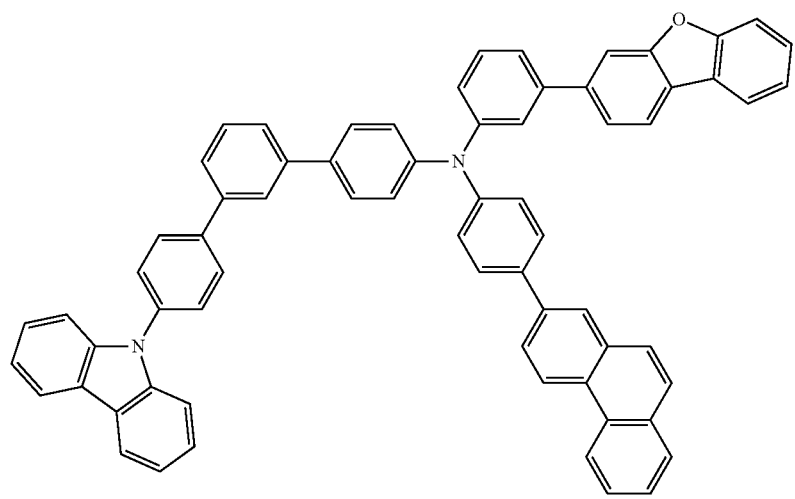

-continued
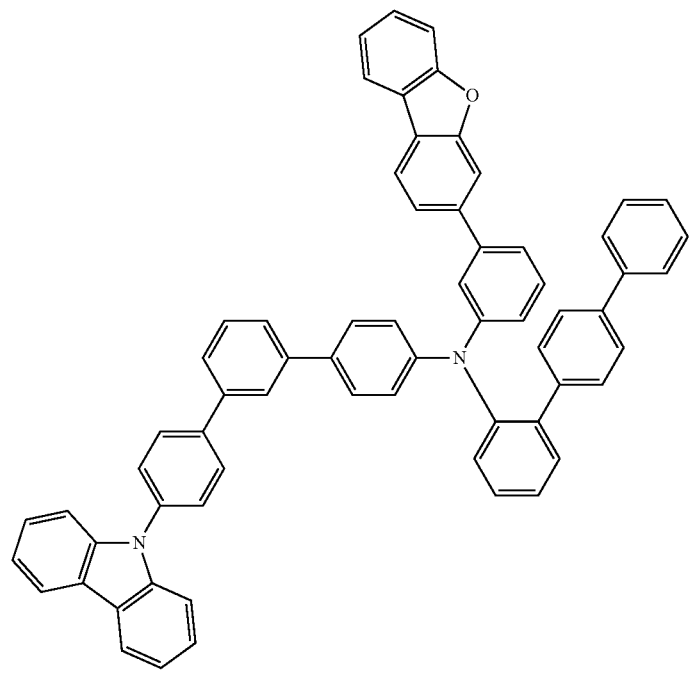
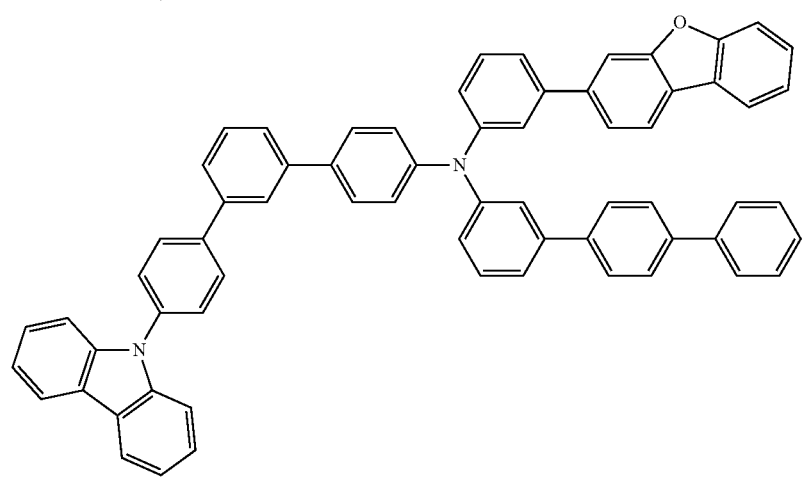
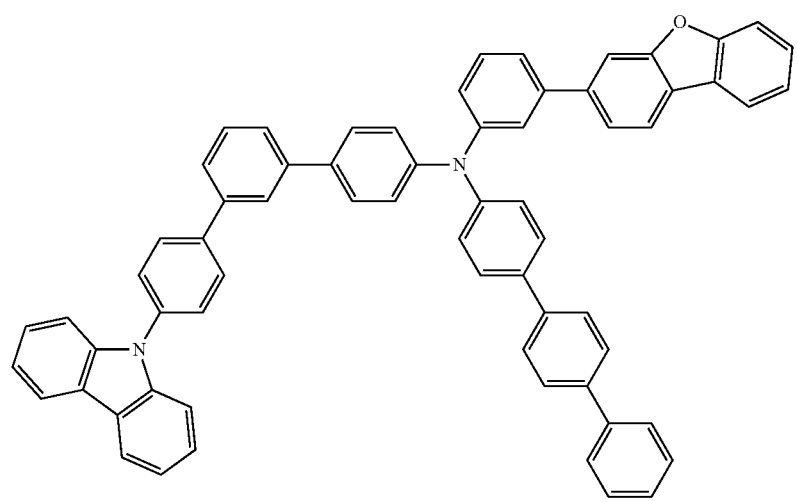

-continued
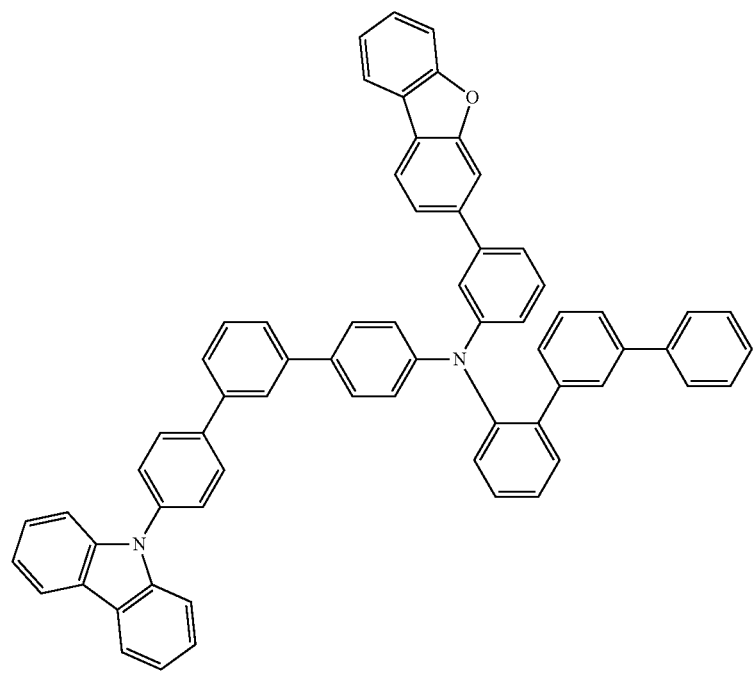
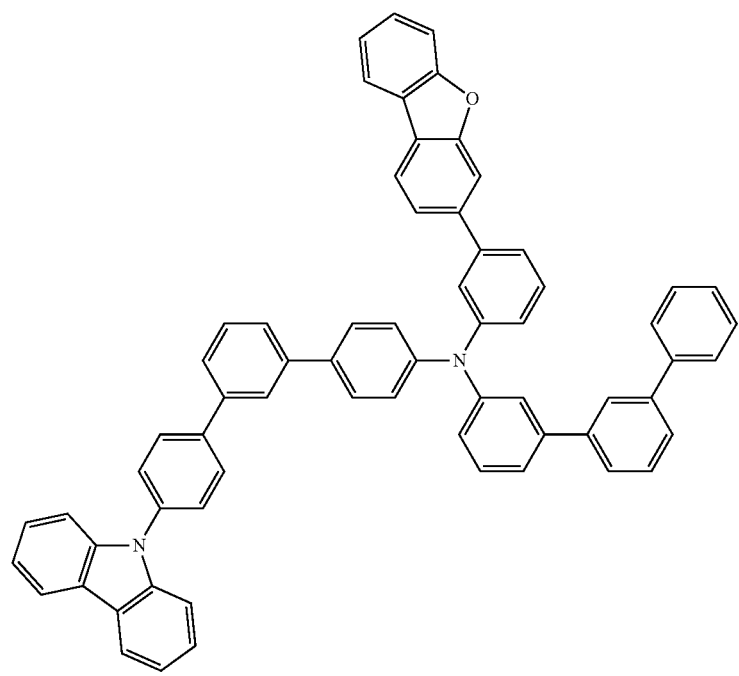

-continued
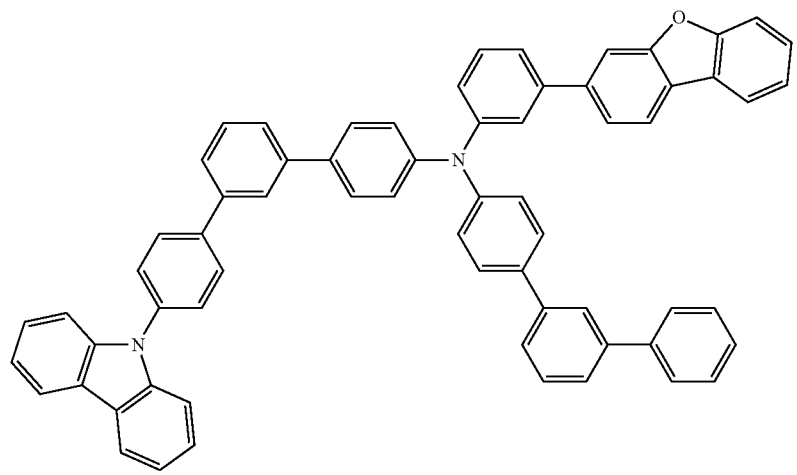
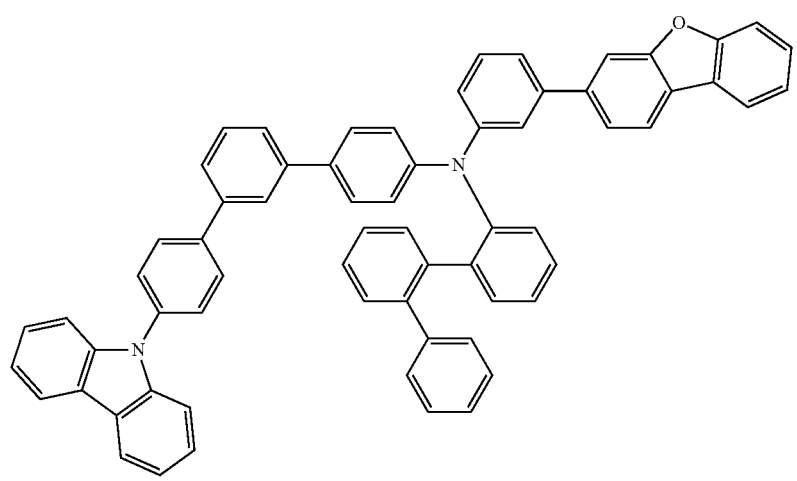
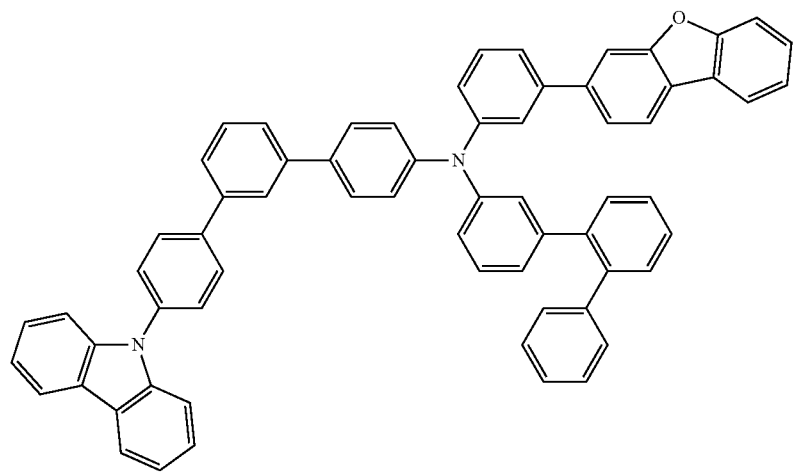

-continued
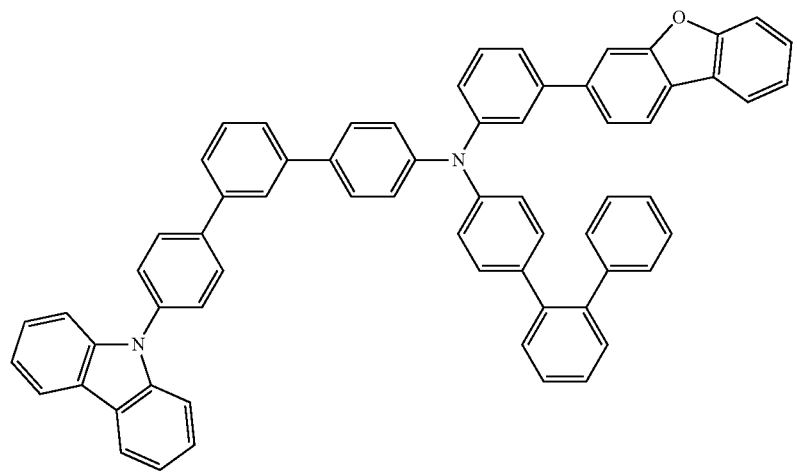
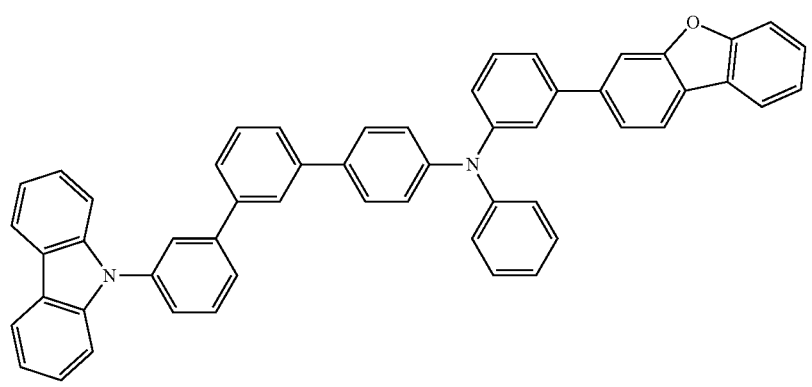
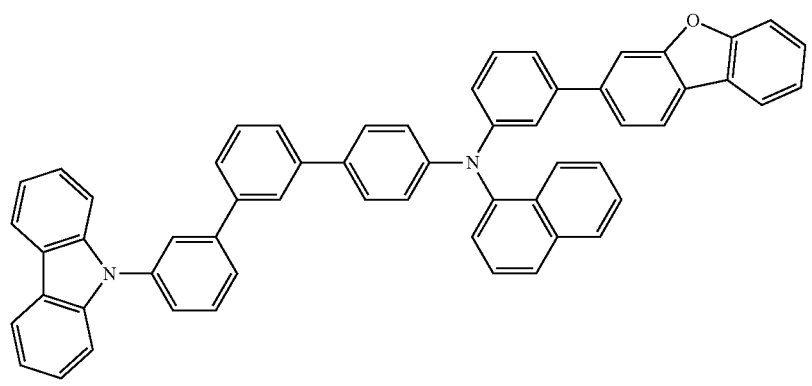
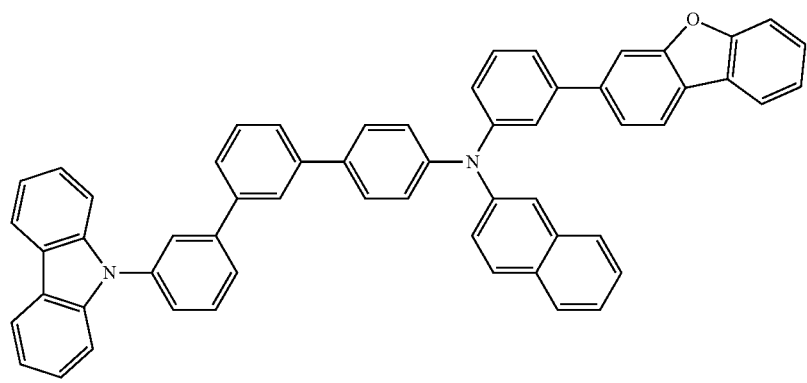

-continued
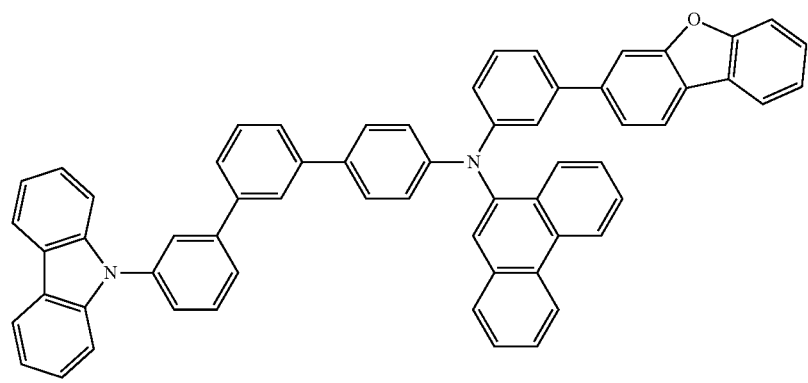
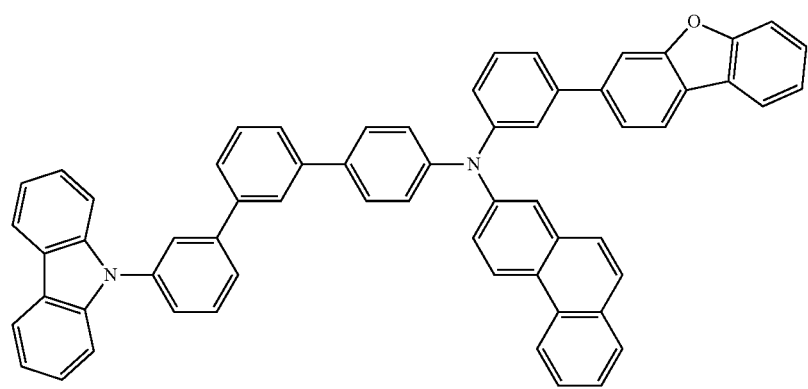
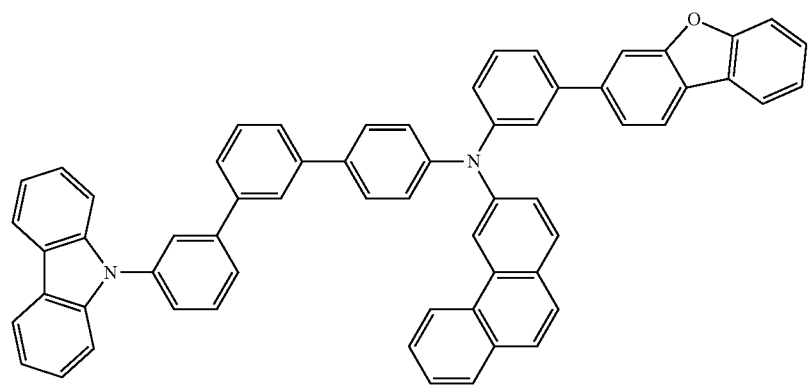
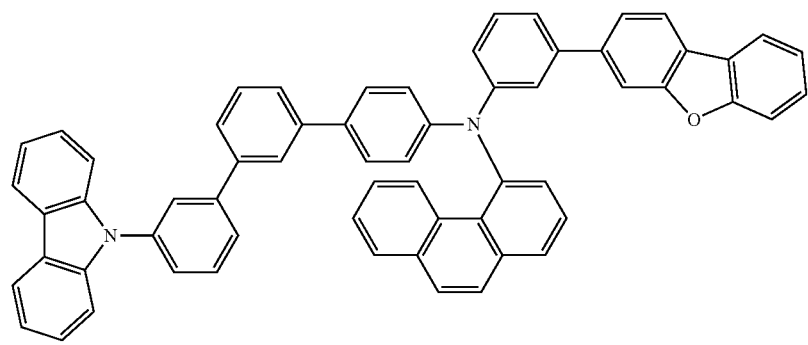

-continued
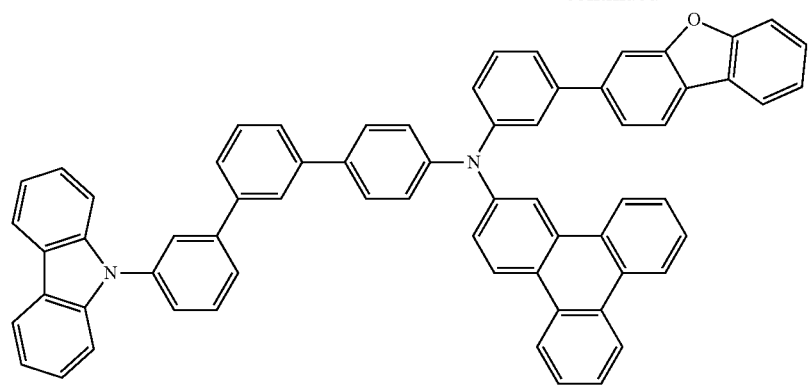
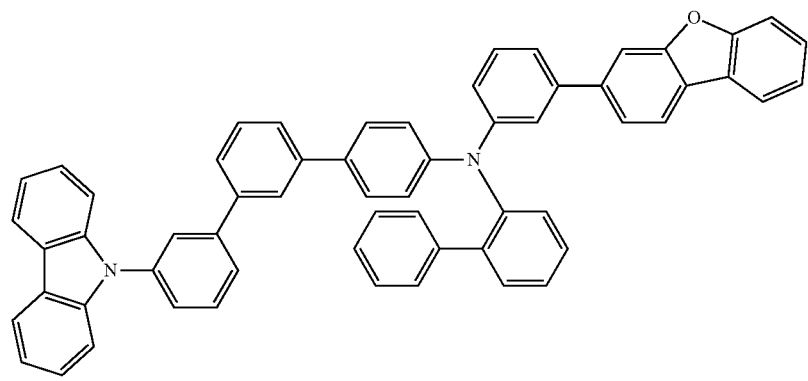
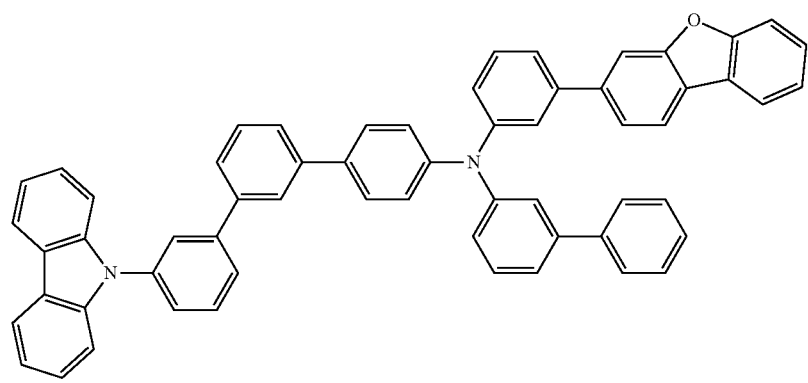
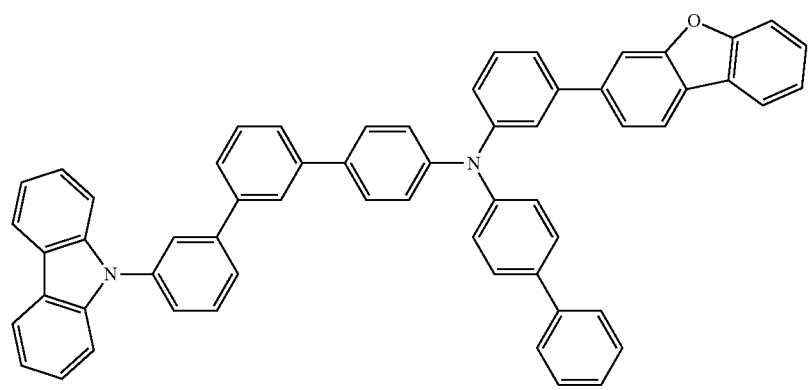

-continued
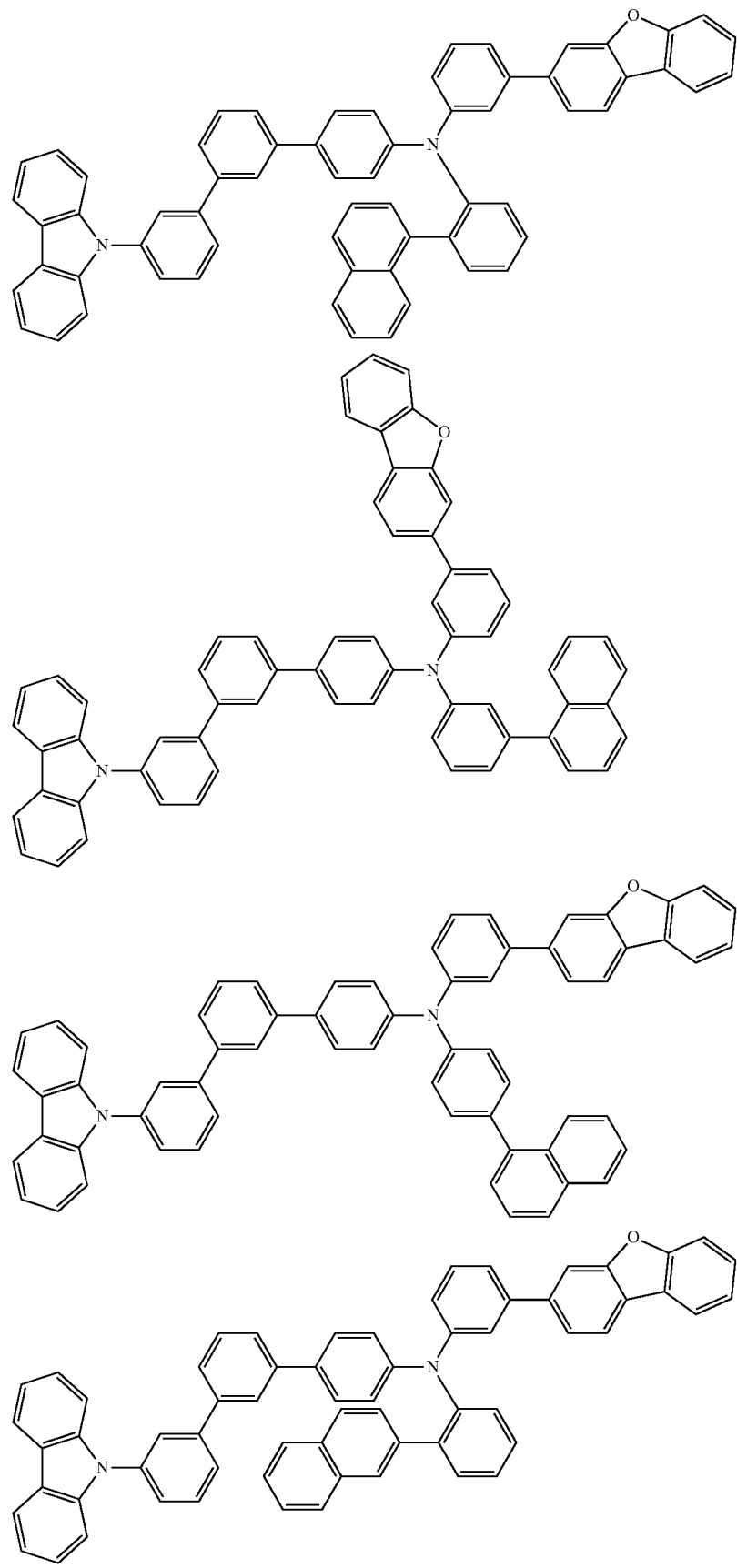

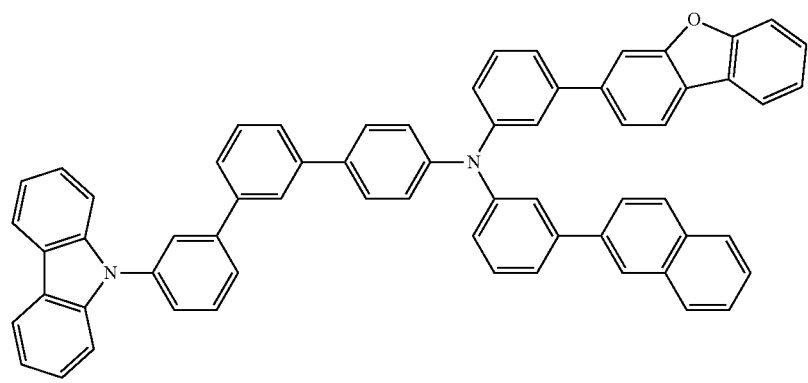
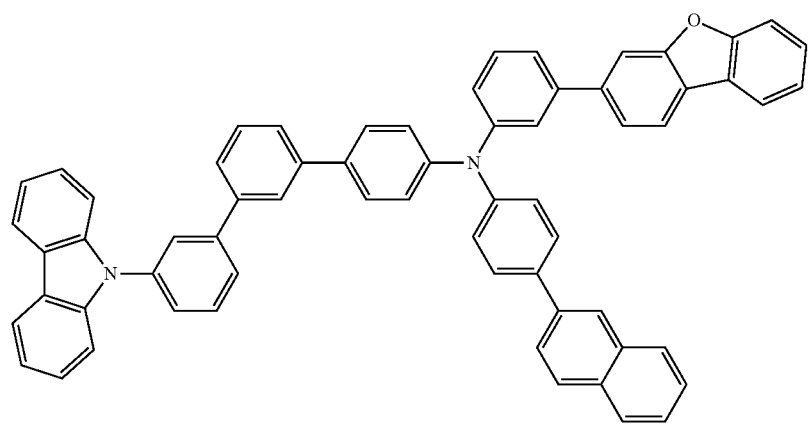
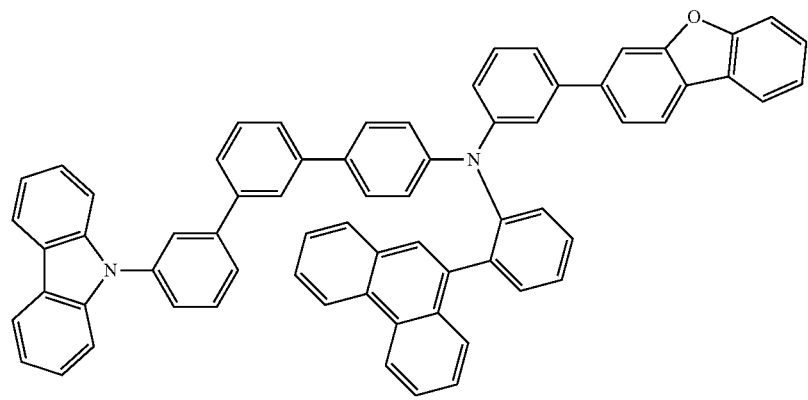
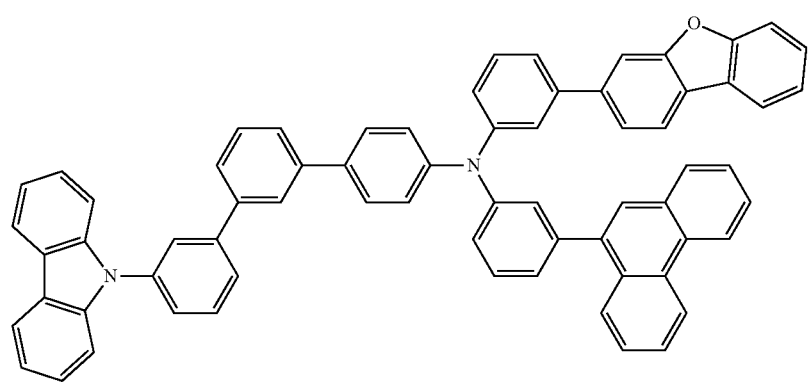

-continued
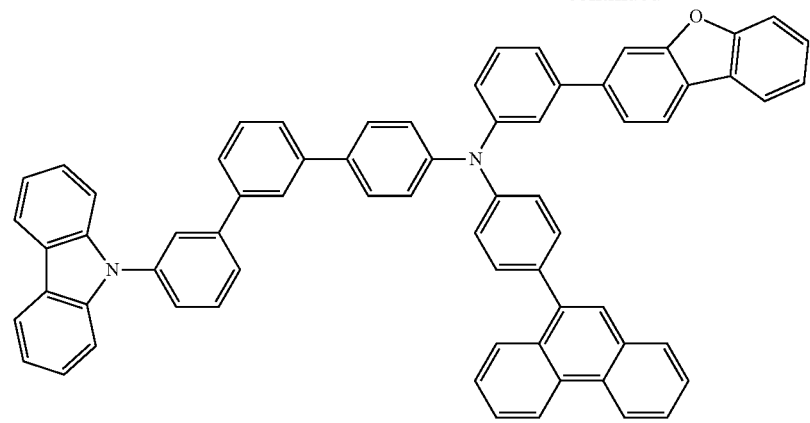
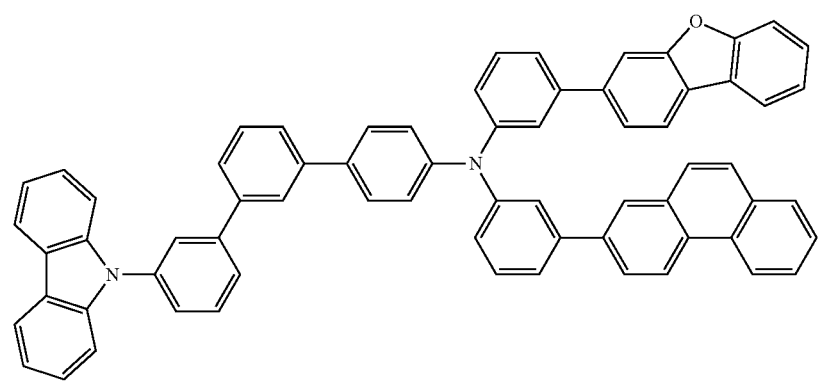
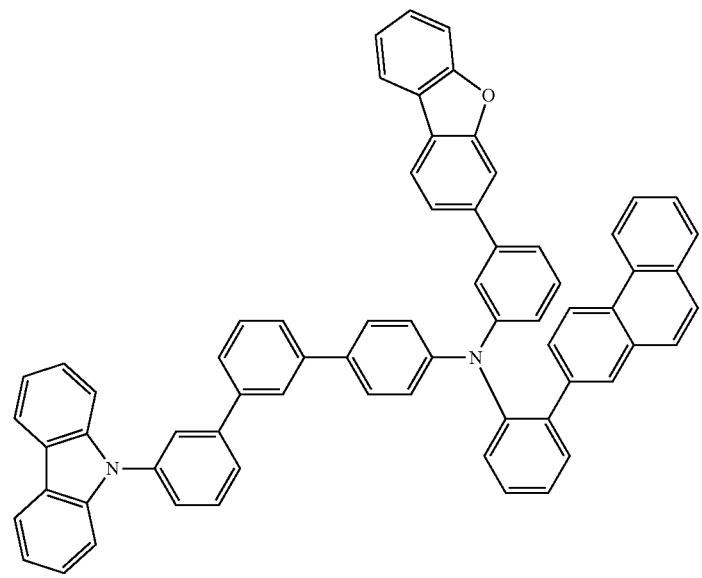

-continued
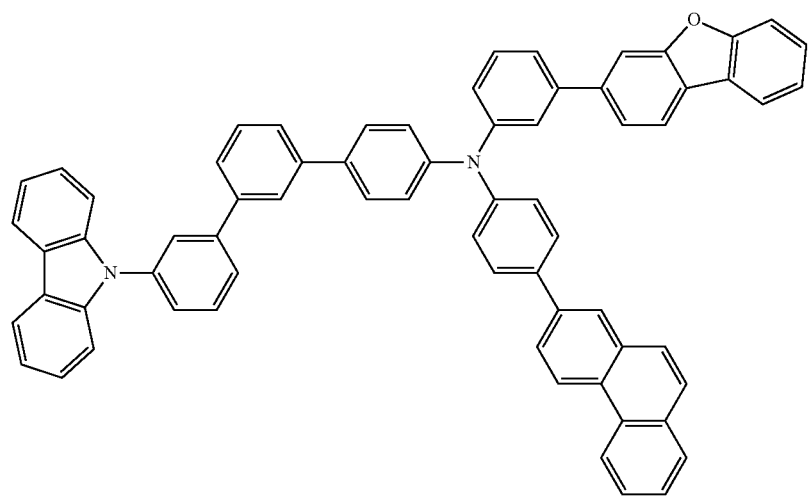
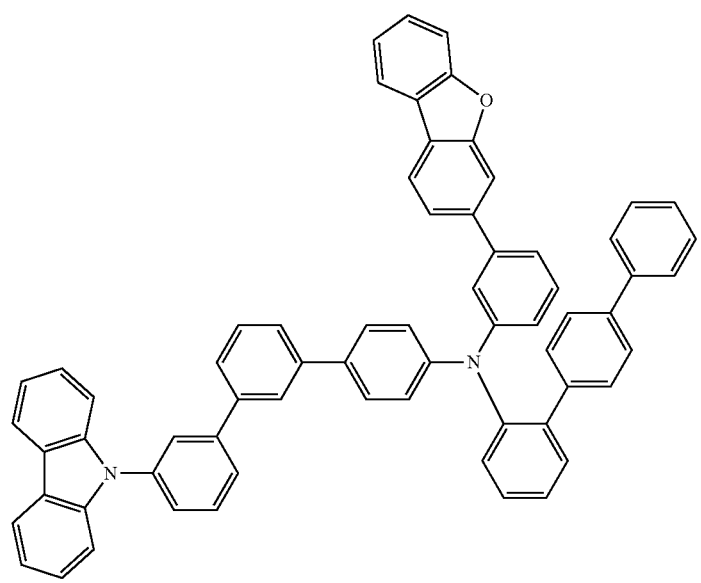
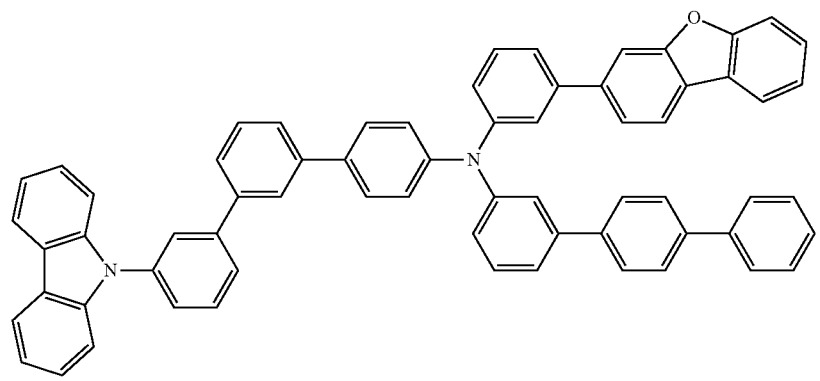

-continued
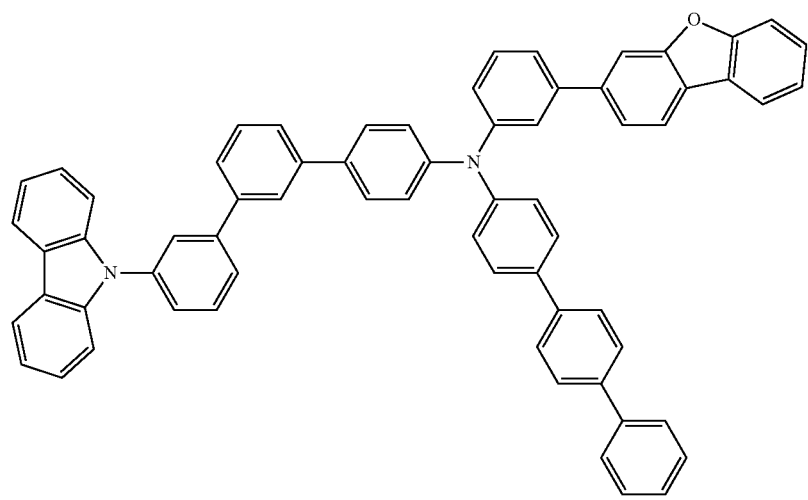
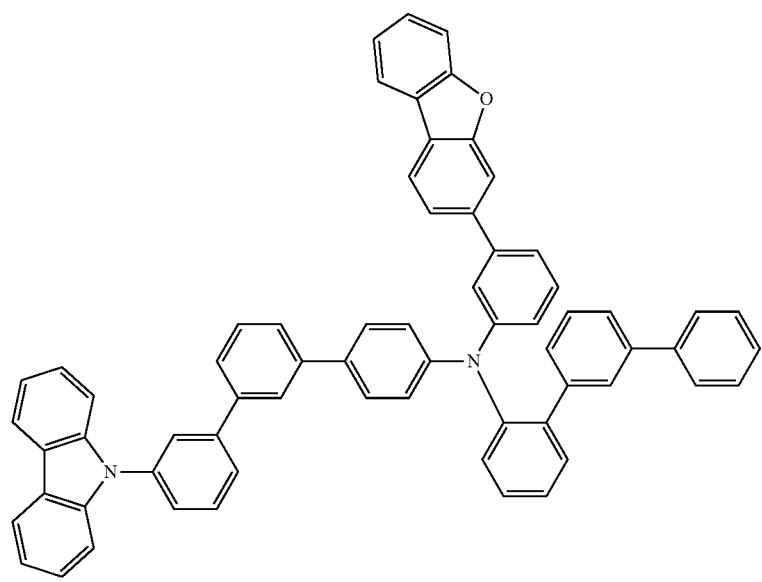
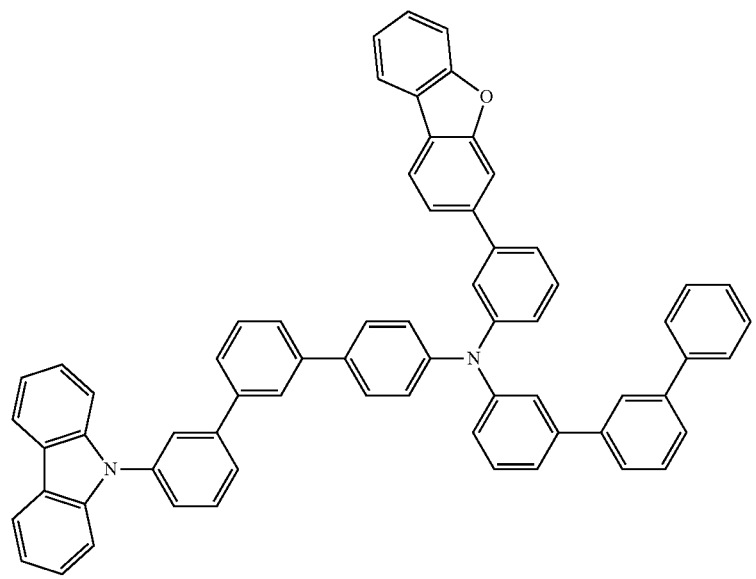

-continued
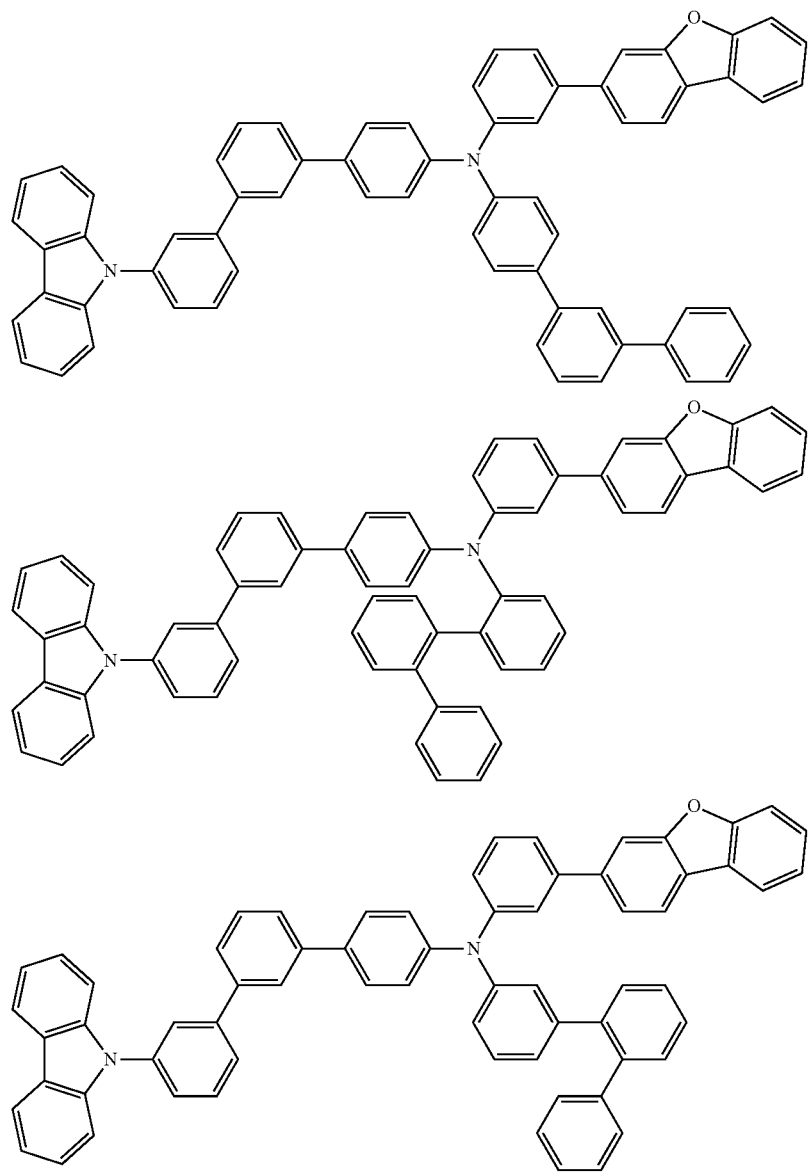
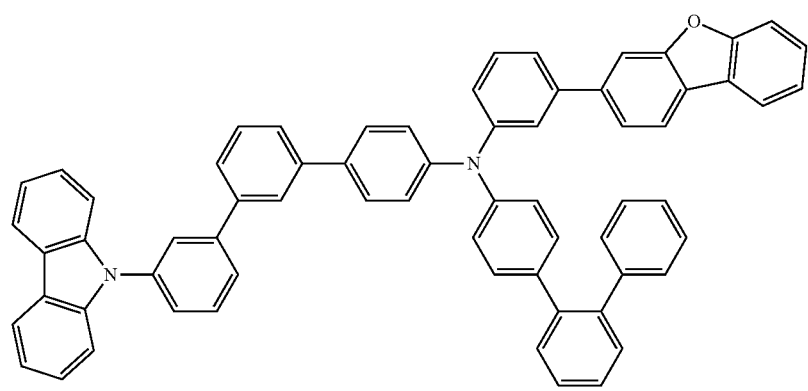

-continued
261
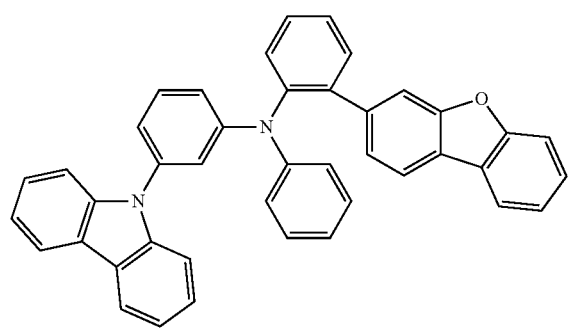
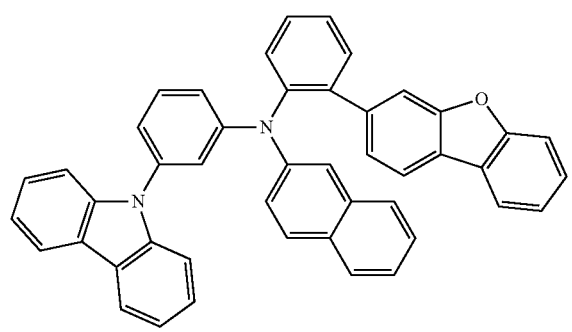
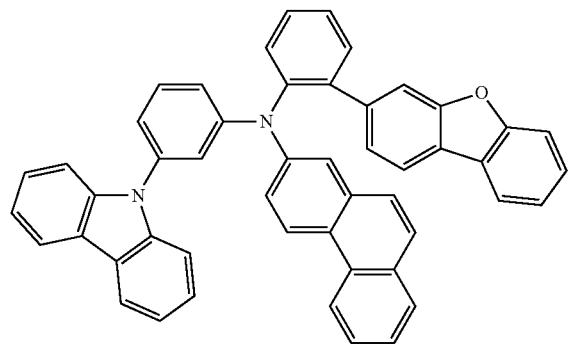
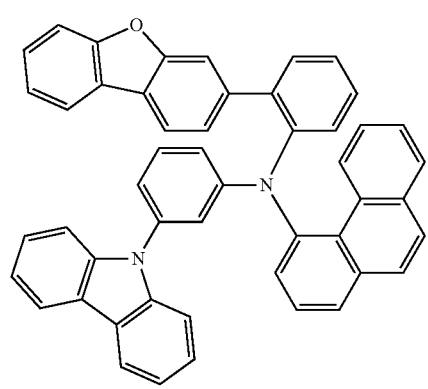
262
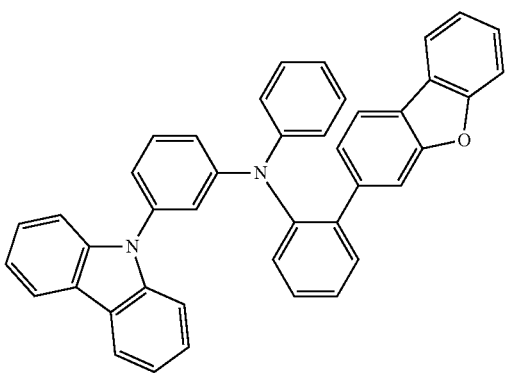
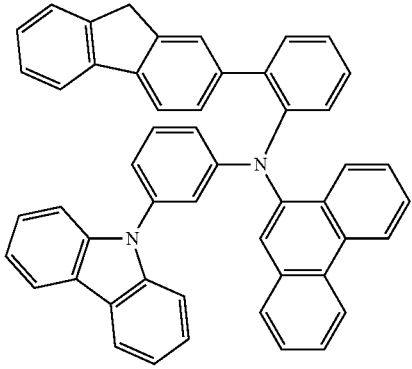
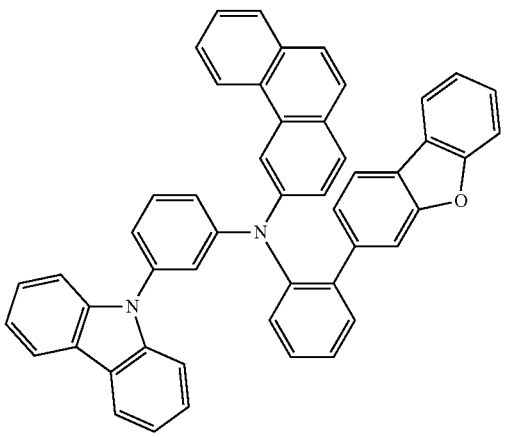
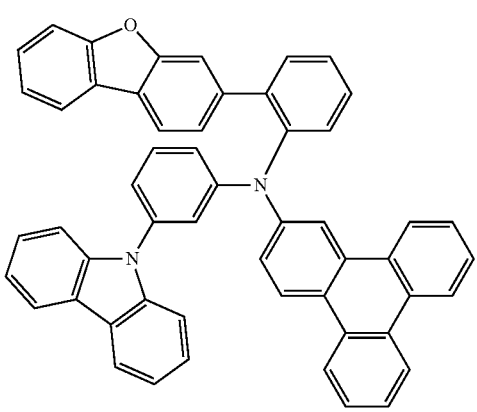

-continued
| 263 | 264 |
|---|---|
| 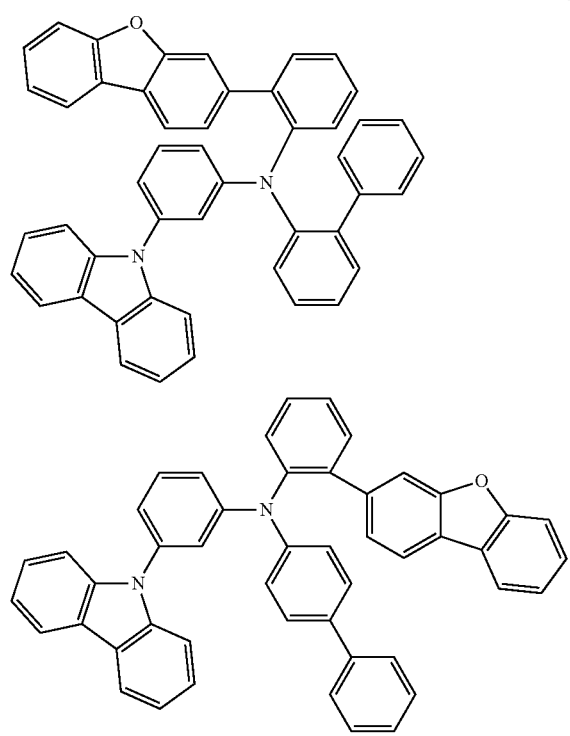 | 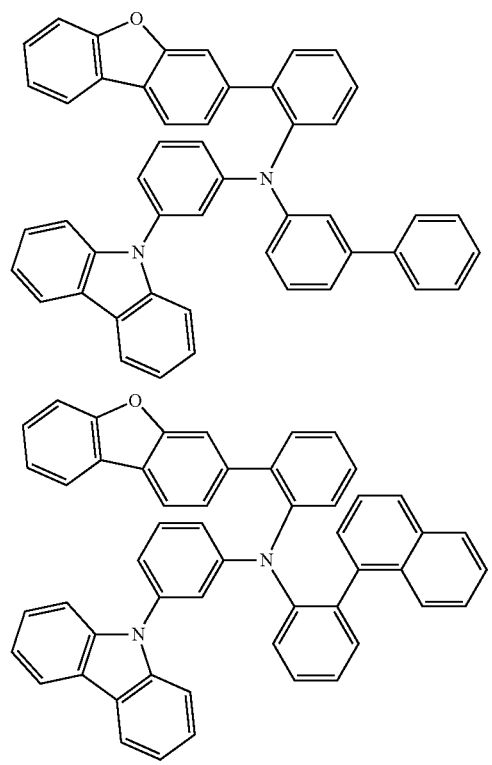 |
| 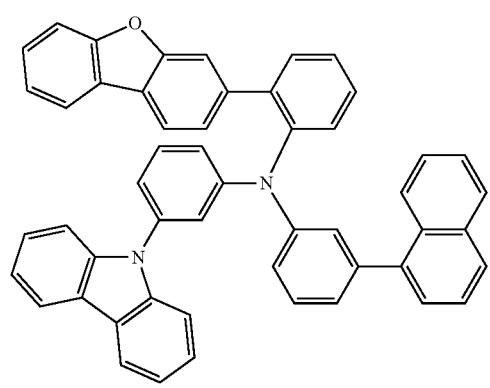 | 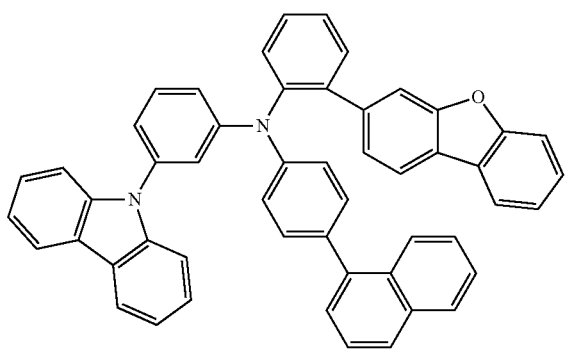 |
| 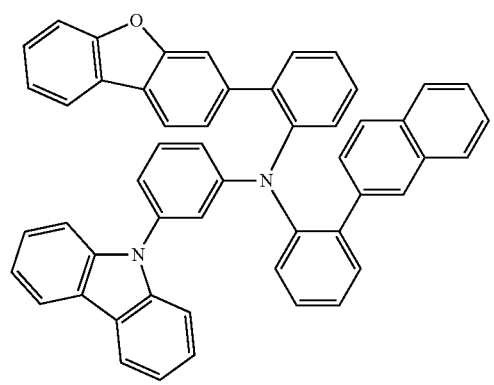 | 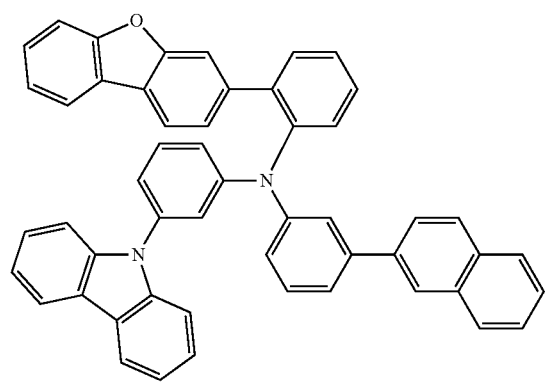 |

265
266
-continued
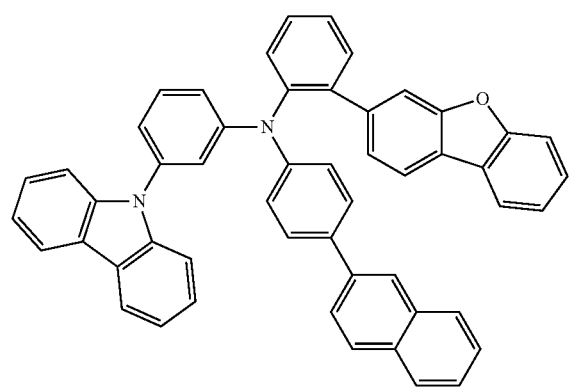
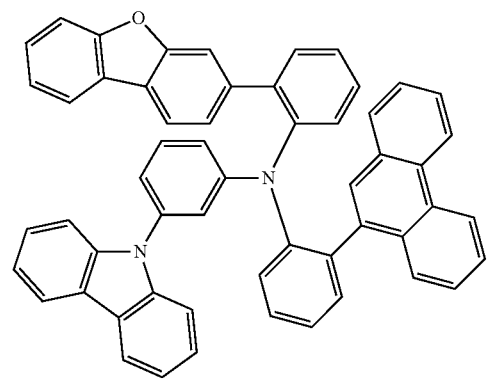
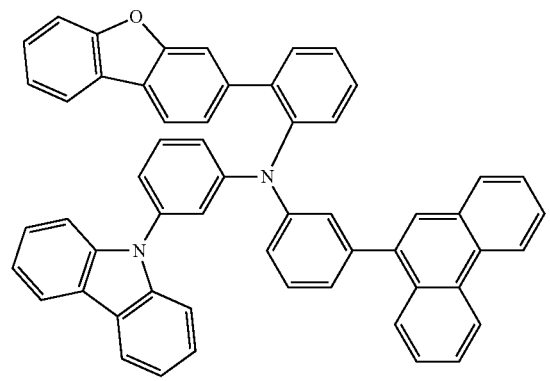
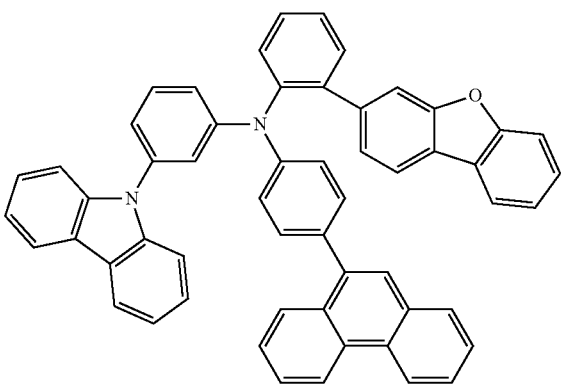
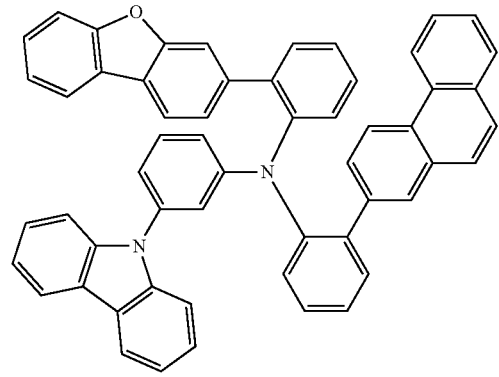
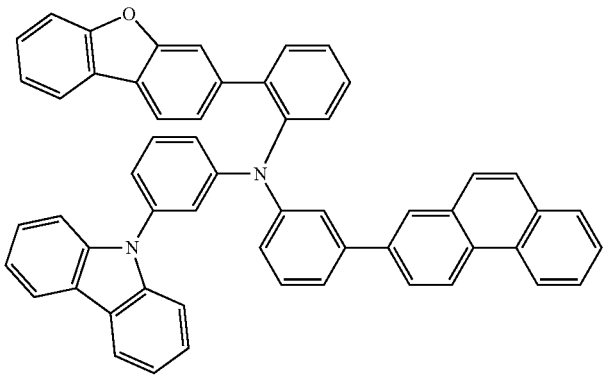
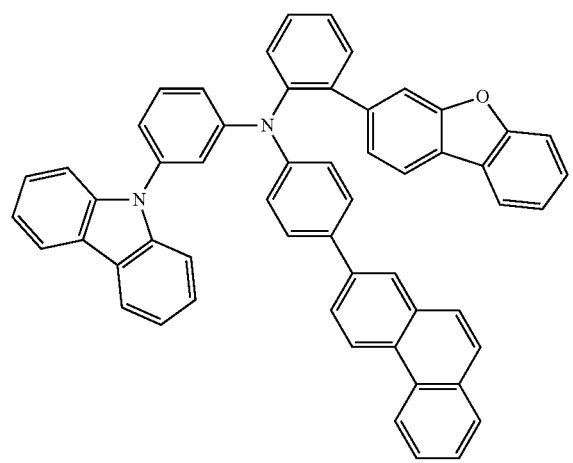
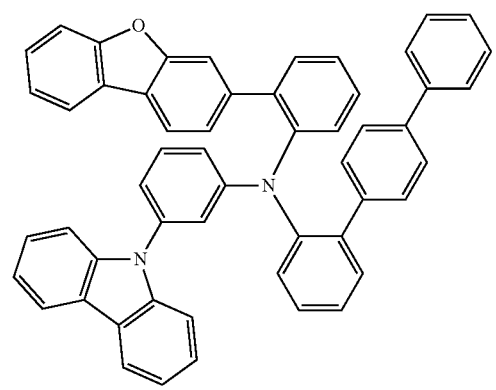

267
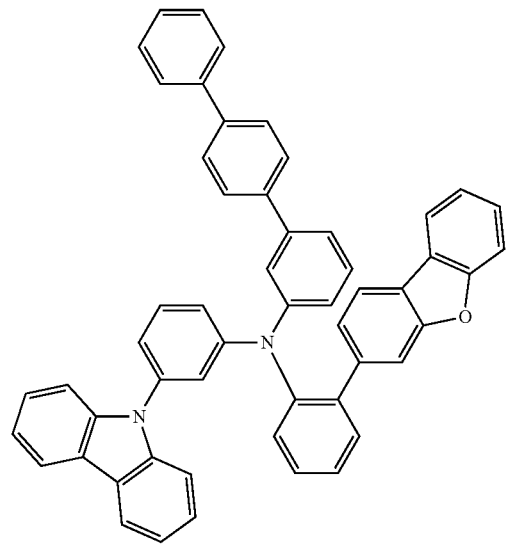
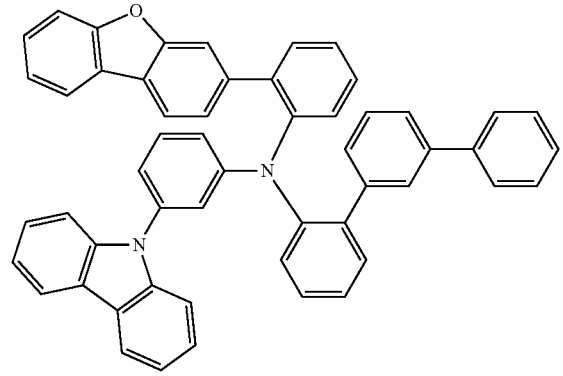
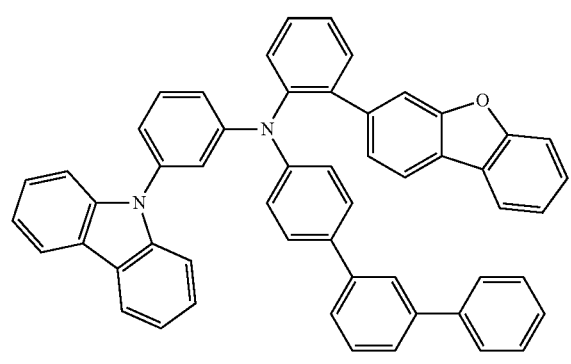
268
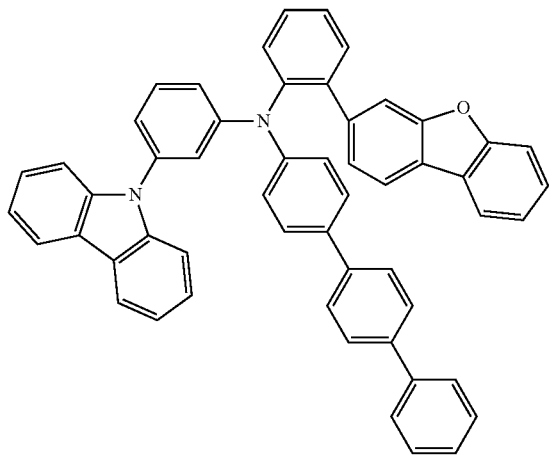
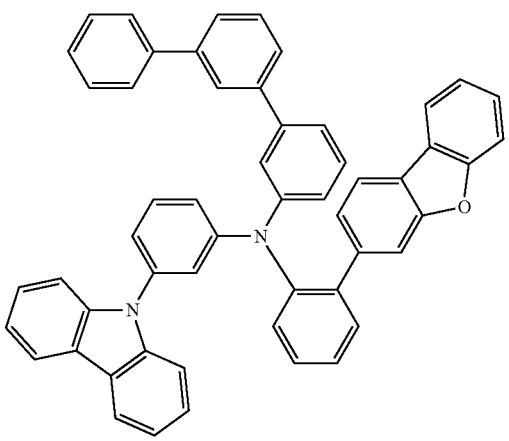
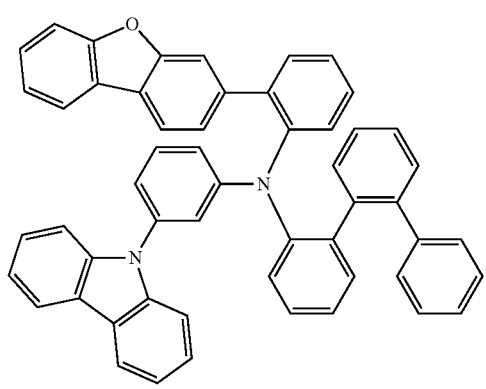

269
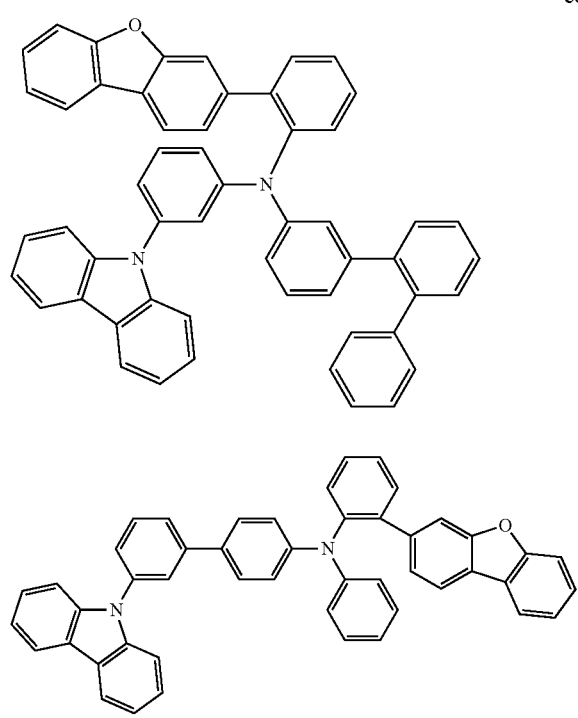
270
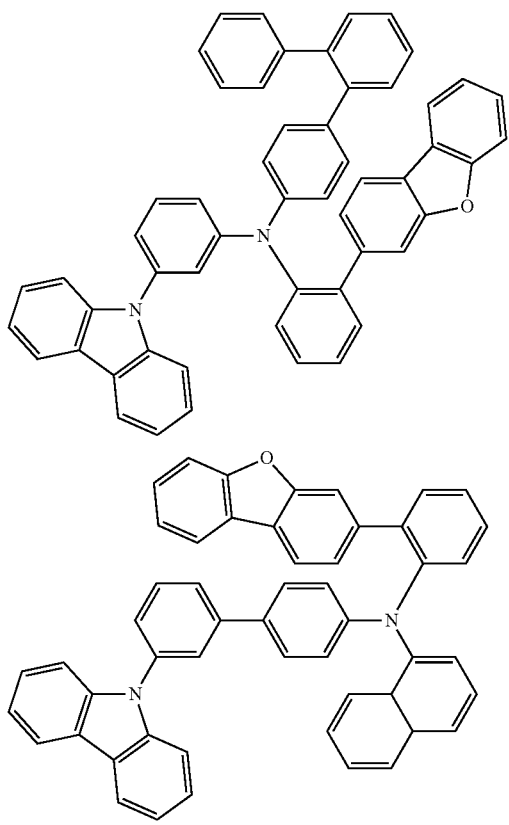
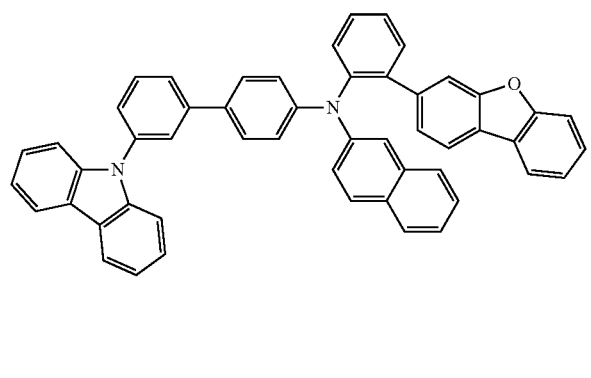
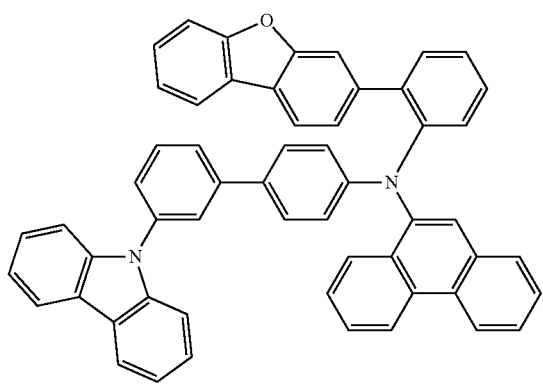
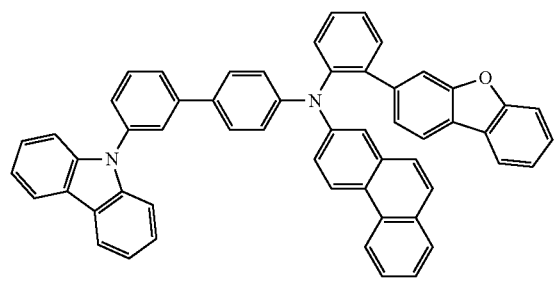
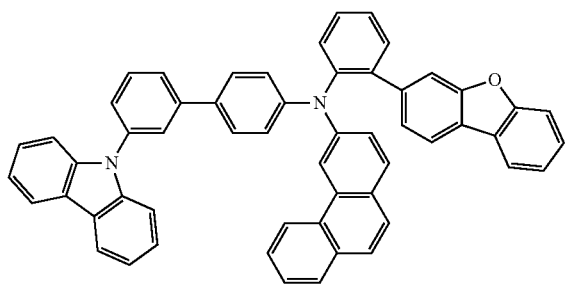

271 272
-continued
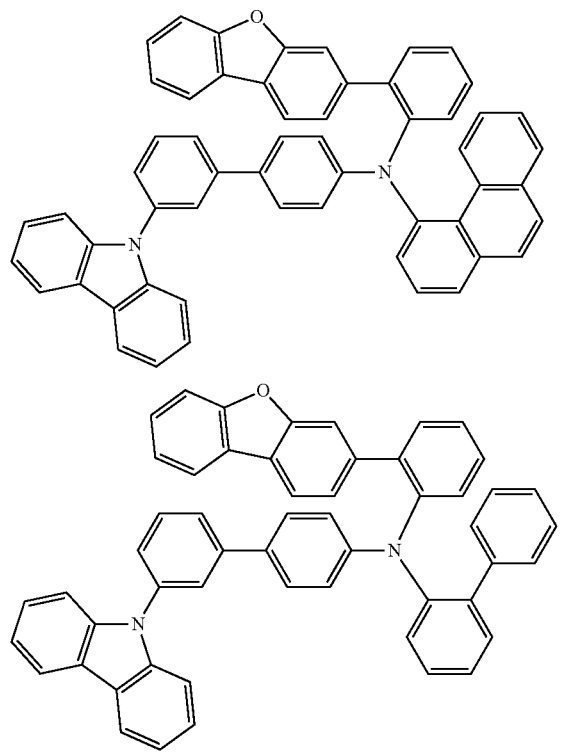
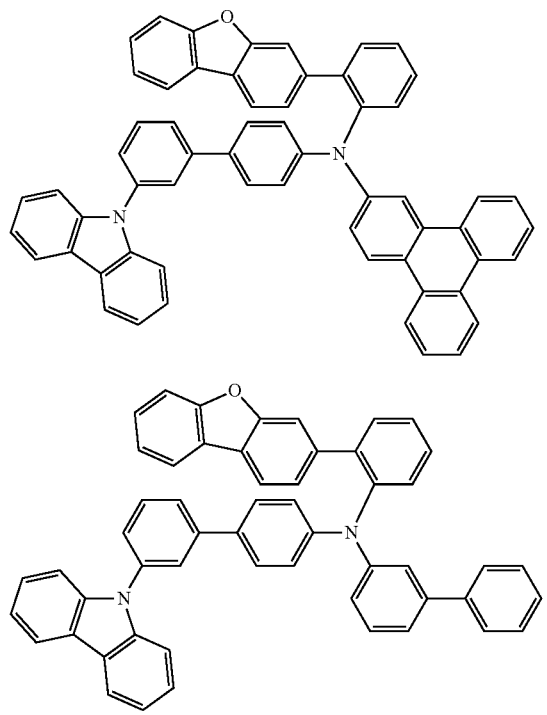
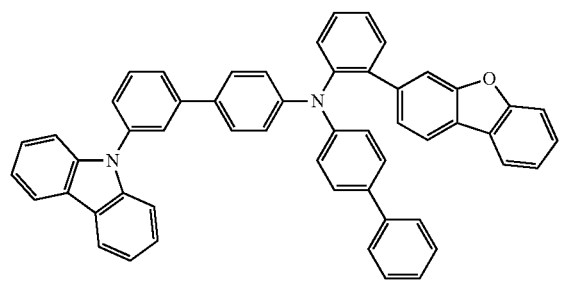
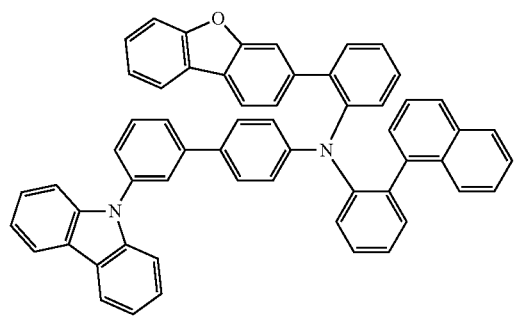
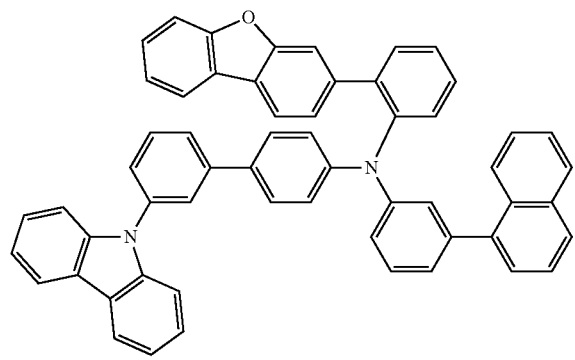
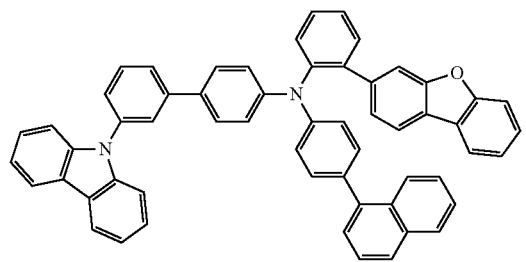

273
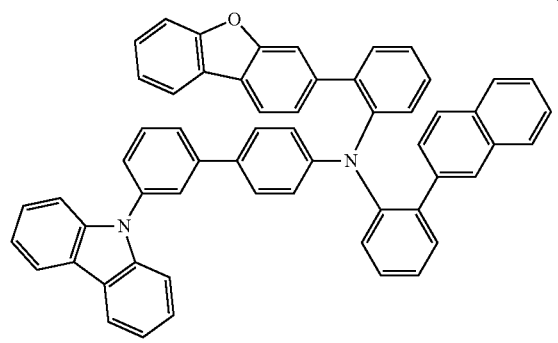
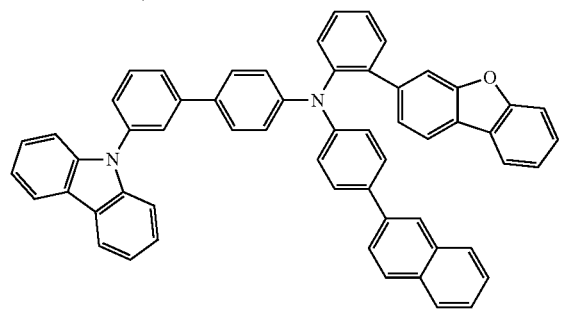
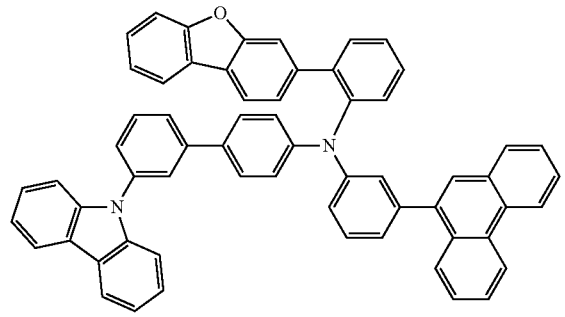
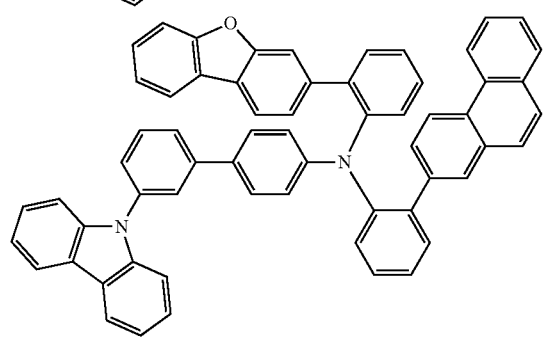
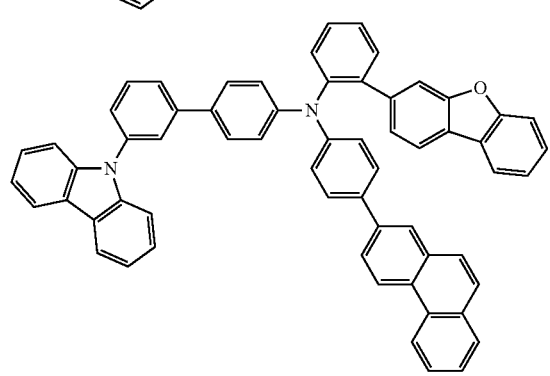
274
-continued
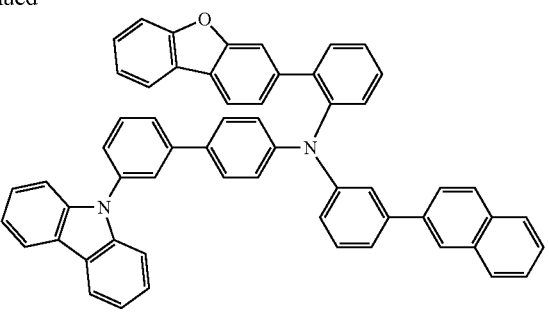
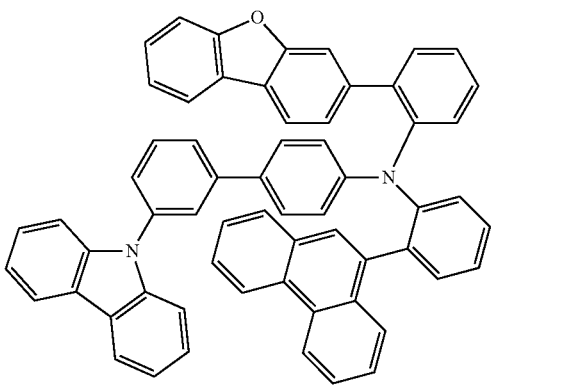
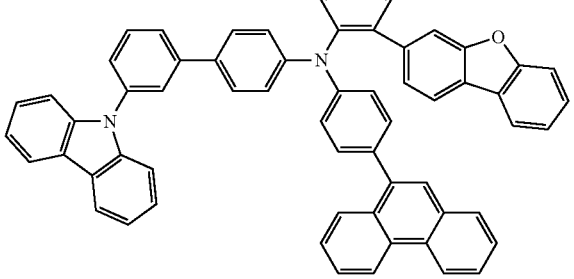
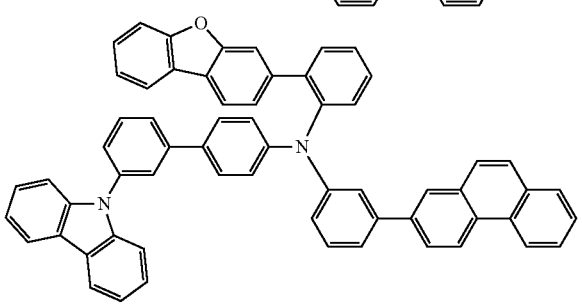
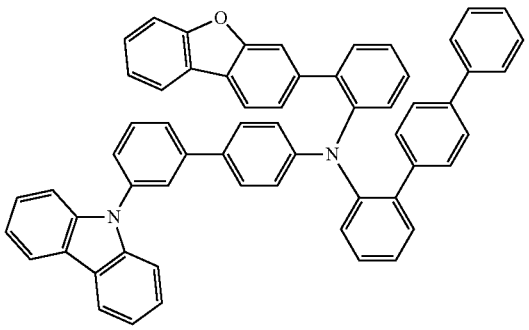

-continued
275
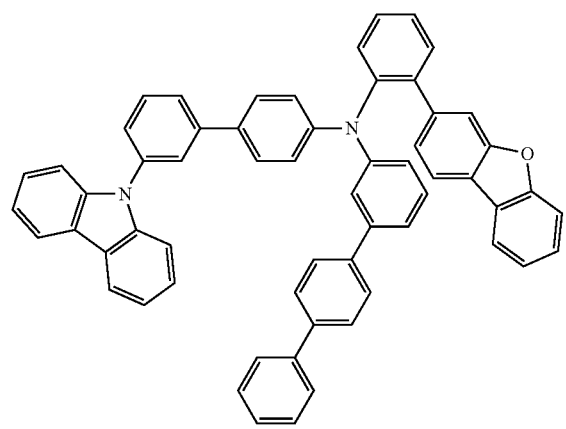
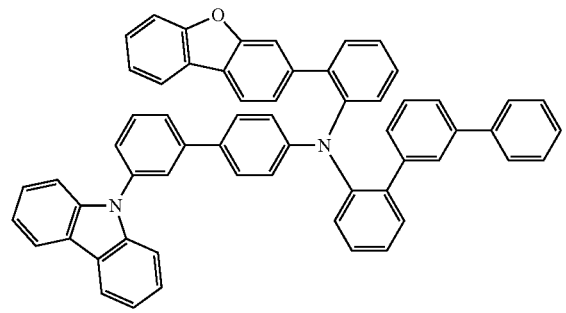
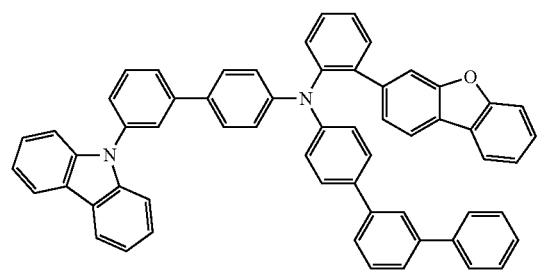
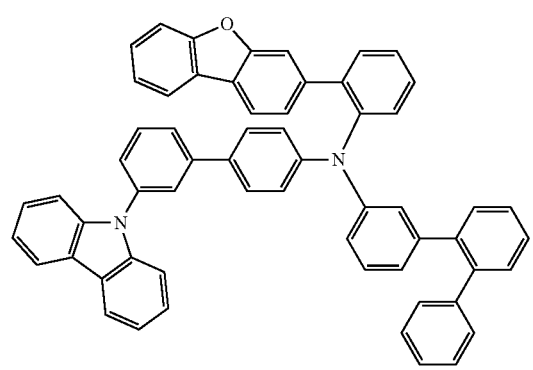
276
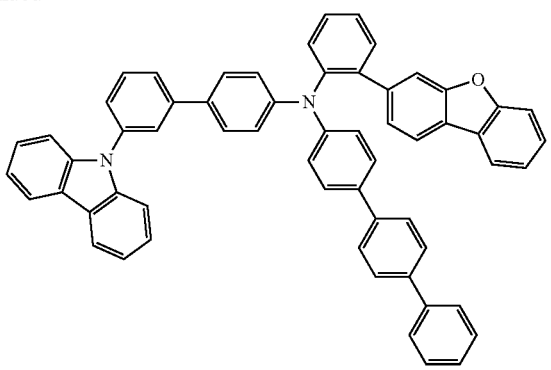
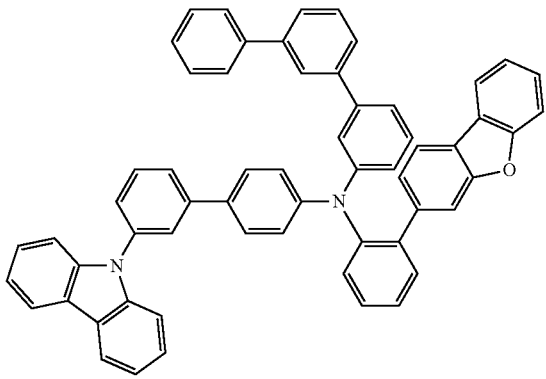
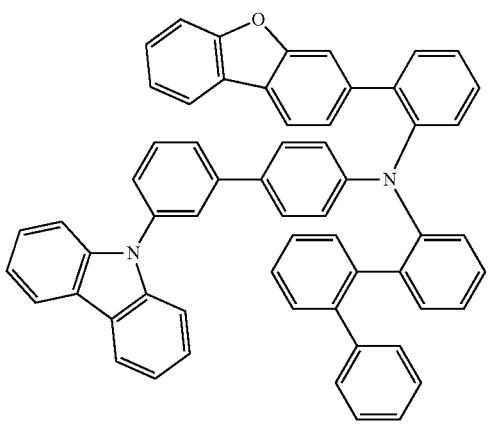
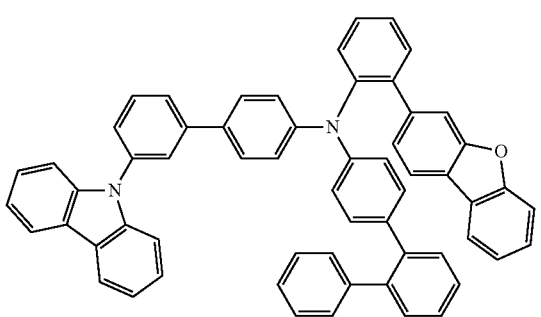

-continued
277
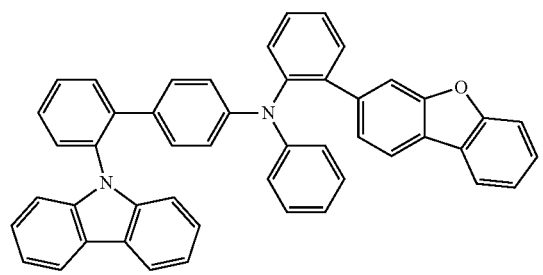
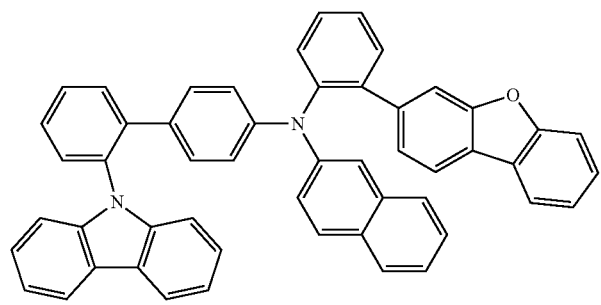
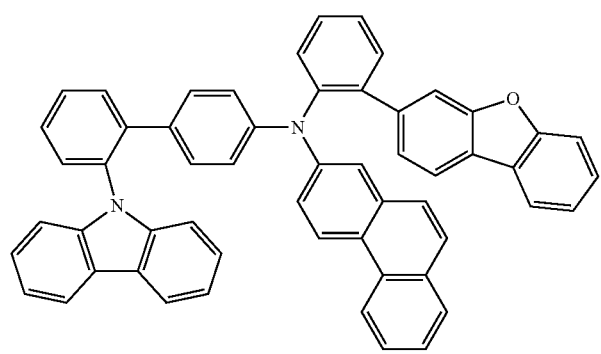
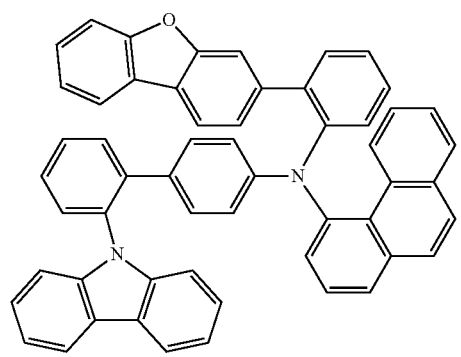
278
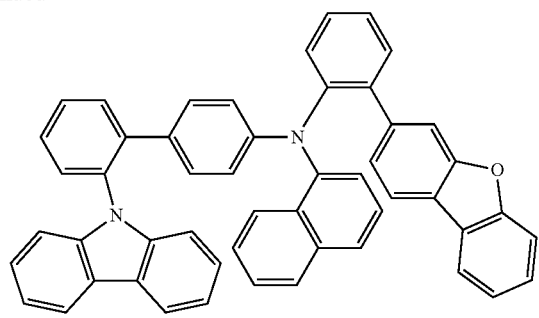
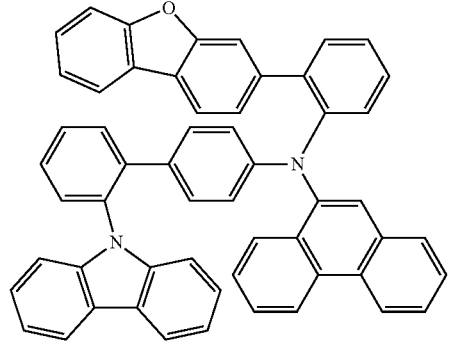
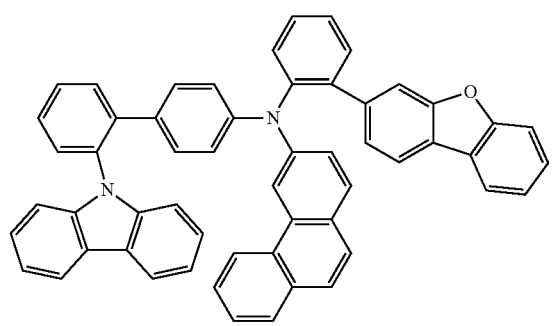
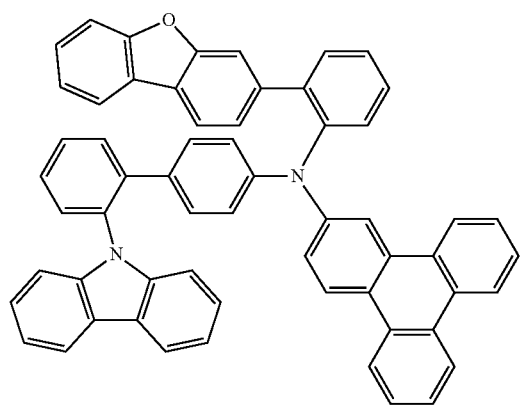

279
280
-continued
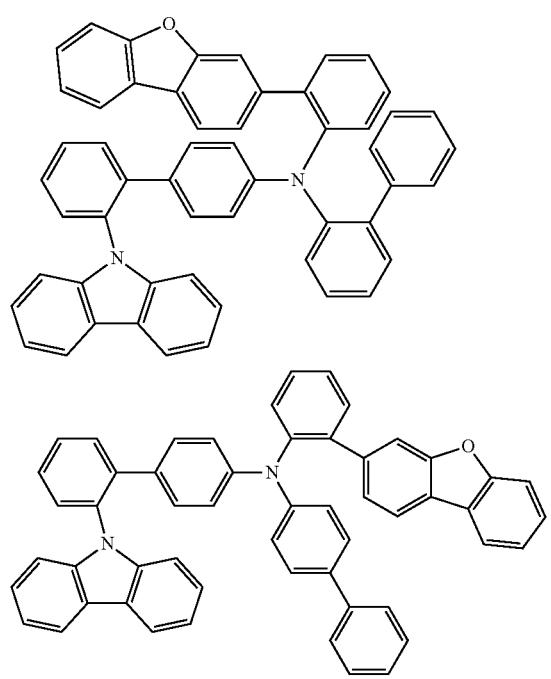
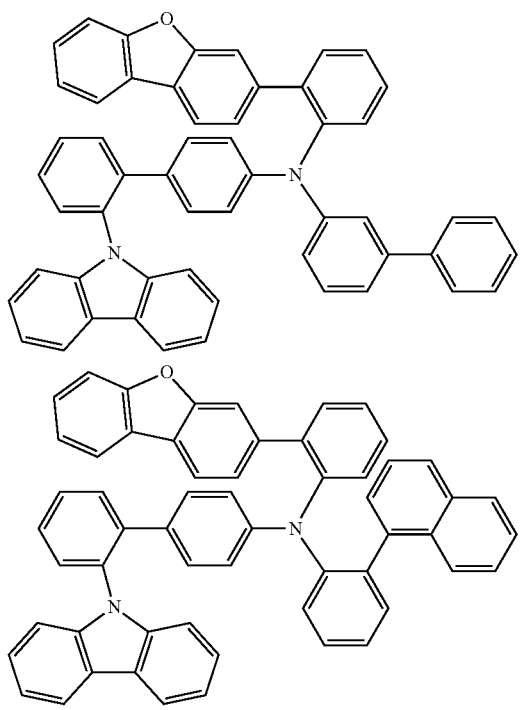
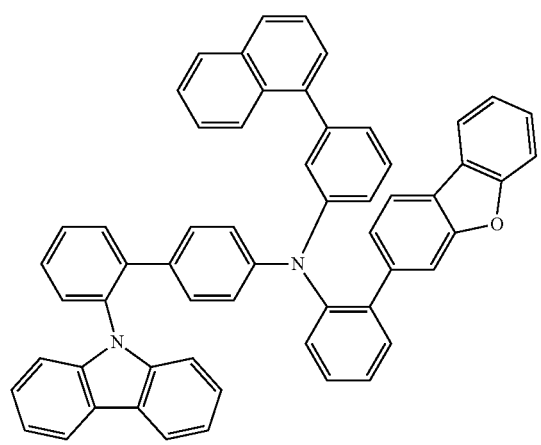
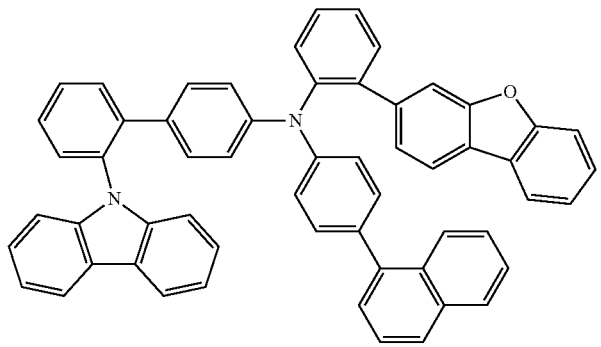
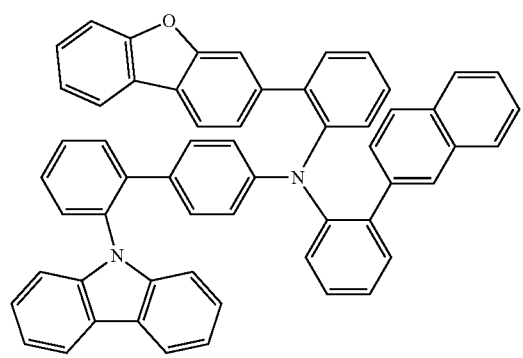
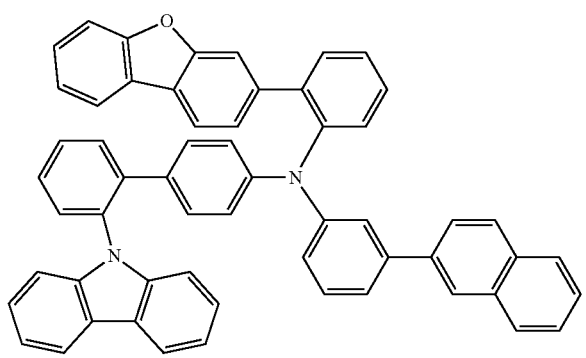

281
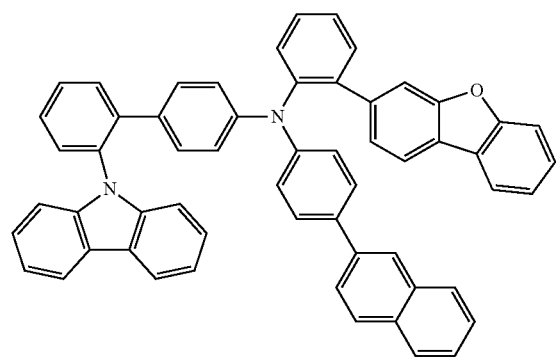
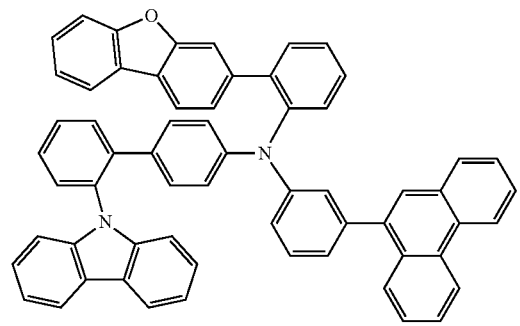
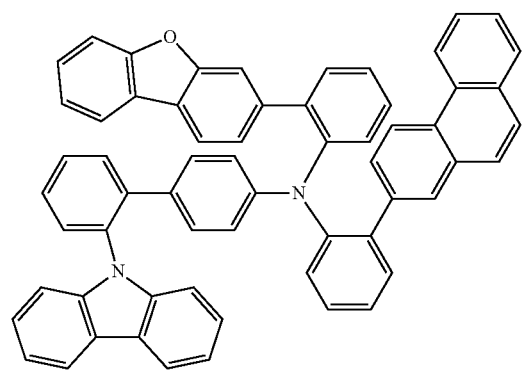
282
-continued
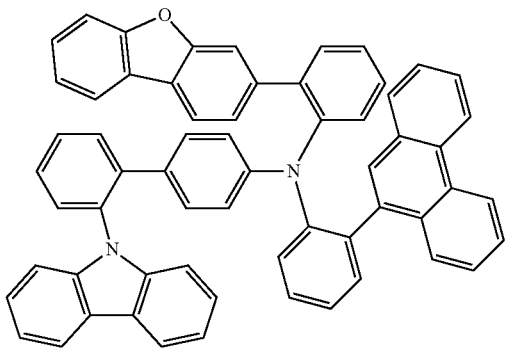
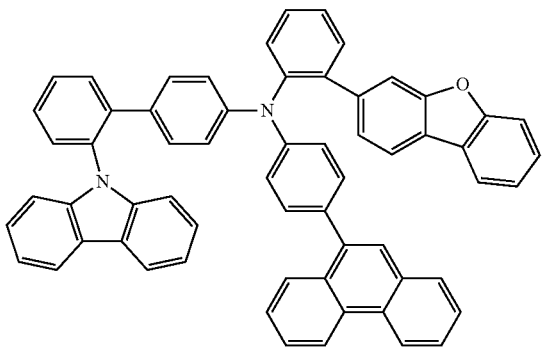
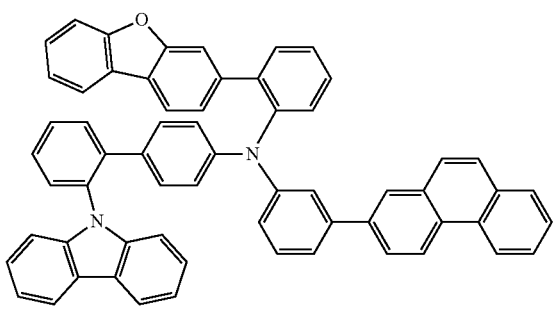
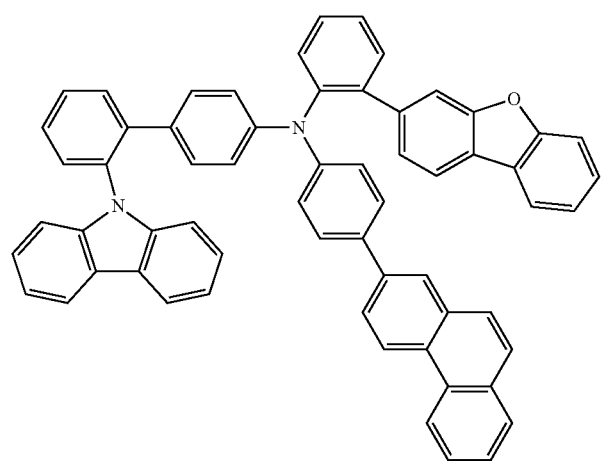

-continued
283
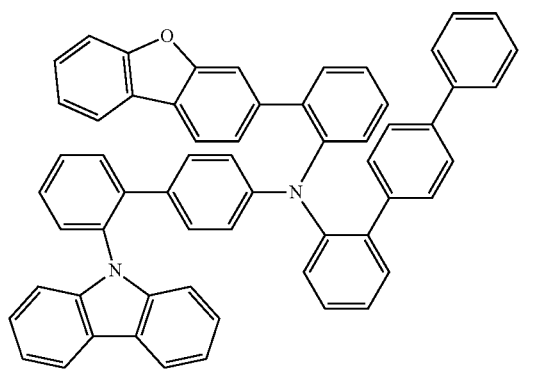
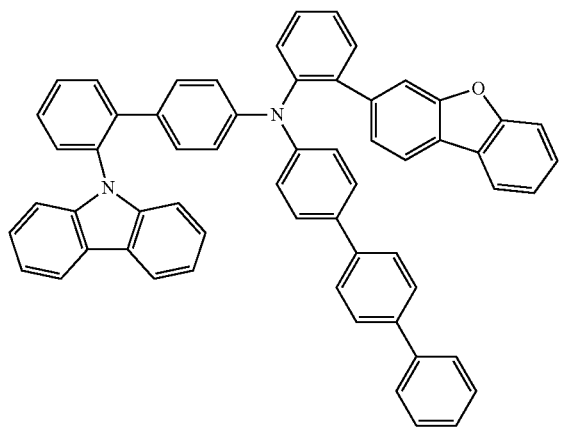
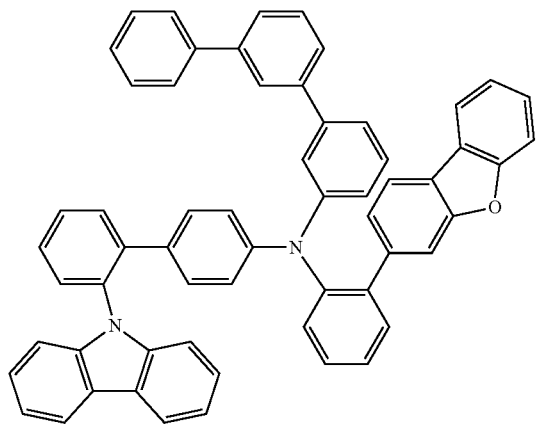
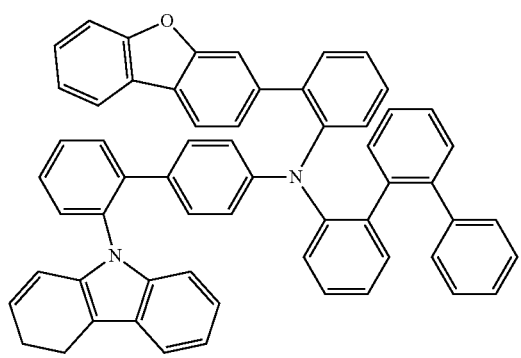
284
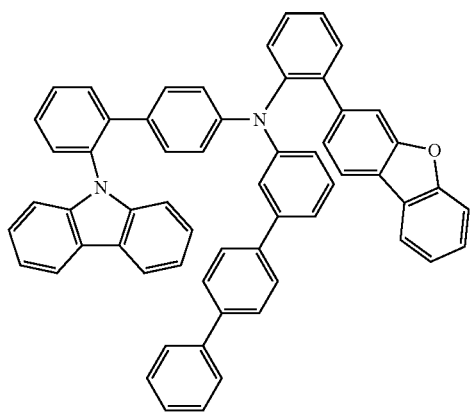
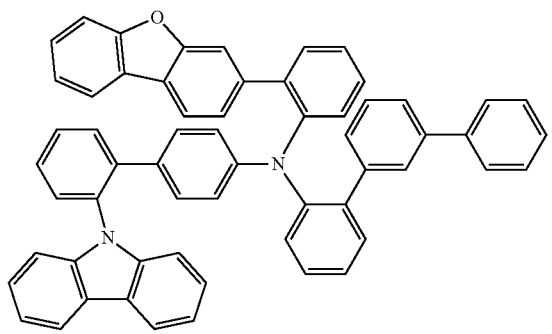
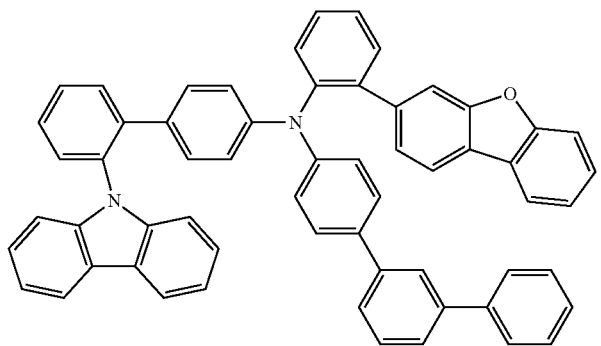
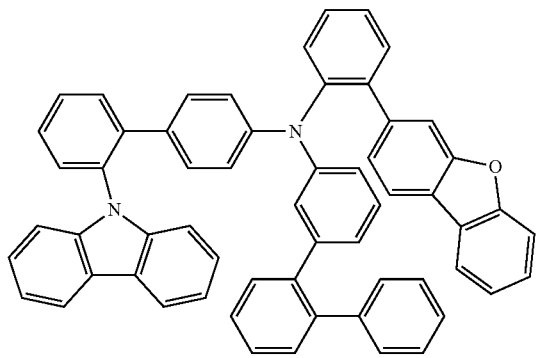

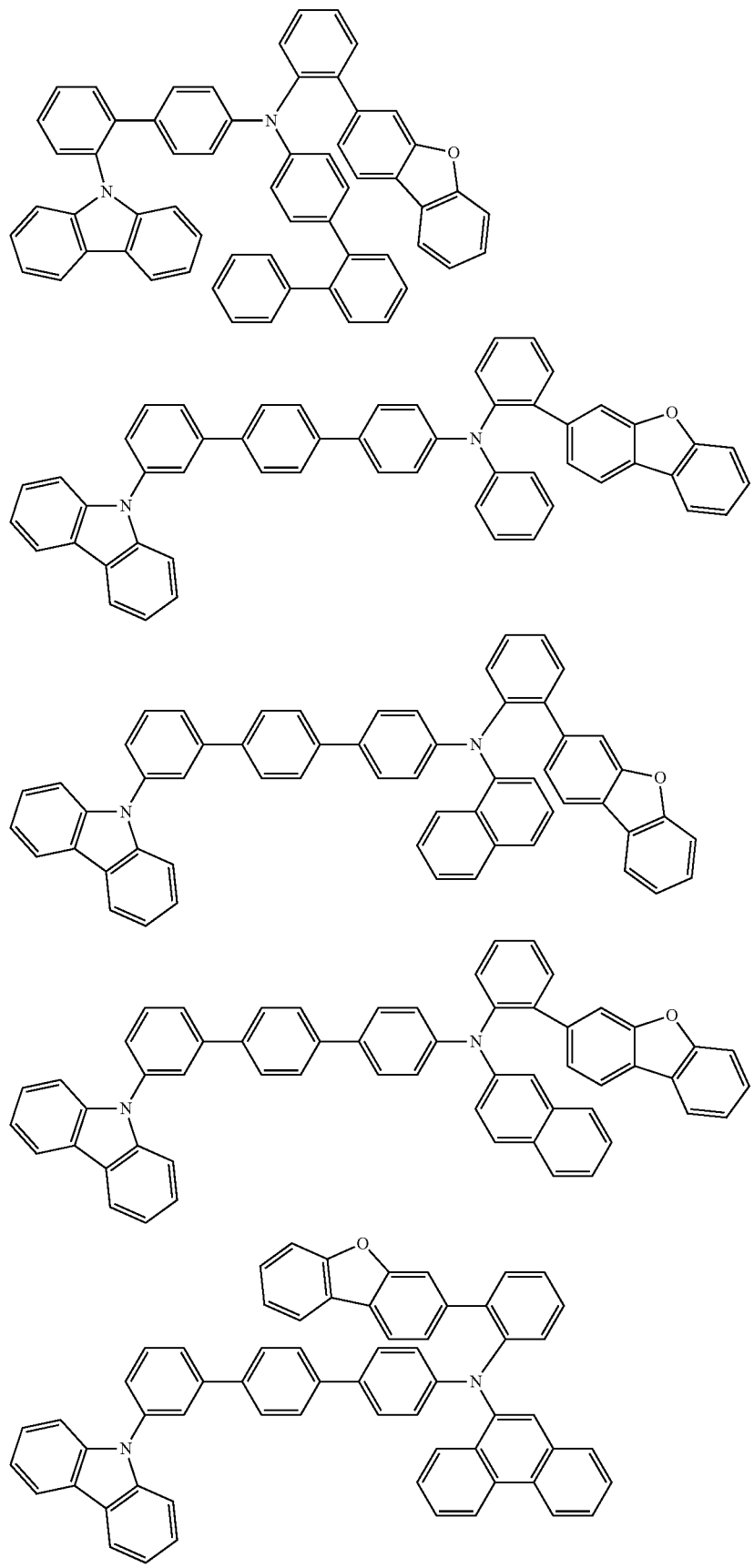

-continued
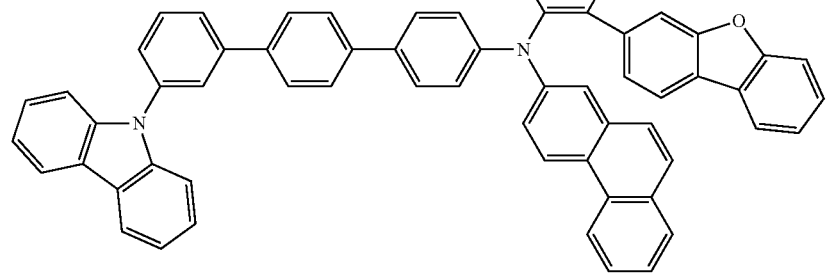
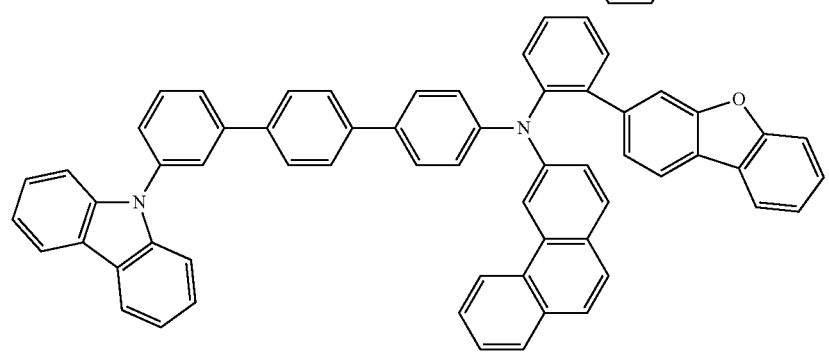
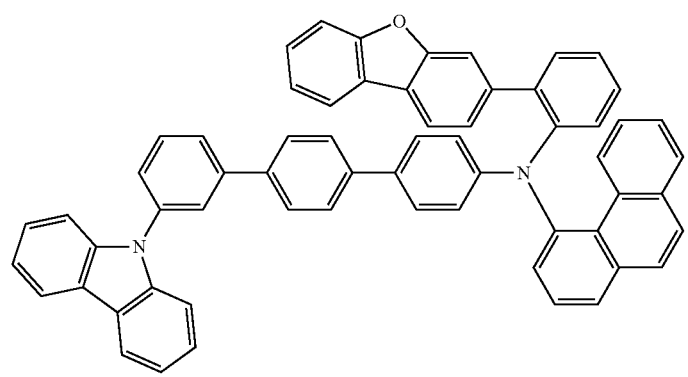
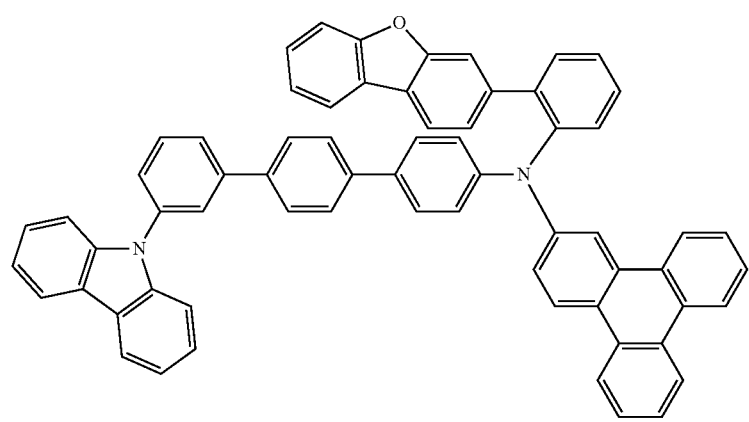

-continued
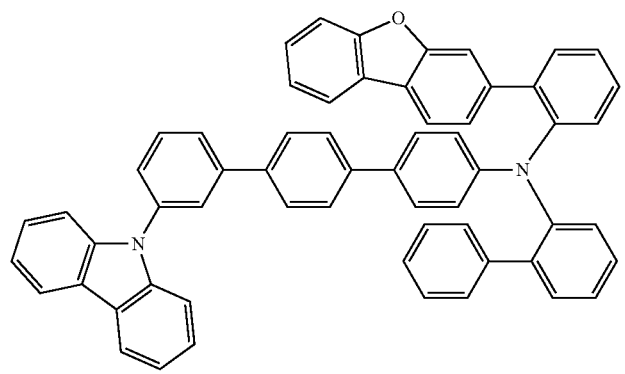
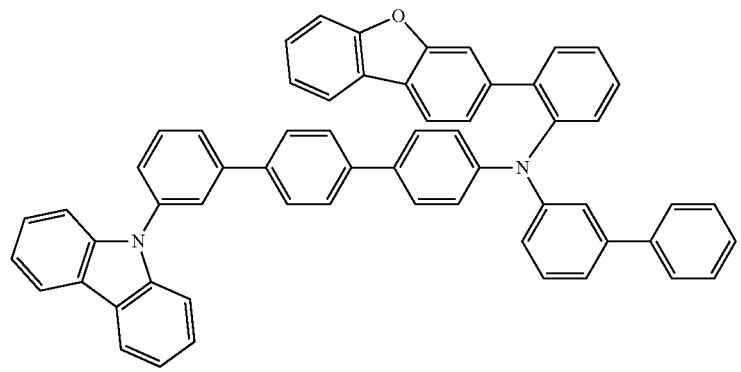
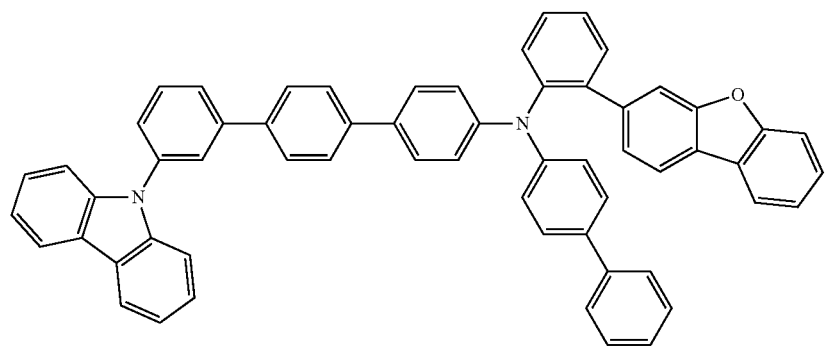
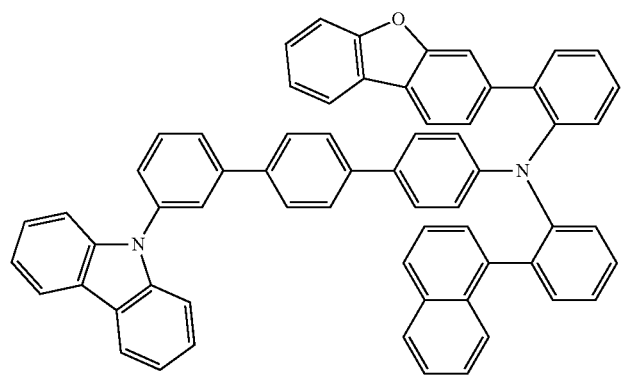

-continued
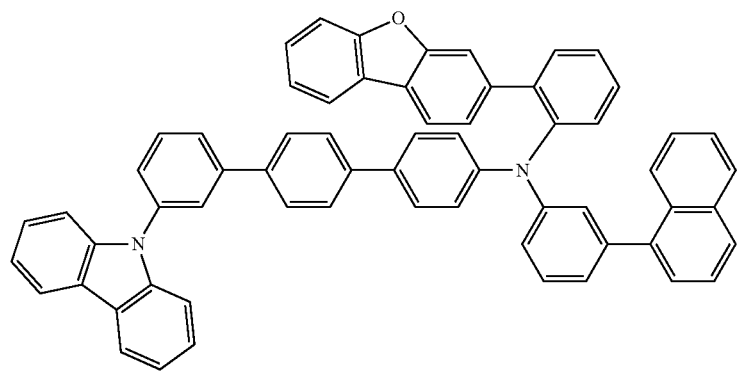
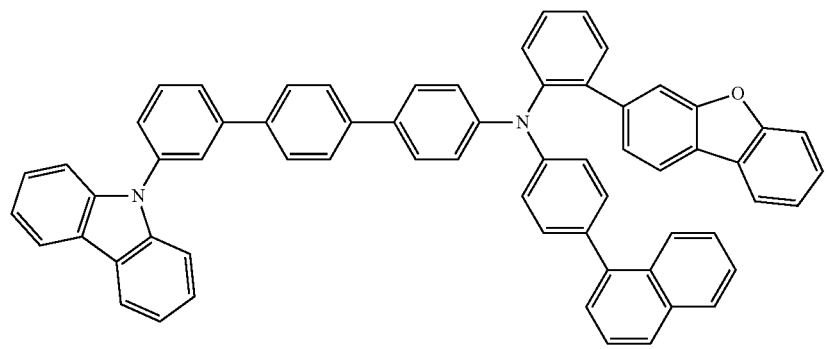
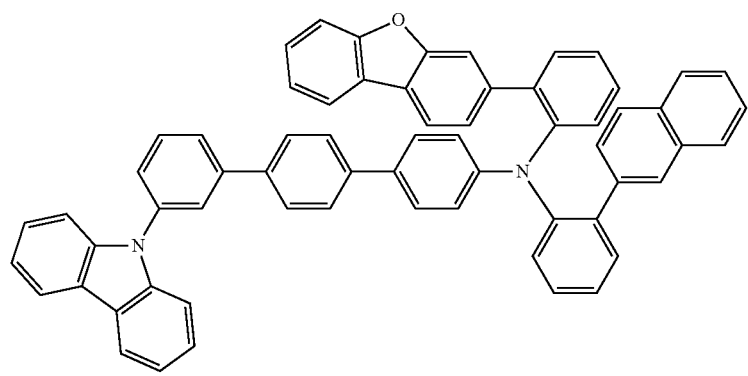
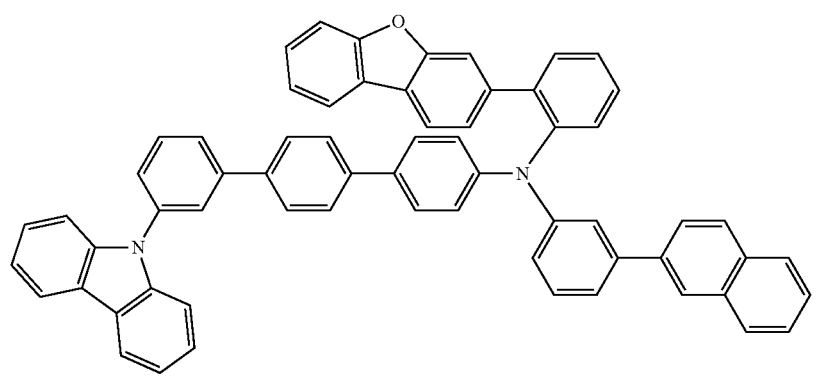

-continued
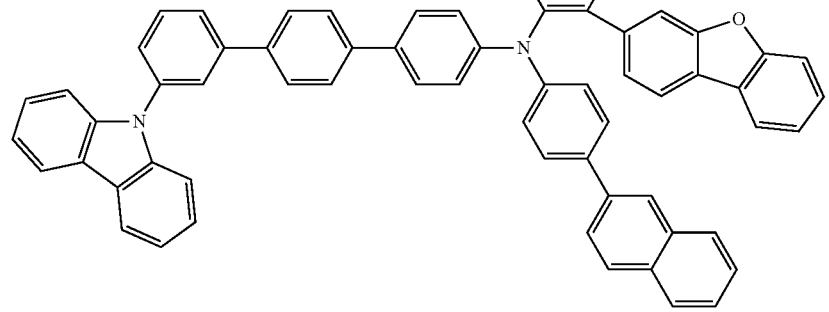
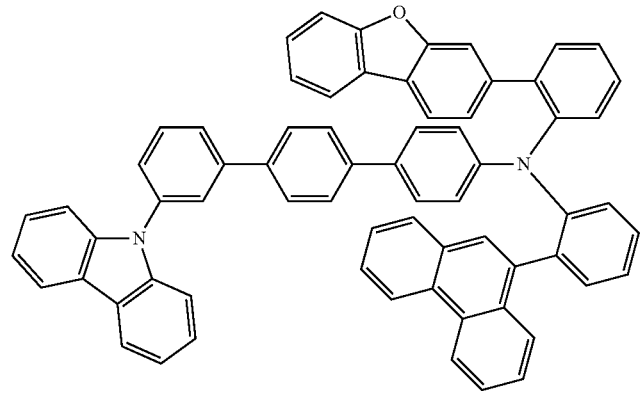
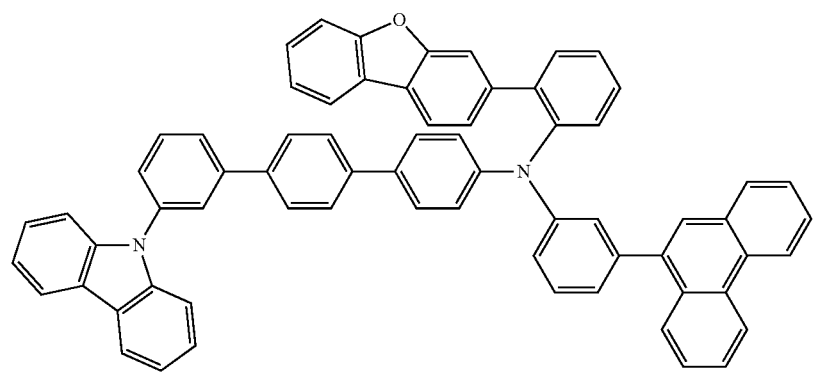
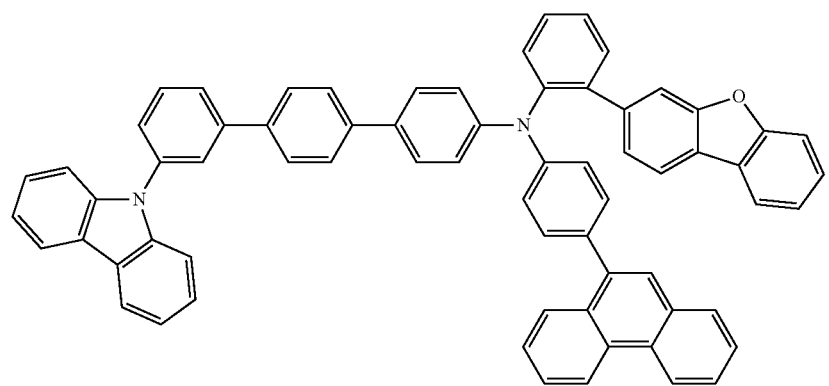

-continued
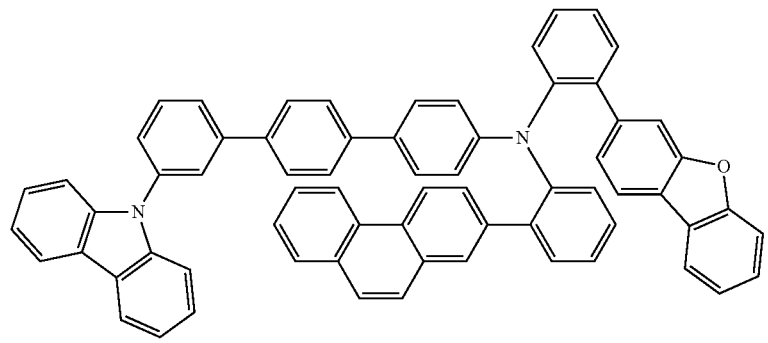
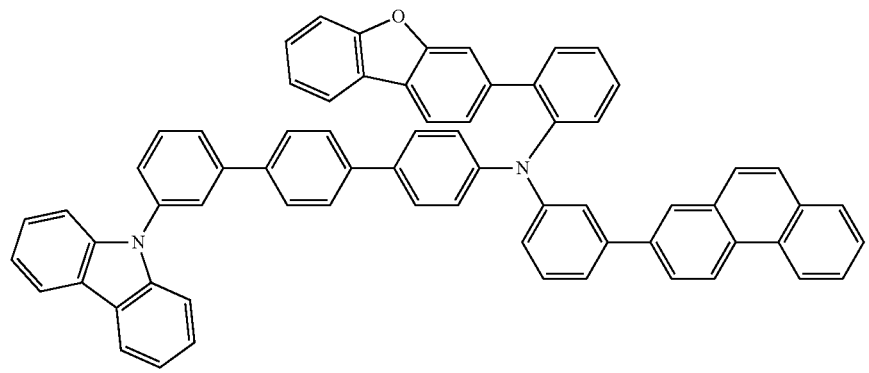
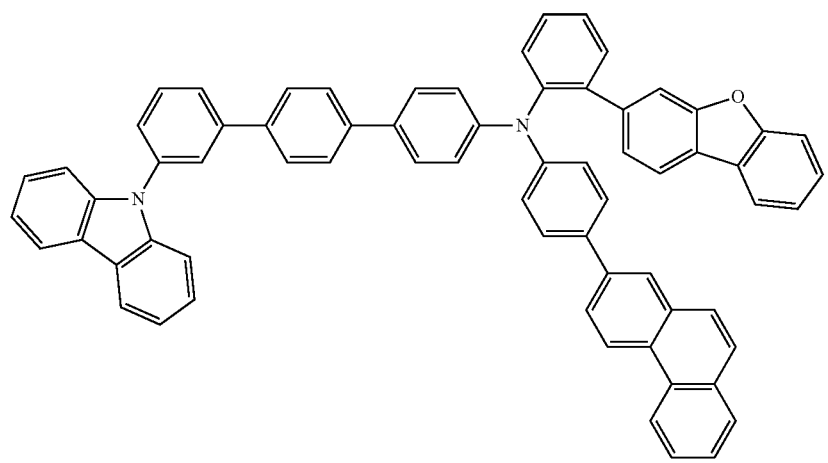
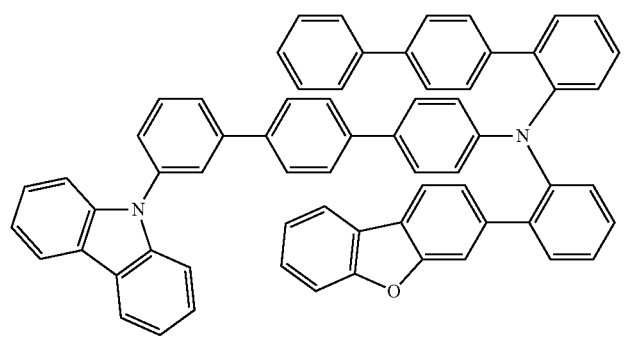

-continued
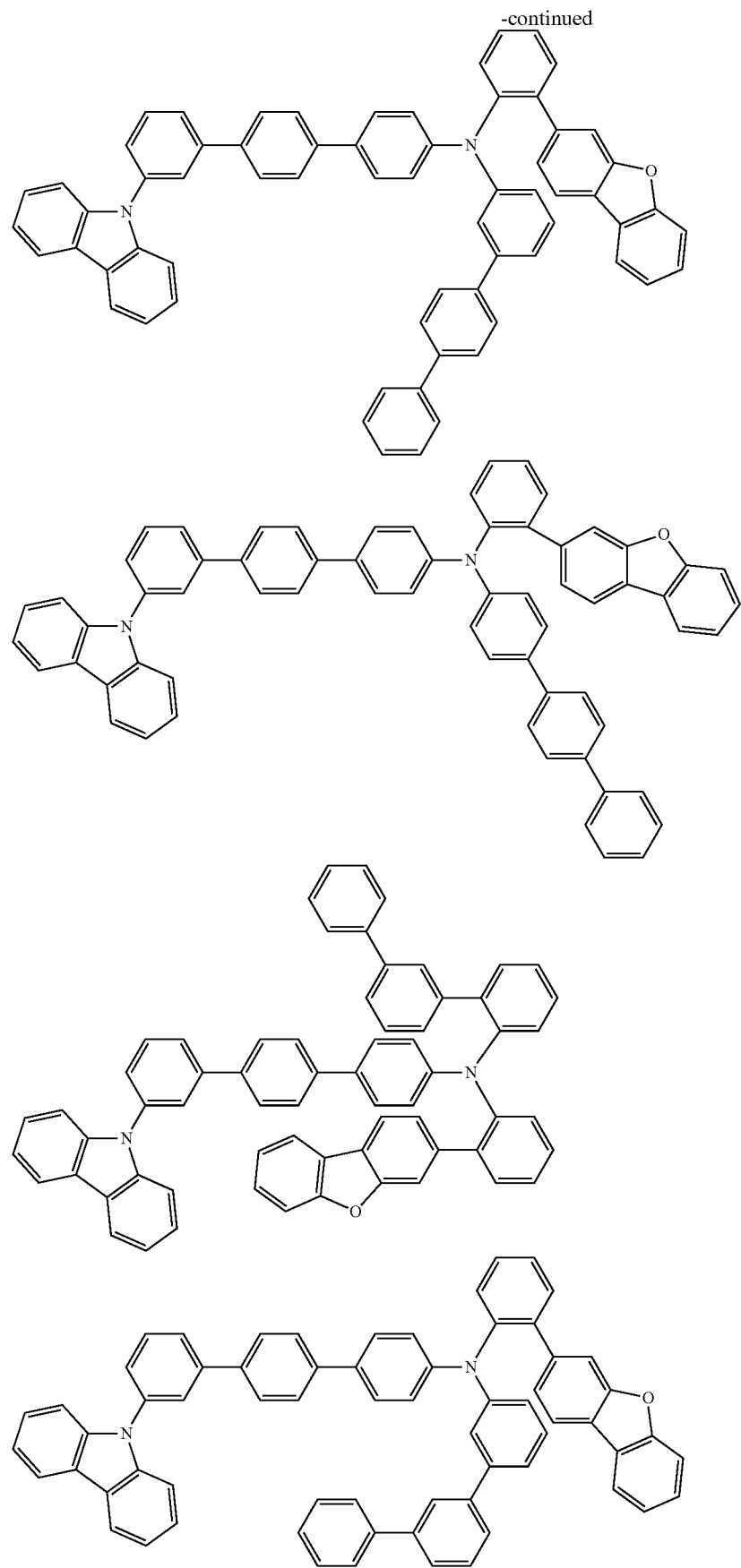

-continued
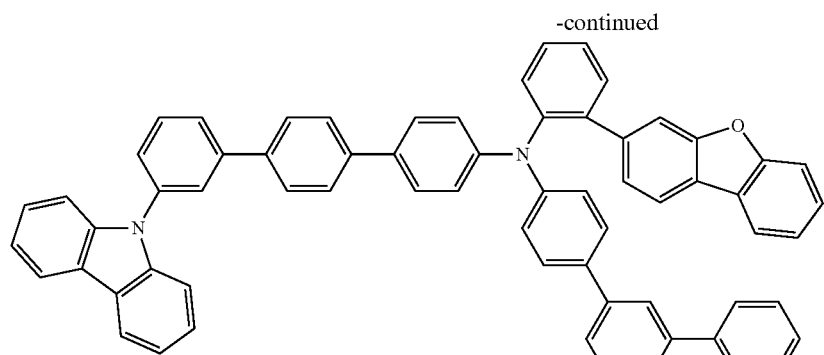
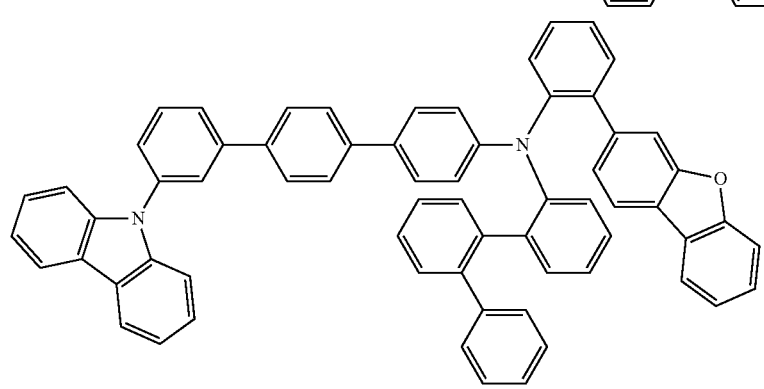
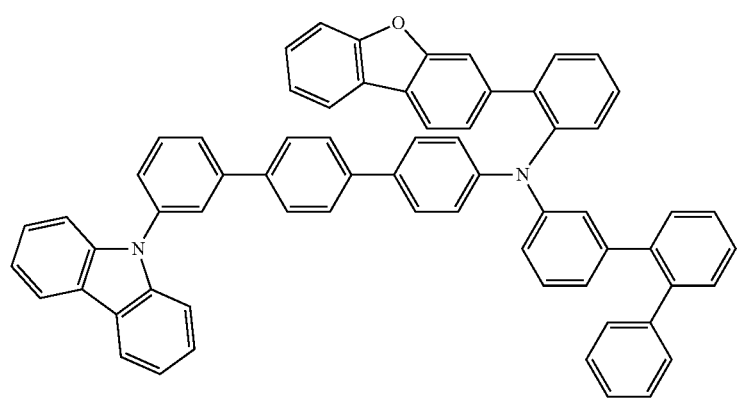
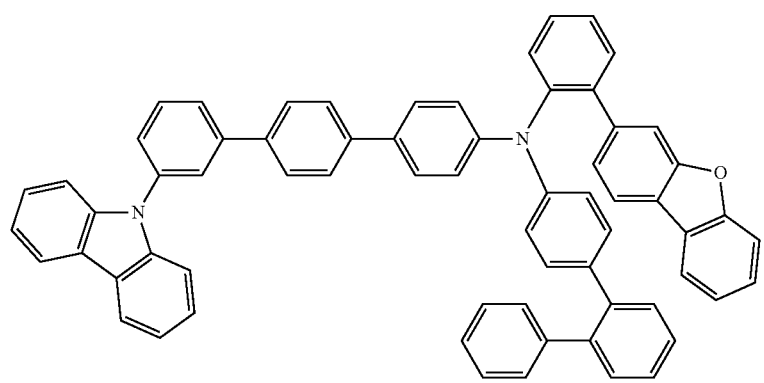

-continued
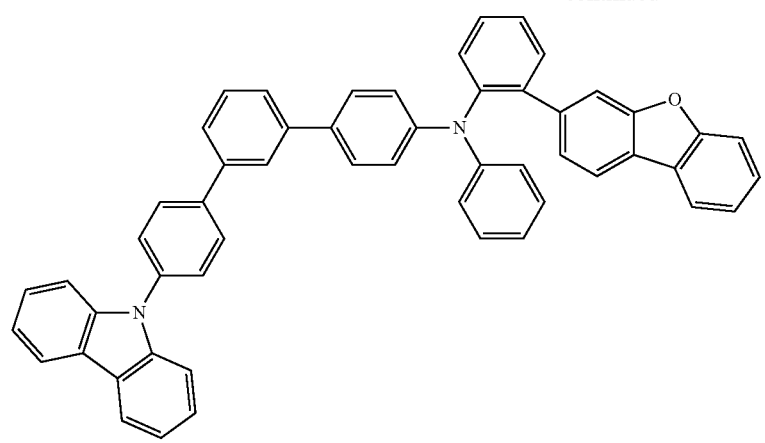
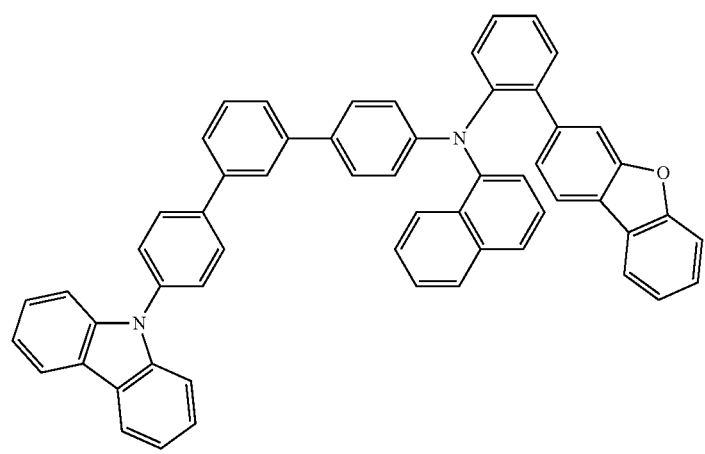
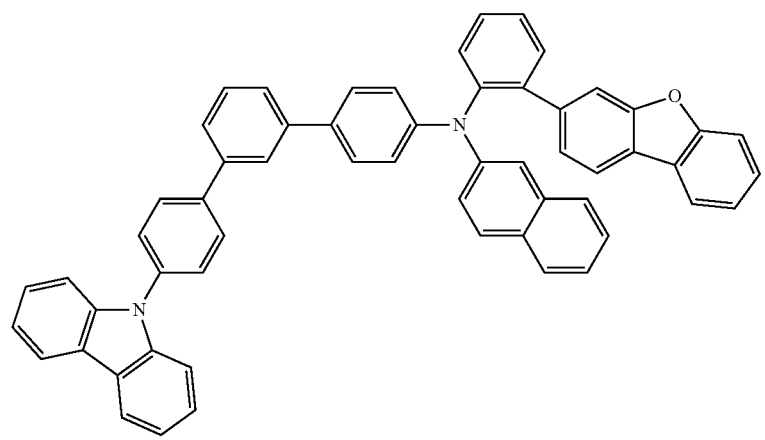

-continued
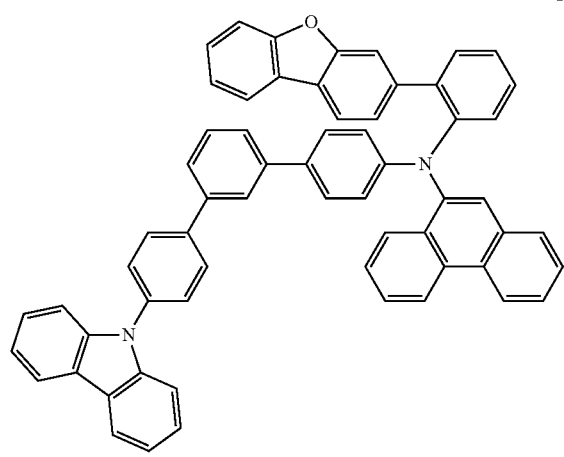
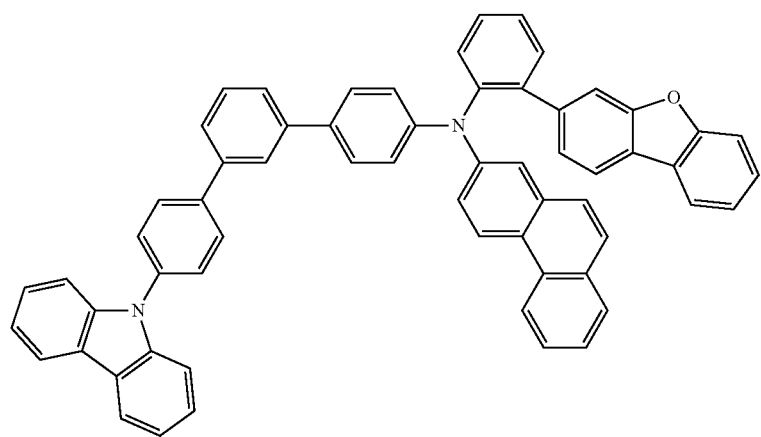
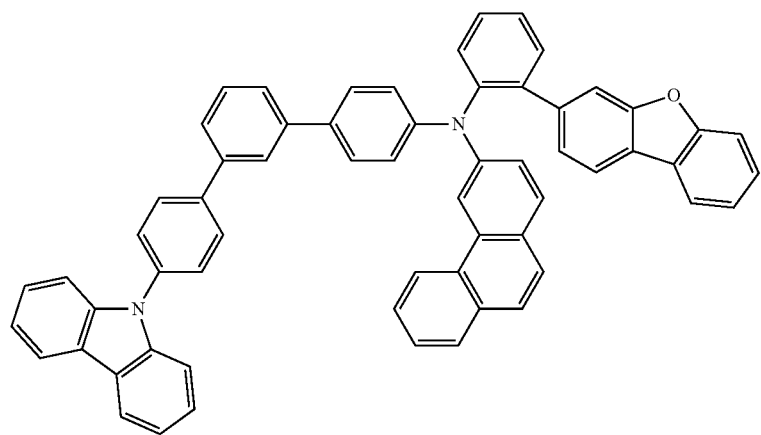

-continued
305
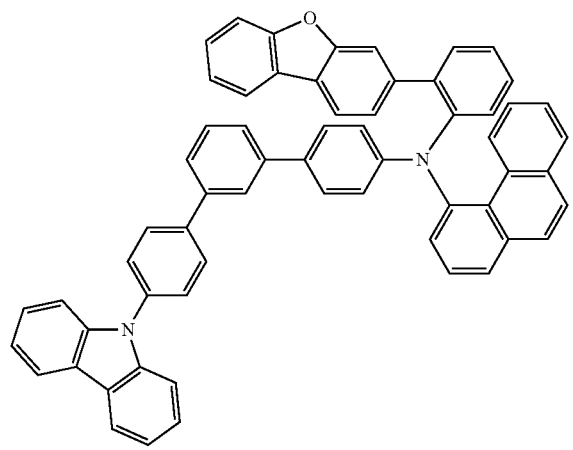
306
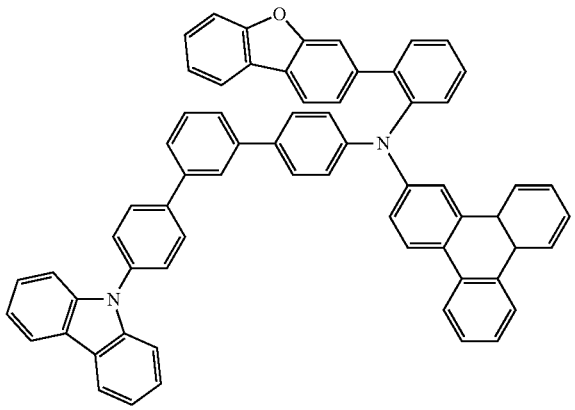
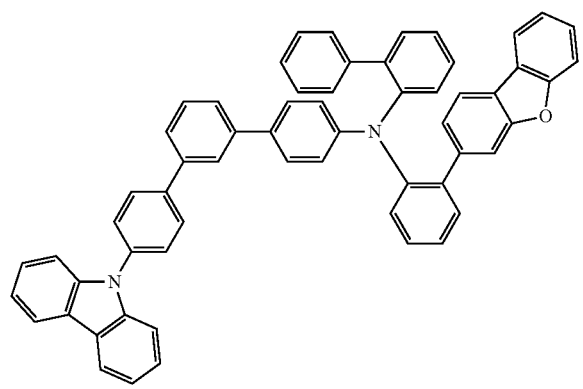
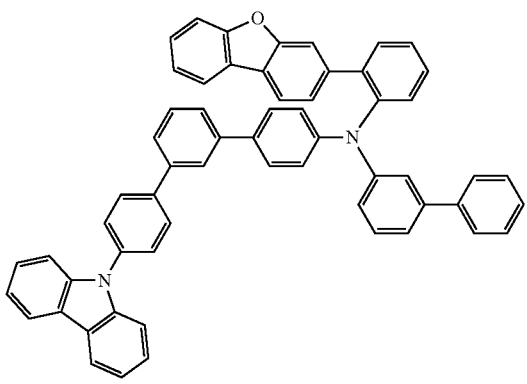
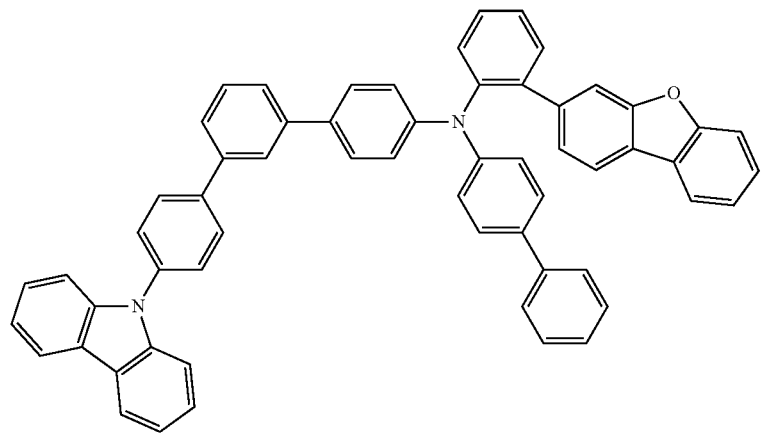

-continued
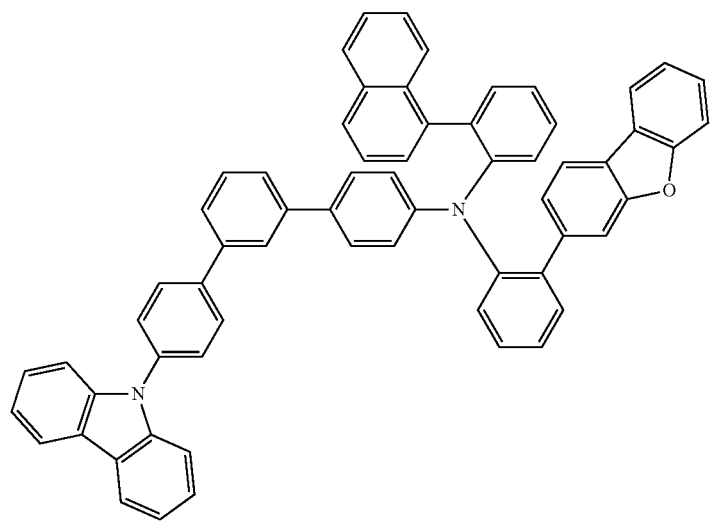
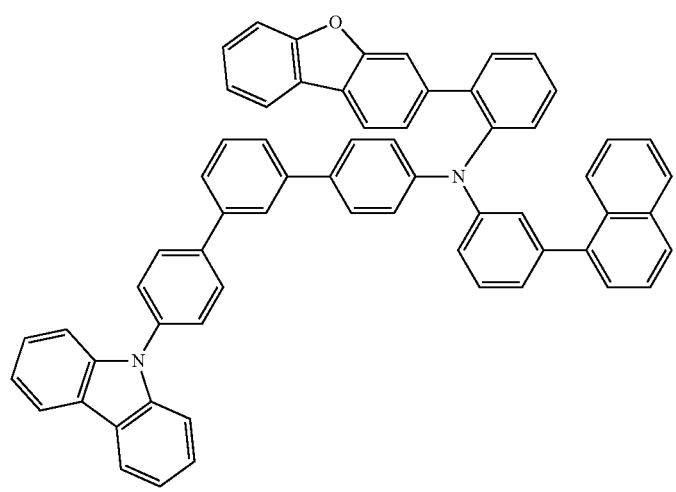
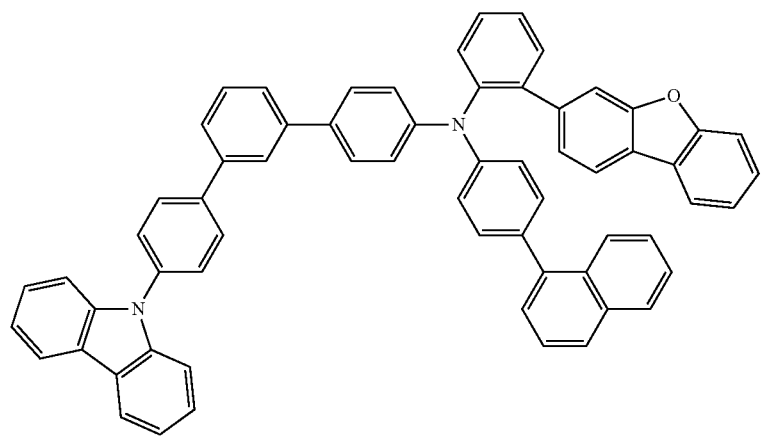

309 310
-continued
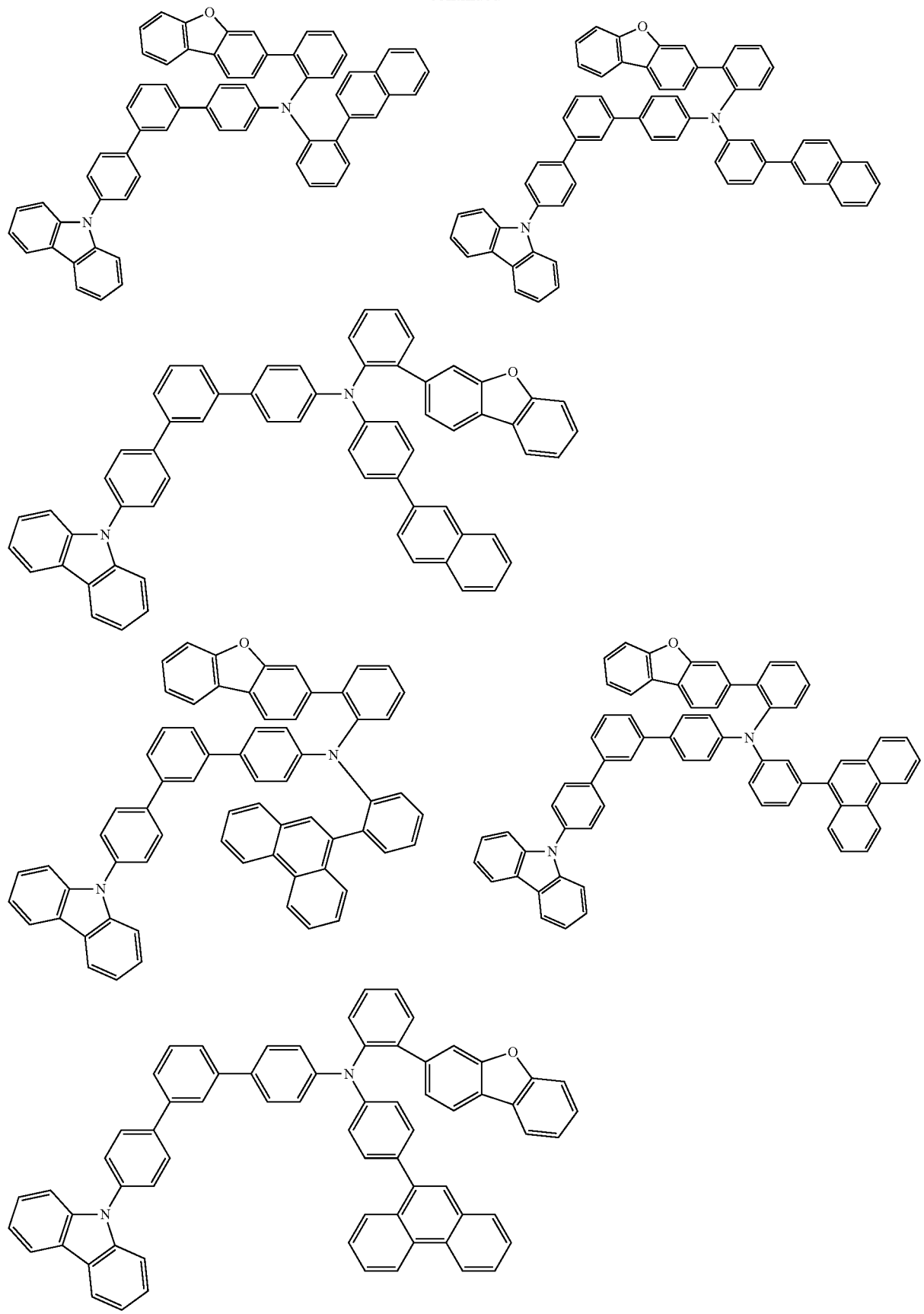

-continued
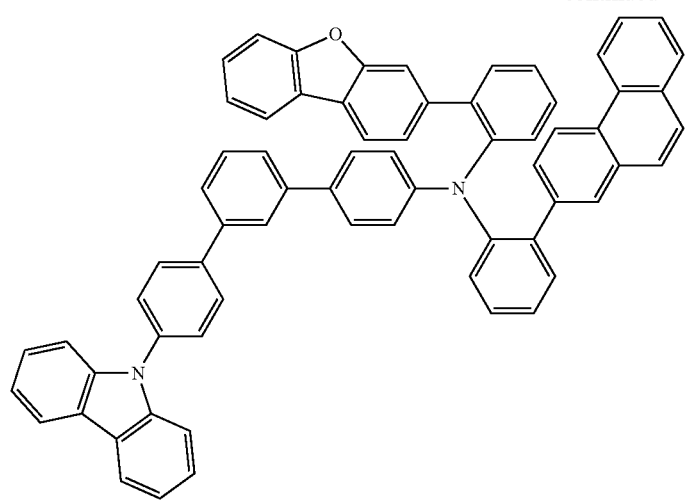
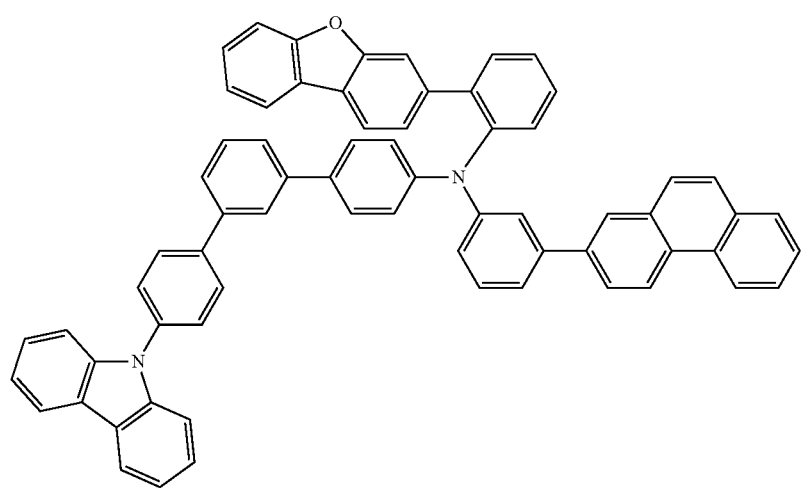
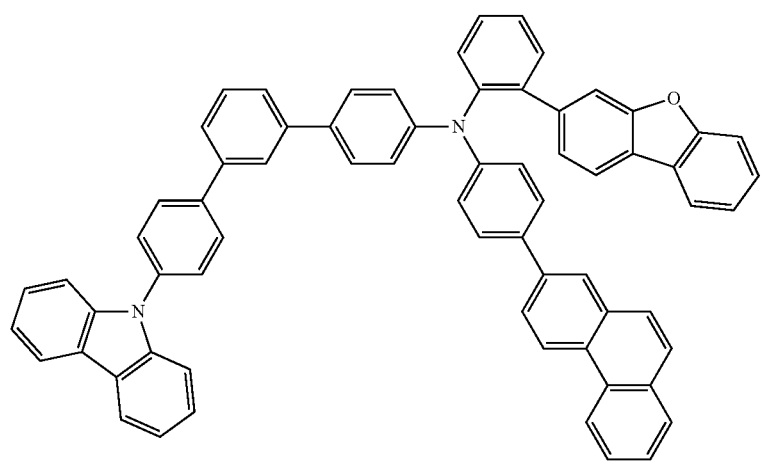

313 314
-continued
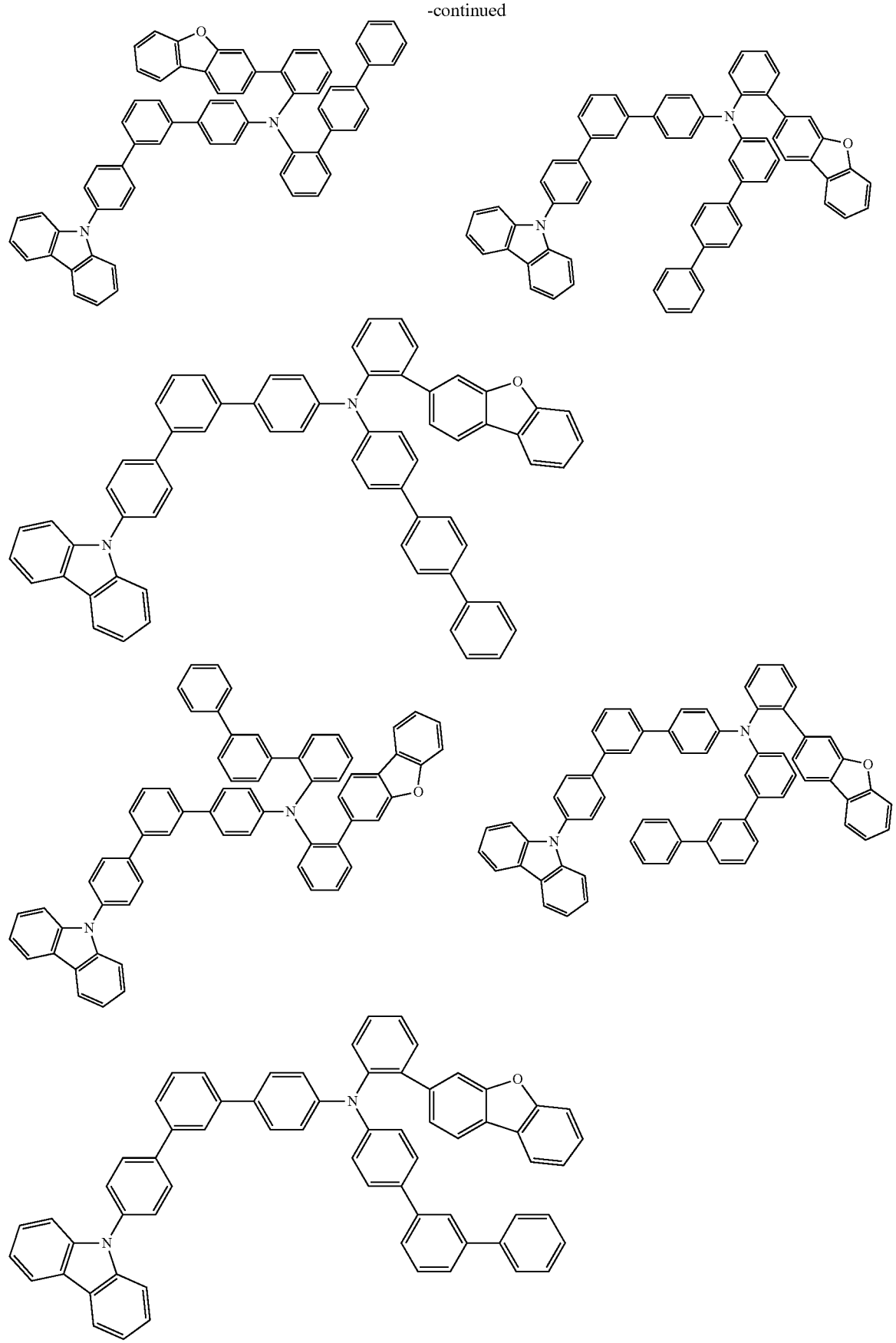

-continued
315
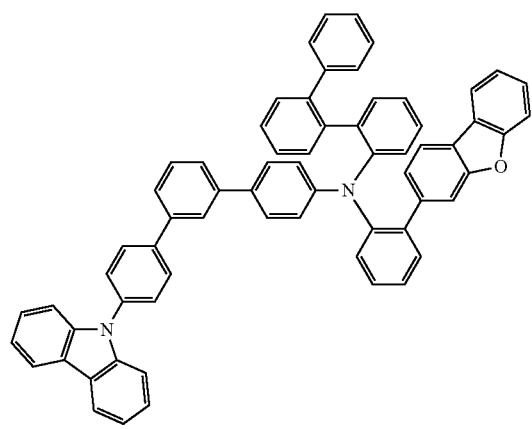
316
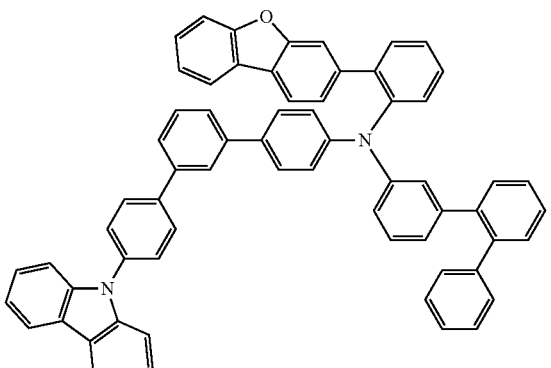
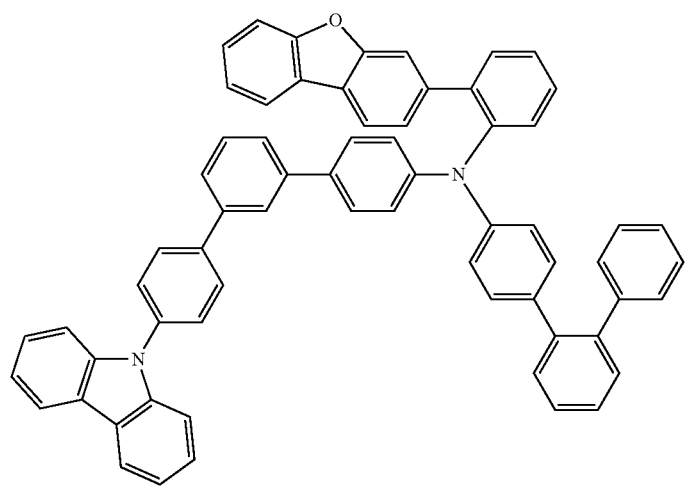
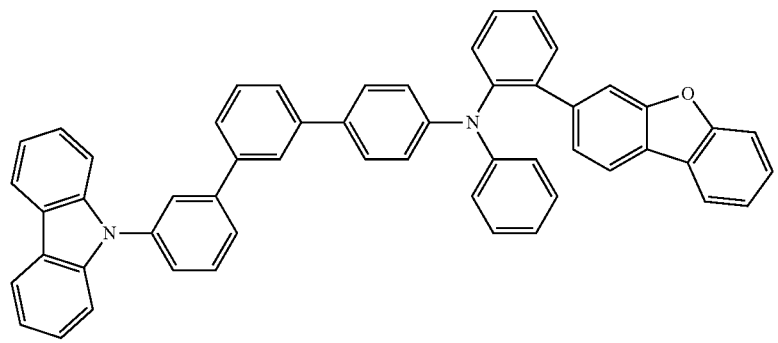
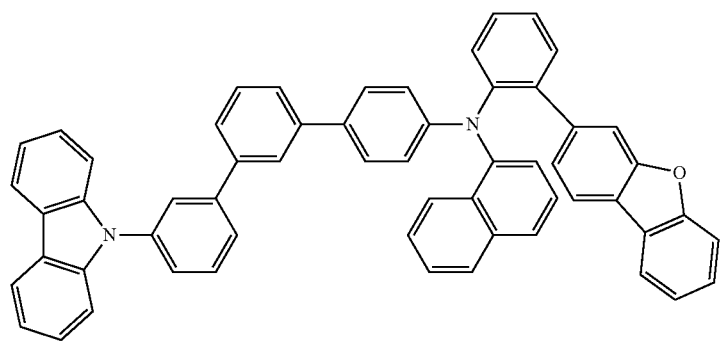

-continued
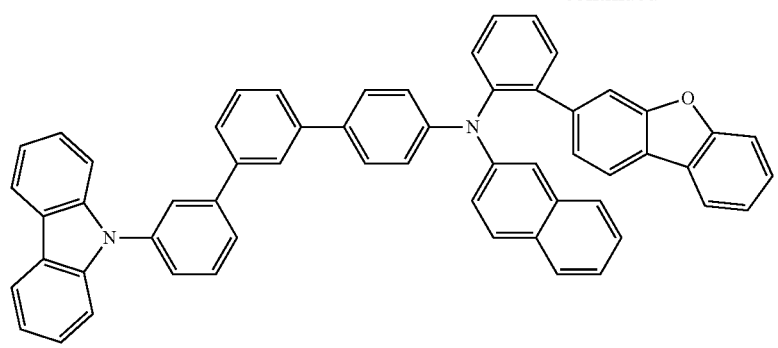
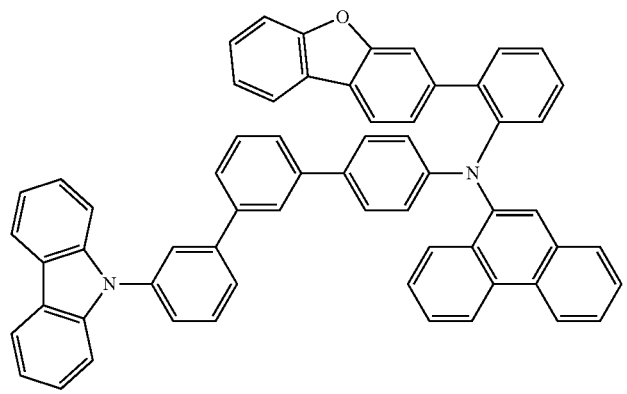
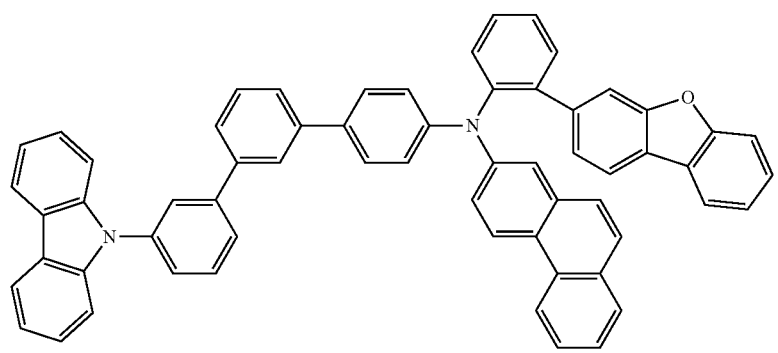
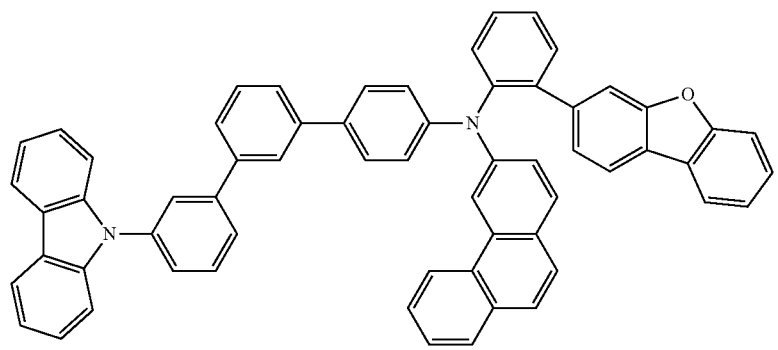

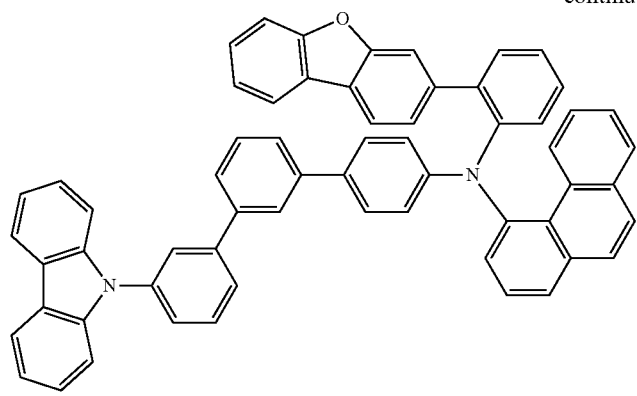
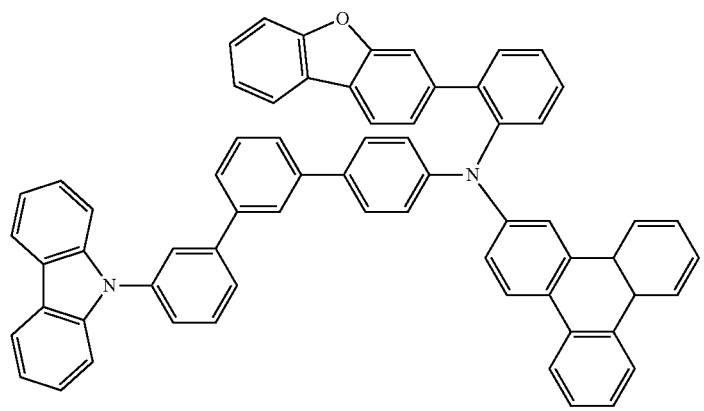
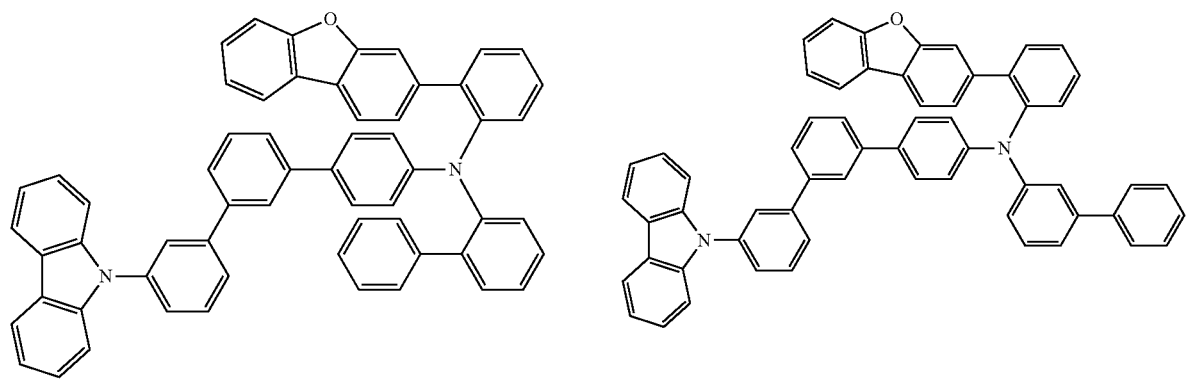
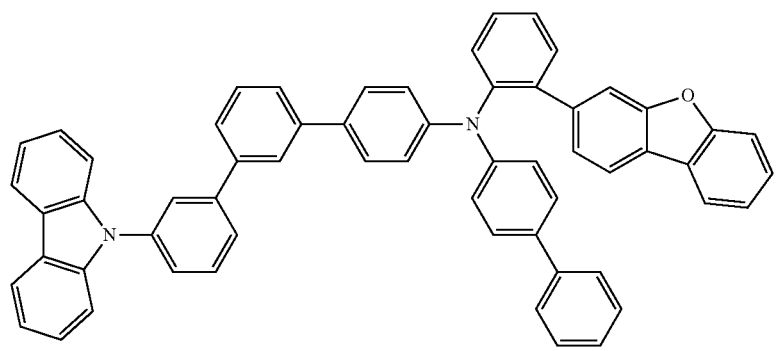

321 322
-continued
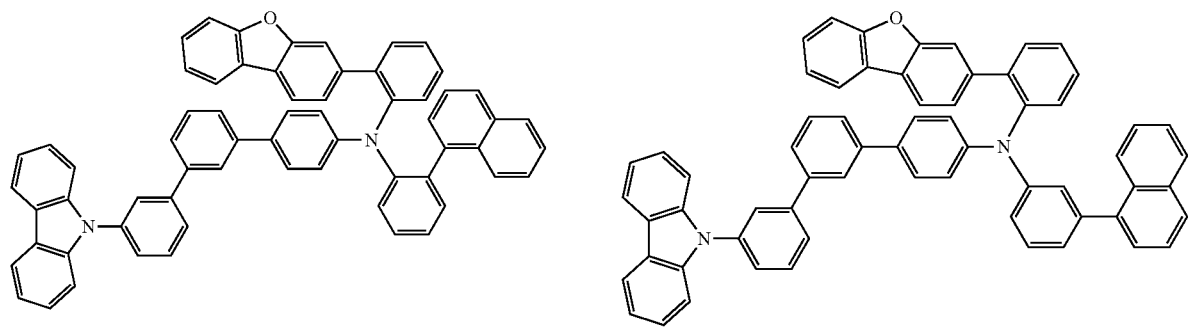
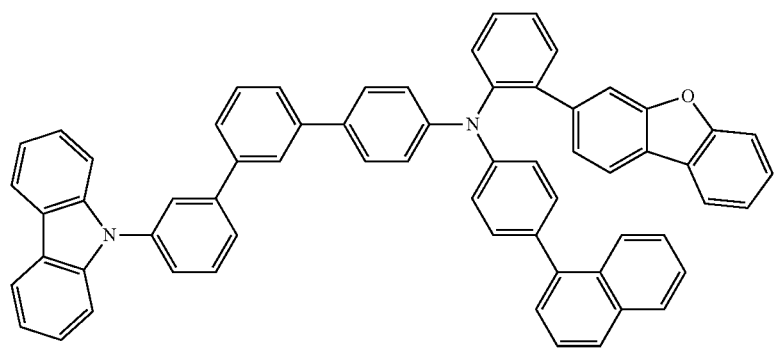
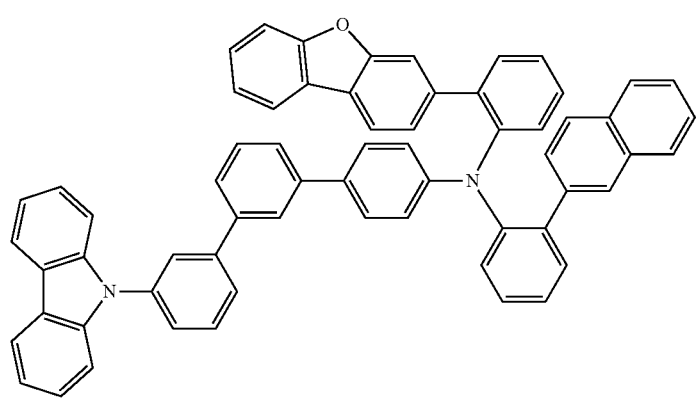
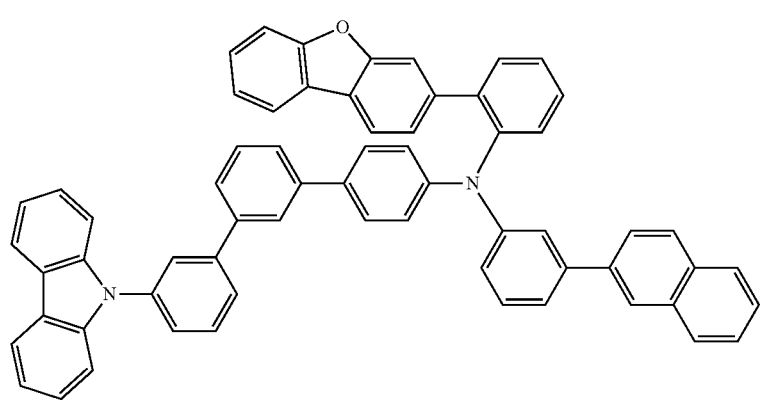

-continued
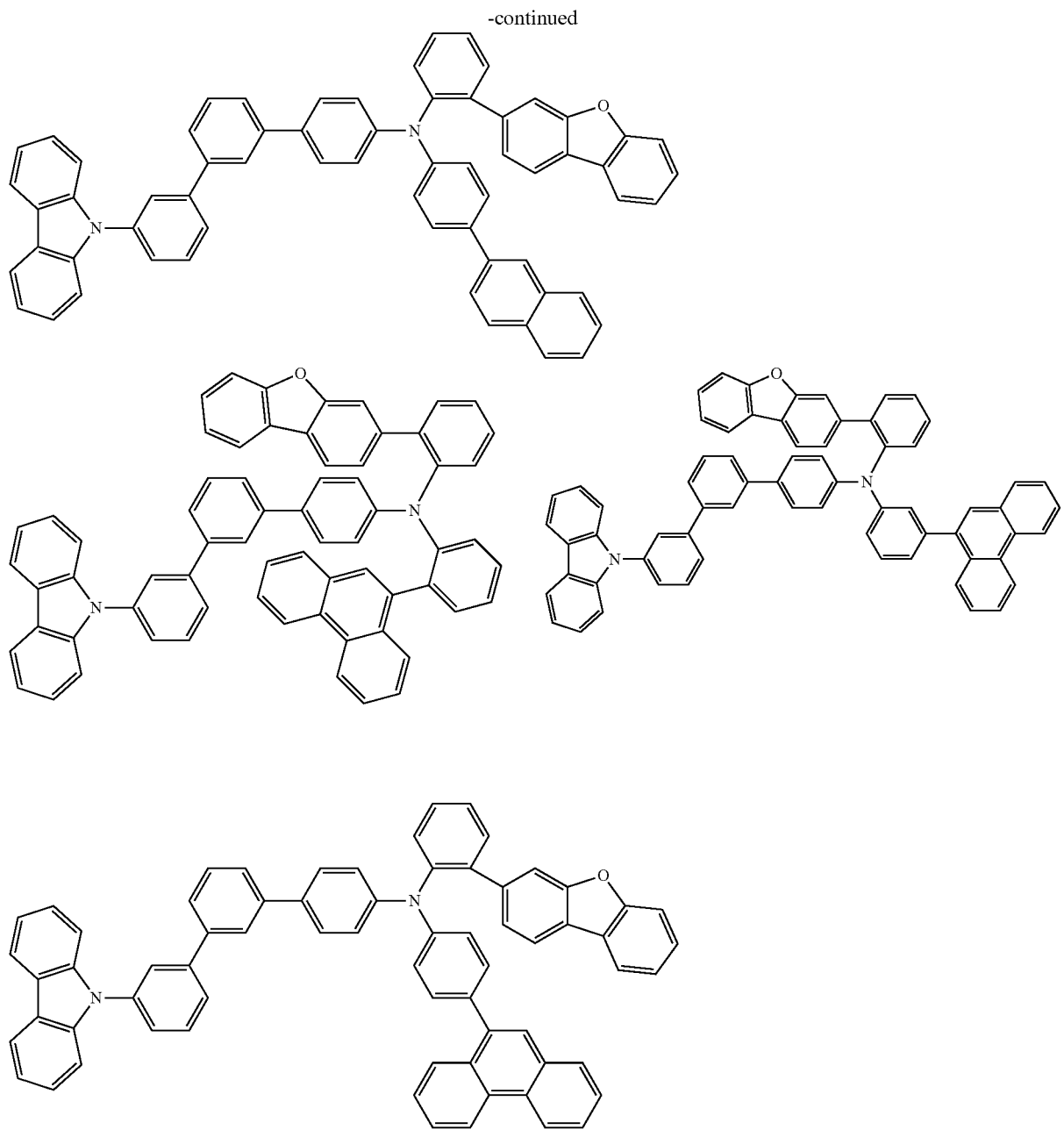
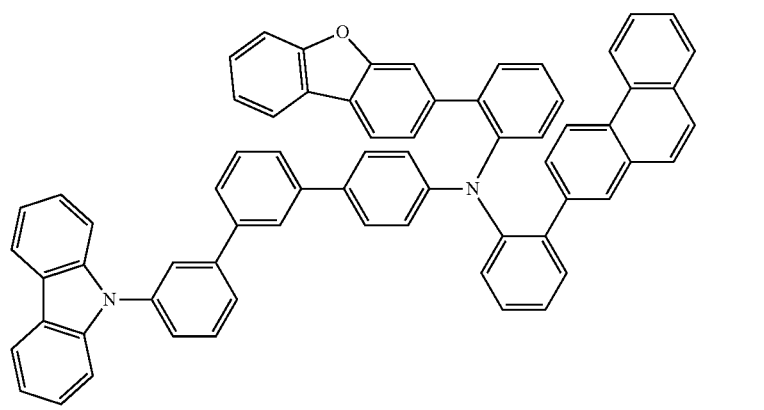

-continued
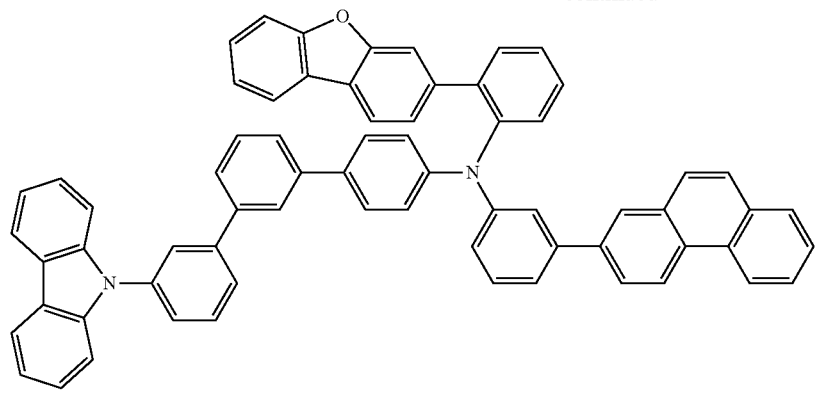
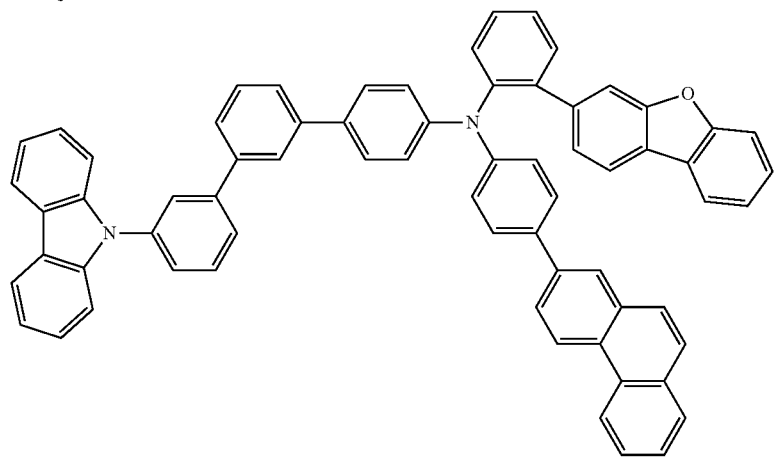
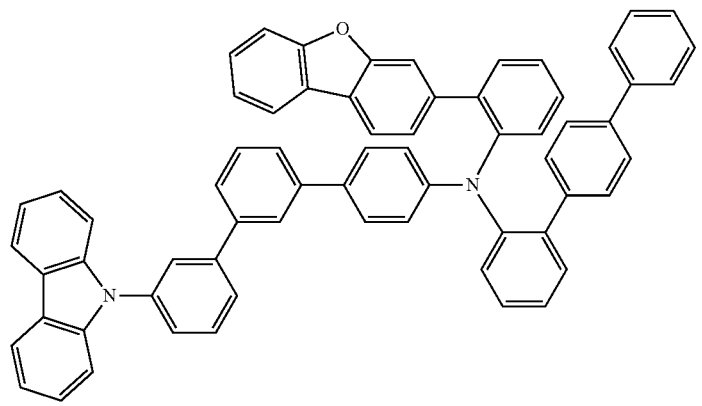
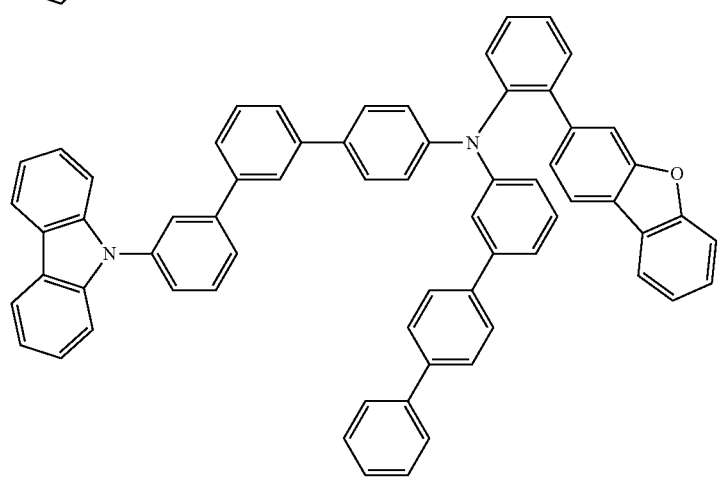

-continued
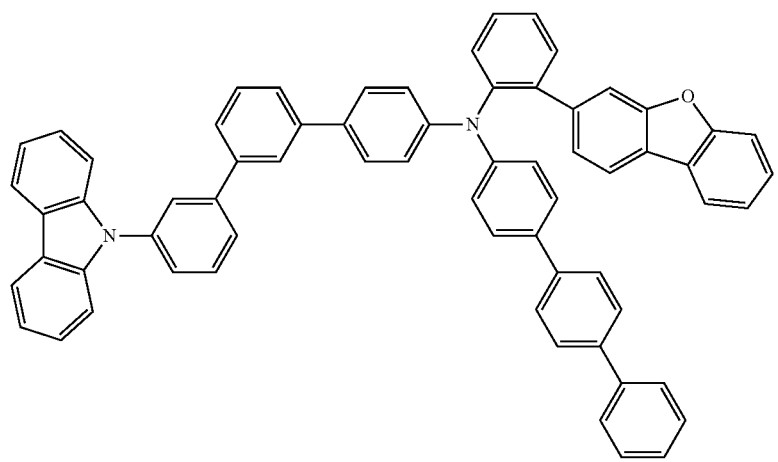
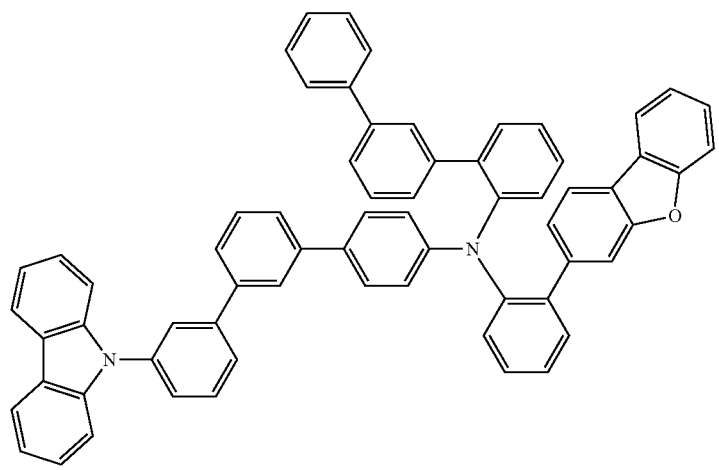
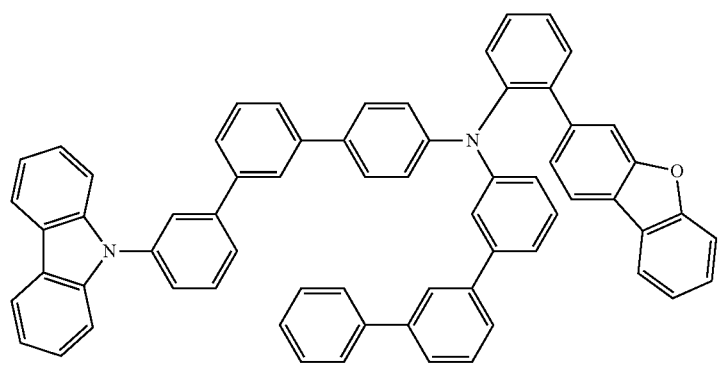
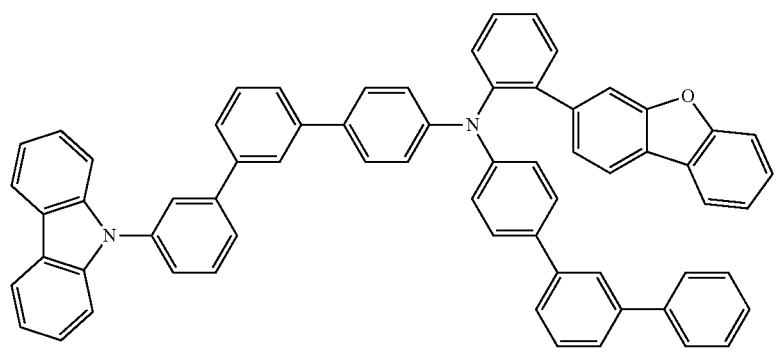

-continued
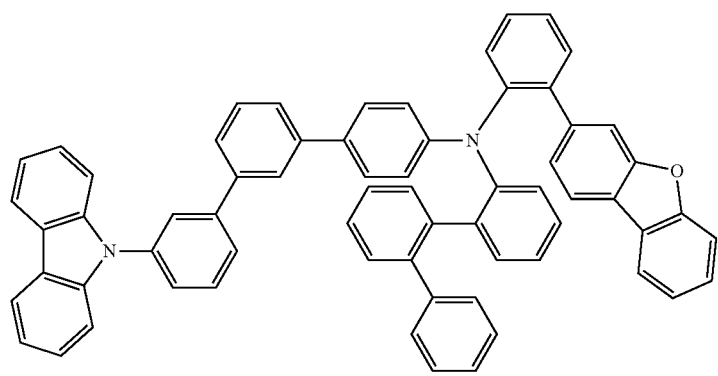
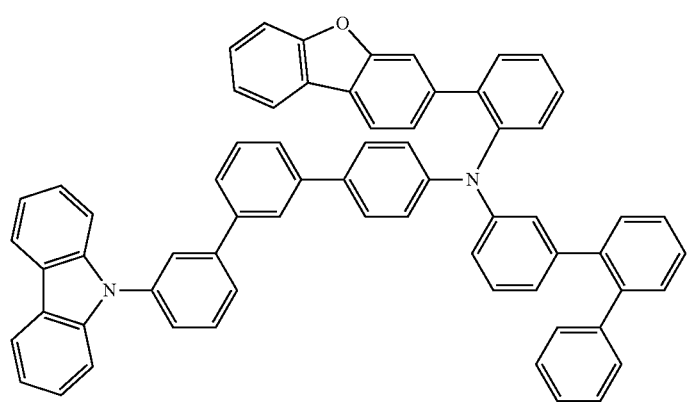
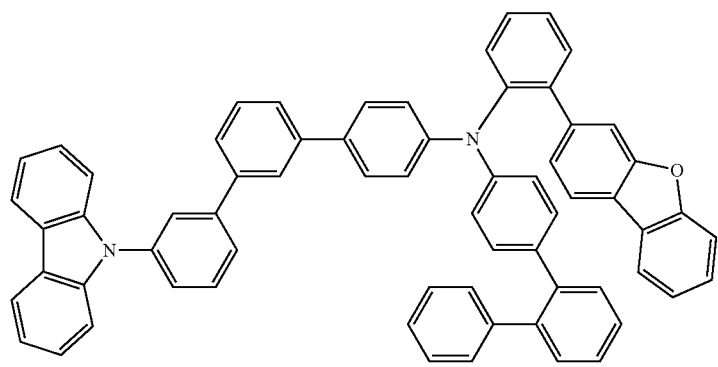 [SMILES: c1ccc(-c2ccccc2-c2ccc(N(c3ccc(-c4cccc(-c5cccc(-n6c7ccccc7c7ccccc76)c5)c4)cc3)c3ccccc3-c3ccc4c(c3)oc3ccccc34)cc2)cc1]

331 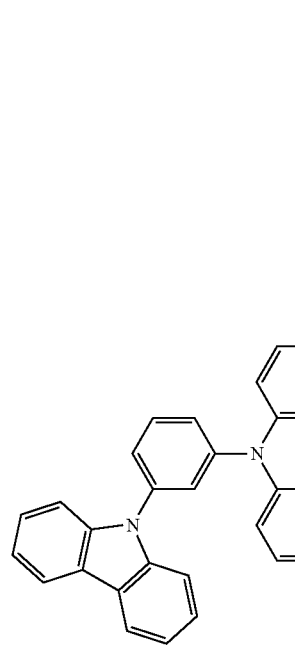 332 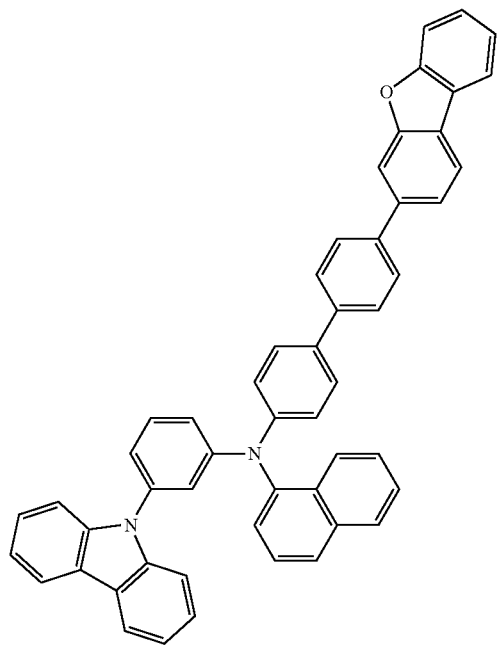
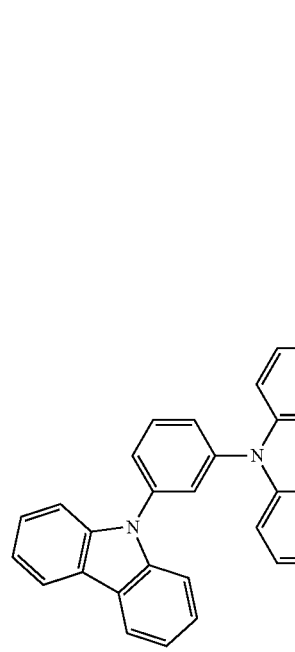 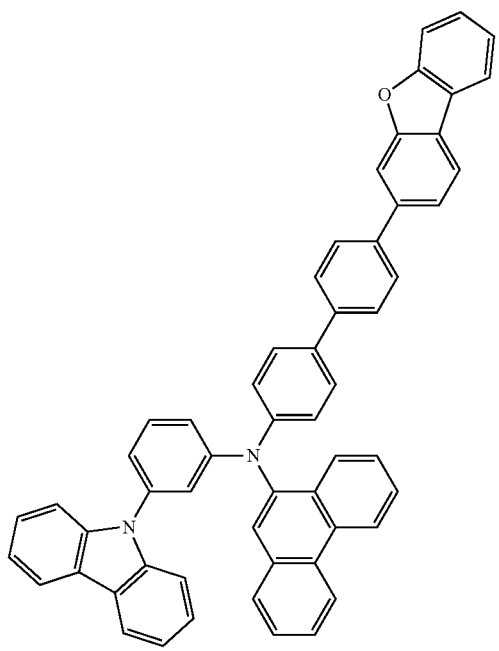

333 334
-continued
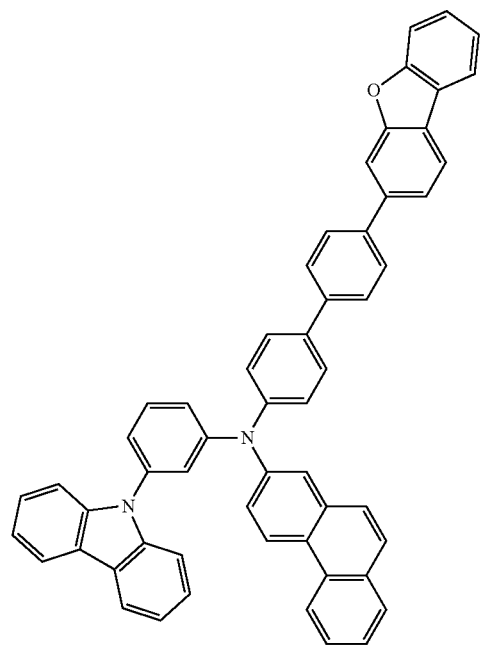
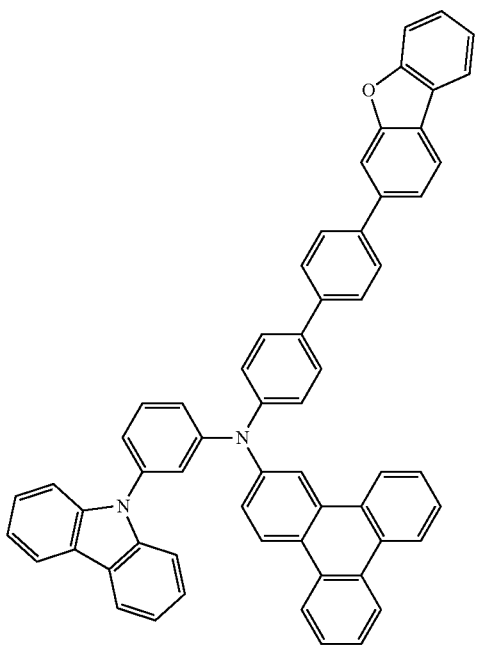
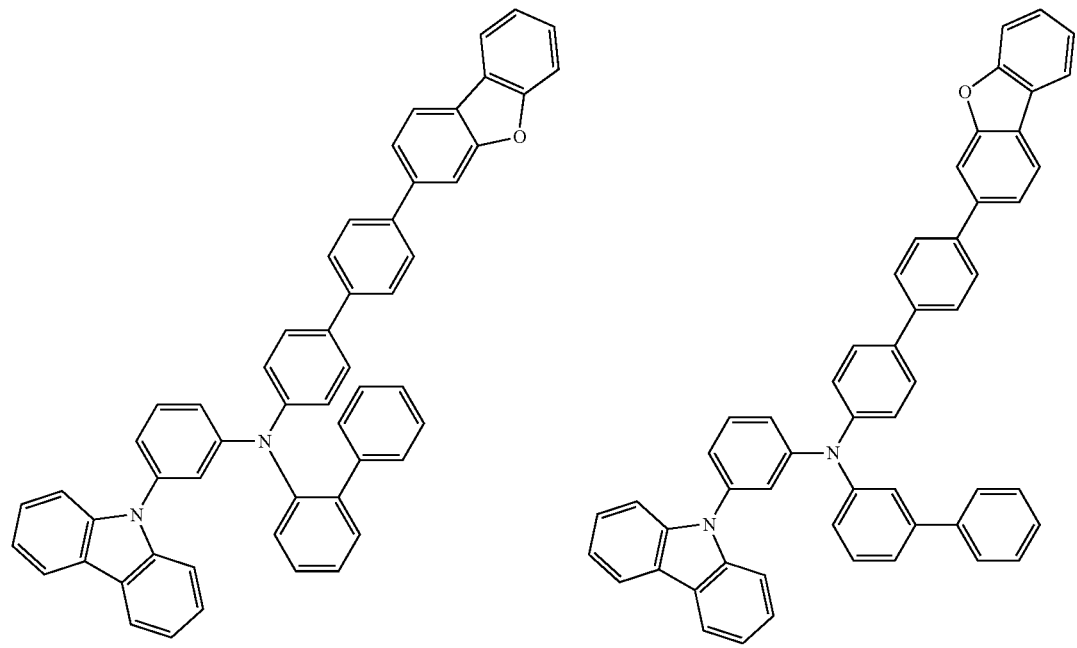

-continued
335
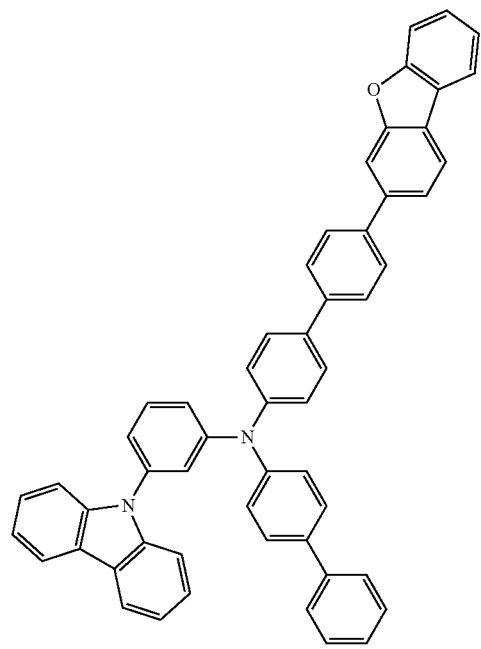
336
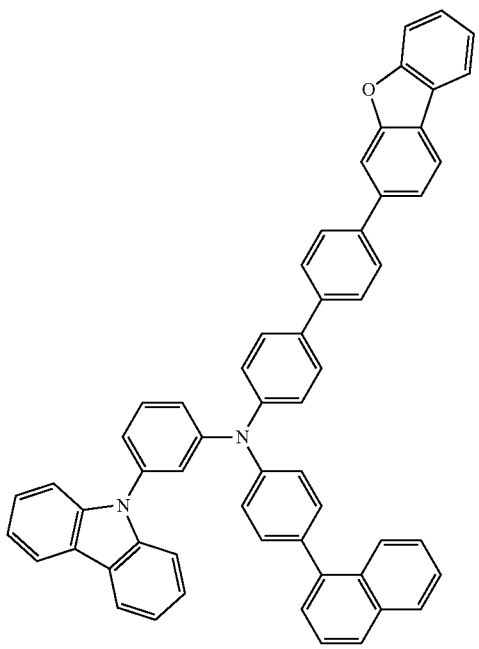
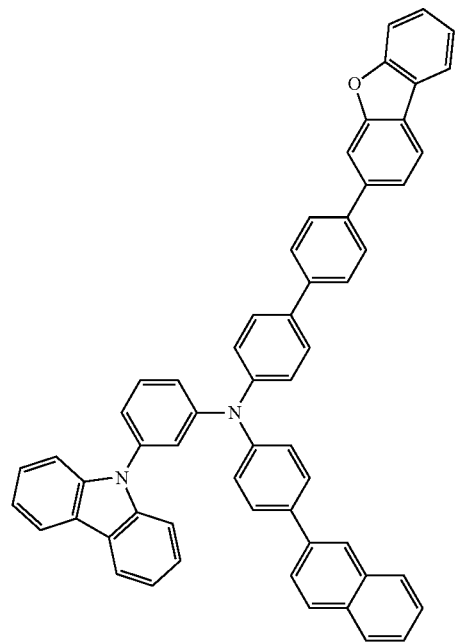
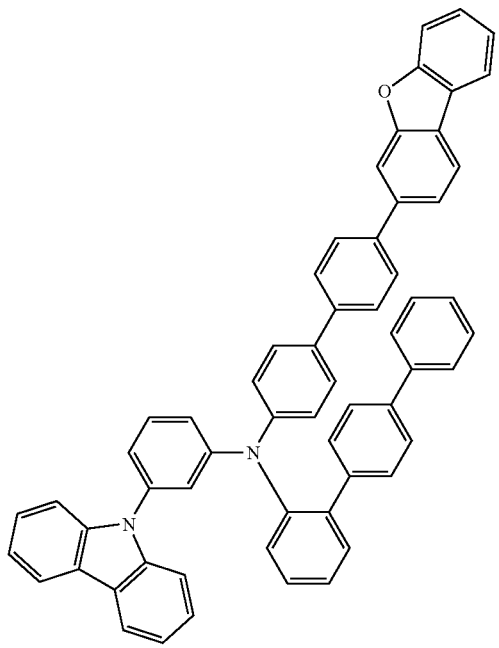

337 338
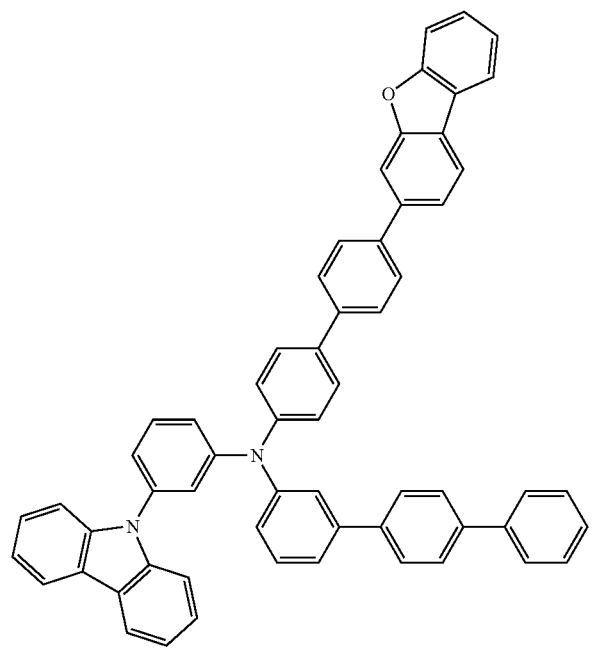
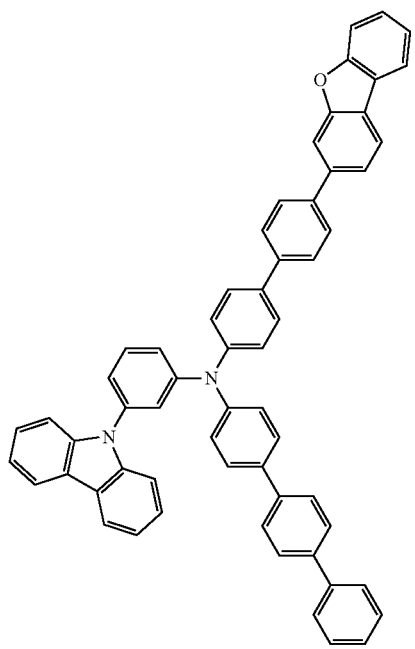
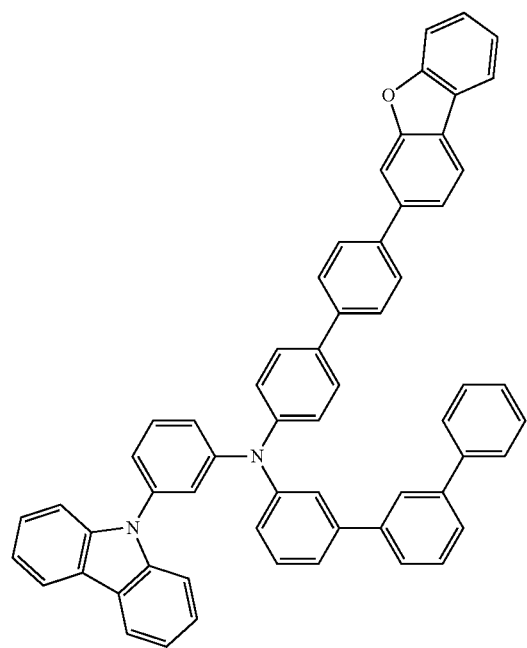
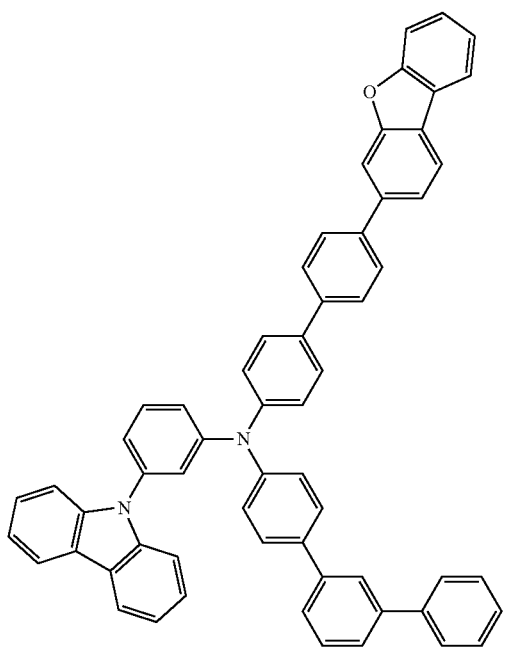

-continued
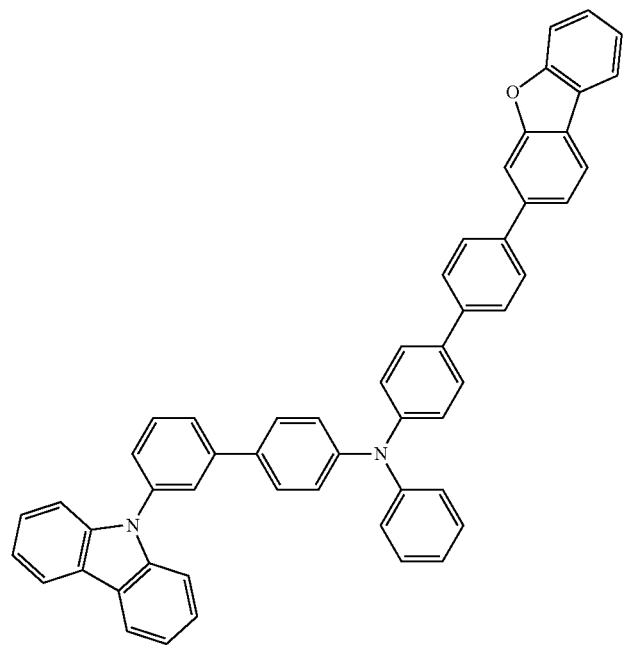
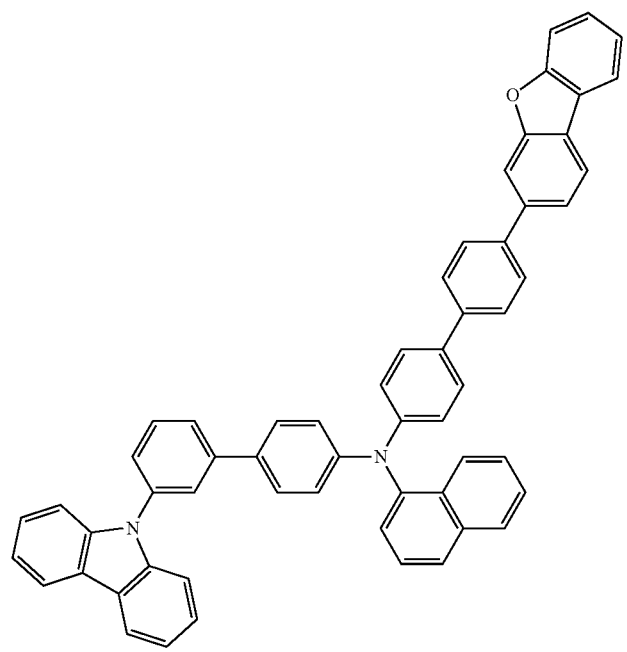

-continued
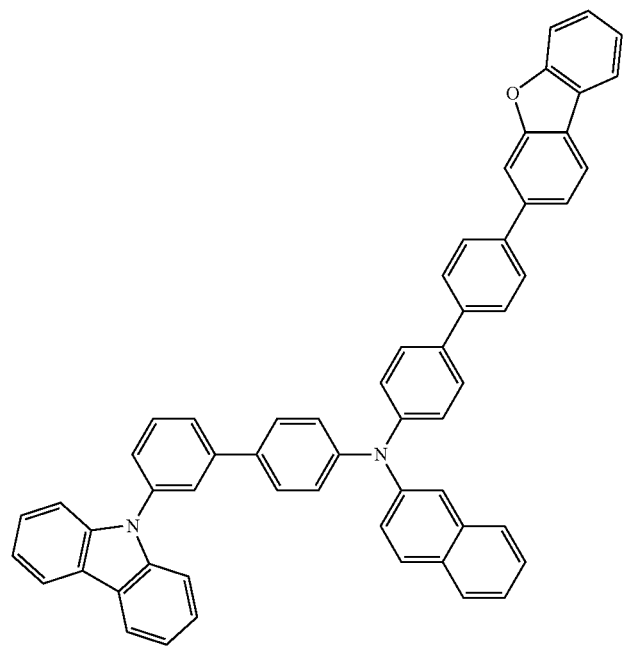
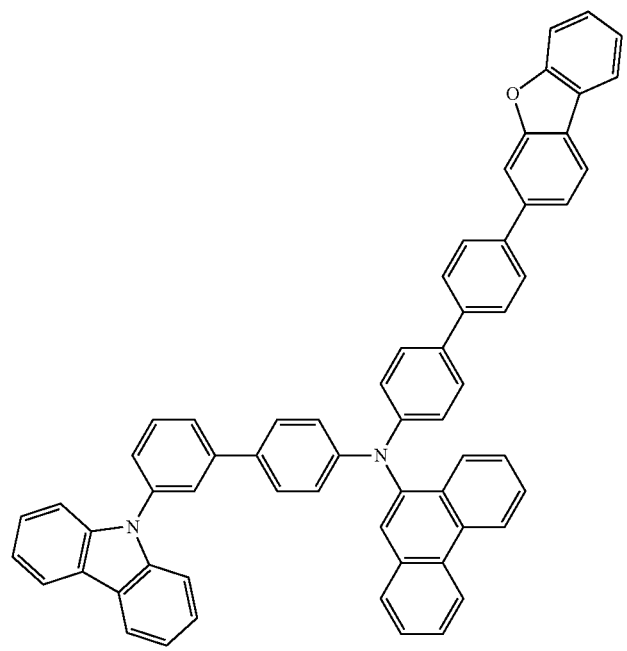

-continued
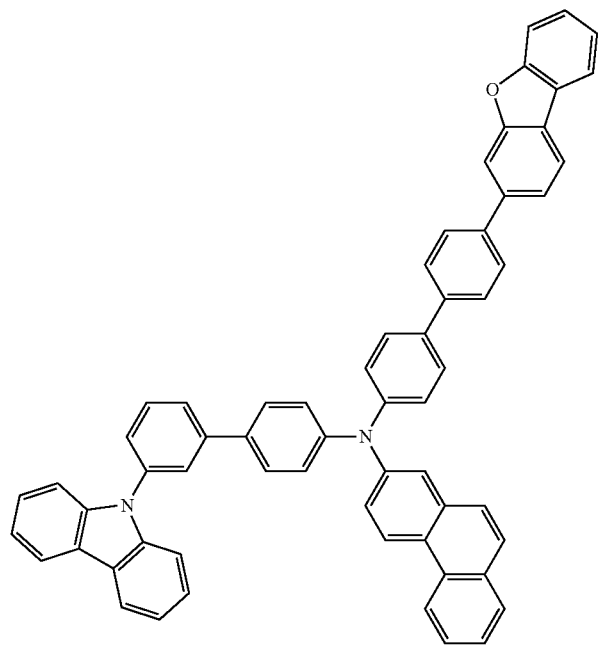
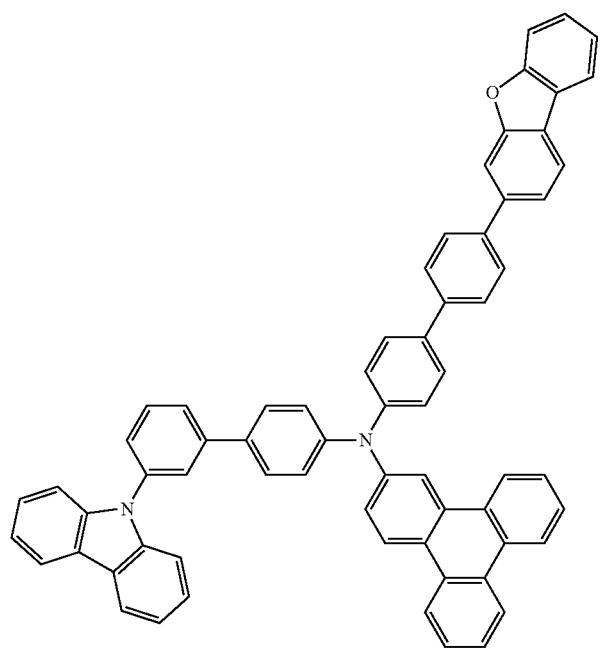

-continued
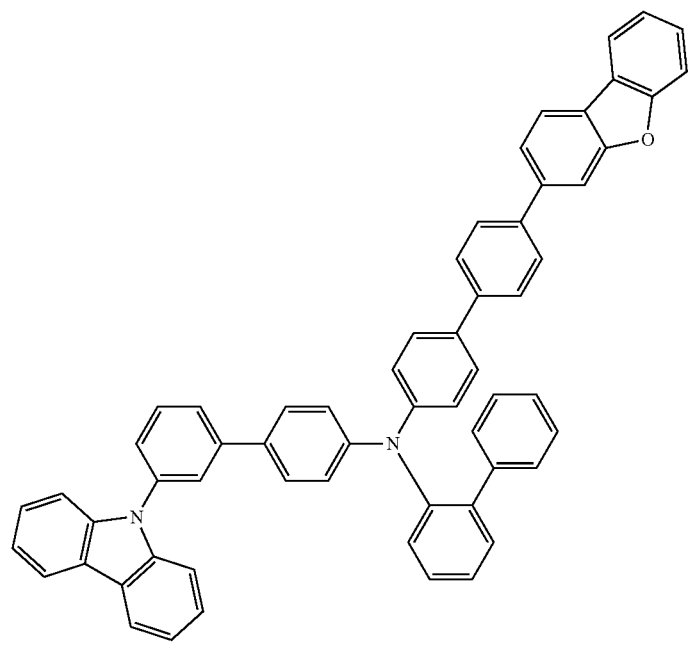
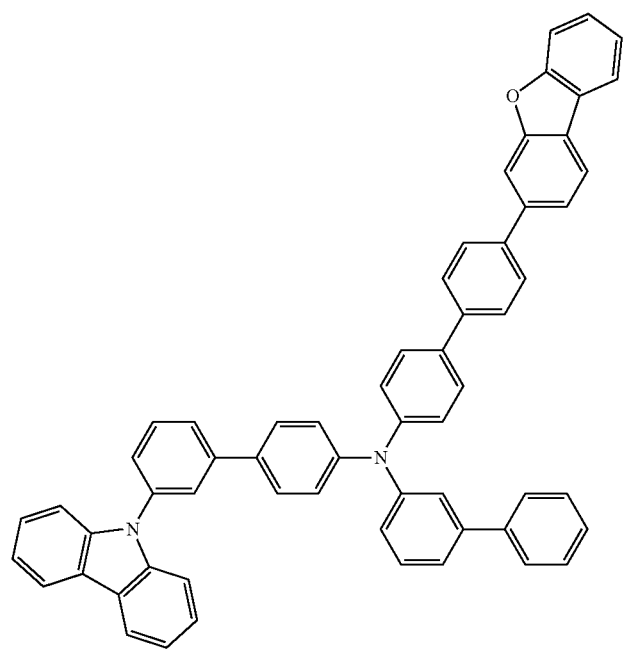

-continued
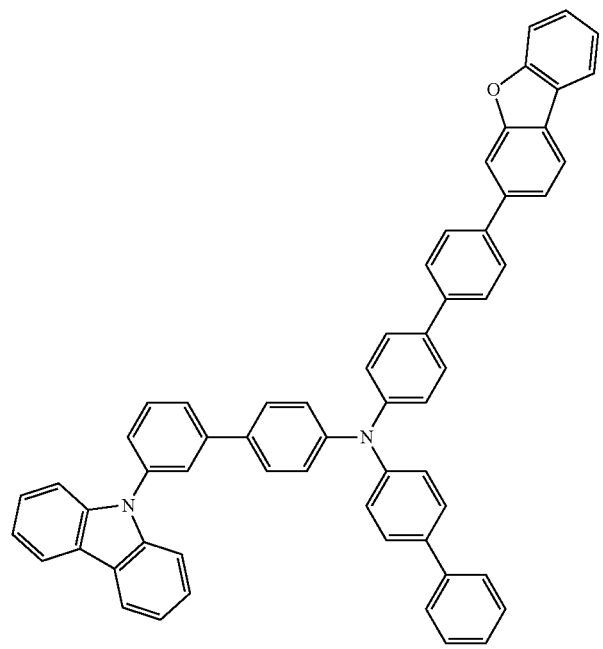
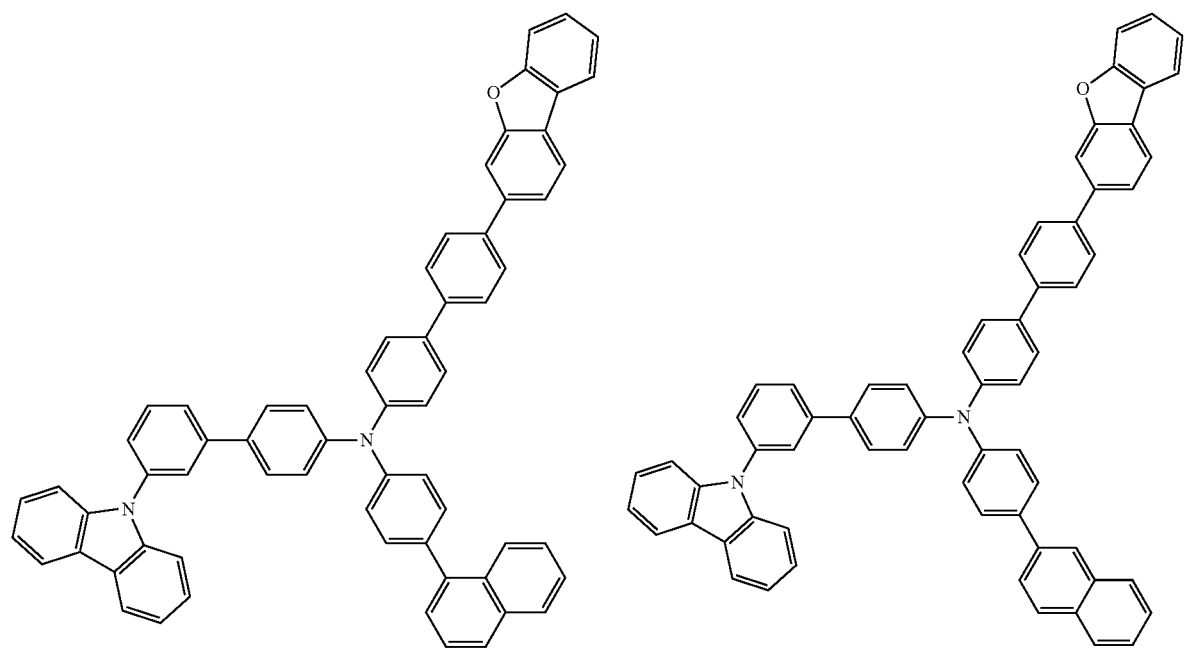

-continued
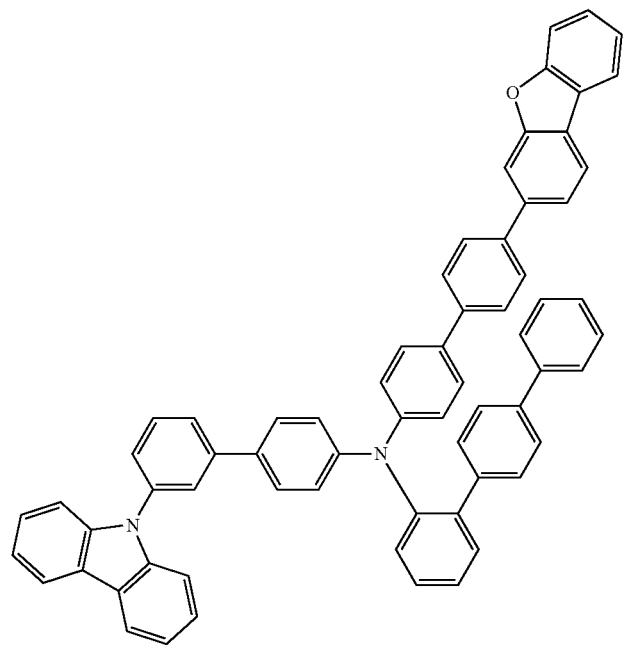
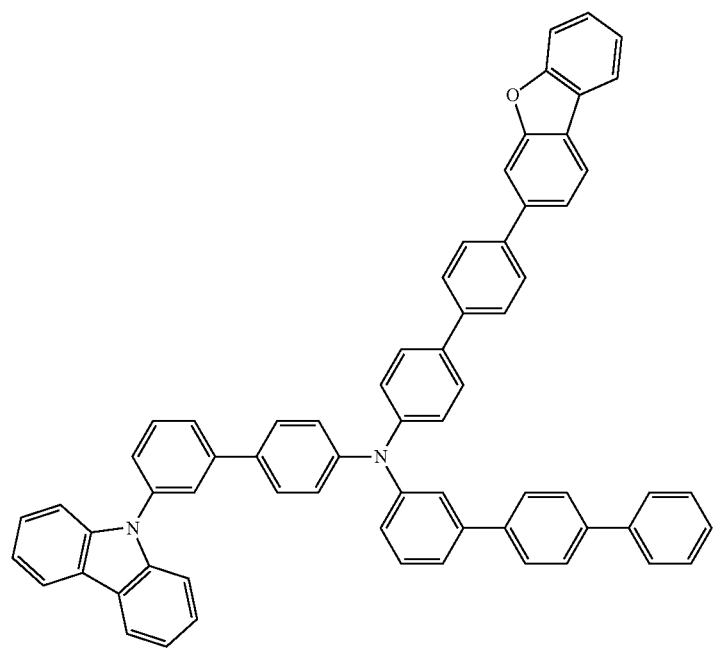

-continued
| 351 | 352 |
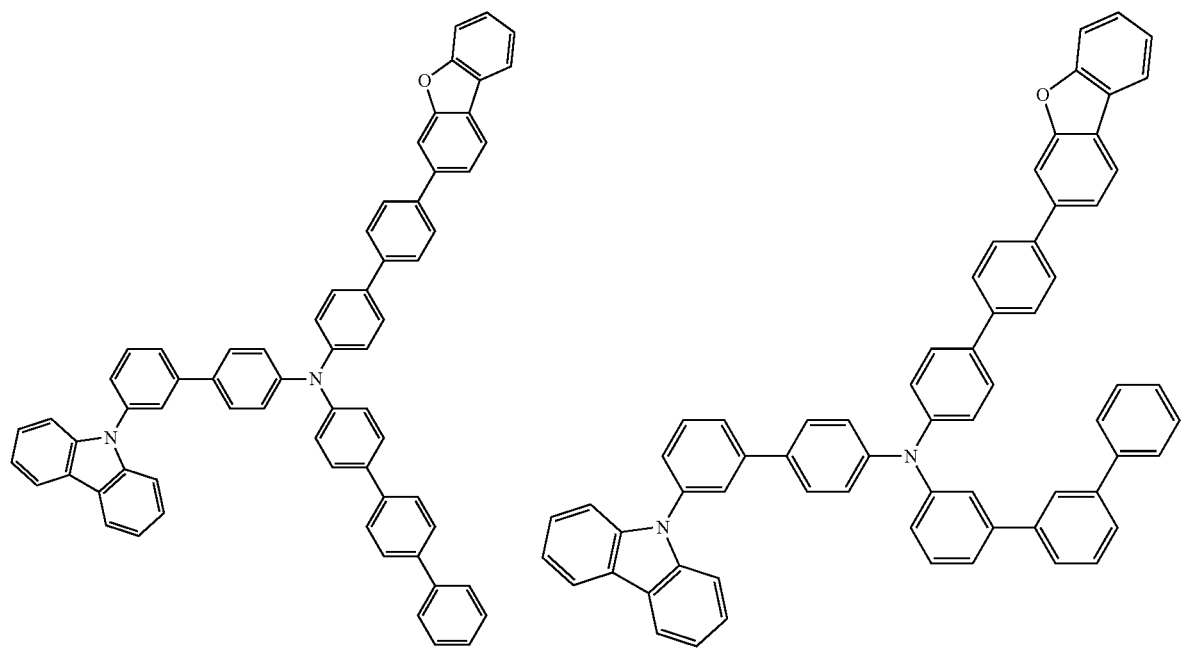
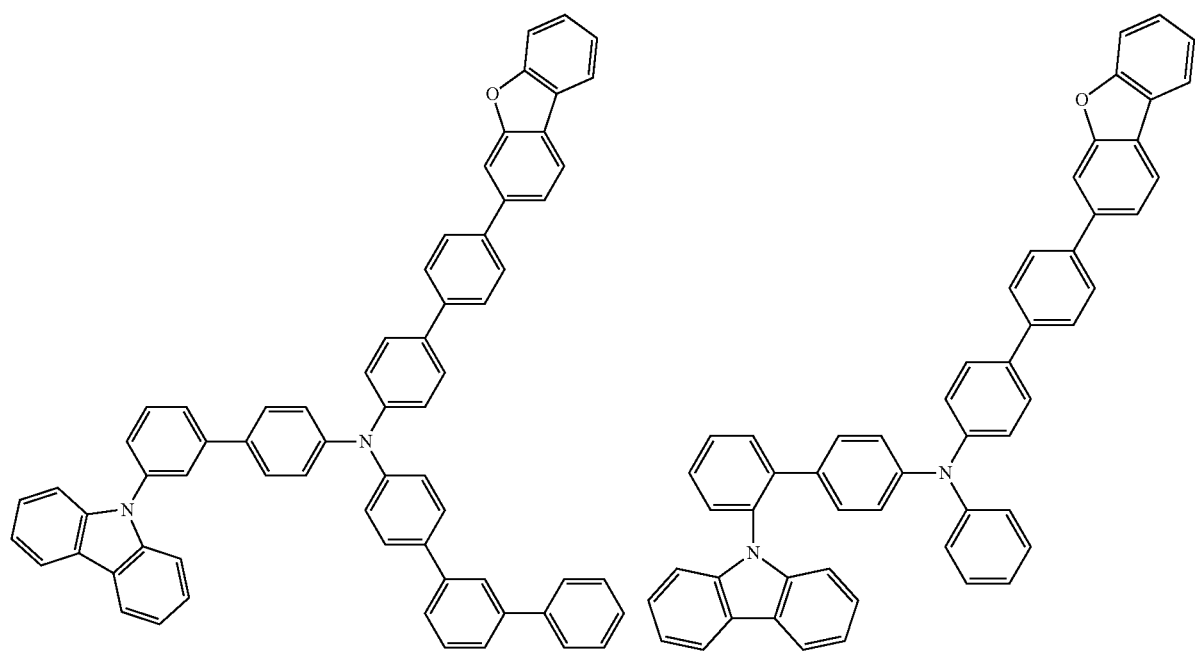

353
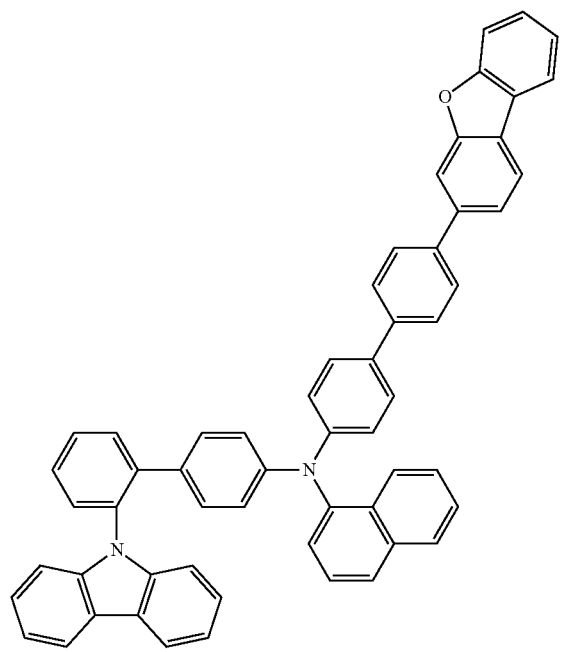
354
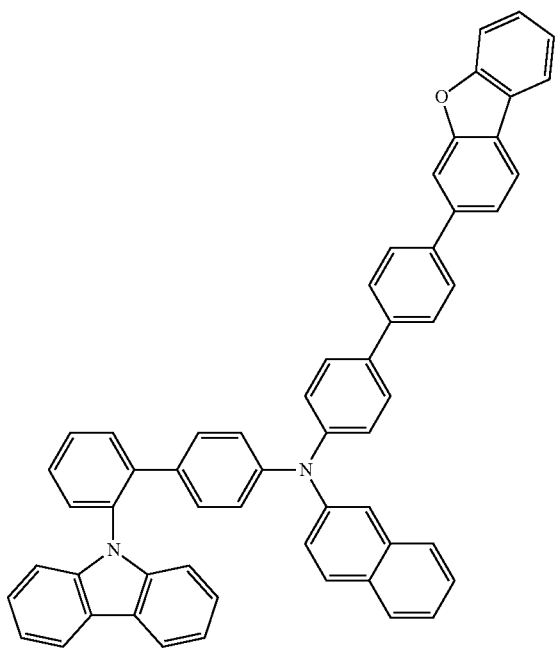
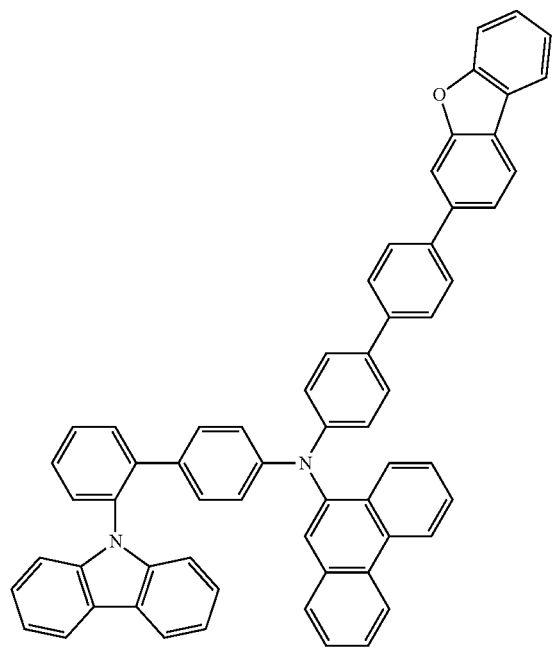
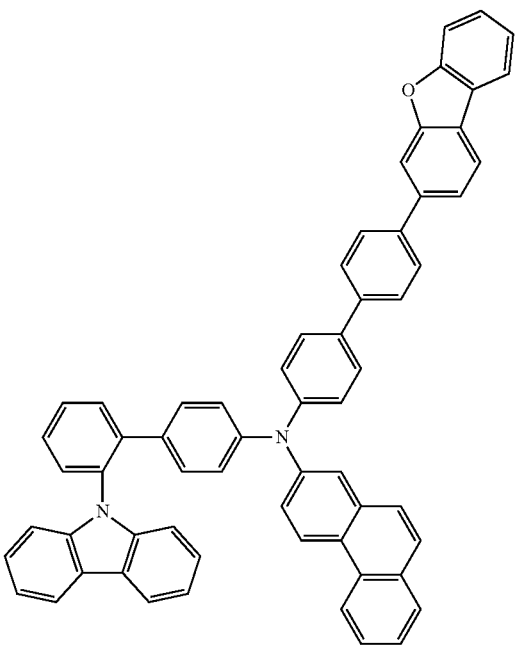

-continued
355
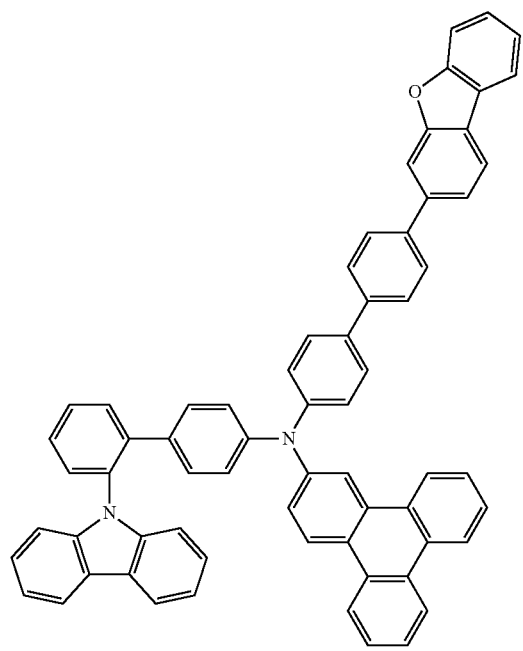
356
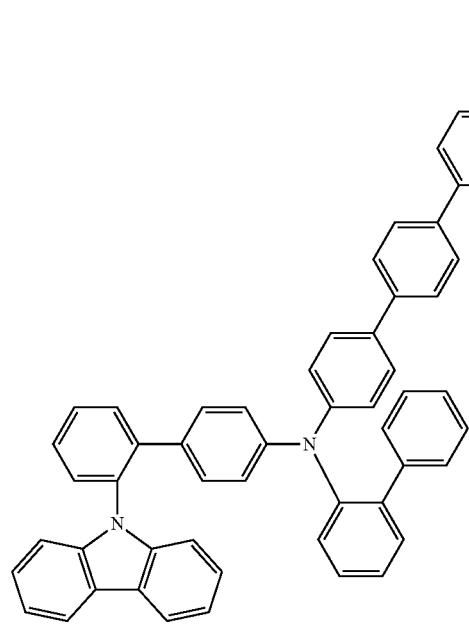
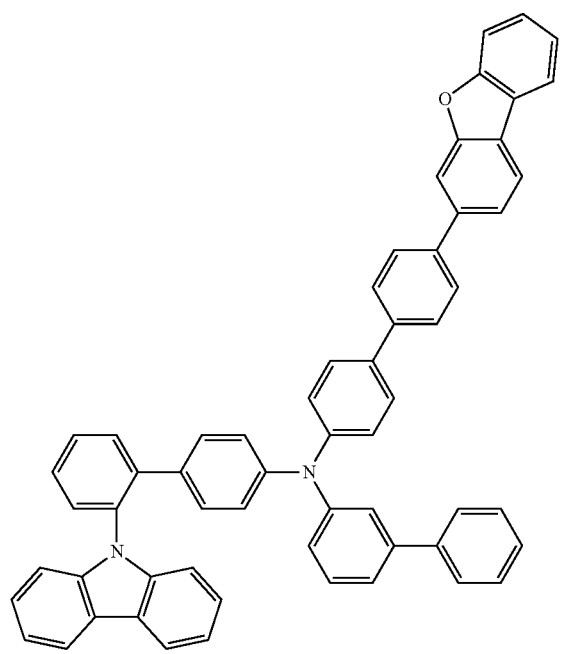
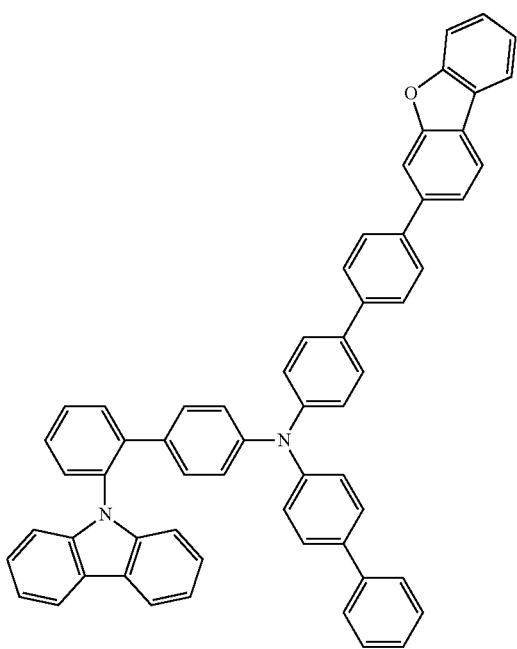

357
358
-continued
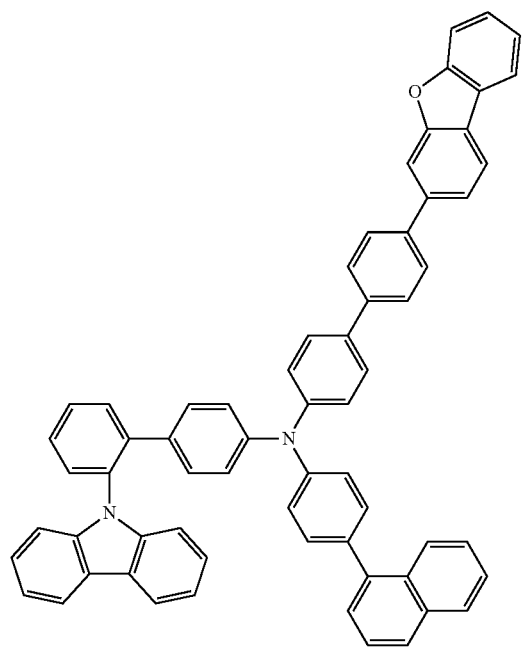
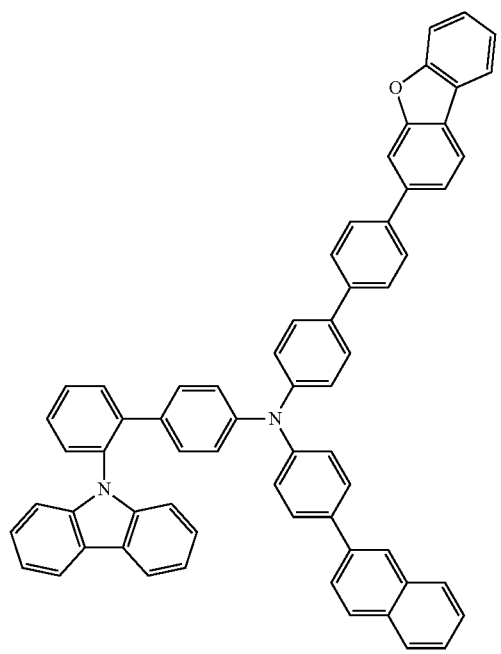
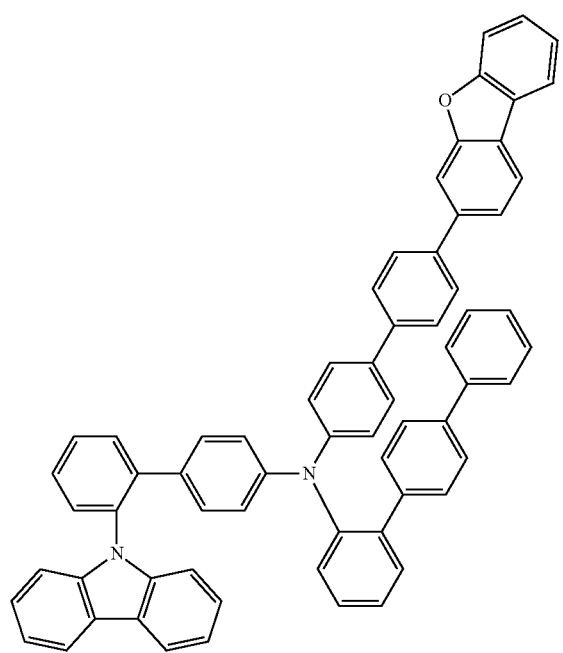

359 360
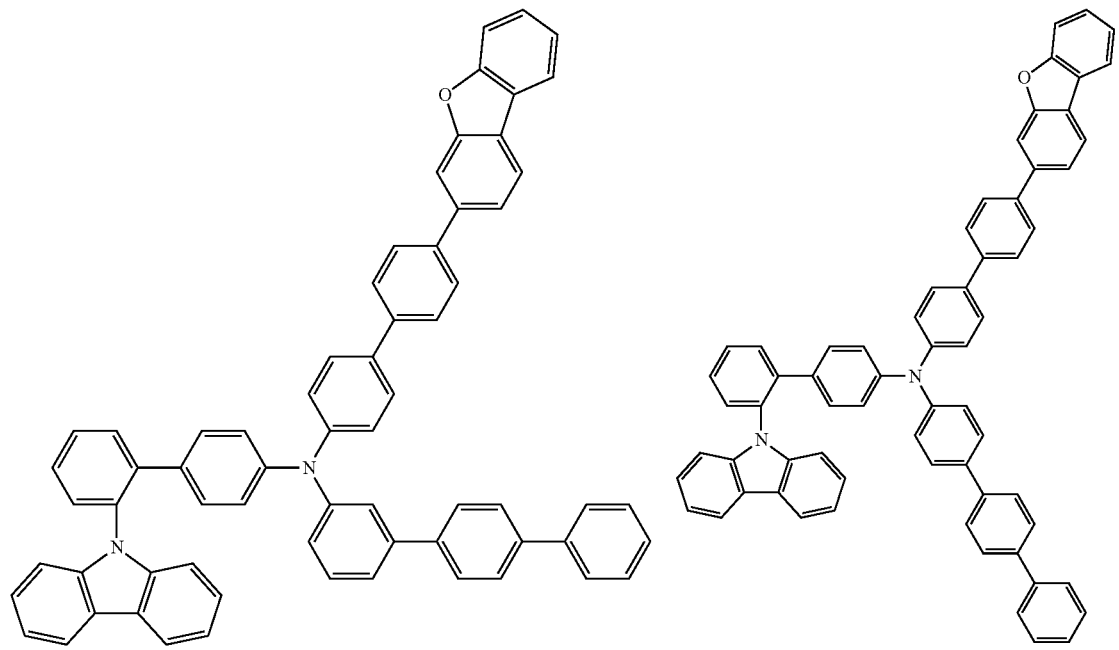
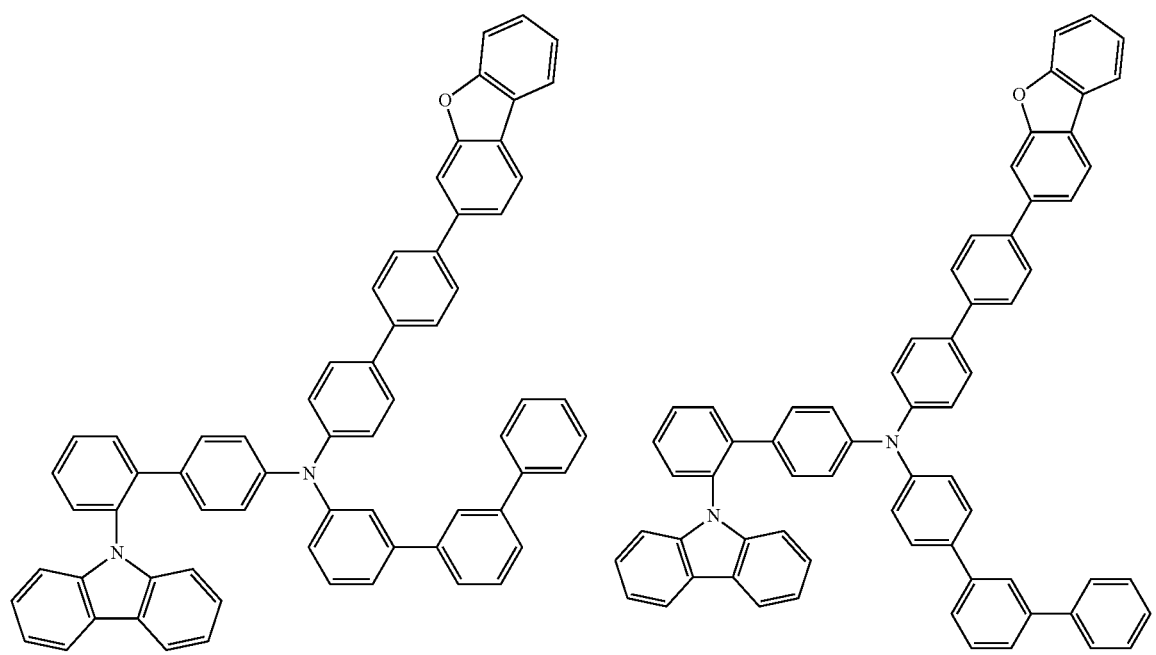

-continued
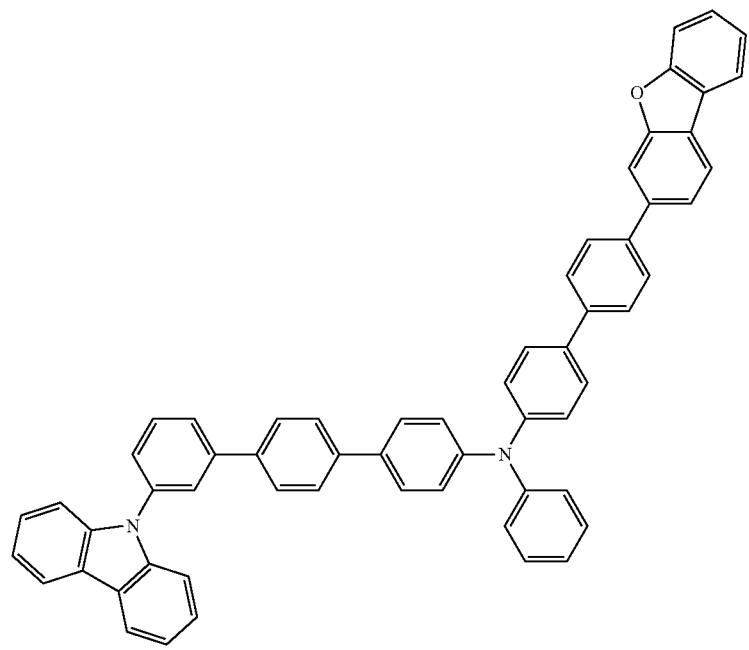
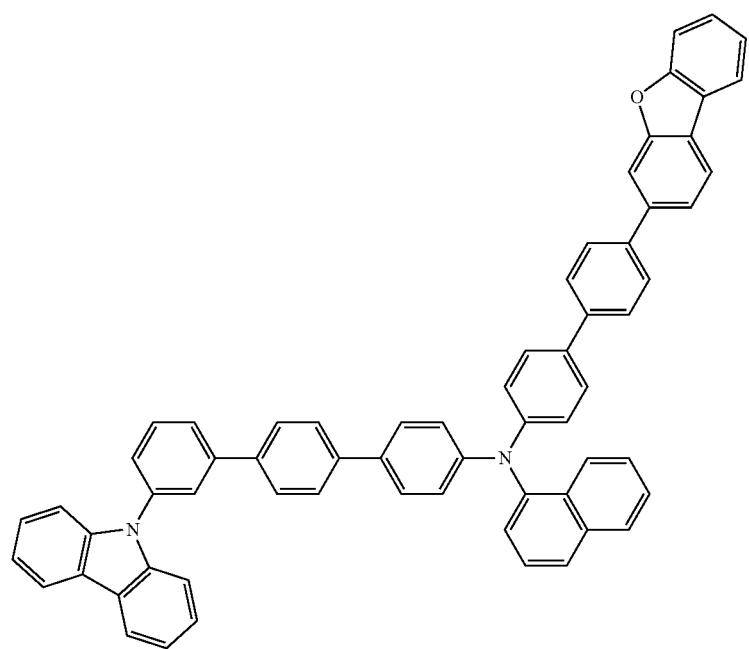

-continued
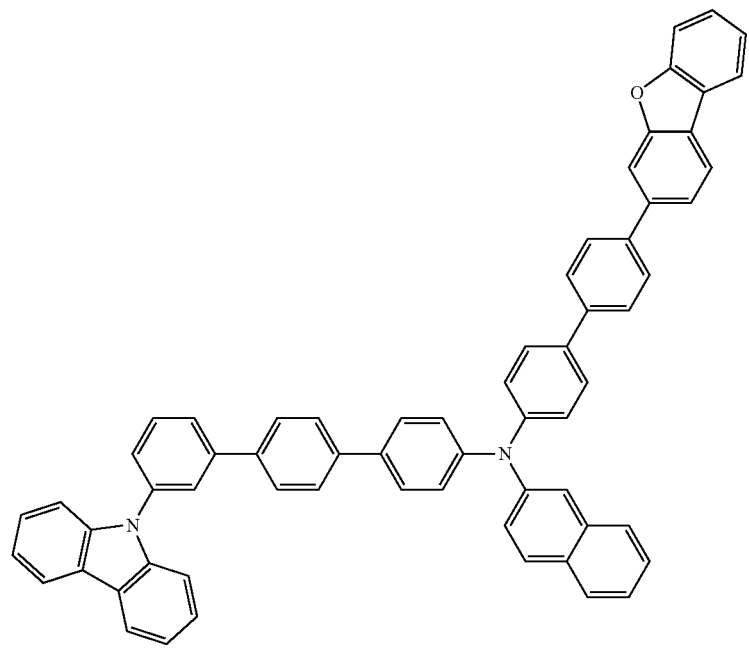
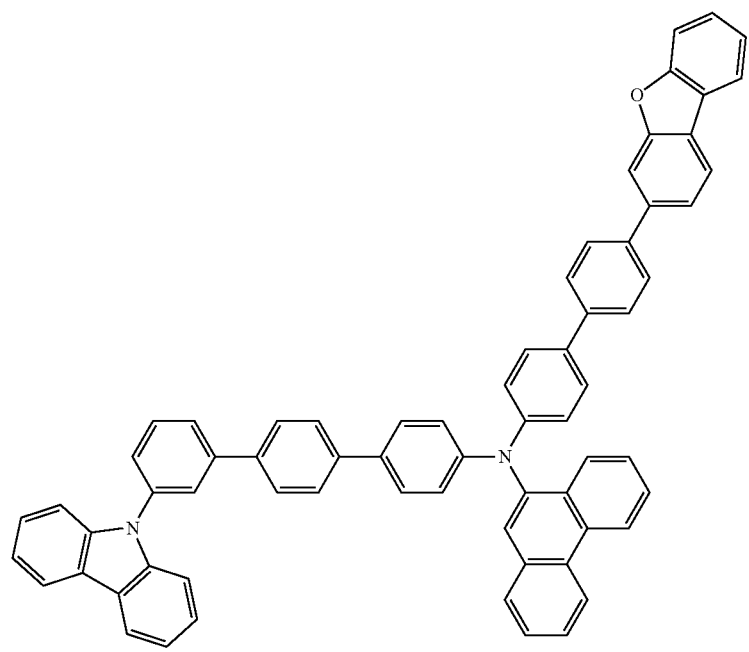

-continued
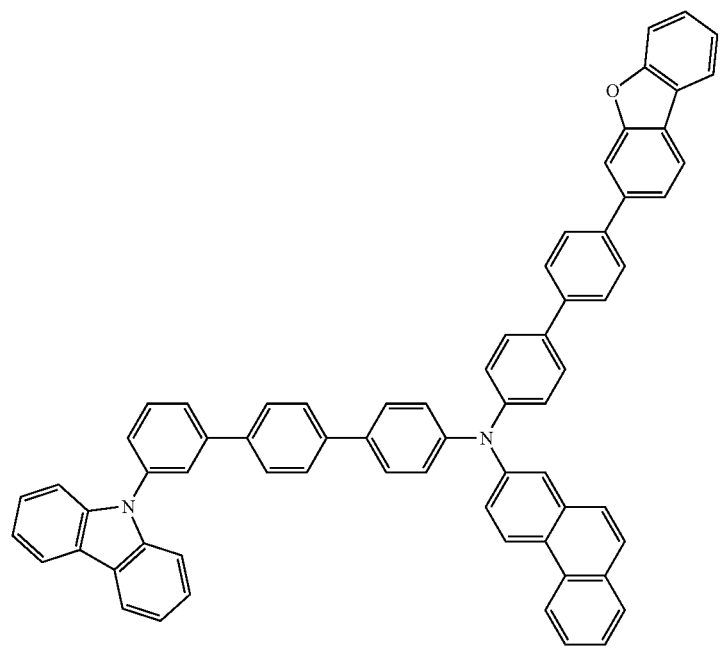
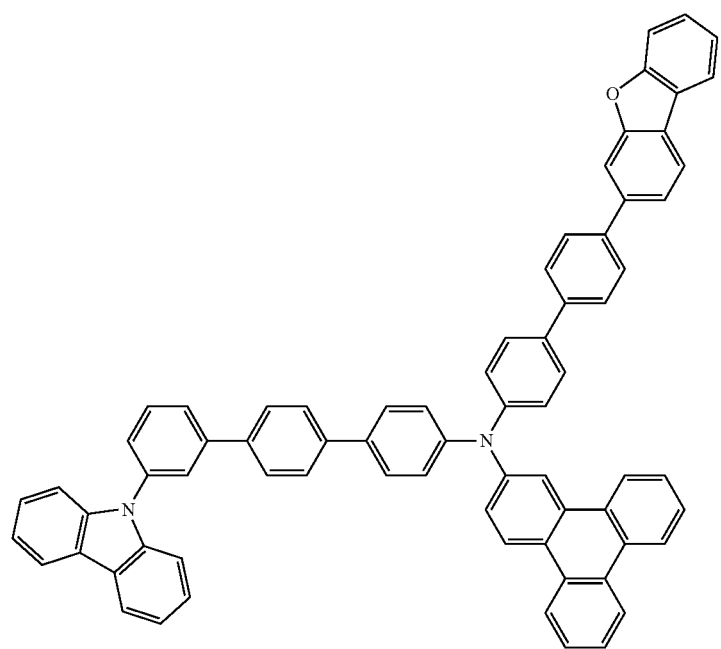

-continued
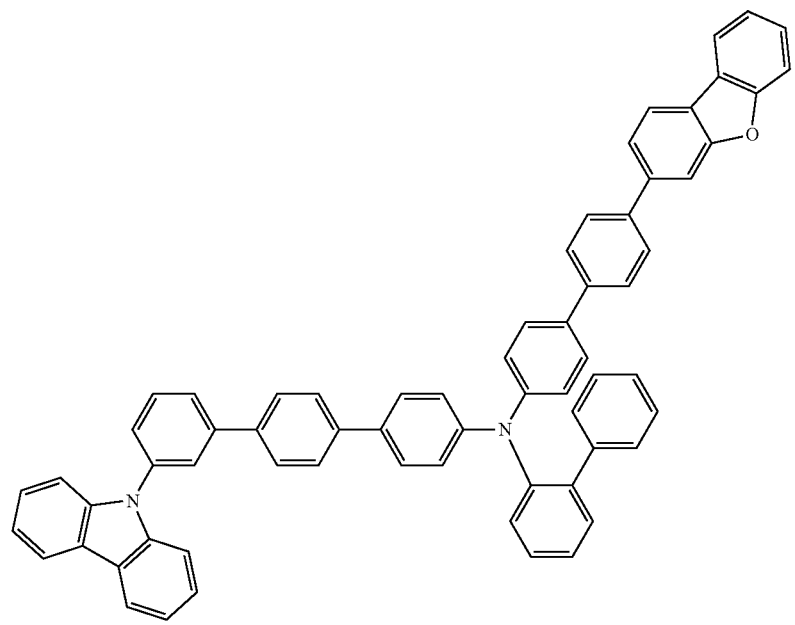
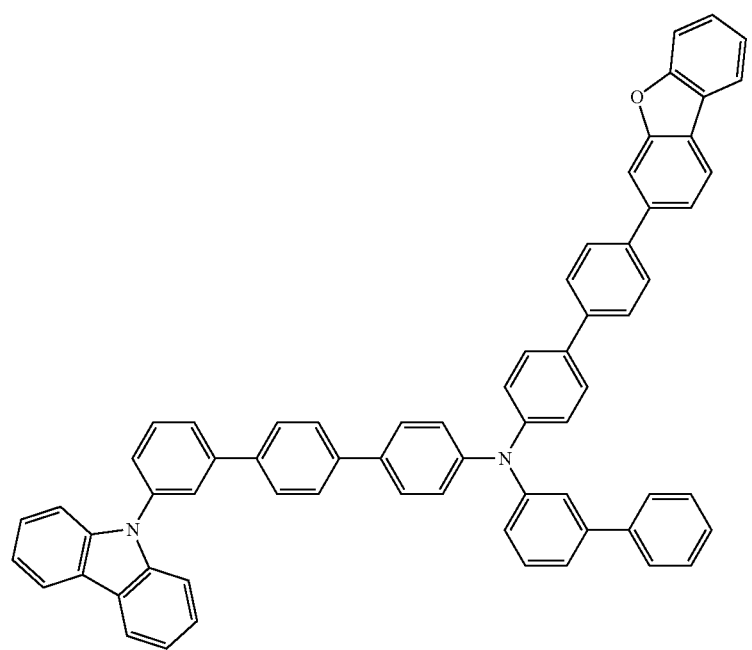

-continued
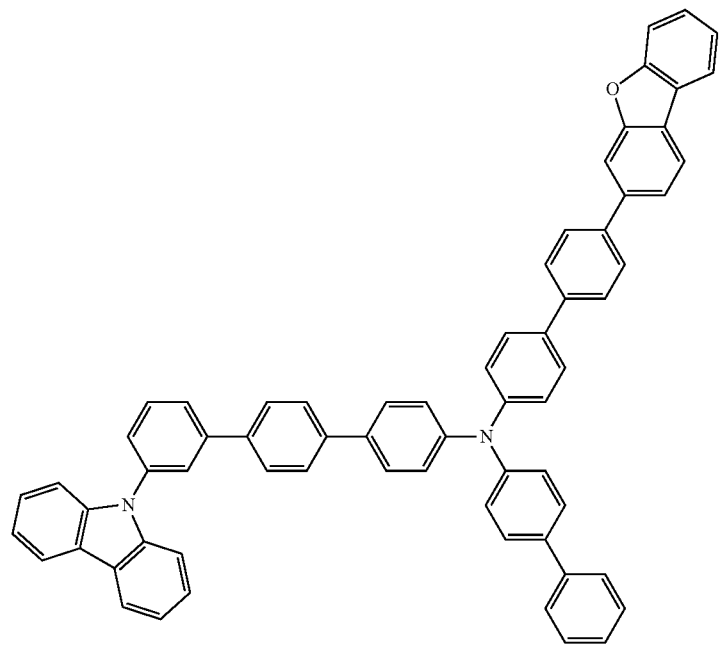
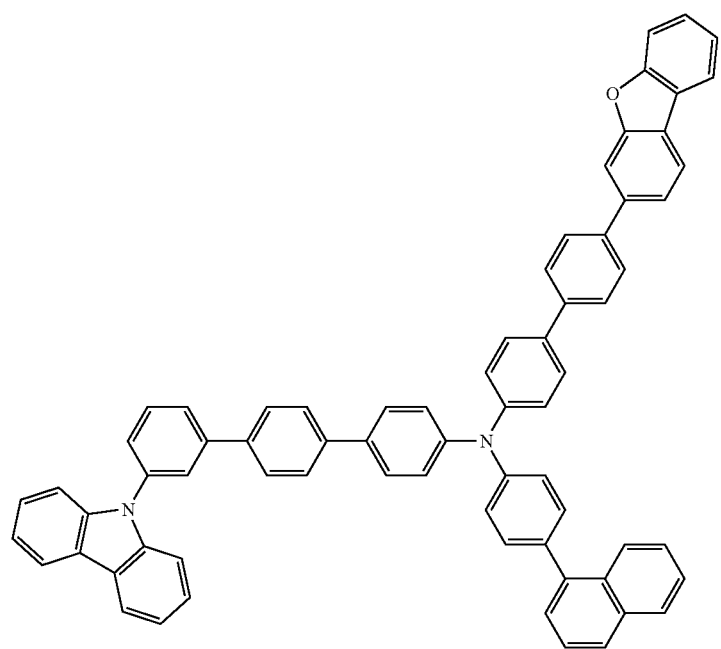

-continued
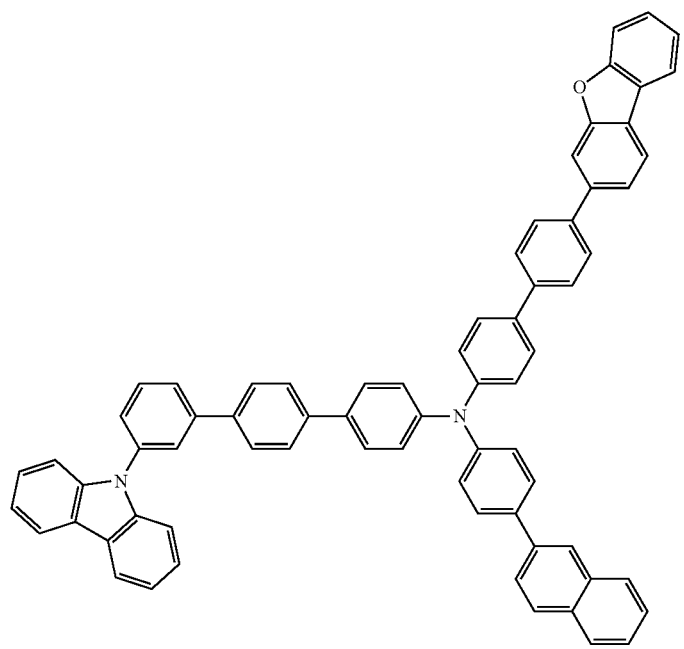
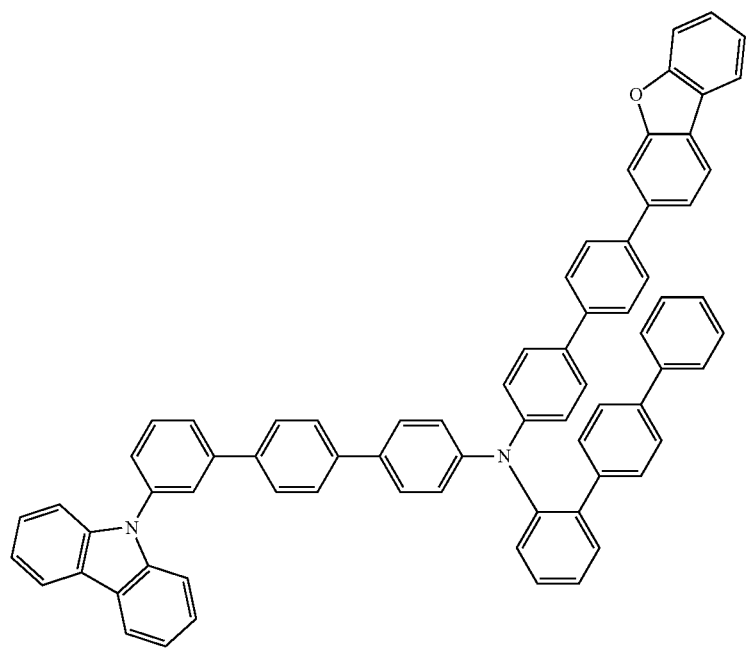

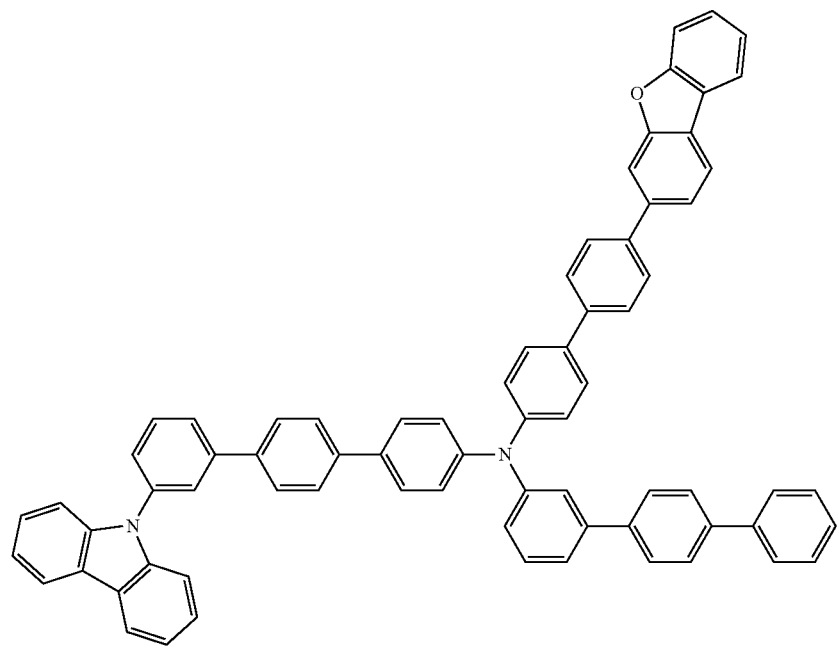
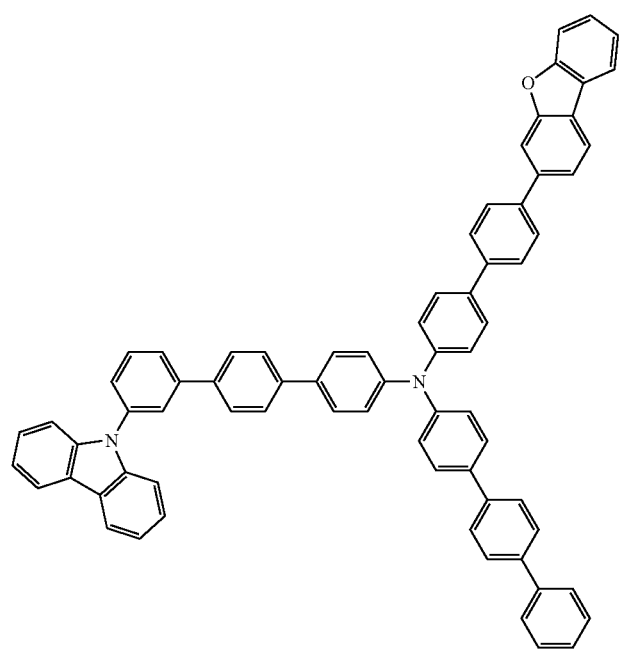

-continued
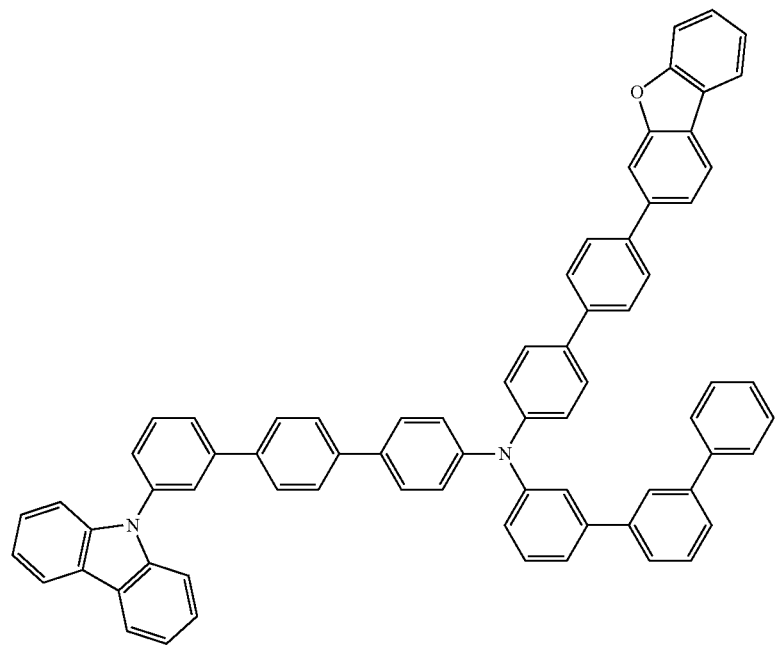
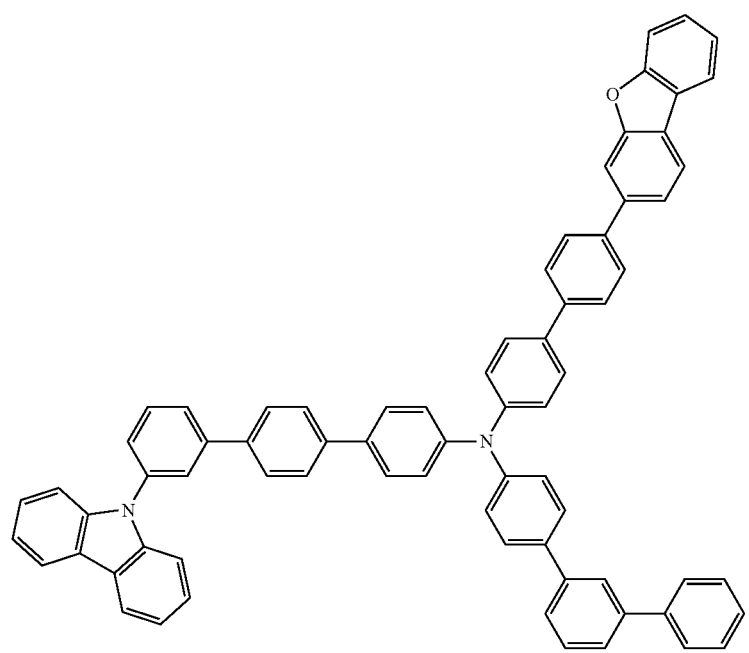

-continued
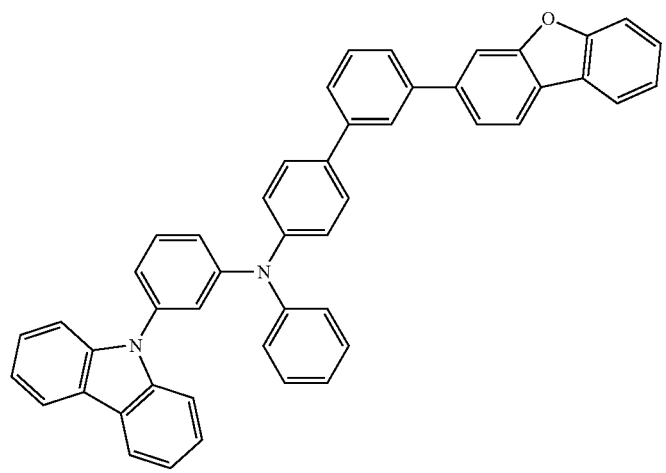
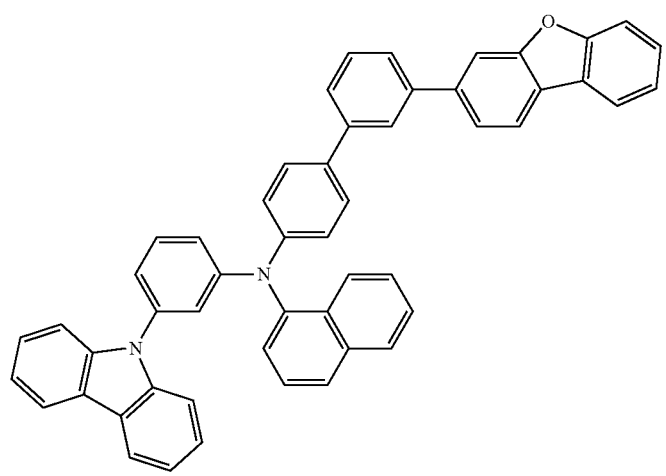
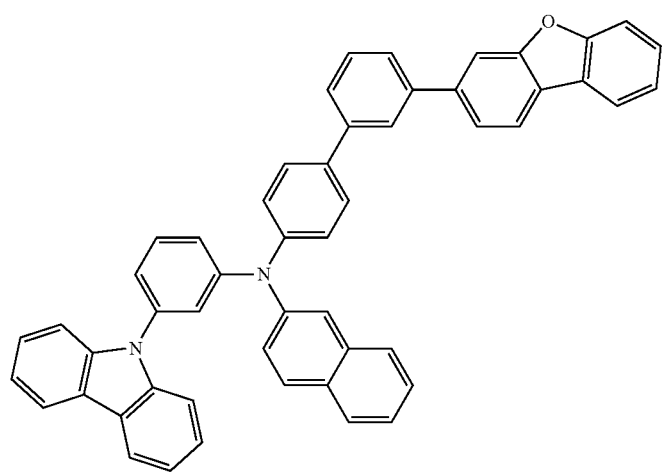

-continued
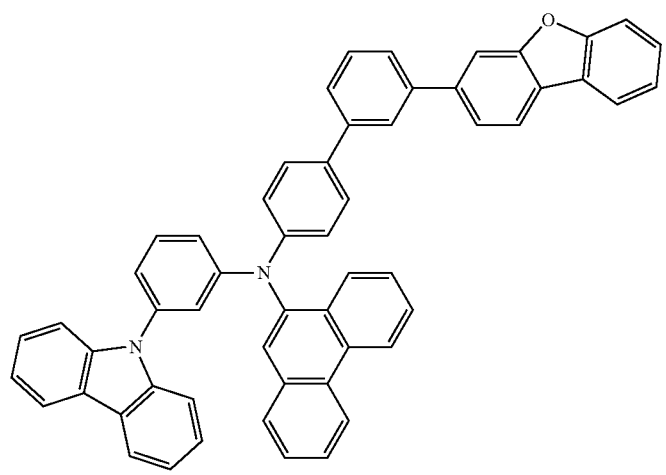
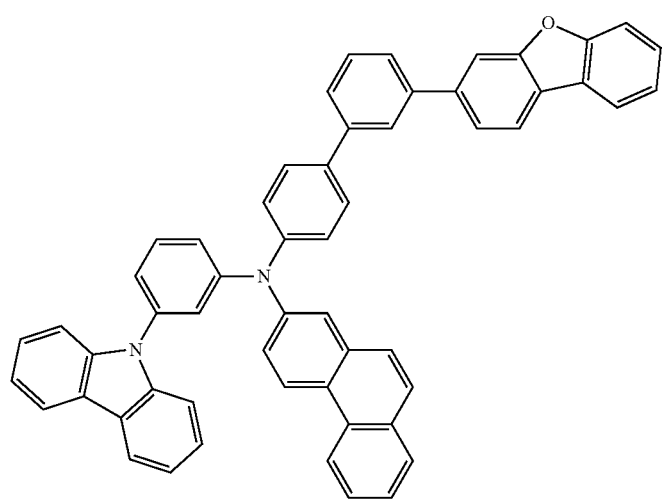
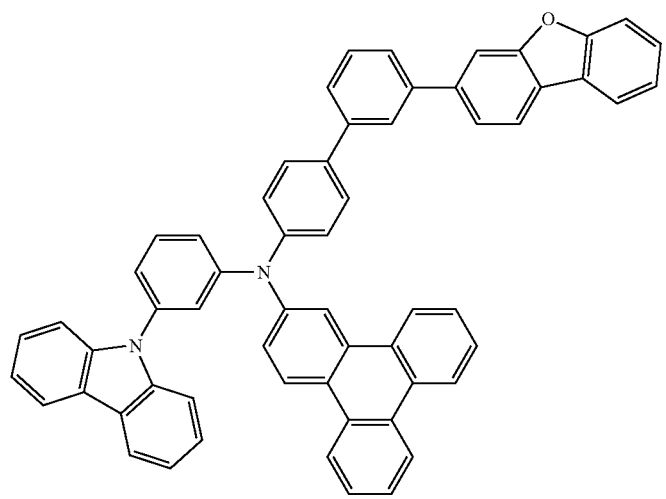

-continued
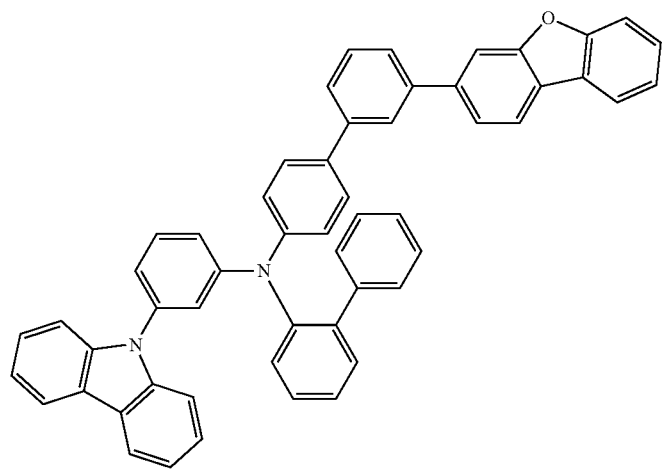
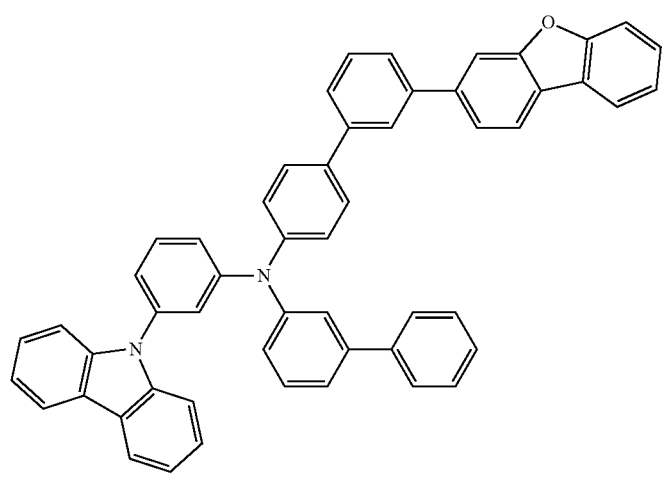
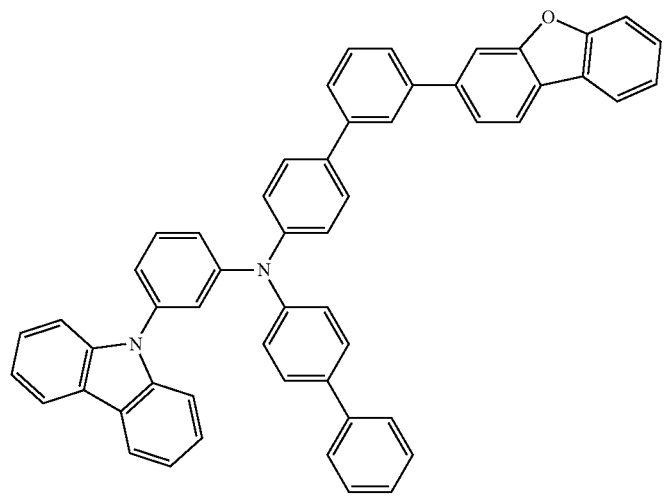

-continued
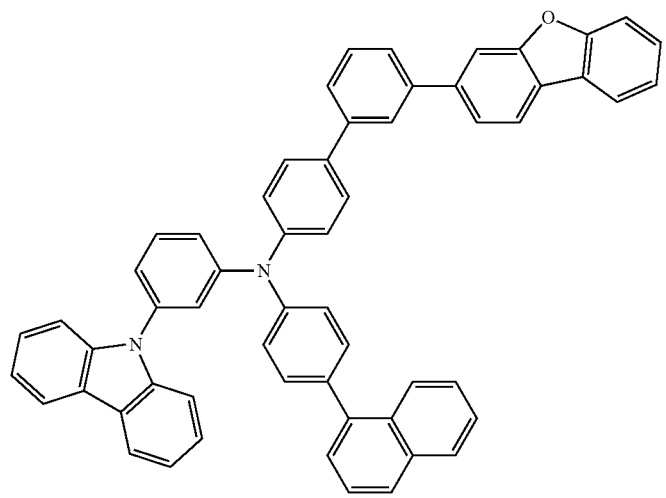
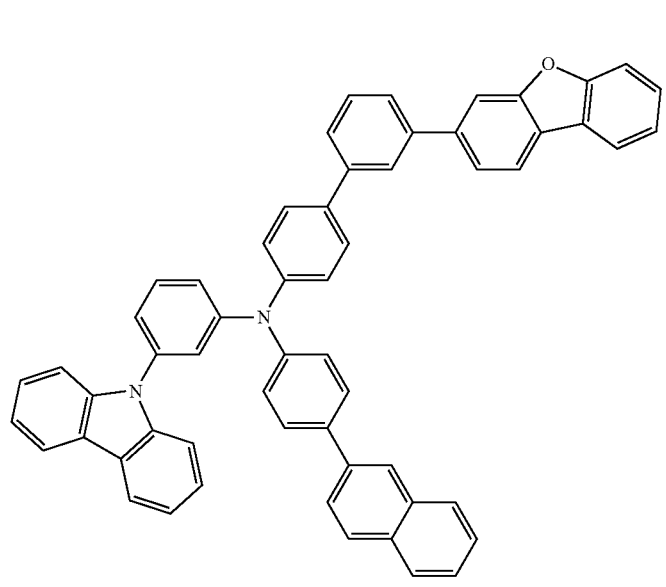
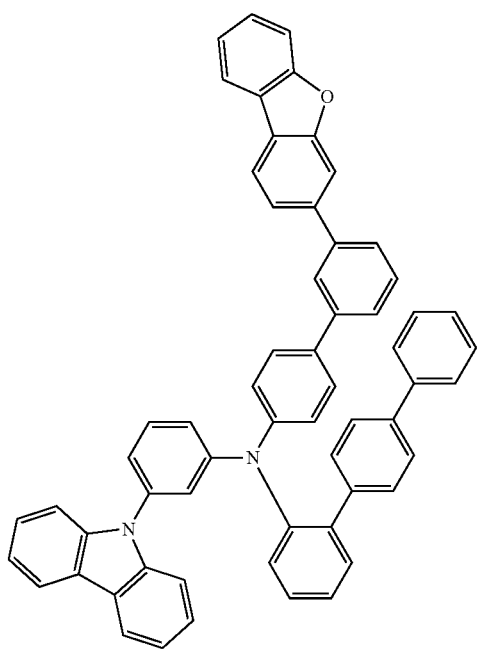
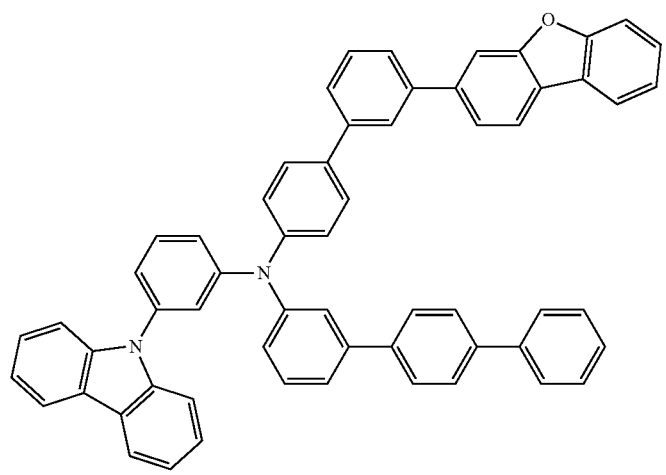

-continued
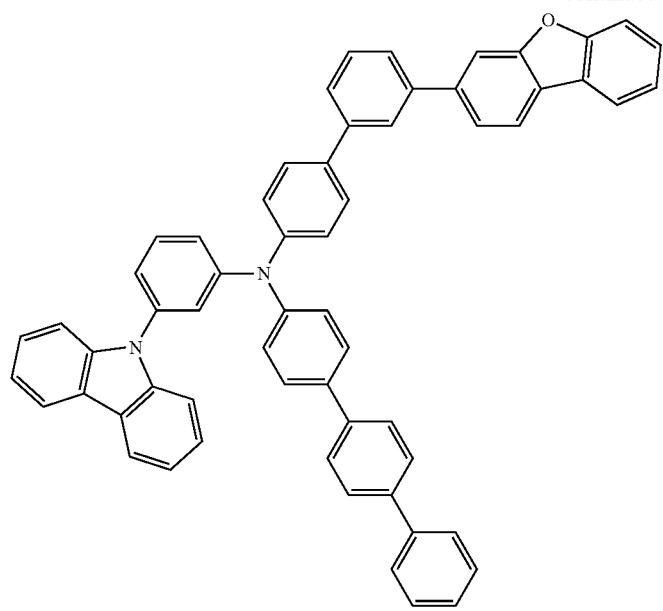
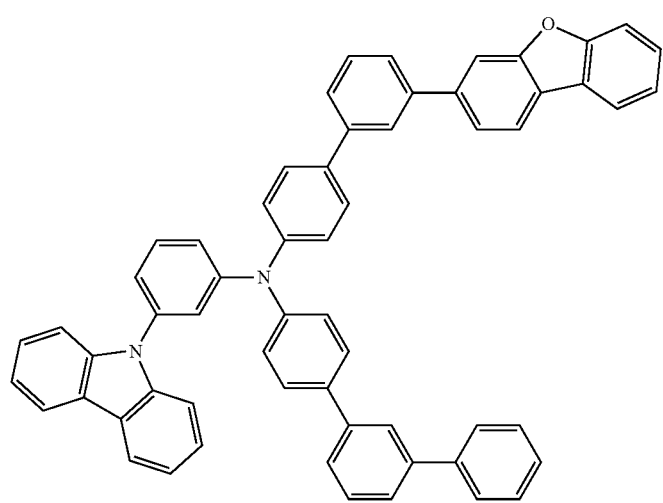
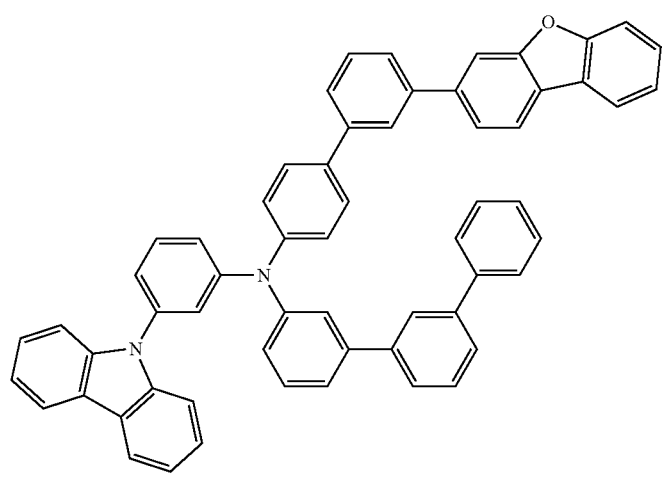

-continued
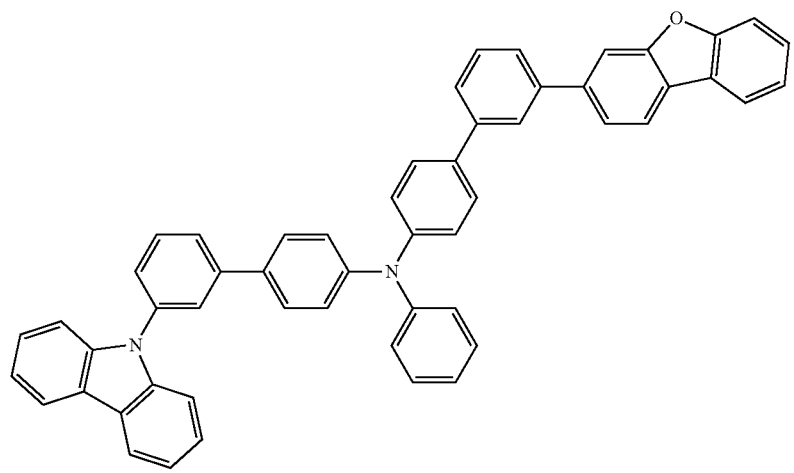
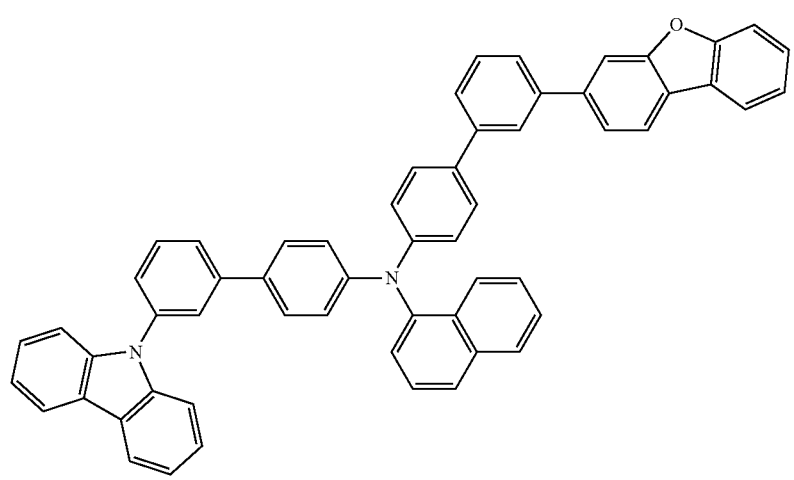
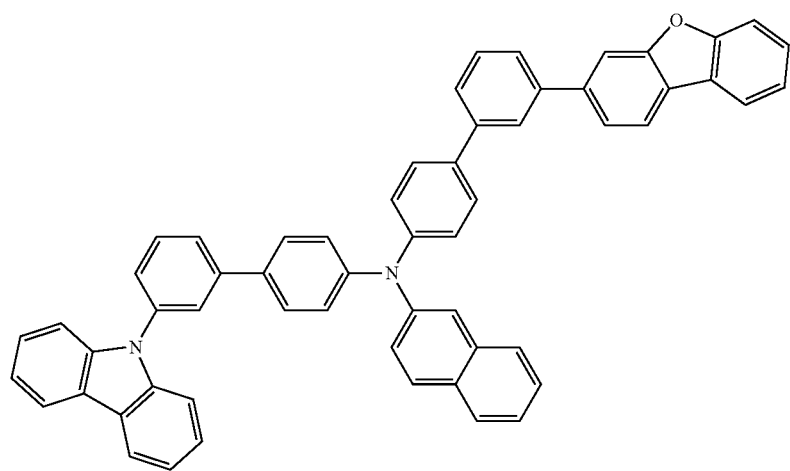

-continued
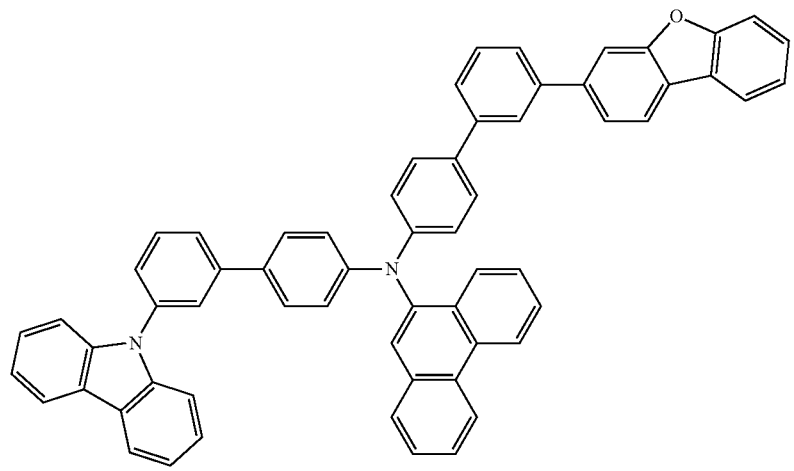
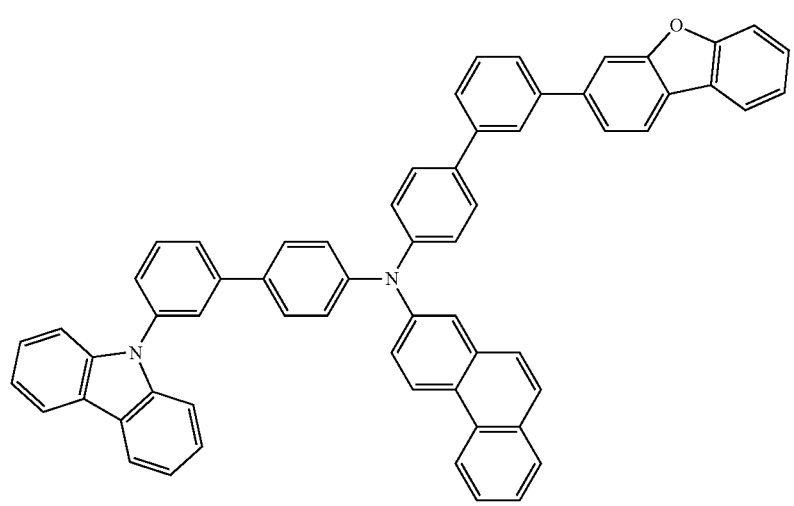
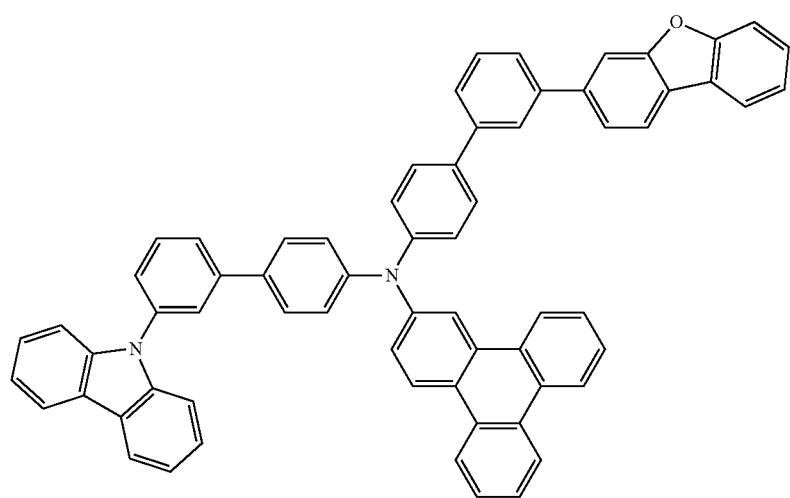

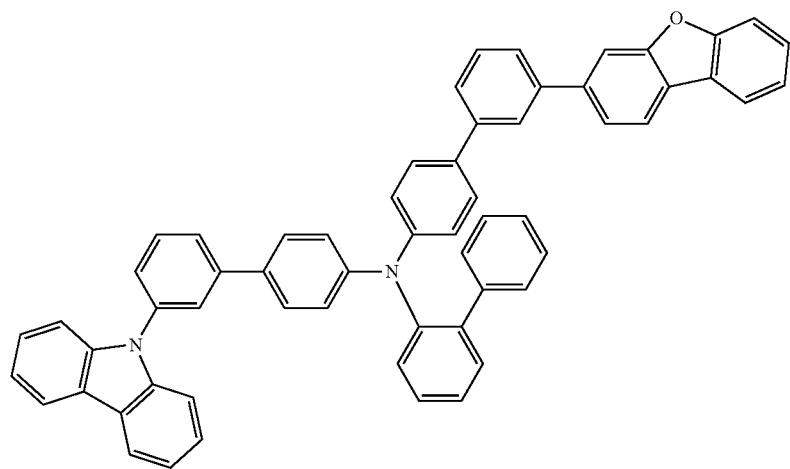
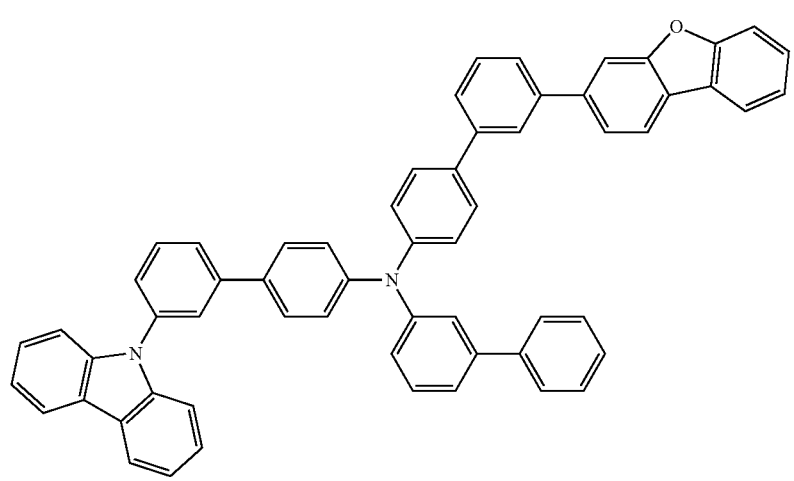
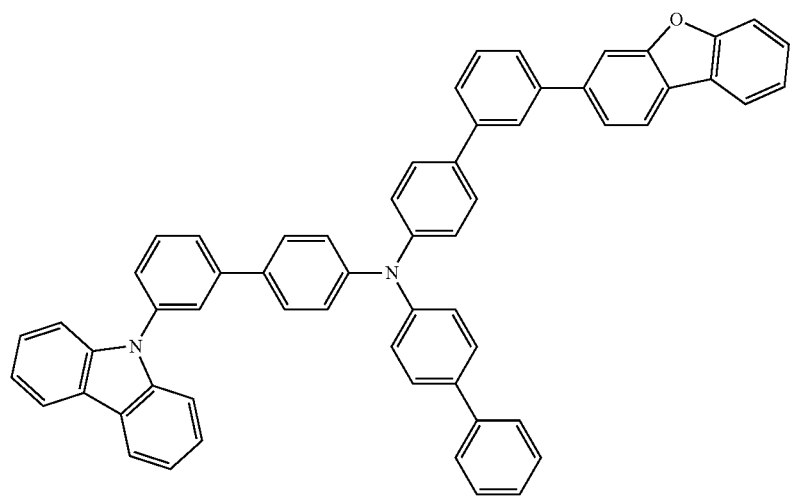

-continued
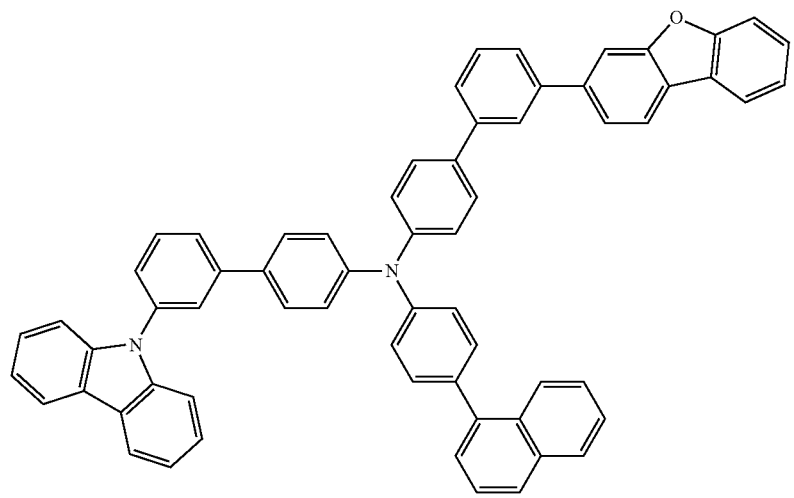
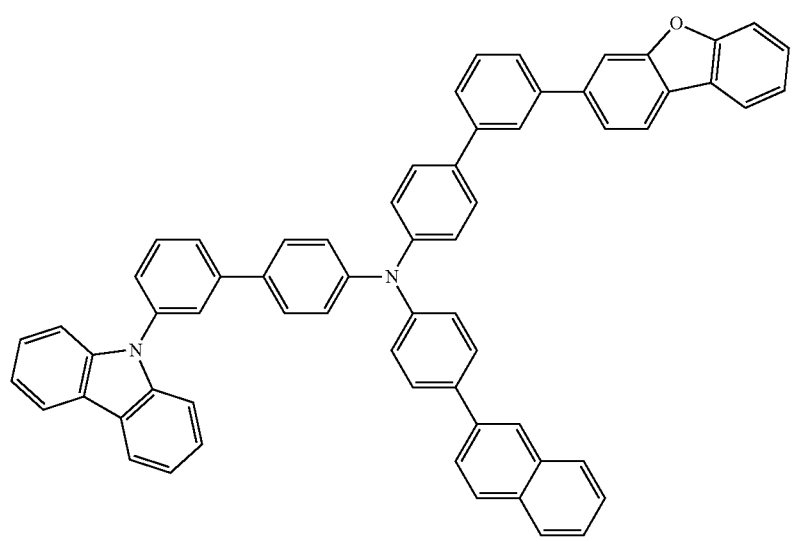
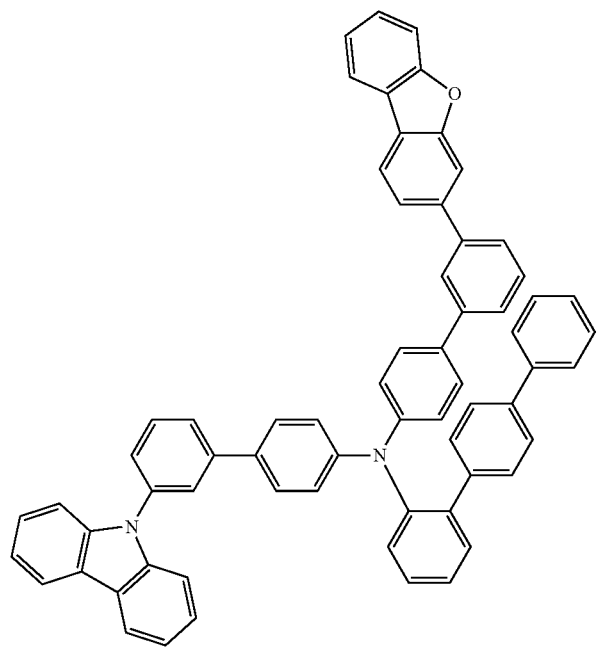

-continued
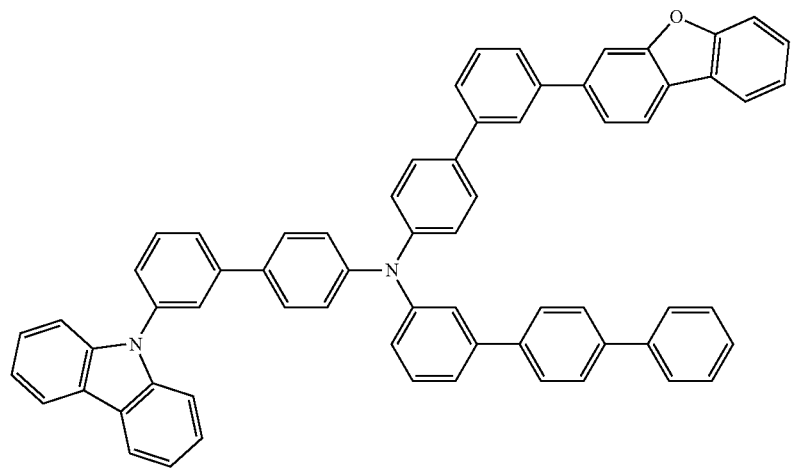
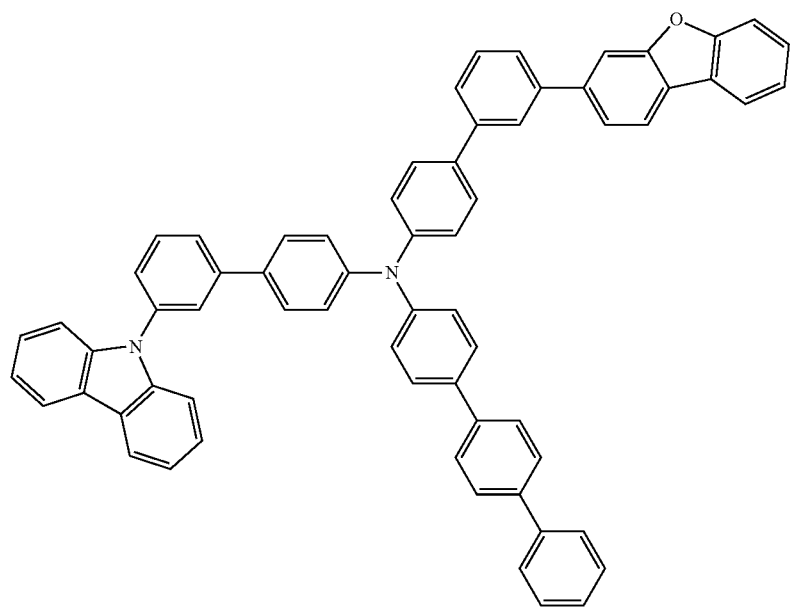
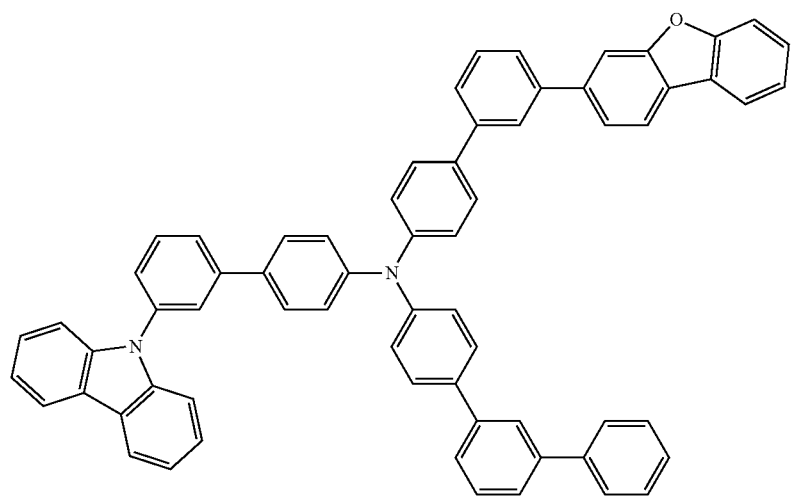

-continued
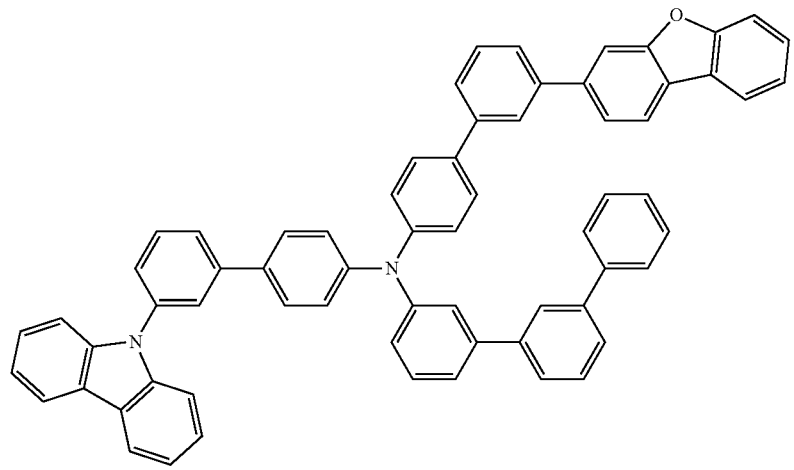
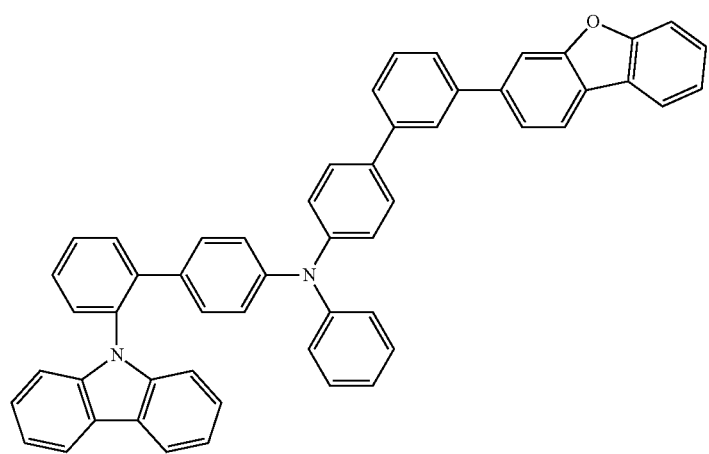
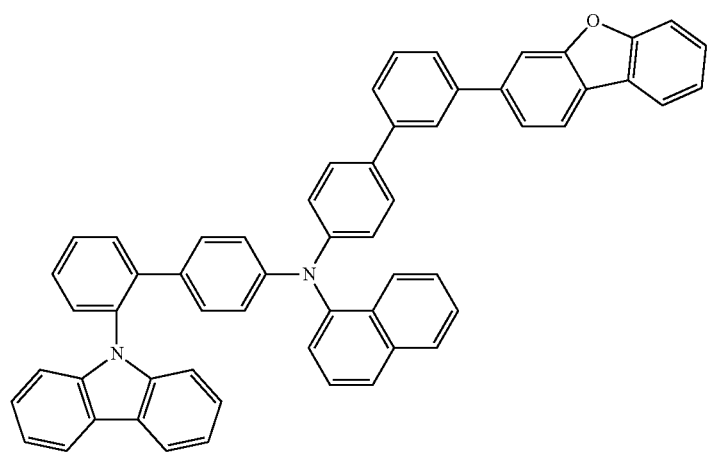

-continued
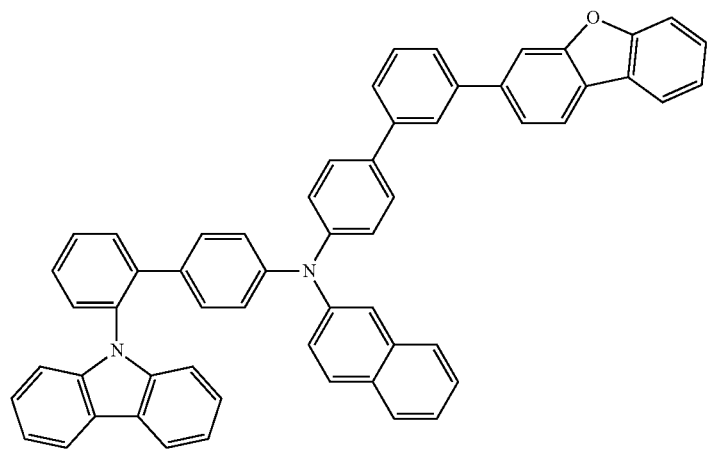
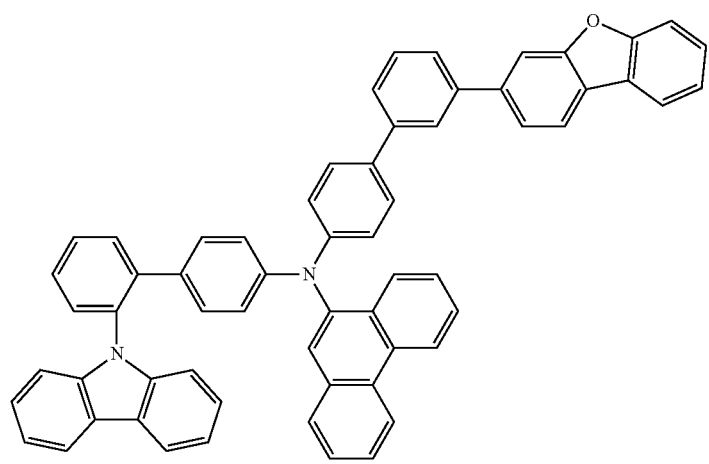
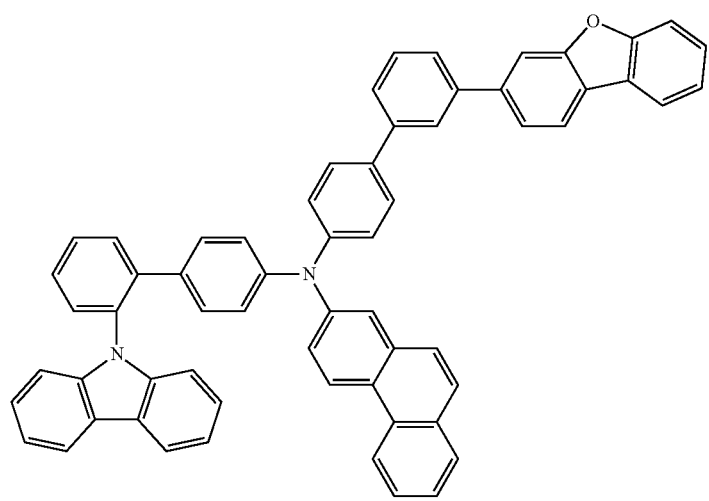

-continued
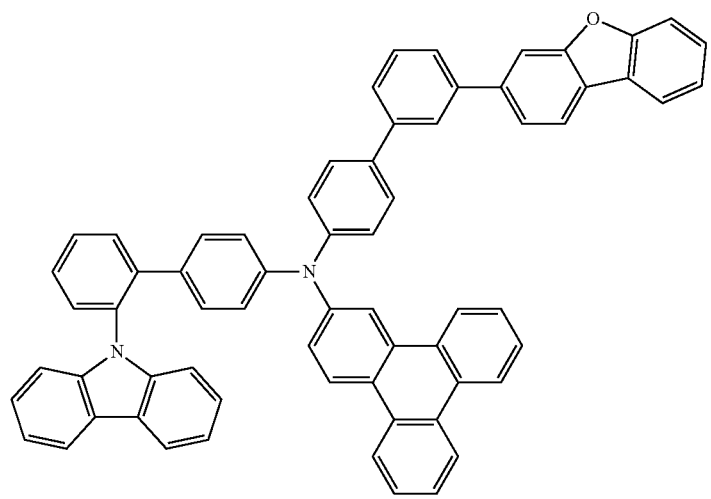
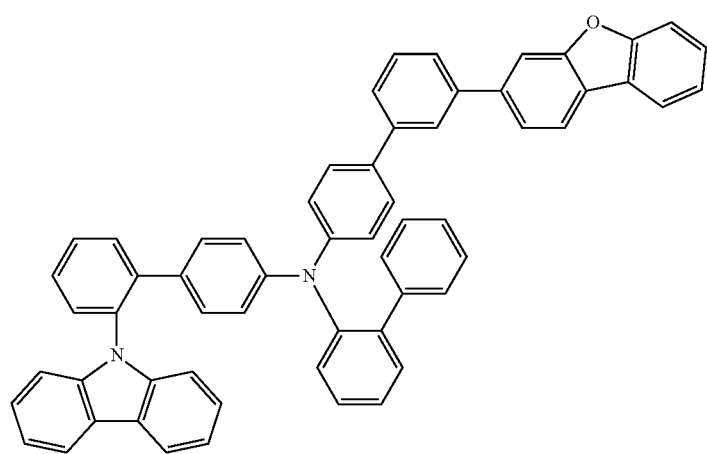
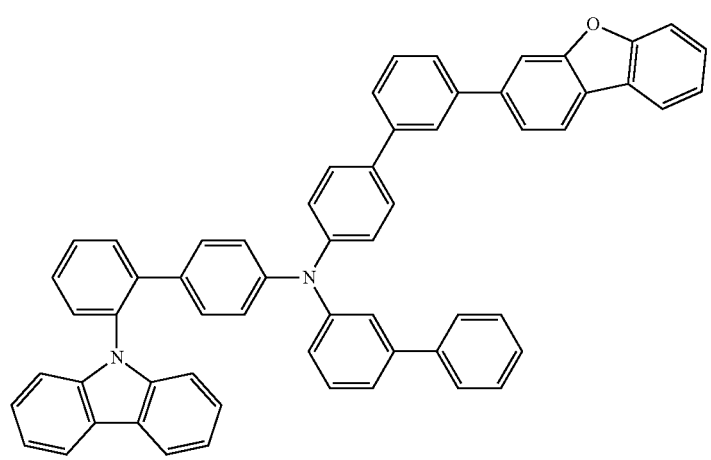

-continued
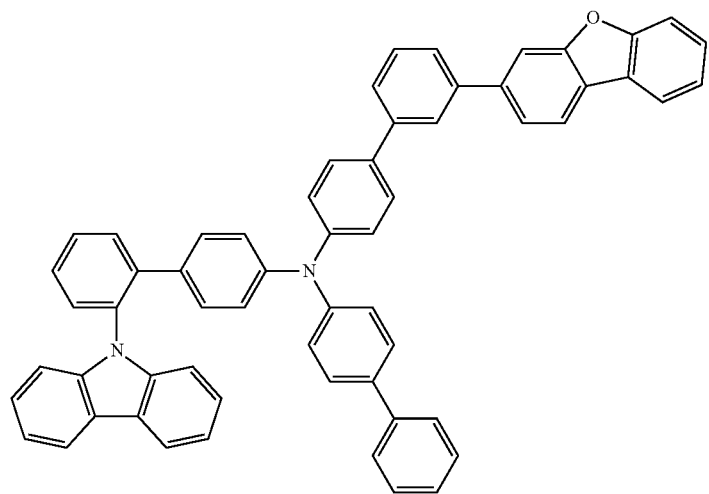
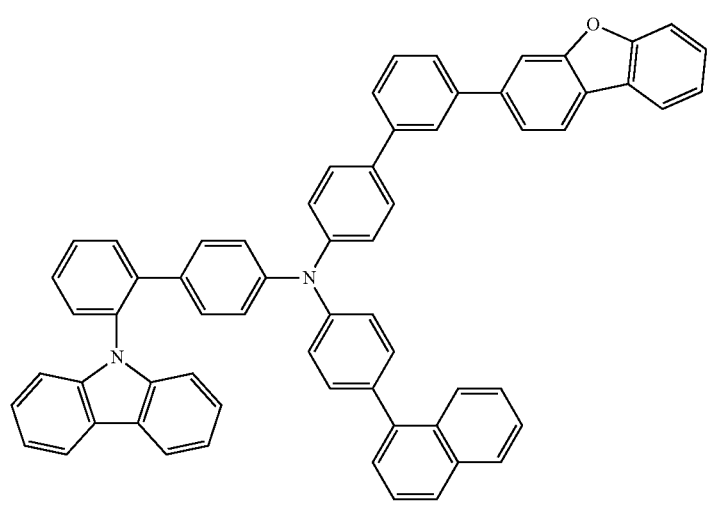
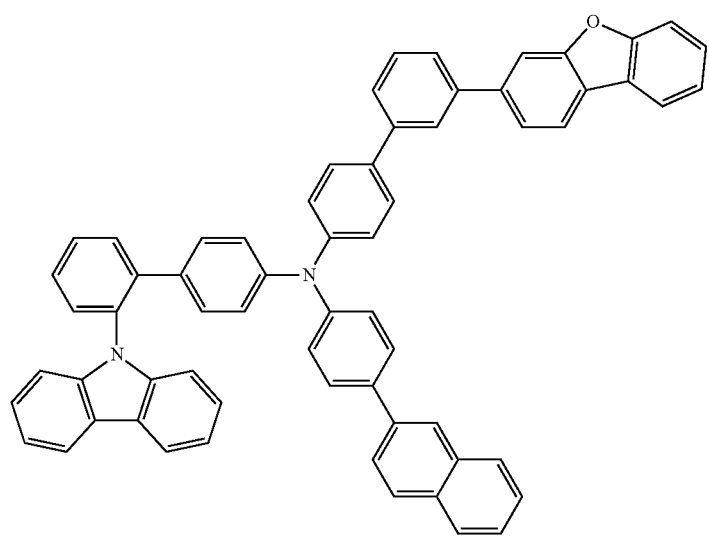

-continued
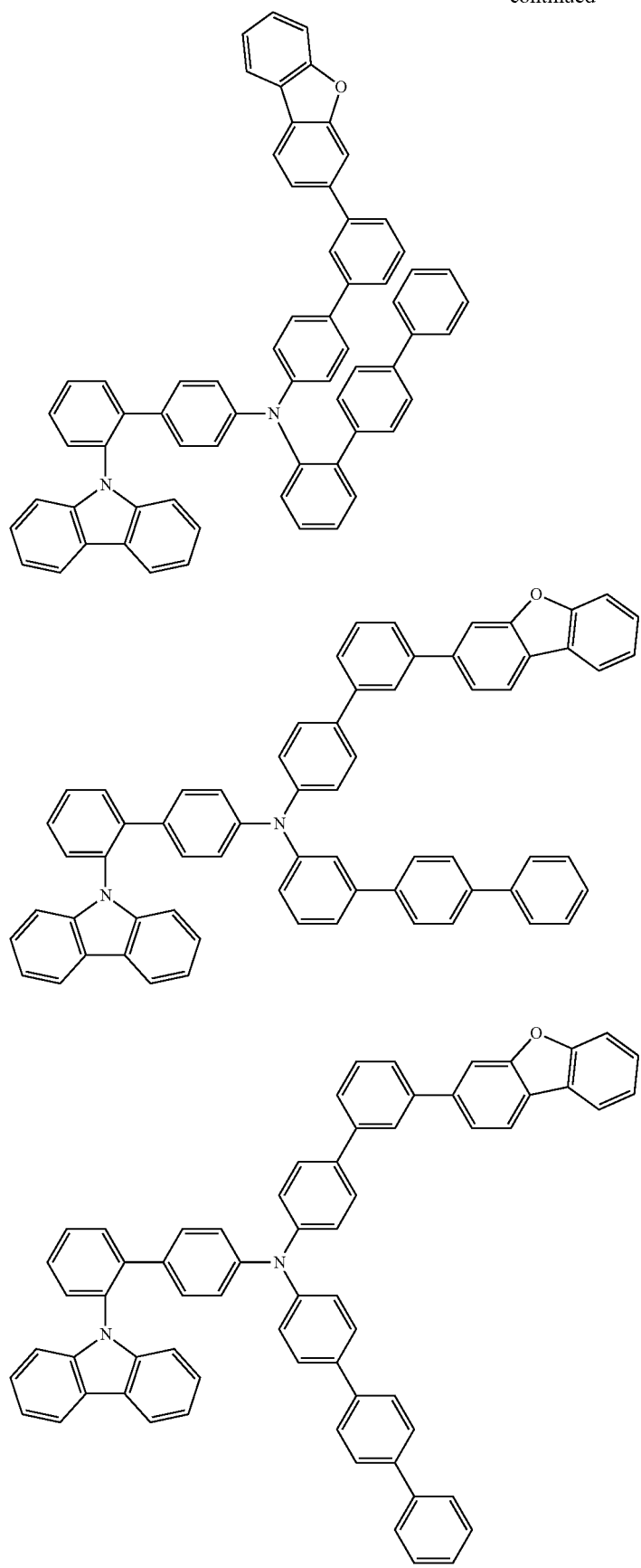

-continued
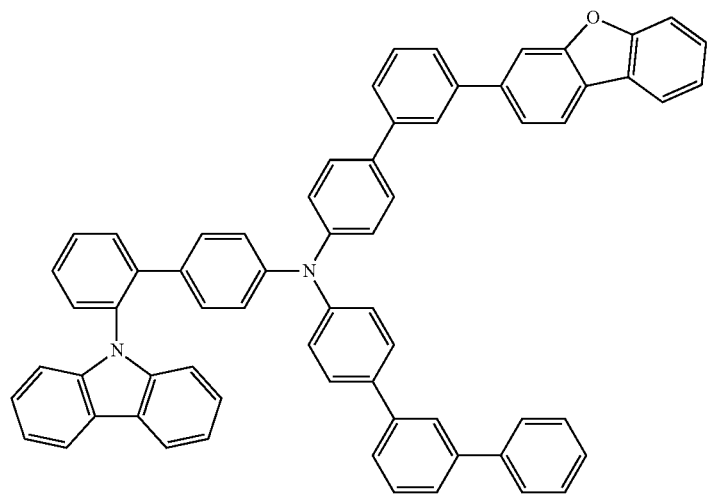
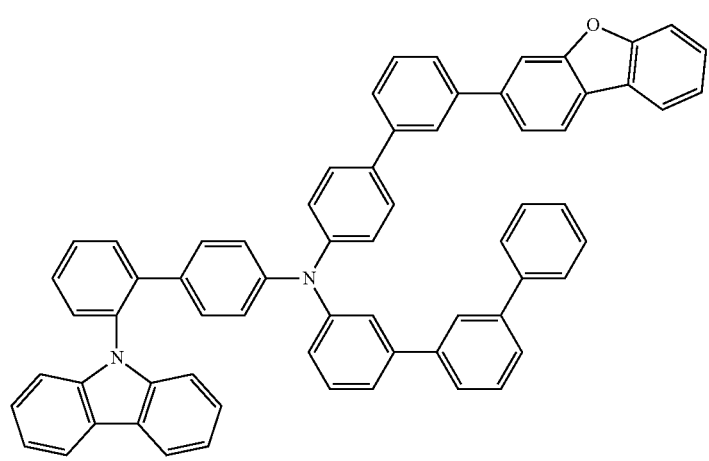
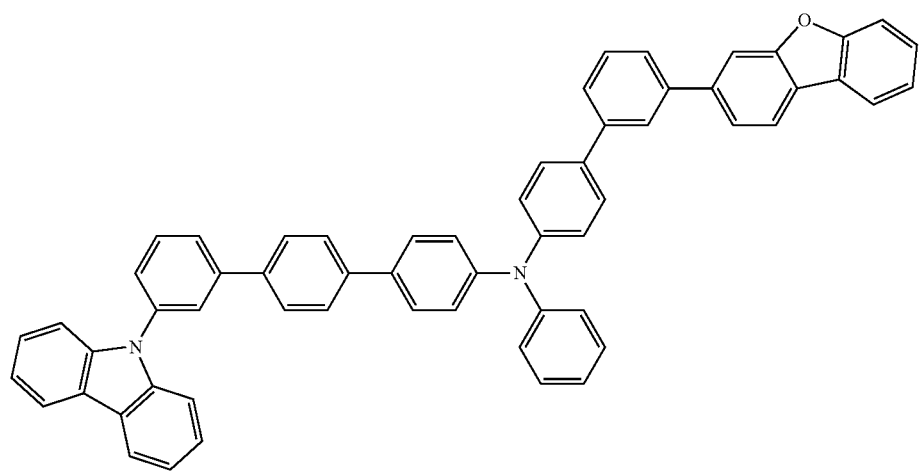

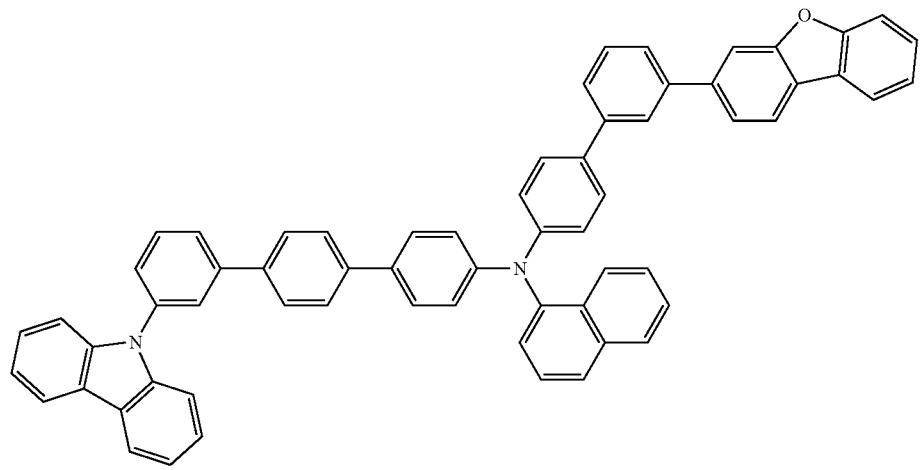
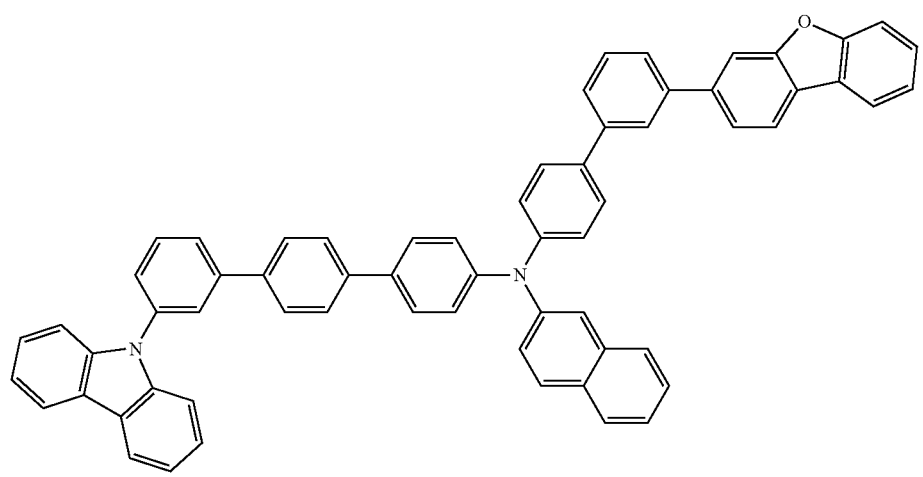
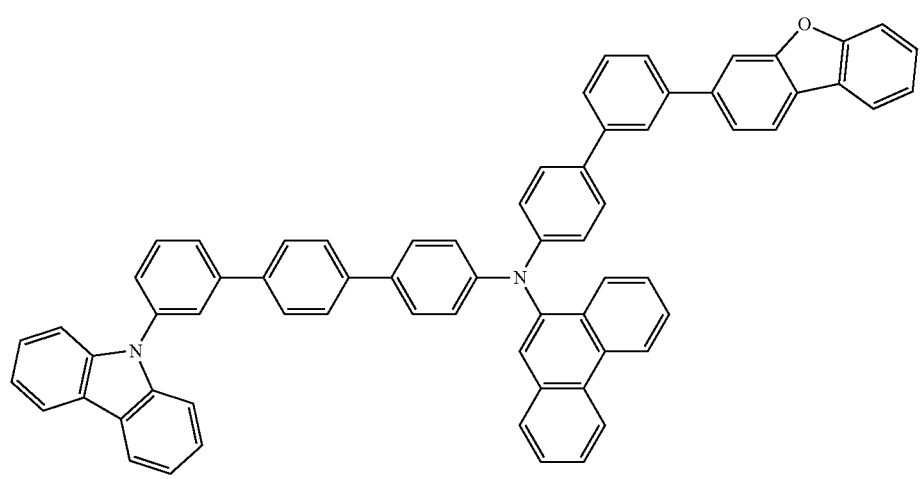

-continued
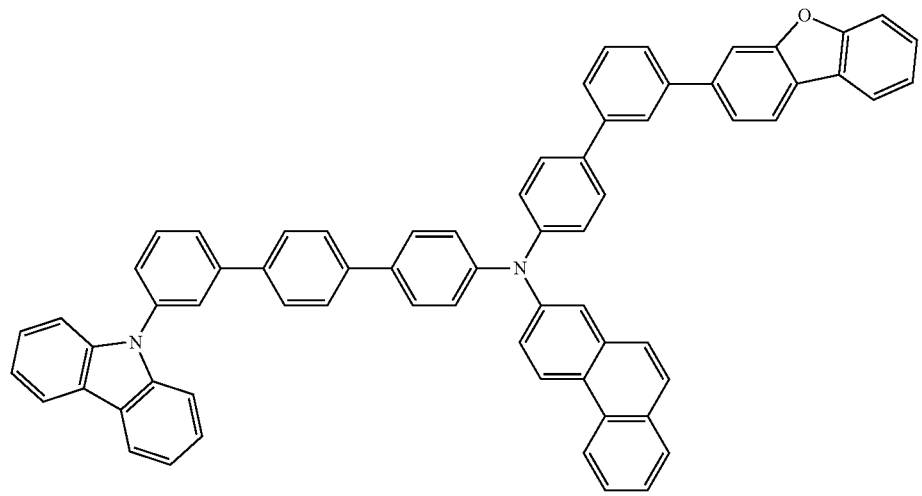
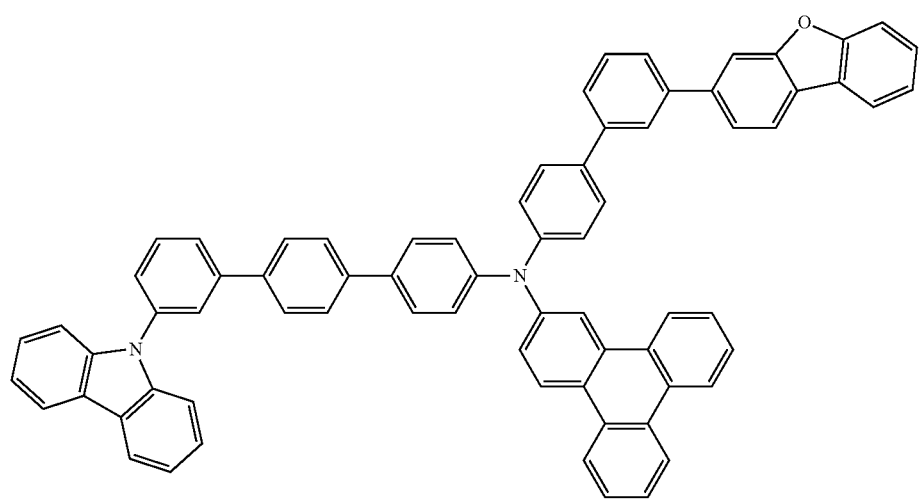
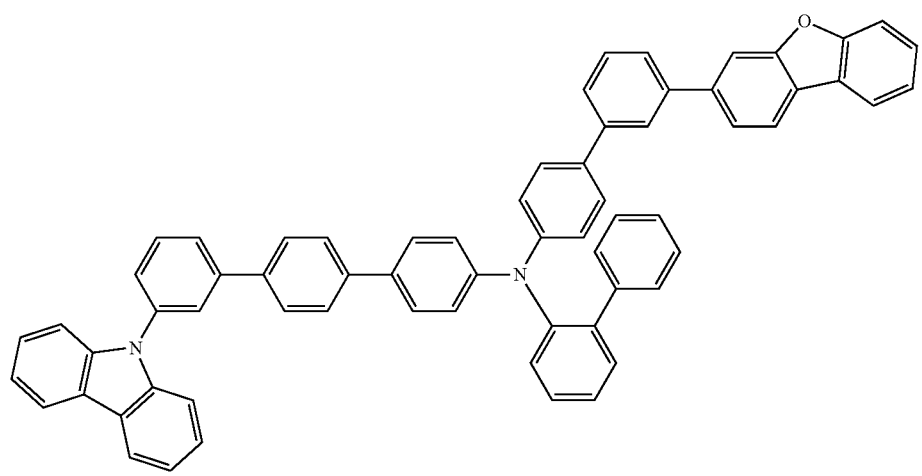

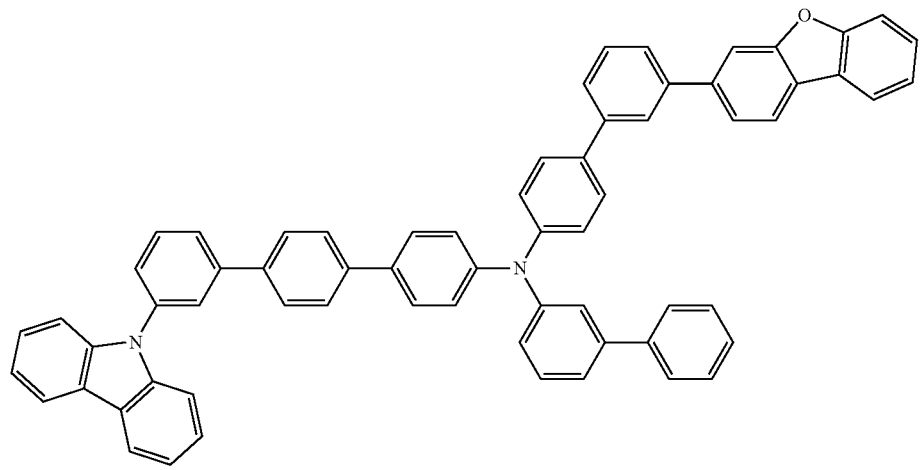
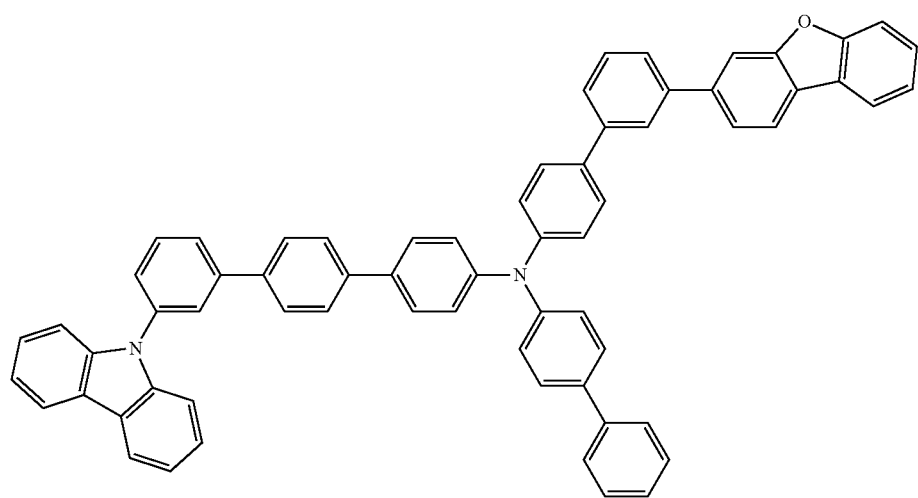
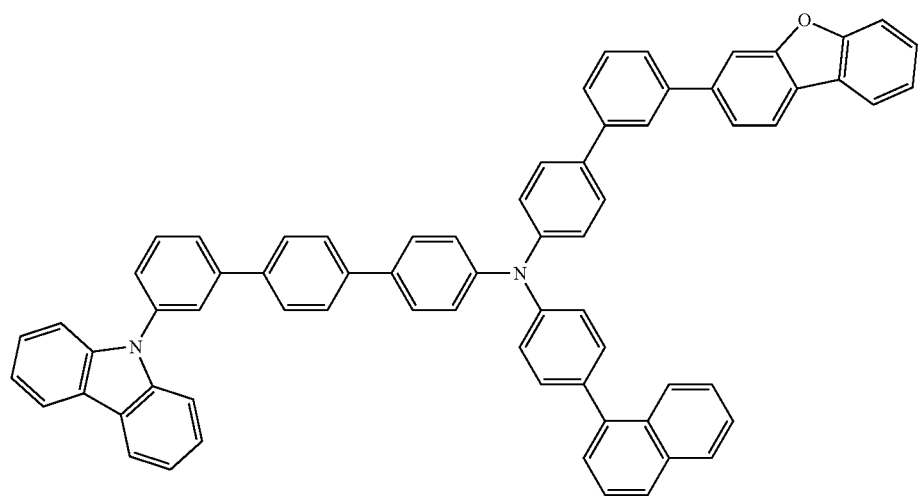

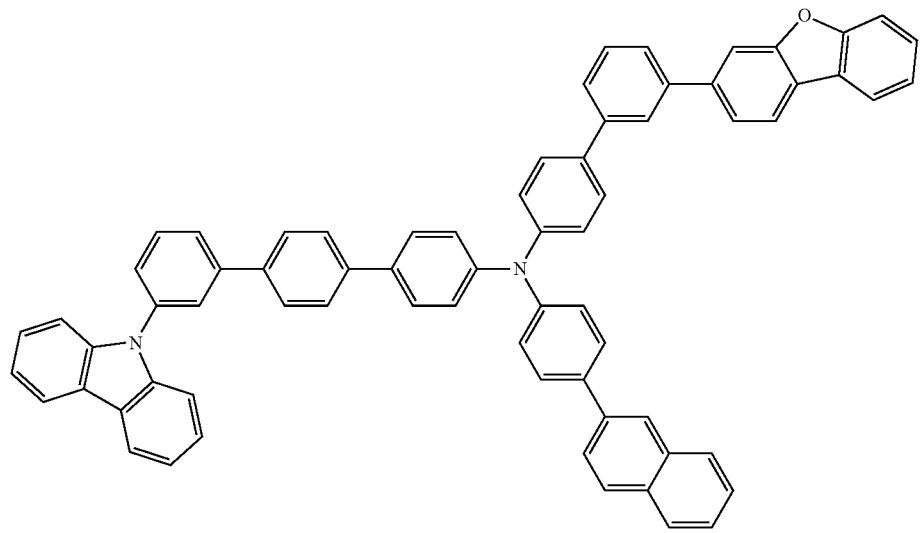
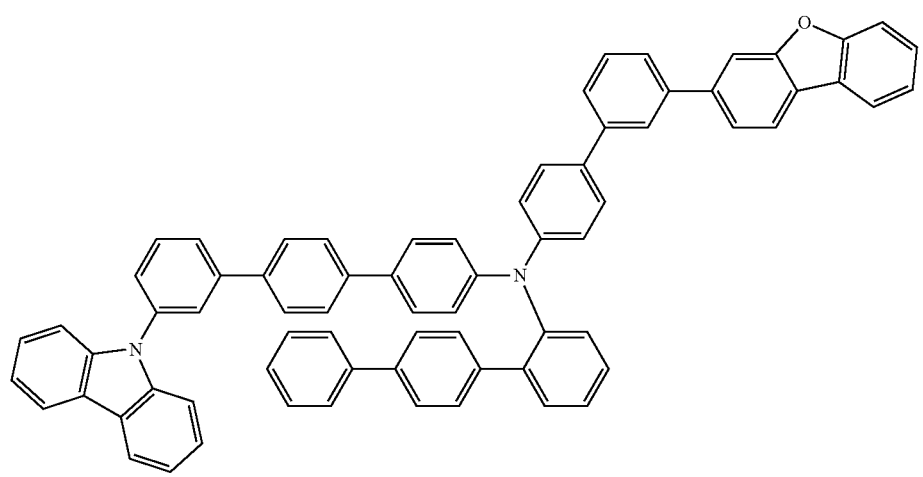
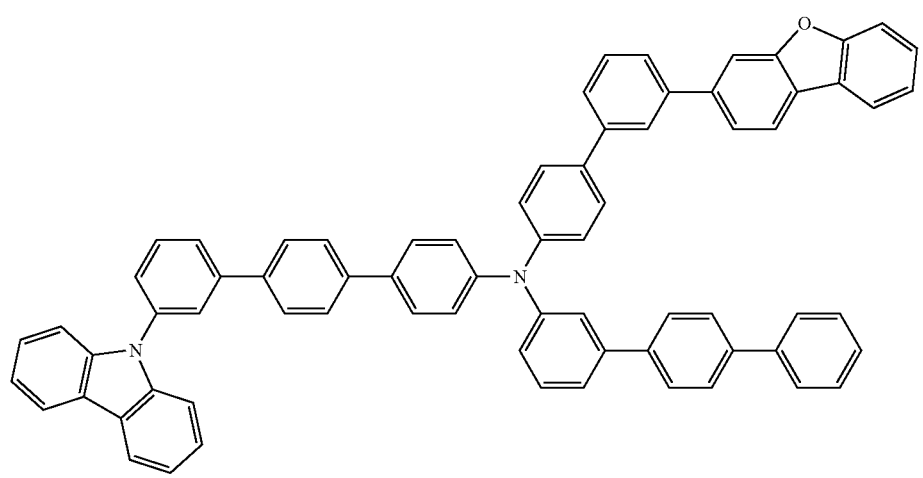

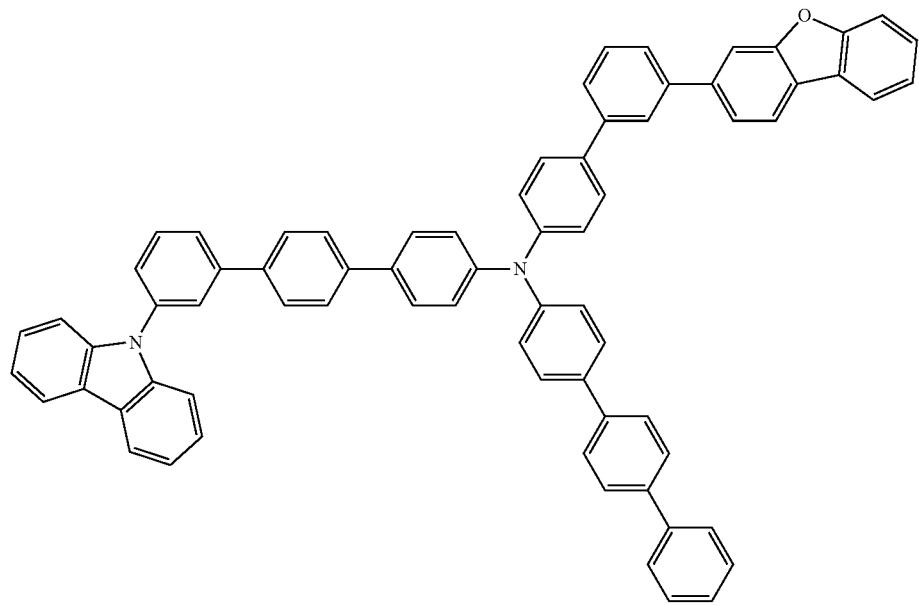
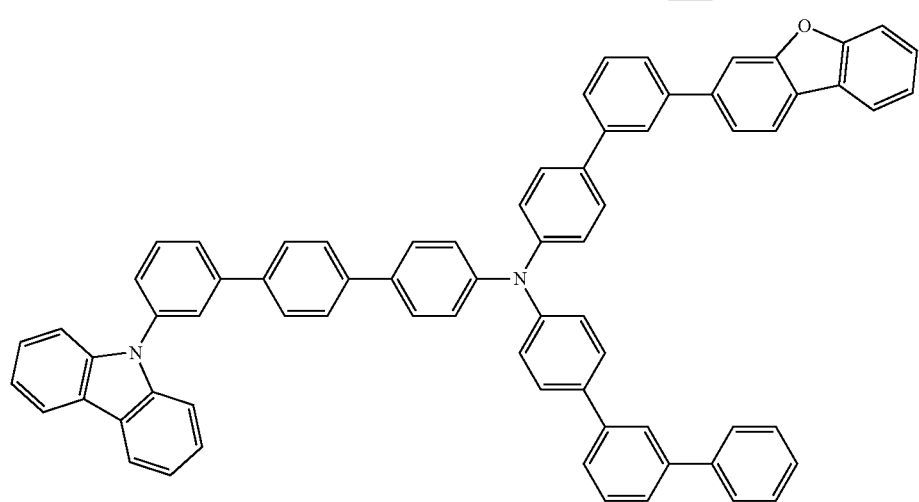
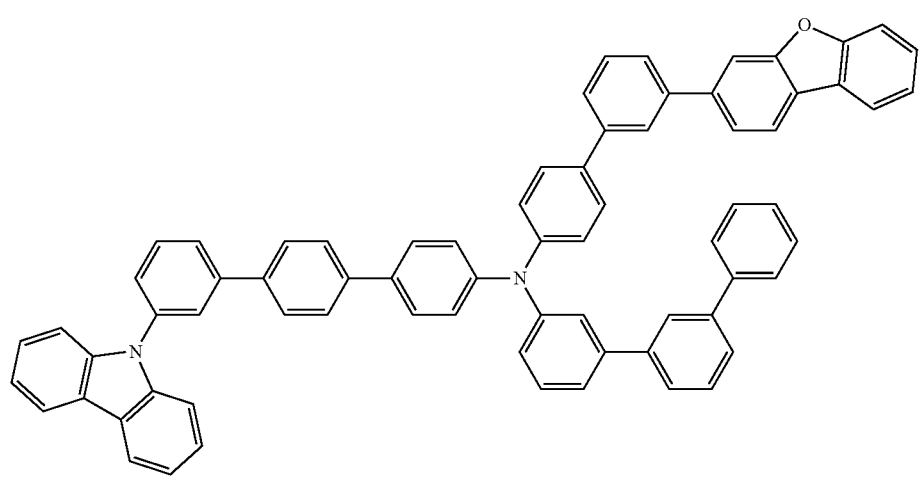

-continued
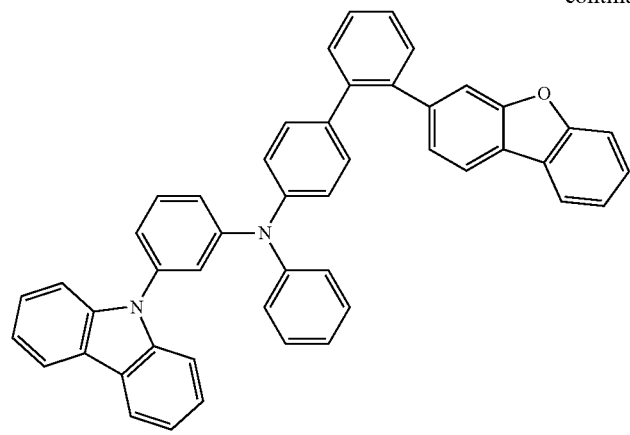
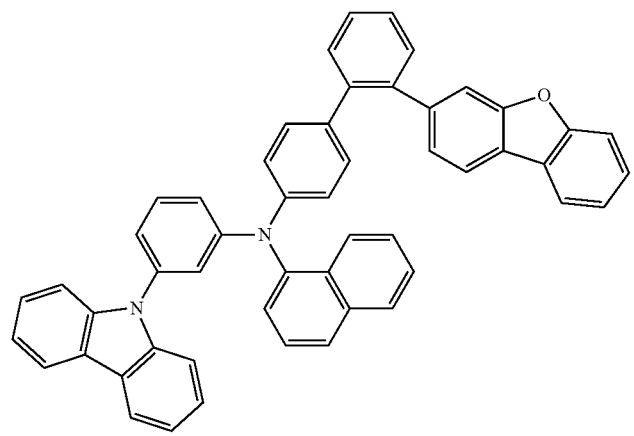
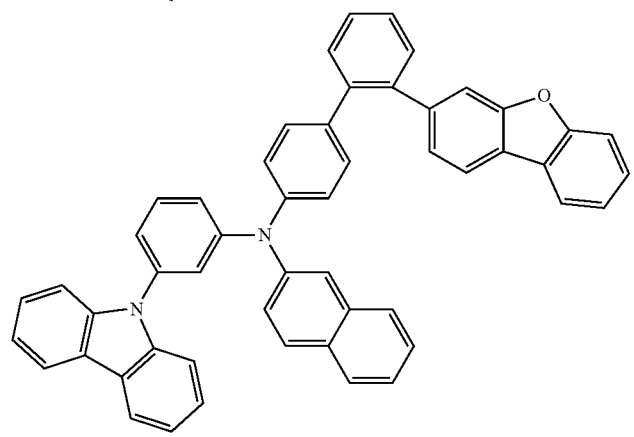
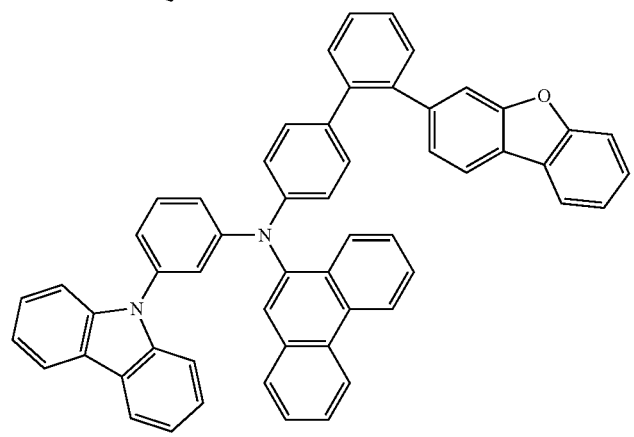

-continued
421
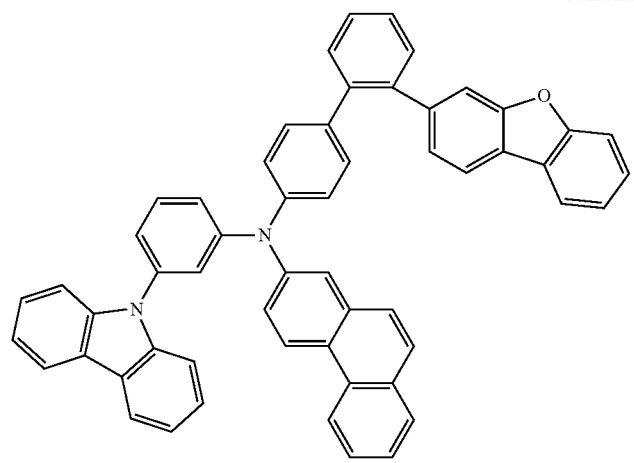
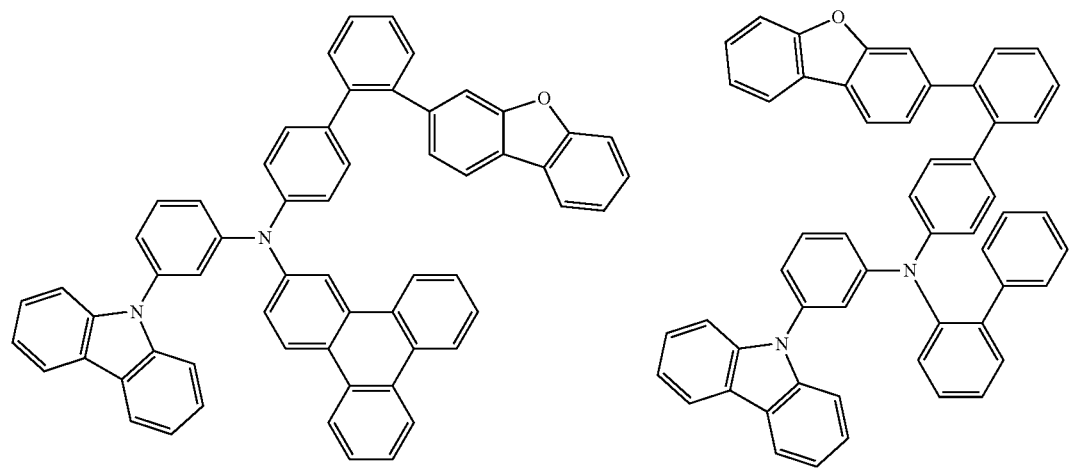
422
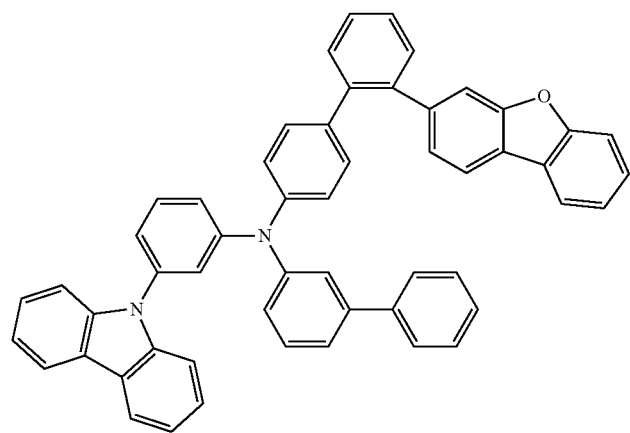

423 424
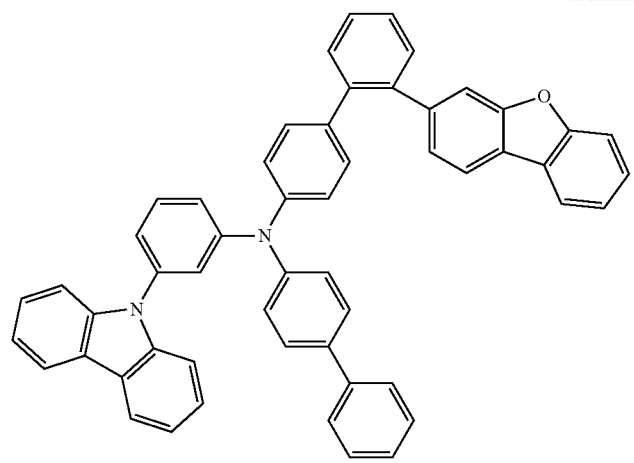
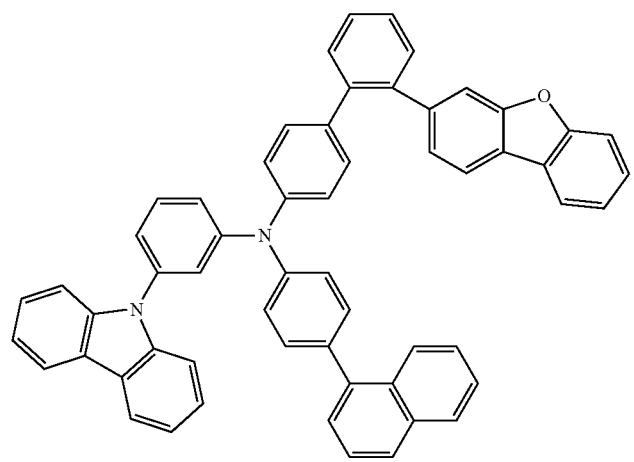
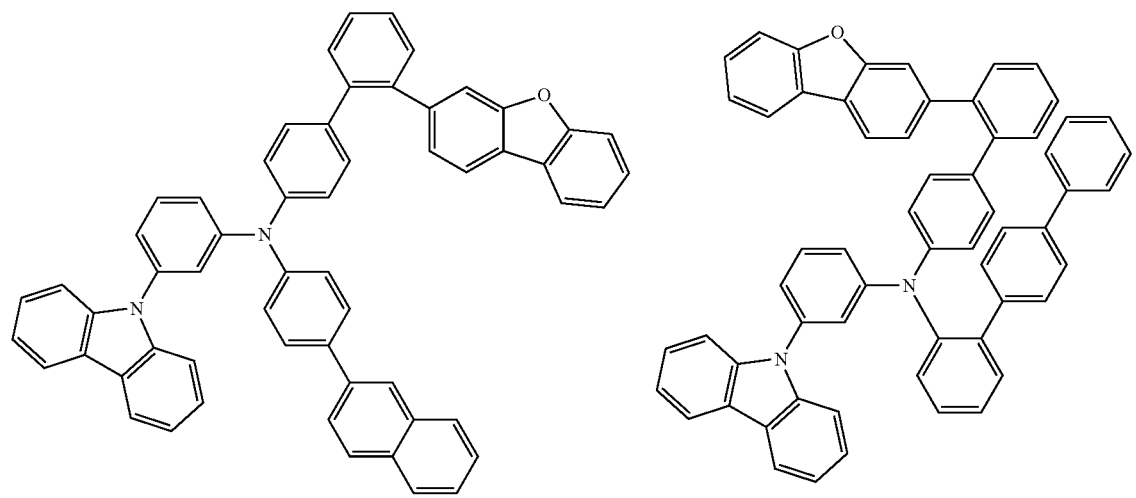

425
-continued
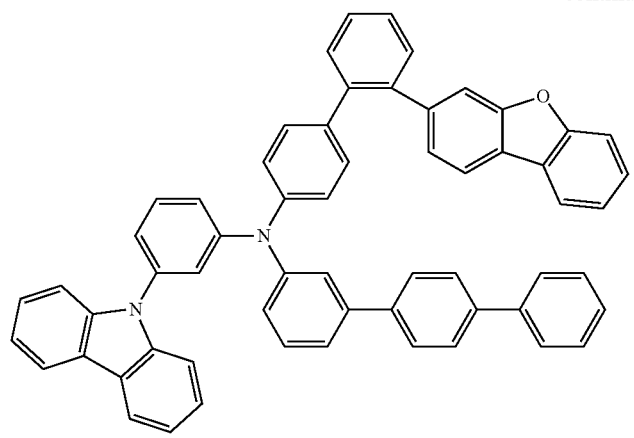
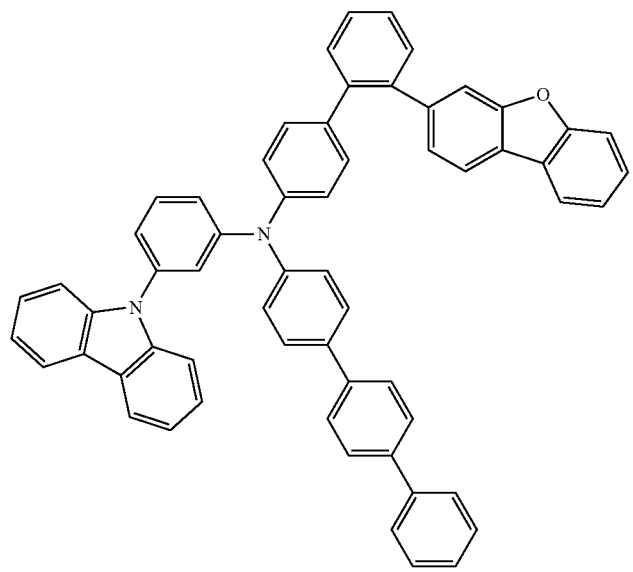
426
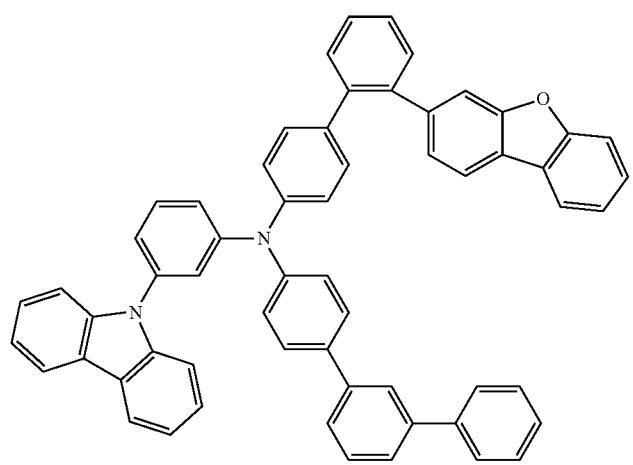
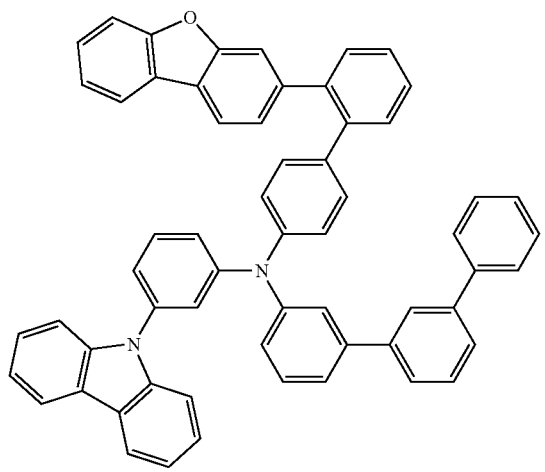

-continued
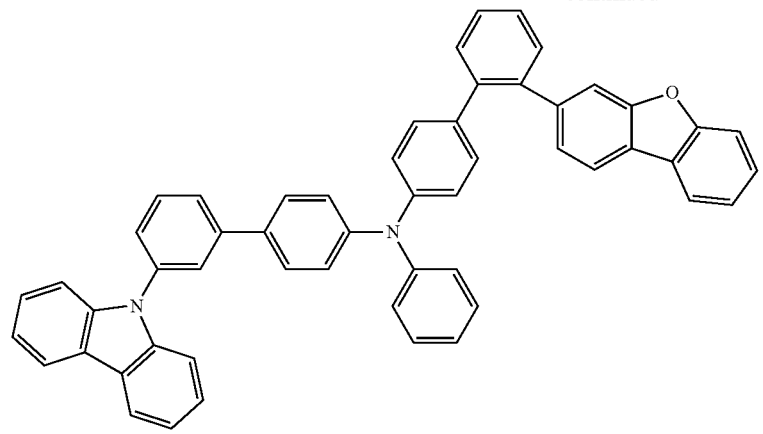
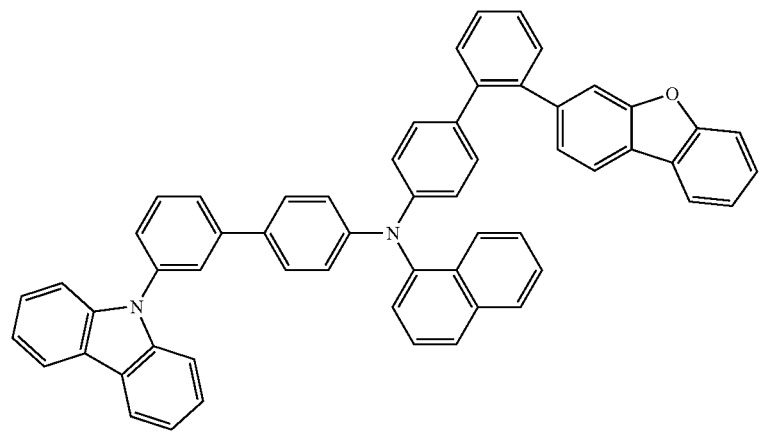
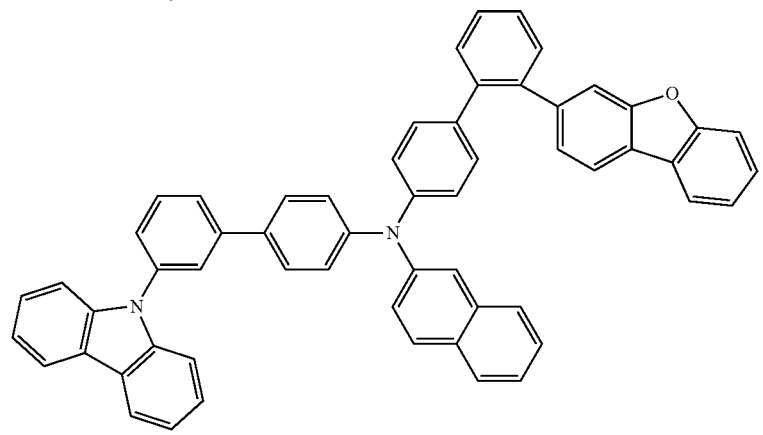
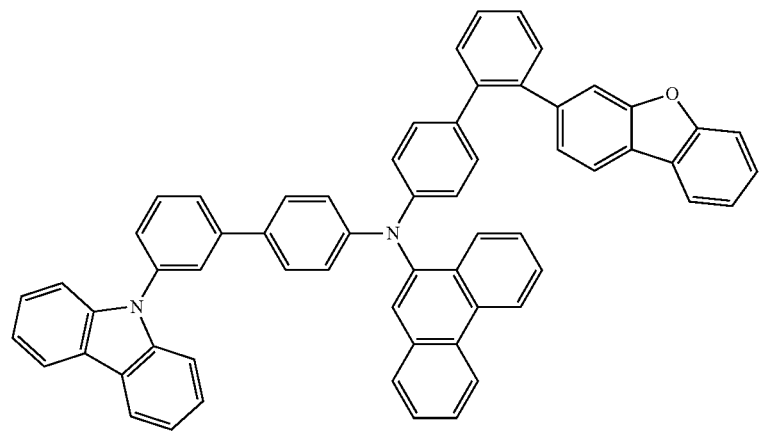

-continued
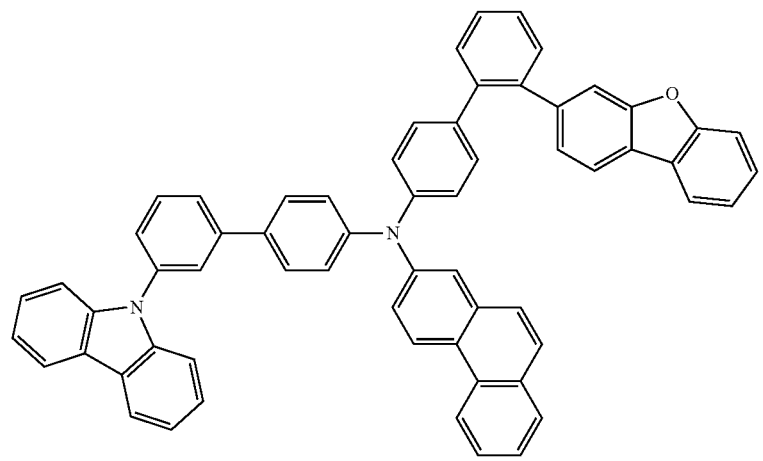
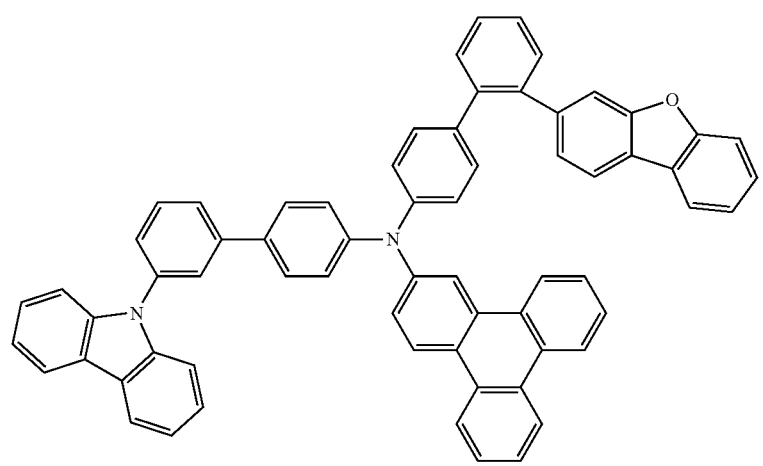
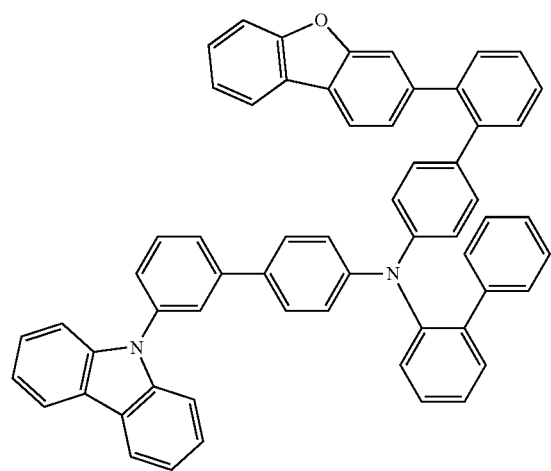

-continued
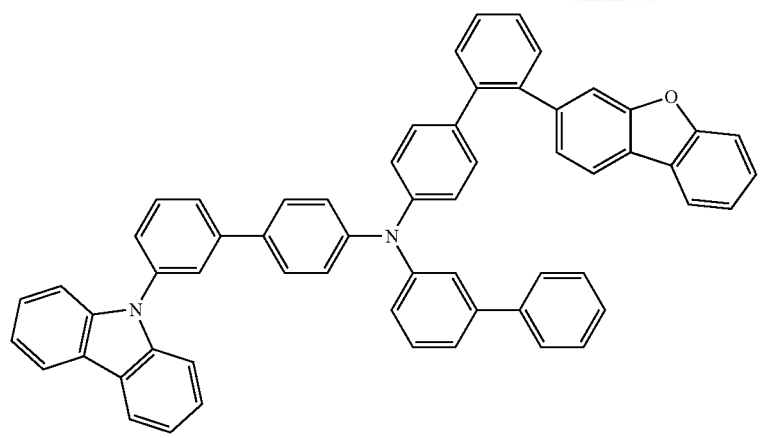
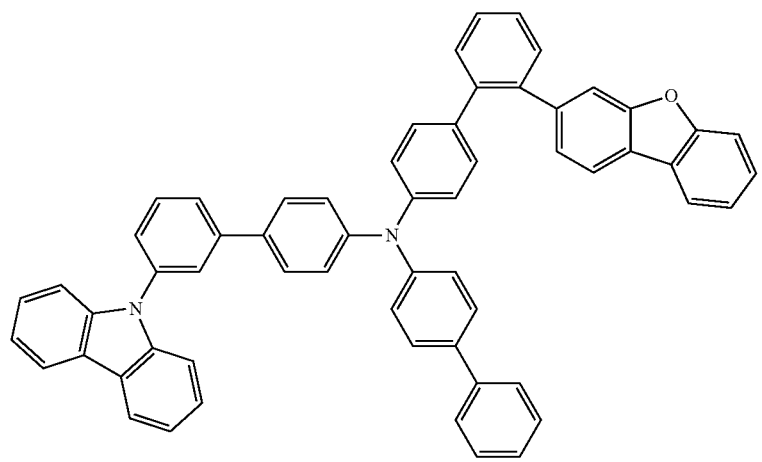
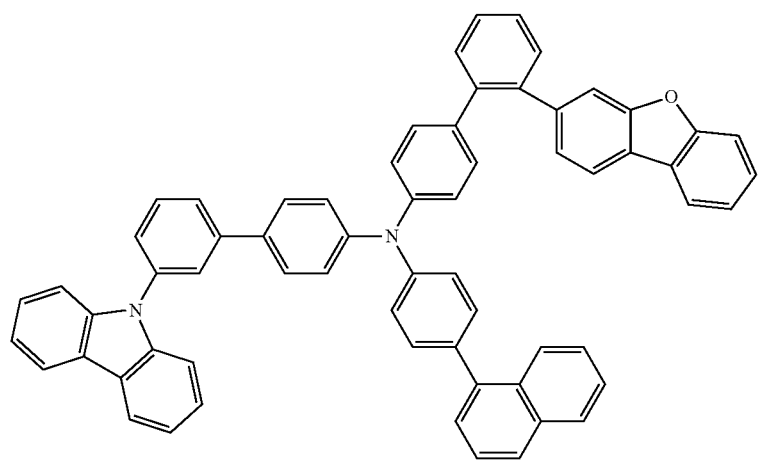

-continued
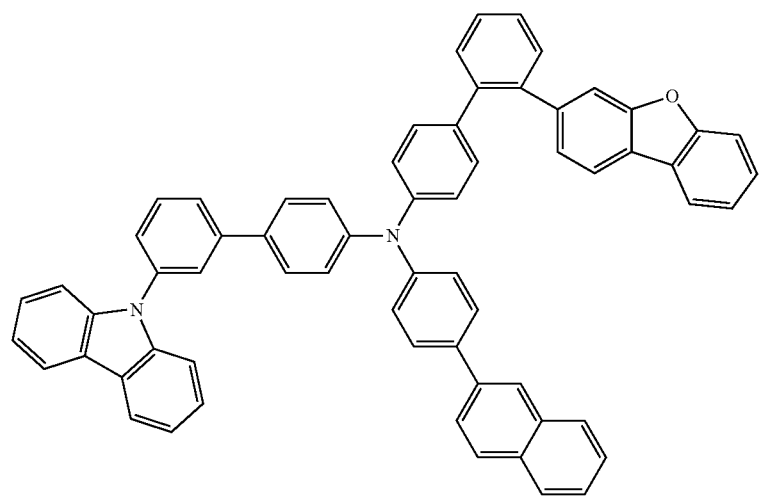
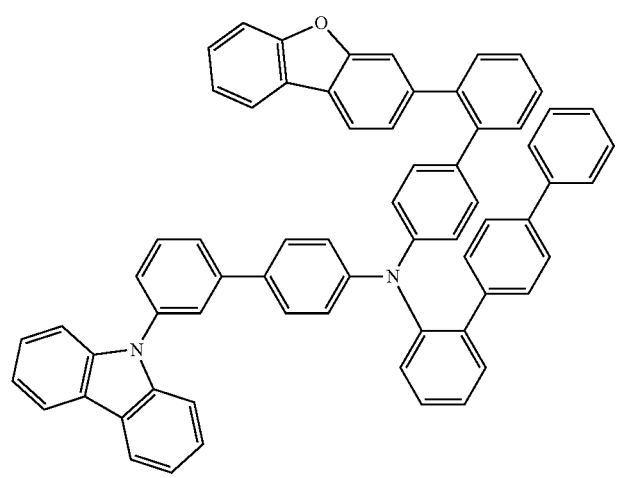
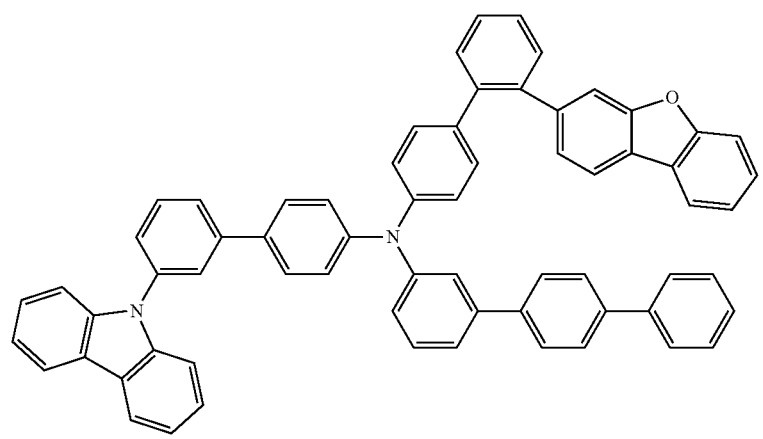

-continued
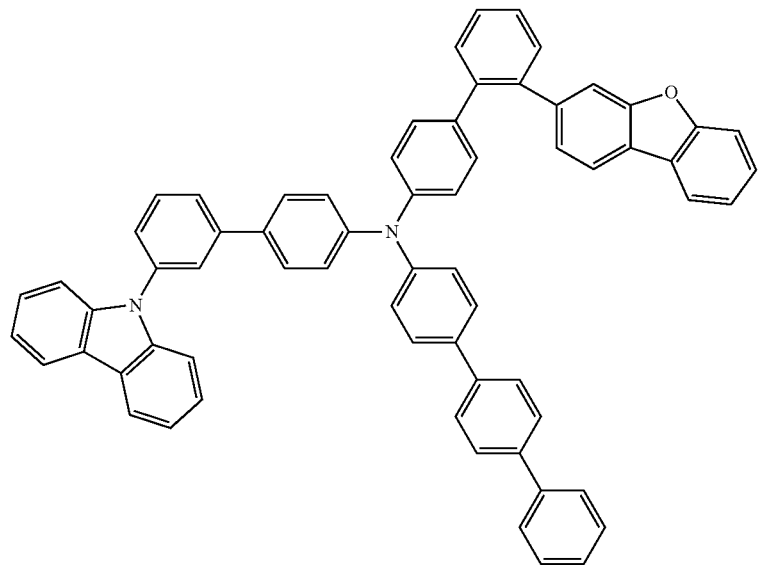
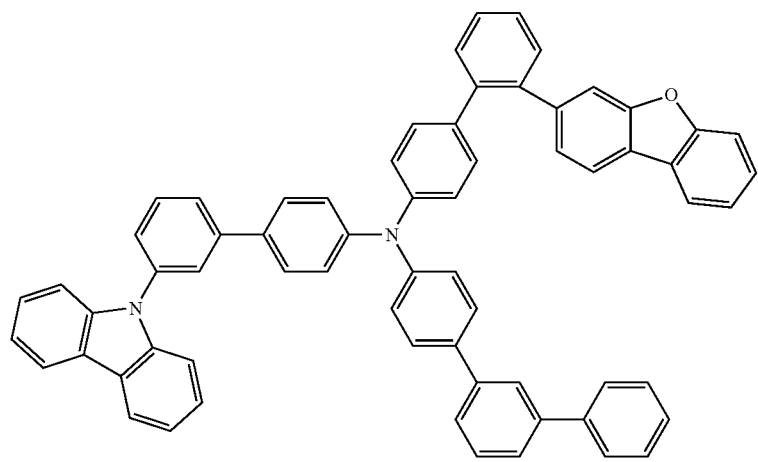
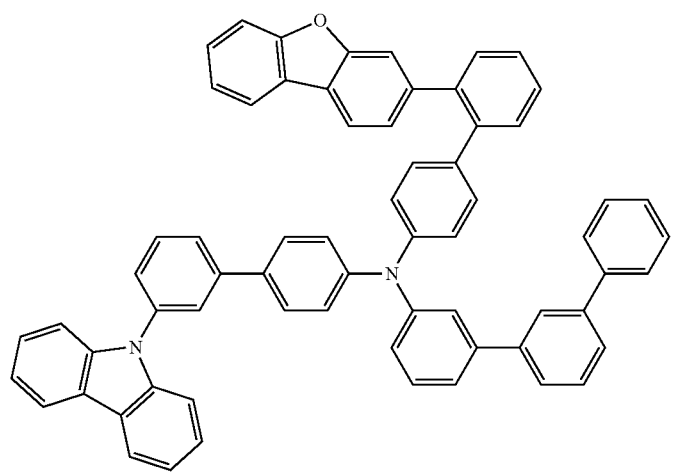

-continued
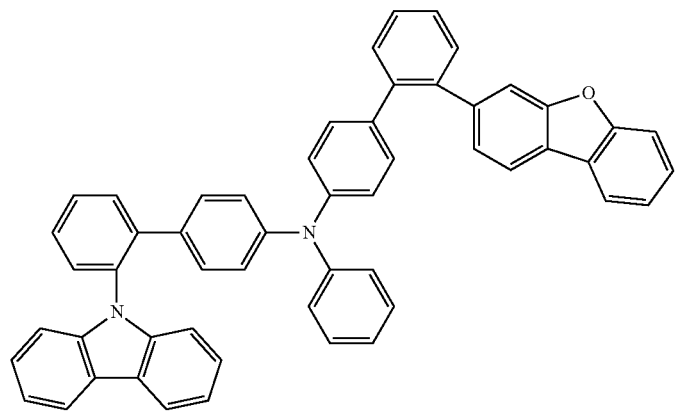
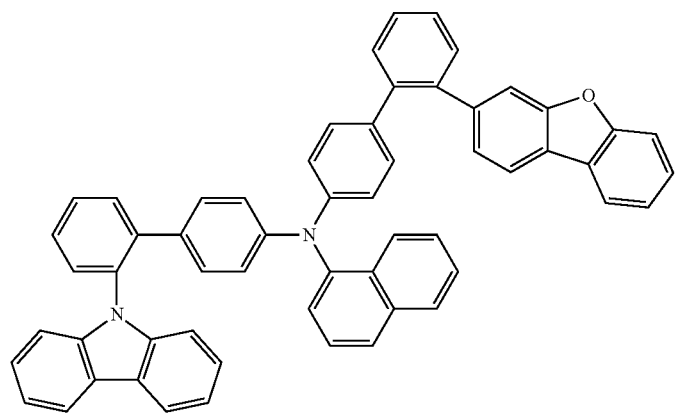
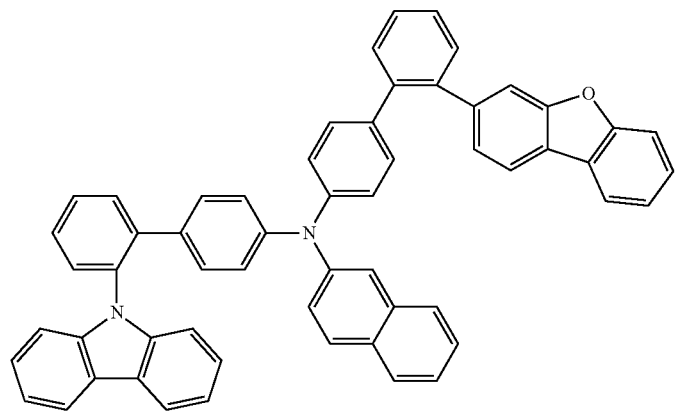
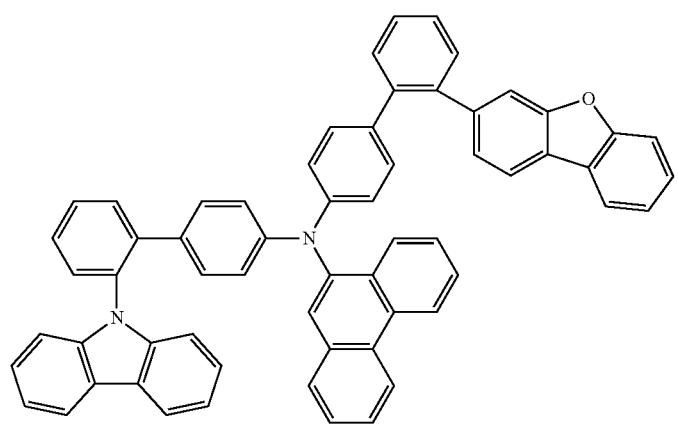

439 440
-continued
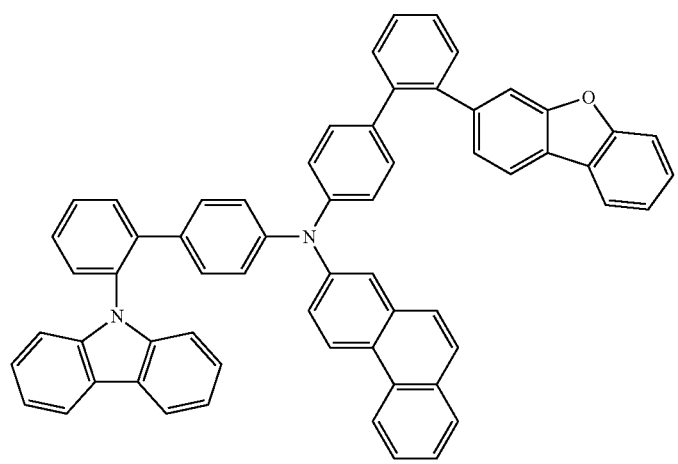
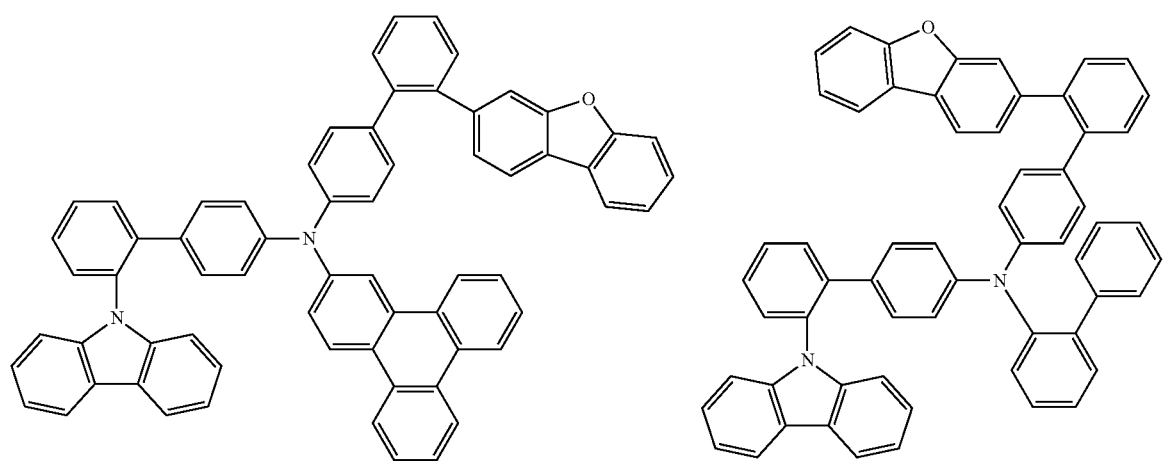
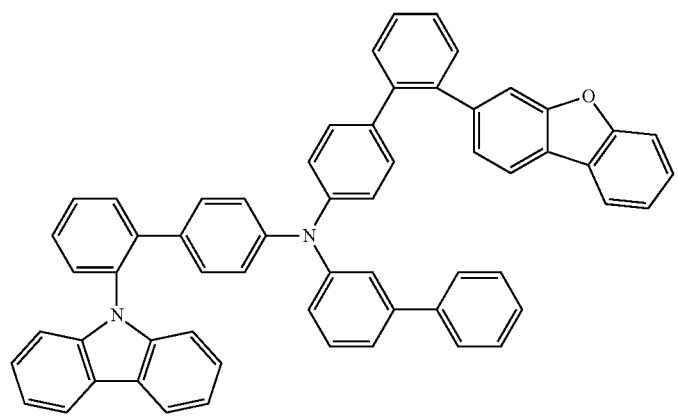

-continued
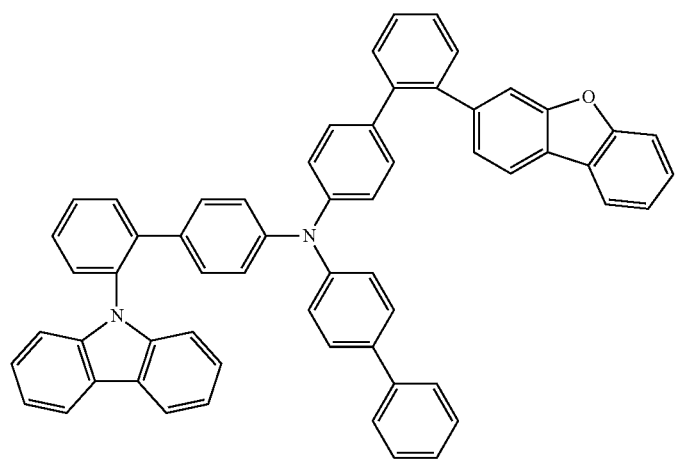
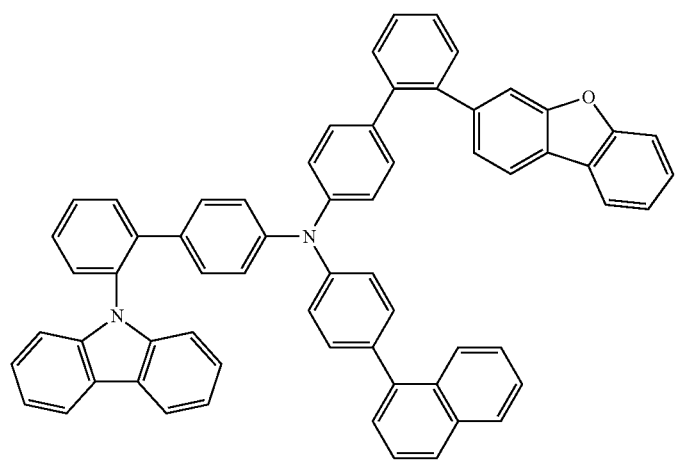
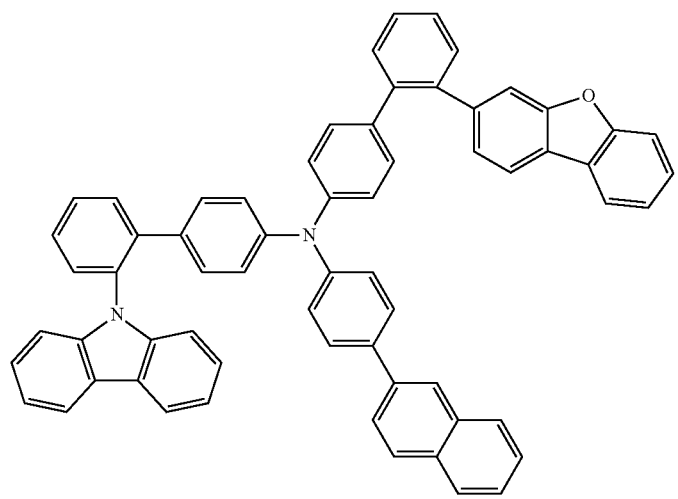

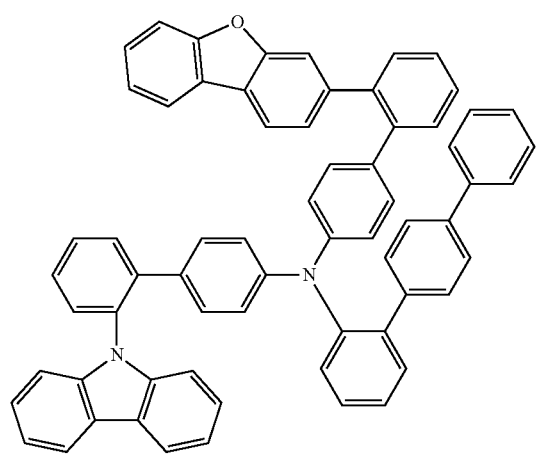
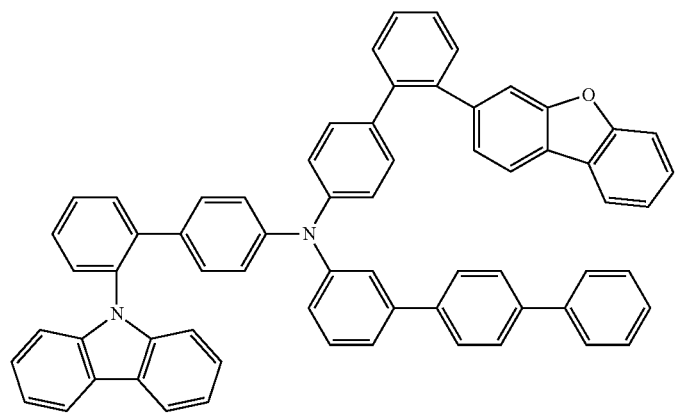
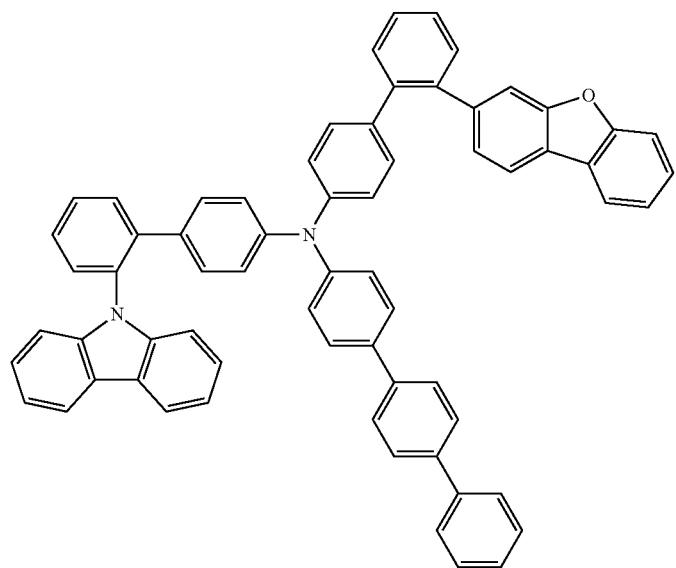

-continued
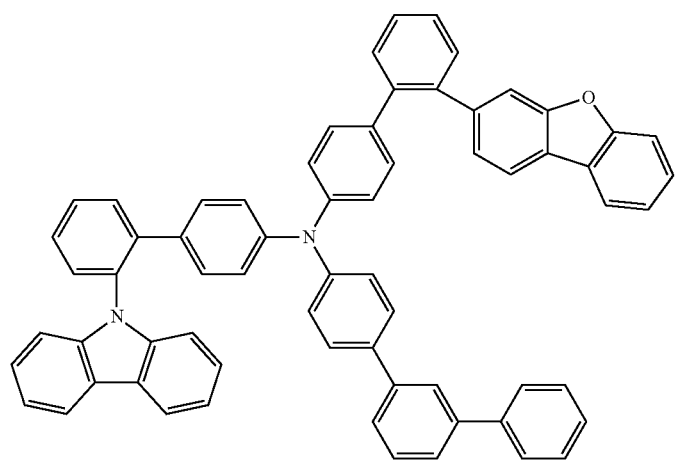
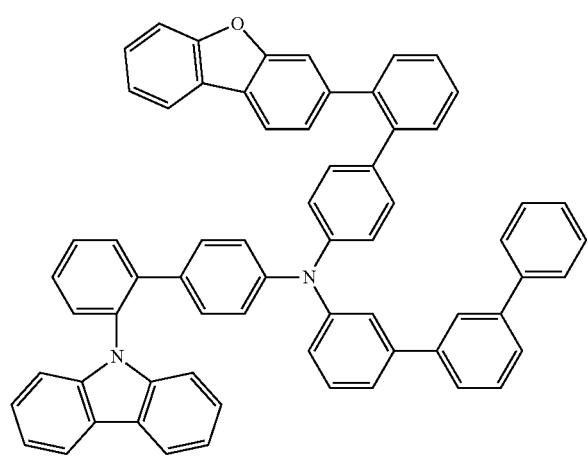
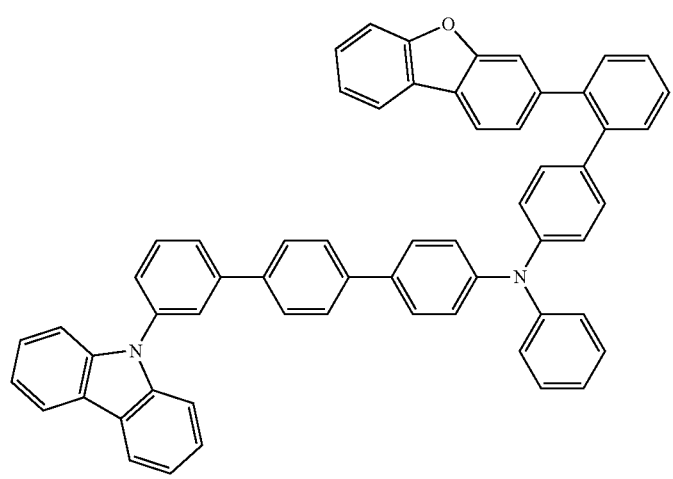

-continued
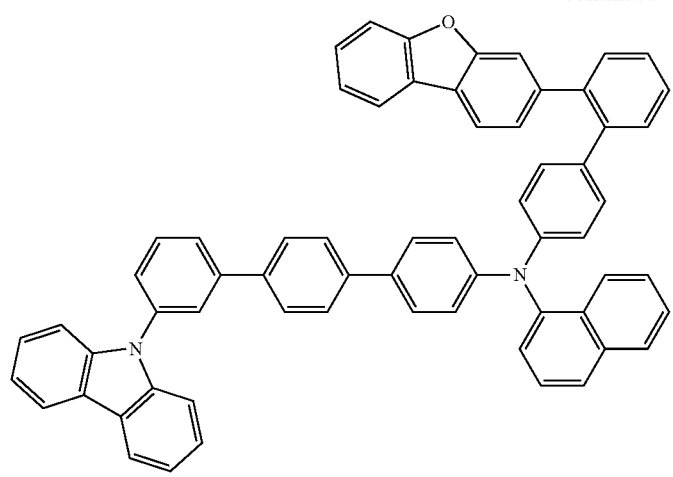
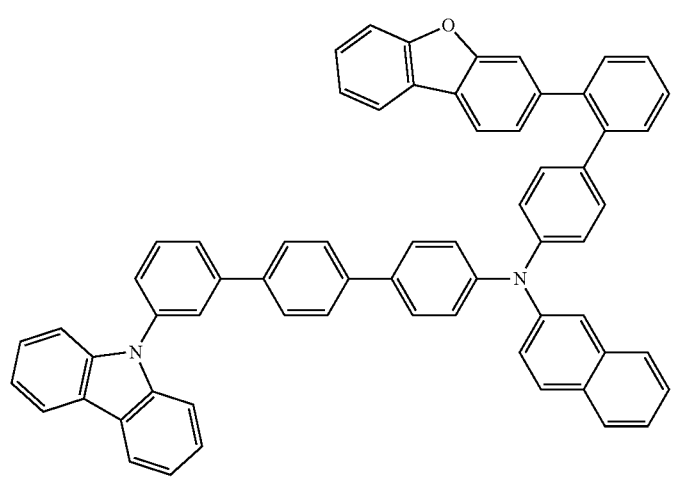
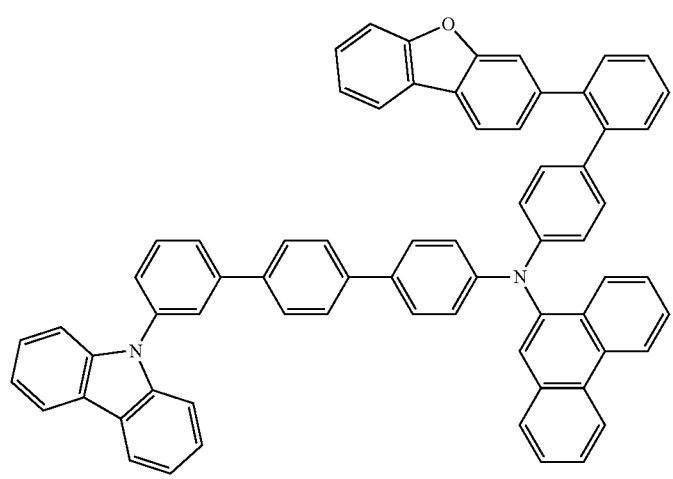

-continued
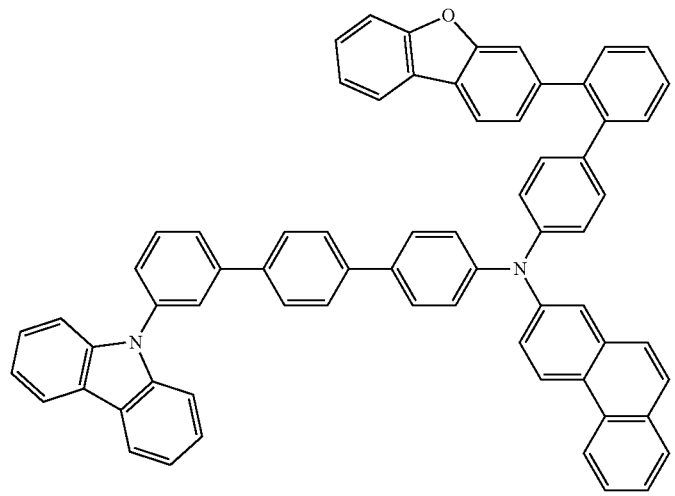
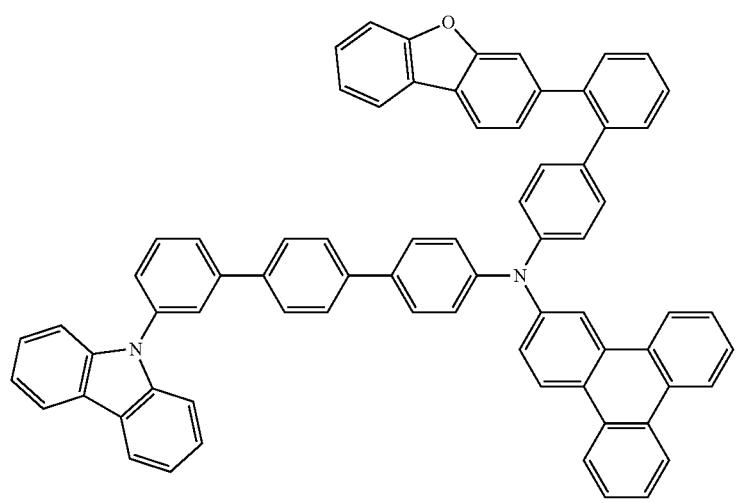
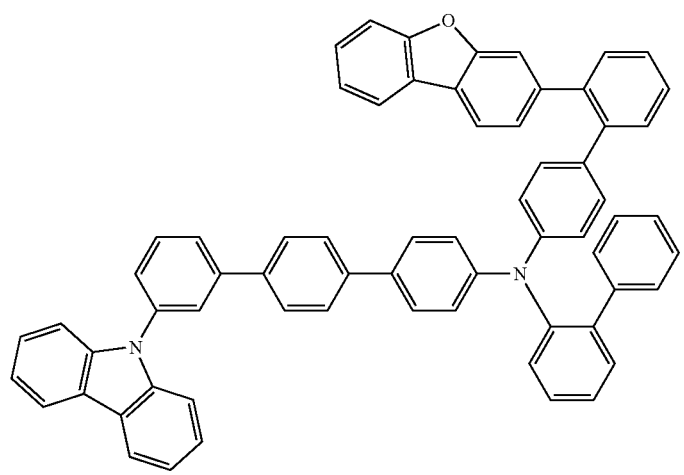

-continued
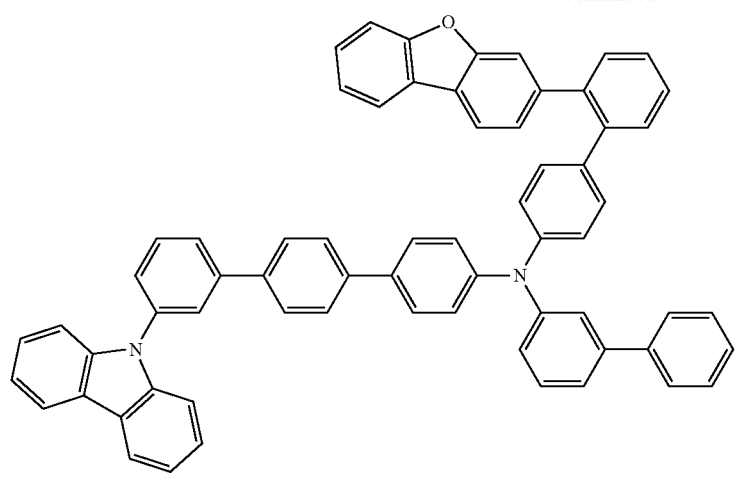
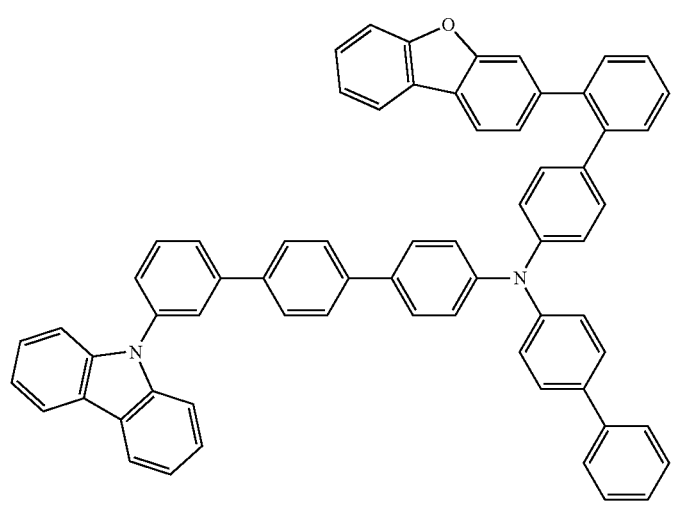
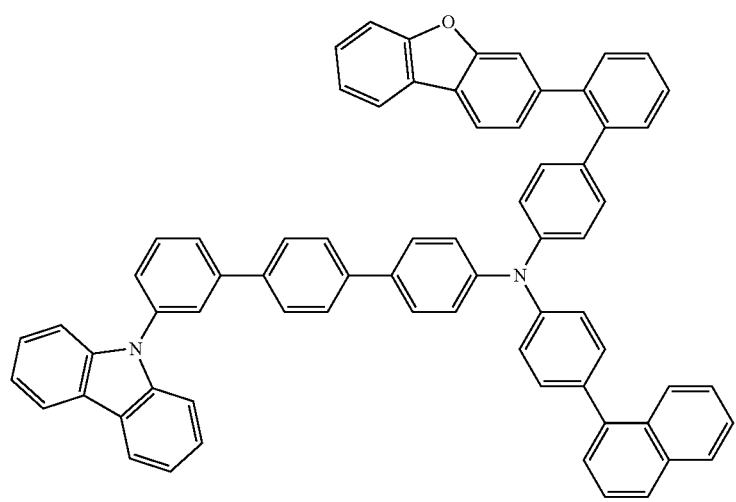

-continued
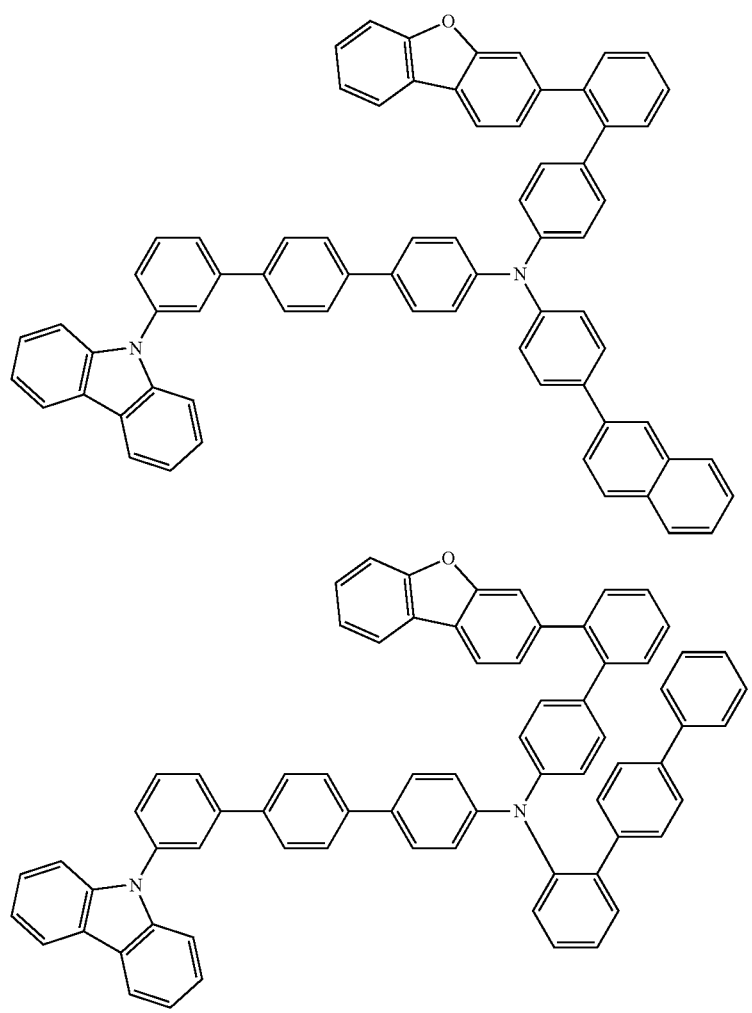
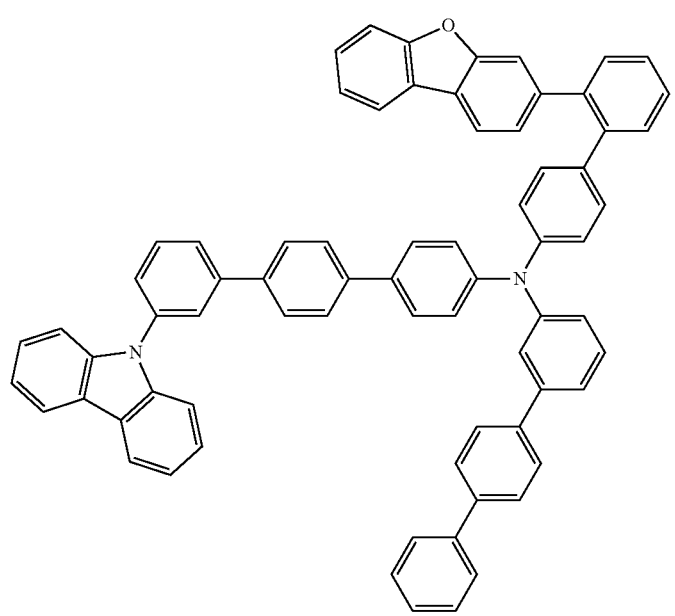

-continued
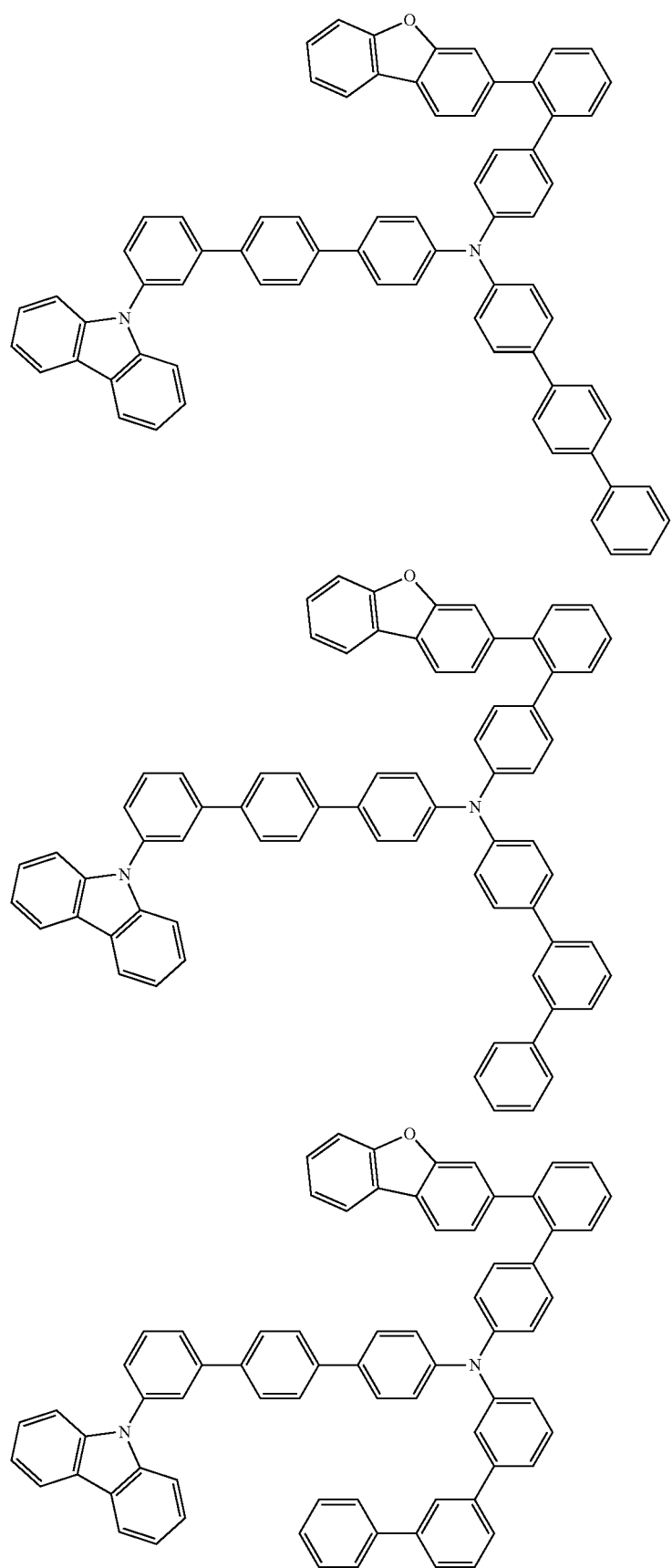 [SMILES: c1ccc(-c2ccc(-c3ccc(N(c4ccc(-c5ccc(-c6cccc(-n7c8ccccc8c8ccccc87)c6)cc5)cc4)c4ccc(-c5ccccc5-c5ccc6c(c5)oc5ccccc56)cc4)cc3)cc2)cc1 ; c1ccc(-c2cccc(-c3ccc(N(c4ccc(-c5ccc(-c6cccc(-n7c8ccccc8c8ccccc87)c6)cc5)cc4)c4ccc(-c5ccccc5-c5ccc6c(c5)oc5ccccc56)cc4)cc3)c2)cc1 ; c1ccc(-c2cccc(-c3cccc(N(c4ccc(-c5ccc(-c6cccc(-n7c8ccccc8c8ccccc87)c6)cc5)cc4)c4ccc(-c5ccccc5-c5ccc6c(c5)oc5ccccc56)cc4)c3)c2)cc1]

-continued
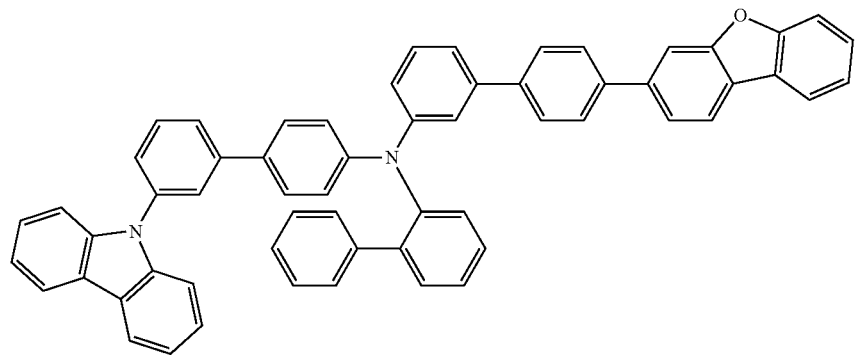
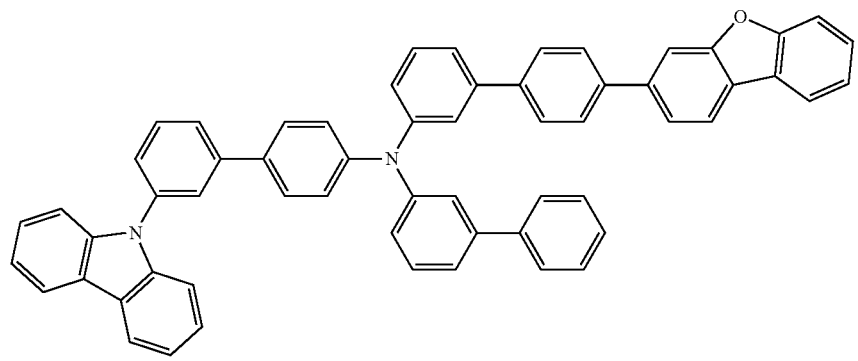
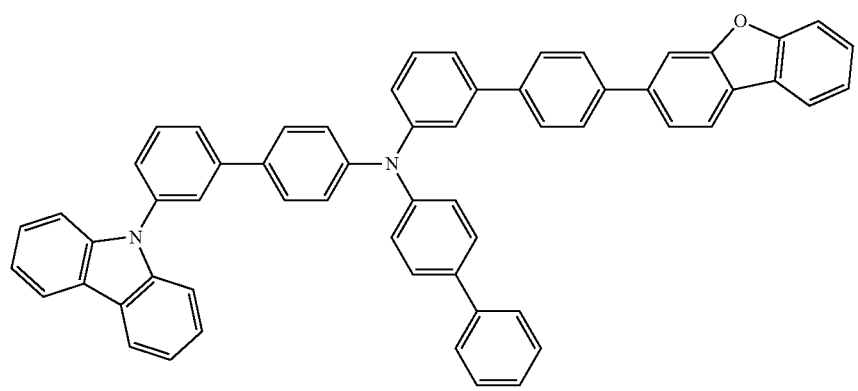
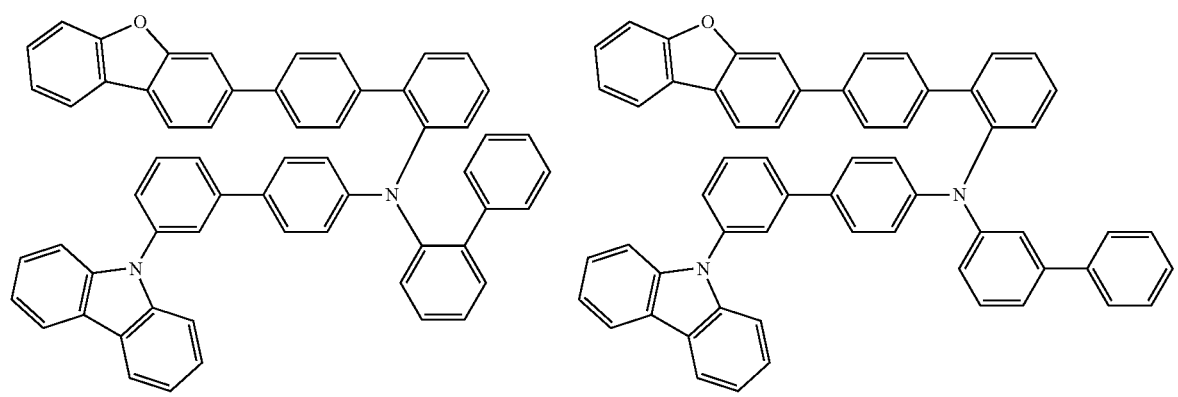

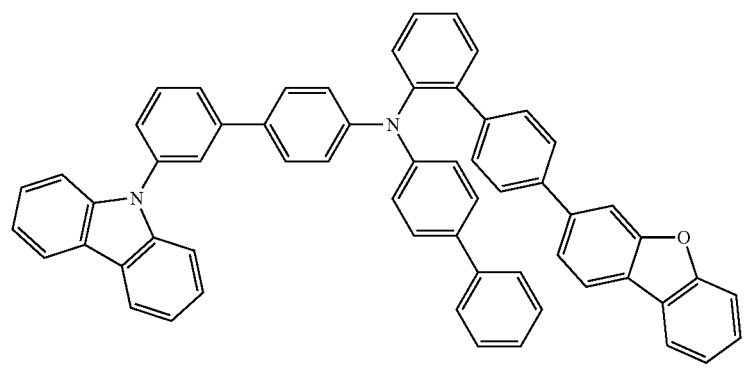
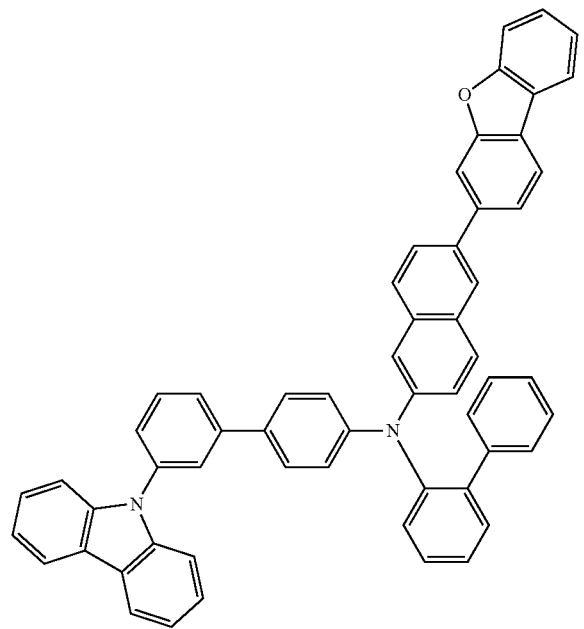
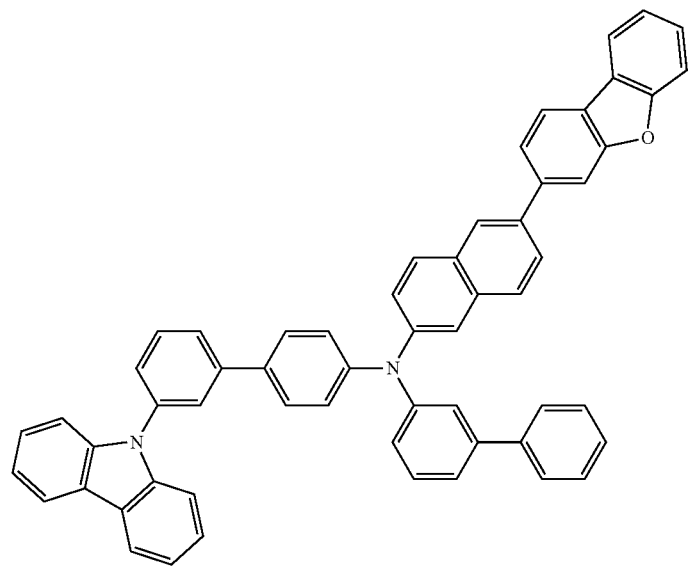

-continued
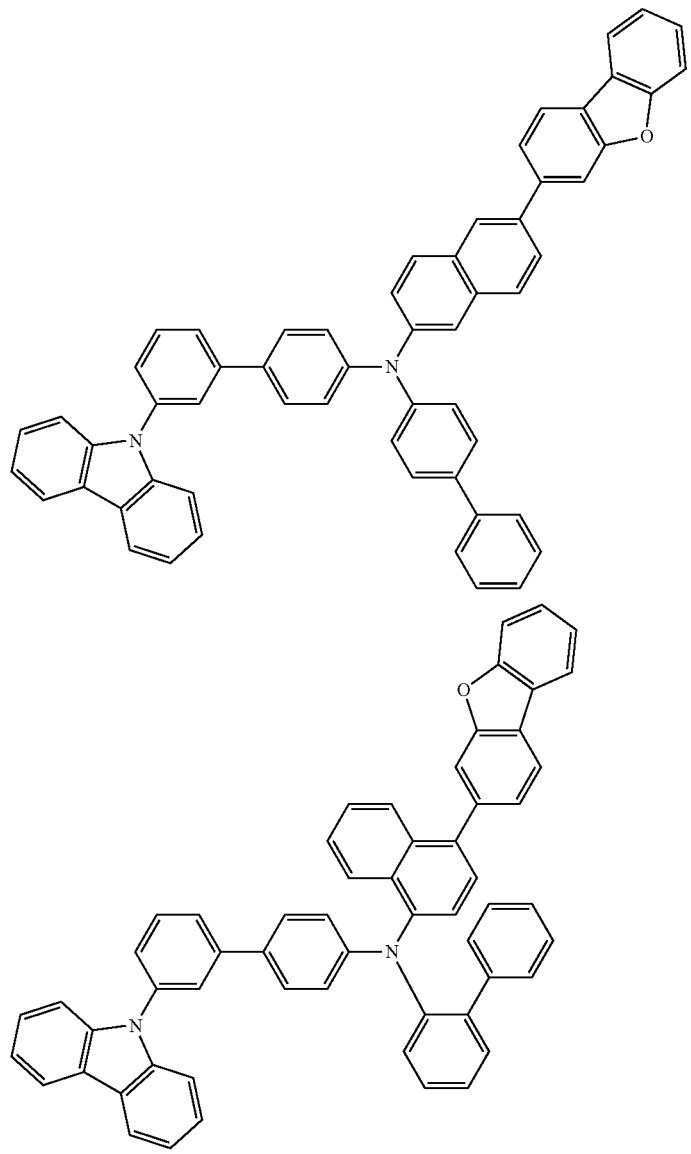
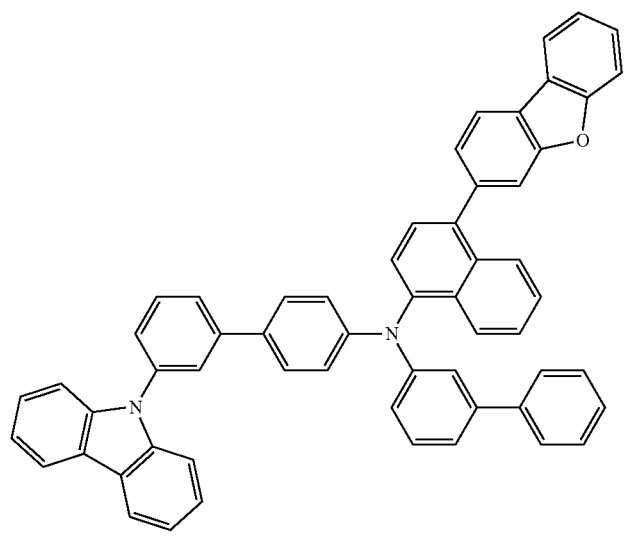

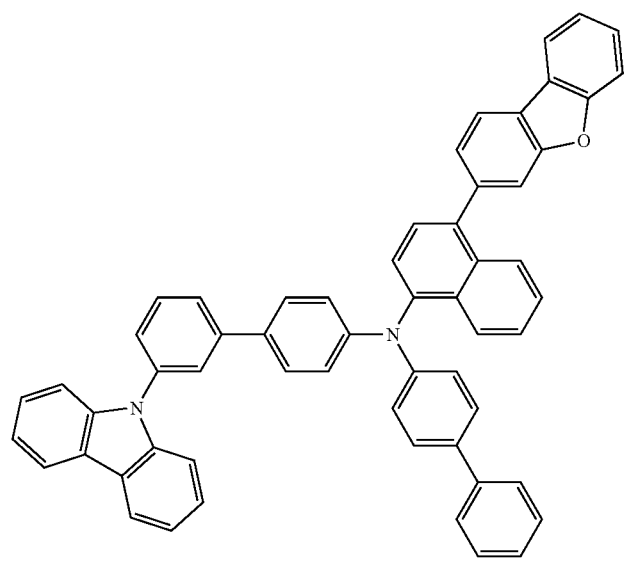
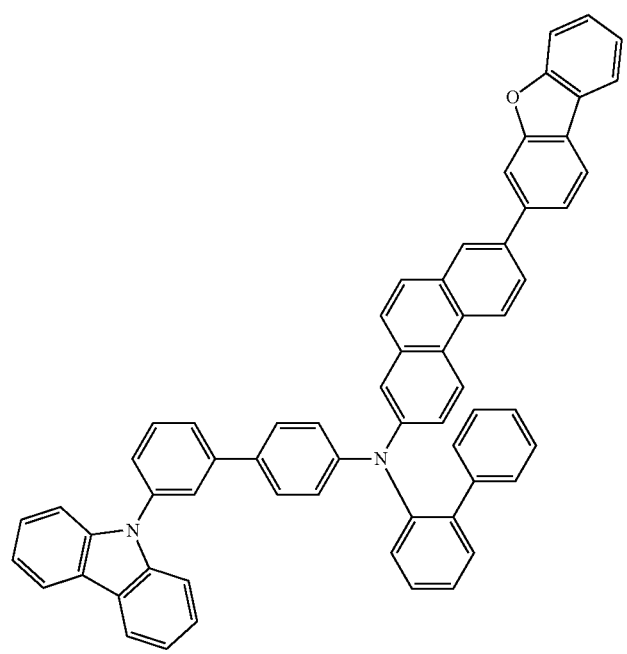

-continued
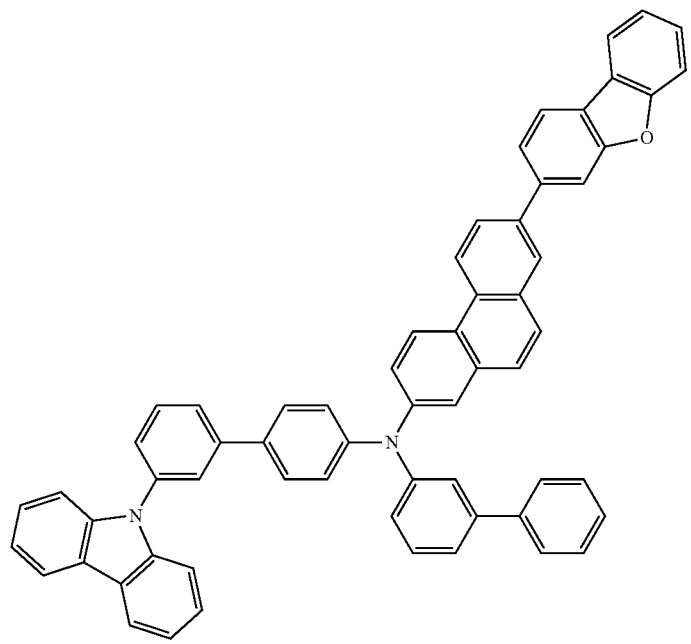
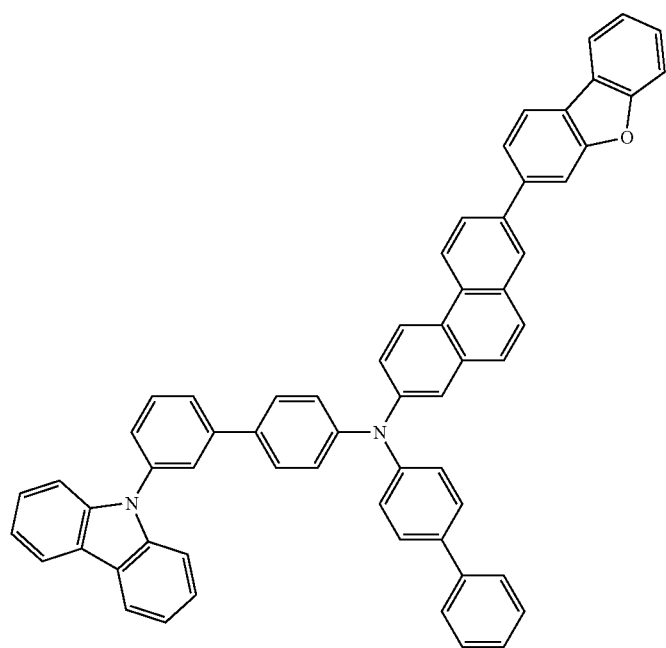

467 468
-continued
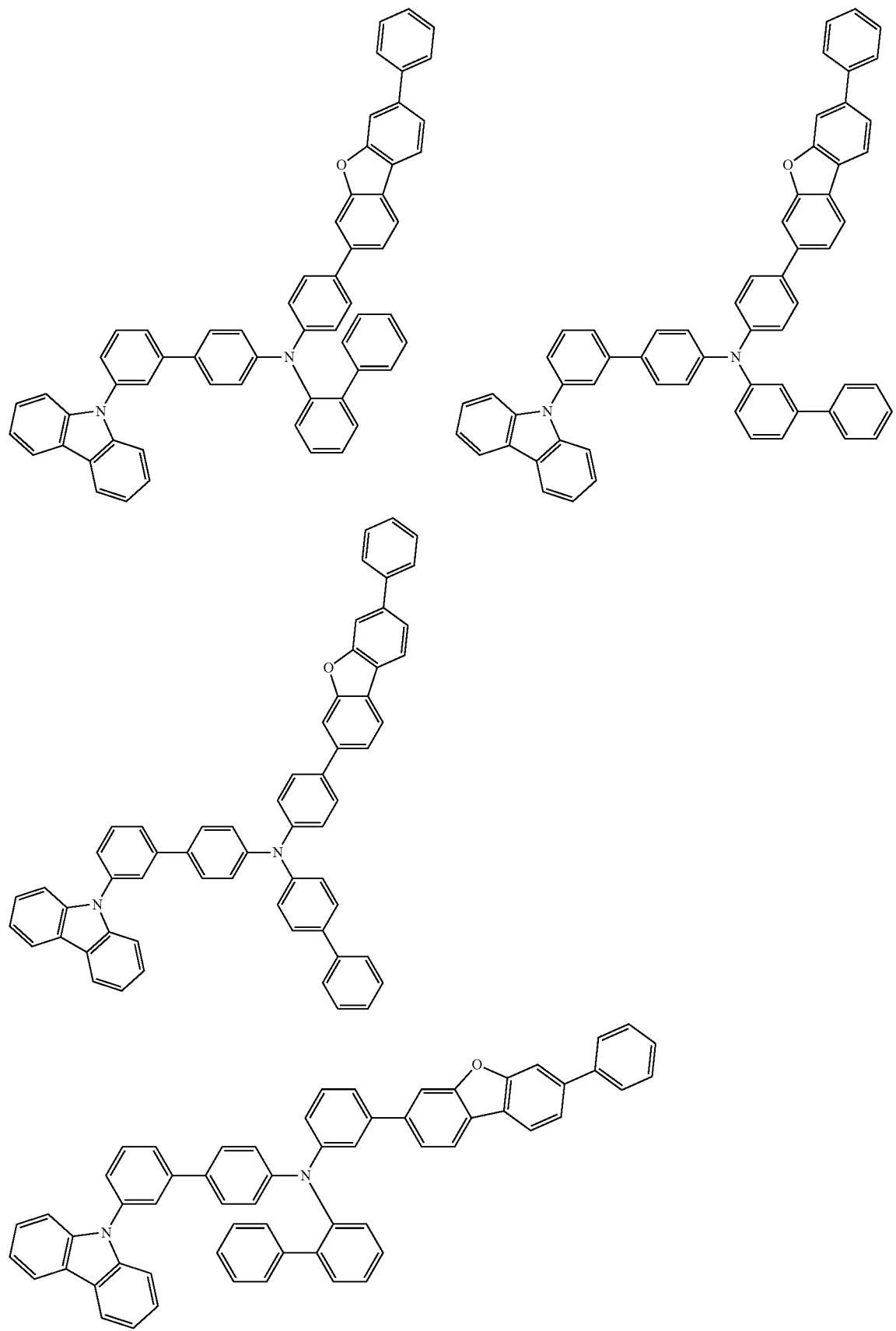

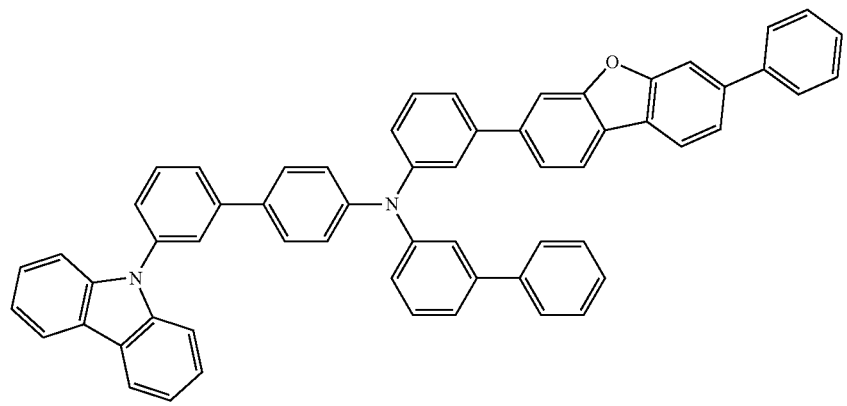
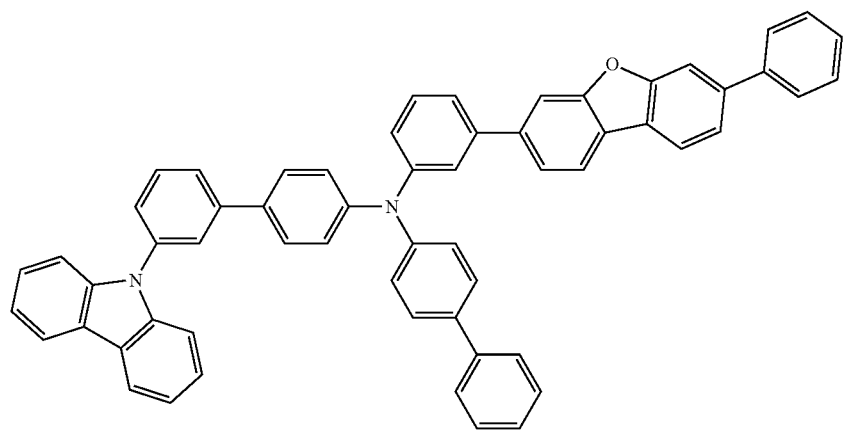
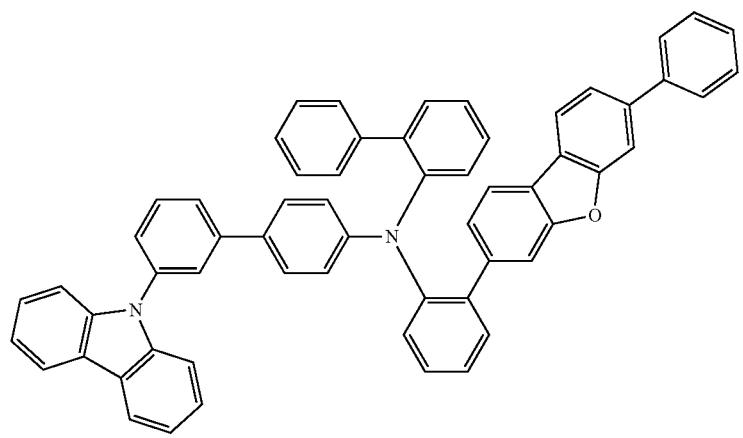
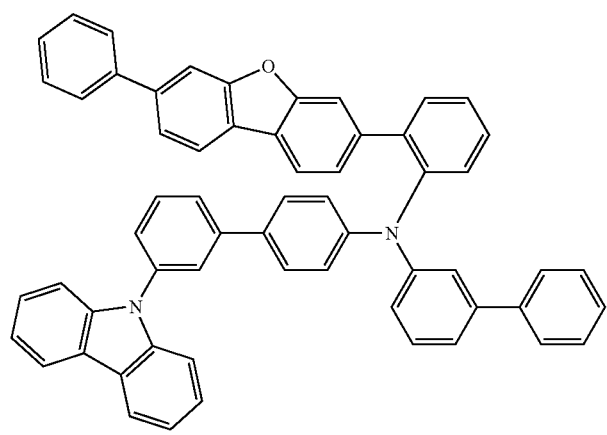

471
472
-continued
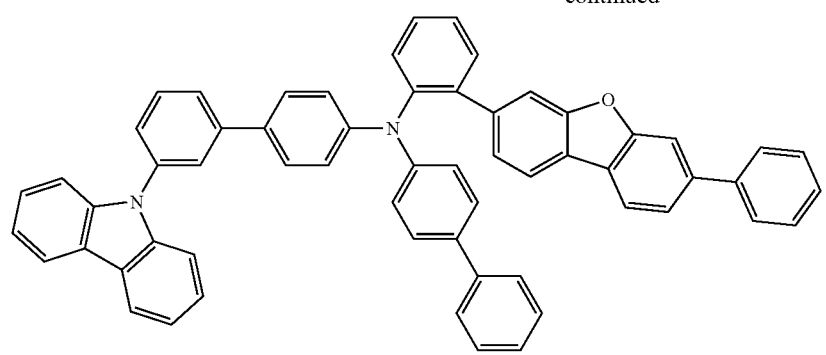
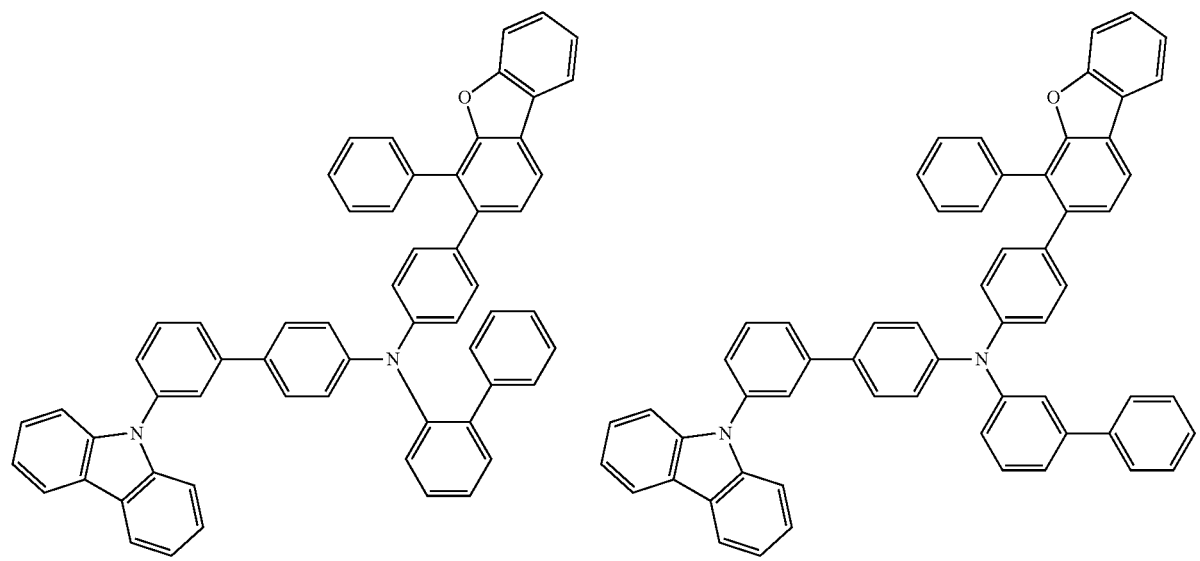
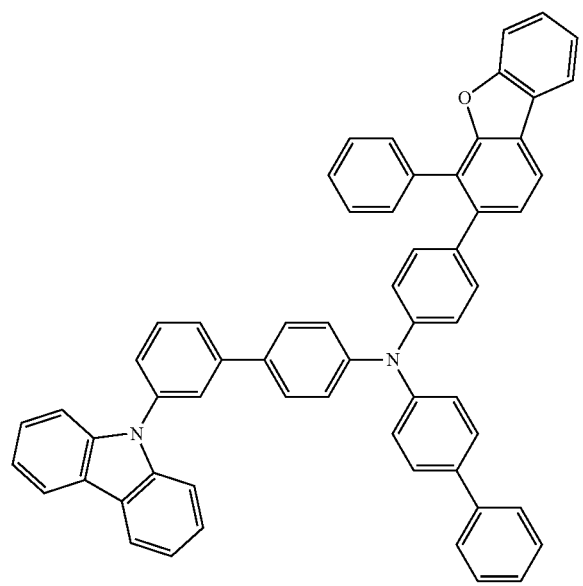

-continued
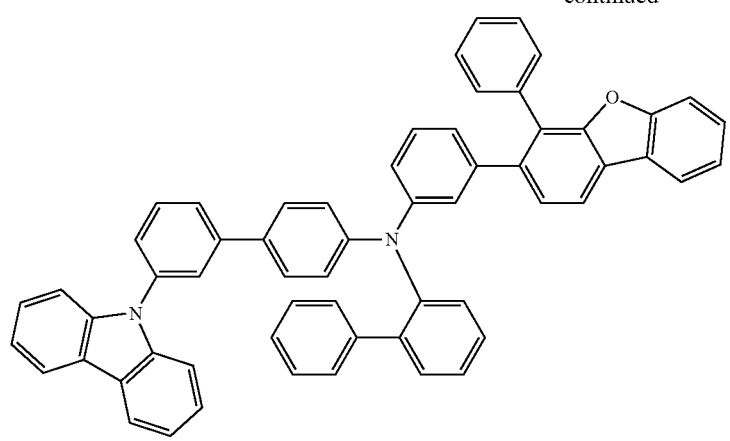
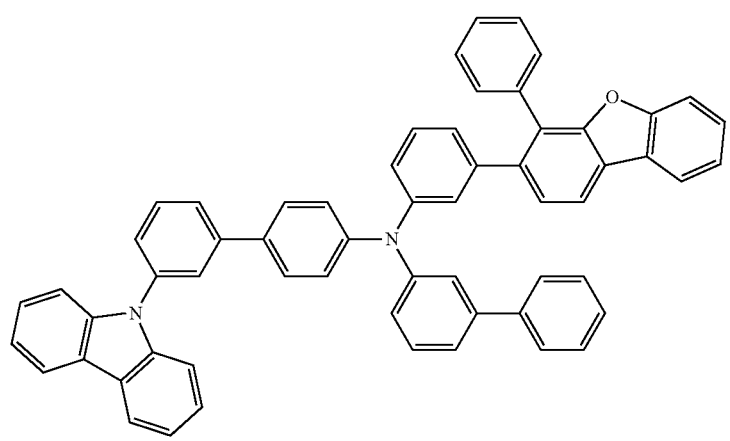
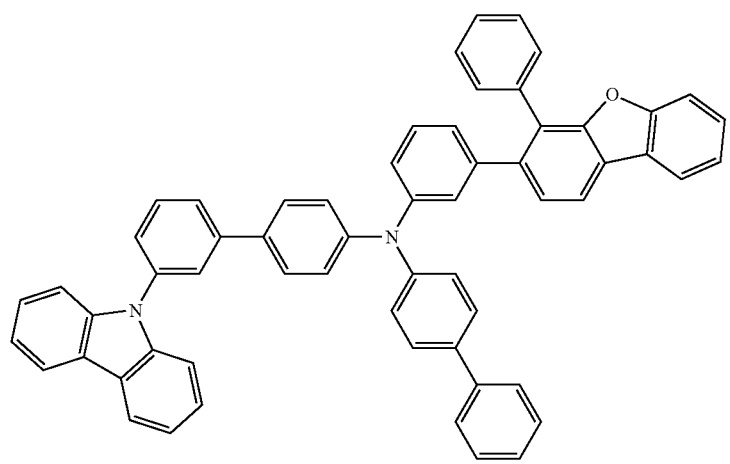

-continued
475 476
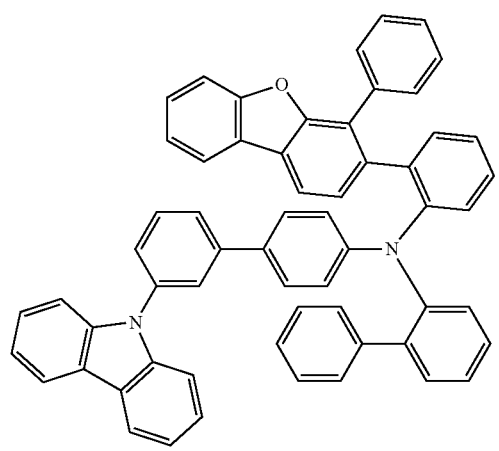
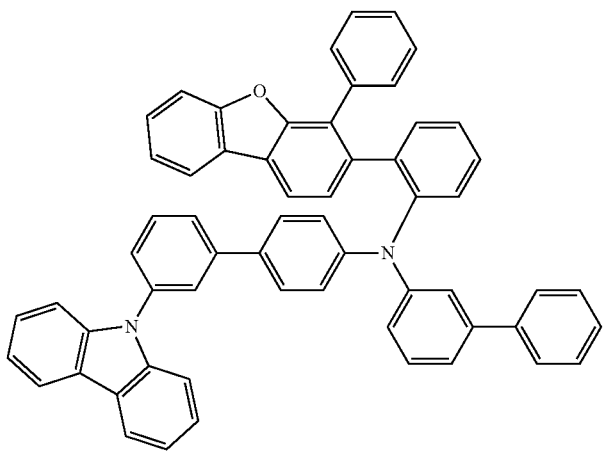
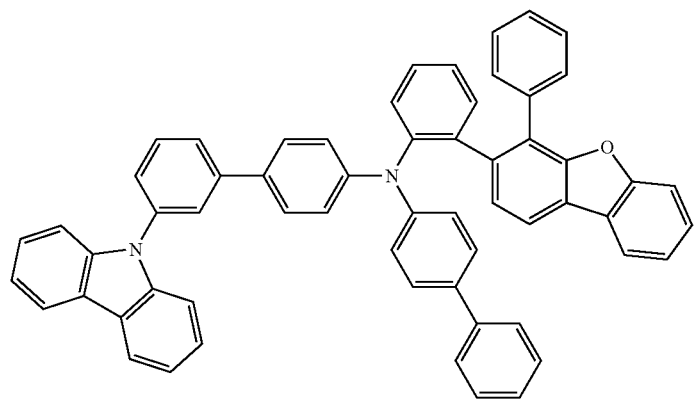
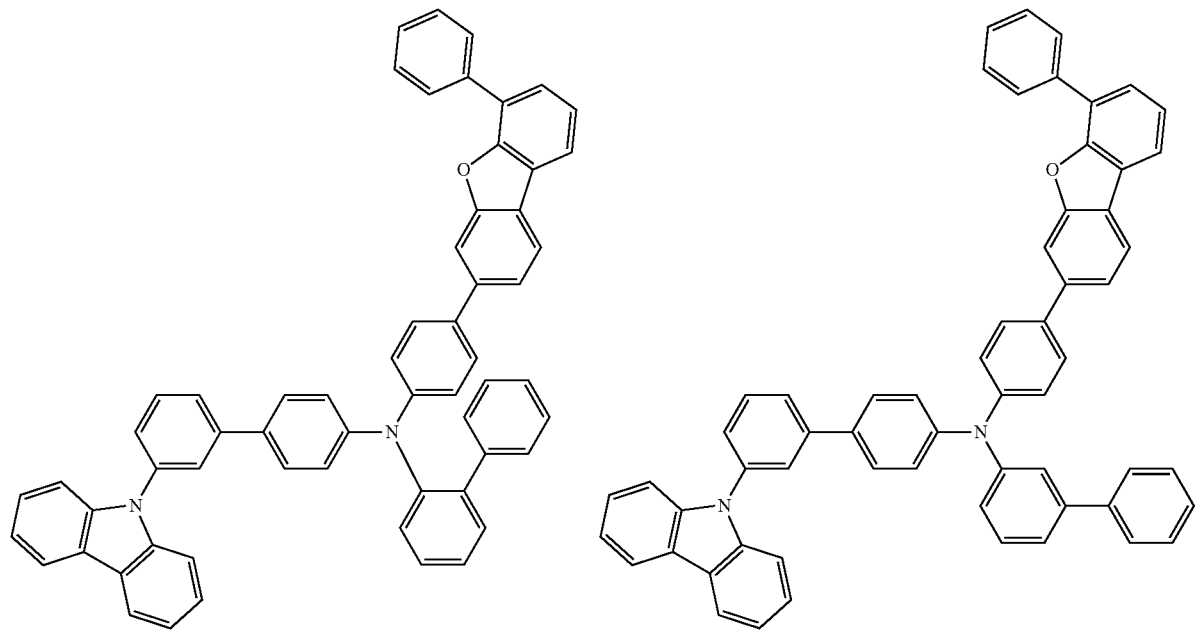

-continued
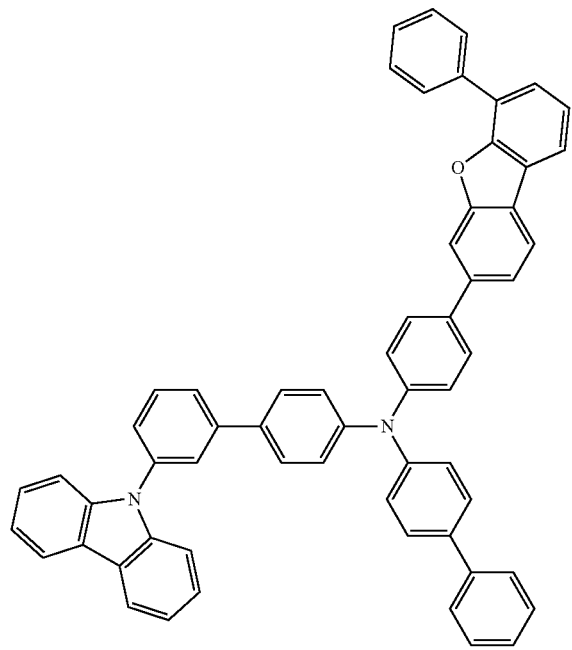
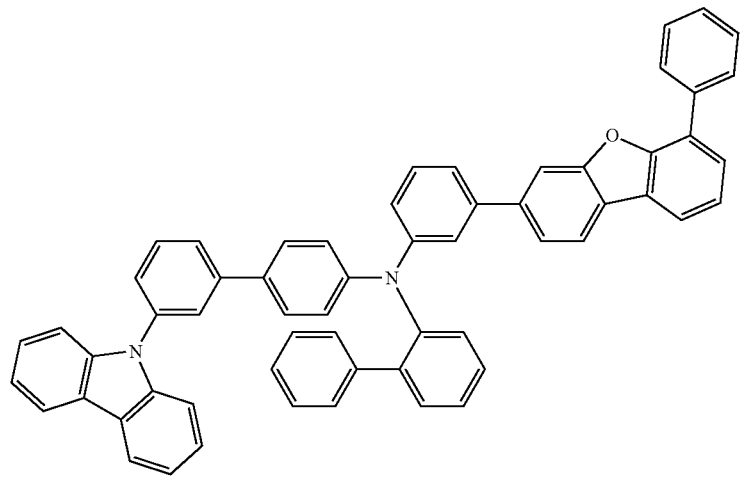
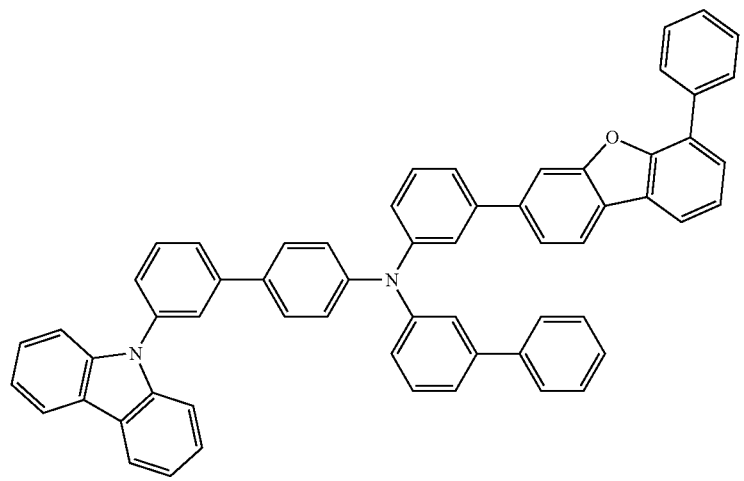

-continued
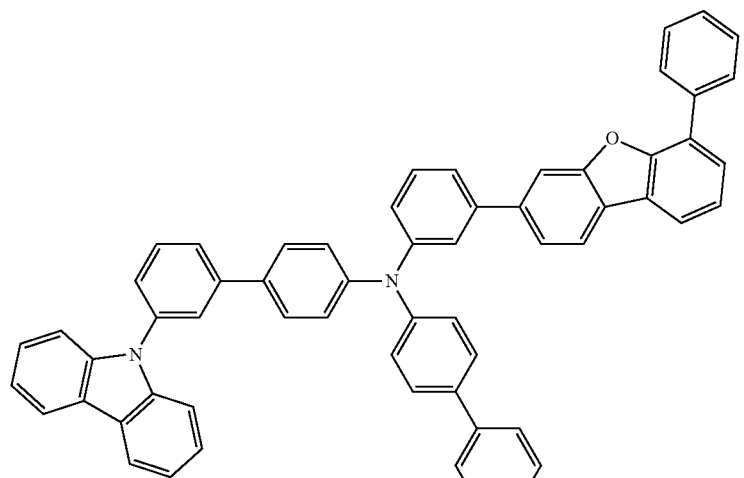
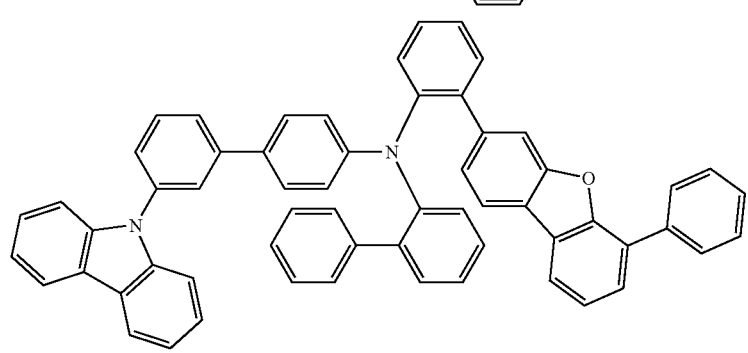
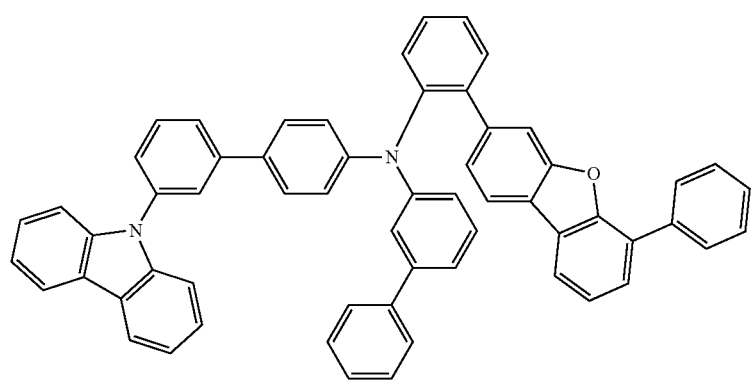
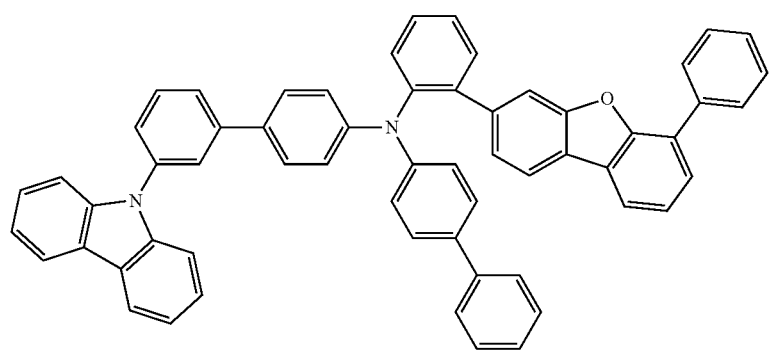

-continued
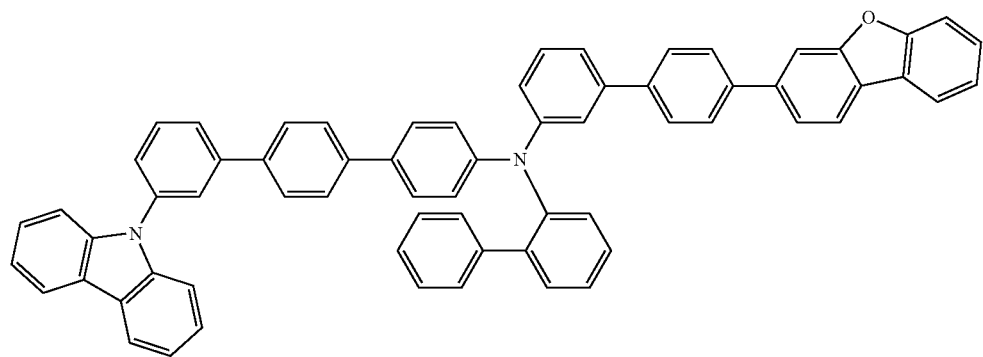
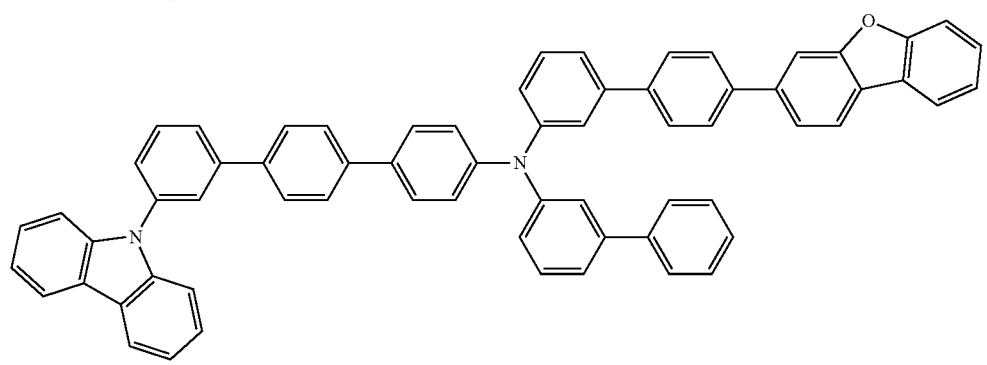
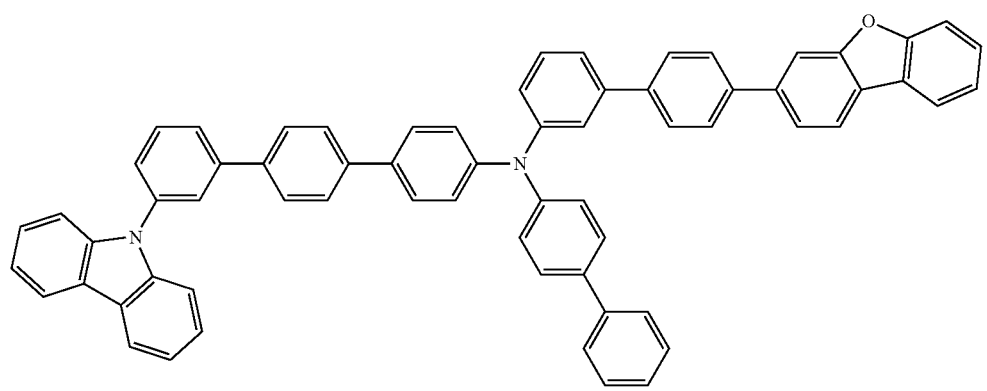
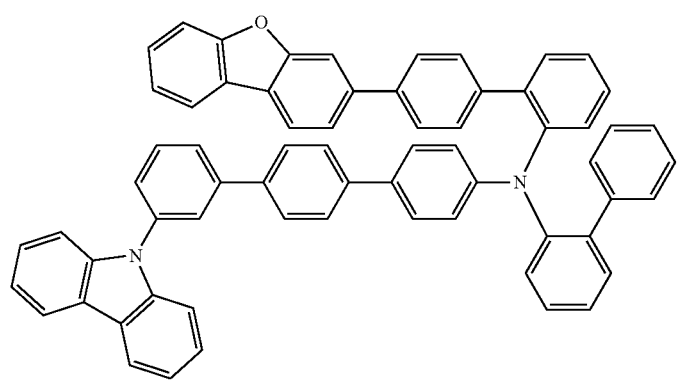

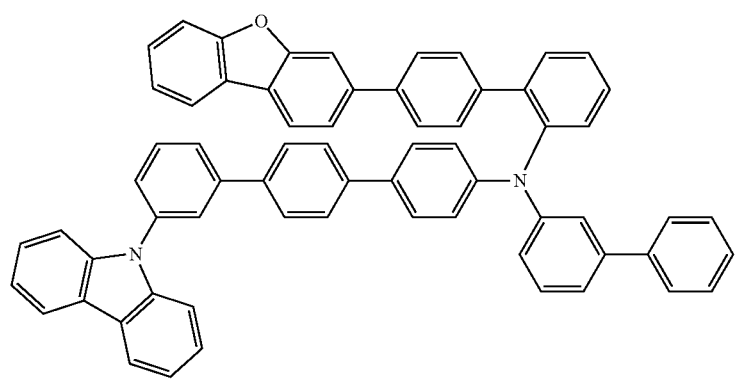
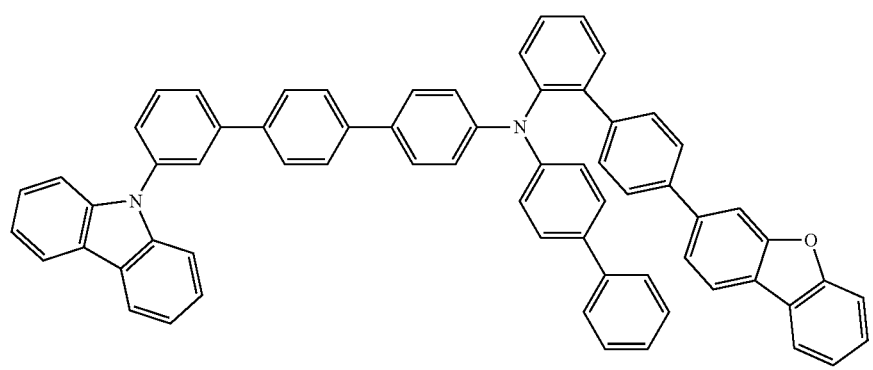
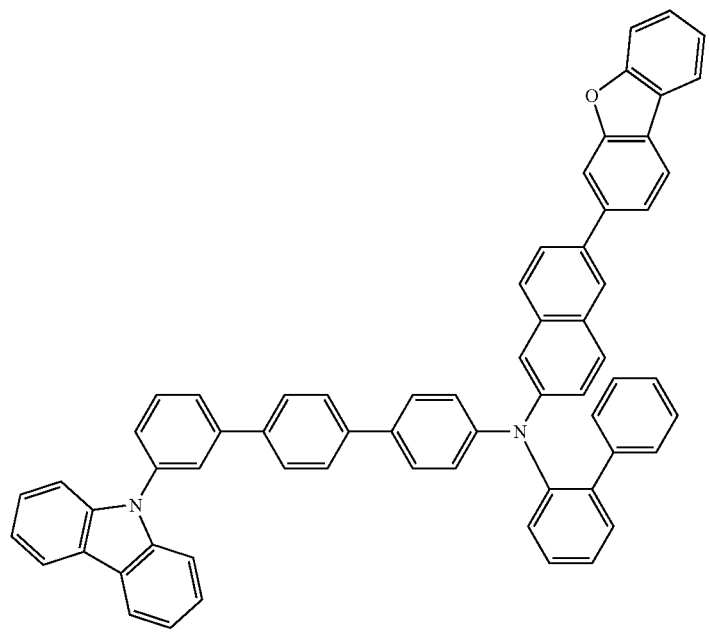

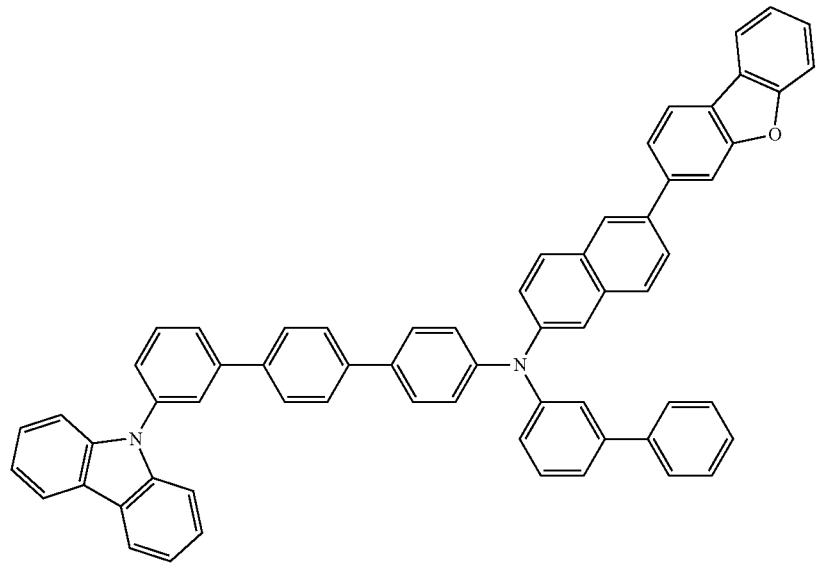
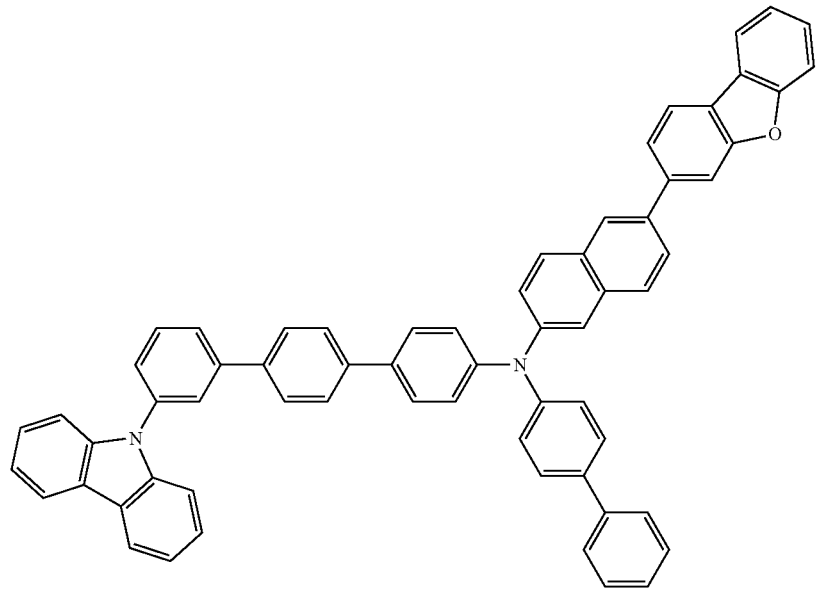
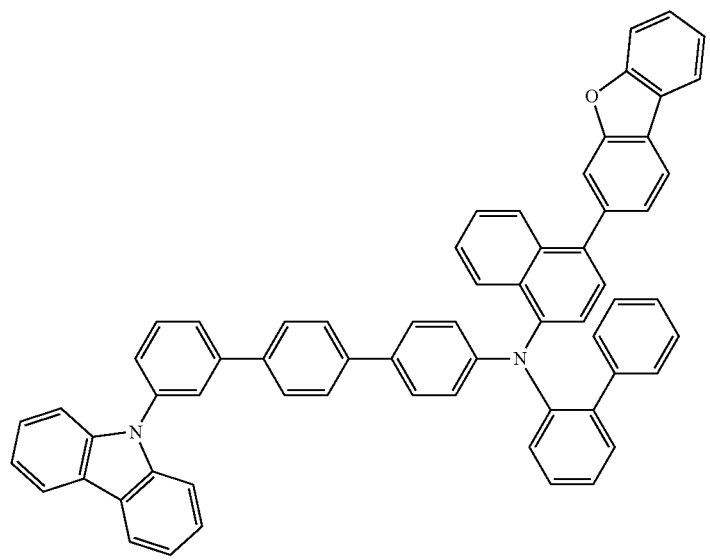

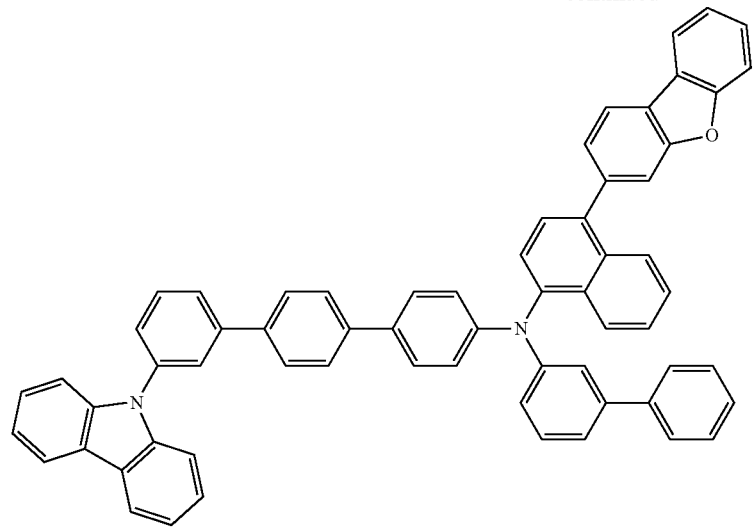
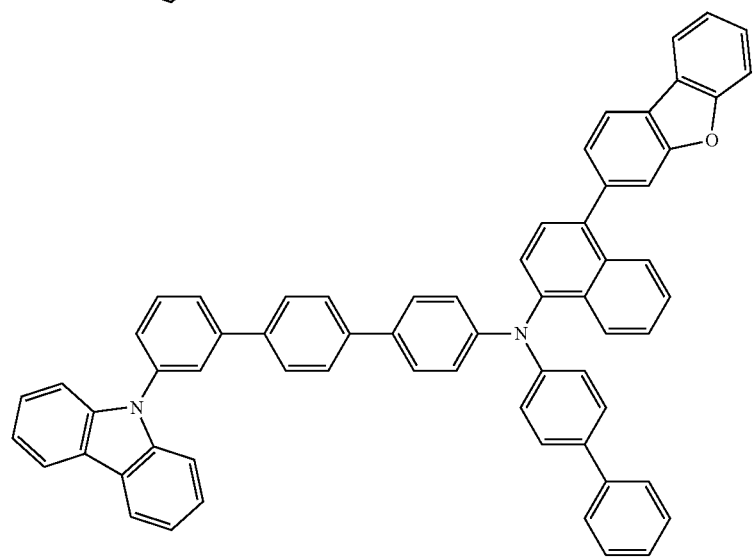
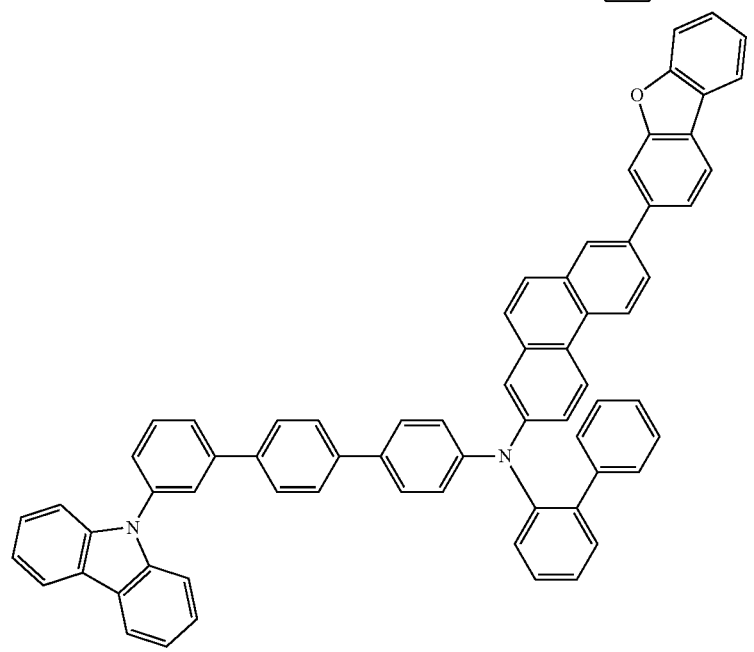

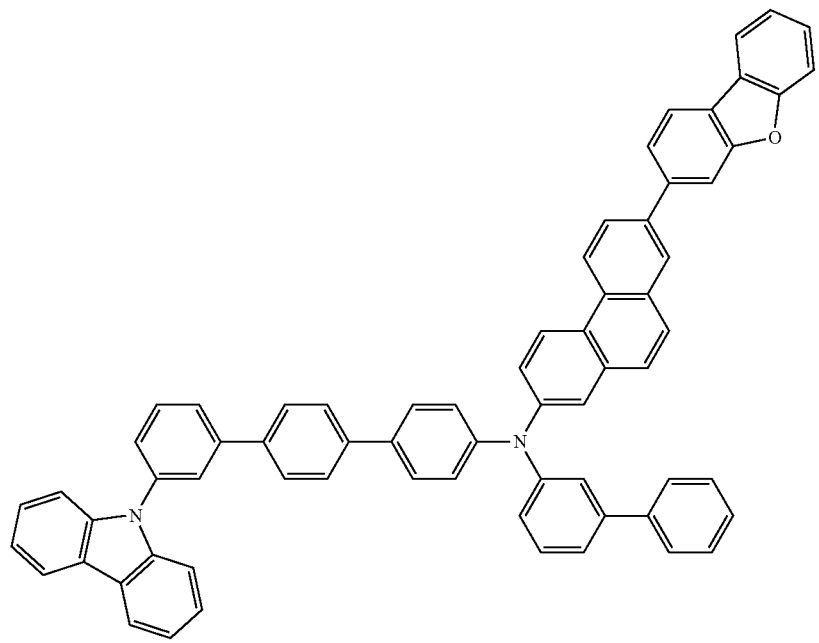
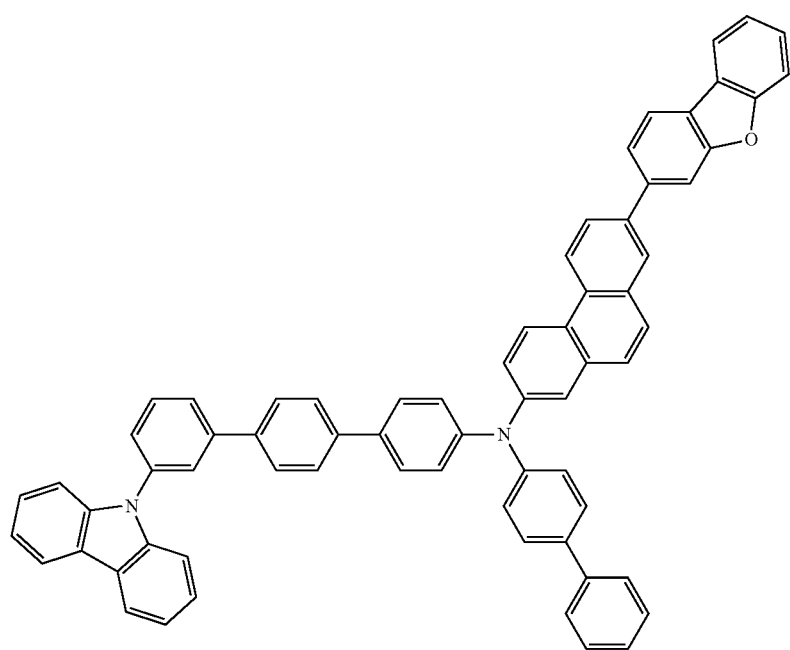

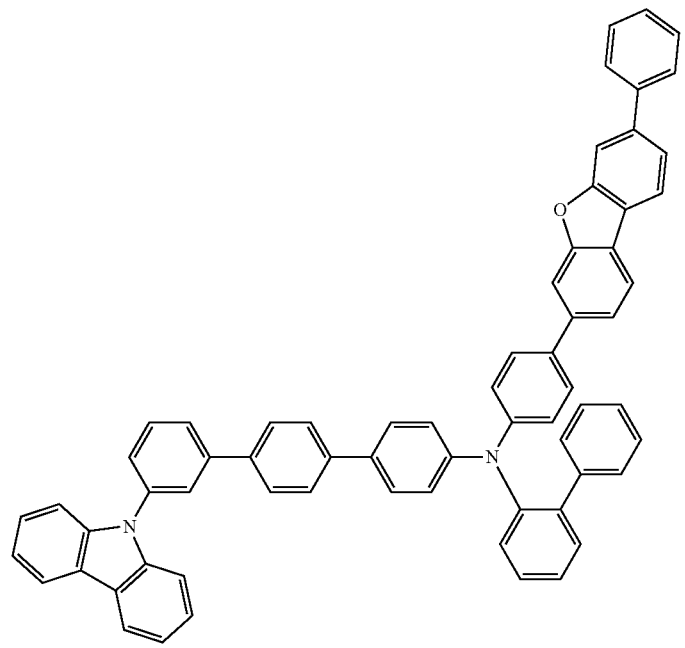
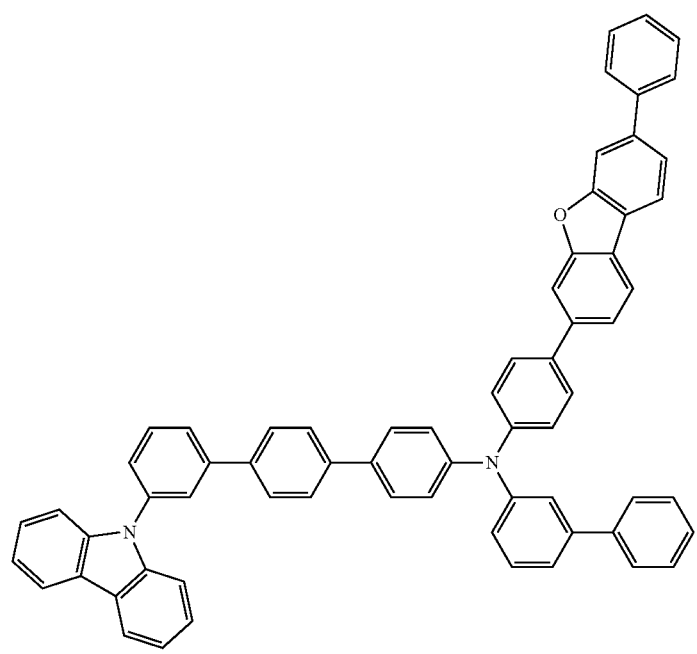

-continued
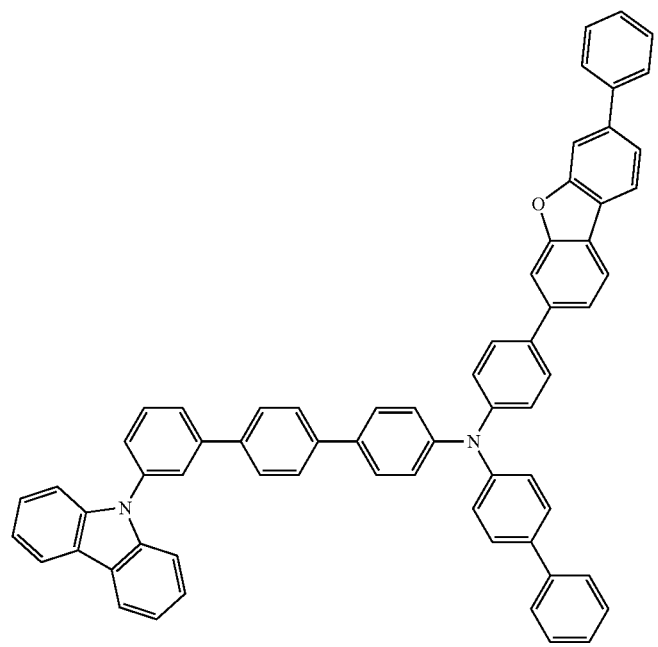
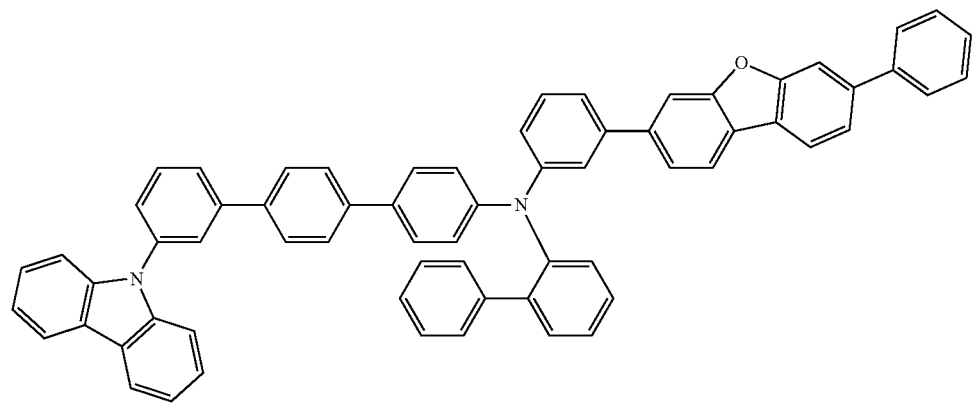
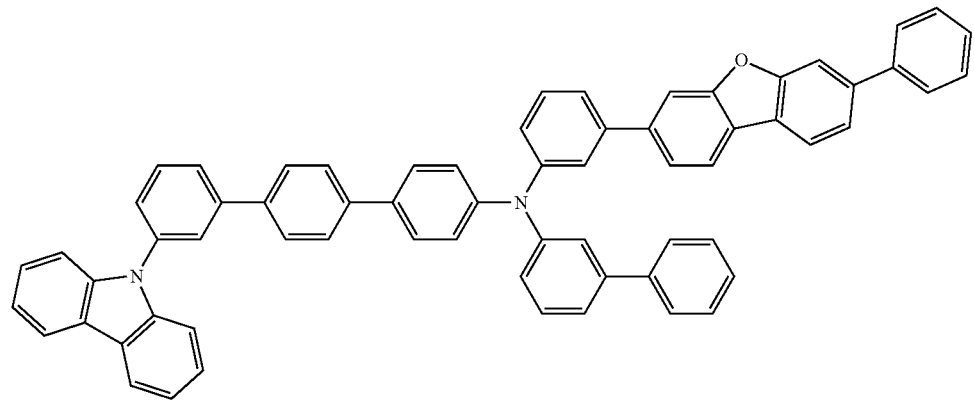

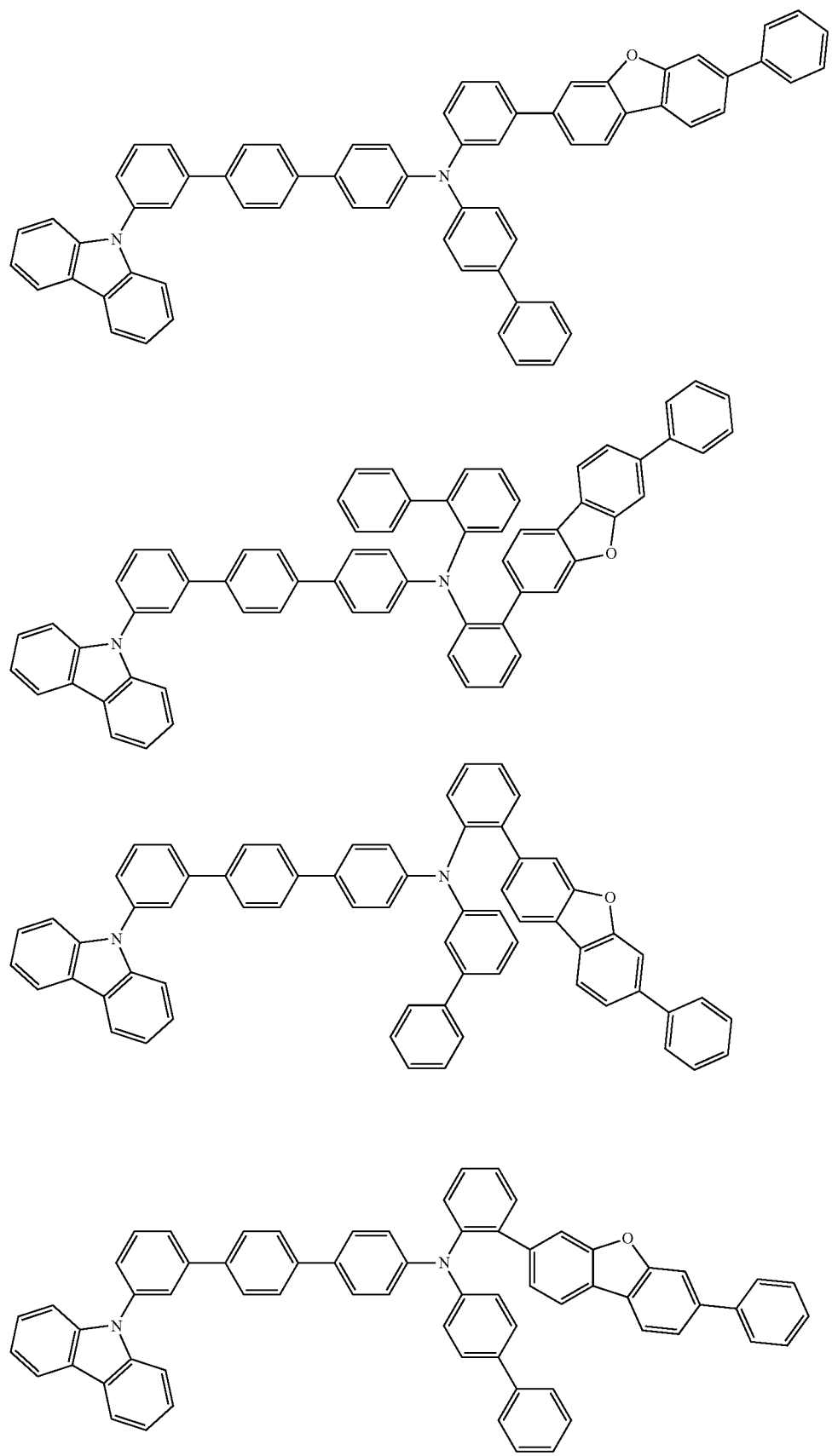

-continued
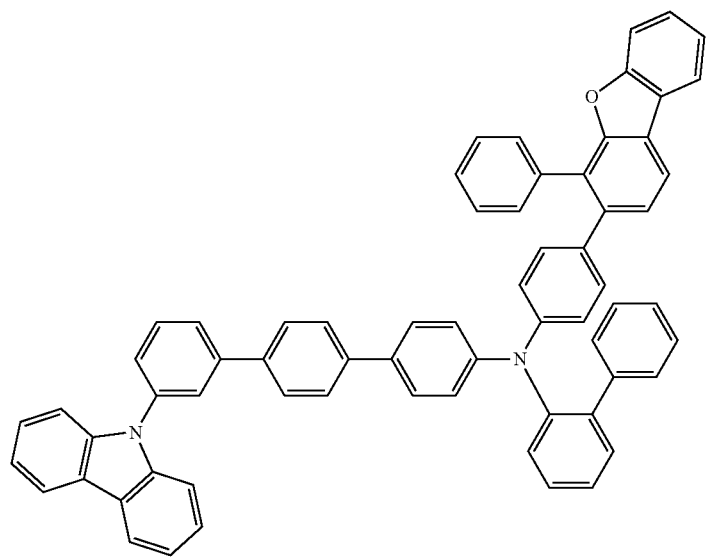
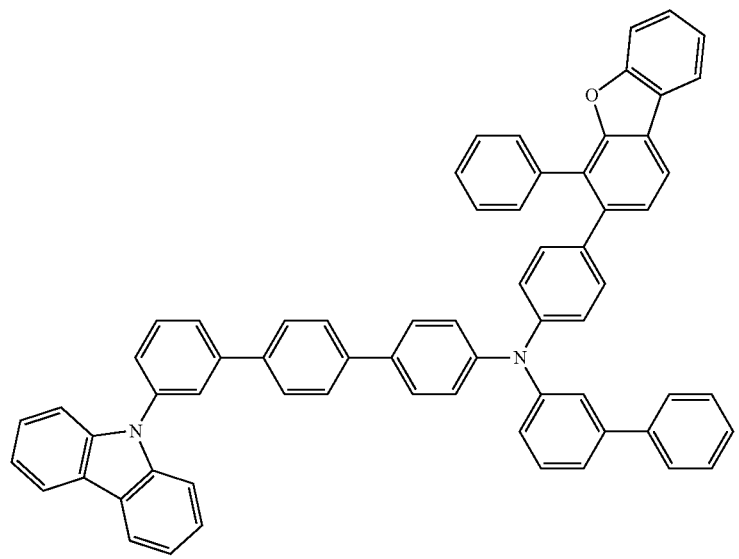
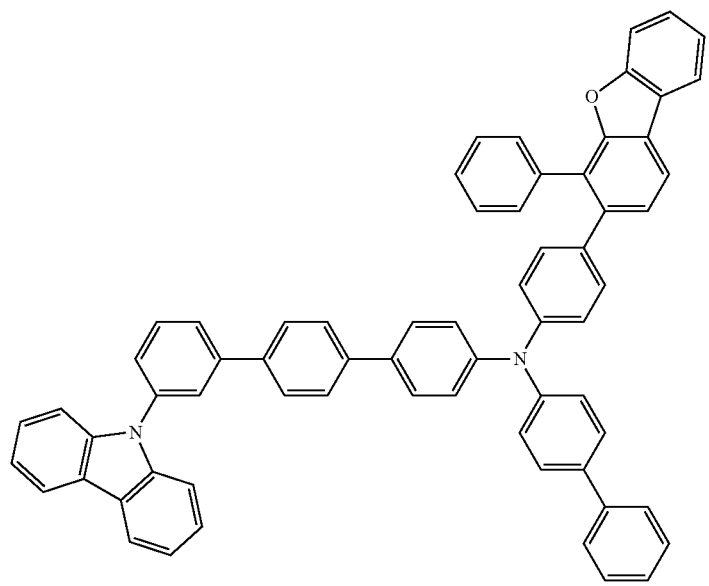

-continued
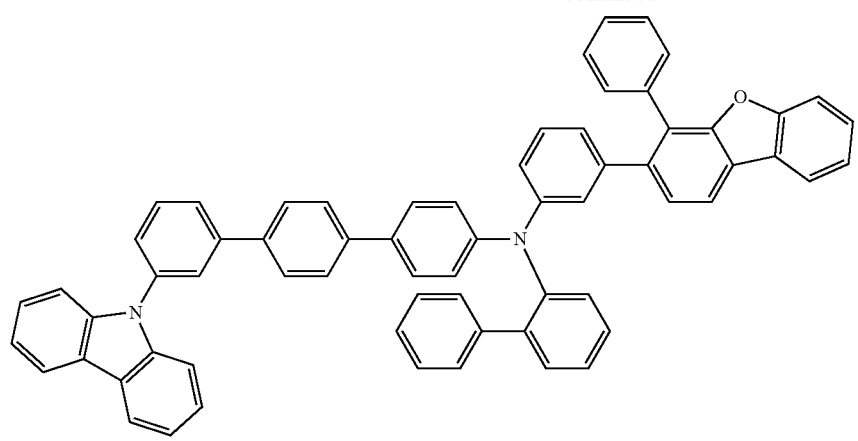
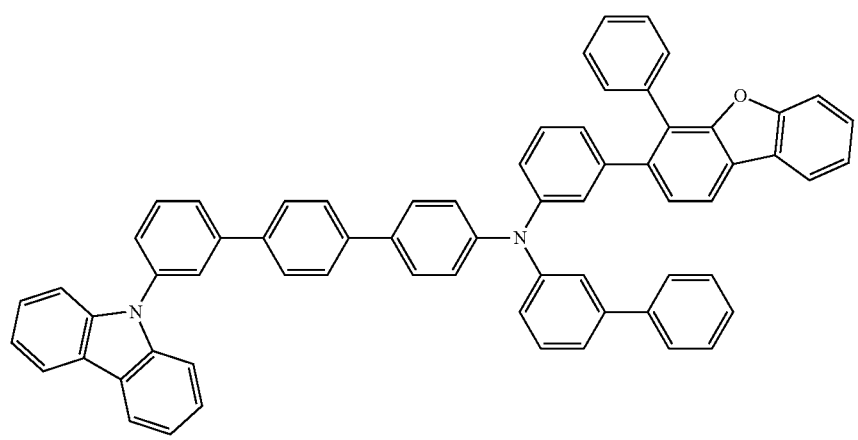
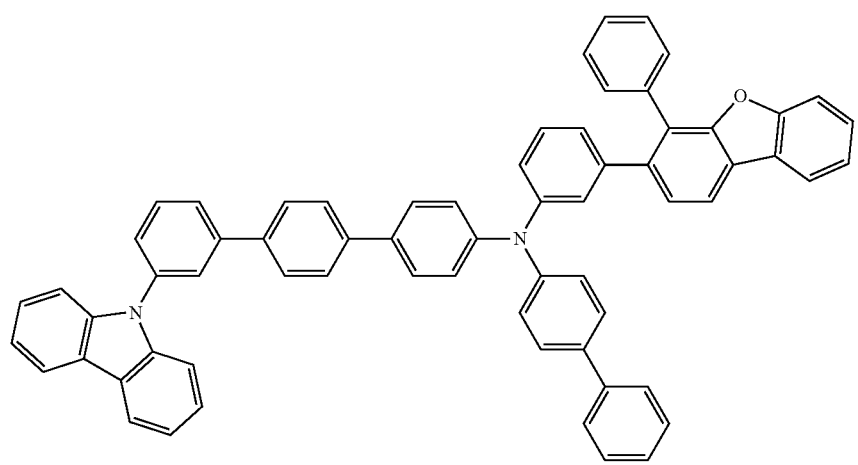

-continued
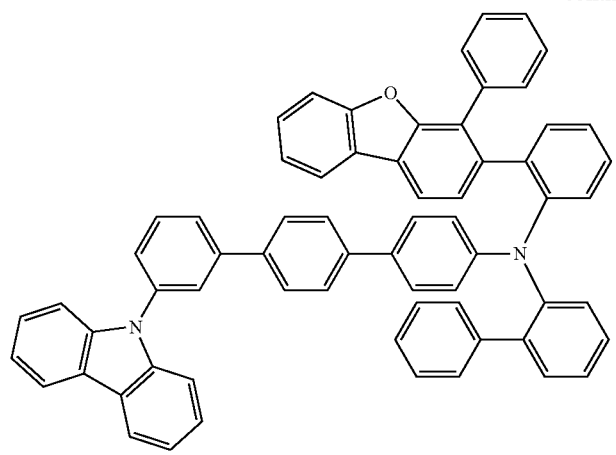
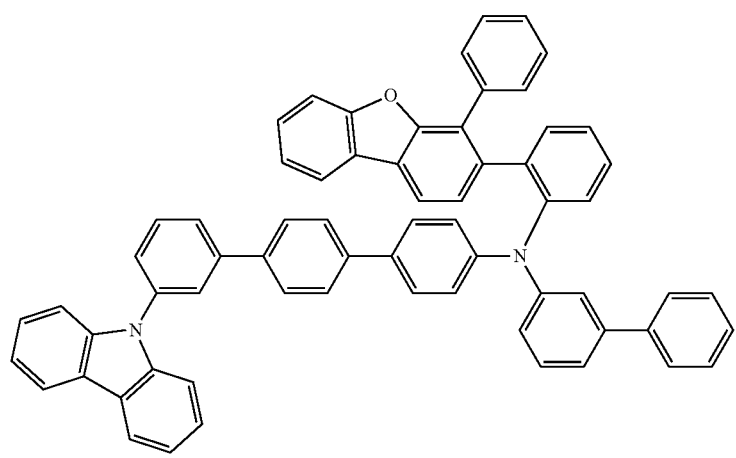
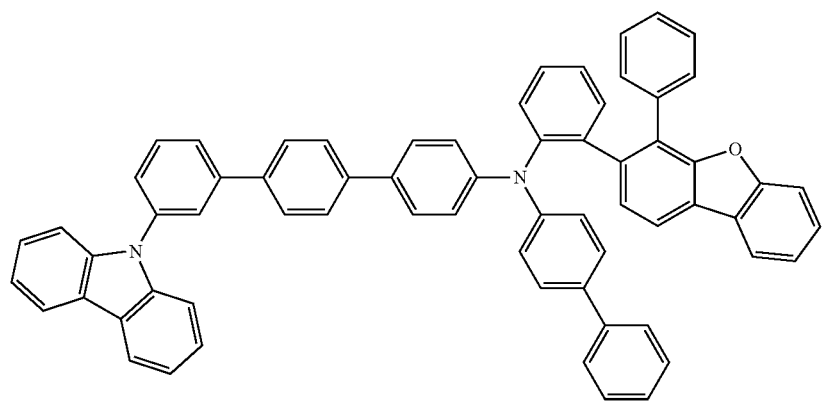

-continued
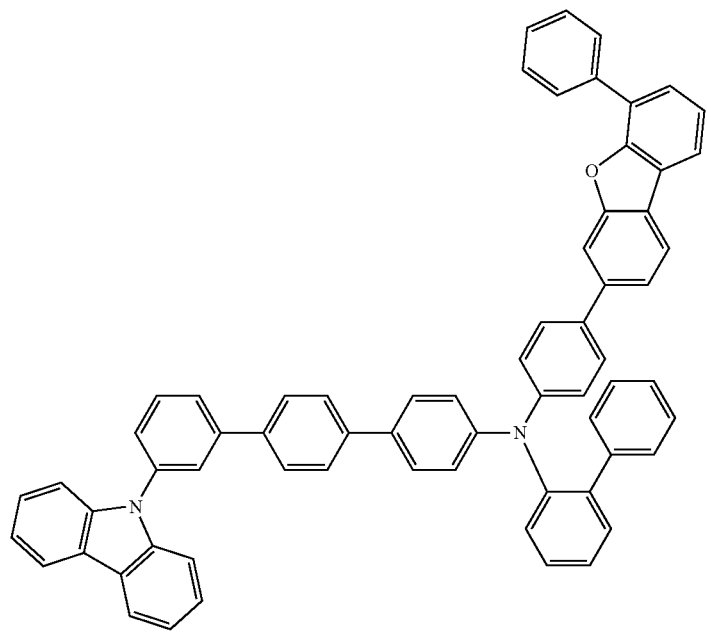
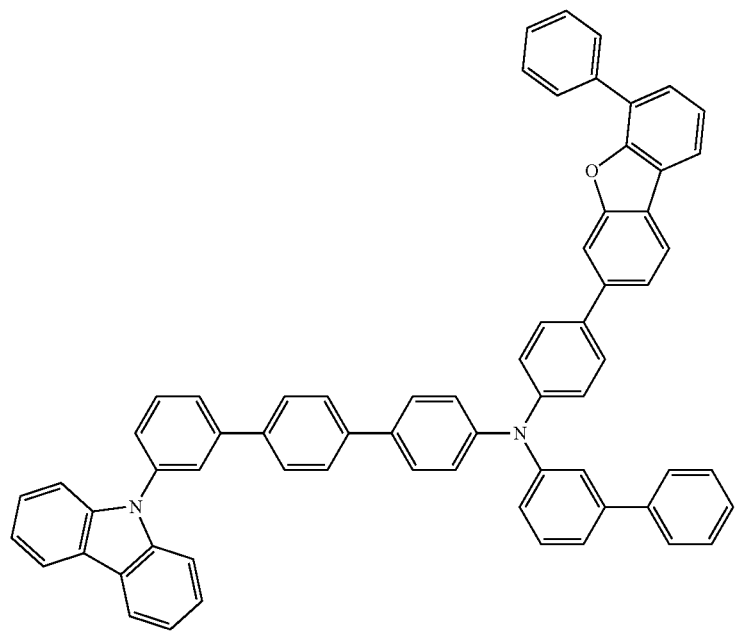

-continued
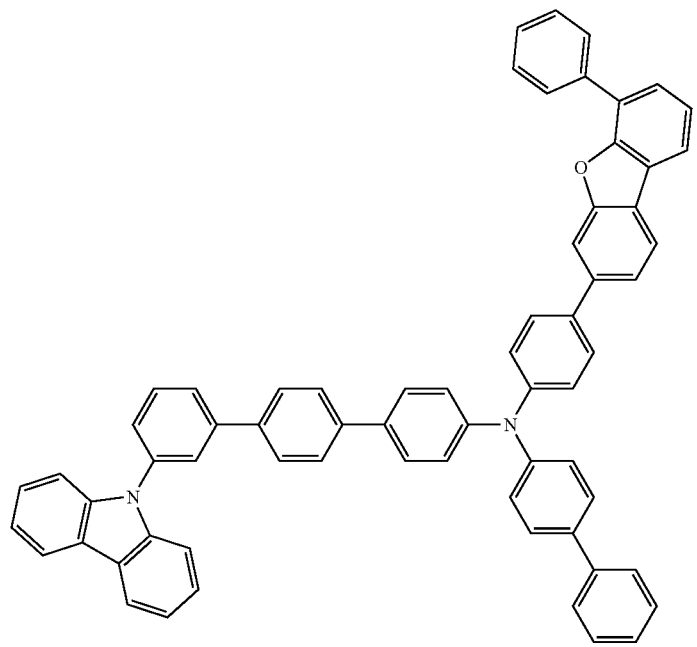
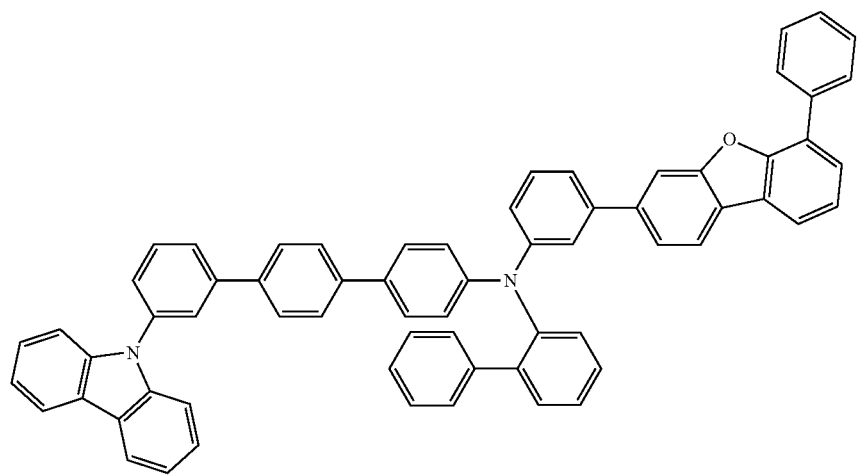
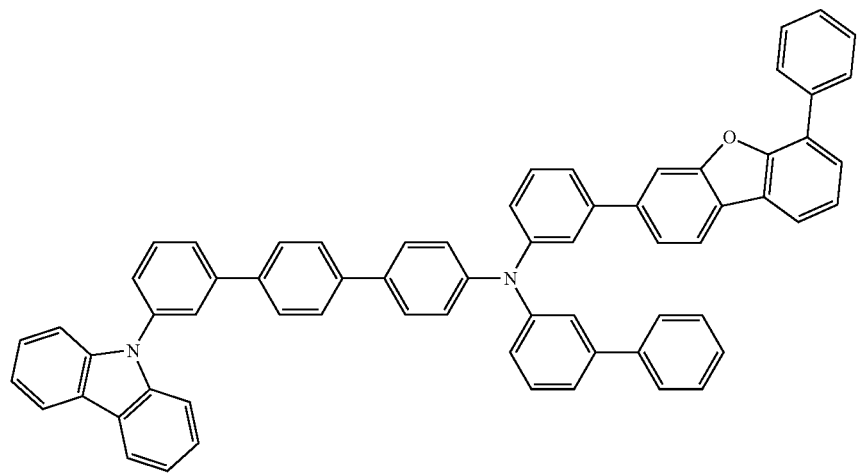

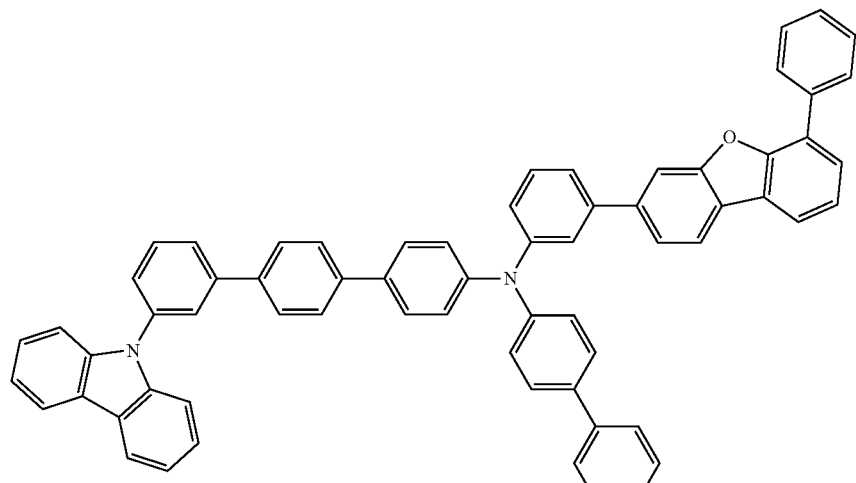
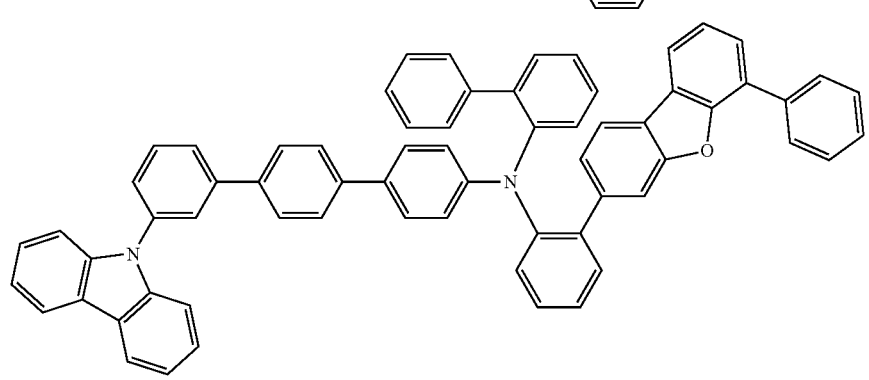
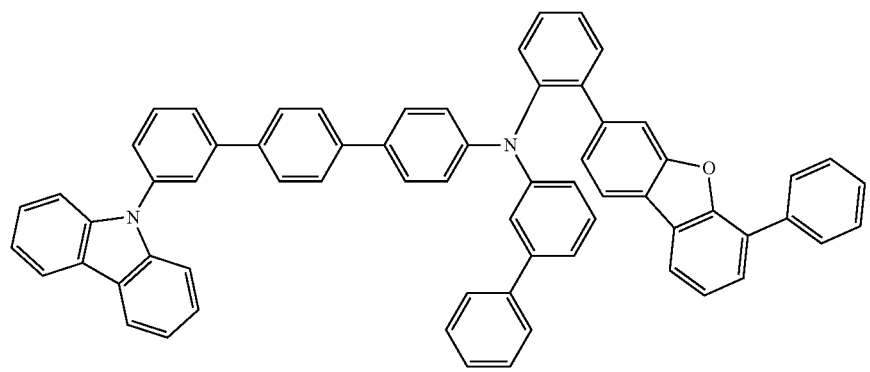
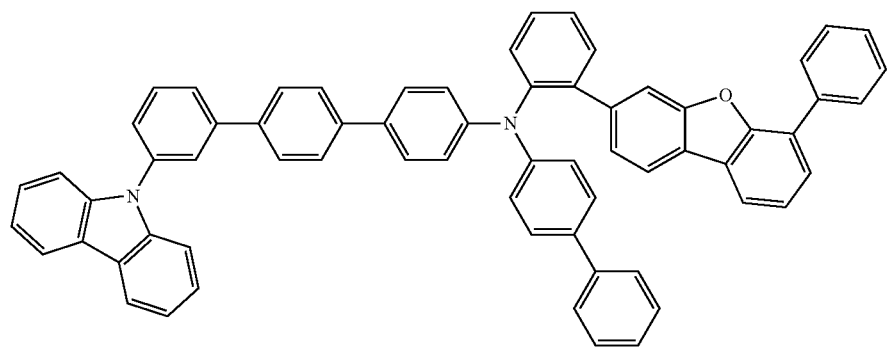

-continued
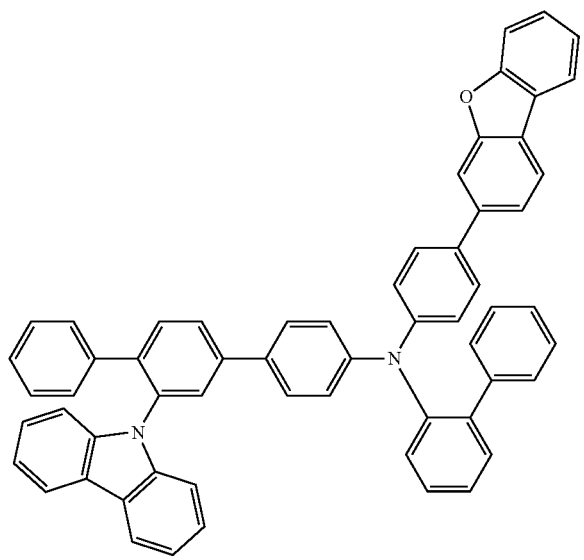
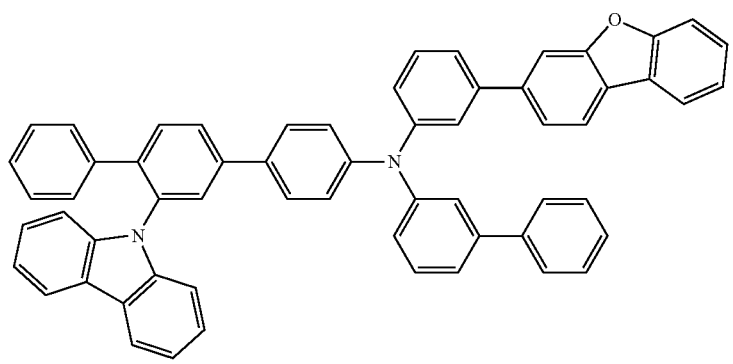
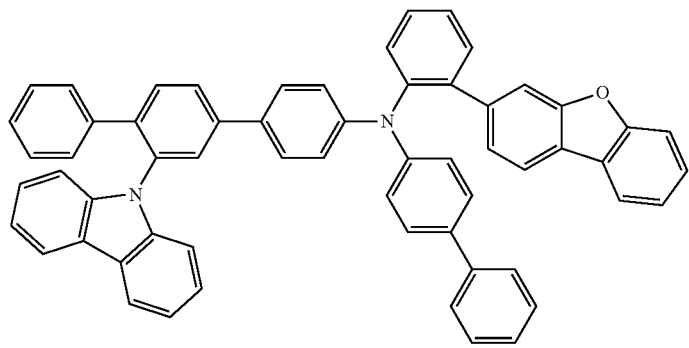

511 512
-continued
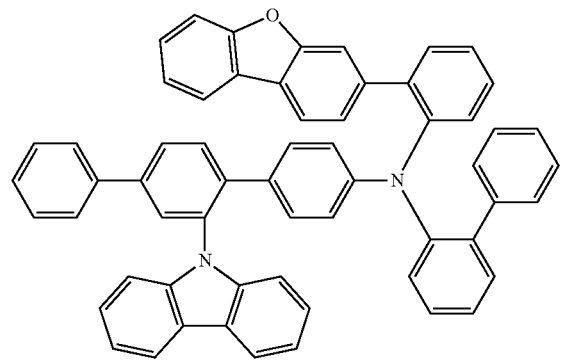
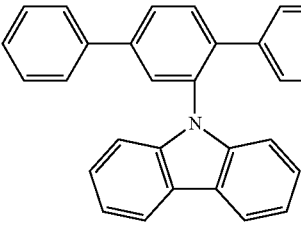
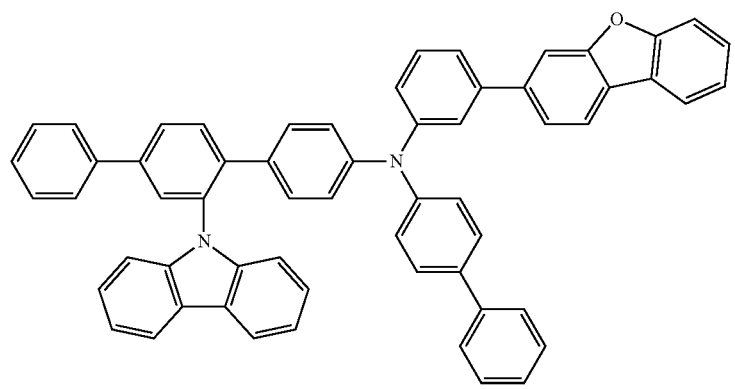
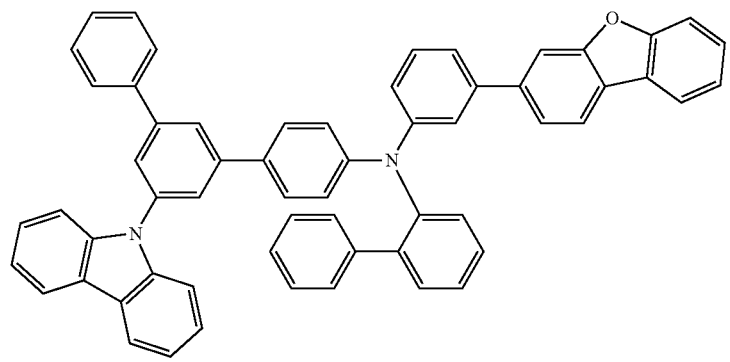
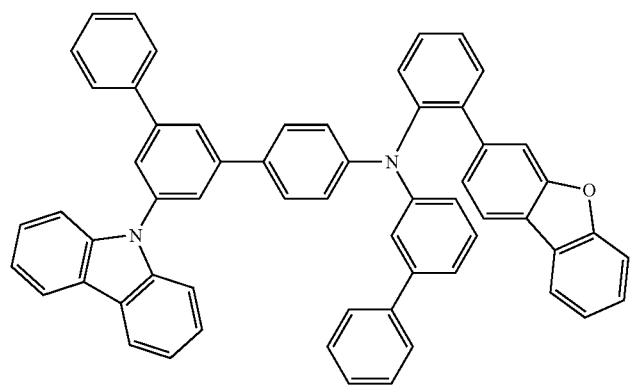

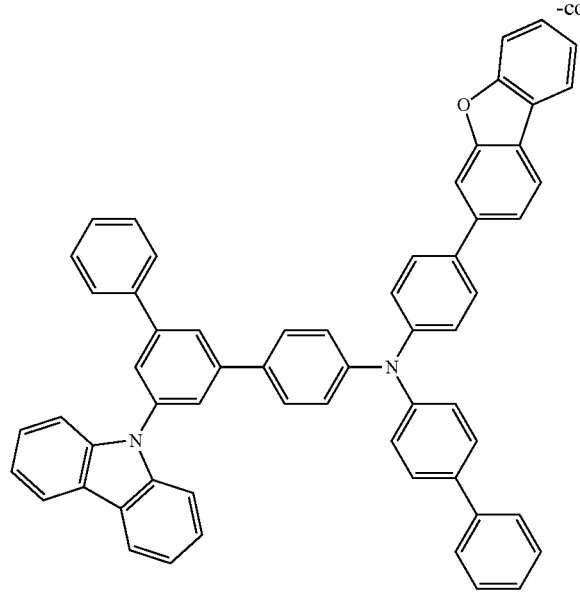

As described above, in the compound (1) of the invention, a 3-dibenzofuranyl group or its related group is directly or indirectly bonded to the central nitrogen atom, and, a N-carbazolyl group or its related group is bonded to the central nitrogen atom via a specific linker represented by formula (L3-1) or (L3-2). The long lifetime of the organic EL devices are largely attributable to this structure.

The above structure is considered to make the ionization potential deep. Therefore, when used as a hole transporting material, the supply of holes into a light emitting layer is enhanced to reduce the load to a hole transporting layer during the operation of an organic EL device and improve the durability of the compound against excitons is improved, this increasing the durability to the load.

The production method of the compound (1) is not particularly limited. One of ordinary skill in the art can easily produce the compound (1) by the method described in the examples mentioned below or by a method modifying the method described in the following examples with reference to known synthesis methods.

Material for Organic Electroluminescence Devices

The material for organic electroluminescence devices comprises the compound (1) (inclusive of the preferred embodiment thereof mentioned above, the same applies below). The content of the compound (1) in the material for organic electroluminescence devices is, but not particularly limited, 1% by mass or more (inclusive of 100% by mass), preferably 10% by mass or more (inclusive of 100% by mass), more preferably 50% by mass or more (inclusive of 100% by mass), still more preferably 80% by mass or more (inclusive of 100% by mass), and particularly preferably 90% by mass or more (inclusive of 100% by mass). The material for organic electroluminescence devices may consist of the compound (1) only. The material for organic electroluminescence device is useful for the production of an organic EL device.

Organic Electroluminescence Device

The organic EL device of the invention will be described below.

The organic EL device comprises an organic layer between a cathode and an anode. The organic layer comprises a light emitting layer and at least one layer of the organic layer comprises the compound (1).

Examples of the organic layer which comprises the compound (1) include a hole transporting region formed between an anode and a light emitting layer, such as a hole transporting layer, a hole injecting layer, an electron blocking layer, and an exciton blocking layer, a light emitting layer, a space layer, and an electron transporting region formed between a cathode and a light emitting layer, such as an electron transporting layer, an electron injecting layer, and a hole blocking layer, although not limited thereto. The compound (1) is used for the production of a fluorescent or phosphorescent EL device as a material for a hole transporting region or a light emitting layer, preferably as a material for a hole transporting region, and more preferably as a material for a hole transporting layer.

The organic EL device of the invention may be any of a fluorescent or phosphorescent single color emitting device, a white-emitting device of fluorescent-phosphorescent hybrid type, a simple-type emitting device having a single emission unit, and a tandem emitting device having two or more emission units, with a fluorescent device being preferred. The "emission unit" referred to herein is the smallest unit for emitting light by the recombination of injected holes and injected electrons, which comprises an organic layer, wherein at least one layer is a light emitting layer.

Representative device structures of the simple-type organic EL device are shown below:

(1) Anode/Emission Unit/Cathode

The emission unit may be a laminated structure comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the simple-type emission unit are shown below, wherein the layers in parentheses are optional:

(a) (Hole injecting layer/)Hole transporting layer/Fluorescent emitting layer (/Electron transporting layer);
(b) (Hole injecting layer/)Hole transporting layer/Phosphorescent emitting layer (/Electron transporting layer);

(c) (Hole injecting layer/)Hole transporting layer/First fluorescent emitting layer/Second fluorescent emitting layer (/Electron transporting layer);
(d) (Hole injecting layer/)Hole transporting layer/First phosphorescent emitting layer/Second phosphorescent emitting layer (/Electron transporting layer);
(e) (Hole injecting layer/)Hole transporting layer/Phosphorescent emitting layer/Space layer/Fluorescent emitting layer (/Electron transporting layer);
(f) (Hole injecting layer/)Hole transporting layer/First phosphorescent emitting layer/Second phosphorescent emitting layer/Space layer/Fluorescent emitting layer (/Electron transporting layer);
(g) (Hole injecting layer/)Hole transporting layer/First phosphorescent emitting layer/Space layer/Second phosphorescent emitting layer/Space layer/Fluorescent emitting layer (/Electron transporting layer);
(h) (Hole injecting layer/)Hole transporting layer/Phosphorescent emitting layer/Space layer/First fluorescent emitting layer/Second fluorescent emitting layer (/Electron transporting layer);
(i) (Hole injecting layer/)Hole transporting layer/Electron blocking layer/Fluorescent emitting layer (/Electron transporting layer);
(j) (Hole injecting layer/)Hole transporting layer/Electron blocking layer/Phosphorescent emitting layer (/Electron transporting layer);
(k) (Hole injecting layer/)Hole transporting layer/Exciton blocking layer/Fluorescent emitting layer (/Electron transporting layer);
(l) (Hole injecting layer/)Hole transporting layer/Exciton blocking layer/Phosphorescent emitting layer (/Electron transporting layer);
(m) (Hole injecting layer/)First hole transporting layer/Second hole transporting layer/Fluorescent emitting layer (/Electron transporting layer);
(n) (Hole injecting layer/)First hole transporting layer/Second hole transporting layer/Phosphorescent emitting layer (/Electron transporting layer);
(o) (Hole injecting layer/)Hole transporting layer/Fluorescent emitting layer/Hole blocking layer (/Electron transporting layer);
(p) (Hole injecting layer/)Hole transporting layer/Phosphorescent emitting layer/Hole blocking layer (/Electron transporting layer);
(q) (Hole injecting layer/)Hole transporting layer/Fluorescent emitting layer/Triplet blocking layer (/Electron transporting layer); and
(r) (Hole injecting layer/)Hole transporting layer/Phosphorescent emitting layer/Triplet blocking layer (/Electron transporting layer).

The emission colors of the phosphorescent emitting layers or the fluorescent emitting layer may be different. For example, the emission unit (f) may be (Hole injecting layer/)Hole transporting layer/First phosphorescent emitting layer (red emission)/Second phosphorescent emitting layer (green emission)/Space layer/Fluorescent emitting layer (blue emission)/Electron transporting layer.

An electron blocking layer may be disposed between each light emitting layer and the hole transporting layer or between each light emitting layer and the space layer, if necessary. Also, a hole blocking layer may be disposed between each light emitting layer and the electron transporting layer, if necessary. With such an electron blocking layer or a hole blocking layer, electrons and holes are confined in the light emitting layer to increase the charge recombination in the light emitting layer, thereby improving the emission efficiency.

Representative device structure of the tandem-type organic EL device is shown below:
(2) Anode/First Emission Unit/Intermediate Layer/Second Emission Unit/Cathode.

The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer supplies electrons to the first emission unit and holes to the second emission unit and may be formed by known materials.

A schematic structure of an example of the organic EL device is shown in FIG. 1, wherein the organic EL device 1 comprises a substrate 2, an anode 3, a cathode 4, and an emission unit 10 disposed between the anode 3 and the cathode 4. The emission unit 10 comprises a light emitting layer 5. An anode-side organic layer 6 (for example, a hole injecting layer or a hole transporting layer) may be disposed between the light emitting layer 5 and the anode 3, and a cathode-side organic layer 7 (for example, an electron injecting layer or an electron transporting layer) may be disposed between the light emitting layer 5 and the cathode 4. An electron blocking layer (not shown) may be disposed on the anode 3 side of the light emitting layer 5, and a hole blocking layer (not shown) may be disposed on the cathode 4 side of the light emitting layer 5. With these blocking layers, electrons and holes are confined in the light emitting layer 5 to increase the exciton generation in the light emitting layer 5.

In the present invention, a host is referred to as a fluorescent host when combinedly used with a fluorescent dopant (fluorescent emitting material) and as a phosphorescent host when combinedly used with a phosphorescent dopant (phosphorescent emitting material). Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not mean a material that cannot be used as a material for a fluorescent emitting layer. The same applies to the fluorescent host.

Substrate

The substrate is a support for the emitting device and made of, for example, glass, quartz, and plastics. The substrate may be a flexible substrate, for example, a plastic substrate made of polycarbonate, polyarylate, polyether sulfone, polypropylene, polyester, polyvinyl fluoride, or polyvinyl chloride. An inorganic deposition film is also usable.

Anode

The anode is formed on the substrate preferably from a metal, an alloy, an electrically conductive compound, and a mixture thereof, each having a large work function, for example, 4.0 eV or more. Examples of the material for the anode include indium oxide-tin oxide (ITO: indium tin oxide), indium oxide-tin oxide doped with silicon or silicon oxide, indium oxide-zinc oxide, indium oxide doped with tungsten oxide and zinc oxide, and graphene. In addition, gold (Au), platinum (Pt), nickel (Ni), tungsten (W), chromium (Cr), molybdenum (Mo), iron (Fe), cobalt (Co), copper (Cu), palladium (Pd), titanium (Ti), and a nitride of the above metal (for example, titanium nitride) are also usable.

These anode materials are made into a film generally by a sputtering method. For example, a film of indium oxide-zinc oxide is formed by sputtering an indium oxide target doped with 1 to 10% by mass of zinc oxide, and a film of indium oxide doped with tungsten oxide and zinc oxide is formed by sputtering an indium oxide target doped with 0.5 to 5% by mass of tungsten oxide and 0.1 to 1% by mass of zinc oxide. In addition, a vacuum vapor deposition method, a coating method, an inkjet method, and a spin coating method are usable.

A hole injecting layer to be optionally formed in contact with the anode is formed from a material which is capable of easily injecting holes independently of the work function of the anode. Therefore, the anode can be formed by a material generally known as an electrode material, for example, a metal, an alloy, an electroconductive compound, a mixture thereof, and a group 1 element and a group 2 element of the periodic table.

A material having a small work function belonging to a group 1 or a group 2 of the periodic table, for example, an alkali metal, such as lithium (Li) and cesium (Cs), an alkaline earth metal, such as magnesium (Mg), calcium (Ca), and strontium (Sr), and an alloy thereof, such as MgAg and AlLi, are also usable as an anode material. In addition, a rare earth metal, such as europium and ytterbium, and an alloy thereof are also usable. The alkali metal, the alkaline earth metal, and the alloy thereof is made into the anode by a vacuum vapor deposition or a sputtering method. When a silver paste is used, a coating method and an inkjet method are usable.

Hole Injecting Layer

The hole injecting layer comprises a material having a high hole injecting ability (hole injecting material). The compound (1) may be used in the hole injecting layer solely or in combination with the following material.

Examples of the hole injecting material other than the compound (1) include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

The following low molecular aromatic amine compound is also usable as the hole injecting layer material: 4,4',4"-tris(N,N-diphenylamino)triphenylamine (TDATA), 4,4',4"-tris[N-(3-methylphenyl)-N-phenylamino]triphenylamine (MTDATA), 4,4'-bis[N-(4-diphenylaminophenyl)-N-phenylamino]biphenyl (DPAB), 4,4'-bis(N-{4-[N'-(3-methylphenyl)-N'-phenylamino]phenyl}-N-phenylamino)biphenyl (DNTPD), 1,3,5-tris[N-(4-diphenylaminophenyl)-N-phenylamino]benzene (DPA3B), 3-[N-(9-phenylcarbazole-3-yl)-N-phenylamino]-9-phenylcarbazole (PCzPCA1), 3,6-bis[N-(9-phenylcarbazole-3-yl)-N-phenylamino]-9-phenylcarbazole (PCzPCA2), and 3-[N-(1-naphthyl)-N-(9-phenylcarbazole-3-yl)amino]-9-phenylcarbazole (PCzPCN1).

A macromolecular compound, such as an oligomer, a dendrimer, a polymer, is also usable as the hole injecting layer material. Examples thereof include poly(N-vinylcarbazole) (PVK), poly(4-vinyltriphenylamine) (PVTPA), poly[N-(4-{N'-[4-(4-diphenylamino)phenyl]phenyl-N'-phenylamino}phenyl)methacrylamide](PTPDMA), and poly[N,N'-bis(4-butylphenyl)-N,N'-bis(phenyl)benzidine] (Poly-TPD). An acid-added macromolecular compound, such as poly(3,4-ethylenedioxythiophene)/poly(styrene-sulfonic acid) (PEDOT/PSS) and polyaniline/poly(styrene-sulfonic acid) (PAni/PSS), is also usable.

In addition, an acceptor material, such as a hexaazatriphenylene (HAT) compound represented by formula (K), is preferably used in combination with the compound (1):

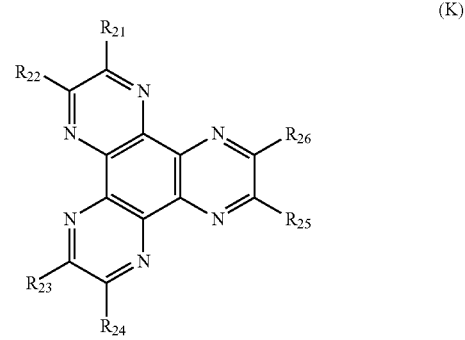

(K)

wherein:

$R_{21}$ to $R_{26}$ may be the same or different and each of $R_{21}$ to $R_{26}$ is independently a cyano group, —$CONH_2$, a carboxyl group, or —$COOR_{27}$ wherein $R_{27}$ is an alkyl group having 1 to 20 carbon atoms or a cycloalkyl group having 3 to 20 ring carbon atoms, or adjacent two selected from $R_{21}$ and $R_{22}$, $R_{23}$ and $R_{24}$, and $R_{25}$ and $R_{26}$ may be bonded to each other to form a group represented by —CO—O—CO—.

Examples of $R_{27}$ include a methyl group, an ethyl group, a n-propyl group, an isopropyl group, a n-butyl group, an isobutyl group, a t-butyl group, a cyclopentyl group, and a cyclohexyl group.

Hole Transporting Layer

The hole transporting layer comprises a material having a high hole transporting ability (hole transporting material). The compound (1) is preferably used in the hole transporting layer alone or in combination with the compound mentioned below.

When used in the hole transporting layer (electron blocking layer) adjacent to the light emitting layer, the compound of the invention reduces the energy barrier for injecting holes into the light emitting layer and has a high durability against excitons. If the energy barrier for injecting holes into the light emitting layer is reduced, the accumulation of positive charges in the hole transporting layer/light emitting layer interface is prevented to reduce the load to the device. Since the compound of the invention has a high durability against excitons, the deterioration of the organic EL device is considered to be also reduced, thereby prolonging the lifetime of the organic EL device.

Examples of the hole transporting material other than the compound (1) includes an aromatic amine compound, a carbazole derivative, and an anthracene derivative.

Examples of the aromatic amine compound include 4,4'-bis[N-(1-naphthyl)-N-phenylamino]biphenyl (NPB), N,N'-bis(3-methylphenyl)-N,N'-diphenyl-[1,1'-biphenyl]-4,4'-diamine (TPD), 4-phenyl-4'-(9-phenylfluorene-9-yl) triphenylamine (BAFLP), 4,4'-bis[N-(9,9-dimethylfluorene-2-yl)-N-phenylamino]biphenyl (DFLDPBi), 4,4',4"-tris(N,N-diphenylamino)triphenylamine (TDATA), 4,4',4"-tris[N-(3-methylphenyl)-N-phenylamino]triphenylamine (MTDATA), and 4,4'-bis[N-(spiro-9,9'-bifluorene-2-yl)-N-phenylamino]biphenyl (BSPB). The above compounds have a hole mobility of $10^{-6}$ $cm^2/Vs$ or more.

Also usable in the hole transporting layer is a carbazole derivative, such as 4,4'-di(9-carbazolyl)biphenyl (CBP), 9-[4-(9-carbazolyl)phenyl]-10-phenylanthracene (CzPA), and 9-phenyl-3-[(4-(10-phenyl-9-anthryl)phenyl]-9H-carbazole (PCzPA), and an anthracene derivative, such as 2-t-butyl-9,10-di(2-naphthyl)anthracene (t-BuDNA), 9,10-di(2-naphthyl)anthracene (DNA), and 9,10-diphenylanthracene (DPAnth). In addition, a macromolecular compound, such as poly(N-vinylcarbazole) (PVK) and poly(4-vinyltriphenylamine) (PVTPA) are usable.

Compounds other than those mentioned above are also usable, if their hole transporting ability is higher than their electron transporting ability.

The hole transporting layer may be a single layer or a laminate of two or more layers. For example, the hole transporting layer may be a two-layered structure comprising a first hole transporting layer (anode side) and a second hole transporting layer (cathode side). In such a two-layered structure, the compound (1) may be used in one of the first hole transporting layer and the second hole transporting layer, or used in both layers, wherein the compound (1) used in the first hole transporting layer is different from the compound (1) used in the second hole transporting layer.

In an embodiment of the invention, the compound (1) is preferably used in the first hole transporting layer. In another embodiment, the compound (1) is preferably used in the second hole transporting layer. In still another embodiment, the compound (1) is preferably used in both the first hole transporting layer and the second hole transporting layer.

Dopant Material of Light Emitting Layer

The light emitting layer comprises a highly light-emitting material (dopant material) and may be formed from a various kind of materials. For example, a fluorescent emitting material and a phosphorescent emitting material are usable as the dopant material. The fluorescent emitting material is a compound capable of emitting light from a singlet excited state, and the phosphorescent emitting material is a compound capable of emitting light from a triplet excited state.

Examples of blue fluorescent emitting material usable in the light emitting layer include a pyrene derivative, a styrylamine derivative, a chrysene derivative, a fluoranthene derivative, a fluorene derivative, a diamine derivative, and a triarylamine derivative, such as N,N'-bis[4-(9H-carbazole-9-yl)phenyl]-N,N'-diphenylstilbene-4,4'-diamine (YGA2S), 4-(9H-carbazole-9-yl)-4'-(10-phenyl-9-anthryl)triphenylamine (YGAPA), and 4-(10-phenyl-9-anthryl)-4'-(9-phenyl-9H-carbazole-3-yl)triphenylamine (PCBAPA).

Examples of green fluorescent emitting material usable in the light emitting layer include an aromatic amine derivative, such as N-(9,10-diphenyl-2-anthryl)-N,9-diphenyl-9H-carbazole-3-amine (2PCAPA), N-[9,10-bis(1,1'-biphenyl-2-yl)-2-anthryl]-N,9-diphenyl-9H-carbazole-3-amine (2PCABPhA), N-(9,10-diphenyl-2-anthryl)-N,N',N'-triphenyl-1,4-phenylenediamine (2DPAPA), N-[9,10-bis(1,1'-biphenyl-2-yl)-2-anthryl]-N,N',N'-triphenyl-1,4-phenylenediamine (2DPABPhA), N-[9,10-bis(1,1'-biphenyl-2-yl)]-N-[4-(9H-carbazole-9-yl)phenyl]-N-phenylanthracene-2-amine (2YGABPhA), and N,N,9-triphenylanthracene-9-amine (DPhAPhA).

Examples of red fluorescent emitting material usable in the light emitting layer include a tetracene derivative and a diamine derivative, such as N,N,N',N'-tetrakis(4-methylphenyl)tetracene-5,11-diamine (p-mPhTD) and 7,14-diphenyl-N,N,N',N'-tetrakis(4-methylphenyl)acenaphtho[1,2-a]fluoranthene-3,10-diamine (p-mPhAFD).

Examples of blue phosphorescent emitting material usable in the light emitting layer include a metal complex, such as an iridium complex, an osmium complex, and a platinum complex. Examples thereof include bis[2-(4',6'-difluorophenyl)pyridinato-N,C2']iridium(III) tetrakis(1-pyrazolyl)borato (FIr$_6$), bis[2-(4',6'-difluorophenyl)pyridinato-N,C2']iridium(III) picolinato (FIrpic), bis[2-(3',5'-bistrifluoromethylphenyl)pyridinato-N, C2']iridium(III) picolinato (Ir(CF$_3$ppy)$_2$(pic)), and bis[2-(4',6'-difluorophenyl)pyridinato-N,C2']iridium(III) acetylacetonato (FIracac).

Examples of green phosphorescent emitting material usable in the light emitting layer include an iridium complex, such as tris(2-phenylpyridinato-N,C2')iridium(III) (Ir(ppy)$_3$), bis(2-phenylpyridinato-N,C2')iridium(III) acetylacetonato (Ir(ppy)$_2$(acac)), bis(1,2-diphenyl-1H-benzimidazolato)iridium(III) acetylacetonato (Ir(pbi)$_2$(acac)), and bis(benzo[h]quinolinato)iridium(III) acetylacetonato (Ir(bzq)$_2$(acac)).

Examples of red phosphorescent emitting material usable in the light emitting layer include a metal complex, such as an iridium complex, a platinum complex, a terbium complex, and a europium complex. Examples thereof include an organometallic complex, such as bis[2-(2'-benzo[4,5-a]thienyl)pyridinato-N,C3']iridium(III) acetylacetonato (Ir(btp)$_2$(acac)), bis(1-phenylisoquinolinato-N,C2')iridium(III) acetylacetonato (Ir(piq)$_2$(acac)), (acetylacetonato)bis[2,3-bis(4-fluorophenyl)quinoxalinato]iridium(III) (Ir(Fdpq)$_2$(acac)), and 2,3,7,8,12,13,17,18-octaethyl-21H,23H-porphyrin platinum(II) (PtOEP).

A rare earth metal complex, such as tris(acetylacetonato)(monophenanthroline)terbium(III) (Tb(acac)$_3$(Phen)), tris(1,3-diphenyl-1,3-prop anedionato)(monophenanthroline)europium(III) (Eu(DBM)$_3$(Phen)), and tris[1-(2-thenoyl)-3,3,3-trifluoroacetonato] (monophenanthroline)europium(III) (Eu(TTA)$_3$(Phen)), emits light from the rare earth metal ion (electron transition between different multiple states), and therefore, usable as a phosphorescent emitting material.

Host Material for Light Emitting Layer

The light emitting layer may be a layer wherein the above dopant material is dispersed in another material (host material). The compound (1) may be used as a host material and other various materials may be used as a host material. The host material preferably has a lowest unoccupied molecular orbital level (LUMO level) higher than that of the dopant material and a highest occupied molecular orbital level (HOMO level) lower than that of the dopant material.

The host material other the compound (1) may include, for example, (1) a metal complex, such as an aluminum complex, a beryllium complex, and a zinc complex;

(2) a heterocyclic compound, such as an oxadiazole derivative, a benzimidazole derivative, and a phenanthroline derivative;

(3) a fused aromatic compound, such as a carbazole derivative, an anthracene derivative, a phenanthrene derivative, a pyrene derivative, and a chrysene derivative; and (4) an aromatic amine compound, such as a triarylamine derivative and a fused aromatic polycyclic amine derivative.

Examples thereof include:

a metal complex, such as tris(8-quinolinolato)aluminum (III) (Alq), tris(4-methyl-8-quinolinolato)aluminum(III) (Almq$_3$), bis(10-hydroxybenzo[h]quinolinato)beryllium(II) (BeBq$_2$), bis(2-methyl-8-quinolinolato) (4-phenylphenolato)aluminum(III) (BAlq), bis(8-quinolinolato)zinc(II) (Znq), bis[2-(2-benzoxazolyl)phenolato]zinc(II) (ZnPBO), and bis[2-(2-benzothiazolyl)phenolato]zinc(II) (ZnBTZ);

a heterocyclic compound, such as 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-biphenylyl)-4-phenyl-5-(4-tert-butylphenyl)-1,2,4-triazole (TAZ), 2,2',2"-(1,3,5-benzenetriyl)tris(1-phenyl-1H-benzimidazole) (TPBI), bathophenanthroline (BPhen), and bathocuproin (BCP);

a fused aromatic compound, such as 9-[4-(10-phenyl-9-anthryl)phenyl]-9H-carbazole (CzPA), 3,6-diphenyl-9-[4-(10-phenyl-9-anthryl)phenyl]-9H-carbazole (DPCzPA), 9,10-bis(3,5-diphenylphenyl)anthracene (DPPA), 9,10-di(2-naphthyl)anthracene (DNA), 2-tert-butyl-9,10-di(2-naphthyl)anthracene (t-BuDNA), 9,9'-bianthryl (BANT), 9,9'-(stilbene-3,3'-diyl)diphenanthrene (DPNS), 9,9'-(stilbene-4,4'-diyl)diphenanthrene (DPNS2), 3,3',3"-(benzene-1,3,5-triyl)tripyrene (TPB3), 9,10-diphenylanthracene (DPAnth), and 6,12-dimethoxy-5,11-diphenylchrysene; and an aromatic amine compound, such as N,N-diphenyl-9-[4-(10-phenyl-9-anthryl)phenyl]-9H-carbazole-3-amine (CzA1PA), 4-(10-phenyl-9-anthryl)triphenylamine (DPhPA), N,9-diphenyl-N-[4-(10-phenyl-9-anthryl)phenyl]-9H-carbazole-3-amine (PCAPA), N,9-diphenyl-N-{4-[4-(10-phenyl-9-anthryl)phenyl]phenyl}-9H-carbazole-3-amine (PCAPBA), N-(9,10-diphenyl-2-anthryl)-N,9-diphenyl-9H-carbazole-3-amine (2PCAPA), 4,4'-bis[N-(1-anthryl)-N-phenylamino]biphenyl (NPB or α-NPD), N,N'-bis(3-methylphenyl)-N,N'-diphenyl-[1,1'-biphenyl]-4,4'-diamine (TPD), 4,4'-bis[N-(9,9-dimethylfluorene-2-yl)-N-phenylamino]biphenyl (DFLDPBi), and 4,4'-bis[N-(spiro-9,9'-bifluorene-2-yl)-N-phenylamino]biphenyl (BSPB).

The host material may be used alone or in combination of two or more.

In particular, as a host material for a blue fluorescent device, the following anthracene compound is preferably used.

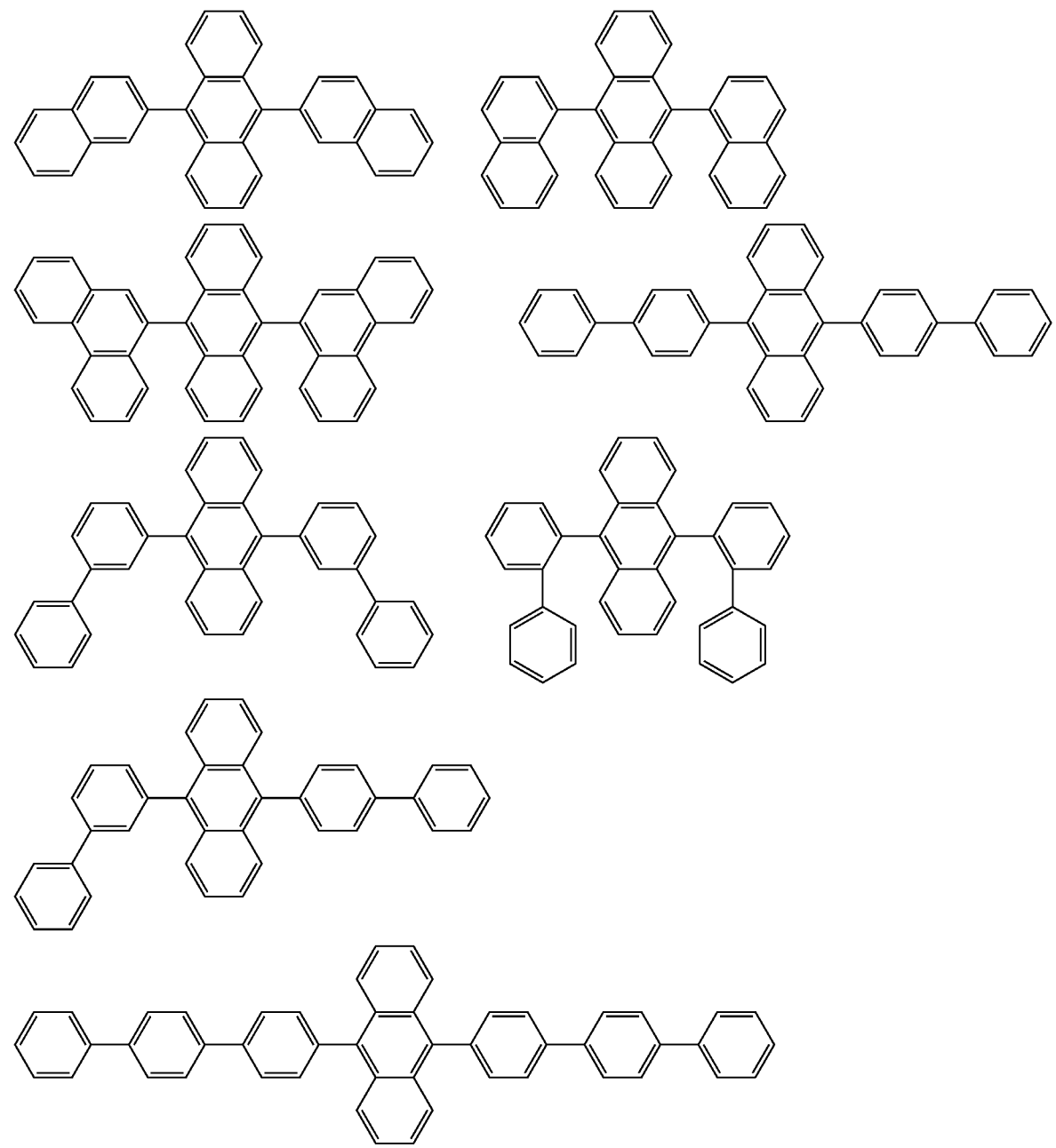

-continued
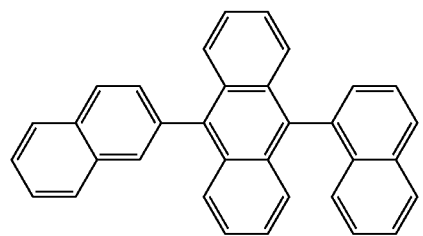
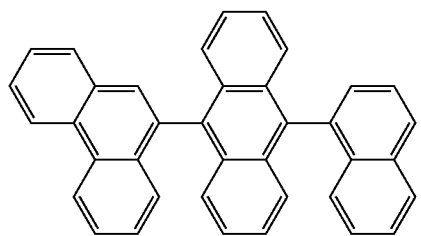
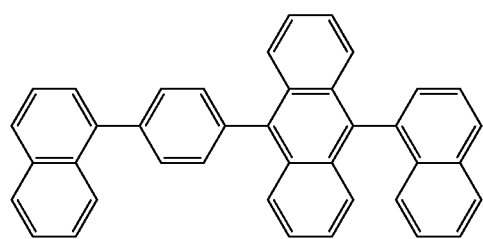
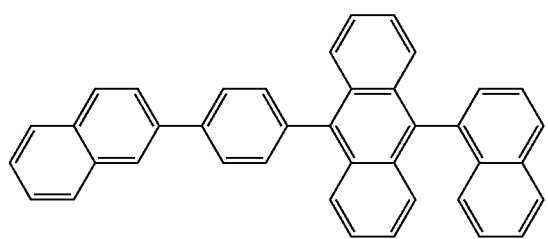
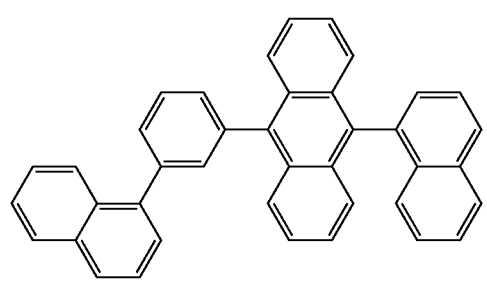
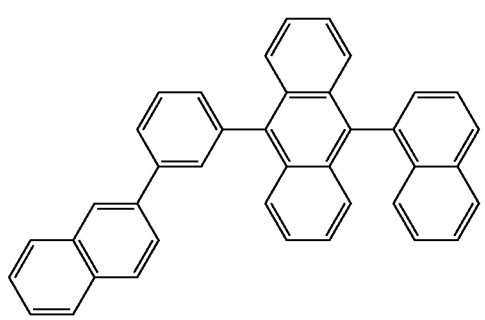
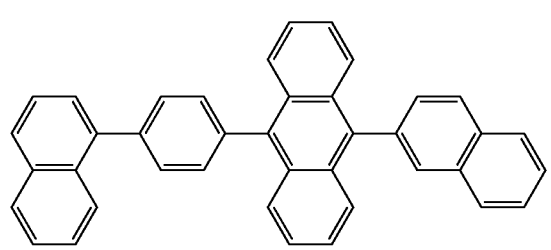
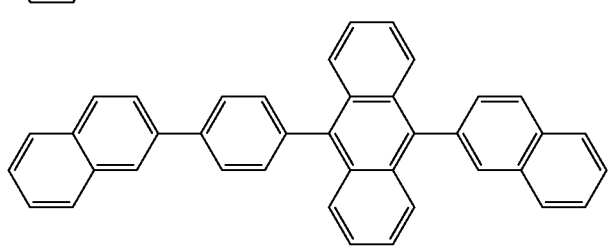
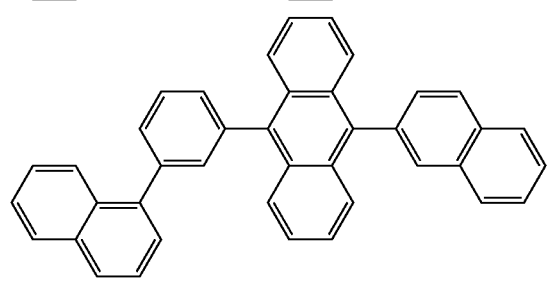
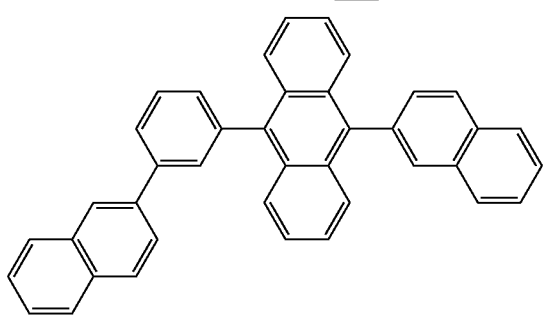
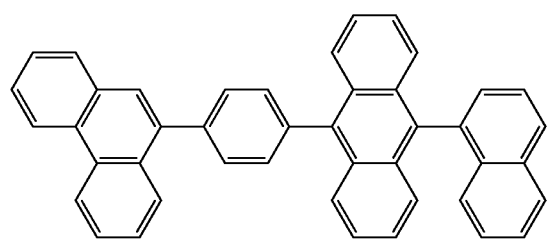
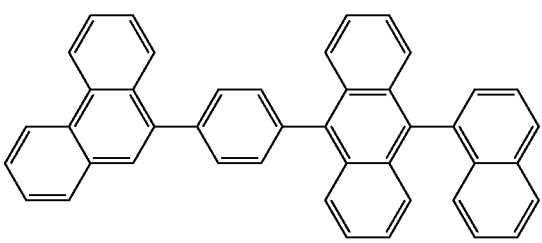

525 526
-continued
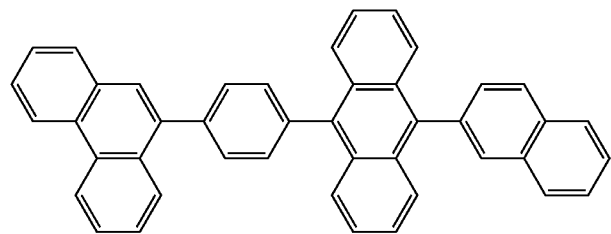
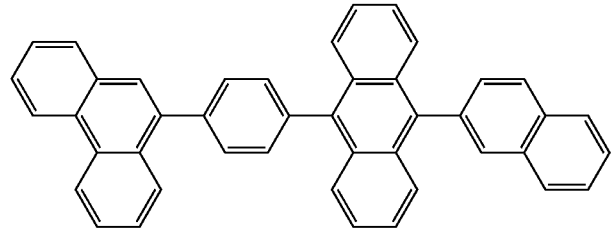
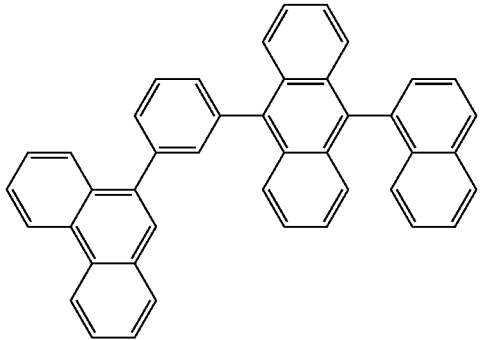
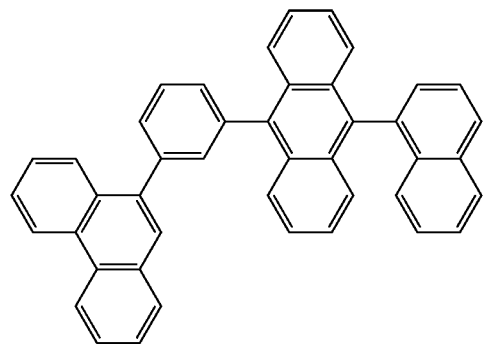
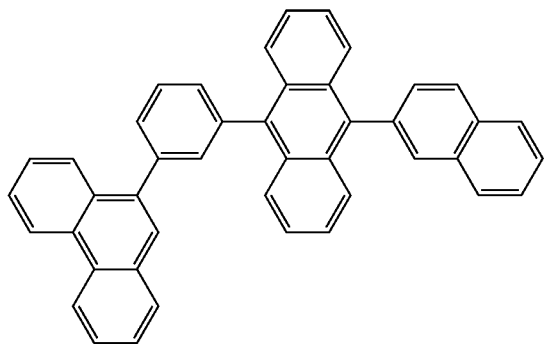
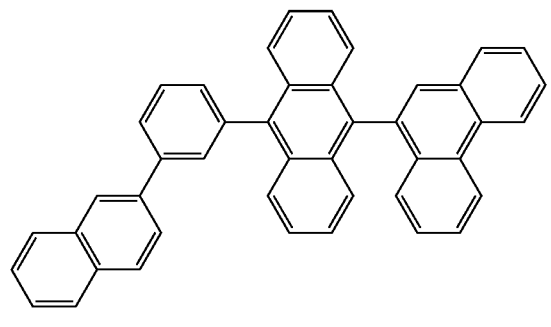
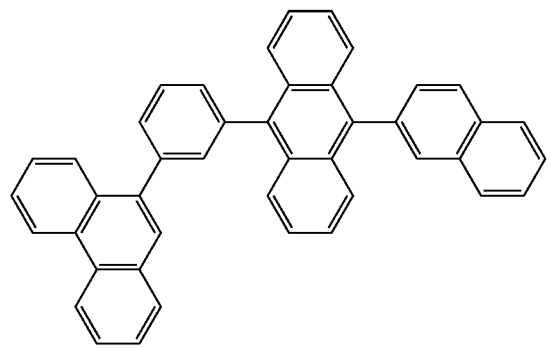
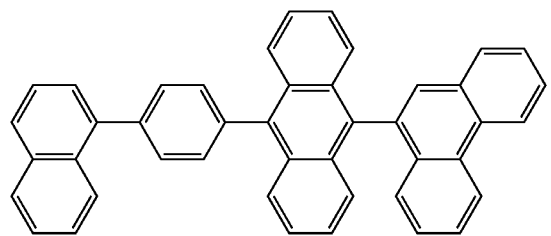
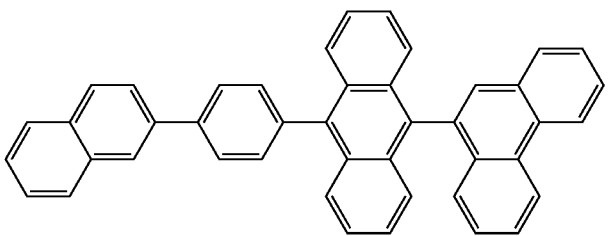

-continued
| 527 | 528 |
|---|---|
| 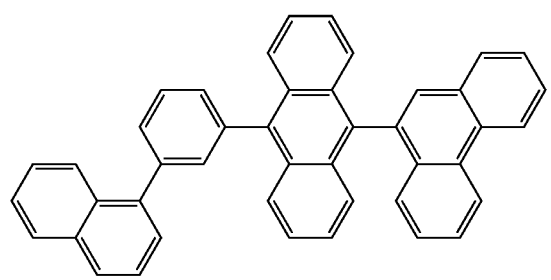 | 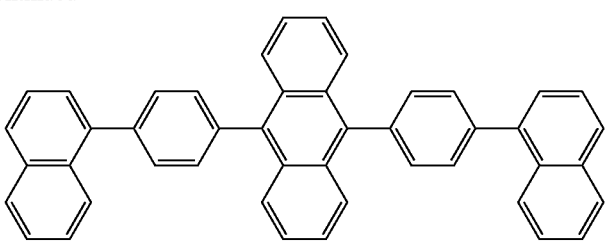 |
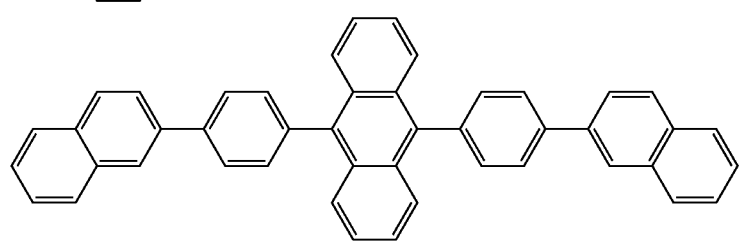
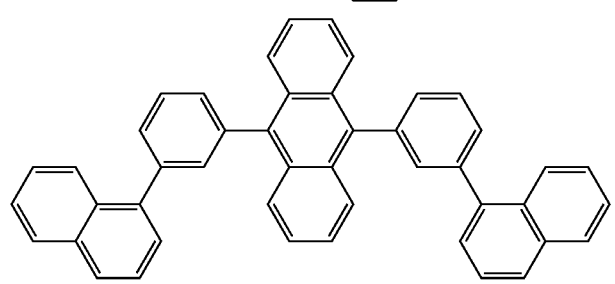
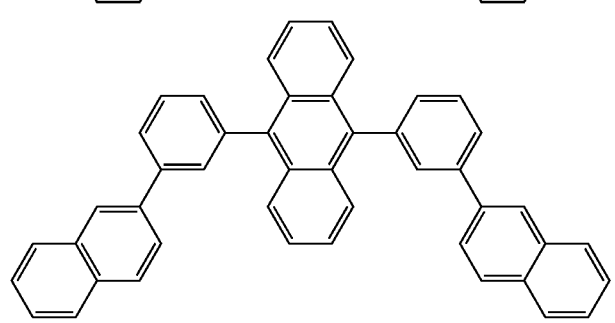
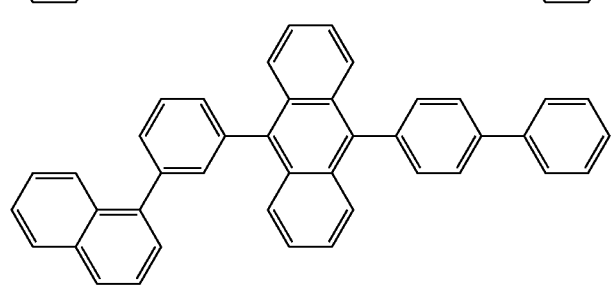
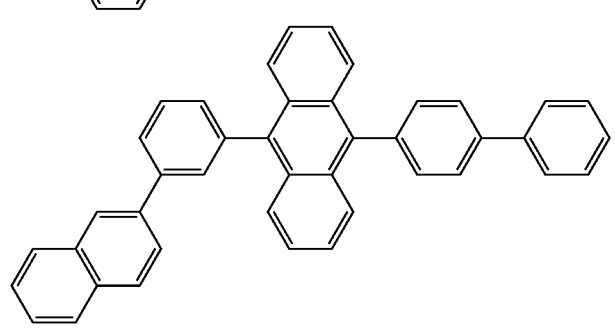
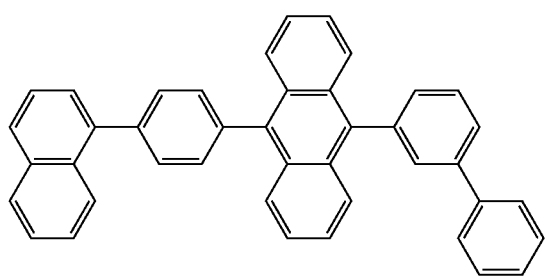

-continued
529          530
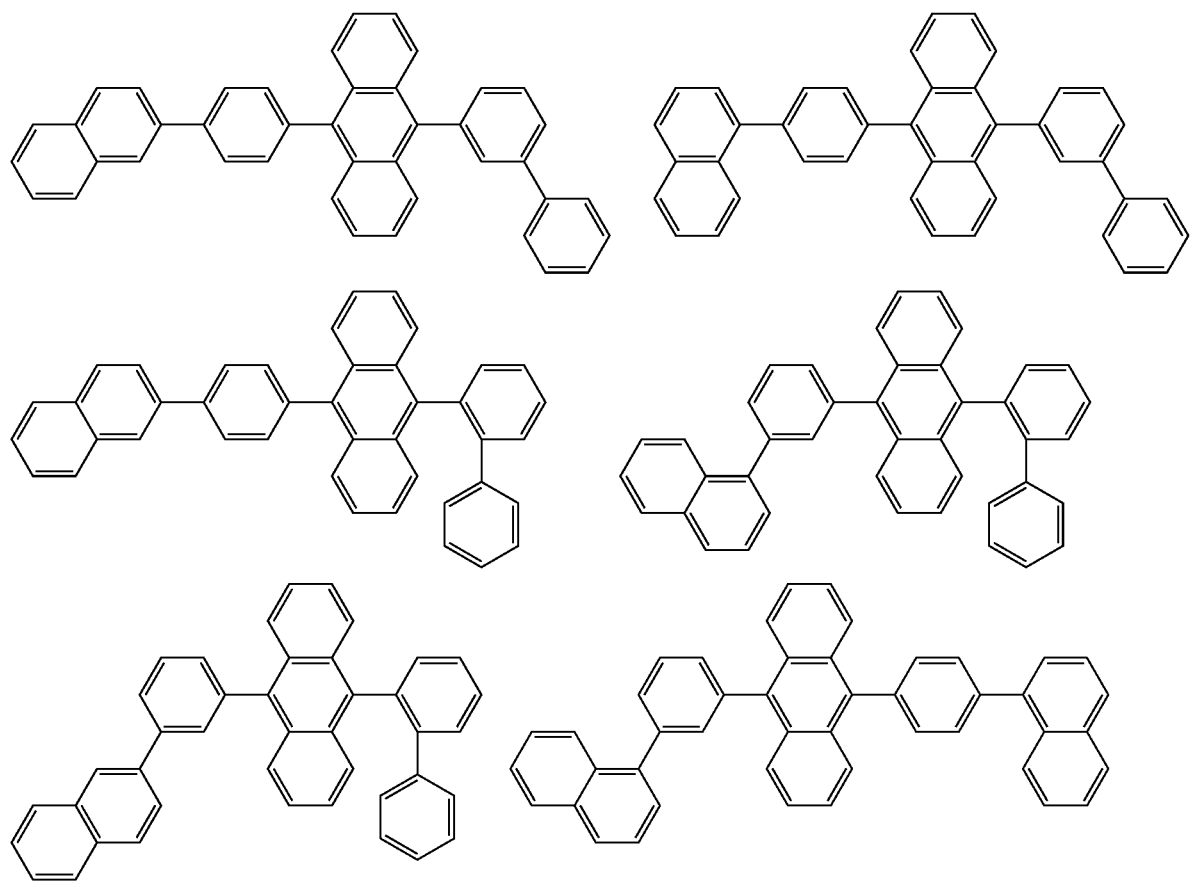
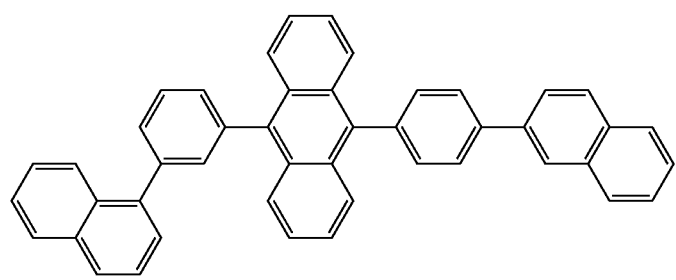
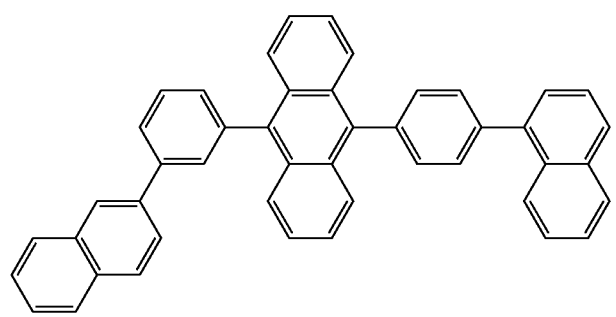

531
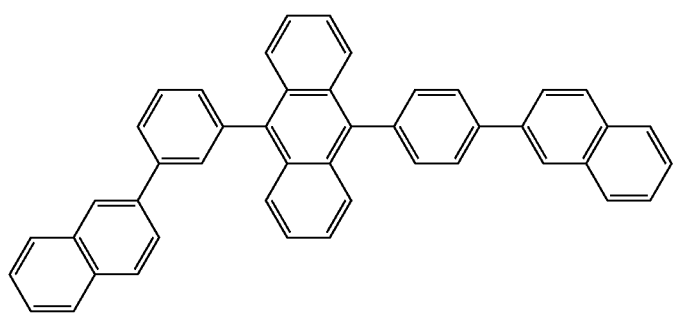
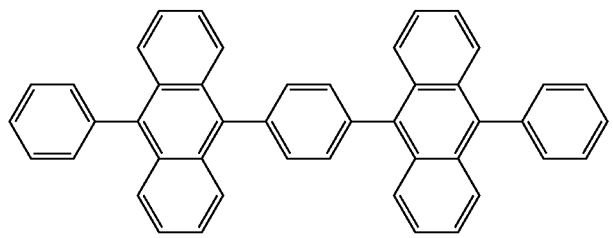
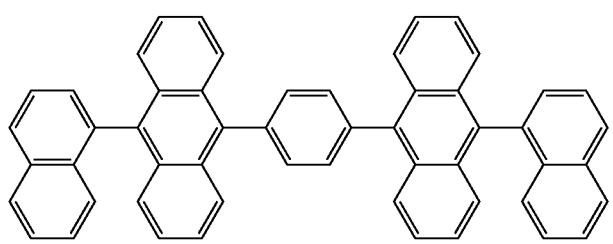
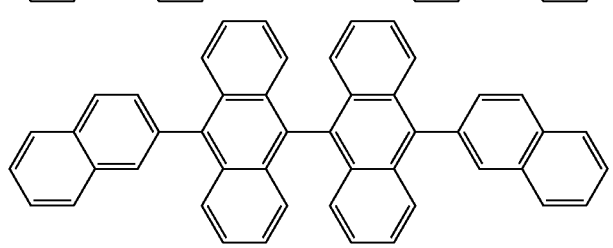
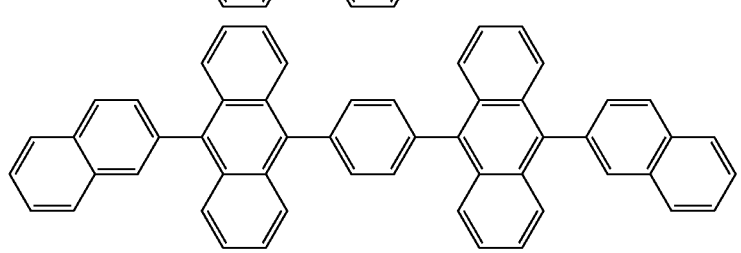
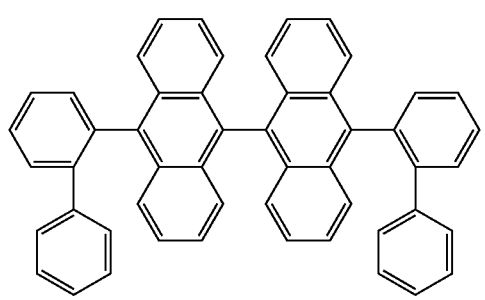
532
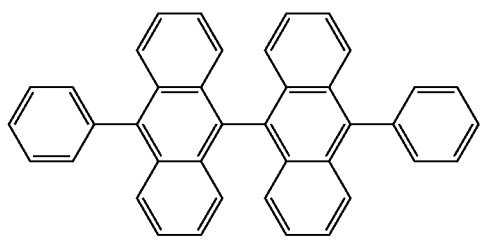
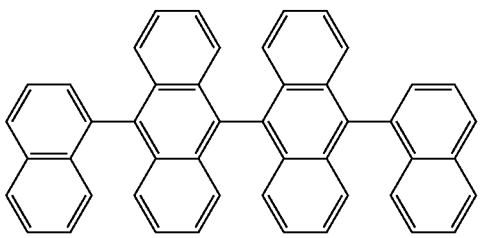
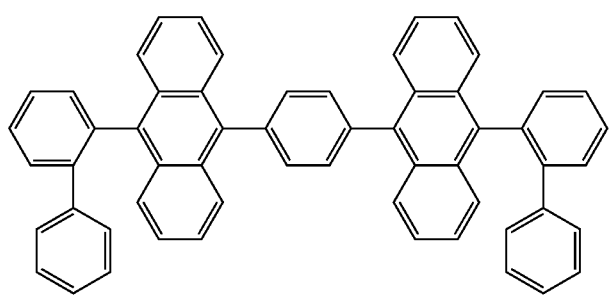

-continued
| 533 | 534 |
|---|---|
| 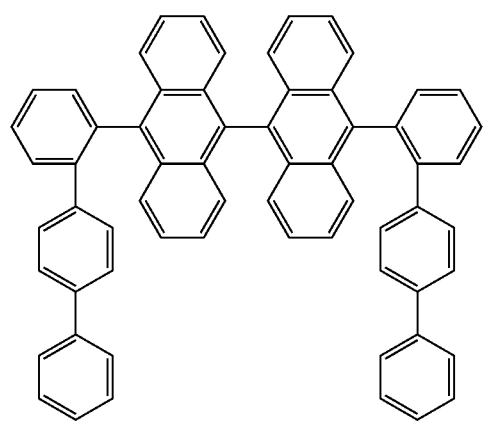 | 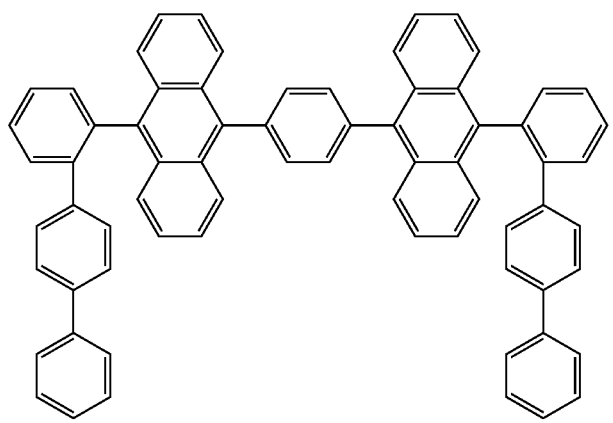 |
| 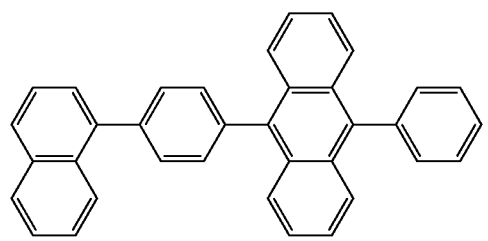 | 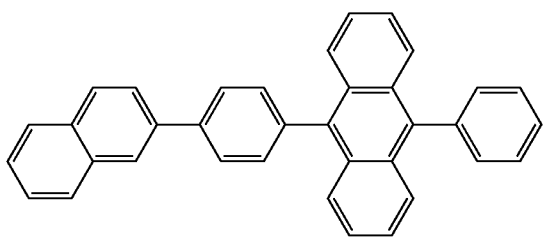 |
| 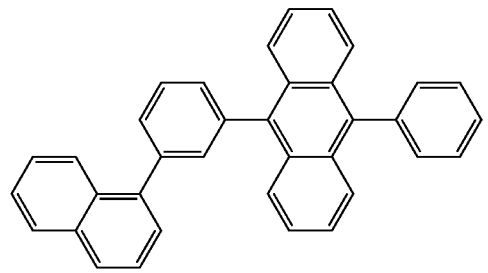 | 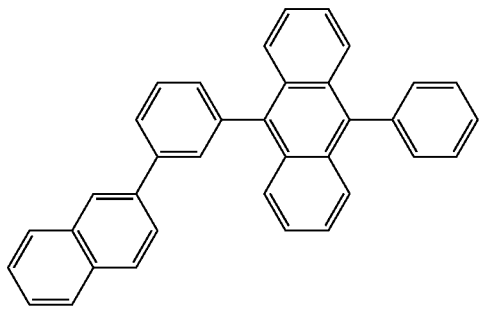 |
| 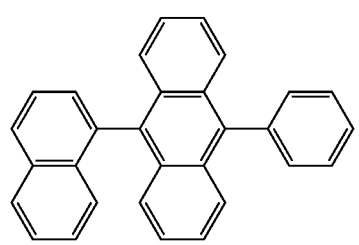 | 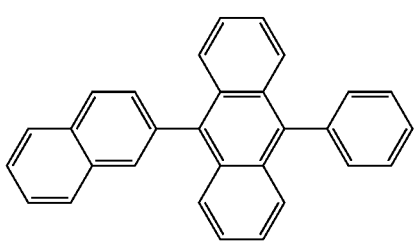 |
| 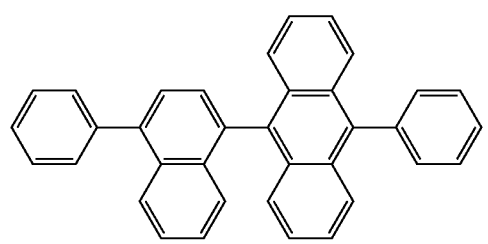 | 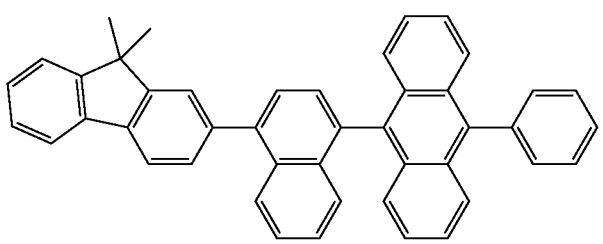 |
| 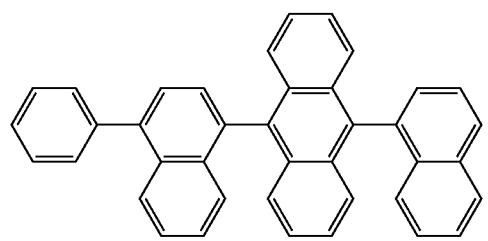 | 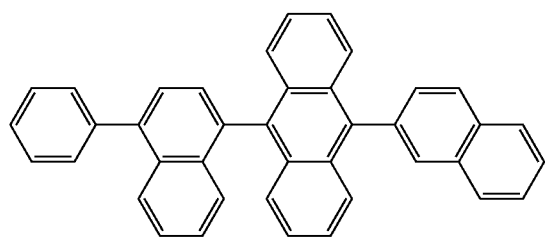 |

535 536
-continued
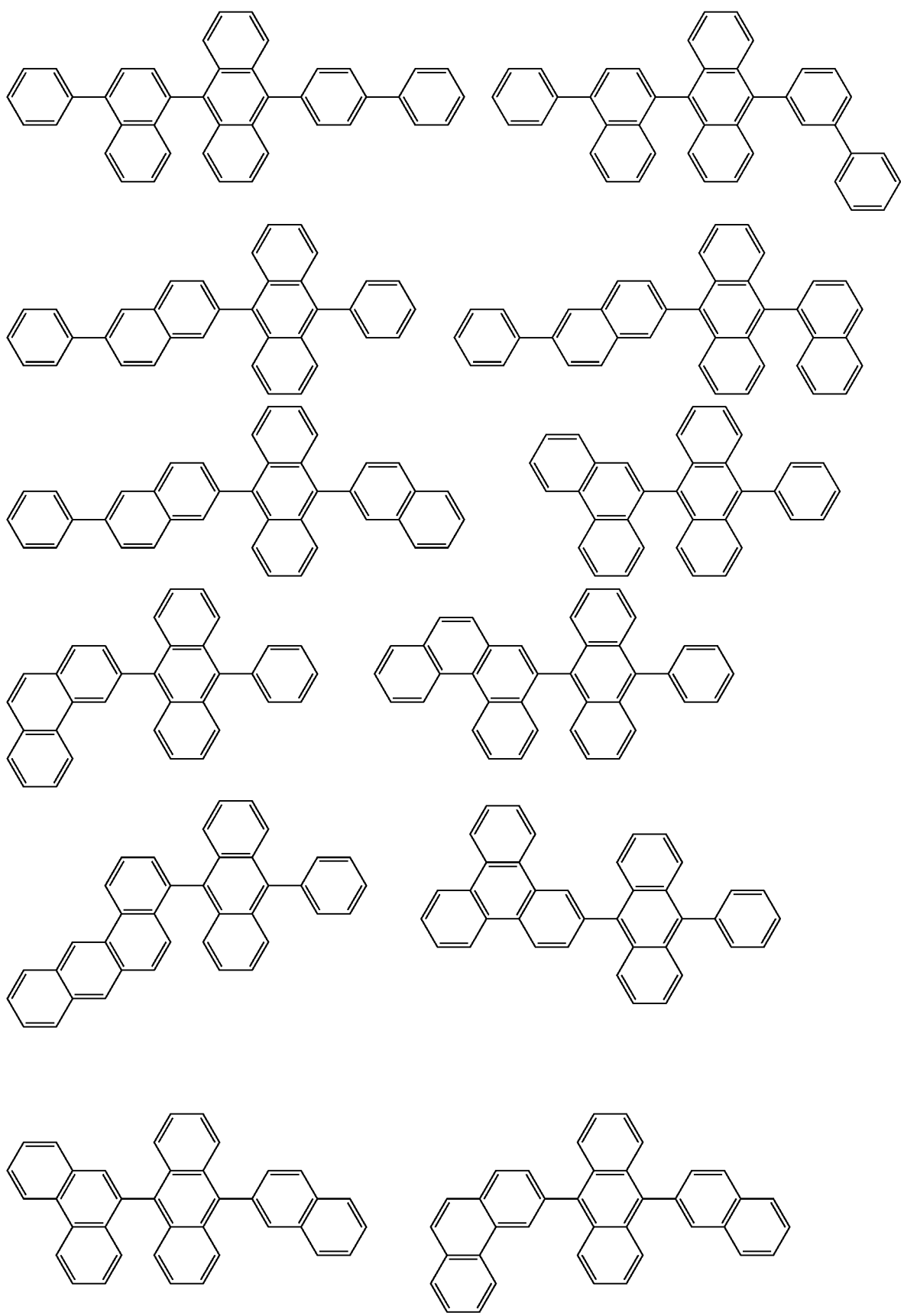

-continued
| 537 | 538 |
|---|---|
| 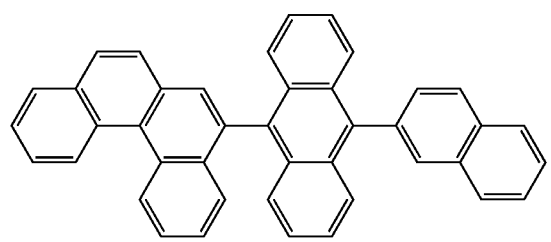 | 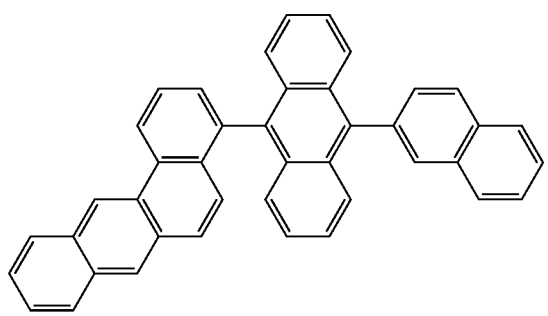 |
| 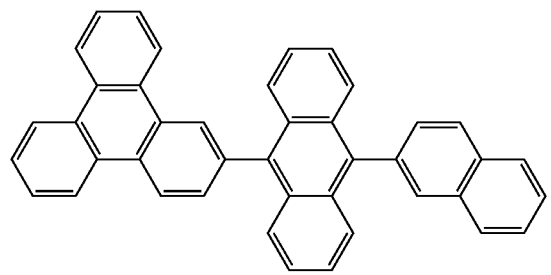 | 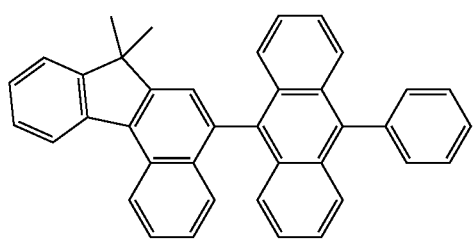 |
| 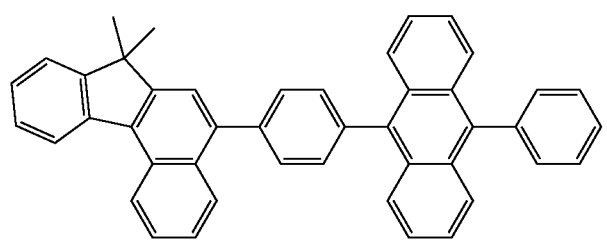 | 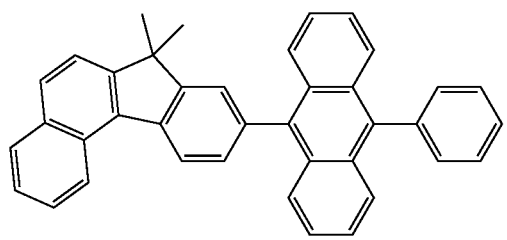 |
| 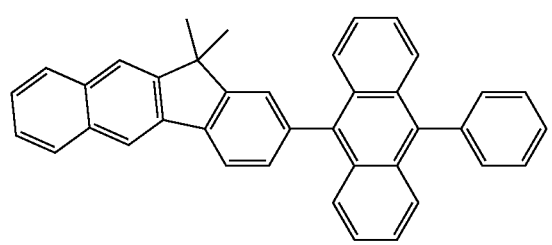 | 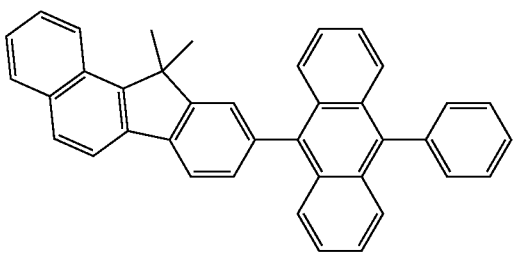 |
| 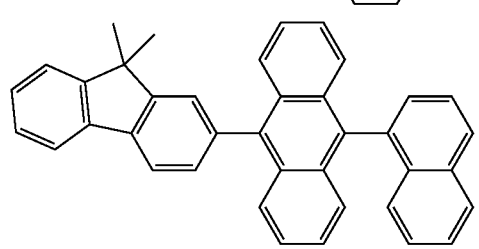 | 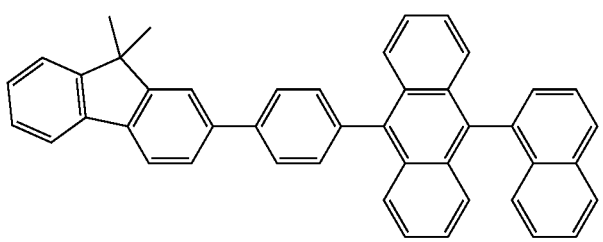 |
| 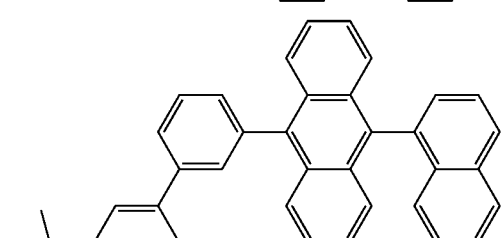 | 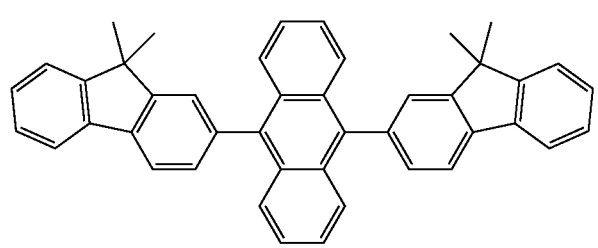 |

-continued
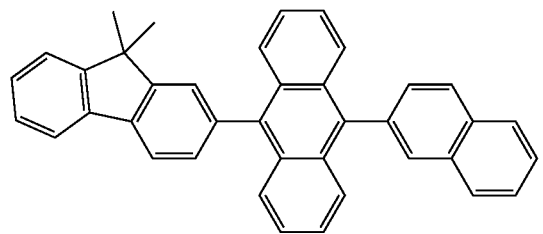
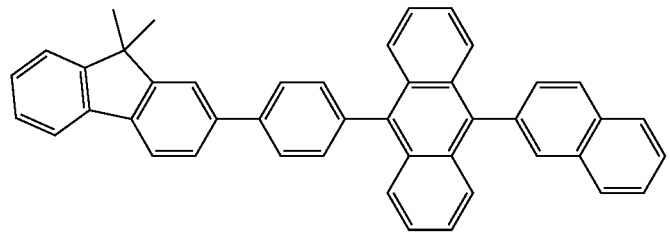
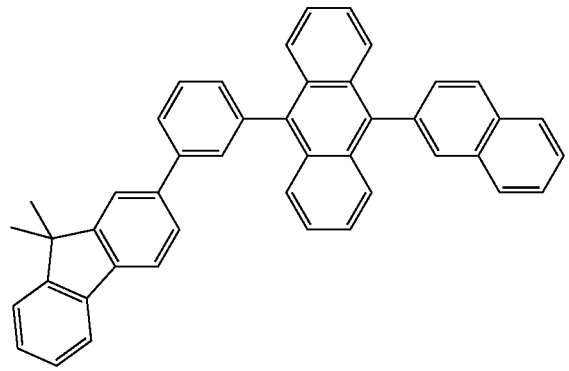
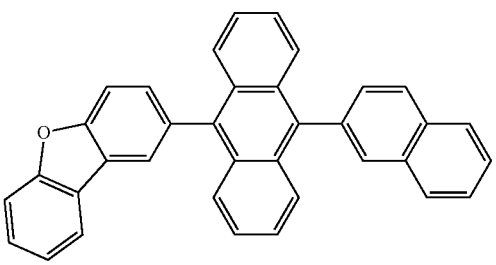
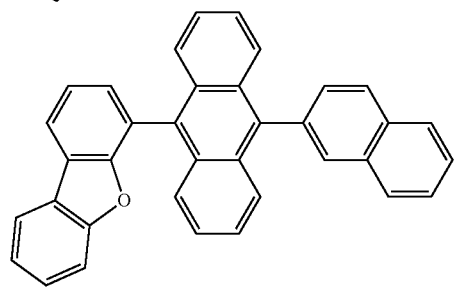
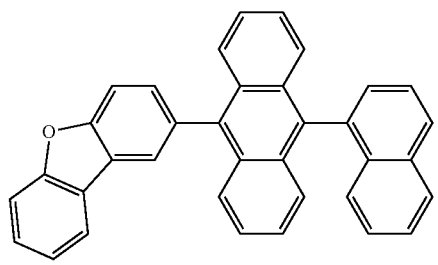
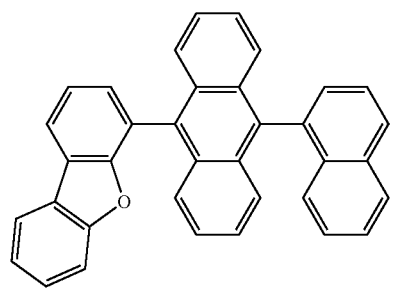
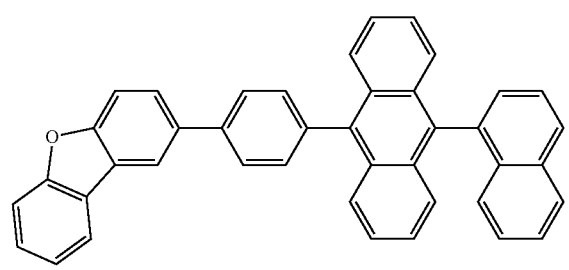
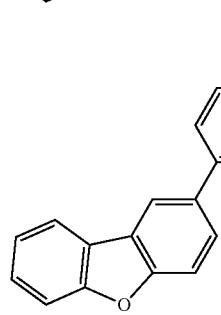
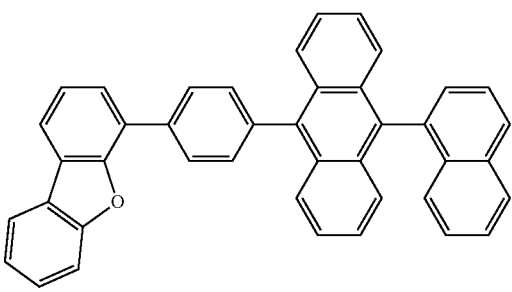

541
542
-continued
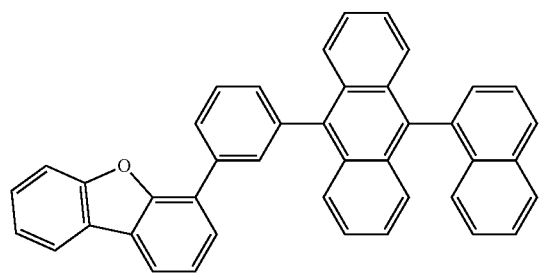
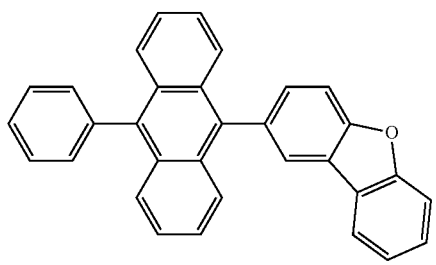
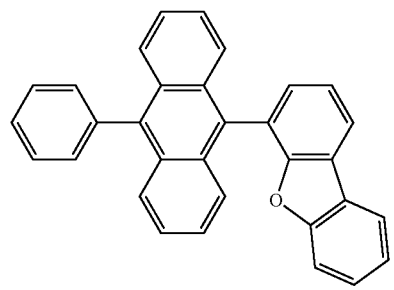
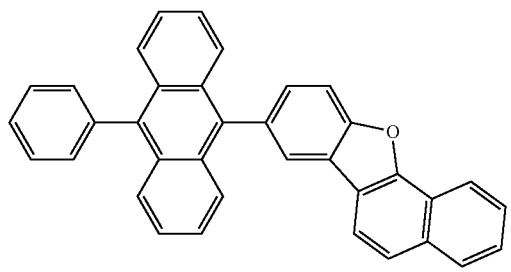
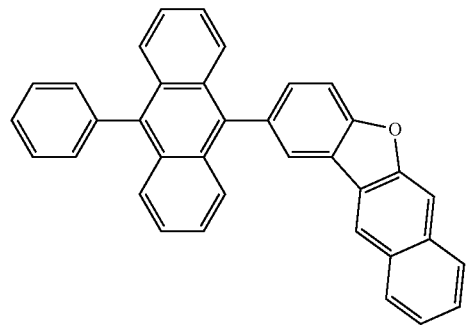
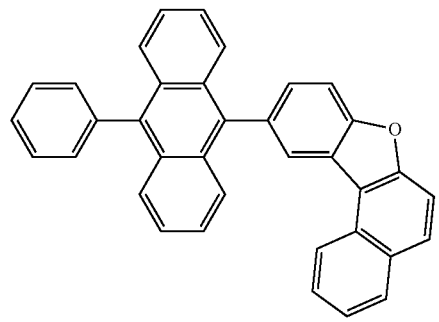
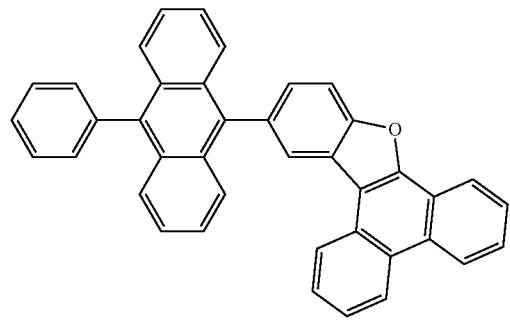
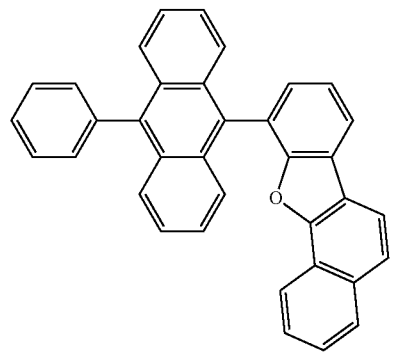
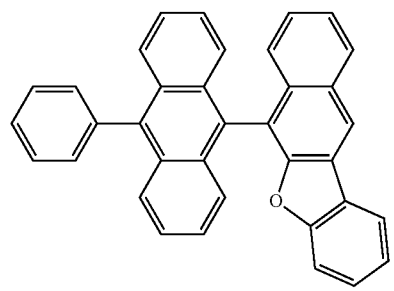
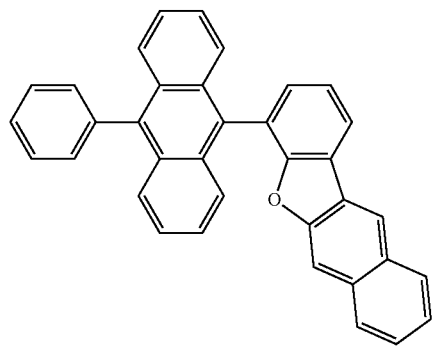

543
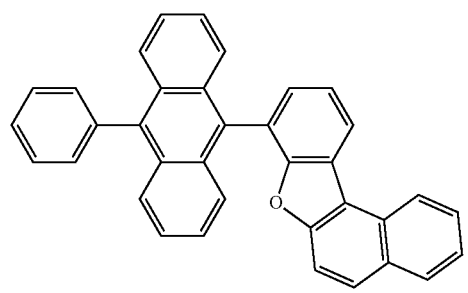
544
-continued
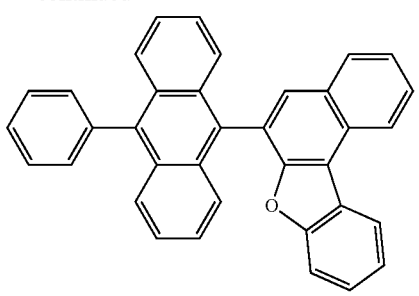
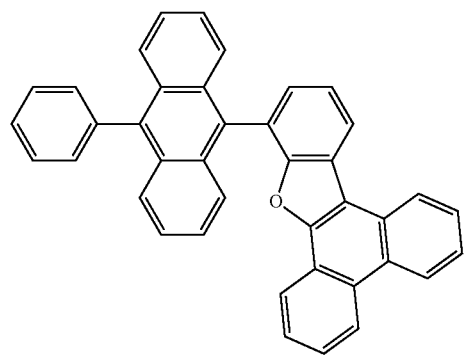
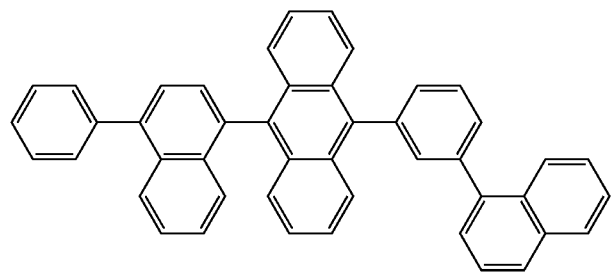
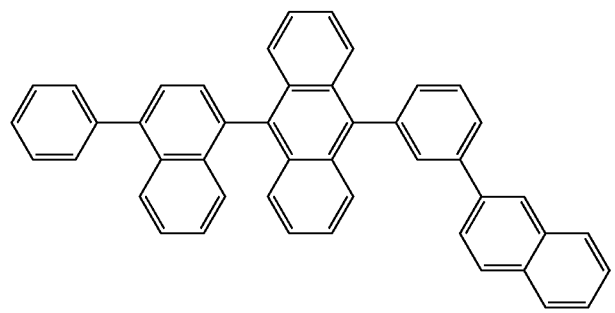
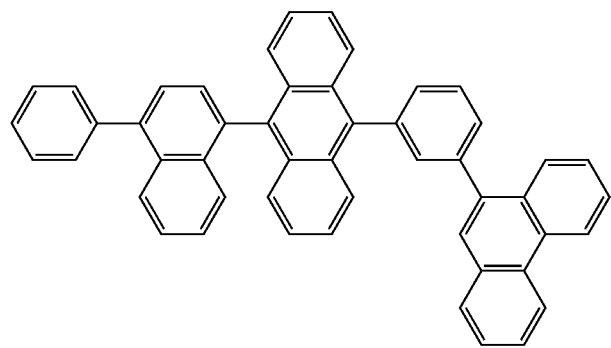

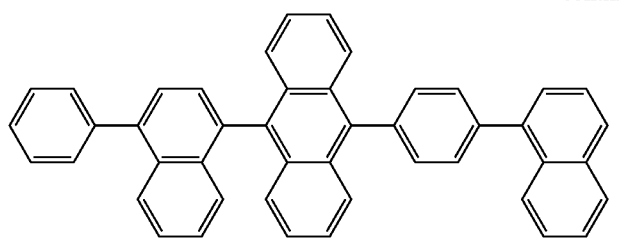

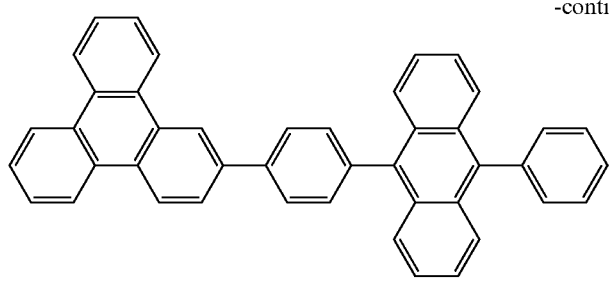
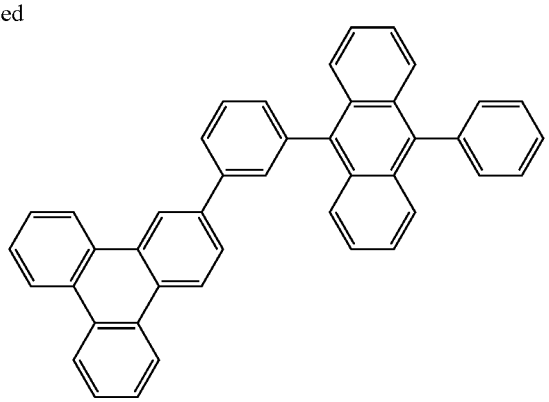

Electron Transporting Layer

The electron transporting layer comprises a material having a high electron transporting ability (electron transporting material). Examples thereof are:
(1) a metal complex, such as an aluminum complex, a beryllium complex, and a zinc complex;
(2) a heteroaromatic compound, such as an imidazole derivative, a benzimidazole derivative, an azine derivative, a carbazole derivative, and a phenanthroline derivative; and
(3) a macromolecular compound.

Examples of the metal complex include tris(8-quinolinolato)aluminum (III) (Alq), tris(4-methyl-8-quinolinolato) aluminum (Almq$_3$), bis(10-hydroxybenzo[h]quinolinato)beryllium (BeBq$_2$), bis(2-methyl-8-quinolinato)(4-phenylphenolato)aluminum (III) (BAlq), bis(8-quinolinato)zinc(II) (Znq), bis[2-(2-benzoxazolyl)phenolato]zinc(II) (ZnPBO), and bis[2-(2-benzothiazolyl)phenolato]zinc(II) (ZnBTZ).

Examples of the heteroaromatic compound include 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-tert-butylphenyl)-4-phenyl-5-(4-biphenylyl)-1,2,4-triazole (TAZ), 3-(4-tert-butylphenyl)-4-(4-ethylphenyl)-5-(4-biphenylyl)-1,2,4-triazole (p-EtTAZ), bathophenanthroline (BPhen), bathocuproine (BCP), and 4,4'-bis(5-methylbenzoxazole-2-yl)stilbene (BzOs).

Examples of the macromolecular compound include poly[(9,9-dihexylfluorene-2,7-diyl)-co-(pyridine-3,5-diyl)] (PF-Py), and poly[(9,9-dioctylfluorene-2,7-diyl)-co-(2,2'-bipyridine-6,6'-diyl)] (PF-BPy).

The above compounds have an electron mobility of $10^{-6}$ cm$^2$/Vs or more. Materials other than those mentioned above are also usable in the electron transporting layer if their electron transporting ability is higher than their hole transporting ability. The electron transporting layer may be a single layer or a laminate of two or more layers each comprising the material mentioned above.

Electron Injecting Layer

The electron injecting layer is a layer comprising a material having a high electron injecting ability, for example, an alkali metal, an alkaline earth metal, and a compound of these metals, such as lithium (Li), cesium (Cs), calcium (Ca), lithium fluoride (LiF), cesium fluoride (CsF), calcium fluoride (CaF$_2$), and lithium oxide (LiOx). In addition, an electron transporting material which is doped with an alkali metal, an alkaline earth metal or a compound thereof, for example, Alq doped with magnesium (Mg), is also usable. By using such a material, electrons are efficiently injected from the cathode.

A composite material comprising an organic compound and an electron donor is also usable in the electron injecting layer. Such a composite material is excellent in the electron injecting ability and the electron transporting ability, because the organic compound receives electrons from the electron donor. The organic compound is preferably a compound excellent in transporting the received electrons. Examples thereof include the materials for the electron transporting layer mentioned above, such as the metal complex and the aromatic heterocyclic compound. Any compound capable of giving its electron to the organic compound is usable as the electron donor. Preferred examples thereof are an alkali metal, an alkaline earth metal, and a rare earth metal, such as lithium, cesium, magnesium, calcium, erbium, and ytterbium; an alkali metal oxide and an alkaline earth metal oxide, such as, lithium oxide, calcium oxide, and barium oxide; a Lewis base, such as magnesium oxide; and an organic compound, such as tetrathiafulvalene (TTF).

Cathode

The cathode is formed preferably from a metal, an alloy, an electrically conductive compound, or a mixture thereof, each having a small work function, for example, a work function of 3.8 eV or less. Examples of the material for the cathode include an element belonging to a group 1 or group 2 of the periodic table, i.e., an alkali metal, such as lithium (Li) and cesium (Cs), an alkaline earth metal, such as magnesium (Mg), calcium (Ca), and strontium (Sr), an alloy containing these metals (for example, MgAg and AlLi), a rare earth metal, such as europium (Eu) and ytterbium (Yb), and an alloy containing a rare earth metal.

The alkali metal, the alkaline earth metal, and the alloy thereof is made into the cathode by a vacuum vapor deposition or a sputtering method. A coating method and an inkjet method are usable when a silver paste is used.

When the electron injecting layer is formed, the material for the cathode is selected irrespective of whether the work function is large or small and various electroconductive materials, such as Al, Ag, ITO, graphene, and indium oxide-tin oxide doped with silicon or silicon oxide, are usable. These electroconductive materials are made into films by a sputtering method, an inkjet method, and a spin coating method.

Insulating Layer

Since electric field is applied to the ultra-thin films of organic EL devices, the pixel defects due to leak and short circuit tends to occur. To prevent the defects, an insulating thin film layer may be interposed between the pair of electrodes.

Examples of the material for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. These materials may be used in combination or may be used in each layer of laminated layers.

Space Layer

For example, in an organic EL device having a fluorescent emitting layer and a phosphorescent emitting layer, a space layer is disposed between the fluorescent emitting layer and the phosphorescent emitting layer to prevent the diffusion of excitons generated in the phosphorescent emitting layer to the fluorescent emitting layer or to control the carrier (charge) balance. The space layer may be disposed between two or more phosphorescent emitting layers.

Since the space layer is disposed between the light emitting layers, a material combining the electron transporting ability and the hole transporting ability is preferably used for forming the space layer. To prevent the diffusion of triplet energy in the adjacent phosphorescent emitting layer, the triplet energy of the material for the space layer is preferably 2.6 eV or more. The materials described with respect to the hole transporting layer are usable as the material for the space layer.

Blocking Layer

A blocking layer, such as an electron blocking layer, a hole blocking layer, and a triplet blocking layer, may be provided in the portion adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer. The triplet blocking layer prevents the diffusion of excitons generated in the light emitting layer to adjacent layers and has a function of confining the excitons in the light emitting layer.

Each layer of the organic EL device is formed by a known method, such as a vapor deposition method and a coating method. For example, each layer is formed by a known vapor deposition method, such as a vacuum vapor deposition method and a molecular beam evaporation method (MBE method), and a known coating method using a solution of a compound for forming a layer, such as a dipping method, a spin coating method, a casting method, a bar coating method, and a roll coating method.

The thickness of each layer is not particularly limited and preferably 5 nm to 10 μm, more preferably 10 nm to 0.2 μm, because an excessively small thickness may cause defects such as pin holes and an excessively large thickness may require a high driving voltage.

The organic EL device can be used in an electronic device, for example, as display parts, such as organic EL panel module, display devices of television sets, mobile phones, personal computer, etc., and light emitting sources of lighting equipment and vehicle lighting equipment.

EXAMPLES

The present invention will be described below in more details with reference to the examples. However, it should be noted that the scope of the invention is not limited thereto.

Intermediate Synthesis A: Synthesis of Intermediate A

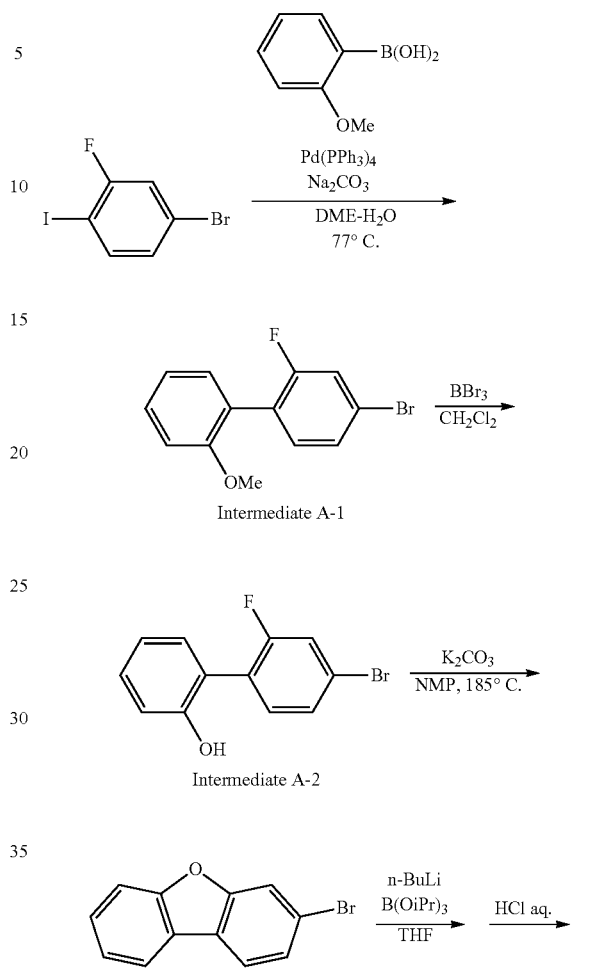

(A-1) Synthesis of Intermediate A-1

In argon atmosphere, a mixture of 1-bromo-3-fluoro-4-iodobenzene (1037 g, 3.45 mol), 2-methoxyphenylboronic acid (620 g, 4.14 mol), tetrakis(triphenylphosphine)palladium(0) (80 g, 69 mmol), sodium carbonate (1096 g, 10.3 mol), 1,2-dimethoxyethane (DME) (5.2 L), and water (5.2 L) was stirred at 77° C. for 42 h. The reaction liquid was cooled to room temperature. After adding water, the reaction liquid was extracted with ethyl acetate and the organic layer was concentrated under reduced pressure. The obtained residue was purified by silica gel column chromatography to obtain Intermediate A-1 (685 g). The yield was 70%.

(A-2) Synthesis of Intermediate A-2

In argon atmosphere, a solution of Intermediate A-1 synthesized in the step (A-1) (675 g, 2.40 mol) in dichloromethane (6 L) was cooled in an iced water bath, into which boron tribromide (240 g, 2.64 mol) was gradually added.

The temperature was raised to room temperature and the stirring was continued for 14 h. Then, methanol (500 mL) was added while cooling the reaction liquid in an iced water bath. After adding water, the resultant reaction liquid was separated into an aqueous layer and an organic layer, and the organic layer was concentrated under reduced pressure. The obtained residue was purified by silica gel column chromatography to obtain Intermediate A-2 (561 g). The yield was 87%.

(A-3) Synthesis of Intermediate A-3

In argon atmosphere, a solution of Intermediate A-2 synthesized in the step (A-2) (561 g, 2.10 mol) and potassium carbonate (580 g, 4.20 mol) in N-methyl-2-pyrrolidone (NMP) (6 L) was stirred at 185° C. for 1.5 h. The reaction liquid was cooled and stirred after adding water. The generated solid matter was collected by filtration and washed with water. The obtained solid was dissolved into toluene and the insoluble was removed by filtration. The filtrate was concentrated. The crystal obtained by adding heptane was collected by filtration to obtain Intermediate A-3 (414 g). The yield was 80%.

(A-4) Synthesis of Intermediate A

In argon atmosphere, into a solution of Intermediate A-3 synthesized in the step (A-3) (10 g, 40.4 mmol) in tetrahydrofuran (THF) (200 mL), a 2.7 M hexane solution of n-butyllithium (16.7 mL, 44.6 mmol) was added at −63° C. The resultant solution was stirred for 2.5 h. Then, after adding triisopropyl borate (16.4 g, 87.2 mmol) at −65° C. and returning the temperature to room temperature, the solution was stirred for 3.3 h. After adding a 4 M hydrochloric acid (100 mL), the reaction liquid was stirred at room temperature for one hour. The obtained reaction liquid was extracted with dichloromethane. The dichloromethane layer was washed with an aqueous solution of sodium hydrogen carbonate and a saturated brine, dried over anhydrous magnesium sulfate, and concentrated. The obtained residue was crystallized from toluene and hexane to obtain Intermediate A (5.66 g). The yield was 66%.

Intermediate Synthesis B: Synthesis of Intermediate B

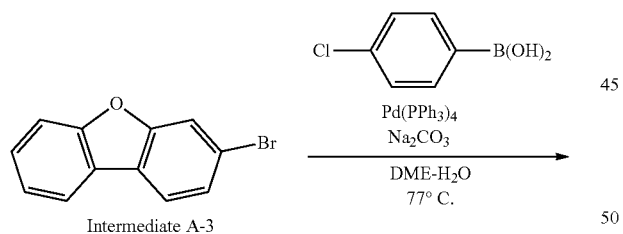

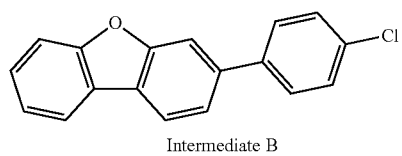

Intermediate B

In argon atmosphere, a mixture of Intermediate A-3 synthesized in the step (A-3) (309 g, 1.25 mol), 4-chlorophenylboronic acid (353 g, 2.26 mol), tetrakis(triphenylphosphine) palladium(0) (29 g, 25 mmol), sodium carbonate (398 g, 3.76 mol), DME (1.9 L), and water (1.9 L) was stirred at 77° C. for 42 h. The reaction liquid was cooled to room temperature. After adding water, the reaction liquid was extracted with ethyl acetate, and the organic layer was concentrated under reduced pressure. The obtained residue was purified by silica gel column chromatography and recrystallization to obtain Intermediate B (255 g). The yield was 73%.

Intermediate Synthesis C: Synthesis of Intermediate C

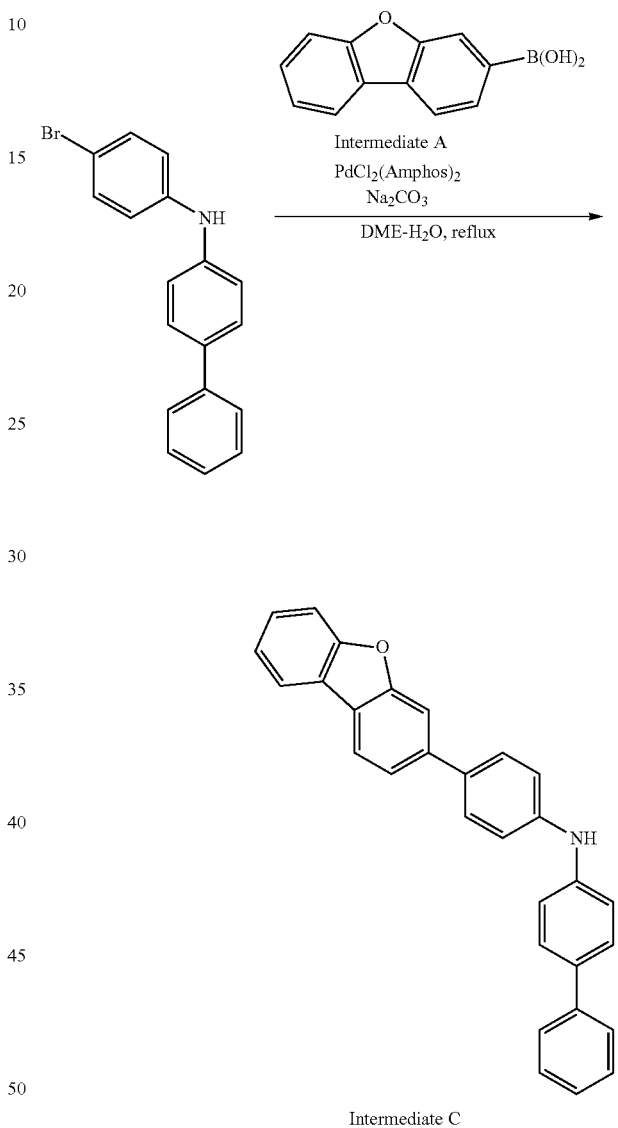

In argon atmosphere, a solution of N-(4-bromophenyl)-4-biphenylamine (5.00 g, 15.4 mmol), Intermediate A (3.27 g, 15.4 mmol), PdCl$_2$(Amphos)$_2$ (0.218 g, 0.308 mmol), and an 2 M aqueous solution of sodium carbonate (23.1 mL) in DME (100 mL) was refluxed for 4 h under heating. The reaction liquid was cooled to room temperature and concentrated under reduced pressure. After adding water, the resultant aqueous solution was extracted with toluene. The toluene layer was purified by silica gel column chromatography and recrystallization to obtain Intermediate C (3.93 g). The yield was 62%.

"Amphos" mentioned above is [4-(N,N-Dimethylamino)phenyl]di-tert-butylphosphine.

Intermediate Synthesis D: Synthesis of Intermediate D

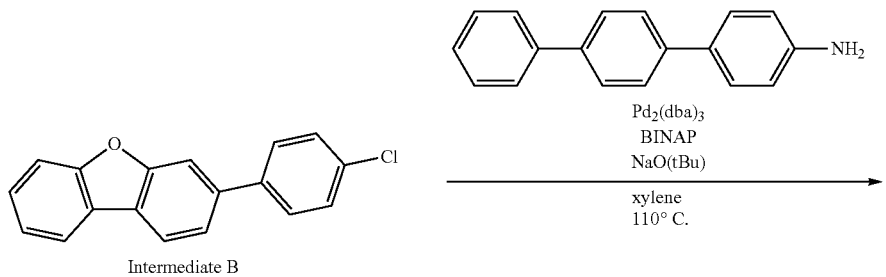

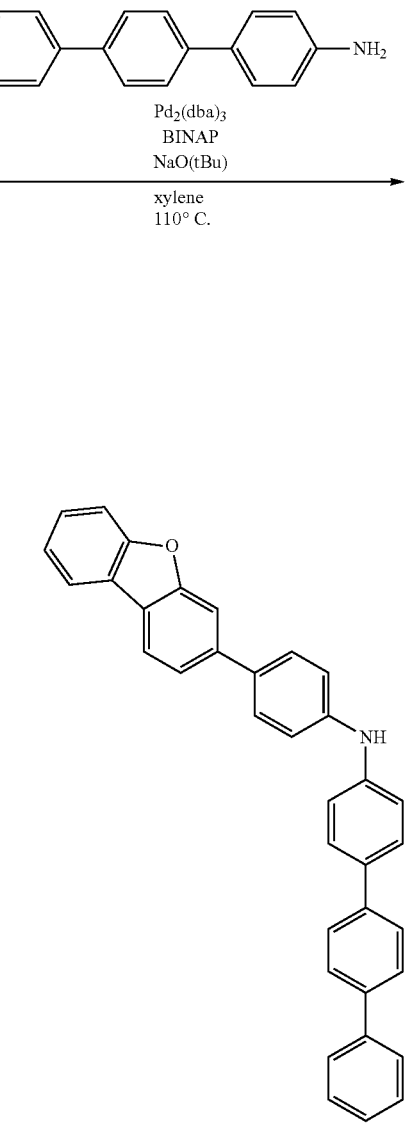

Intermediate D

In argon atmosphere, a mixture of Intermediate B (4.18 g, 15.0 mmol), 4-amino-p-terphenyl (7.36 g, 30.0 mmol), tris(dibenzylideneacetone)dipalladium(0) (0.206 g, 0.225 mmol), BINAP (0.280 g, 0.45 mmol), sodium t-butoxide (2.88 g, 30 mmol), and toluene (1.5 L) was stirred at 105° C. for 70 h. The reaction liquid was cooled to room temperature. After adding water, the reaction liquid was extracted with toluene and the organic layer was concentrated under reduced pressure. The obtained residue was purified by silica gel column chromatography and recrystallization to obtain Intermediate D (4.02 g). The yield was 55%.

BINAP mentioned above is 2,2'-bis(diphenylphosphino)-1,1'-binaphthyl.

Intermediate Synthesis E: Synthesis of Intermediate E

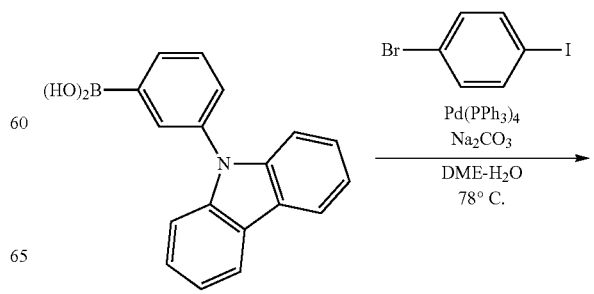

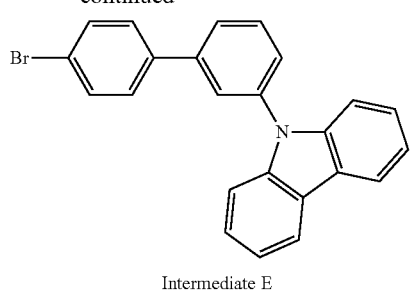

Intermediate E

In argon atmosphere, a solution of 3-(9-carbazolyl)phenylboronic acid (208 g, 725 mmol), 1-bromo-4-iodobenzene (246 g, 868 mmol), tetrakis(triphenylphosphine)palladium (0) (16.7 g, 14 mmol), and sodium carbonate (154 g, 1.45 mol) in a mixed solvent of DME (4.1 L) and water (710 mL) was stirred at 78° C. for 18 h. After cooling to room temperature and adding methanol, the generated solid was collected by filtration, which was purified by silica gel column chromatography and recrystallization to obtain Intermediate E (187 g). The yield was 64%.

Intermediate Synthesis F: Synthesis of Intermediate F

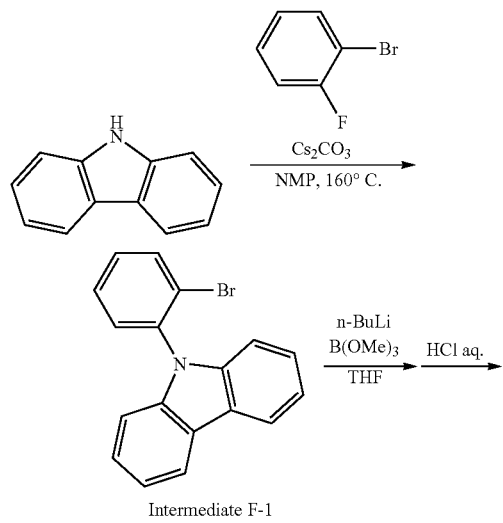

Intermediate F-1

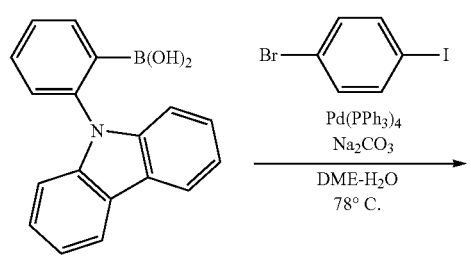

Intermediate F-2

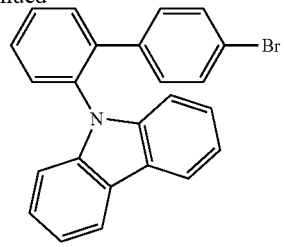

Intermediate F (F-1) Synthesis of Intermediate F-1

Into a solution of carbazole (10 g, 59.8 mmol) and cesium carbonate (39.0 g, 120 mmol) in NMP (59.8 mL), 1-bromo-2-fluorobenzene (7.80 mL, 71.8 mmol) was added. The resultant solution was stirred at 160° C. for 16 h under heating. The reaction liquid was cooled to room temperature and the insoluble was removed by filtration after adding toluene. The obtained solution was washed with water, dried over anhydrous sodium sulfate, and purified by silica gel column chromatography. The obtained residue was crystallized to obtain Intermediate F-1 (18.3 g). The yield was 94%.

(F-2) Synthesis of Intermediate F-2

In argon atmosphere, a solution of Intermediate F-1 synthesized in the step (F-1) (8.0 g, 24.8 mmol) in THF (124 mL) was cooled in a dry ice/acetone bath, to which a 1.6 M hexane solution of n-butyllithium (17.1 mL, 27.3 mmol) was added dropwise, and the resultant solution was stirred for 2 h. After adding a solution of trimethyl borate (3.33 mL, 29.8 mmol) in THF (10 mL) dropwise, the stirring was continued for one hour, and then, the dry ice/acetone bath was removed and the temperature was raised to room temperature. The reaction liquid was cooled in an iced water bath and stirred for one hour after adding a 2 M hydrochloric acid and then the temperature was raised to room temperature. The obtained reaction liquid was extracted with ethyl acetate. The organic layer was washed with water, dried over anhydrous sodium sulfate, and concentrated under reduced pressure. The obtained residue was crystallized to obtain Intermediate F-2 (4.91 g). The yield was 69%.

(F-3) Synthesis of Intermediate F

Intermediate F was synthesized in the same manner as in Intermediate Synthesis E except for using Intermediate F-2 synthesized in the step (F-2) in place of 3-(9-carbazolyl)phenylboronic acid.

Intermediate Synthesis G: Synthesis of Intermediate G

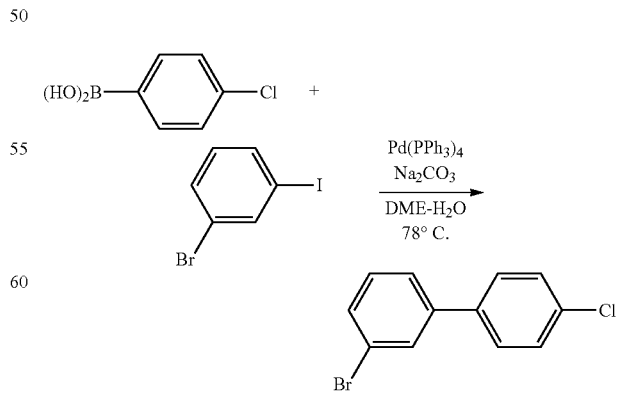

Intermediate G

In argon atmosphere, a solution of 4-chlorophenylboronic acid (200 g, 1.27 mol), 1-bromo-3-iodobenzene (362 g, 1.27 mol), tetrakis(triphenylphosphine)palladium(0) (29.5 g, 25 mmol), and sodium carbonate (407 g, 3.83 mol) in a mixed solvent of DME (5.6 L) and water (1.9 L) was stirred at 78° C. for 17 h. After cooling to room temperature, the solution was extracted and the extract was concentrated under reduced pressure. The obtained residue was purified by silica gel column chromatography to obtain Intermediate G (172 g). The yield was 50%.

Intermediate Synthesis H: Synthesis of Intermediate H

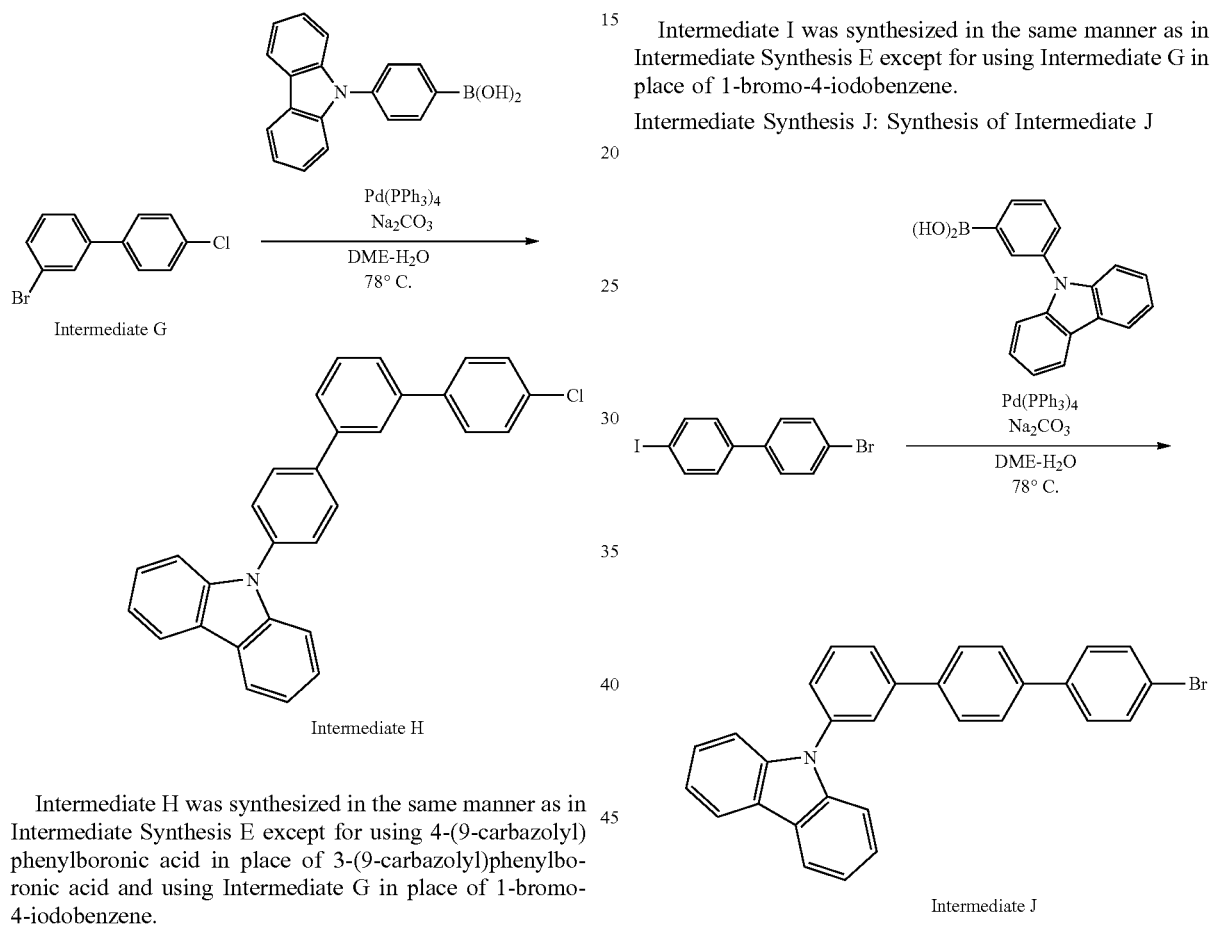

Intermediate H was synthesized in the same manner as in Intermediate Synthesis E except for using 4-(9-carbazolyl)phenylboronic acid in place of 3-(9-carbazolyl)phenylboronic acid and using Intermediate G in place of 1-bromo-4-iodobenzene.

Intermediate Synthesis I: Synthesis of Intermediate I

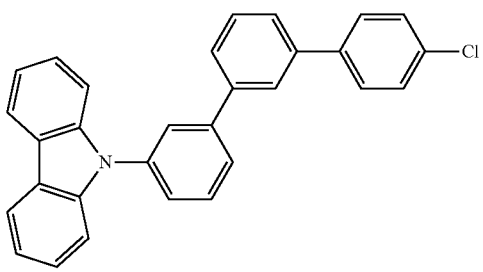

Intermediate I was synthesized in the same manner as in Intermediate Synthesis E except for using Intermediate G in place of 1-bromo-4-iodobenzene.

Intermediate Synthesis J: Synthesis of Intermediate J

Intermediate J was synthesized in the same manner as in Intermediate Synthesis E except for using 4-bromo-4'-iodobiphenyl in place of 1-bromo-4-iodobenzene.

Intermediate Synthesis K: Synthesis of Intermediate K

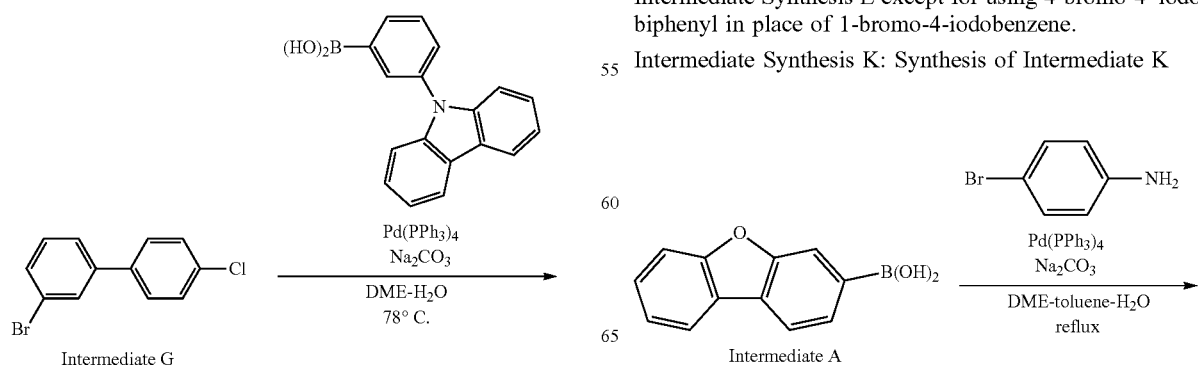

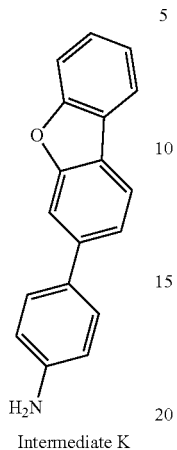

Intermediate K

Under nitrogen atmosphere, a mixture of Intermediate A (5.13 g, 24.2 mmol), 4-bromoaniline (4.16 g, 24.2 mmol), tetrakis(triphenylphosphinepalladium)(0) (0.562 g, 0.486 mmol), a 2 M aqueous solution of sodium carbonate (36.4 mL, 72.8 mmol), DME (60 mL), and toluene (60 mL) was refluxed for 6.5 h under heating. After cooling to room temperature, the reaction liquid was phase-separated. The water layer was extracted with ethyl acetate. The organic layer was washed with water, dried over anhydrous sodium sulfate, and concentrated under reduced pressure. The obtained residue was purified by silica gel column chromatography to obtain Intermediate K (4.96 g). The yield was 79%.

Intermediate Synthesis L: Synthesis of Intermediate L

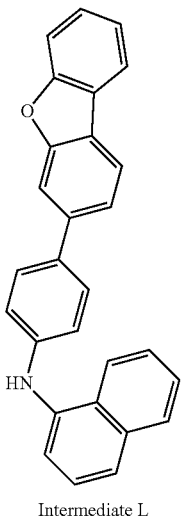

Intermediate L

In argon atmosphere, a mixture of Intermediate K (3.88 g, 15.0 mmol), 1-bromonaphthalene (3.10 g, 15.0 mmol), tris(dibenzylideneacetone)dipalladium(0) (0.206 g, 0.225 mmol), BINAP (0.280 g, 0.45 mmol), sodium t-butoxide (2.88 g, 30 mmol), and xylene (1.5 L) was stirred at 110° C. for 10 h. The reaction liquid was cooled to room temperature and extracted with toluene after adding water. The extract was concentrated under reduced pressure. The obtained residue was purified by silica gel column chromatography and recrystallization to obtain Intermediate L (3.52 g). The yield was 61%.

Intermediate Synthesis M: Synthesis of Intermediate M

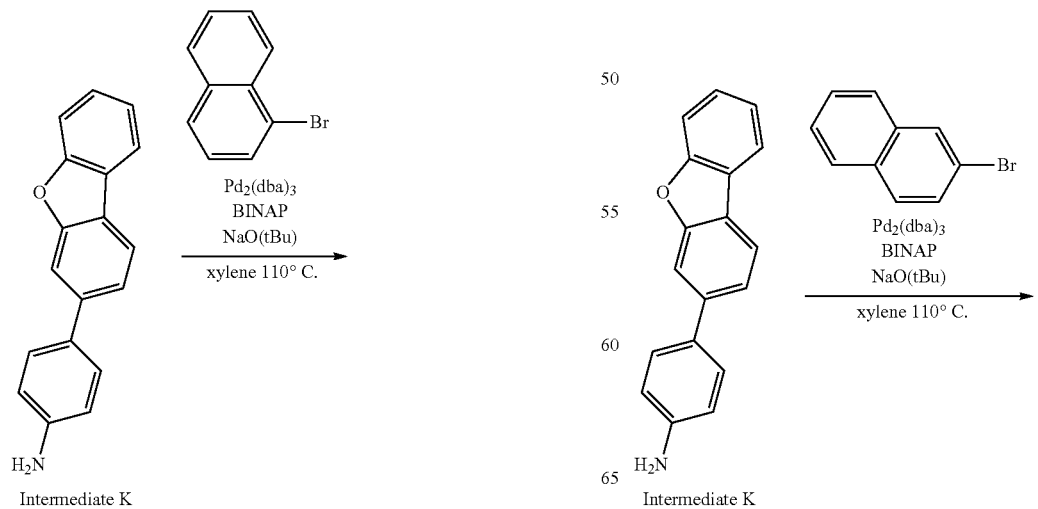

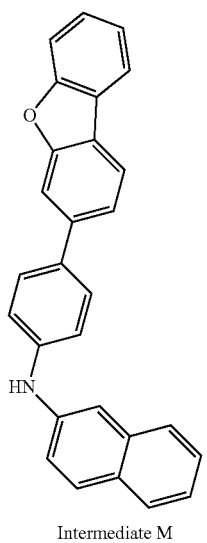

Intermediate M

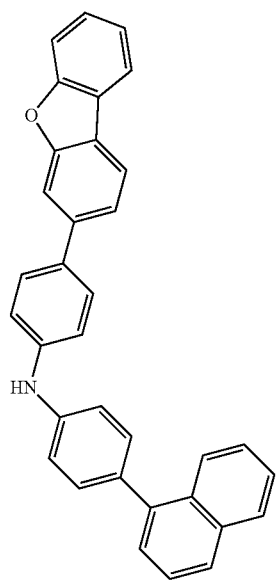

Intermediate N

Intermediate M was synthesized in the same manner as in Intermediate Synthesis L except for using 2-bromonaphthalene in place of 1-bromonaphthalene.

Intermediate Synthesis N: Synthesis of Intermediate N

Intermediate N was synthesized in the same manner as in Intermediate Synthesis L except for using 1-(4-bromophenyl)naphthalene in place of 1-bromonaphthalene.

Intermediate Synthesis O: Synthesis of Intermediate O

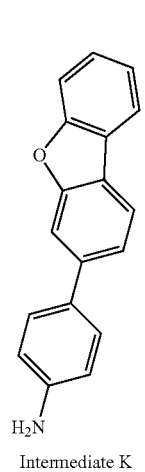

Intermediate K

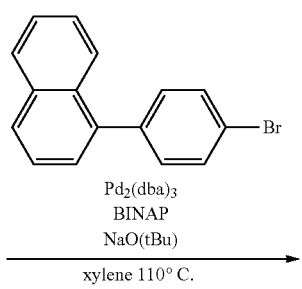

Pd₂(dba)₃
BINAP
NaO(tBu)

xylene 110° C.

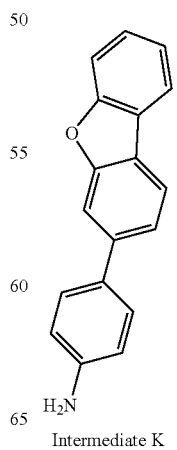

Intermediate K

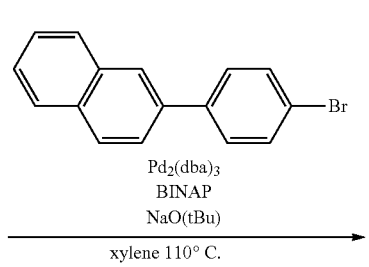

Pd₂(dba)₃
BINAP
NaO(tBu)

xylene 110° C.

563

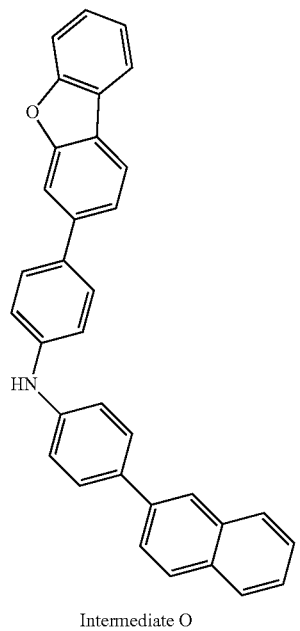

Intermediate O

Intermediate O was synthesized in the same manner as in Intermediate Synthesis L except for using 2-(4-bromophenyl)naphthalene in place of 1-bromonaphthalene.

Intermediate Synthesis P: Synthesis of Intermediate P

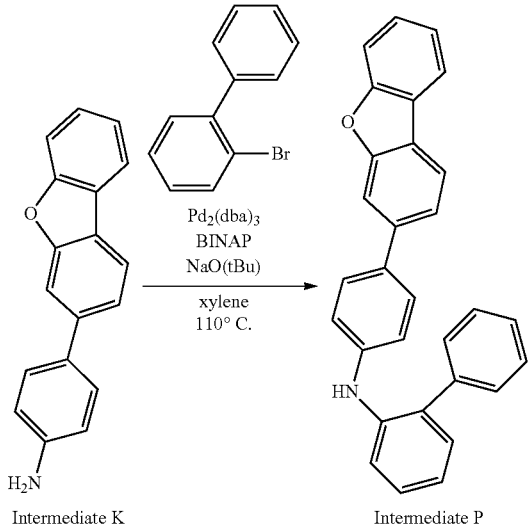

Intermediate K    Intermediate P

Intermediate P was synthesized in the same manner as in Intermediate Synthesis L except for using 2-bromobiphenyl in place of 1-bromonaphthalene.

564

Synthesis Example 1: Synthesis of Compound 1

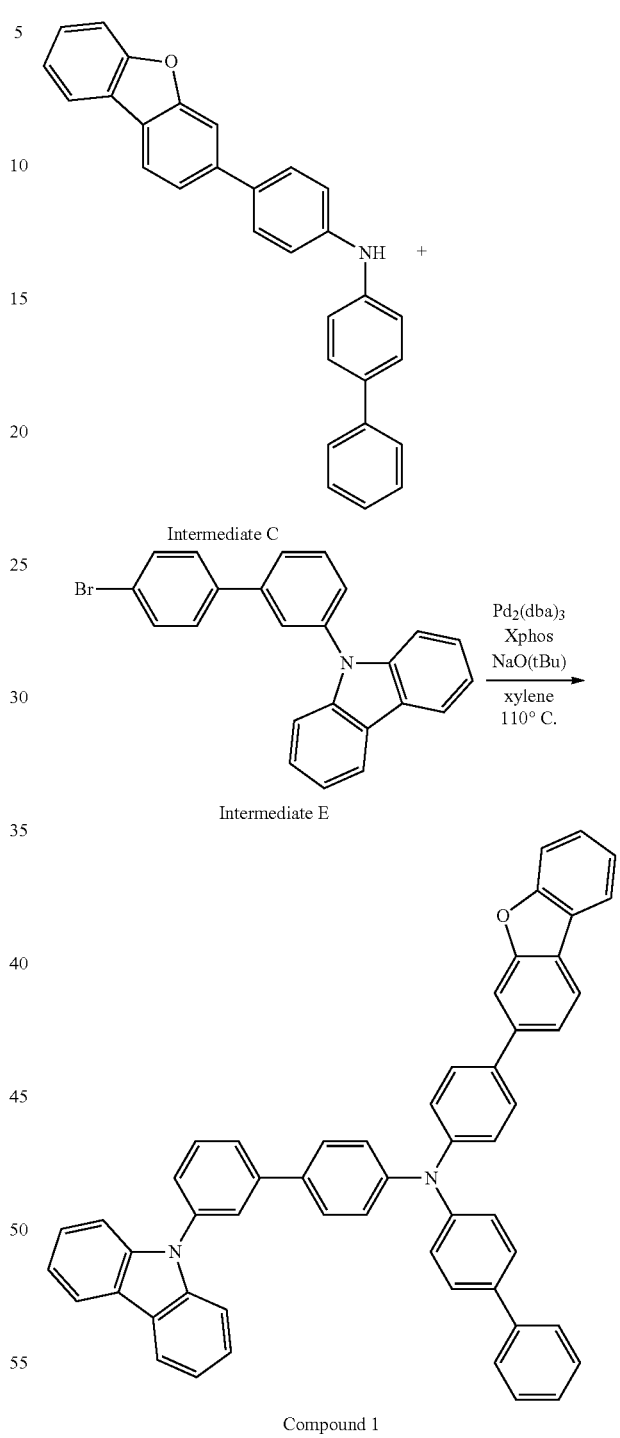

In argon atmosphere, a mixture of Intermediate C (3.20 g, 7.78 mmol), Intermediate E (3.10 g, 7.78 mmol), tris(dibenzylideneacetone)dipalladium(0) (0.142 g, 0.156 mmol), XPhos (0.297 g, 0.622 mmol), sodium t-butoxide (2.242 g, 23.33 mmol), and xylene (50 mL) was stirred at 110° C. for 4.5 h. The reaction liquid was cooled to room temperature and then stirred after adding NH silica gel (aminosilica gel). After removing silica gel by filtration, the filtrate was concentrated under reduced pressure. The obtained residue was purified by silica gel column chromatography and recrystallization to obtain a white solid (3.22 g). The yield was 57%. XPhos mentioned above is 2-dicyclohexylphosphino-2',4', 6'-triisopropylbiphenyl.

The obtained product was identified as Compound 1 by the result of mass spectrometric analysis (m/e=728 to the molecular weight of 728.28).

Synthesis Example 2: Synthesis of Compound 2

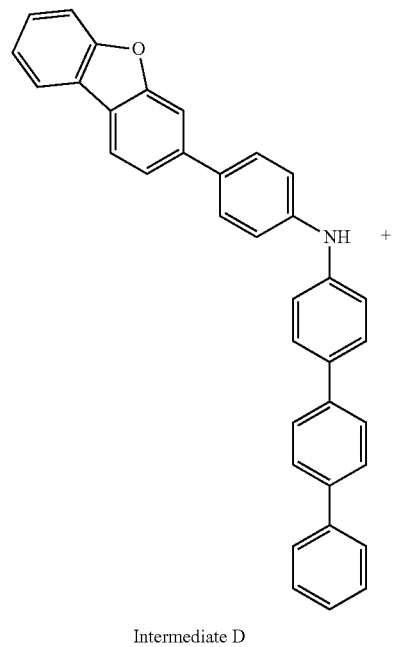

Intermediate D

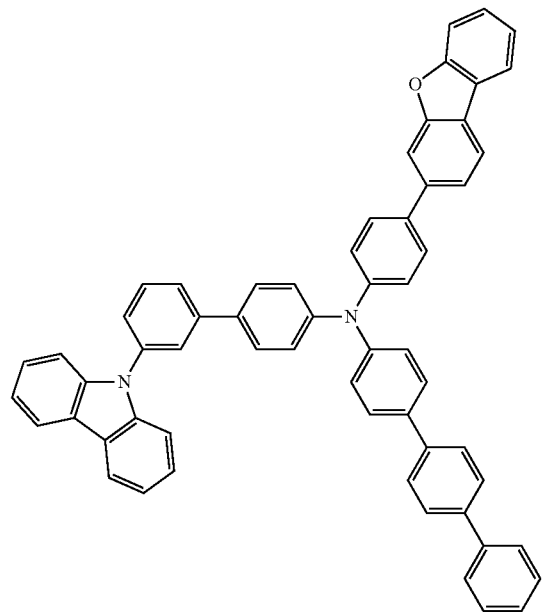

Compound 2

The procedure of Synthesis Example 1 was repeated except for using Intermediate D in place of Intermediate C.

The obtained product was identified as Compound 2 by the result of mass spectrometric analysis (m/e=804 to the molecular weight of 804.31).

Synthesis Example 3: Synthesis of Compound 3

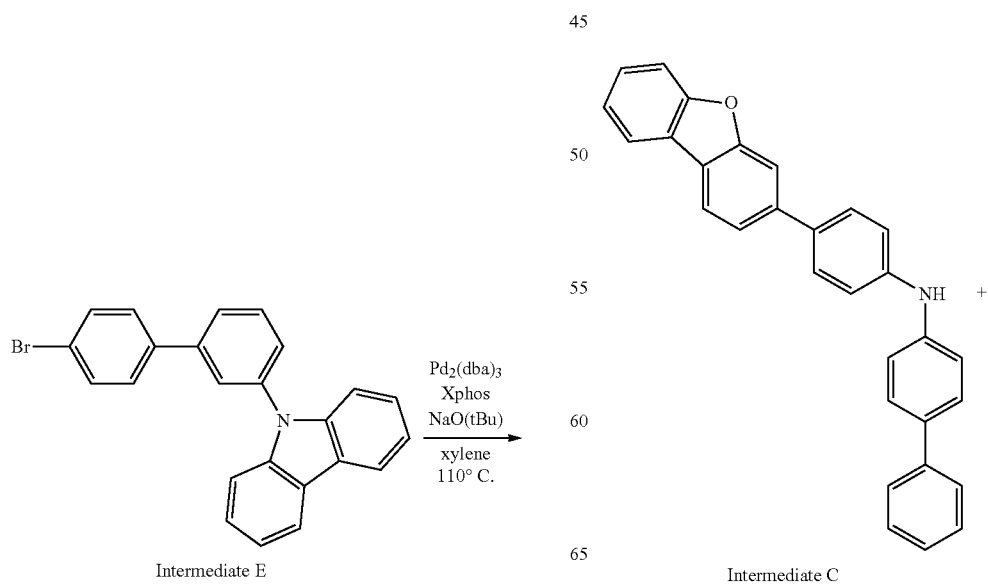

Intermediate E

Intermediate C

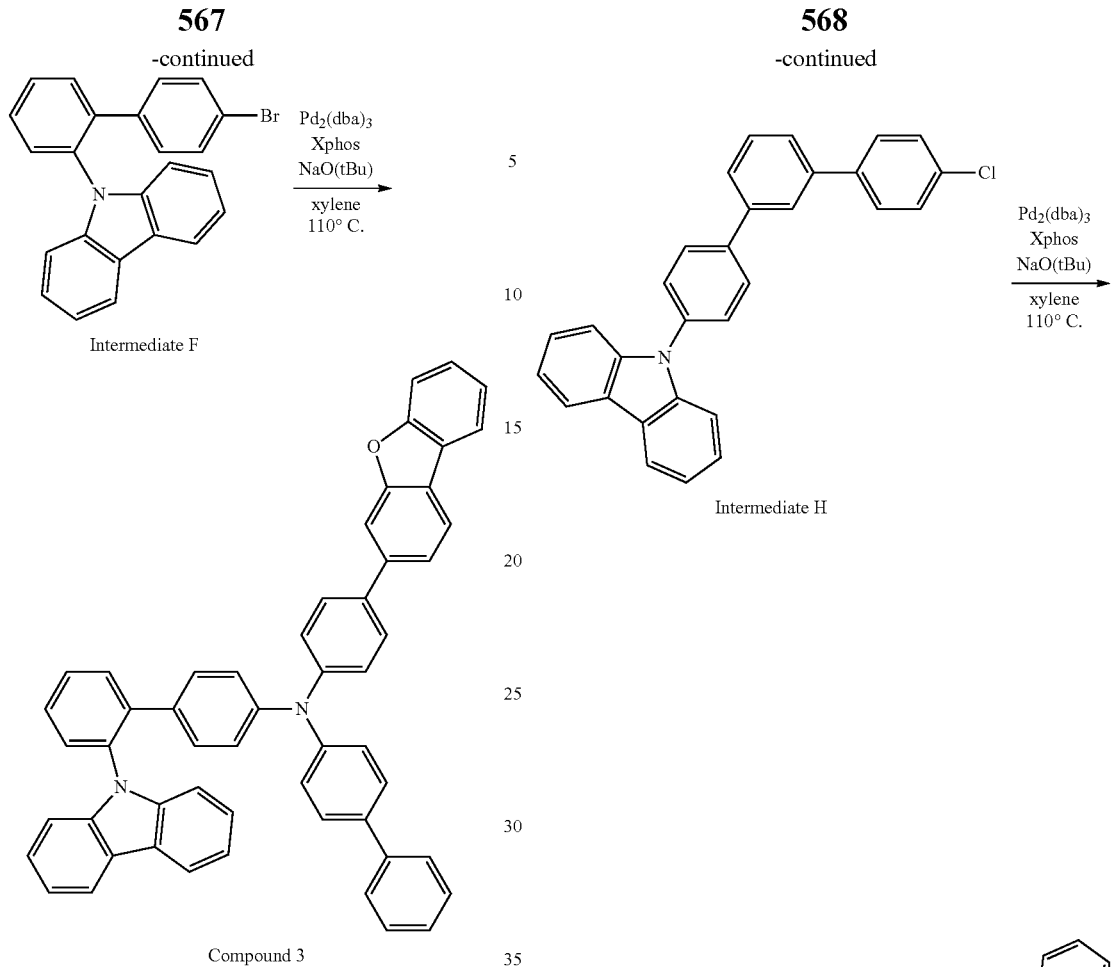

The procedure of Synthesis Example 1 was repeated except for using Intermediate F in place of Intermediate E. The obtained product was identified as Compound 3 by the result of mass spectrometric analysis (m/e=728 to the molecular weight of 728.28).

Synthesis Example 4: Synthesis of Compound 4

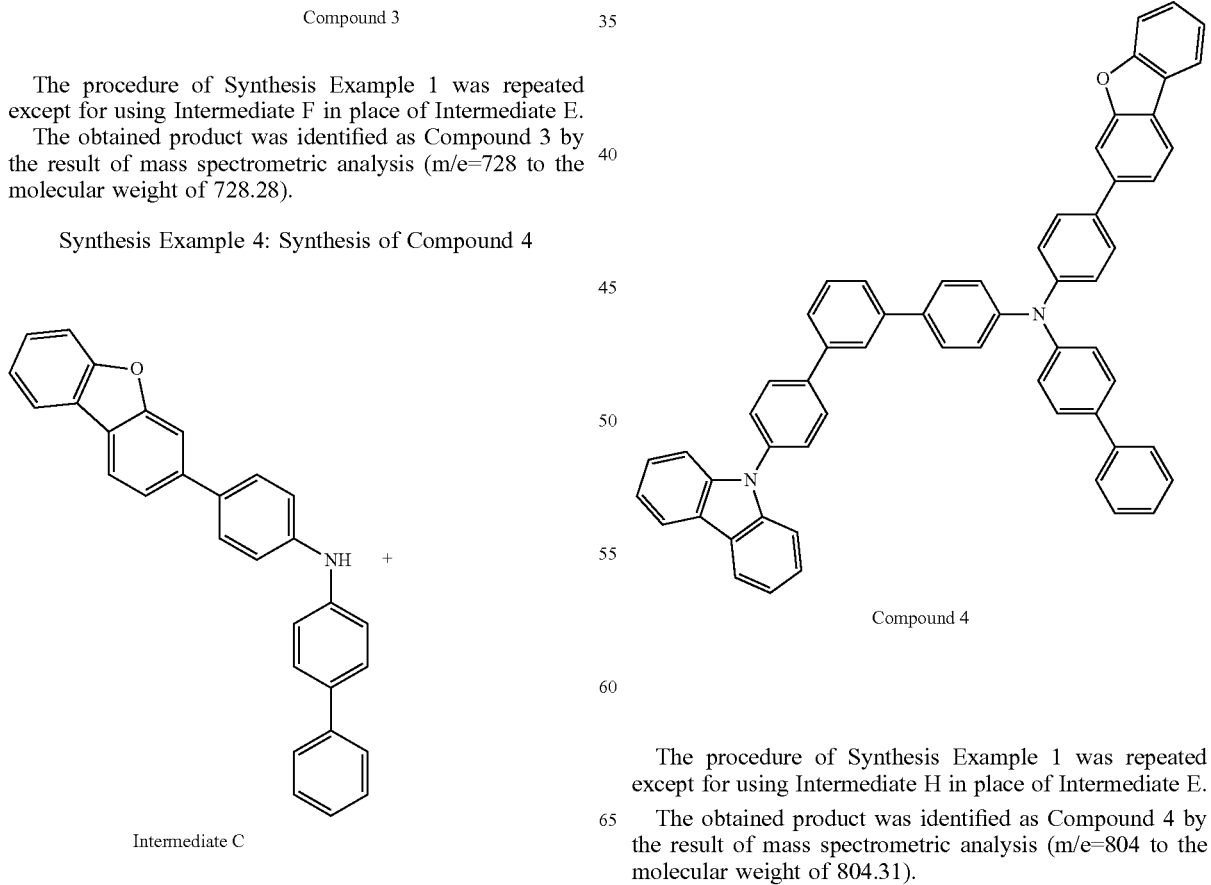

The procedure of Synthesis Example 1 was repeated except for using Intermediate H in place of Intermediate E. The obtained product was identified as Compound 4 by the result of mass spectrometric analysis (m/e=804 to the molecular weight of 804.31).

Synthesis Example 5: Synthesis of Compound 5

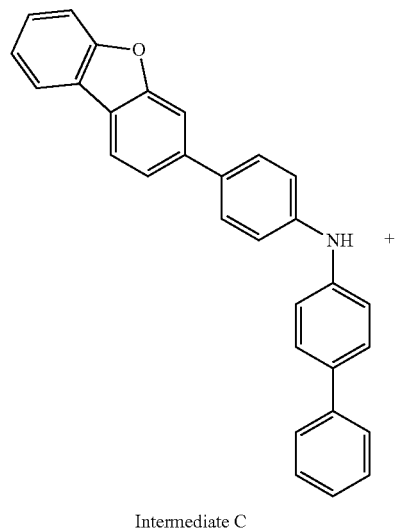

Intermediate C

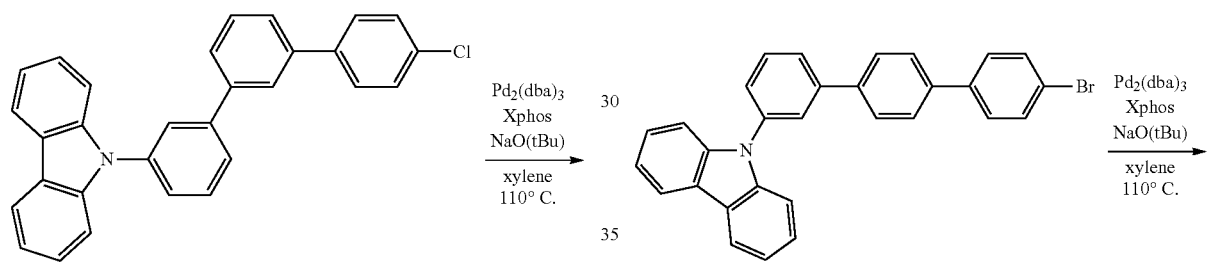

Intermediate I

Compound 5

The procedure of Synthesis Example 1 was repeated except for using Intermediate I in place of Intermediate E.

The obtained product was identified as Compound 5 by the result of mass spectrometric analysis (m/e=804 to the molecular weight of 804.31).

Synthesis Example 6: Synthesis of Compound 6

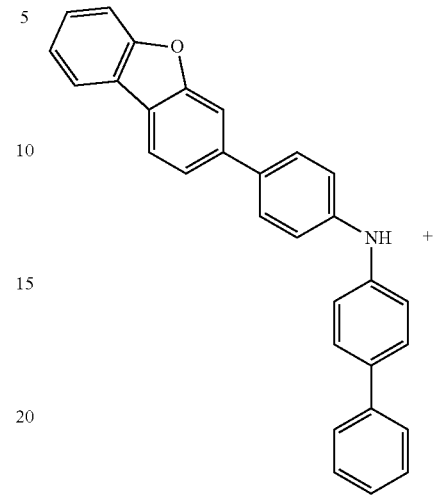

Intermediate C

Intermediate J

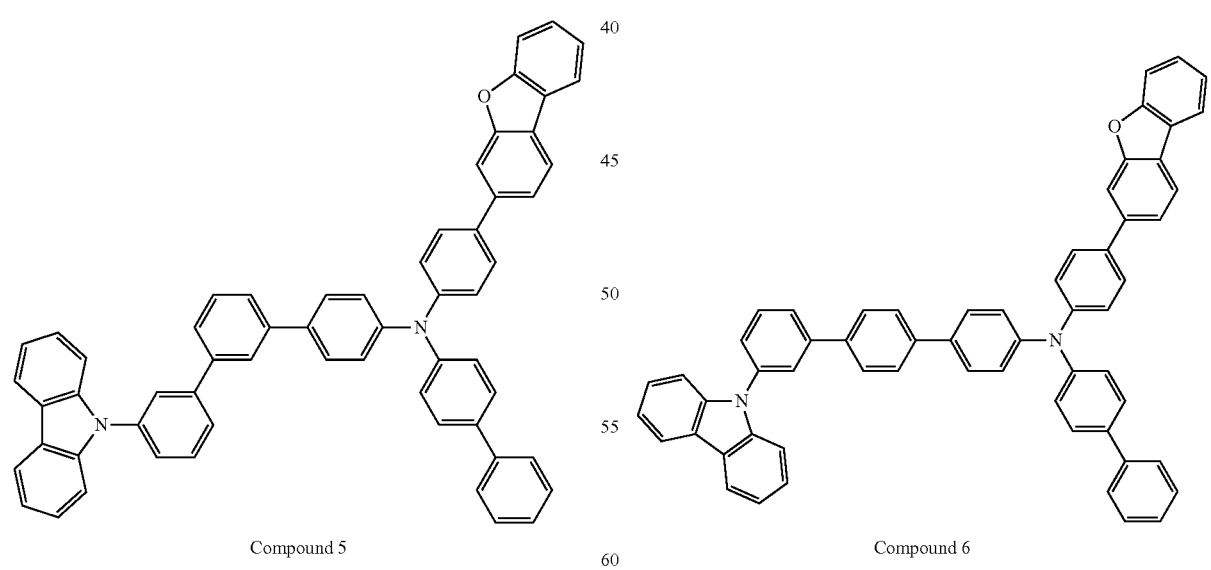

Compound 6

The procedure of Synthesis Example 1 was repeated except for using Intermediate J in place of Intermediate E.

The obtained product was identified as Compound 6 by the result of mass spectrometric analysis (m/e=804 to the molecular weight of 804.31).

Synthesis Example 7: Synthesis of Compound 7

Synthesis Example 8: Synthesis of Compound 8

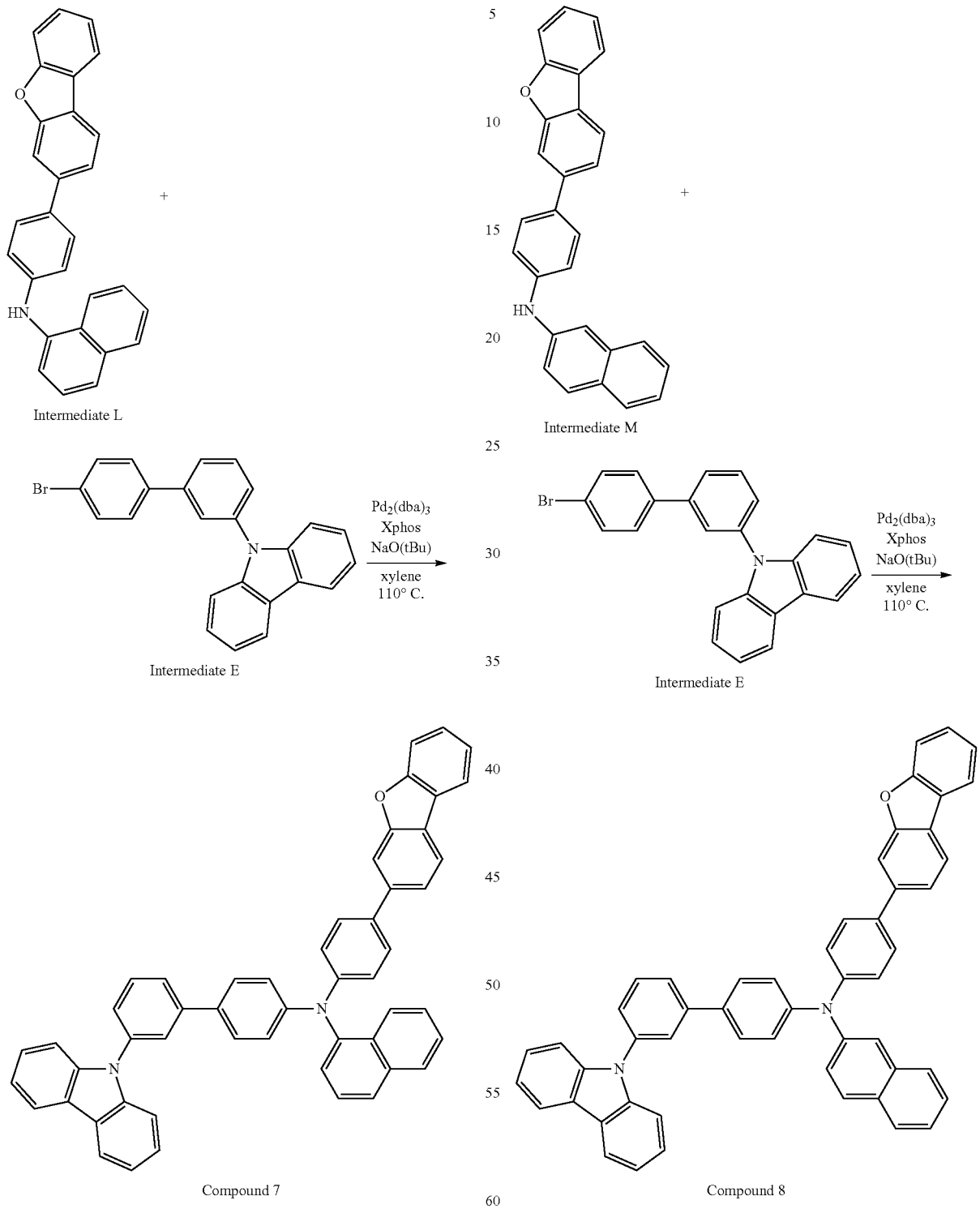

The procedure of Synthesis Example 1 was repeated except for using Intermediate L in place of Intermediate C.

The obtained product was identified as Compound 7 by the result of mass spectrometric analysis (m/e=702 to the molecular weight of 702.27).

The procedure of Synthesis Example 1 was repeated except for using Intermediate M in place of Intermediate C.

The obtained product was identified as Compound 8 by the result of mass spectrometric analysis (m/e=702 to the molecular weight of 702.27).

Synthesis Example 9: Synthesis of Compound 9

Synthesis Example 10: Synthesis of Compound 10

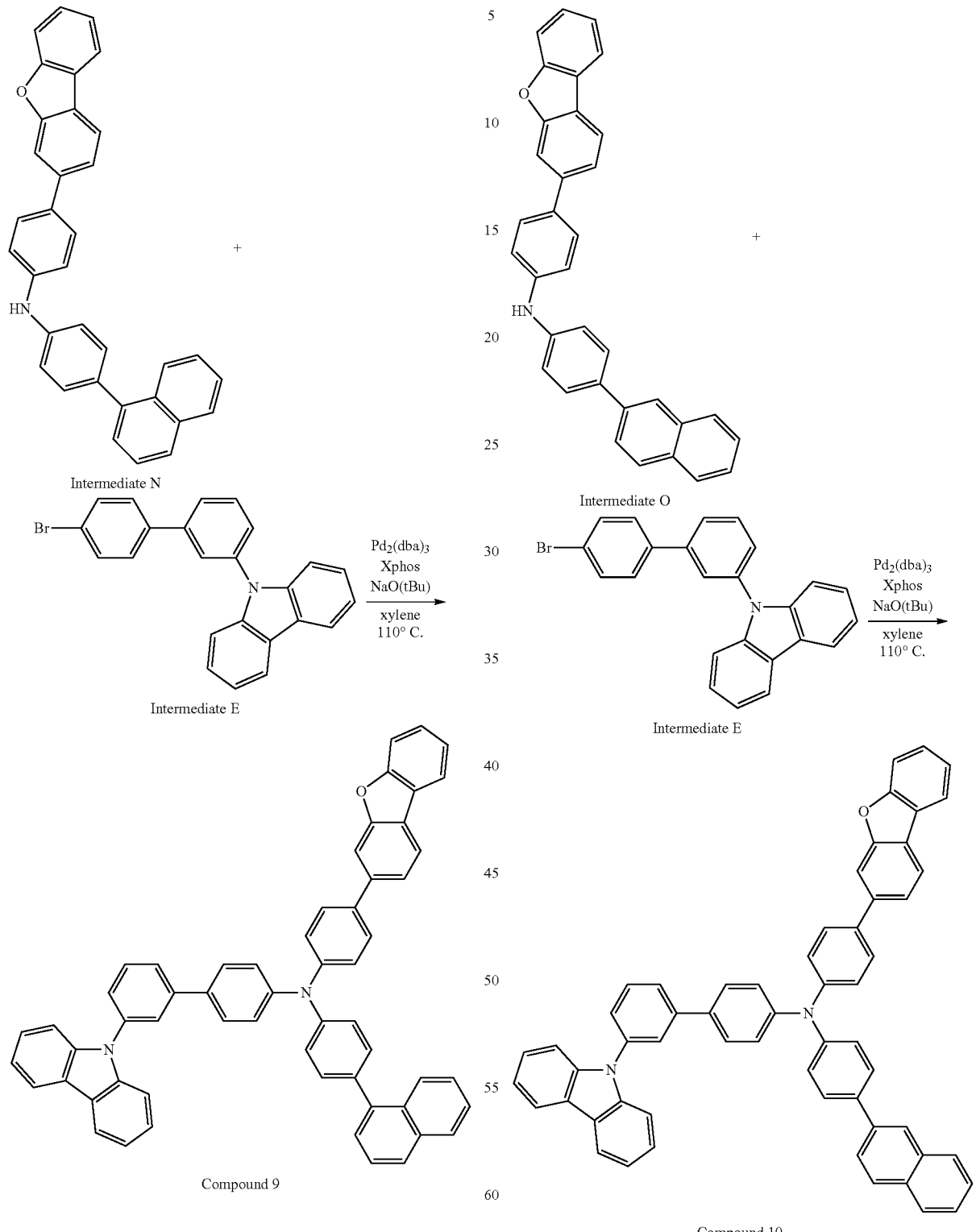

Compound 9

Compound 10

The procedure of Synthesis Example 1 was repeated except for using Intermediate N in place of Intermediate C.

The obtained product was identified as Compound 9 by the result of mass spectrometric analysis (m/e=778 to the molecular weight of 778.30).

The procedure of Synthesis Example 1 was repeated except for using Intermediate O in place of Intermediate C.

575

The obtained product was identified as Compound 10 by the result of mass spectrometric analysis (m/e=778 to the molecular weight of 778.30).

Synthesis Example 11: Synthesis of Compound 11

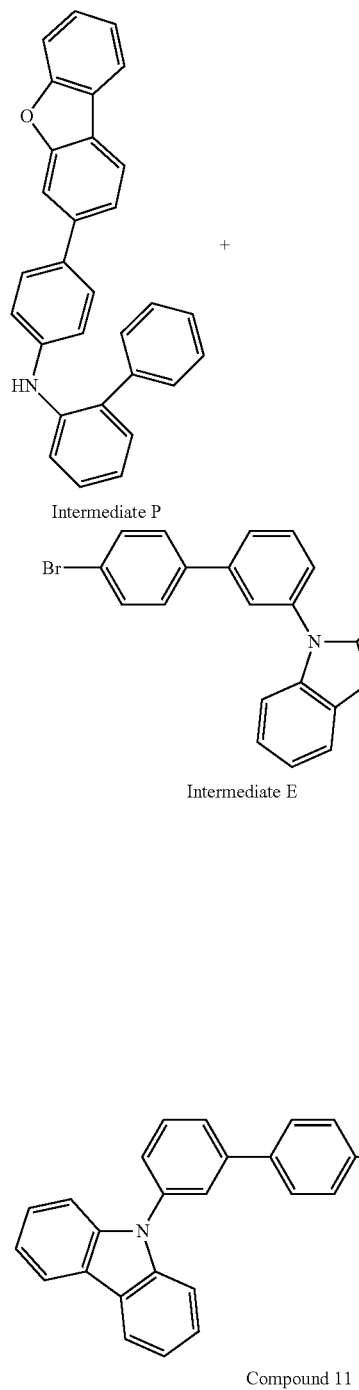

Intermediate P

Intermediate E

Compound 11

The procedure of Synthesis Example 1 was repeated except for using Intermediate P in place of Intermediate C.

The obtained product was identified as Compound 11 by the result of mass spectrometric analysis (m/e=728 to the molecular weight of 728.28).

576

Synthesis Example 12: Synthesis of Compound 12

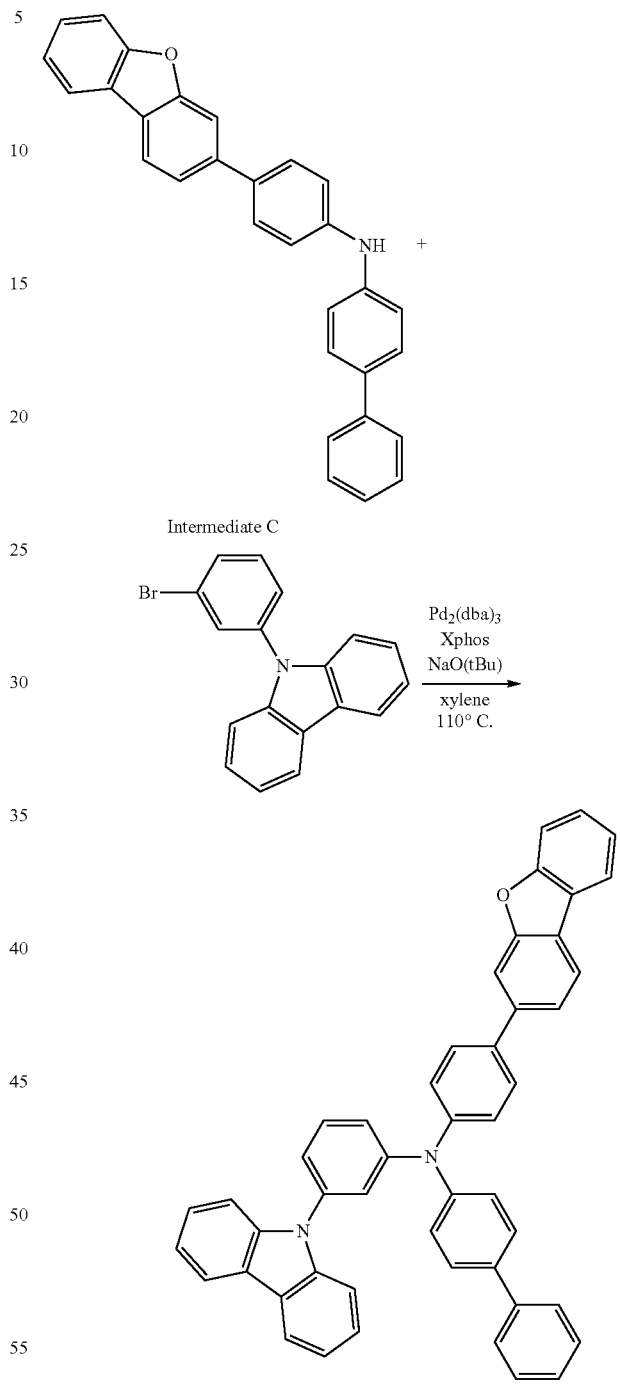

Intermediate C

Compound 12

The procedure of Synthesis Example 1 was repeated except for using 9-(3-bromophenyl)carbazole in place of Intermediate E.

The obtained product was identified as Compound 12 by the result of mass spectrometric analysis (m/e=652 to the molecular weight of 652.25).

Synthesis Example 13: Synthesis of Compound 13

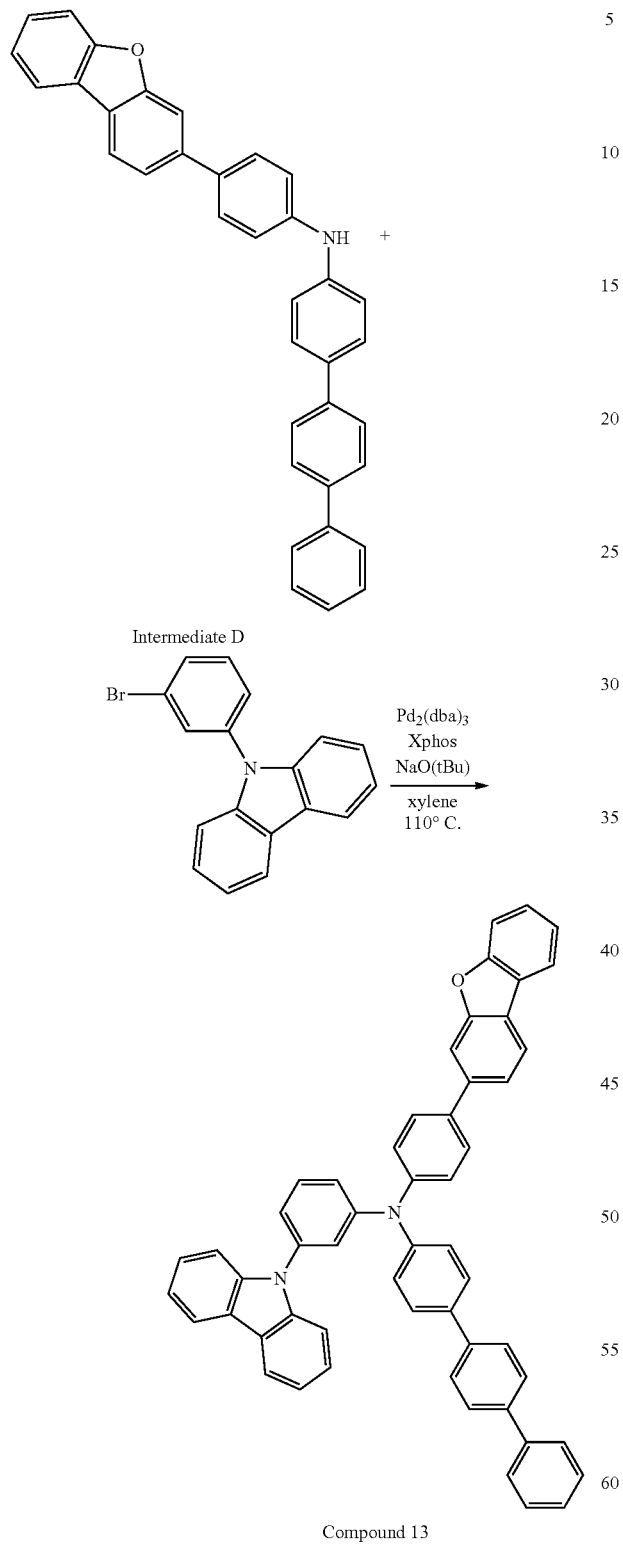

Intermediate D

Compound 13

The procedure of Synthesis Example 2 was repeated except for using 9-(3-bromophenyl)carbazole in place of Intermediate E.

The obtained product was identified as Compound 13 by the result of mass spectrometric analysis (m/e=728 to the molecular weight of 728.28).

Example 1

Production of Organic EL Device

A 25 mm×75 mm×1.1 mm glass substrate having ITO transparent electrode (anode) (product of Geomatec Company) was ultrasonically cleaned in isopropyl alcohol for 5 min and then UV/ozone cleaned for 30 min. The thickness of ITO transparent electrode was 130 nm.

The cleaned glass substrate having an ITO transparent electrode line was mounted to a substrate holder of a vacuum vapor deposition apparatus. First, the compound HI-1 was vapor-deposited on the surface having the ITO transparent electrode line so as to cover the transparent electrode to form an HI-1 film with a thickness of 5 nm, thereby forming a hole injecting layer.

On the hole injecting layer, the compound HT-1 (first hole transporting material) was vapor-deposited to form an HT-1 film with a thickness of 80 nm, thereby forming a first hole transporting layer.

On the first hole transporting layer, the compound 1 synthesized in Synthesis Example 1 was vapor-deposited to form an HT-2 film with a thickness of 10 nm, thereby forming a second hole transporting layer.

Then, on the second hole transporting layer, the compound BH-1 (host material) and the compound BD-1 (dopant material) were vapor co-deposited to form a co-deposited film with a thickness of 25 nm. The concentration of the compound BD-1 was 4.0% by mass. The co-deposited film works as a light emitting layer.

Then, on the light emitting layer, the compound ET-1 was vapor-deposited to form an ET-1 film with a thickness of 10 nm, thereby forming a first electron transporting layer.

On the first electron transporting layer, the compound ET-2 was vapor-deposited to form an ET-2 film with a thickness of 15 nm, thereby forming a second electron transporting layer.

On the second electron transporting layer, LiF was vapor-deposited to form a LiF film with a thickness of 1 nm, thereby forming an electron injecting electrode (cathode).

Then, metallic Al was vapor-deposited on the LiF film to form a metallic Al film with a thickness of 80 nm, thereby forming a metallic Al cathode.

Evaluation of Organic EL Device

The organic EL device thus produced was operated at a current density of 10 mA/cm$^2$ and the spectral radiance spectrum was measured by using a spectroradiometer CS-1000 manufactured by Konica Minolta. The emission peak wavelength λp (unit of measure: nm) was determined from the obtained spectral radiance spectrum.

In addition, the time taken until the luminance was reduced to 95% of the initial luminance (LT95) was measured by operating the organic EL device at a current density of 50 mA/cm$^2$.

The results are shown in Table 1.

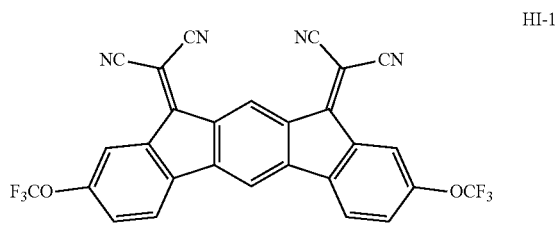

HI-1

HT-1
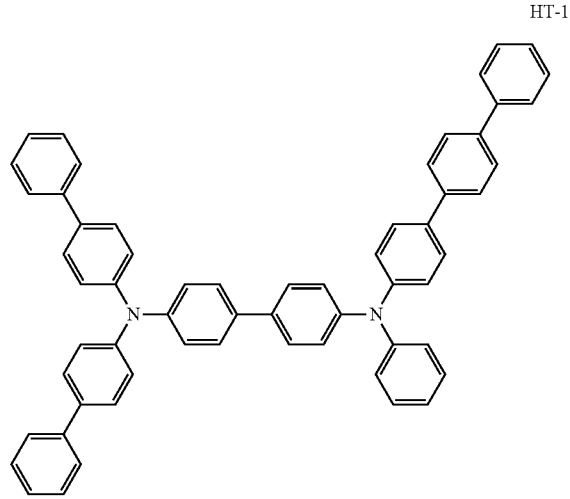
Compound 1
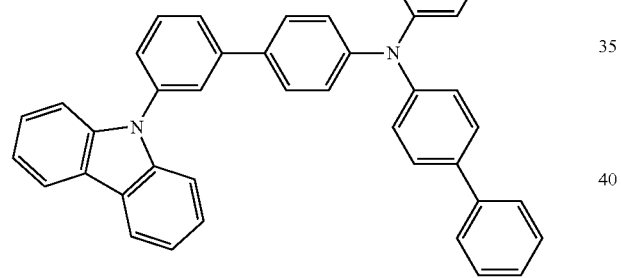
BH-1
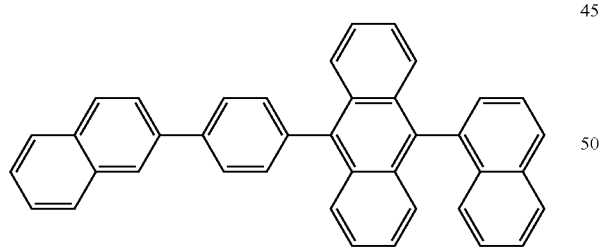
BD-1
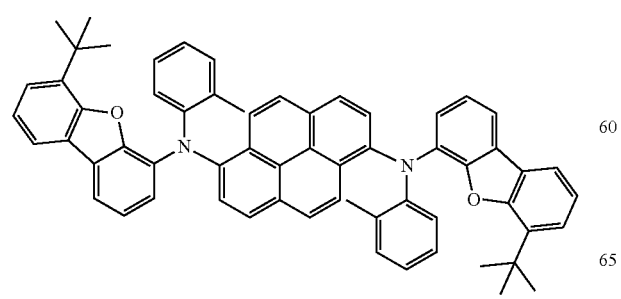
ET-1
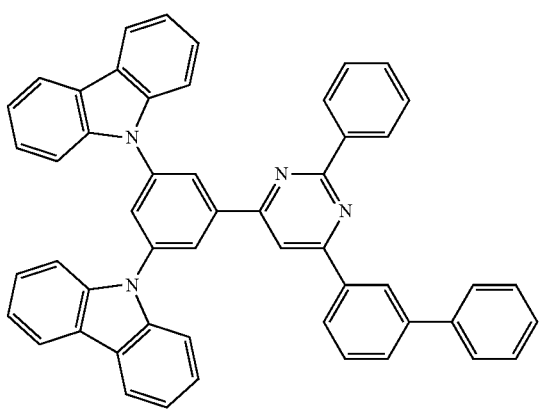
ET-2
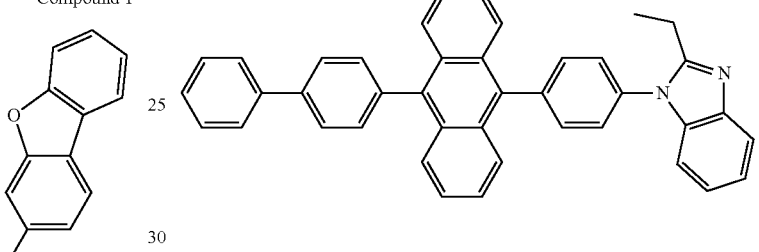
Examples 2 to 13, Comparative Examples 1 to 4
Each organic EL device was produced in the same manner as in Example 1 except for using each of the compounds 2 to 13 and the comparative compounds 1 to 4 in place of the compound 1 and evaluated in the same manner as in Example 1. The results are shown in Table 1.
Compound 2
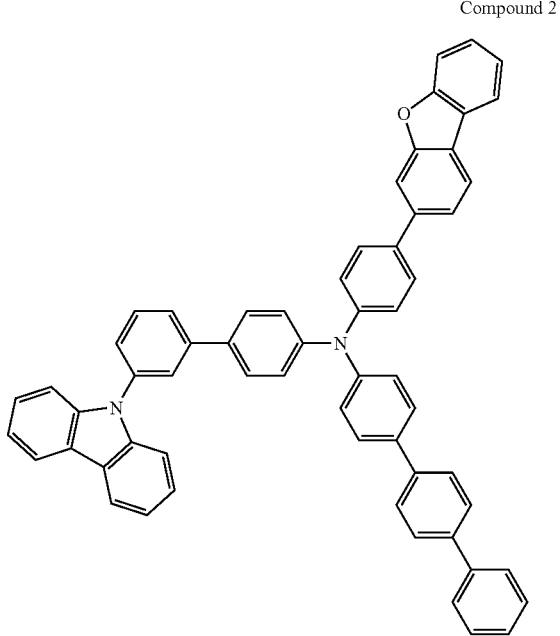

Compound 3
Compound 4
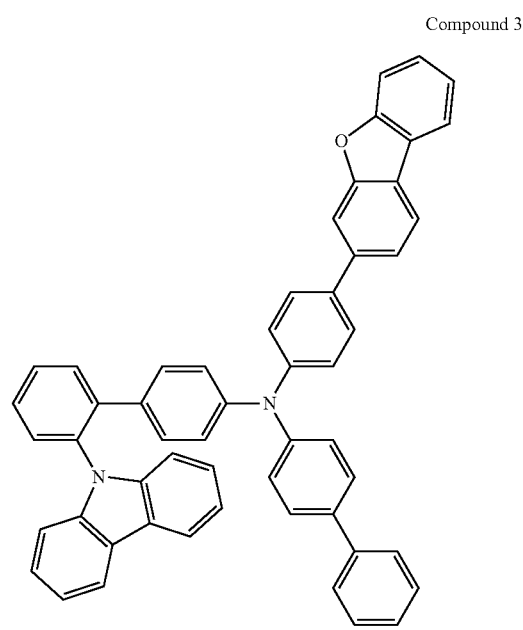
Compound 5
Compound 6
Compound 7
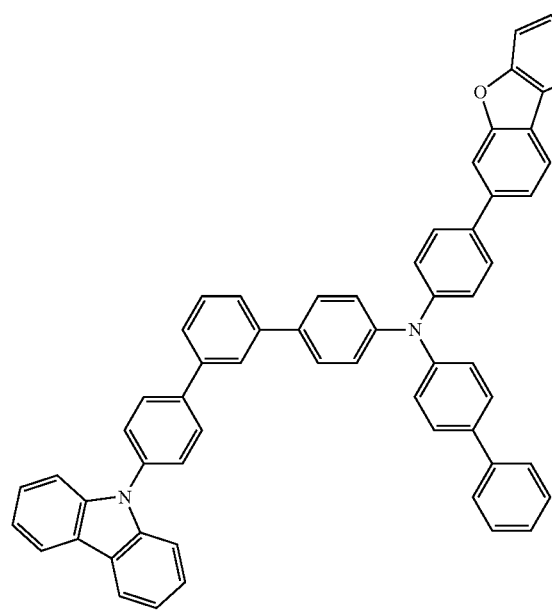

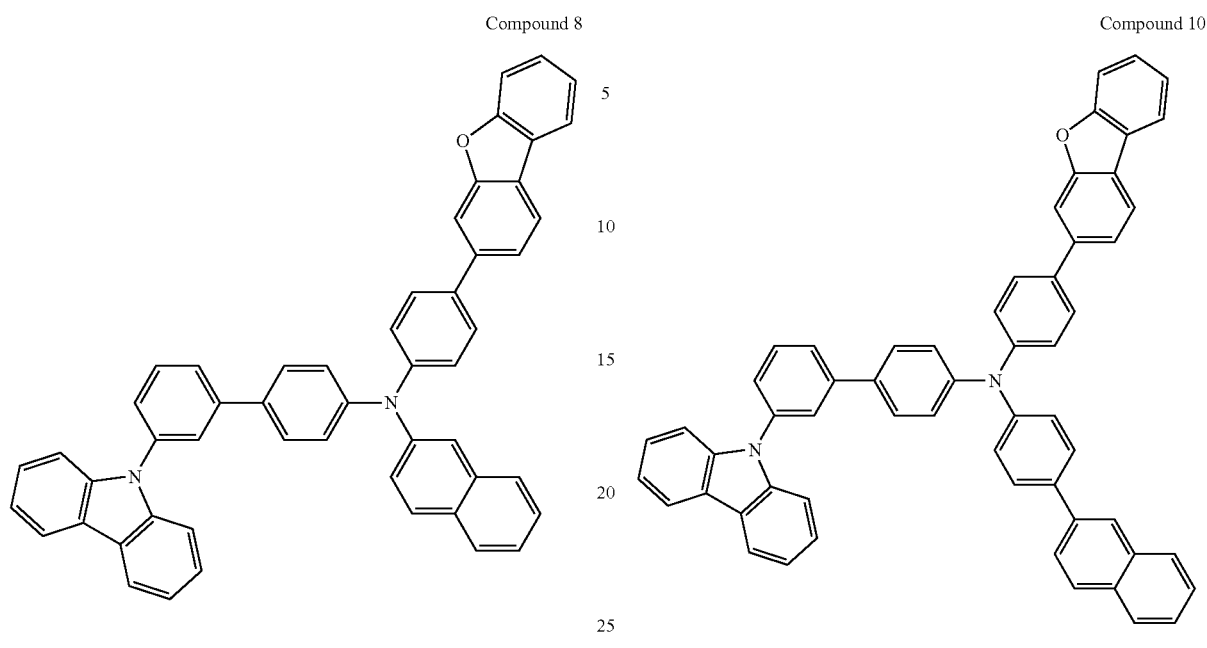
Compound 8
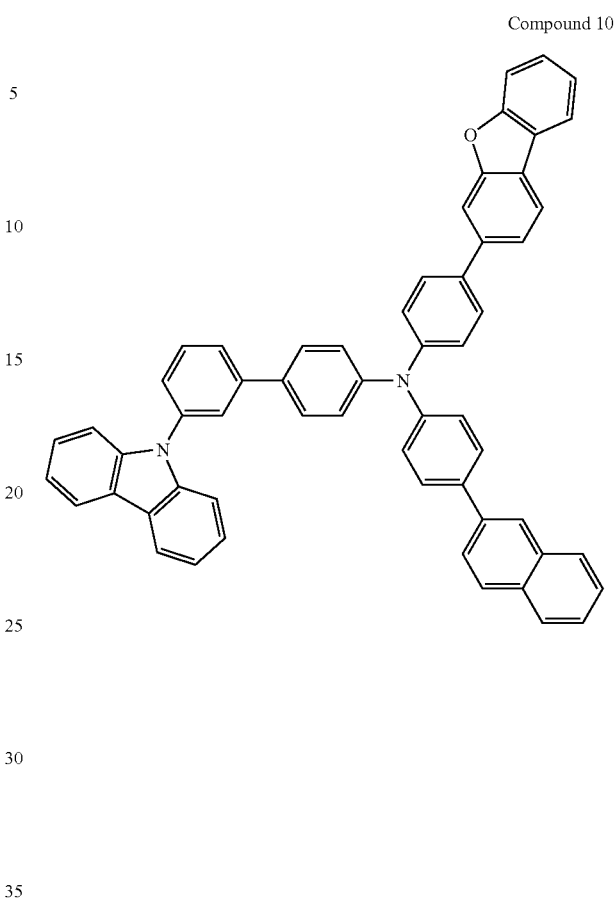
Compound 10
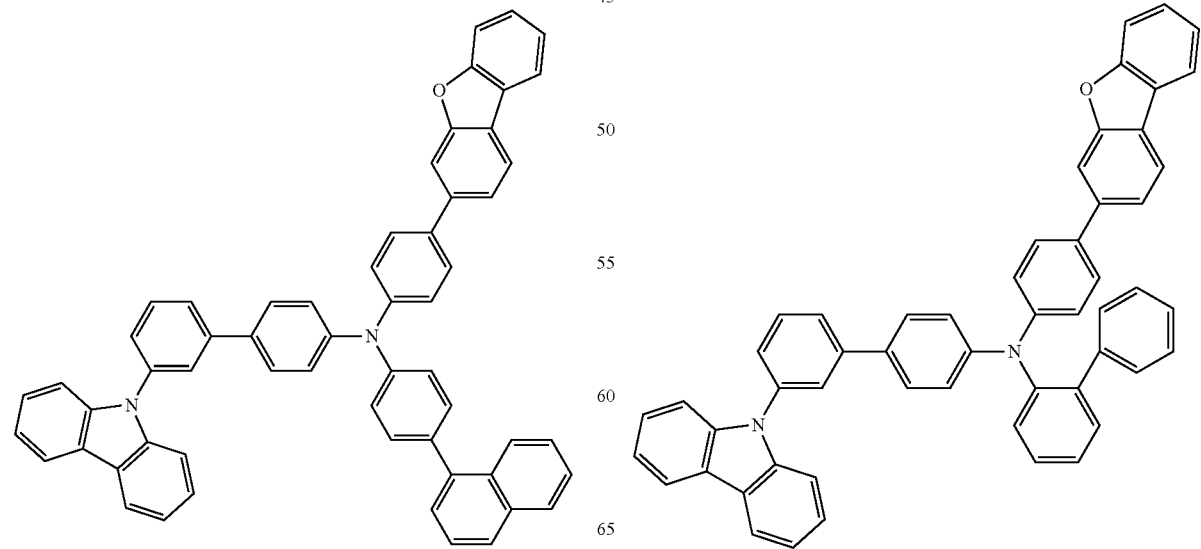
Compound 9
Compound 11

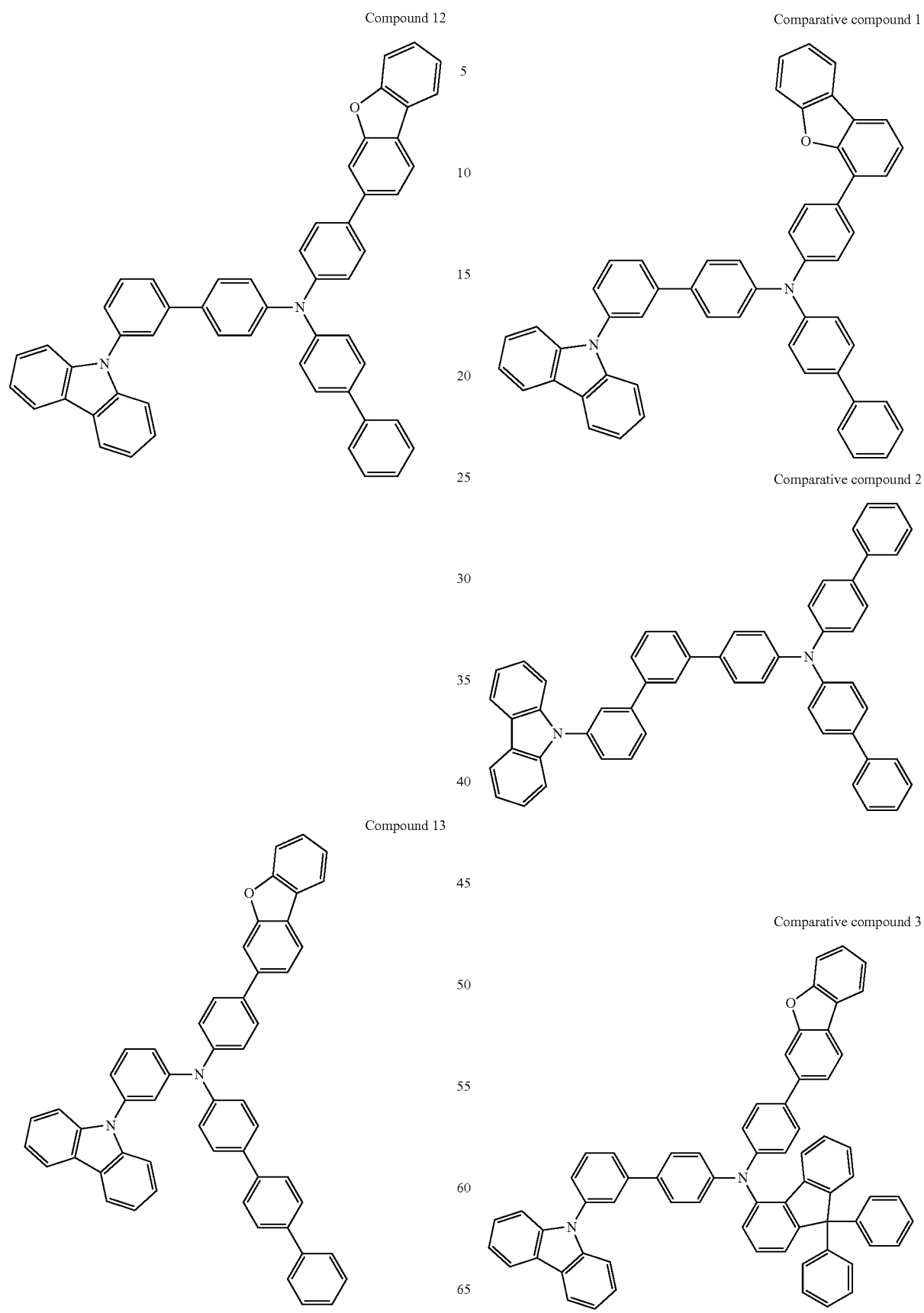

-continued

Comparative compound 4

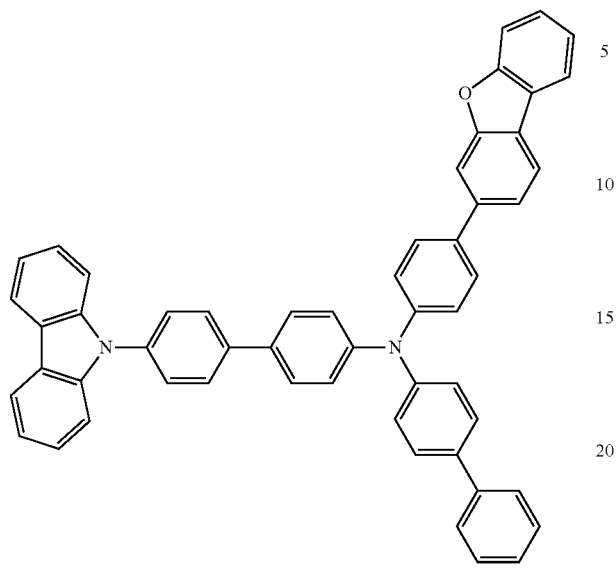

TABLE 1

|  | Compound of second hole transporting layer | LT95 (h) | Emission peak wavelength λp (nm) |
| --- | --- | --- | --- |
| Examples | | | |
| 1 | Compound 1 | 140 | 455 |
| 2 | Compound 2 | 150 | 455 |
| 3 | Compound 3 | 145 | 455 |
| 4 | Compound 4 | 145 | 455 |
| 5 | Compound 5 | 150 | 455 |
| 6 | Compound 6 | 150 | 455 |
| 7 | Compound 7 | 130 | 455 |
| 8 | Compound 8 | 130 | 455 |
| 9 | Compound 9 | 140 | 455 |
| 10 | Compound 10 | 135 | 455 |
| 11 | Compound 11 | 130 | 455 |
| 12 | Compound 12 | 140 | 455 |
| 13 | Compound 13 | 150 | 455 |
| Comparative Examples | | | |
| 1 | Comparative compound 1 | 100 | 455 |
| 2 | Comparative compound 2 | 50 | 455 |
| 3 | Comparative compound 3 | 40 | 455 |
| 4 | Comparative compound 4 | 90 | 455 |

As seen from Table 1, as compared with the comparative compounds 1 to 4, the compounds 1 to 13 in an embodiment of the invention provided the organic EL devices each having an improved device lifetime.

REFERENCE SIGNS LIST

1: Organic EL device
2: Substrate
3: Anode
4: Cathode
5: Light emitting layer
6: Anode-side organic layer
7: Cathode-side organic layer
10: Emission unit

The invention claimed is:
1. A compound represented by formula (1):

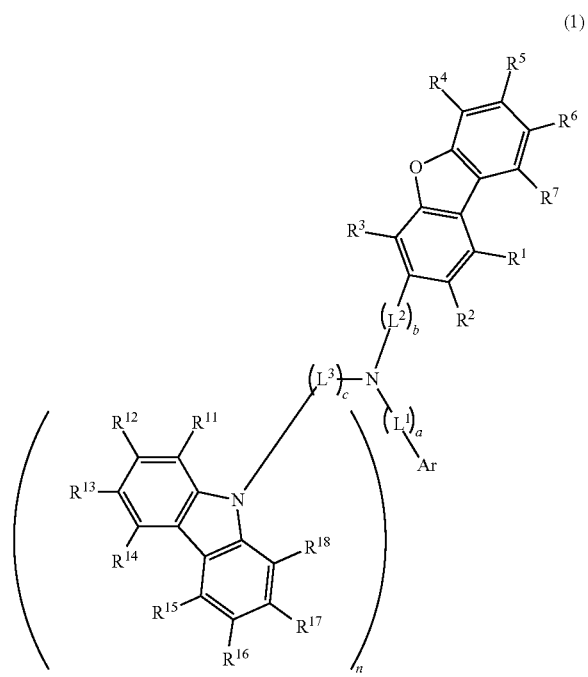

(1)

wherein:
$R^1$ to $R^7$ and $R^{11}$ to $R^{18}$ are each independently
a hydrogen atom,
a substituted or unsubstituted alkyl group having 1 to 30 carbon atoms,
a substituted or unsubstituted cycloalkyl group having 3 to 30 ring carbon atoms,
a substituted or unsubstituted aryl group having 6 to 30 ring carbon atoms,
a substituted or unsubstituted aralkyl group having 7 to 36 carbon atoms,
a mono- or di-substituted amino group having a substituent selected from the group consisting of a substituted or unsubstituted alkyl group having 1 to 30 carbon atoms and a substituted or unsubstituted aryl group having 6 to 30 ring carbon atoms,
a substituted or unsubstituted alkoxy group having 1 to 30 carbon atoms,
a substituted or unsubstituted aryloxy group having 6 to 30 ring carbon atoms,
a mono-, di- or tri-substituted silyl group having a substituent selected from the group consisting of a substituted or unsubstituted alkyl group having 1 to 30 carbon atoms and a substituted or unsubstituted aryl group having 6 to 30 ring carbon atoms,
a substituted or unsubstituted haloalkyl group having 1 to 30 carbon atoms,
a substituted or unsubstituted haloalkoxy group having 1 to 30 carbon atoms, a substituted or unsubstituted heteroaryl group having 5 to 30 ring atoms, a halogen atom, a cyano group, or a nitro group;

$R^1$ and $R^2$, adjacent two selected from $R^4$ to $R^7$, adjacent two selected from $R^{11}$ to $R^{14}$ and adjacent two selected from $R^{15}$ to $R^{18}$ may be bonded to each other to form a ring structure;

Ar is a substituted or unsubstituted aryl group having 6 to 30 ring carbon atoms, wherein the aryl group is composed of only one or more six-membered rings;

n is 1 or 2;

a is 0, 1, 2, or 3;

when a is 0, Ar is directly bonded to the central nitrogen atom;

when a is 2 or 3, two or three $L^1$'s may be the same or different;

b is 1, 2, or 3;

when b is 2 or 3, two or three $L^2$'s may be the same or different;

c is 1, 2, or 3;

when c is 1, $L^3$ is a group represented by formula (L3-1) or (L3-2);

when c is 2 or 3, two or three $L^3$'s may be the same or different, one or more $L^3$ is selected from the group consisting of formula (L3-1) and (L3-2) and any remaining $L^3$ is a substituted or unsubstituted aromatic hydrocarbon group having 6 to 18 ring carbon atoms:

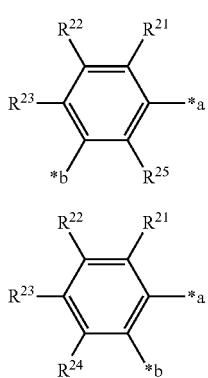

wherein:

$R^{21}$ to $R^{25}$ are each independently as defined above with respect to $R^1$ to $R^7$, wherein $R^{21}$ to $R^{23}$ are not a heteroaryl group;

when c is 1, *a is directly bonded to the central nitrogen atom and *b is directly bonded to the nitrogen atom of the carbazole structure;

when c is 2 or 3, *a is directly bonded to the central nitrogen atom or is bonded to L3 and *b is directly bonded to the nitrogen atom of the carbazole structure or bonded to L3 and $L^1$ and $L^2$ are each independently a substituted or unsubstituted aromatic hydrocarbon group having 6 to 18 ring carbon atoms.

2. The compound according to claim 1, which is represented by formula (2):

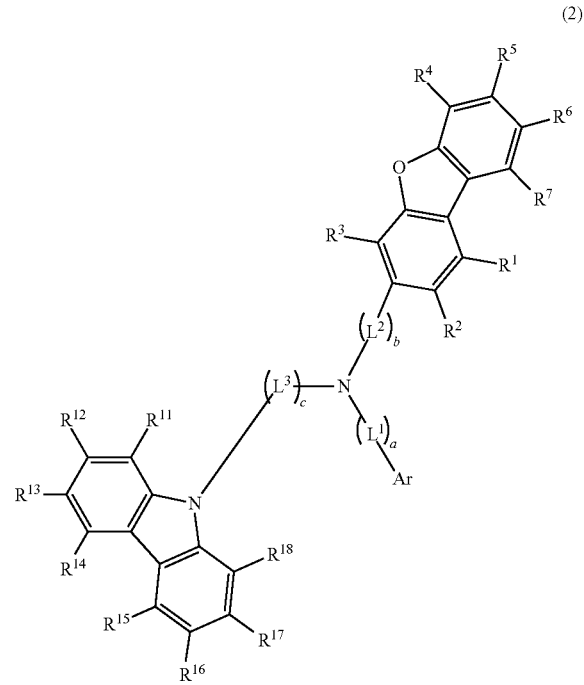

3. The compound according to claim 1, wherein the aryl group of the substituted or unsubstituted aryl group having 6 to 30 ring carbon atoms represented by Ar is a phenyl group, a biphenylyl group, a terphenylyl group, a naphthyl group, an anthryl group, a benzanthryl group, a phenanthryl group, a benzophenanthryl group, a phenalenyl group, a picenyl group, a pentaphenyl group, a pyrenyl group, a chrysenyl group, a benzochrysenyl group, a perylenyl group, or a triphenylenyl group.

4. The compound according to claim 1, wherein the aryl group of the substituted or unsubstituted aryl group having 6 to 30 ring carbon atoms represented by Ar is a phenyl group, a biphenylyl group, a terphenylyl group, a naphthyl group, a phenanthryl group, or a triphenylenyl group.

5. The compound according to claim 1, wherein the aryl group of the substituted or unsubstituted aryl group having 6 to 30 ring carbon atoms represented by Ar is selected from the group consisting of:

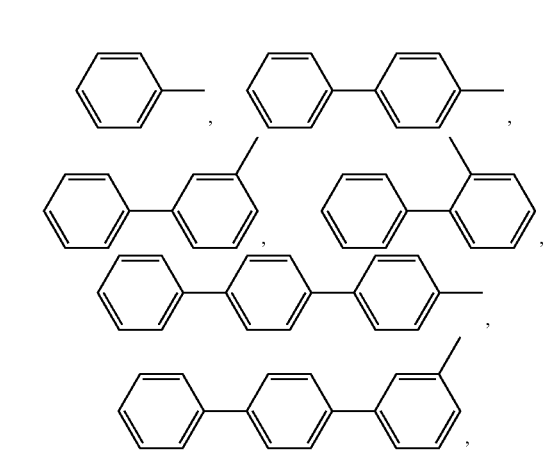

-continued

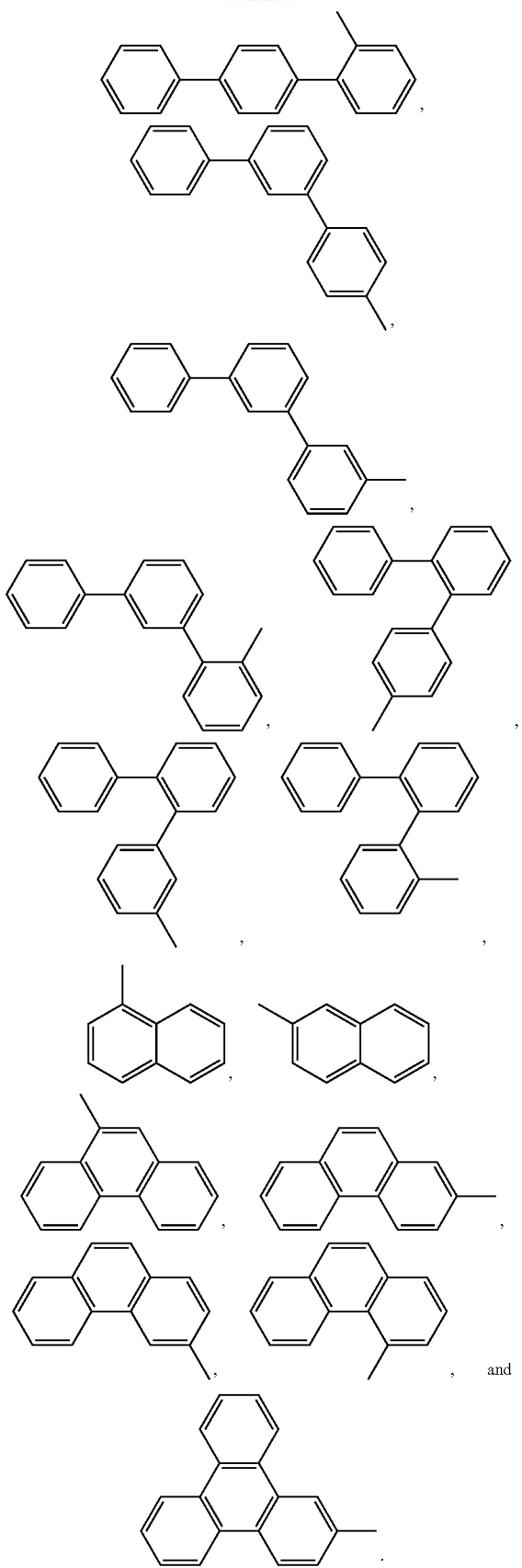

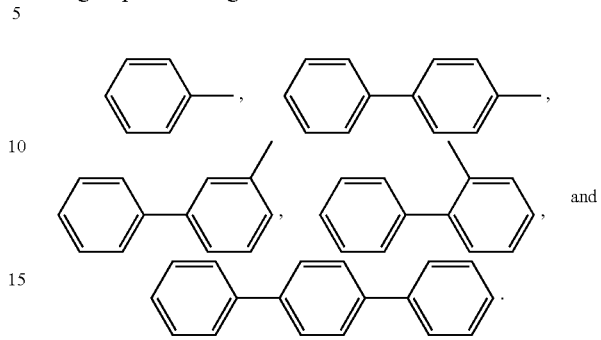

6. The compound according to claim 1, wherein the aryl group of the substituted or unsubstituted aryl group having 6 to 30 ring carbon atoms represented by Ar is selected from the group consisting of:

7. The compound according to claim 1, wherein the aromatic hydrocarbon group of the substituted or unsubstituted aromatic hydrocarbon group having 6 to 18 ring carbon atoms represented by each of $L^1$ and $L^2$ is independently a phenylene group, a biphenylylene group, a terphenylylene group, a naphthylene group, an anthrylene group, a benzanthrylene group, a phenanthrylene group, a benzophenanthrylene group, a picenylene group, a pentaphenylene group, a pyrenylene group, a chrysenylene group, a benzochrysenylene group, or a triphenylenylene group.

8. The compound according to claim 1, wherein the aromatic hydrocarbon group of the substituted or unsubstituted aromatic hydrocarbon group having 6 to 18 ring carbon atoms represented by each of $L^1$ and $L^2$ is independently a phenylene group, a biphenylylene group, a terphenylylene group, a naphthylene group, or a phenanthrylene group.

9. The compound according to claim 1, wherein:
the aromatic hydrocarbon group of the substituted or unsubstituted aromatic hydrocarbon group having 6 to 18 ring carbon atoms represented by $L^1$ is a phenylene group, a biphenylylene group, or a naphthylene group; and
the aromatic hydrocarbon group of the substituted or unsubstituted aromatic hydrocarbon group having 6 to 18 ring carbon atoms represented by $L^2$ is a phenylene group or a biphenylylene group.

10. The compound according to claim 1, wherein:
the aromatic hydrocarbon group of the substituted or unsubstituted aromatic hydrocarbon group having 6 to 18 ring carbon atoms represented by $L^1$ is a phenylene group; and
the aromatic hydrocarbon group of the substituted or unsubstituted aromatic hydrocarbon group having 6 to 18 ring carbon atoms represented by $L^2$ is a phenylene group or a biphenylylene group.

11. The compound according to claim 1, wherein the aromatic hydrocarbon group of the substituted or unsubstituted aromatic hydrocarbon group having 6 to 18 ring carbon atoms represented by each of $L^1$ and $L^2$ is a phenylene group.

12. The compound according to claim 1, wherein:
the aromatic hydrocarbon group of the substituted or unsubstituted aromatic hydrocarbon group having 6 to 18 ring carbon atoms represented by $L^1$ is an o-phenylene group, a m-phenylene group, or a p-phenylene group; and the aromatic hydrocarbon group of the substituted or unsubstituted aromatic hydrocarbon group having 6 to 18 ring carbon atoms represented by $L^2$ is an o-phenylene group, a m-phenylene group, a p-phenylene group, a 4,4'-biphenylylene group, a 4,3'-biphenylylene group, a 4,2'-biphenylylene group, a 1,4-naphthylene group, a 2,6-naphthylene group, or a 2,7-phenanthrylene group.

13. The compound according to claim 1, wherein $-(L^3)_c-$ in formula (1) is selected from the group consisting of:

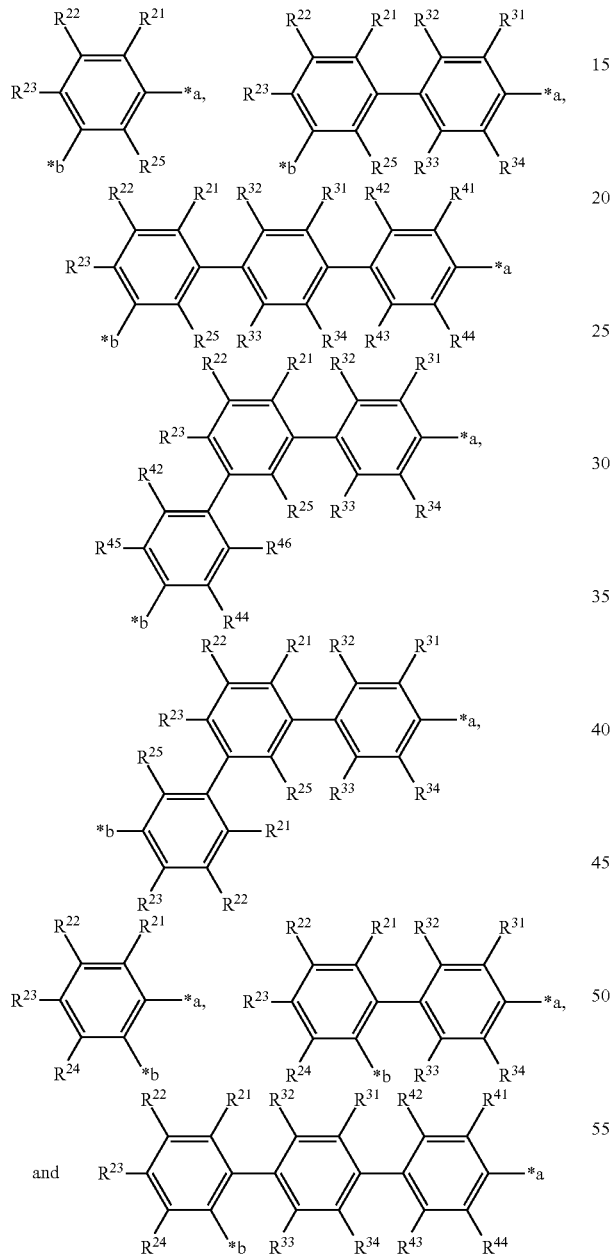

wherein:
$R^{21}$ to $R^{25}$, $R^{31}$ to $R^{34}$, and $R^{41}$ to $R^{46}$ are each independently as defined above with respect to $R^1$ to $R^7$,
*a is directly bonded to the central nitrogen atom, and
*b is directly bonded to the nitrogen atom of the carbazole structure.

14. The compound according to claim 1, wherein $-(L^3)_c-$ in formula (1) is selected from the group consisting of:

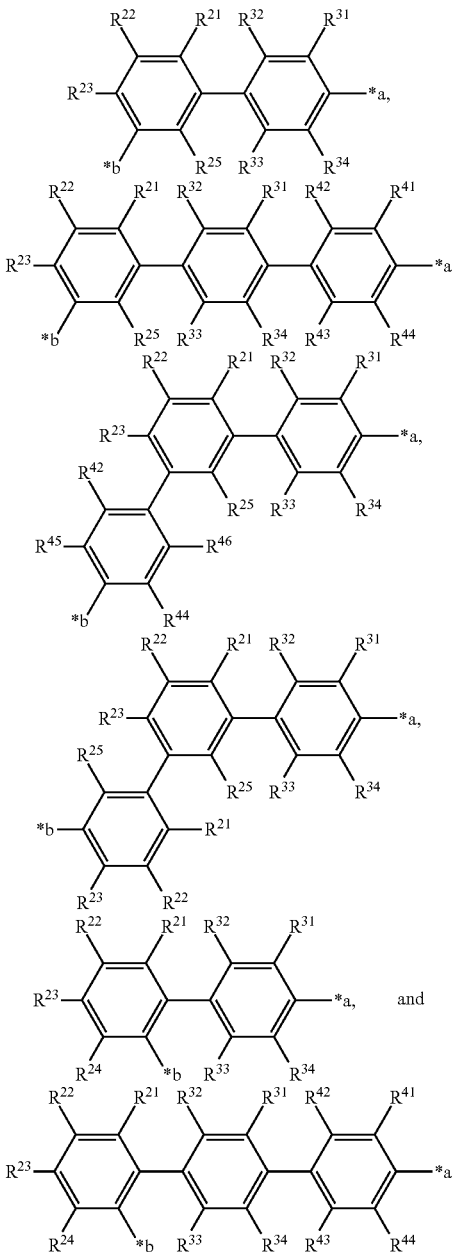

wherein:
$R^{21}$ to $R^{25}$, $R^{31}$ to $R^{34}$, and $R^{41}$ to $R^{46}$ are each independently as defined above with respect to $R^1$ to $R^7$,
*a is directly bonded to the central nitrogen atom, and
*b is directly bonded to the nitrogen atom of the carbazole structure.

15. The compound according to claim 1, wherein a is 0 or 1.

16. The compound according to claim 1, wherein a is 0.

17. The compound according to claim 1, wherein b is 1 and c is 2 or 3.

18. The compound according to claim 1, wherein:
the aryl group of the substituted or unsubstituted aryl group having 6 to 30 ring carbon atoms represented by Ar is selected from the group consisting of:

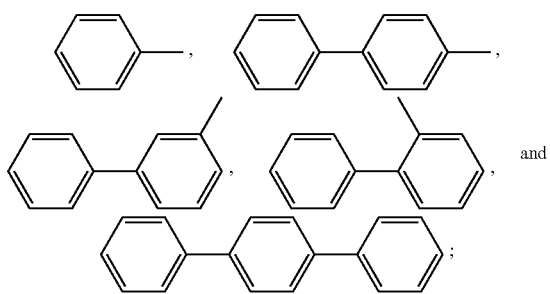

the aromatic hydrocarbon group of the substituted or unsubstituted aromatic hydrocarbon group having 6 to 18 ring carbon atoms represented by L¹ is a phenylene group;

the aromatic hydrocarbon group of the substituted or unsubstituted aromatic hydrocarbon group having 6 to 18 ring carbon atoms represented by L² is a phenylene group or a biphenylylene group;

-(L³)$_c$- in formula (1) is selected from the group consisting of:

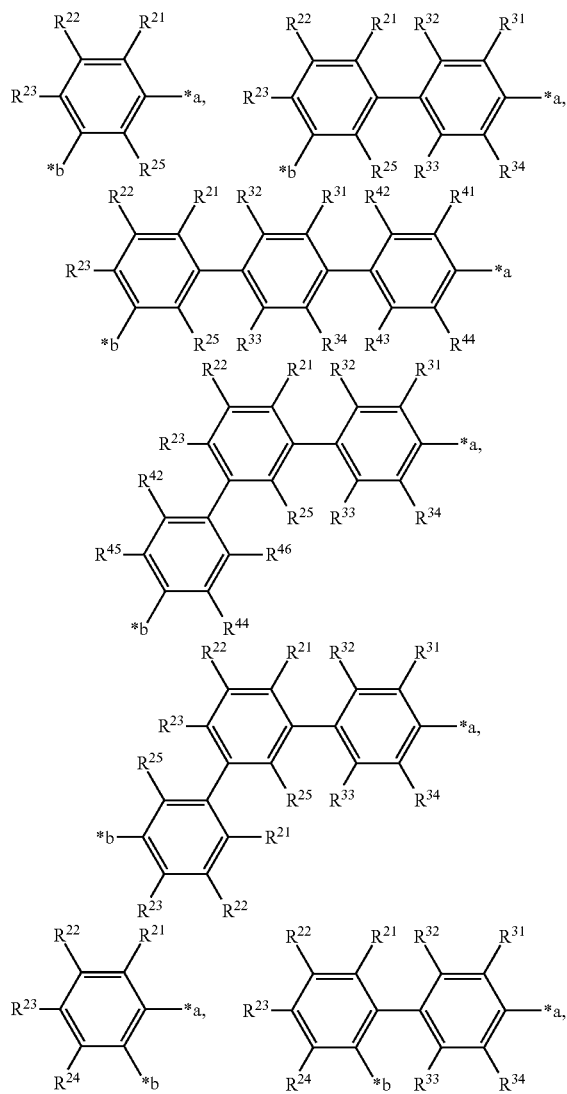

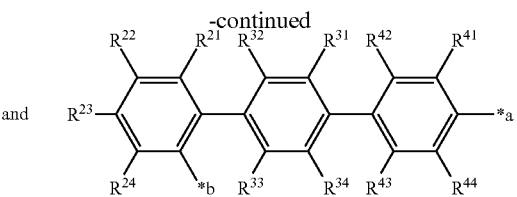

wherein:

R²¹ to R²⁵, R³¹ to R³⁴, and R⁴¹ to R⁴⁶ are each independently as defined above with respect to R¹ to R⁷,

*a is directly bonded to the central nitrogen atom, and

*b is directly bonded to the nitrogen atom of the carbazole structure; and a is 1 and b is 1.

19. The compound according to claim 1, wherein:

the aryl group of the substituted or unsubstituted aryl group having 6 to 30 ring carbon atoms represented by Ar is selected from the group consisting of:

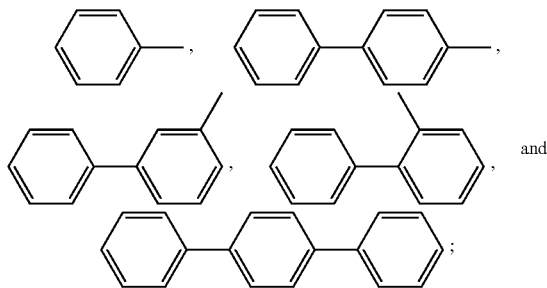

the aromatic hydrocarbon group of the substituted or unsubstituted aromatic hydrocarbon group having 6 to 18 ring carbon atoms represented by each of L¹ and L² is a phenylene group;

-(L³)$_c$- in formula (1) is selected from the group consisting of:

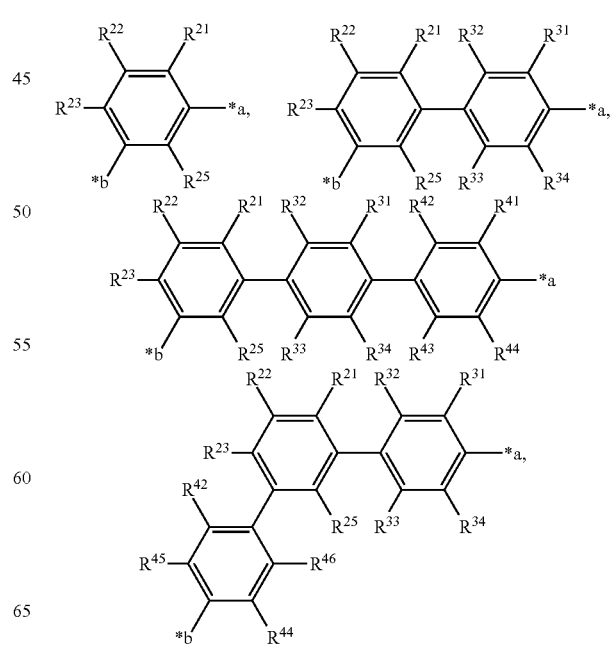

-continued

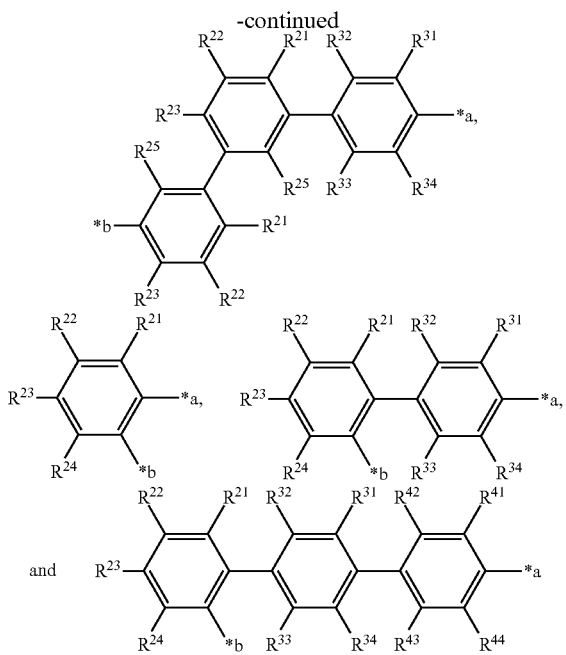

wherein:
$R^{21}$ to $R^{25}$, $R^{31}$ to $R^{34}$, and $R^{41}$ to $R^{46}$ are each independently defined as defined above with respect to $R^1$ to $R^7$,

*a is directly bonded to the central nitrogen atom, and

*b is directly bonded to the nitrogen atom of the carbazole structure; and a is 1 and b is 1.

20. The compound according to claim 1, wherein $R^1$ to $R^7$ and $R^{11}$ to $R^{18}$ are all hydrogen atoms.

21. A material for an organic electroluminescence device, the material comprising the compound according to claim 1.

22. An organic electroluminescence device, comprising a cathode, an anode, and an organic layer disposed between the cathode and the anode, wherein the organic layer comprises a light emitting layer and at least one layer of the organic layer comprises the compound according to claim 1.

23. The organic electroluminescence device according to claim 22, wherein the organic layer comprises a hole transporting region and the hole transporting region comprises the compound.

24. The organic electroluminescence device according to claim 22, wherein the hole transporting region comprises a first hole transporting layer at an anode side and a second hole transporting layer at a cathode side, and one or both of the first hole transporting layer and the second hole transporting layer comprises the compound.

25. An electronic device, comprising the organic electroluminescence device according to claim 22.

* * * * *